US009096527B2

(12) United States Patent
Biswas et al.

(10) Patent No.: US 9,096,527 B2
(45) **Date of Patent: *Aug. 4, 2015**

(54) TRPM8 ANTAGONISTS AND THEIR USE IN TREATMENTS

(71) Applicant: AMGEN INC., Thousand Oaks, CA (US)

(72) Inventors: Kaustav Biswas, Agoura Hills, CA (US); James Brown, Moorpark, CA (US); Jian J. Chen, Camarillo, CA (US); Vijay Keshav Gore, Aliso Veijo, CA (US); Scott Harried, Pittsburgh, PA (US); Daniel B. Horne, Simi Valley, CA (US); Matthew R. Kaller, Ventura, CA (US); Qingyian Liu, Camarillo, CA (US); Vu Van Ma, Oak Park, CA (US); Holger Monenschein, San Diego, CA (US); Thomas T. Nguyen, Newbury Park, CA (US); David J. St. Jean, Jr., Camarillo, CA (US); Chester Chenguang Yuan, Newbury Park, CA (US); Wenge Zhong, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/187,677

(22) Filed: Feb. 24, 2014

(65) Prior Publication Data

US 2014/0171639 A1 Jun. 19, 2014

Related U.S. Application Data

(63) Continuation of application No. 13/529,860, filed on Jun. 21, 2012, now Pat. No. 8,710,043.

(60) Provisional application No. 61/500,843, filed on Jun. 24, 2011.

(51) Int. Cl.

| | |
|---|---|
| ***C07D 498/04*** | (2006.01) |
| ***C07D 401/12*** | (2006.01) |
| ***C07D 471/04*** | (2006.01) |
| ***C07D 213/81*** | (2006.01) |
| ***C07D 213/82*** | (2006.01) |
| ***C07D 213/40*** | (2006.01) |
| ***C07D 213/61*** | (2006.01) |
| ***C07D 401/14*** | (2006.01) |
| ***C07D 403/12*** | (2006.01) |

(Continued)

(52) U.S. Cl.

CPC ............ *C07D 213/82* (2013.01); *C07D 213/40* (2013.01); *C07D 213/61* (2013.01); *C07D 213/81* (2013.01); *C07D 401/12* (2013.01); *C07D 401/14* (2013.01); *C07D 403/12* (2013.01); *C07D 405/12* (2013.01); *C07D 405/14* (2013.01); *C07D 409/12* (2013.01); *C07D 413/12* (2013.01); *C07D 417/12* (2013.01); *C07D 471/04* (2013.01); *C07D 487/04* (2013.01); *C07D 498/04* (2013.01)

(58) Field of Classification Search

CPC .. C07D 213/61; C07D 213/81; C07D 213/82; C07D 401/12; C07D 401/14; C07D 403/12; C07D 405/12; C07D 405/14; C07D 409/12; C07D 413/12; C07D 417/12; C07D 471/04; C07D 487/04

See application file for complete search history.

(56) References Cited

U.S. PATENT DOCUMENTS

| | | | |
|---|---|---|---|
| 2,483,250 | A | 9/1949 | Suter |
| 3,995,044 | A | 11/1976 | Kabbe et al. |

(Continued)

FOREIGN PATENT DOCUMENTS

| | | | |
|---|---|---|---|
| CA | 2135536 | A1 | 5/1995 |
| CA | 2761639 | A1 | 12/2010 |

(Continued)

OTHER PUBLICATIONS

International Search Report and Written Opinion for analogous PCT Application No. PCT/US2012/043566, mailed on Feb. 18, 2013.

(Continued)

*Primary Examiner* — Savitha Rao
(74) *Attorney, Agent, or Firm* — Bernard P. Friedrichsen

(57) ABSTRACT

Compounds of Formula I are useful as antagonists of TRPM8. Such compounds are useful in treating a number of TRPM8 mediated disorders and conditions and may be used to prepare medicaments and pharmaceutical compositions useful for treating such disorders and conditions. Examples of such disorders include, but are not limited to, migraines and neuropathic pain. Compounds of Formula I have the following structure:

I

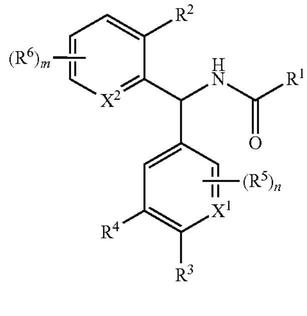

where the definitions of the variables are provided herein.

38 Claims, No Drawings

(51) Int. Cl.

| | |
|---|---|
| ***C07D 405/12*** | (2006.01) |
| ***C07D 405/14*** | (2006.01) |
| ***C07D 409/12*** | (2006.01) |
| ***C07D 413/12*** | (2006.01) |
| ***C07D 417/12*** | (2006.01) |
| ***C07D 487/04*** | (2006.01) |

(56) References Cited

U.S. PATENT DOCUMENTS

| | | | |
|---|---|---|---|
| 4,006,239 | A | 2/1977 | Mayer et al. |
| 5,081,131 | A | 1/1992 | Tomcufcik et al. |
| 5,223,499 | A | 6/1993 | Greenlee et al. |
| 5,296,495 | A | 3/1994 | Matsuo et al. |
| 5,344,813 | A | 9/1994 | Theobald et al. |
| 5,380,721 | A | 1/1995 | Johnson et al. |
| 5,395,840 | A | 3/1995 | Miiller et al. |
| 5,468,882 | A | 11/1995 | Schohe-Loop et al. |
| 5,698,554 | A | 12/1997 | Ishida et al. |
| 5,728,699 | A | 3/1998 | Toriyabe et al. |
| 5,817,677 | A | 10/1998 | Linz et al. |
| 5,891,872 | A | 4/1999 | Doll et al. |
| 5,892,030 | A | 4/1999 | Alig |
| 5,910,595 | A | 6/1999 | Durrwachter |
| 5,916,906 | A | 6/1999 | Shaskan |
| 5,977,090 | A | 11/1999 | Slusher et al. |
| 6,075,029 | A | 6/2000 | Klein et al. |
| 6,200,993 | B1 | 3/2001 | Cote et al. |
| 6,268,384 | B1 | 7/2001 | Novak et al. |
| 6,302,921 | B1 | 10/2001 | Delroisse et al. |
| 6,329,405 | B1 | 12/2001 | Kurata et al. |
| 6,369,227 | B1 | 4/2002 | Lam et al. |
| 6,413,979 | B1 | 7/2002 | Hayama et al. |
| 6,448,281 | B1 | 9/2002 | Beaulieu et al. |
| 6,451,752 | B1 | 9/2002 | Delroisse et al. |
| 6,555,561 | B2 | 4/2003 | Bloom et al. |
| 6,617,351 | B1 | 9/2003 | Arnold et al. |
| 6,630,495 | B1 | 10/2003 | Cooke et al. |
| 6,630,509 | B2 | 10/2003 | Fagerhag et al. |
| 6,696,467 | B2 | 2/2004 | Mattei et al. |
| 6,903,128 | B2 | 6/2005 | Duplantier et al. |
| 7,087,617 | B2 | 8/2006 | Corbett et al. |
| 7,091,371 | B2 | 8/2006 | Ducray et al. |
| 7,179,823 | B1 | 2/2007 | Momose et al. |
| 7,273,856 | B2 | 9/2007 | Sisto et al. |
| 7,291,641 | B2 | 11/2007 | Chabrier De Lassauniere et al. |
| 7,351,713 | B2 | 4/2008 | Chan Chun Kong et al. |
| 7,375,093 | B2 | 5/2008 | Tice et al. |
| 7,405,221 | B2 | 7/2008 | Kopka et al. |
| 7,550,499 | B2 | 6/2009 | Tuerdi et al. |
| 7,601,868 | B2 | 10/2009 | Ishihara et al. |
| 7,618,959 | B2 | 11/2009 | Axten et al. |
| 7,625,937 | B2 | 12/2009 | Ali et al. |
| 7,834,023 | B2 | 11/2010 | Scarborough et al. |
| 7,888,376 | B2 | 2/2011 | Salvati et al. |
| 7,947,718 | B2 | 5/2011 | Carruthers et al. |
| 7,964,204 | B2 | 6/2011 | Lahm et al. |
| 7,968,542 | B2 | 6/2011 | Miyaji et al. |
| 8,017,635 | B2 | 9/2011 | Lyga et al. |
| 8,268,754 | B2 | 9/2012 | Mita et al. |
| 2002/0019527 | A1 | 2/2002 | Wang et al. |
| 2002/0042516 | A1 | 4/2002 | Tom et al. |
| 2003/0050211 | A1 | 3/2003 | Hage et al. |
| 2003/0195212 | A1 | 10/2003 | Lundstedt et al. |
| 2005/0026991 | A1 | 2/2005 | Cholody et al. |
| 2005/0038035 | A1 | 2/2005 | Takasugi et al. |
| 2005/0159450 | A1 | 7/2005 | Dargazanli et al. |
| 2006/0063775 | A1 | 3/2006 | Pajouhesh et al. |
| 2006/0117994 | A1 | 6/2006 | Ryu et al. |
| 2006/0173183 | A1 | 8/2006 | Powers et al. |
| 2007/0066604 | A1 | 3/2007 | Herold et al. |
| 2007/0155738 | A1 | 7/2007 | Steeneck et al. |
| 2007/0185152 | A1 | 8/2007 | Yamashita et al. |
| 2008/0045589 | A1 | 2/2008 | Kelley |
| 2008/0051418 | A1 | 2/2008 | Maekawa et al. |
| 2008/0146612 | A1 | 6/2008 | Thompson et al. |
| 2008/0214552 | A1 | 9/2008 | Fischer et al. |
| 2008/0293674 | A1 | 11/2008 | Schwarz et al. |
| 2008/0293687 | A1 | 11/2008 | Gibson et al. |
| 2008/0312278 | A1 | 12/2008 | Schadt et al. |
| 2009/0069320 | A1 | 3/2009 | Reich et al. |
| 2009/0082358 | A1 | 3/2009 | Nishimura et al. |
| 2009/0239876 | A1 | 9/2009 | Clements et al. |
| 2009/0275550 | A1 | 11/2009 | Barrow et al. |
| 2009/0286765 | A1 | 11/2009 | Blackaby et al. |
| 2010/0063100 | A1 | 3/2010 | Chen et al. |
| 2010/0125062 | A1 | 5/2010 | Allen et al. |
| 2010/0179166 | A1 | 7/2010 | Bell et al. |
| 2010/0261723 | A1 | 10/2010 | Finlay |
| 2010/0261728 | A1 | 10/2010 | Norman et al. |
| 2010/0292263 | A1 | 11/2010 | Wood |
| 2011/0028507 | A1 | 2/2011 | Kim et al. |
| 2011/0028509 | A1 | 2/2011 | Crosignani et al. |
| 2011/0105532 | A1 | 5/2011 | Heil et al. |
| 2011/0105549 | A1 | 5/2011 | Wood et al. |
| 2011/0212969 | A1 | 9/2011 | Blackburn et al. |
| 2011/0269761 | A1 | 11/2011 | Langkopf et al. |
| 2011/0301193 | A1 | 12/2011 | Errico et al. |
| 2012/0004198 | A1 | 1/2012 | Liao et al. |
| 2013/0158034 | A1 | 6/2013 | Brown et al. |

FOREIGN PATENT DOCUMENTS

| | | | |
|---|---|---|---|
| CN | 1733708 | | 2/2006 |
| CN | 101343313 | | 6/2009 |
| CN | 101466676 | A | 6/2009 |
| EP | 0459730 | A2 | 12/1991 |
| EP | 528172 | A1 | 1/1993 |
| EP | 1099442 | A2 | 5/2001 |
| EP | 1099701 | A1 | 5/2001 |
| EP | 1500650 | A1 | 1/2005 |
| EP | 2272841 | A1 | 1/2011 |
| FR | 2692895 | A1 | 6/1992 |
| JP | 53141271 | A1 | 12/1978 |
| JP | 07285962 | A1 | 10/1995 |
| JP | 2001354563 | A1 | 12/2001 |
| JP | 2002302439 | A1 | 10/2002 |
| JP | 2004115450 | A1 | 4/2004 |
| JP | 2004175872 | A1 | 6/2004 |
| JP | 2004203871 | A1 | 7/2004 |
| JP | 2007091708 | A1 | 8/2007 |
| WO | WO 9212973 | | 1/1992 |
| WO | WO 9312796 | A1 | 7/1993 |
| WO | WO 9701546 | A1 | 1/1996 |
| WO | WO 9620173 | A1 | 7/1996 |
| WO | WO 9710219 | A1 | 3/1997 |
| WO | WO 9715567 | A1 | 5/1997 |
| WO | WO 9722588 | A1 | 6/1997 |
| WO | WO 9962486 | A1 | 12/1999 |
| WO | WO 0035889 | A1 | 6/2000 |
| WO | WO 0116271 | A1 | 3/2001 |
| WO | WO 0158869 | A2 | 8/2001 |
| WO | WO 0181316 | A2 | 11/2001 |
| WO | WO 02051396 | A1 | 7/2002 |
| WO | WO 02079189 | A2 | 10/2002 |
| WO | WO 02088073 | A1 | 11/2002 |
| WO | WO 03045385 | A1 | 6/2003 |
| WO | WO 03051275 | A2 | 6/2003 |
| WO | WO 03082278 | A1 | 10/2003 |
| WO | WO 2004013100 | A2 | 2/2004 |
| WO | WO 2004/026840 | A1 | 4/2004 |
| WO | WO 2004039795 | A2 | 5/2004 |
| WO | WO 2004058755 | A2 | 7/2004 |
| WO | WO 2005005392 | A1 | 1/2005 |
| WO | WO 2005007656 | A1 | 1/2005 |
| WO | WO 2005021545 | A1 | 3/2005 |
| WO | WO 2005023794 | A2 | 3/2005 |
| WO | WO 2005/046683 | | 5/2005 |
| WO | WO 2005042524 | A1 | 5/2005 |
| WO | WO 2005080373 | A1 | 9/2005 |
| WO | WO 2005080390 | A1 | 9/2005 |
| WO | WO 2005113553 | A2 | 12/2005 |
| WO | WO 2005115374 | A1 | 12/2005 |
| WO | WO 2006002383 | A2 | 1/2006 |

(56) References Cited

FOREIGN PATENT DOCUMENTS

| | | | |
|---|---|---|---|
| WO | WO 2006068594 | A1 | 6/2006 |
| WO | WO 2006094246 | A2 | 9/2006 |
| WO | WO 2007002559 | A1 | 1/2007 |
| WO | WO 2007/017093 | A1 | 2/2007 |
| WO | WO 2007054215 | A1 | 5/2007 |
| WO | WO 2007054302 | A1 | 5/2007 |
| WO | WO 2007060028 | A1 | 5/2007 |
| WO | WO 2007062314 | A2 | 5/2007 |
| WO | WO 2007068381 | A1 | 6/2007 |
| WO | WO 2007068383 | A1 | 6/2007 |
| WO | WO 2007086799 | A1 | 8/2007 |
| WO | WO 2007097470 | A2 | 8/2007 |
| WO | WO 2007141504 | A1 | 12/2007 |
| WO | WO 2008003746 | A1 | 1/2008 |
| WO | WO 2008/022938 | | 2/2008 |
| WO | WO 2008014602 | A1 | 2/2008 |
| WO | WO 2008056687 | A1 | 5/2008 |
| WO | WO 2008063667 | A1 | 5/2008 |
| WO | WO 2008063670 | A1 | 5/2008 |
| WO | WO 2008073825 | A1 | 6/2008 |
| WO | WO 2008080015 | A2 | 7/2008 |
| WO | WO 2008112156 | A1 | 9/2008 |
| WO | WO 2009023179 | A2 | 2/2009 |
| WO | WO 2009117269 | A1 | 9/2009 |
| WO | WO 2009156089 | A1 | 12/2009 |
| WO | WO 2010027236 | A2 | 3/2010 |
| WO | WO 2010046780 | A2 | 4/2010 |
| WO | WO 2010114471 | A1 | 10/2010 |
| WO | WO 2010137351 | A1 | 12/2010 |
| WO | WO 2010141330 | A1 | 12/2010 |
| WO | WO 2011014649 | A1 | 2/2011 |
| WO | WO 2011023703 | A1 | 3/2011 |
| WO | WO 2011054436 | A2 | 5/2011 |
| WO | WO 2011085126 | A2 | 7/2011 |
| WO | WO 2011106632 | A1 | 9/2011 |
| WO | WO 2011142359 | A1 | 11/2011 |
| WO | WO 2011146300 | A1 | 11/2011 |
| WO | WO 2011147765 | A1 | 12/2011 |
| WO | WO 2012052540 | A1 | 4/2012 |
| WO | WO 2012061698 | A2 | 5/2012 |
| WO | WO 2012078855 | A1 | 6/2012 |
| WO | WO 2012079624 | A1 | 6/2012 |
| WO | WO 2012082862 | A2 | 6/2012 |
| WO | WO 2012083190 | A1 | 6/2012 |
| WO | WO 2012118850 | A1 | 9/2012 |
| WO | WO 2012120398 | A1 | 9/2012 |

OTHER PUBLICATIONS

International Search Report for PCT Application No. PCT/US2012/043569, mailed on Sep. 24, 2012.

Albrecht, W. L. et al, "3-Substituted Imidazo[1,5-a]pyridines," *Journal of Heterocyclic Chemistry*, 16(7), pp. 1349-1351 (1979).

Bensel, N. et al, "BenseneIStraightforward Synthesis of N-Protected Benzylic Amines by Carbamoalkylation of Aromatic Compounds," *Tetrahedron Letters*, 40, pp. 879-882 (1999).

Boyer, J. H. et al, "Diazotization of 2-Pyridylmethylamine," *Journal of Organic Chemistry*, 23, pp. 1053-1054 (1958).

Childers, W. E. et al., "Advances in the Development of Novel Analgesics," *Expert Opinion on Therapeutic Patents*, 18(8), pp. 1027-1067 (2008).

Chung, J.-U. et al, "α-Substituted N-(4-tert-Butylbenzy1)-N'-[4-(methylsulfonylamino)-benzyl]thiourea Analogues as Potent and StereospecificTRPV1 Antagonists," *Bioorganic & Medicinal Chemistry*, 15, pp. 6043-6053 (2007).

DeFalco, J. et al., "TRPM8 Biology and Medicinal Chemistry," *Current Topics in Medicinal Chemistry*, 11(17), pp. 2237-2252 (2011).

Dou, X.-Y. et al, "Rhodium-Catalyzed Arylation of α-Amido Sulfones with Arylboronic Acids in a Water-Toluene Biphasic System," *Inorganica Chimica Acta*, 369, pp. 284-287 (2011).

Gomtsyan, A. et al, "α-Methylation at Benzylic Fragment of N-Aryl-N'-benzyl Ureas provides TRPV1 antagonists with better pharmacokinetic properties and higher efficacy in inflammatory pain model," *Bioorganic & Medicinal Chemistry Letters*, 17, pp. 3894-3899 (2007).

Heymans, F. et al., "Quantitative Structure-Activity Relationships for N-[(N',N'-Disubstituted-amino)acetyl]arylamines for Local Anesthetic Activity and Acute Toxicity," *Journal of Medicinal Chemistry*, 23(2), pp. 184-193 (1980).

Hou, G. et al., "Iridium,-Monodentate Phophoramidite-Catalyzed Asymmetric Hydrogenation of Substituted Benzophenone N-H Imines," *Journal of the American Chemical Society*, 132(7) pp. 2124-2125 and S1-S52 (2010).

Kovtun, Y. P. et al, "Improved Method for the Preparation of 3-Aryl- and 3-Styrylimidazo[1,5-a]pyridines," *Chemistry of Heterocyclic Compounds* (New York) (Translation of Khimiya Geterotsiklicheskikh Soedinenii), 36(5), pp. 557-559 (2000).

Kraznov, V. A. et al., "Synthesis and Anticonvulsive Activity of Fluorine-Substituted Benzyhydrylamides," Pharmaceutical Chemistry Journal, 31(7), pp. 368-369 (1997).

Laurent, M. et al, "A Practical Synthesis of para Di- and Mono-Substituted Benzhydrylamines from Benzhydrol Precursors," *Synthesis*, 5, pp. 667-672 (2000).

Lespagnol, A. et al, "Amides with a papaverine structure." *Bulletin de la Societe Chimique de France*, (2), pp. 699-702, (1972).

Liu, Z. et al, "Catalytic Asymmetric Addition of Arylboronic acids to N-Boc Imines Generated in situ using C2-Symmetric Cationic N-Heterocyclic Carbenes (NHCs) Pd2þ diaquo complexes," *Tetrahedron*, 66, pp. 2619-2623 (2010).

Maki, T. et al., "4,5,6,7-Tetrachlorobenzo[d][1,3,2]dioxaboro-2-ol as an Effective Catalyst for the Amide Condensation of Sterically Demanding Carboxylic Acids," *Organic Letters*, 8(7), pp. 1431-1434 and S1-S29 (2006).

Metzger, F. et al. "Sulphonylurea Binding in Rat Isolated Glomeruli: Pharmacological Characterization and Dependence on Cell Metabolism and Cytoskeleton," *Nauyn-Schmiedberg's Archives of Pharmacology*, 355(2), pp. 141-149 (1997).

Muccioli, G.G. et al, "1-Benzhydryl-3-phenylurea and 1-Benzhydryl-3-phenylthiourea Derivatives: New Templates among the CB1 Cannabinoid Receptor Inverse Agonists," *Journal of Medicinal Chemistry*, 48, pp. 7486-7490 (2005).

Pacchiano, F. et al, "Ureido-Substituted Benzenesulfonamides Potently Inhibit Carbonic Anhydrase IX and Show Antimetastatic Activity in a Model of Breast Cancer Metastasis," *Journal of Medicinal Chemistry*, 54, pp. 1896-1902 (2011).

Raja, E. K. et al., "Superelectrophilic Chemistry of Amino-Nitriles and Related Substrates," *Tetrahedron*, 67(25), pp. 4494-4497 (2011).

Sasse, A. et al, "(Partial) Agonist/Antagonist Properties of Novel Diarylalkyl Carbamates on Histamine H3 Receptors," *Bioorganic & Medicinal Chemistry*, 8, pp. 1139-1149 (2000).

Trivedi, B.K. et al, "Inhibitors of Acyl-CoA:Cholesterol Acyltransferase. 4. A Novel Series of Urea ACAT Inhibitors as Potential Hypocholesterolemic Agents," *Journal of Medicinal Chemistry*, 36(22), pp. 3300-3307 (1993).

Weil, A, "Conservation of Functional and Pharmacological Properties in the Distantly Related Temperature Sensors TRPV1 and TRPM8," *Molecular Pharmacology*, 68(2), pp. 518-527 (2005).

Wrobleski, S.T. et al.,"Rational Design and Synthesis of an Orally Active Indolopyridone as a Novel Conformationally Constrained Cannabinoid Ligand Possessing Antiinflammatory Properties," *Journal of Medicinal Chemistry*, 46(11), pp. 2110-2116 (2003).

XP002690876, Database PubChem Compound [Online]"ACIM78XL-Compound Summary" Database Accession No. CID2437712 (Jul. 15, 2005) (Cited in International Search Report for PCT Application No. PCT/US2012/043566).

XP002690877, Database Registry [Online] Chemical Abstracts Service, Columbus, Ohio, US "6-Methoxy-N-[phenyl(pyridin-2-yl)methyl]quinoline-2-carboxamide," Database Accession No. 1241062-82-7 (Sep. 15, 2010) (Cited in International Search Report for PCT Application No. PCT/US2012/043566).

XP002691556, Database PubChem Compound [Online] "Zinc58157967—Compound Summary" Database Accession No.

(56) References Cited

OTHER PUBLICATIONS

CID52501511 (May 20, 2011) (Cited in International Search Report for PCT Application No. PCT/US2012/043566).
XP002690878, Database Registry [Online] Chemical Abstracts Service, Columbus, Ohio, US "1,6-Dihydro-1-methyl-6-oxo-N-(phenyl-2-pyridinylmethyl)-3-pyridinecarboxamide," Database Accession No. 1280882-39-4 (Apr. 17, 2011) (Cited in International Search Report for PCT Application No. PCT/US2012/043566).
XP002690879, Database Registry [Online] Chemical Abstracts Service, Columbus, Ohio, US "2-Methyl-N-(phenyl-3-pyridinylmethyl)-1H-benzimidazole-6-carboxamide," Database Accession No. 1214549-94-6 (Mar. 25, 2010) (Cited in International Search Report for PCT Application No. PCT/US2012/043566).
Prosecution History of Copending U.S. Appl. No. 13/529,880, filed Jun. 21, 2012, and published on Jun. 20, 2013 as US Patent Application Publication No. US 2013/0158034 A1.
Patani, G. A. et al., "Bioisosterism: A Rational Approach in Drug Design", Chem Rev. 96, pp. 3147-3176 (1996).
Steffen Paulekuhn, G. et al., "Trends in Active Pharmaceutical Ingredient Salt Selection based on Analysis of the Orange Book Database", J. Med. Chem. 50, pp. 6665-6672 (2007).
U.S. Appl. No. 13/529,880, filed Jun. 21, 2012, Amgen Inc.
A-1658-CN-PCT English Translation First Office Action (Nov. 13, 2014).

TRPM8 ANTAGONISTS AND THEIR USE IN TREATMENTS

CROSS REFERENCES TO RELATED APPLICATIONS

This application is a continuation of, and claims priority to, U.S. patent application Ser. No. 13/529,860, filed on Jun. 21, 2012, pending, which claims the benefit of, and priority to, U.S. Provisional Application No. 61/500,843, filed on Jun. 24, 2011, both of which are hereby incorporated by reference in their entireties and for all purposes as if fully set forth herein.

FIELD OF THE INVENTION

The present invention relates to compounds that have TRPM8 antagonist properties and are useful in preparing medicaments and compositions and in treating diseases and conditions such as those mediated by TRPM8. The compounds and compositions may be used to treat various diseases or conditions modulated by TRPM8 such as, but not limited to, migraines and neuropathic pain.

BACKGROUND OF THE INVENTION

Cold sensation is derived from activation of the somatosensory system by a cold stimulus. Calcium imaging and patch clamp experiments in dissociated trigeminal and dorsal root ganglia neurons have revealed cold stimuli induced calcium influx, suggesting the direct opening of a calcium-permeable ion channels by cold (Thut et al., 2003; Reid, 2005). A recently cloned non-selective cation channel, TRPM8 (transient receptor potential melastatin 8) or trp-p8 (identified as a prostate-specific gene, up-regulated in prostate cancer and other malignancies, (Tsavaler et al., 2001)) is activated by cold stimulus of 10 to 24° C. temperature (McKemy et al., 2002; Peier et al., 2002). In addition, TRPM8 is also activated by compounds that elicit cool sensation such as menthol, icilin (AG-3-5) (McKemy et al., 2002), and the endogenous lipid $PIP_2$ (Rohacs et al., 2005). Correlating with the cold sensitivity of both A delta and C-fibers, TRPM8 is highly expressed in sensory neurons of the trigeminal and dorsal root ganglia (McKemy et al., 2002; Peier et al., 2002; Thut et al., 2003). TRPM8 is also expressed in nerve fibers innervating urinary bladder in guinea pigs (Tsukimi et al., 2005) and humans (Mukerji et al., 2006) and believed to contribute to the bladder hypersensitivity.

Activation mechanism of TRPM8 by menthol and icilin appears to differ. Icilin requires calcium for robust activation of TRPM8, whereas menthol and cold do not (Chuang et al., 2004). Typically, activation by all these agonists follows a period of calcium-dependent desensitization. The domain swap analysis of chicken and rat TRPM8 and further mutational studies revealed that determinants of icilin sensitivity map to a region of TRPM8 that corresponds to the capsaicin binding site in TRPV1 transmembrane domain 3 to 4 region (Chuang et al., 2004).

Cold allodynia and mechanical hyperalgesia are associated with neuropathic pain in humans and in rodent models of neuropathic and chemotherapy-induced pain. TRPM8 is shown to mediate the analgesia by agonists such as menthol and icilin (by desensitization of the receptor) during experimental neuropathic pain in rodents (Proudfoot et al., 2006). Further, attenuation of cold sensation and cold allodynia after chronic constriction injury model of neuropathic pain in TRPM8 knockout mice (Colburn et al., 2007; Dhaka et al., 2007) suggests that antagonists of TRPM8 may be considered as pain therapeutics for chemotherapy-induced pain, neuropathic pain and bladder disorders.

Mint oil that contains menthol, an agonist of TRPM8 has been reported to alleviate pain in post-herpetic neuralgia (Davies et al., 2002), a neuropathic pain condition. Furthermore, oral or intracerebroventricular injection of menthol decreased nociceptive responses to hot-plate test and acetic acid-induced writhing in mice (Galeotti et al., 2002). These responses are believed to be mediated by the activation and desensitization of the TRPM8. These observations and the knockout mice studies indicate that TRPM8 modulation by antagonists might be beneficial for patients experiencing neuropathic pain.

A need exists for TRPM8 antagonist compounds that can be used to treat diseases and conditions mediated by TRPM8 such as, but not limited to, migraines and neuropathic pain and those other conditions described herein.

SUMMARY OF THE INVENTION

The present invention comprises a new class of compounds useful in the treatment of diseases, such as TRPM8-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of TRPM8-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

In one aspect, the compounds of the invention are represented by the following general structure:

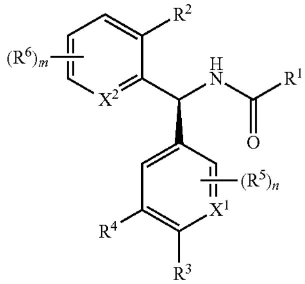

or pharmaceutically acceptable salt thereof, wherein $R^1$, $R^2$, $R^3$, $R^4$, $R^5$, $R^6$, $X^1$, $X^2$, m and n are defined below.

In another aspect, the invention provides compounds of Formula I having the structure:

I

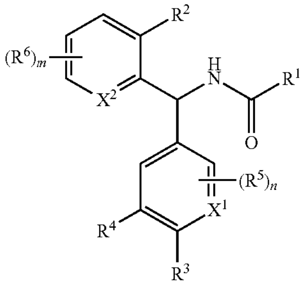

a pharmaceutically-acceptable salt thereof, a tautomer thereof, a pharmaceutically-acceptable salt of the tautomer, a stereoisomer thereof, or a mixture thereof, wherein:

m is 0, 1, 2 or 3;

n is 0 or 1;

$X^1$ is $C(R^4)$ or N;

$X^2$ is CH, CF, or N;

$R^1$ is $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)$OR^a$, $C_{1-4}$haloalk, cyano, nitro, —C(=O)$R^a$, —C(=O)$OR^a$, —C(=O)$NR^aR^a$, —C(=$NR^a$)$NR^aR^a$, —$OR^a$, —OC(=O)$R^a$, —OC(=O)$NR^aR^a$, —OC(=O)N($R^a$)S(=O)$_2R^a$, —$OC_{2-6}$alk$NR^aR^a$, —$OC_{2-6}$alk$OR^a$, —$SR^a$, =S, —S(=O)$R^a$, —S(=O)$_2R^a$, —S(=O)$_2NR^aR^a$, —S(=O)$_2$N($R^a$)C(=O)$R^a$, —S(=O)$_2$N($R^a$)C(=O)$OR^a$, —S(=O)$_2$N($R^a$)C(=O)$NR^aR^a$, —$NR^aR^a$, —N($R^a$)C(=O)$R^a$, —N($R^a$)C(=O)$OR^a$, —N($R^a$)C(=O)$NR^aR^a$, —N($R^a$)C(=$NR^a$)$NR^aR^a$, —N($R^a$)S(=O)$_2R^a$, —N($R^a$)S(=O)$_2NR^aR^a$, —$NR^aC_{2-6}$alk$NR^aR^a$ and —$NR^aC_{2-6}$alk$OR^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, $C_{1-6}$alk, $C_{1-4}$haloalk, cyano, nitro, —C(=O)$R^a$, —C(=O)$OR^a$, —C(=O)$NR^aR^a$, —C(=$NR^a$)$NR^aR^a$, —$OR^a$, —OC(=O)$R^a$, —$SR^a$, —S(=O)$R^a$, —S(=O)$_2R^a$, —S(=O)$_2NR^aR^a$, —$NR^aR^a$, and —N($R^a$)C(=O)$R^a$;

$R^2$ is H, halo, cyano, $R^c$, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$ and —$NR^aC_{2-6}$alk$OR^a$; or $R^2$ is $C_{1-6}$alk substituted by 0, 1, 2 or 3 substituents selected from $C_{1-4}$haloalk, halo, cyano, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$ and —$NR^aC_{2-6}$alk$OR^a$, or $R^2$ is $C_{1-6}$alk substituted by 0, 1, 2 or 3 halo substituents and additionally substituted by 0 or 1 substituents selected from $R^c$;

$R^3$ is H, $C_{1-8}$alk, $C_{1-8}$alkOH, $C_{1-4}$haloalk, halo, cyano, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$ or —$NR^aC_{2-6}$alk$OR^a$;

$R^4$ is independently, at each instance, H, $C_{1-6}$alk, —$C_{1-3}$haloalk, —$OC_{1-6}$alk, —$OC_{1-3}$haloalk, —N($C_{1-6}$alk)$C_{1-6}$alk, —$NHC_{1-6}$alk, —NC(=O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, halo, $OR^a$, $CH_3$ or $CF_3$;

$R^6$ is F, $C_{1-6}$alk, or $OR^a$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 heteroatoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

In some such embodiments, the compound of Formula I has the Formula IA:

IA

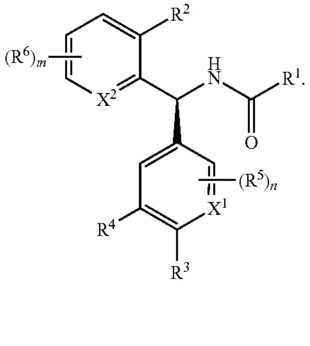

In some embodiments of the compounds of Formula IA, $X^2$ is selected from CH or N;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —S$R^a$, —S(═O)$R^a$, —S(═O)$_2R^a$, —S(═O)$_2$N$R^aR^a$, —N$R^aR^a$, and —N($R^a$)C(═O)$R^a$;

$R^3$ is H, $C_{1-8}$alk, $C_{1-4}$haloalk, halo, cyano, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ or —N$R^a$$C_{2-6}$alkO$R^a$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, $CH_3$ or $CF_3$; and $R^6$ is F.

In another aspect, the invention provides pharmaceutical compositions that include the compound of any of the embodiments or the pharmaceutically-acceptable salt thereof, the tautomer thereof, the pharmaceutically-acceptable salt of the tautomer, or the mixture thereof, and a pharmaceutically-acceptable diluent or carrier.

In yet another aspect, the invention provides methods of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. Such methods typically include administering the compound according to any of the embodiments or the pharmaceutically-acceptable salt thereof, the tautomer thereof, the pharmaceutically-acceptable salt of the tautomer, or the mixture thereof to the subject. In some such embodiments, the subject is suffering from neuropathic paid whereas in other embodiments the subject is suffering from migraines or migraine pain.

The compounds of the invention may also be used to prepare pharmaceutical compositions and medicaments. Therefore, in some embodiments, the invention provides the use of the compound according to any of the embodiments or the pharmaceutically-acceptable salt thereof, the tautomer thereof, the pharmaceutically-acceptable salt of the tautomer, or the mixture thereof in the preparation of a medicament.

In another aspect, the invention provides the use of the compound according to any of the embodiments or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. In some such embodiments, the compound is used to treat neuropathic paid. In other embodiments, the compound is used to treat migraines or migraine pain The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alk" means an alkyl group comprising a minimum of a and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

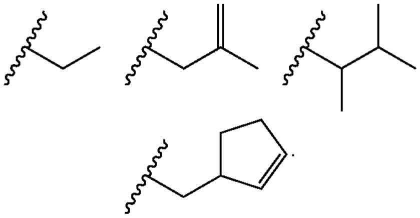

Where the term "$C_{\alpha-\beta}$alkyl" and "$C_{\alpha-\beta}$cycloalkyl" are used, they relate to acyclic saturated alkyls and cyclic saturated alkyls, respectively.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

The term "cyano" refers to a nitrile group which may be written as —C≡N.

"Halo" or "halogen" means a halogen atoms selected from F, Cl, Br and I.

"$C_{V-W}$haloalk" means an alk group, as described above, wherein any number, but at least one, of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

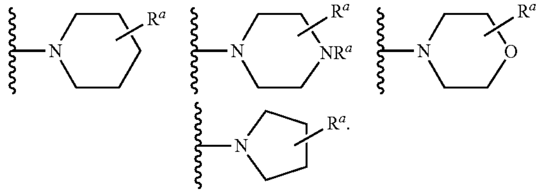

The group $N(C_{\alpha-\beta}alk)C_{\alpha-\beta}alk$, wherein α and β are as defined above, include substituents where the two $C_{\alpha-\beta}$alk groups together form a ring, optionally including a N, O or S atom, and include groups such as:

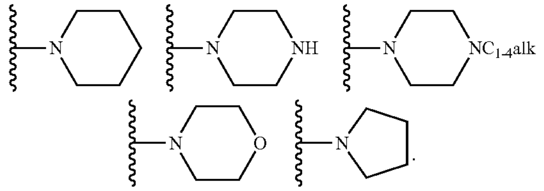

"Heterocycle" means a ring comprising at least one carbon atom and at least one other atom selected from N, O and S. Examples of heterocycles that may be found in the claims include, but are not limited to, the following:

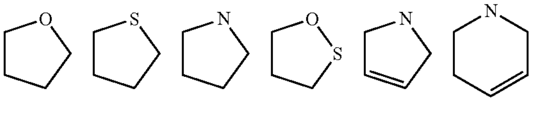

-continued

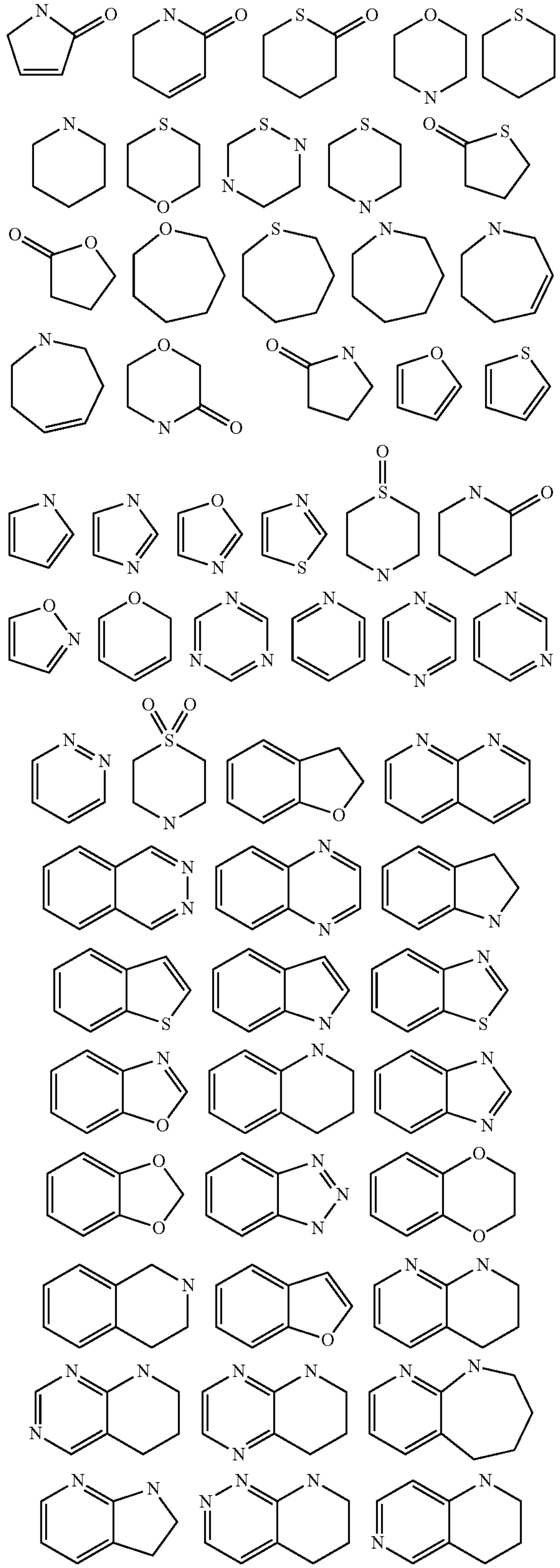

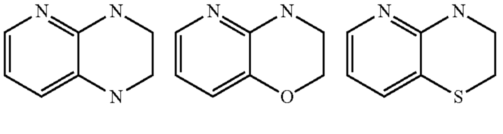

and

-continued

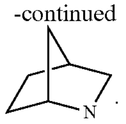

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

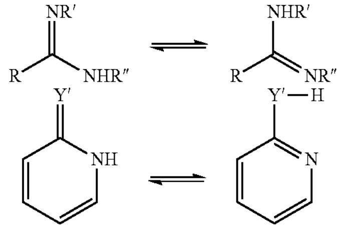

-continued

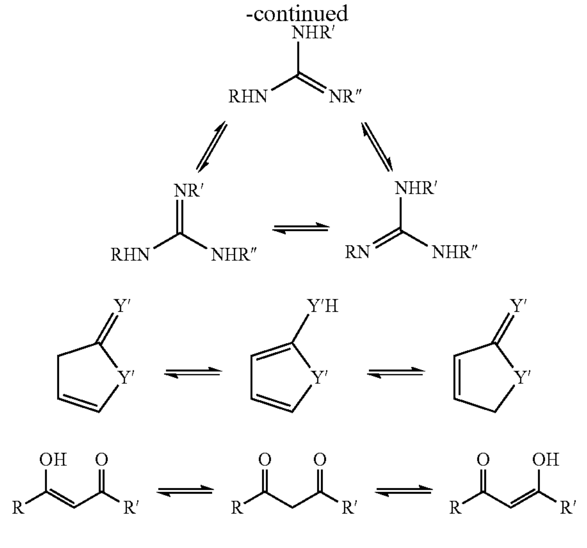

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

The specification and claims contain listing of species using the language like "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

One aspect of the current invention relates to compounds having the general structure:

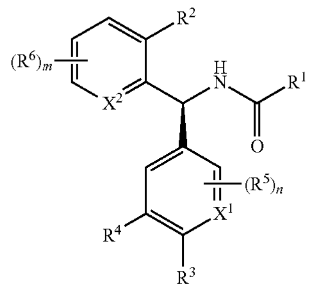

or any pharmaceutically-acceptable salt thereof, wherein:

m is 0, 1, 2 or 3;

n is 0 or 1;

$X^1$ is C($R^4$) or N;

$X^2$ is C or N;

Y is NH or O;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —S$R^a$, —S(═O)$R^a$, —S(═O)$_2R^a$, —S(═O)$_2$N$R^aR^a$, —N$R^aR^a$, and —N($R^a$)C(═O)$R^a$;

$R^2$ is selected from H, halo, cyano, $R^c$, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ and —N$R^a$$C_{2-6}$alkO$R^a$; or $R^2$ is $C_{1-6}$alk substituted by 0, 1, 2 or 3 substituents selected from $C_{1-4}$haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ and —N$R^a$$C_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN- $R^aR^a$, —$OC_{2-6}alkOR^a$, —$SR^a$, —S(═O)$R^b$, —S(═O)$_2R^b$, —S(═O)$_2NR^aR^a$, —$NR^aR^a$, —N($R^a$)C(═O)$R^b$, —N($R^a$)C(═O)O$R^b$, —N($R^a$)C(═O)$NR^aR^a$, —N($R^a$)C(═$NR^a$)$NR^aR^a$, —N($R^a$)S(═O)$_2R^b$, —N($R^a$)S(═O)$_2NR^aR^a$, —$NR^aC_{2-6}alkNR^aR^a$ or —$NR^aC_{2-6}alkOR^a$;

$R^4$ is independently, at each instance, H, $C_{1-6}$alk, —$C_{1-3}$ haloalk, —$OC_{1-6}$alk, —$OC_{1-3}$haloalk, —N($C_{1-6}$alk)$C_{1-6}$alk, —$NHC_{1-6}$alk, —NC(═O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, $CH_3$ or $CF_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

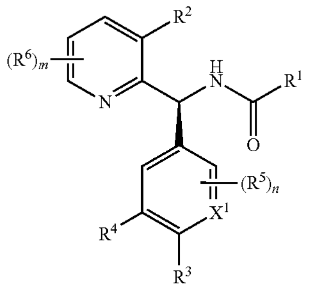

or any pharmaceutically-acceptable salt thereof, wherein:

m is 0, 1, 2 or 3;

n is 0 or 1;

$X^1$ is C($R^4$) or N;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)$NR^aR^a$, —C(═$NR^a$)$NR^aR^a$, —$OR^a$, —OC(═O)$R^a$, —OC(═O)$NR^aR^a$, —OC(═O)N($R^a$)S(═O)$_2R^a$, —$OC_{2-6}alkNR^aR^a$, —$OC_{2-6}alkOR^a$, —$SR^a$, —S(═O)$R^a$, —S(═O)$_2R^a$, —S(═O)$_2NR^aR^a$, —S(═O)$_2$N($R^a$)C(═O)$R^a$, —S(═O)$_2$N($R^a$)C(═O)O$R^a$, —S(═O)$_2$N($R^a$)C(═O)$NR^aR^a$, —$NR^aR^a$, —N($R^a$)C(═O)$R^a$, —N($R^a$)C(═O)O$R^a$, —N($R^a$)C(═O)$NR^aR^a$, —N($R^a$)C(═$NR^a$)$NR^aR^a$, —N($R^a$)S(═O)$_2R^a$, —N($R^a$)S(═O)$_2NR^aR^a$, —$NR^aC_{2-6}alkNR^aR^a$ and —$NR^aC_{2-6}alkOR^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(═O)$R^a$, —C(═O)O$R^a$, —C(═O)$NR^aR^a$, —C(═$NR^a$)$NR^aR^a$, —$OR^a$, —OC(═O)$R^a$, —$SR^a$, —S(═O)$R^a$, —S(═O)$_2R^a$, —S(═O)$_2NR^aR^a$, —$NR^aR^a$, and —N($R^a$)C(═O)$R^a$;

$R^2$ is selected from H, halo, cyano, Re, —C(═O)$R^b$, —C(═O)O$R^b$, —C(═O)$NR^aR^a$, —C(═$NR^a$)$NR^aR^a$, —$OR^a$, —OC(═O)$R^b$, —OC(═O)$NR^aR^a$, —$OC_{2-6}$alkN-$R^aR^a$, —$OC_{2-6}alkOR^a$, —$SR^a$, —S(═O)$R^b$, —S(═O)$_2R^b$, —S(═O)$_2NR^aR^a$, —$NR^aR^a$, —N($R^a$)C(═O)$R^b$, —N($R^a$)C(═O)O$R^b$, —N($R^a$)C(═O)$NR^aR^a$, —N($R^a$)C(═$NR^a$)$NR^aR^a$, —N($R^a$)S(═O)$_2R^b$, —N($R^a$)S(═O)$_2NR^aR^a$, —$NR^aC_{2-6}alkNR^aR^a$ and —$NR^aC_{2-6}alkOR^a$; or $R^2$ is $C_{1-6}$alk substituted by 0, 1, 2 or 3 substituents selected from $C_{1-4}$haloalk, halo, cyano, nitro, —C(═O)$R^b$, —C(═O)O$R^b$, —C(═O)$NR^aR^a$, —C(═$NR^a$)$NR^aR^a$, —$OR^a$, —OC(═O)$R^b$, —OC(═O)$NR^aR^a$, —$OC_{2-6}alkNR^aR^a$, —$OC_{2-6}alkOR^a$, —$SR^a$, —S(═O)$R^b$, —S(═O)$_2R^b$, —S(═O)$_2NR^aR^a$, —$NR^aR^a$, —N($R^a$)C(═O)$R^b$, —N($R^a$)C(═O)O$R^b$, —N($R^a$)C(═O)$NR^aR^a$, —N($R^a$)C(═$NR^a$)$NR^aR^a$, —N($R^a$)S(═O)$_2R^b$, —N($R^a$)S(═O)$_2NR^aR^a$, —$NR^aC_{2-6}alkNR^aR^a$ and —$NR^aC_{2-6}alkOR^a$, or $R^2$ is $C^{1-6}$alk substituted by 0, 1, 2 or 3 halo substituents and additionally substituted by 0 or 1 substituents selected from $R^c$;

$R^3$ is H, $C_{8-8}$alk, $C_{1-4}$haloalk, halo, cyano, —C(═O)$R^b$, —C(═O)O$R^b$, —C(═O)$NR^aR^a$, —C(═$NR^a$)$NR^aR^a$, —$OR^a$, —OC(═O)$R^b$, —OC(═O)$NR^aR^a$, —$OC_{2-6}$alkN-$R^aR^a$, —$OC_{2-6}alkOR^a$, —$SR^a$, —S(═O)$R^b$, —S(═O)$_2R^b$, —S(═O)$_2NR^aR^a$, —$NR^aR^a$, —N($R^a$)C(═O)$R^b$, —N($R^a$)C(═O)O$R^b$, —N($R^a$)C(═O)$NR^aR^a$, —N($R^a$)C(═$NR^a$)$NR^aR^a$, —N($R^a$)S(═O)$_2R^b$, —N($R^a$)S(═O)$_2NR^aR^a$, —$NR^aC_{2-6}alkNR^aR^a$ or —$NR^aC_{2-6}alkOR^a$;

$R^4$ is independently, at each instance, H, $C_{1-6}$alk, —$C_{1-3}$ haloalk, —$OC_{1-6}$alk, —$OC_{1-3}$haloalk, —N($C_{1-6}$alk)$C_{1-6}$alk, —$NHC_{1-6}$alk, —NC(═O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, $CH_3$ or $CF_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

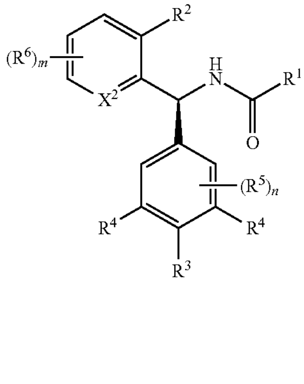

or any pharmaceutically-acceptable salt thereof, wherein:

m is 0, 1, 2 or 3;

n is 0 or 1;

$X^2$ is C or N;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —S$R^a$, —S(═O)$R^a$, —S(═O)$_2R^a$, —S(═O)$_2$N$R^aR^a$, —N$R^aR^a$, and —N($R^a$)C(═O)$R^a$;

$R^2$ is selected from H, halo, cyano, $R^e$, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ and —N$R^a$$C_{2-6}$alkO$R^a$; or $R^2$ is $C_{1-6}$alk substituted by 0, 1, 2 or 3 substituents selected from $C_{1-4}$haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ and —N$R^a$$C_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ or —N$R^a$$C_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(═O)$C_{1-6}$alk, —N($C_{1-6}$alk)$C_{1-6}$alk, F, Cl, Br, CN, OH or $NH_2$;

$R^5$ is F, $CH_3$ or $CF_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

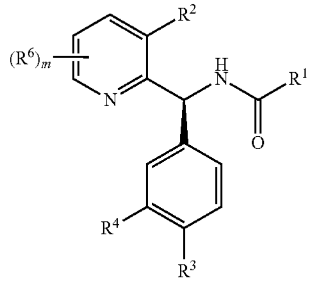

or any pharmaceutically-acceptable salt thereof, wherein:

m is 0, 1, 2 or 3;

$R^1$ is a direct-bonded, partially-saturated or unsaturated 5- or 6-membered monocyclic ring containing 1 or 2 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk and cyano;

$R^2$ is selected from F and $CF_3$;

$R^3$ is $CH_3$, $CF_3$, F or Cl;

$R^4$ is H or F;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

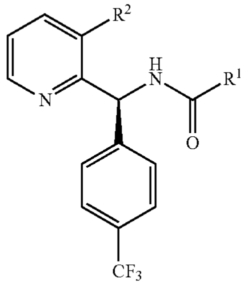

or any pharmaceutically-acceptable salt thereof, wherein:

m is 0, 1, 2 or 3;

$R^1$ is a direct-bonded, partially-saturated or unsaturated 5- or 6-membered monocyclic ring containing 1 or 2 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk and cyano; and $R^2$ is selected from F and $CF_3$.

Another aspect of the current invention relates to compounds having the general structure:

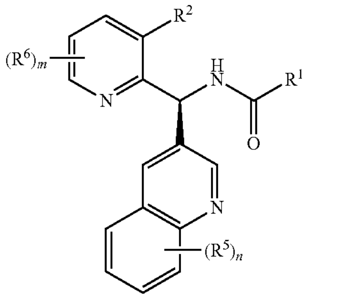

or any pharmaceutically-acceptable salt thereof, wherein:

m is 0, 1, 2 or 3;

n is 0 or 1;

$X^1$ is C($R^4$) or N;

$X^2$ is C or N;

Y is NH or O;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —S$R^a$, —S(═O)$R^a$, —S(═O)$_2R^a$, —S(═O)$_2$N$R^aR^a$, —N$R^aR^a$, and —N($R^a$)C(═O)$R^a$;

$R^2$ is selected from H, halo, cyano, $R^c$, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ and —N$R^a$$C_{2-6}$alkO$R^a$; or $R^2$ is $C_{1-6}$alk substituted by 0, 1, 2 or 3 substituents selected from $C_{1-4}$haloalk, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ and —N$R^a$$C_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —O$C_{2-6}$alkN$R^aR^a$, —O$C_{2-6}$alkO$R^a$, —S$R^a$, —S(═O)$R^b$, —S(═O)$_2R^b$, —S(═O)$_2$N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^a$$C_{2-6}$alkN$R^aR^a$ or —N$R^a$$C_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(═O)$C_{1-6}$alk, —N($C_{1-6}$alk)$C_{1-6}$alk, F, Cl, Br, CN, OH or $NH_2$;

$R^5$ is F, $CH_3$ or $CF_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

In another embodiment, in conjunction with any above or below embodiments, $R^1$ is $C_{1-6}$alk substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$.

In another embodiment, in conjunction with any above or below embodiments, $R^1$ is $C_{1-2}$alk-linked saturated, partially-saturated or unsaturated 3-, 4-, 5-, 6- or 7-membered monocyclic ring containing 0, 1, 2, 3 or 4 atoms selected from N, O and S, but containing no more than one O or S atom, the ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$.

In another embodiment, in conjunction with any above or below embodiments, $R^1$ is a direct-bonded saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —S$R^a$, —S(═O)$R^a$, —S(═O)$_2R^a$, —S(═O)$_2$N$R^aR^a$, —N$R^aR^a$, and —N($R^a$)C(═O)$R^a$.

In another embodiment, in conjunction with any above or below embodiments, $R^1$ is a direct-bonded partially-saturated or unsaturated 5- or 6-membered monocyclic ring containing 1, 2, 3 or 4 atoms selected from N, O and S, but containing no more than one O or S atom, the ring being substituted by 0, 1, 2 or 3 substituents independently selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$.

In another embodiment, in conjunction with any above or below embodiments, $R^1$ is a direct-bonded partially-saturated or unsaturated 6-membered monocyclic ring containing 1 or 2 N atoms, substituted by 0, 1, 2 or 3 substituents independently selected from halo, oxo, $C_{1-6}$alk, $C_{1-4}$haloalk, cyano and —O$R^a$.

In another embodiment, in conjunction with any above or below embodiments, $R^1$ is a direct-bonded unsaturated 10-membered bicyclic ring containing 1 or 2 N atoms, substituted by 0, 1, 2 or 3 substituents independently selected from halo, oxo, $C_{1-6}$alk, $C_{1-4}$haloalk, cyano and —O$R^a$.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound as described above.

Another aspect of the invention relates to a pharmaceutical composition comprising a compound according to Claim 1 and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

ADDITIONAL EMBODIMENTS

The embodiments listed below are presented in numbered form for convenience and are in addition to the embodiments described above.

1. In a first additional embodiment, the invention provides a compound of Formula I having the structure:

I

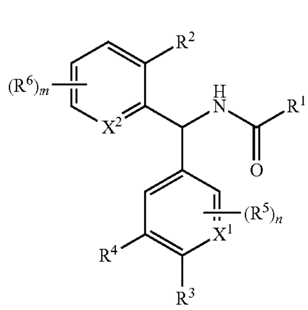

a pharmaceutically-acceptable salt thereof, a tautomer thereof, a pharmaceutically-acceptable salt of the tautomer, a stereoisomer thereof, or a mixture thereof, wherein:

m is 0, 1, 2 or 3;

n is 0 or 1;

$X^1$ is C($R^4$) or N;

$X^2$ is CH, CF, or N;

$R^1$ is $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, =S, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$$C_{2-6}$alkN$R^aR^a$ and —N$R^a$$C_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$$C_{2-6}$alkN$R^aR^a$ and —N$R^a$$C_{2-6}$alkO$R^a$, or $R^2$ is $C_{1-6}$alk substituted by 0, 1, 2 or 3 halo substituents and additionally substituted by 0 or 1 substituents selected from $R^c$;

$R^3$ is H, $C_{1-8}$alk, $C_{1-8}$alkOH, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$$C_{2-6}$alkN$R^aR^a$ or —N$R^a$$C_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, halo, O$R^a$, $CH_3$ or $CF_3$;

$R^6$ is F, $C_{1-6}$alk, or O$R^a$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 heteroatoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

2. The compound of embodiment 1 or the pharmaceutically-acceptable salt thereof, the tautomer thereof, the pharmaceutically-acceptable salt of the tautomer, or the mixture thereof, wherein the compound of Formula I has the Formula IA:

IA

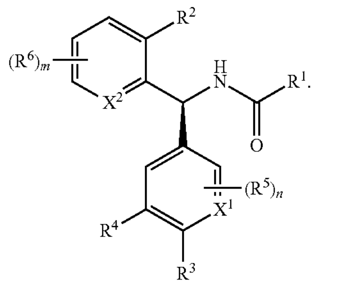

3. The compound of embodiment 2 or the pharmaceutically-acceptable salt thereof, the tautomer thereof, the pharmaceutically-acceptable salt of the tautomer, or the mixture thereof, wherein $X^2$ is selected from CH or N;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$$C_{2-6}$alkN$R^aR^a$ or —N$R^a$$C_{2-6}$alkO$R^a$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, $CH_3$ or $CF_3$; and $R^6$ is F.

4. The compound of embodiment 3 or the pharmaceutically-acceptable salt thereof.

5. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is the saturated, partially-saturated or unsaturated 3-, 4-, 5-, 6- or 7-membered monocyclic or 7-, 8-, 9-, 10- or 11-membered bicyclic ring and the monocyclic or bicyclic ring is substituted by 0, 1, 2, or 3 substituents, wherein the substituents are selected from F, Cl, Br, I, oxo, cyano, $—CH_3$, $—CH_2CH_3$, $—CH_2CH_2CH_3$, $—C(H)(CH_3)_2$, $—CH_2C(H)(CH_3)_2$, $—CH_2C(H){=}CH_2$, $—CH_2CO_2H$, $—CH_2CF_3$, $—C(OH)(CH_3)_2$, $—SO_2N(H)CH_3$, $—N(H)SO_2CH_3$, $—OCH_3$, $—OCF_3$, —OH, $—OCH_2CO_2H$, $—CH_2OH$, $—CH_2CH_2OH$, $—CH_2C(H)(CH_3)OH$, $—CO_2H$, $—CO_2CH_3$, $—CO_2CH_2CH_3$, $—CO_2C(CH_3)_3$, $—CO_2NH_2$, $—CO_2N(H)CH_3$, $—SO_2CH_3$, $—OC({=}O)CH_3$, $—NH_2$, $—NHC({=}O)CH_3$, $—N(CH_3)_2$, $—N(H)CH_2CH_3$, $—CF_3$, $—CHF_2$, $—CH_2C(H)(CF_3)OH$, $—CH_2C(CH_3)_2OH$, $—CH_2$-phenyl, $—C({=}O)$-phenyl, tetrazolyl, oxadiazolonyl, pyridyl, oxetanyl,

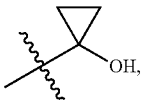 or 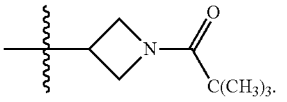

6. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is a phenyl, pyridyl, pyridinonyl, piperidinonyl, pyridazinonyl, pyrazinonyl, pyridazinyl, pyrimidinyl, pyrazinyl, tetradyrofuranyl, tetrahydropyranyl, thiazolyl, furanyl, thiophenyl, pyrazolyl, isoxazolyl, triazolyl, oxazolyl, imidazolyl, pyrrolidinonyl, piperidinyl, cyclohexyl, cyclohexanonyl, quinolinyl, isoquinolinyl, naphthyridinyl, pyrrolopyridinyl, pyrrolopyrimidinyl, benzothiophenyl, pyrazolopyrimidinyl, triazolopyrimidinyl, indazolyl, tetrahydroindazolyl, tetrahydrocyclopentapyrazolyl, dihydropyrazolooxazinyl, indolinonyl, isoindolinonyl, benzooxazolonyl, oxazolopyridinonyl, benzoimidazolonyl, isoindolindionyl, tetrahydroquinolinyl, dihydroquinolinonyl, benzooxazinonyl, dihydrobenzooxazinonyl, dihydroindenonyl, benzothiazolyl, benzimidazolyl, imidazopyridinyl, tetrazolopyridinyl, quinolinonyl, quinoxalinyl, or quinoxalindionyl substituted by 0, 1, 2, or 3 substituents.

7. The compound of embodiment 6 or the pharmaceutically-acceptable salt thereof, the tautomer thereof, the pharmaceutically-acceptable salt of the tautomer, or the mixture thereof, wherein $R^1$ is a phenyl substituted by 0, or 1 substituent.

8. The compound of embodiment 6 or the pharmaceutically-acceptable salt thereof, the tautomer thereof, the pharmaceutically-acceptable salt of the tautomer, or the mixture thereof, wherein $R^1$ is a pyridinonyl substituted by 0, or 1 substituent.

9. The compound of embodiment 6 or the pharmaceutically-acceptable salt thereof, the tautomer thereof, the pharmaceutically-acceptable salt of the tautomer, or the mixture thereof, wherein $R^1$ is a pyridyl substituted by 0, or 1 substituent.

10. The compound of embodiment 6 or the pharmaceutically-acceptable salt thereof, the tautomer thereof, the pharmaceutically-acceptable salt of the tautomer, or the mixture thereof, wherein $R^1$ is a benzooxazolonyl substituted by 0, or 1 substituent.

11. The compound of embodiment 6 or the pharmaceutically-acceptable salt thereof, the tautomer thereof, the pharmaceutically-acceptable salt of the tautomer, or the mixture thereof, wherein $R^1$ is a quinolinyl substituted by 0, or 1 substituent.

12. The compound of embodiment 6 or the pharmaceutically-acceptable salt thereof, the tautomer thereof, the pharmaceutically-acceptable salt of the tautomer, or the mixture thereof, wherein $R^1$ is a benzimidazolyl substituted by 0, or 1 substituent.

13. The compound of embodiment 6 or the pharmaceutically-acceptable salt thereof, the tautomer thereof, the pharmaceutically-acceptable salt of the tautomer, or the mixture thereof, wherein $R^1$ is a group of formula

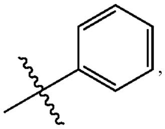, 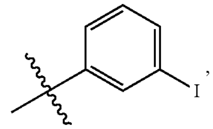, 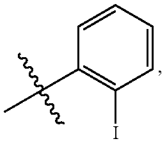,

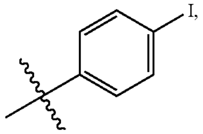 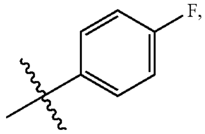

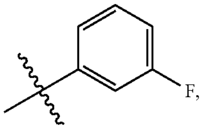 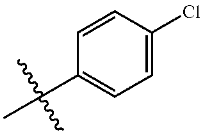,

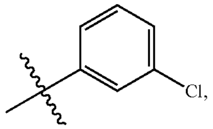 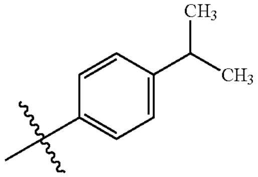,

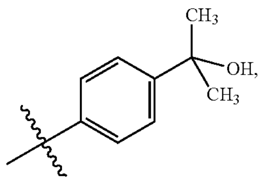 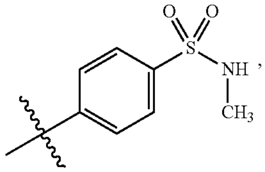

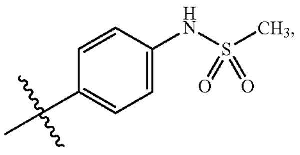 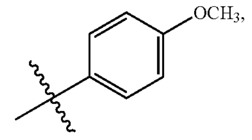

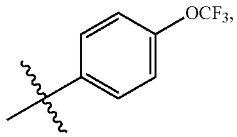 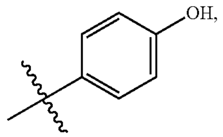

-continued
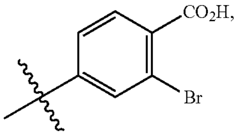
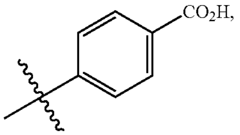
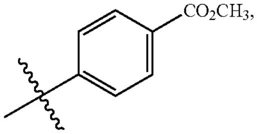
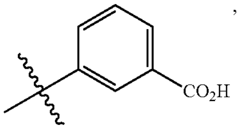
,
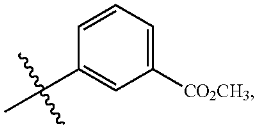
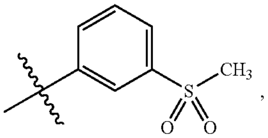
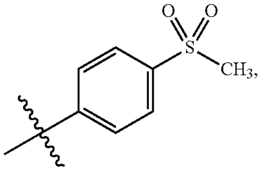
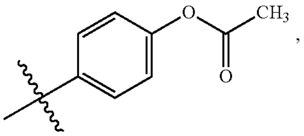
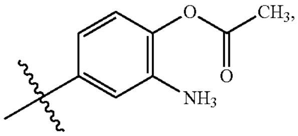
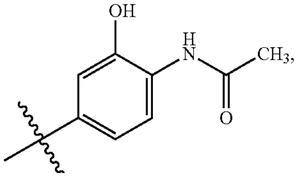
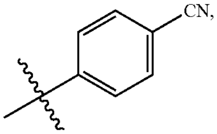
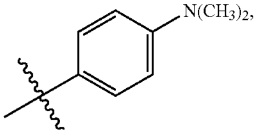
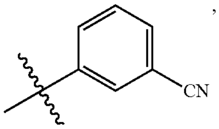
,
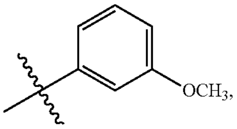
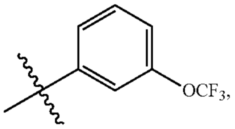
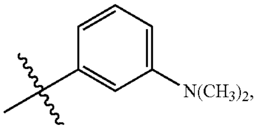
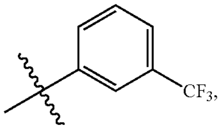
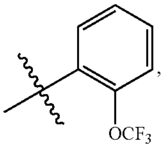
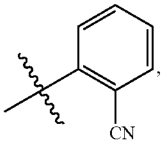
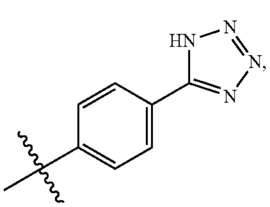
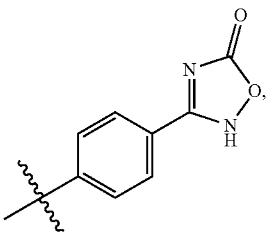
-continued
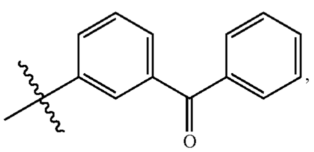
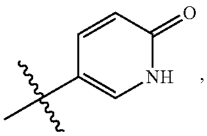
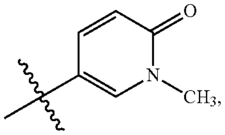
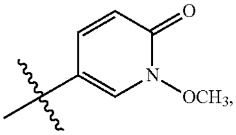
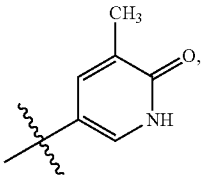
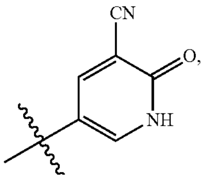
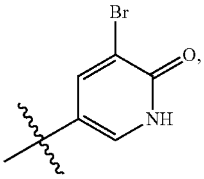
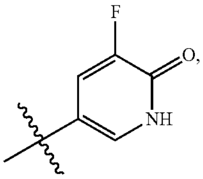
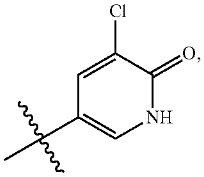
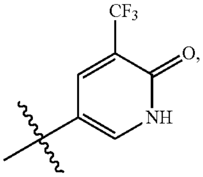
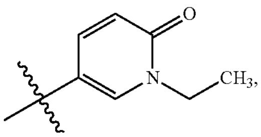
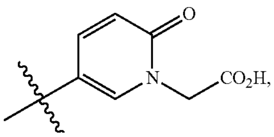
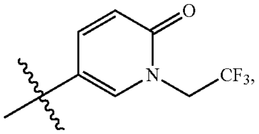
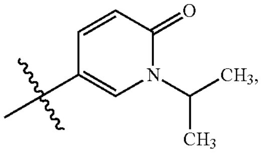
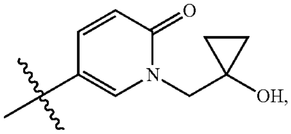
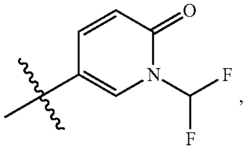
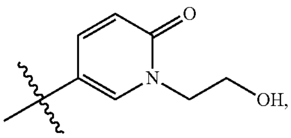
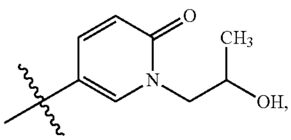
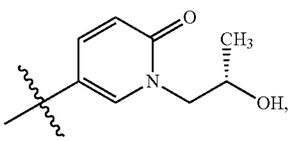

-continued
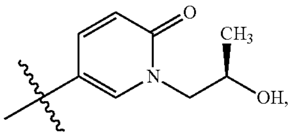
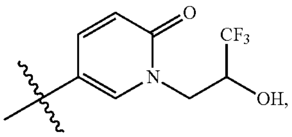
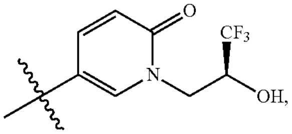
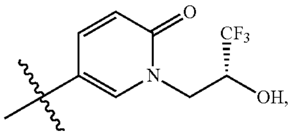
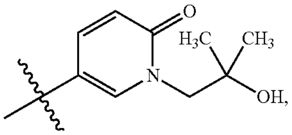
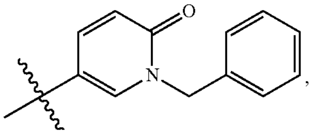
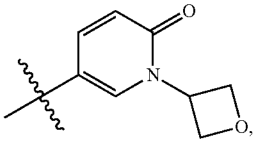
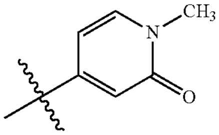
,
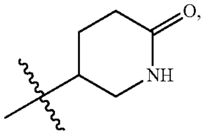
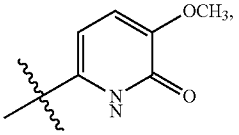
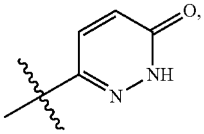
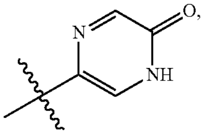
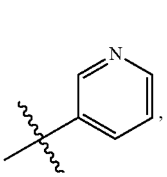
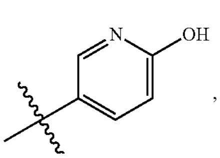
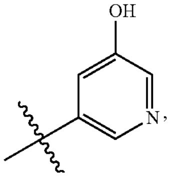
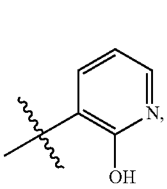
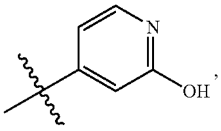
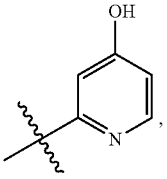
-continued
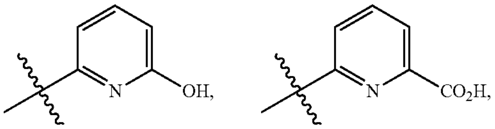
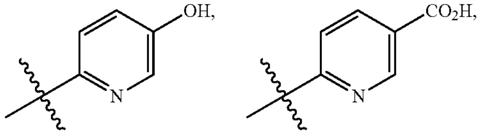
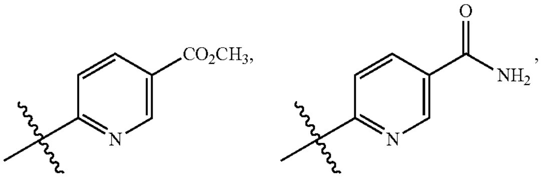
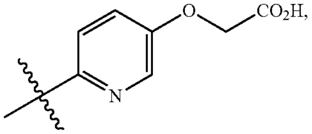
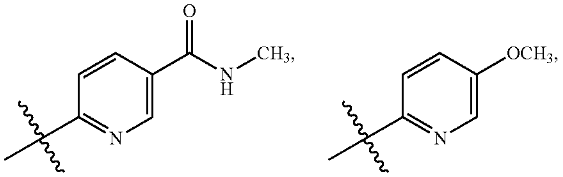
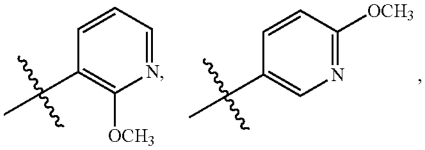
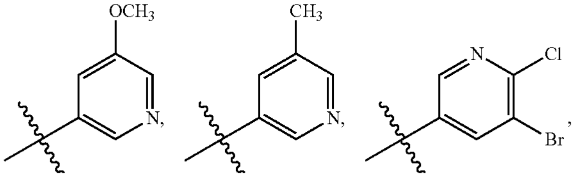
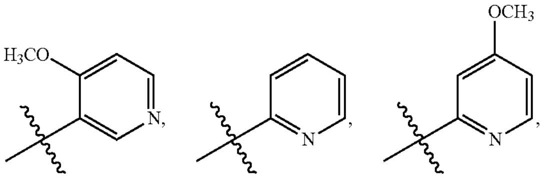
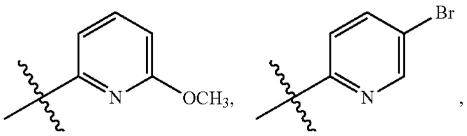
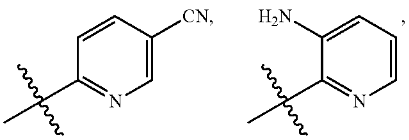
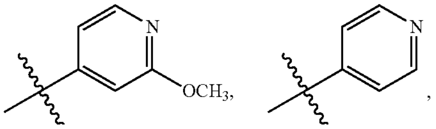

-continued
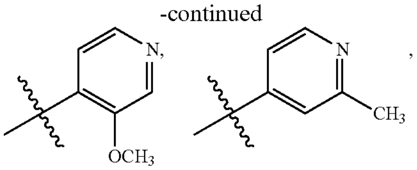
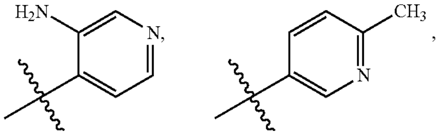
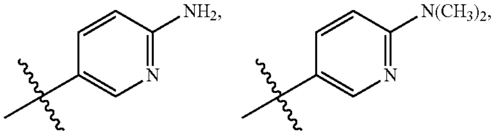
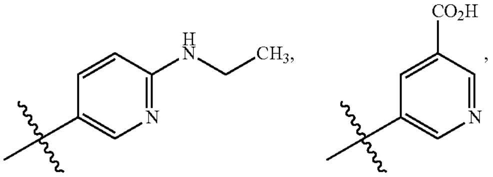
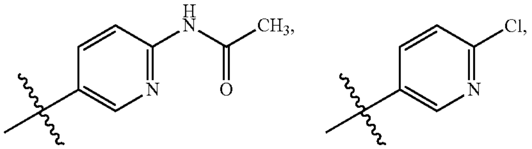
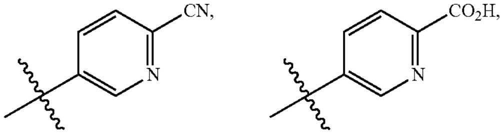
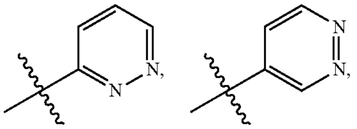
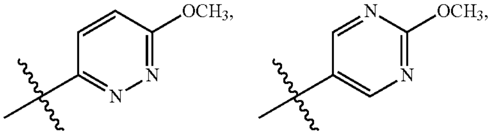
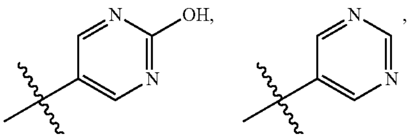
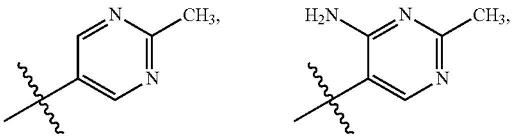
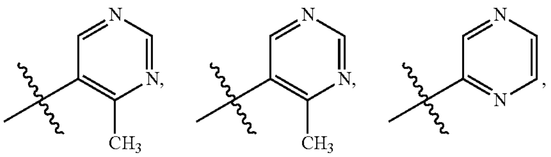
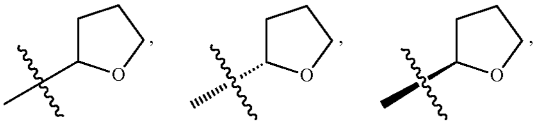
-continued
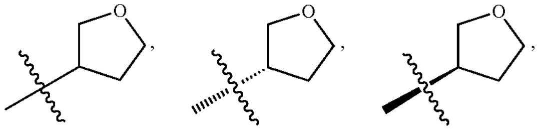
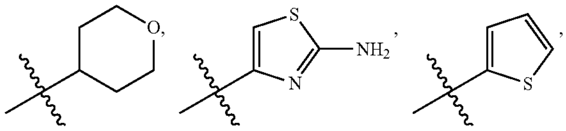
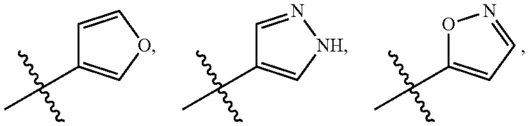
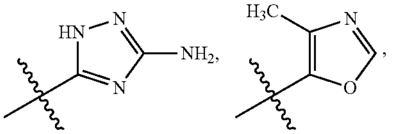
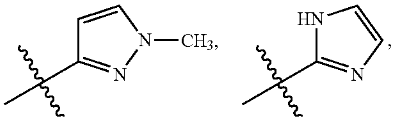
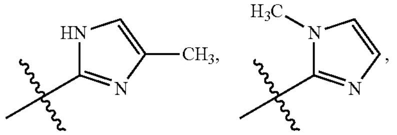
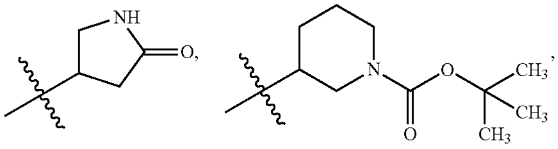
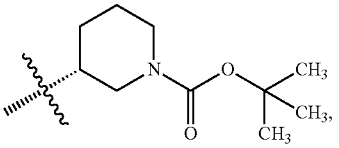
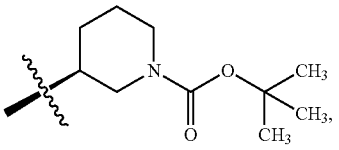
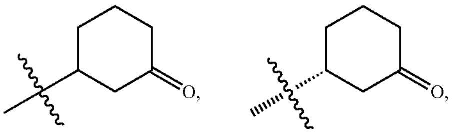
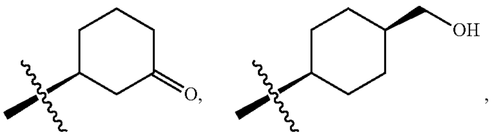
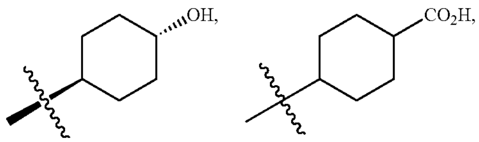

-continued
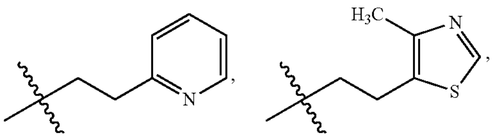
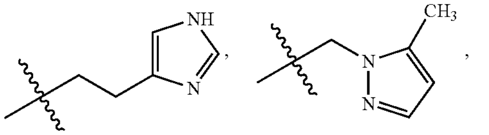
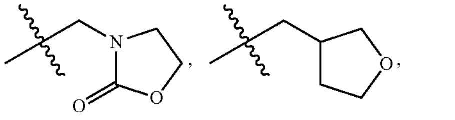
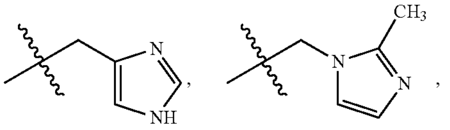
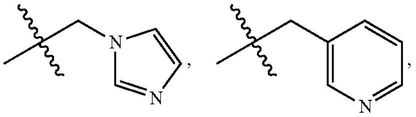
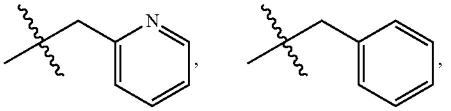
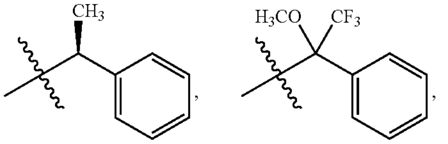
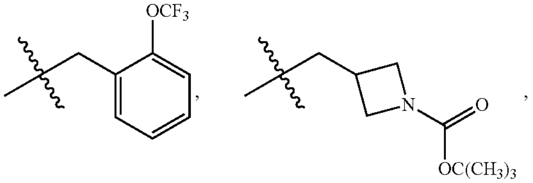
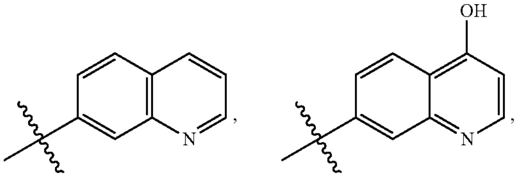
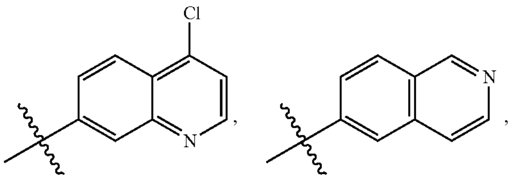
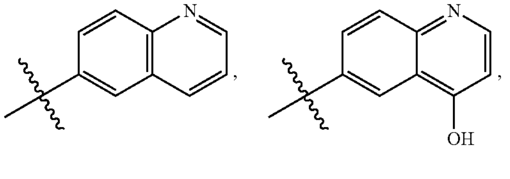
-continued
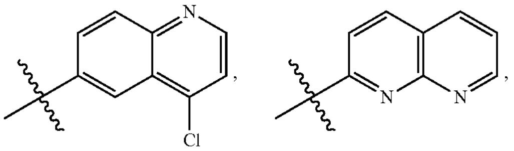
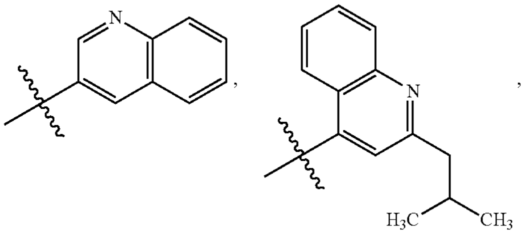
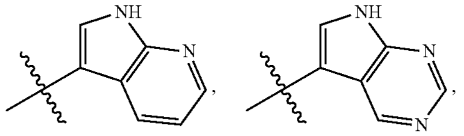
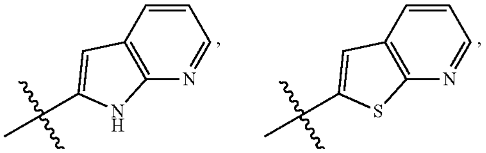
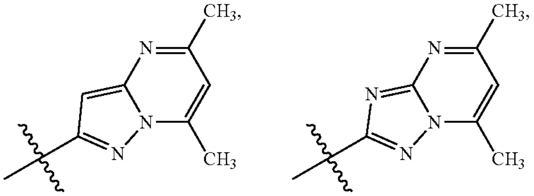
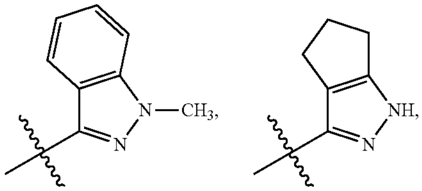
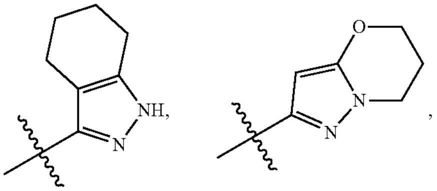
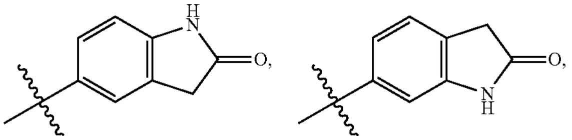
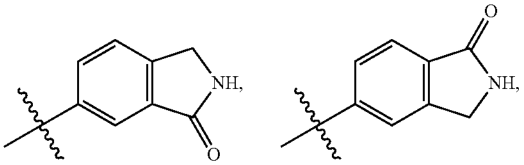
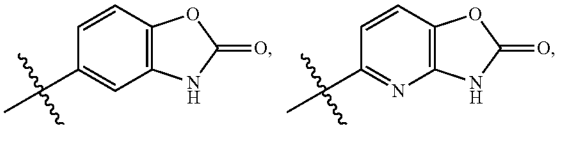

-continued
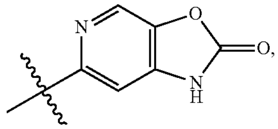
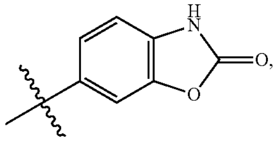
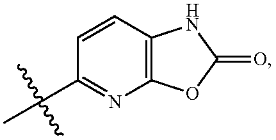
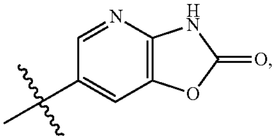
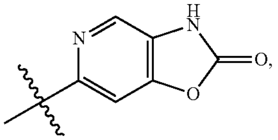
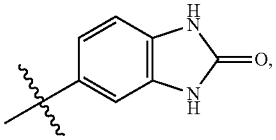
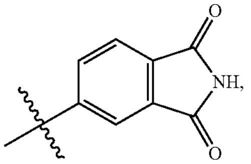
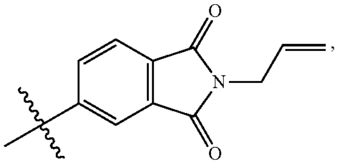
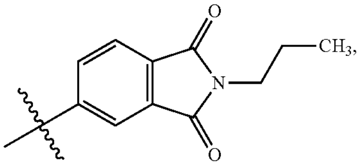
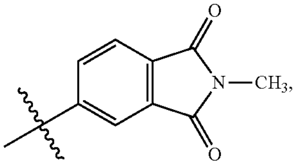
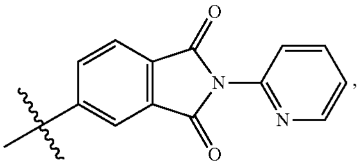
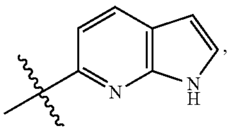
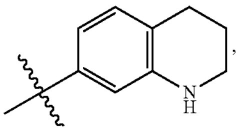
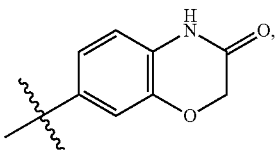
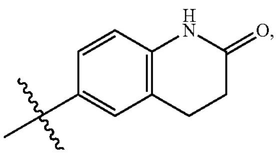
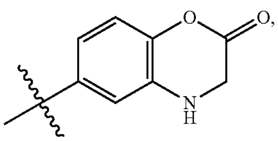
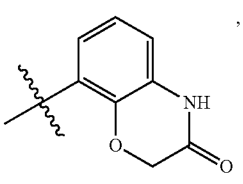
,
-continued
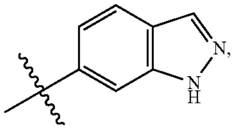
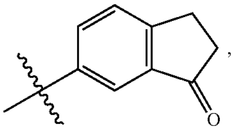
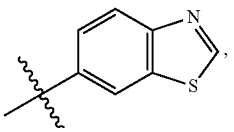
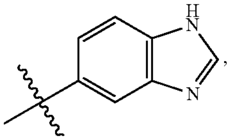
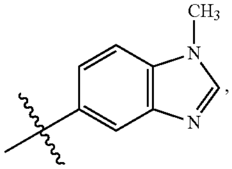
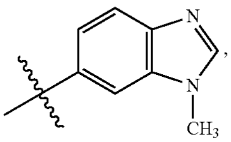
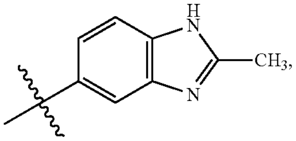
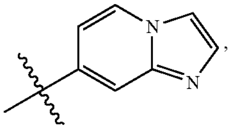
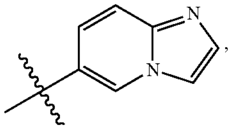
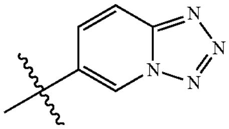
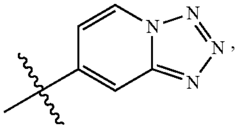
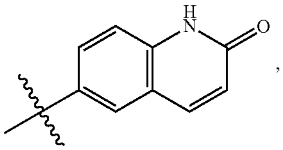
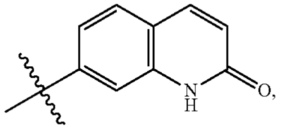
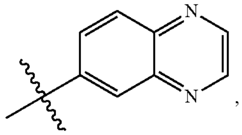
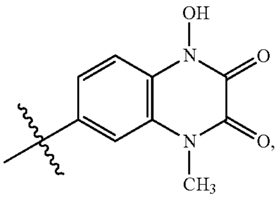
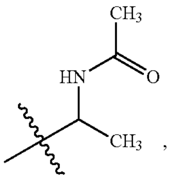
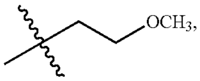
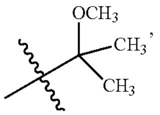
or
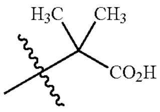
and the symbol , when drawn across a bond, indicates the point of attachment to the rest of the molecule.
14. The compound of embodiment 1 or the pharmaceutically-acceptable salt thereof, the tautomer thereof, the pharmaceutically-acceptable salt of the tautomer, or the mixture thereof, wherein $R^1$ is a group of formula

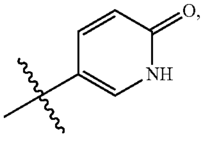,
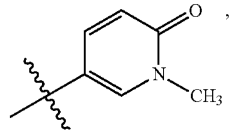,
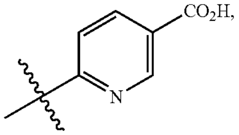,
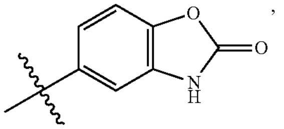,
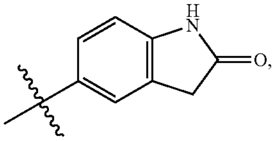,
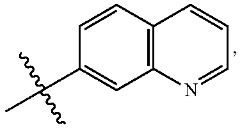,
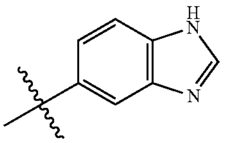, or
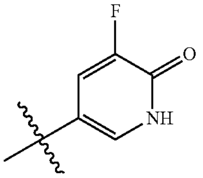

and the symbol , when drawn across a bond, indicates the point of attachment to the rest of the molecule.

15. The compound of embodiment 6 or the pharmaceutically-acceptable salt thereof, the tautomer thereof, the pharmaceutically-acceptable salt of the tautomer, or the mixture thereof, wherein $R^1$ is

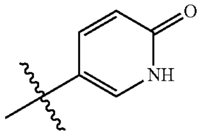 [SMILES: *c1ccc(=O)[nH]c1]

and the symbol , when drawn across a bond, indicates the point of attachment to the rest of the molecule.

16. The compound of embodiment 6 or the pharmaceutically-acceptable salt thereof, the tautomer thereof, the pharmaceutically-acceptable salt of the tautomer, or the mixture thereof, wherein $R^1$ is

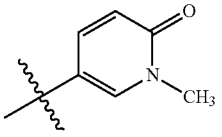 [SMILES: *c1ccc(=O)n(C)c1]

and the symbol , when drawn across a bond, indicates the point of attachment to the rest of the molecule.

17. The compound of any one of embodiments 1-3 or 4-16 or the pharmaceutically-acceptable salt thereof, the tautomer thereof, the pharmaceutically-acceptable salt of the tautomer, or the mixture thereof, wherein $R^5$ is independently, in each instance, F, Cl, $OR^a$, $CH_3$ or $CF_3$.

18. The compound of embodiment 17 or the pharmaceutically-acceptable salt thereof, the tautomer thereof, the pharmaceutically-acceptable salt of the tautomer, or the mixture thereof, wherein $R^5$ is F.

19. The compound of any one of embodiments 1-3, or 5-18 or the pharmaceutically-acceptable salt thereof, the tautomer thereof, the pharmaceutically-acceptable salt of the tautomer, or the mixture thereof, wherein $R^6$ is F, Me, or OMe.

20. The compound of any one of embodiments 1-3 or 5-19 or the pharmaceutically-acceptable salt thereof, the tautomer thereof, the pharmaceutically-acceptable salt of the tautomer, or the mixture thereof, wherein n is 1.

21. The compound of any one of embodiments 1-3 or 5-20 or the pharmaceutically-acceptable salt thereof, the tautomer thereof, the pharmaceutically-acceptable salt of the tautomer, or the mixture thereof, wherein m is 0 or 1.

22. The compound of embodiment 21 or the pharmaceutically-acceptable salt thereof, the tautomer thereof, the pharmaceutically-acceptable salt of the tautomer, or the mixture thereof, wherein m is 1.

23. The compound of embodiment 21 or the pharmaceutically-acceptable salt thereof, the tautomer thereof, the pharmaceutically-acceptable salt of the tautomer, or the mixture thereof, wherein m is 0.

24. The compound of any one of embodiments 1-3 or 5-16 or the pharmaceutically-acceptable salt thereof, the tautomer thereof, the pharmaceutically-acceptable salt of the tautomer, or the mixture thereof, wherein n is 0.

25. The compound of embodiment 24 or the pharmaceutically-acceptable salt thereof, the tautomer thereof, the pharmaceutically-acceptable salt of the tautomer, or the mixture thereof, wherein wherein $R^6$ is F, Me, or OMe.

26. The compound of any one of embodiments 1-3 or 5-25 or the pharmaceutically-acceptable salt thereof, the tautomer thereof, the pharmaceutically-acceptable salt of the tautomer, or the mixture thereof, wherein $R^2$ is —H, halo, cyano, —O—$C_1$-$C_6$alk, or $C_{1-6}$alk substituted by 0, 1, 2 or 3 halo substituents.

27. The compound of embodiment 26 or the pharmaceutically-acceptable salt thereof, the tautomer thereof, the pharmaceutically-acceptable salt of the tautomer, or the mixture thereof, wherein $R^2$ is —H, —F, —Cl, —Br, cyano, —$CF_3$, —$OCH_3$, or $C_{1-6}$alk.

28. The compound of embodiment 26 or the pharmaceutically-acceptable salt thereof, the tautomer thereof, the pharmaceutically-acceptable salt of the tautomer, or the mixture thereof, wherein $R^2$ is —F, —Cl, —Br, cyano, —$CF_3$, —$OCH_3$, or $C_{1-6}$alk.

29. The compound of embodiment 26 or the pharmaceutically-acceptable salt thereof, the tautomer thereof, the pharmaceutically-acceptable salt of the tautomer, or the mixture thereof, wherein $R^2$ is —F.

30. The compound of embodiment 26 or the pharmaceutically-acceptable salt thereof, the tautomer thereof, the pharmaceutically-acceptable salt of the tautomer, or the mixture thereof, wherein $R^2$ is —$CF_3$.

31. The compound of any one of embodiments 1-3 or 5-25 or the pharmaceutically-acceptable salt thereof, the tautomer thereof, the pharmaceutically-acceptable salt of the tautomer, or the mixture thereof, wherein $R^2$ is —$CH_3$, —$CH_2CH_3$, —$CH_2CH_2CH_3$, —$C(CH_3)_3$, —$CH(CH_3)_2$, —$CH_2$—$C(CH_3)_3$, —CH=$CH_2$, —$CH_2$CH=$CH_2$, —C≡C—$CH_3$, or a group of formula $CH_3$

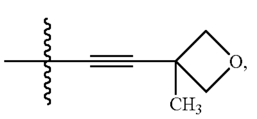, or 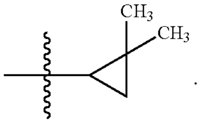.

32. The compound of any one of embodiments 1-3, or 5-31 or the pharmaceutically-acceptable salt thereof, the tautomer thereof, the pharmaceutically-acceptable salt of the tautomer, or the mixture thereof, wherein $R^3$ is H, $C_{1-8}$alk, $C_{1-8}$alkOH, $C_{1-4}$haloalk, halo, or —$OR^a$.

33. The compound of embodiment 32 or the pharmaceutically-acceptable salt thereof, the tautomer thereof, the pharmaceutically-acceptable salt of the tautomer, or the mixture thereof, wherein $R^3$ is H, —$CH_3$, —$CH_2CH_3$, F, Cl, Br, I, —$OCH_3$, —$OCF_3$, —$CH(CH_3)OH$, or —$CF_3$.

34. The compound of embodiment 33 or the pharmaceutically-acceptable salt thereof, the tautomer thereof, the pharmaceutically-acceptable salt of the tautomer, or the mixture thereof, wherein $R^3$ is —$CH_3$, —$CH_2CH_3$, F, Cl, I, —$OCH_3$, —$OCF_3$, —$CH(CH_3)OH$, or —$CF_3$.

35. The compound of embodiment 34 or the pharmaceutically-acceptable salt thereof, the tautomer thereof, the pharmaceutically-acceptable salt of the tautomer, or the mixture thereof, wherein $R^3$ is —$OCF_3$ or —$CF_3$.

36. The compound of embodiment 35 or the pharmaceutically-acceptable salt thereof, the tautomer thereof, the pharmaceutically-acceptable salt of the tautomer, or the mixture thereof, wherein $R^3$ is —$OCF_3$.

37. The compound of embodiment 34 or the pharmaceutically-acceptable salt thereof, the tautomer thereof, the pharmaceutically-acceptable salt of the tautomer, or the mixture thereof, wherein $R^3$ is —$CF_3$.

38. The compound of embodiment 21 or the pharmaceutically-acceptable salt thereof, the tautomer thereof, the pharmaceutically-acceptable salt of the tautomer, or the mixture thereof, wherein $R^3$ is —H.

39. The compound of any one of embodiments 1-3, or 5-38 or the pharmaceutically-acceptable salt thereof, the tautomer thereof, the pharmaceutically-acceptable salt of the tautomer, or the mixture thereof, wherein $R^4$ is H.

40. The compound of any one of embodiments 1-3, or 5-38 or the pharmaceutically-acceptable salt thereof, the tautomer thereof, the pharmaceutically-acceptable salt of the tautomer, or the mixture thereof, wherein $R^4$ is F, Cl, $C_{1-6}$alk, —$OC_{1-6}$alk, or —$C_{1-3}$haloalk.

41. The compound of embodiment 40 or the pharmaceutically-acceptable salt thereof, the tautomer thereof, the pharmaceutically-acceptable salt of the tautomer, or the mixture thereof, wherein $R^4$ is F, Cl, $CF_3$, $CH_3$, or $OCH_3$.

42. The compound of embodiment 41 or the pharmaceutically-acceptable salt thereof, the tautomer thereof, the pharmaceutically-acceptable salt of the tautomer, or the mixture thereof, wherein $R^4$ is F.

43. The compound of any one of embodiments 1-3, or 5-31 or the pharmaceutically-acceptable salt thereof, the tautomer thereof, the pharmaceutically-acceptable salt of the tautomer, or the mixture thereof, wherein $R^3$ and $R^4$ together form a four-atom unsaturated bridge containing 0 or 1 N atoms, wherein the bridge is substituted by 0, 1 or 2 $R^5$ substituents.

44. The compound of any one of embodiments 1-3 or 5-43 or the pharmaceutically-acceptable salt thereof, the tautomer thereof, the pharmaceutically-acceptable salt of the tautomer, or the mixture thereof, wherein $X^2$ is N.

45. The compound of any one of embodiments 1-3 or 5-43 or the pharmaceutically-acceptable salt thereof, the tautomer thereof, the pharmaceutically-acceptable salt of the tautomer, or the mixture thereof, wherein $X^2$ is CH or CF.

46. The compound of embodiment 45 or the pharmaceutically-acceptable salt thereof, the tautomer thereof, the pharmaceutically-acceptable salt of the tautomer, or the mixture thereof, wherein $X^2$ is CH.

47. The compound of embodiment 45 or the pharmaceutically-acceptable salt thereof, the tautomer thereof, the pharmaceutically-acceptable salt of the tautomer, or the mixture thereof, wherein $X^2$ is CF.

48. The compound of any one of embodiments 1-3, or 5-47 or the pharmaceutically-acceptable salt thereof, the tautomer thereof, the pharmaceutically-acceptable salt of the tautomer, or the mixture thereof, wherein $X^1$ is N.

49. The compound of any one of embodiments 1-3, or 5-47 or the pharmaceutically-acceptable salt thereof, the tautomer thereof, the pharmaceutically-acceptable salt of the tautomer, or the mixture thereof, wherein $X^1$ is $C(R^4)$.

50. The compound of embodiment 49 or the pharmaceutically-acceptable salt thereof, the tautomer thereof, the pharmaceutically-acceptable salt of the tautomer, or the mixture thereof, wherein $X^1$ is CH.

51. The compound of any one of embodiments 1-3, or 5-43 or the pharmaceutically-acceptable salt thereof, the tautomer thereof, the pharmaceutically-acceptable salt of the tautomer, or the mixture thereof, wherein $X^1$ is $C(R^4)$ and $X^2$ is N.

52. The compound of any one of embodiments 1-3, or 5-43 or the pharmaceutically-acceptable salt thereof, the tautomer thereof, the pharmaceutically-acceptable salt of the tautomer, or the mixture thereof, wherein $X^1$ is N and $X^2$ is N.

53. The compound of embodiment 1 or the pharmaceutically-acceptable salt thereof, the tautomer thereof, the pharmaceutically-acceptable salt of the tautomer, or the mixture thereof, wherein $X^2$ is N; $R^2$ is F; m is 0; $X^1$ is CH; $R^4$ is F or H; $R^3$ is $CF_3$ or $OCF_3$; and $R^1$ is

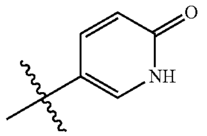 [SMILES: *c1ccc(=O)[nH]c1]

and the symbol , when drawn across a bond, indicates the point of attachment to the rest of the molecule.

54. The compound of embodiment 1, wherein the compound is (S)—N-((3-fluoropyridin-2-yl)(4-(trifluoromethoxy)phenyl)methyl)-6-oxo-1,6-dihydropyridine-3-carboxamide;

(S)-6-oxo-N-((4-(trifluoromethyl)phenyl)(3-(trifluoromethyl)pyridin-2-yl)methyl)-1,6-dihydropyridine-3-carboxamide;

(S)—N-((3-fluoropyridin-2-yl)(4-(trifluoromethyl)phenyl)methyl)-6-oxo-1,6-dihydropyridine-3-carboxamide;

(S)—N-((3-fluoropyridin-2-yl)(4-(trifluoromethyl)phenyl)methyl)-1-methyl-6-oxo-1,6-dihydropyridine-3-carboxamide;

(S)—N-((3-fluoropyridin-2-yl)(4-(trifluoromethyl)phenyl)methyl)-2-oxo-2,3-dihydrobenzo[d]oxazole-5-carboxamide;

(S)—N-((3-fluoropyridin-2-yl)(4-(trifluoromethoxy)phenyl)methyl)-2-oxo-2,3-dihydrobenzo[d]oxazole-5-carboxamide;

(S)—N-((3-fluoropyridin-2-yl)(4-(trifluoromethoxy)phenyl)methyl)-2-oxoindoline-5-carboxamide;

(S)—N-((3-fluoro-4-(trifluoromethoxy)phenyl)(3-fluoropyridin-2-yl)methyl)-6-oxo-1,6-dihydropyridine-3-carboxamide;

(S)—N-((3-fluoro-4-(trifluoromethoxy)phenyl)(3-fluoropyridin-2-yl)methyl)-1-methyl-6-oxo-1,6-dihydropyridine-3-carboxamide; or (S)—N-((4-(trifluoromethyl)phenyl)(3-(trifluoromethyl)pyridin-2-yl)methyl)quinoline-7-carboxamide; or the pharmaceutically-acceptable salt thereof, the tautomer thereof, the pharmaceutically-acceptable salt of the tautomer, or the mixture thereof.

55. The compound of embodiment 1, wherein the compound is (S)—N-((3-fluoropyridin-2-yl)(4-(trifluoromethoxy)phenyl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

56. The compound of embodiment 1, wherein the compound is (S)-6-oxo-N-((4-(trifluoromethyl)phenyl)(3-(trifluoromethyl)pyridin-2-yl)methyl)-1,6-dihydropyridine-3-carboxamide or the pharmaceutically-acceptable salt thereof, the tautomer thereof, the pharmaceutically-acceptable salt of the tautomer, or the mixture thereof.

57. The compound of embodiment 1, wherein the compound is (S)—N-((3-fluoropyridin-2-yl)(4-(trifluoromethyl)phenyl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

58. The compound of embodiment 1, wherein the compound is (S)—N-((3-fluoropyridin-2-yl)(4-(trifluoromethyl)phenyl)methyl)-1-methyl-6-oxo-1,6-dihydropyridine-3-carboxamide or the pharmaceutically-acceptable salt thereof, the tautomer thereof, the pharmaceutically-acceptable salt of the tautomer, or the mixture thereof.

59. The compound of embodiment 1, wherein the compound is (S)—N-((3-fluoropyridin-2-yl)(4-(trifluoromethyl)phenyl)methyl)-2-oxo-2,3-dihydrobenzo[d]oxazole-5-carboxamide or the pharmaceutically-acceptable salt thereof, the tautomer thereof, the pharmaceutically-acceptable salt of the tautomer, or the mixture thereof.

60. The compound of embodiment 1, wherein the compound is (S)—N-((3-fluoropyridin-2-yl)(4-(trifluoromethoxy)phenyl)methyl)-2-oxo-2,3-dihydrobenzo[d]oxazole-5-carboxamide or the pharmaceutically-acceptable salt thereof, the tautomer thereof, the pharmaceutically-acceptable salt of the tautomer, or the mixture thereof.

61. The compound of embodiment 1, wherein the compound is (S)—N-((3-fluoropyridin-2-yl)(4-(trifluoromethoxy)phenyl)methyl)-2-oxoindoline-5-carboxamide or the pharmaceutically-acceptable salt thereof, the tautomer thereof, the pharmaceutically-acceptable salt of the tautomer, or the mixture thereof.

62. The compound of embodiment 1, wherein the compound is (S)—N-((3-fluoro-4-(trifluoromethoxy)phenyl)(3-fluoropyridin-2-yl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

63. The compound of embodiment 1, wherein the compound is (S)—N-((3-fluoro-4-(trifluoromethoxy)phenyl)(3-fluoropyridin-2-yl)methyl)-1-methyl-6-oxo-1,6-dihydropyridine-3-carboxamide or the pharmaceutically-acceptable salt thereof, the tautomer thereof, the pharmaceutically-acceptable salt of the tautomer, or the mixture thereof.

64. The compound of embodiment 1, wherein the compound is (S)—N-((4-(trifluoromethyl)phenyl)(3-(trifluoromethyl)pyridin-2-yl)methyl)quinoline-7-carboxamide or the pharmaceutically-acceptable salt thereof, the tautomer thereof, the pharmaceutically-acceptable salt of the tautomer, or the mixture thereof.

65. The compound of embodiment 1, wherein the compound is (S)—N-((3-fluoro-4-(trifluoromethoxy)phenyl)(pyridin-2-yl)methyl)-6-oxo-1,6-dihydropyridine-3-carboxamide;

(S)—N-((3-fluoro-4-(trifluoromethoxy)phenyl)(2-fluorophenyl)methyl)-6-oxo-1,6-dihydropyridine-3-carboxamide;

(S)-2-oxo-N-(pyridin-2-yl(4-(trifluoromethoxy)phenyl)methyl)-2,3-dihydrobenzo[d]oxazole-5-carboxamide;

(S)-6-oxo-N-(pyridin-2-yl(4-(trifluoromethoxy)phenyl)methyl)-1,6-dihydropyridine-3-carboxamide;

(S)—N-((3-fluoro-4-(trifluoromethoxy)phenyl)(3-(trifluoromethyl)pyridin-2-yl)methyl)-6-oxo-1,6-dihydropyridine-3-carboxamide;

(S)—N-((2-fluoro-4-(trifluoromethoxy)phenyl)(3-fluoropyridin-2-yl)methyl)-6-oxo-1,6-dihydropyridine-3-carboxamide;

(S)—N-((3-fluoro-4-(trifluoromethoxy)phenyl)(pyridin-2-yl)methyl)-1Hbenzo[d]imidazole-5-carboxamide;

(S)-5-fluoro-N-((3-fluoro-4-(trifluoromethoxy)phenyl)(3-fluoropyridin-2-yl)methyl)-6-oxo-1,6-dihydropyridine-3-carboxamide;

(S)—N-((3-fluoro-4-(trifluoromethyl)phenyl)(3-fluoropyridin-2-yl)methyl)-6-oxo-1,6-dihydropyridine-3-carboxamide; or (S)-6-(((3-fluoro-4-(trifluoromethoxy)phenyl)(3-fluoropyridin-2-yl)methyl)carbamoyl)nicotinic acid; or the pharmaceutically-acceptable salt thereof, the tautomer thereof, the pharmaceutically-acceptable salt of the tautomer, or the mixture thereof.

66. The compound of embodiment 1, wherein the compound is (S)—N-((3-fluoro-4-(trifluoromethoxy)phenyl)(pyridin-2-yl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

67. The compound of embodiment 1, wherein the compound is (S)—N-((3-fluoro-4-(trifluoromethoxy)phenyl)(2-fluorophenyl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

68. The compound of embodiment 1, wherein the compound is (S)-2-oxo-N-(pyridin-2-yl(4-(trifluoromethoxy)phenyl)methyl)-2,3-dihydrobenzo[d]oxazole-5-carboxamide or the pharmaceutically-acceptable salt thereof, the tautomer thereof, the pharmaceutically-acceptable salt of the tautomer, or the mixture thereof.

69. The compound of embodiment 1, wherein the compound is (S)-6-oxo-N-(pyridin-2-yl(4-(trifluoromethoxy)phenyl)methyl)-1,6-dihydropyridine-3-carboxamide or the pharmaceutically-acceptable salt thereof, the tautomer thereof, the pharmaceutically-acceptable salt of the tautomer, or the mixture thereof.

70. The compound of embodiment 1, wherein the compound is (S)—N-((3-fluoro-4-(trifluoromethoxy)phenyl)(3-(trifluoromethyl)pyridin-2-yl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

71. The compound of embodiment 1, wherein the compound is (S)—N-((2-fluoro-4-(trifluoromethoxy)phenyl)(3-fluoropyridin-2-yl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

72. The compound of embodiment 1, wherein the compound is (S)—N-((3-fluoro-4-(trifluoromethoxy)phenyl)(pyridin-2-yl)methyl)-1Hbenzo[d]imidazole-5-carboxamide or the pharmaceutically-acceptable salt thereof, the tautomer thereof, the pharmaceutically-acceptable salt of the tautomer, or the mixture thereof.

73. The compound of embodiment 1, wherein the compound is (S)-5-fluoro-N-((3-fluoro-4-(trifluoromethoxy) phenyl)(3-fluoropyridin-2-yl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

74. The compound of embodiment 1, wherein the compound is (S)—N-((3-fluoro-4-(trifluoromethyl)phenyl)(3-fluoropyridin-2-yl)methyl)-6-oxo-1,6-dihydropyridine-3-carboxamide or the pharmaceutically-acceptable salt thereof, the tautomer thereof, the pharmaceutically-acceptable salt of the tautomer, or the mixture thereof.

75. The compound of embodiment 1, wherein the compound is (S)-6-(((3-fluoro-4-(trifluoromethoxy)phenyl)(3-fluoropyridin-2-yl)methyl)carbamoyl)nicotinic acid or the pharmaceutically-acceptable salt thereof, the tautomer thereof, the pharmaceutically-acceptable salt of the tautomer, or the mixture thereof.

76. The compound of embodiment 1, wherein the compound is (S)—N-((3-fluoro-pyridin-2-yl)(4-(trifluoro-methoxy)-phenyl)methyl)-6-oxo-1,6-dihydropyridine-3-carboxamide;
(S)—N-((3-fluoro-pyridin-2-yl)(4-(trifluoro-methoxy)-phenyl)methyl)-quinoline-7-carboxamide;
(S)—N-((3,4-dichlorophenyl)-(3-(trifluoro-methyl)pyridin-2-yl)methyl)-6-hydro-xynicotinamide;
(S)—N-((6-chloro-quinolin-3-yl)(3-(trifluoromethyl)-pyridin-2-yl)-methyl)quinoline-7-carboxamide;
(S)—N-((4-(trifluoro-methoxy)-phenyl)(3-(trifluoromethyl)-pyridin-2-yl)-methyl)quinoline-7-carboxamide;
(S)—N-((4-chloro-phenyl)(3-(trifluoromethyl)-pyridin-2-yl)-methyl)quinoline-7-carboxamide;
(S)—N-((8-chloro-quinolin-3-yl)(3-(trifluoromethyl)-pyridin-2-yl)-methyl)quinoline-7-carboxamide;
(S)—N-((7-methoxyquinolin-3-yl)(3-(trifluoro-methyl)pyridin-2-yl)methyl)-quinoline-7-carboxamide;
(S)—N-((5-chloro-quinolin-3-yl)(3-(trifluoromethyl)-pyridin-2-yl)-methyl)quinoline-7-carboxamide;
(S)—N-((3,4-dichlorophenyl)-(3-(trifluoro-methyl)pyridin-2-yl)methyl)-quinoline-7-carboxamide;
(S)—N-((6-chloro-quinolin-3-yl)(3-(trifluoromethyl)-pyridin-2-yl)-methyl)-isoquinoline-6-carboxamide;
(S)—N-(quinolin-3-yl(3-(trifluoro-methyl)pyridin-2-yl)methyl)-quinoline-7-carboxamide;
(S)—N-((3-chloro-phenyl)(3-(trifluoromethyl)-pyridin-2-yl)-methyl)quinoline-7-carboxamide;
(S)—N-(p-tolyl(3-(trifluoromethyl)-pyridin-2-yl)-methyl) quinoline-7-carboxamide;
(S)—N-(naphthalen-2-yl(3-(trifluoro-methyl)pyridin-2-yl) methyl)-quinoline-7-carboxamide;
(S)—N-((6-chloro-quinolin-3-yl)(3-(trifluoromethyl)-pyridin-2-yl)-methyl)-6-hydro-xynicotinamide;
(S)—N-((3-fluoro-phenyl)(3-(trifluoromethyl)-pyridin-2-yl)-methyl)quinoline-7-carboxamide;
(S)—N-((3-(trifluoromethyl)-phenyl)(3-(trifluoromethyl)-pyridin-2-yl)-methyl)quinoline-7-carboxamide;
(S)—N-((4-methoxyphenyl)-(3-(trifluoro-methyl)pyridin-2-yl)methyl)-quinoline-7-carboxamide;
(S)—N-((8-fluoro-quinolin-3-yl)(3-(trifluoromethyl)-pyridin-2-yl)-methyl)quinoline-7-carboxamide;
(S)—N-(m-tolyl(3-(trifluoromethyl)-pyridin-2-yl)-methyl) quinoline-7-carboxamide;
(S)—N-(quinolin-6-yl(3-(trifluoro-methyl)pyridin-2-yl)methyl)-quinoline-7-carboxamide;
(S)—N-((8-methoxyquinolin-3-yl)(3-(trifluoro-methyl)pyridin-2-yl)methyl)-quinoline-7-carboxamide;
(S)—N-((3-methoxyphenyl)-(3-(trifluoro-methyl)pyridin-2-yl)methyl)-quinoline-7-carboxamide;
(S)—N-((3-fluoro-4-methoxyphenyl)-(3-(trifluoro-methyl) pyridin-2-yl)methyl)-quinoline-7-carboxamide;
N-((1S)-(4-(1-hydroxyethyl)-phenyl)(3-(trifluoromethyl)-pyridin-2-yl)-methyl)quinoline-7-carboxamide;
(S)—N-((4-fluoro-phenyl)(3-(trifluoromethyl)-pyridin-2-yl)-methyl)quinoline-7-carboxamide;
(S)—N-((3-methoxypyridin-2-yl)(4-(trifluoro-methyl)phenyl)-methyl)quinoline-7-carboxamide;
(S)-2-methoxy-N-((4-(trifluoro-methyl)phenyl)-(3-(trifluoro-methyl)pyridin-2-yl)methyl)-nicotinamide;
(S)-6-methoxy-N-((4-(trifluoro-methyl)phenyl)-(3-(trifluoro-methyl)pyridin-2-yl)methyl)-nicotinamide;
(S)—N-((4-(trifluoromethyl)-phenyl)(3-(trifluoromethyl)-pyridin-2-yl)-methyl)-pyridazine-3-carboxamide;
(S)-4-methoxy-N-((4-(trifluoro-methyl)phenyl)-(3-(trifluoro-methyl)pyridin-2-yl)methyl)-picolinamide;
(S)-6-methoxy-N-((4-(trifluoro-methyl)phenyl)-(3-(trifluoro-methyl)pyridin-2-yl)methyl)-picolinamide;
(S)-2-methoxy-N-((4-(trifluoro-methyl)phenyl)-(3-(trifluoro-methyl)pyridin-2-yl)methyl)-isonicotinamide;
N-((3-fluoro-pyridin-2-yl)(4-(trifluoromethyl)-phenyl)methyl)-6-methoxynicotinamide;
N-((3-fluoro-pyridin-2-yl)(4-(trifluoromethyl)-phenyl)methyl)-2-methoxynicotinamide;
(S)-6-methoxy-N-((4-(trifluoro-methyl)phenyl)-(3-(trifluoro-methyl)pyridin-2-yl)methyl)-pyridazine-3-carboxamide;
(S)-5-methoxy-N-((4-(trifluoro-methyl)phenyl)-(3-(trifluoro-methyl)pyridin-2-yl)methyl)-nicotinamide;
(S)-2-methyl-N-((4-(trifluoro-methyl)phenyl)-(3-(trifluoromethyl)pyridin-2-yl)methyl)-isonicotinamide;
(S)-6-methyl-N-((4-(trifluoro-methyl)phenyl)-(3-(trifluoromethyl)pyridin-2-yl)methyl)-nicotinamide;
(S)-6-oxo-N-((4-(trifluoromethyl)-phenyl)(3-(trifluoromethyl)-pyridin-2-yl)-methyl)-1,6-dihydropyridine-3-carboxamide;
(S)-2-methoxy-N-((4-(trifluoro-methyl)phenyl)-(3-(trifluoro-methyl)pyridin-2-yl)methyl)-pyrimidine-5-carboxamide;
(S)—N-((4-(trifluoromethyl)-phenyl)(3-(trifluoromethyl)-pyridin-2-yl)-methyl)-1H-pyrrolo[2,3-b]pyridine-3-carboxamide;
(S)-2-hydroxy-N-((4-(trifluoro-methyl)phenyl)-(3-(trifluoro-methyl)pyridin-2-yl)methyl)-isonicotinamide;
(S)—N-((4-(trifluoromethyl)-phenyl)(3-(trifluoromethyl)-pyridin-2-yl)-methyl)-7H-pyrrolo[2,3-d]pyrimidine-5-carboxamide;
(S)—N-((3-fluoro-pyridin-2-yl)(4-(trifluoromethyl)-phenyl)methyl)-6-methoxynicotinamide;
(S)—N-((3-fluoro-pyridin-2-yl)(4-(trifluoromethyl)-phenyl)methyl)-2-methoxynicotinamide;
(S)-3-methoxy-N-((4-(trifluoro-methyl)phenyl)-(3-(trifluoro-methyl)pyridin-2-yl)methyl)-isonicotinamide;
(S)-1-methyl-2-oxo-N-((4-(trifluoromethyl)-phenyl)(3-(trifluoromethyl)-pyridin-2-yl)-methyl)-1,2-dihydropyridine-4-carboxamide;
(S)-1-methyl-6-oxo-N-((4-(trifluoromethyl)-phenyl)(3-(trifluoromethyl)-pyridin-2-yl)-methyl)-1,6-dihydropyridine-3-carboxamide;
(S)—N-((3-fluoro-pyridin-2-yl)(4-(trifluoromethyl)-phenyl)methyl)-6-oxo-1,6-dihydropyridine-3-carboxamide;
(S)—N-((3-fluoro-pyridin-2-yl)(4-(trifluoromethyl)-phenyl)methyl)-6-methylnicotinamide;

(S)—N-((3-fluoro-pyridin-2-yl)(4-(trifluoromethyl)-phenyl)methyl)-2-methylisonicotinamide;

(S)—N-((3-fluoro-pyridin-2-yl)(4-(trifluoromethyl)-phenyl)methyl)-1H-pyrrolo[2,3-b]pyridine-3-carboxamide;

(S)-4-methoxy-N-((4-(trifluoro-methyl)phenyl)-(3-(trifluoro-methyl)pyridin-2-yl)methyl)-nicotinamide;

(S)-2-oxo-N-((4-(trifluoromethyl)-phenyl)(3-(trifluoromethyl)-pyridin-2-yl)-methyl)indoline-5-carboxamide;

(S)-2-methyl-N-((4-(trifluoro-methyl)phenyl)-(3-(trifluoromethyl)pyridin-2-yl)methyl)-pyrimidine-5-carboxamide;

(S)-5-hydroxy-N-((4-(trifluoro-methyl)phenyl)-(3-(trifluoro-methyl)pyridin-2-yl)methyl)-nicotinamide;

(S)-2-oxo-N-((4-(trifluoromethyl)-phenyl)(3-(trifluoromethyl)-pyridin-2-yl)-methyl)-1,2-dihydropyridine-3-carboxamide;

(S)-4-methyl-N-((4-(trifluoro-methyl)phenyl)-(3-(trifluoromethyl)pyridin-2-yl)methyl)-pyrimidine-5-carboxamide;

(S)-4-hydroxy-N-((4-(trifluoro-methyl)phenyl)-(3-(trifluoro-methyl)pyridin-2-yl)methyl)-pyrimidine-5-carboxamide;

(S)-4-hydroxy-N-((4-(trifluoro-methyl)phenyl)-(3-(trifluoro-methyl)pyridin-2-yl)methyl)-picolinamide;

(S)-6-oxo-N-((4-(trifluoromethyl)-phenyl)(3-(trifluoromethyl)-pyridin-2-yl)-methyl)-1,6-dihydropyridine-2-carboxamide;

(S)-5-hydroxy-N-((4-(trifluoro-methyl)phenyl)-(3-(trifluoro-methyl)pyridin-2-yl)methyl)-picolinamide;

6-oxo-N—((S)-(4-(trifluoromethyl)-phenyl)(3-(trifluoromethyl)-pyridin-2-yl)-methyl)-piperidine-3-carboxamide;

(S)—N-((4-(trifluoromethyl)-phenyl)(3-(trifluoromethyl)-pyridin-2-yl)-methyl)-1H-pyrrolo[2,3-b]pyridine-2-carboxamide;

(S)—N-((4-(trifluoromethyl)-phenyl)(3-(trifluoromethyl)-pyridin-2-yl)-methyl)-1H-pyrrolo[2,3-b]pyridine-6-carboxamide;

(S)—N-((3-fluoro-pyridin-2-yl)(4-(trifluoromethyl)-phenyl)methyl)-1-methyl-6-oxo-1,6-dihydro-pyridine-3-carboxamide;

(S)-2-oxo-N-((4-(trifluoromethyl)-phenyl)(3-(trifluoromethyl)-pyridin-2-yl)-methyl)indoline-6-carboxamide;

(S)—N-((3-fluoro-pyridin-2-yl)(4-(trifluoromethyl)-phenyl)methyl)-2-oxoindoline-5-carboxamide;

(S)—N-((3-fluoro-pyridin-2-yl)(4-(trifluoromethyl)-phenyl)methyl)-2-oxoindoline-6-carboxamide;

(S)—N-((3-fluoro-pyridin-2-yl)(4-(trifluoromethyl)-phenyl)methyl)-2-oxo-1,2-dihydropyridine-3-carboxamide;

(S)—N-((3-fluoro-pyridin-2-yl)(4-(trifluoromethyl)-phenyl)methyl)-3-oxo-3,4-dihydro-2H-benzo[b][1,4]oxazine-7-carboxamide;

(S)—N-((3-fluoro-pyridin-2-yl)(4-(trifluoromethyl)-phenyl)methyl)-4-(N-methylsulfamoyl)benzamide;

(S)—N-((3-fluoro-pyridin-2-yl)(4-(trifluoromethyl)-phenyl)methyl)-2-oxo-3,4-dihydro-2H-benzo[b][1,4]oxazine-6-carboxamide;

(S)—N-((3-fluoro-pyridin-2-yl)(4-(trifluoromethyl)-phenyl)methyl)-2-oxo-2,3-dihydro-benzo[d]oxazole-5-carboxamide;

(S)—N-((3-fluoro-pyridin-2-yl)(4-(trifluoromethyl)-phenyl)methyl)-3-oxo-3,4-dihydro-2H-benzo[b][1,4]oxazine-8-carboxamide;

(S)—N-((3-fluoro-pyridin-2-yl)(4-(trifluoromethyl)-phenyl)methyl)-2-oxo-2,3-dihydro-benzo[d]oxazole-6-carboxamide;

(S)—N-((3-fluoro-pyridin-2-yl)(4-(trifluoro-methoxy)-phenyl)methyl)-2-oxo-2,3-dihydro-benzo[d]oxazole-5-carboxamide;

(S)—N-((3-fluoro-pyridin-2-yl)(4-(trifluoro-methoxy)-phenyl)methyl)-2-oxo-2,3-dihydro-benzo[d]oxazole-6-carboxamide;

(S)—N-((3-fluoro-pyridin-2-yl)(4-(trifluoro-methoxy)-phenyl)methyl)-3-oxo-3,4-dihydro-2H-benzo[b][1,4]oxazine-7-carboxamide;

(S)—N-((3-methylpyridin-2-yl)(4-(trifluoro-methyl)phenyl)-methyl)-6-oxo-1,6-dihydro-pyridine-3-carboxamide;

(S)-1-methyl-N-((3-methylpyridin-2-yl)(4-(trifluoro-methyl)phenyl)-methyl)-6-oxo-1,6-dihydro-pyridine-3-carboxamide;

(S)—N-((3-methylpyridin-2-yl)(4-(trifluoro-methyl)phenyl)-methyl)-2-oxo-2,3-dihydro-benzo[d]oxazole-5-carboxamide;

(S)—N-((3-methylpyridin-2-yl)(4-(trifluoro-methyl)phenyl)-methyl)-3-oxo-3,4-dihydro-2H-benzo[b][1,4]oxazine-7-carboxamide;

(S)—N-((3-fluoro-pyridin-2-yl)(4-(trifluoromethyl)-phenyl)methyl)-imidazo[1,2-a]pyridine-7-carboxamide;

(S)—N-((4-(trifluoromethyl)-phenyl)(3-(trifluoromethyl)-pyridin-2-yl)-methyl)-imidazo[1,2-a]pyridine-7-carboxamide;

(S)—N-((3-fluoro-pyridin-2-yl)(4-(trifluoro-methoxy)-phenyl)methyl)-imidazo[1,2-a]pyridine-7-carboxamide;

S)—N-((3-fluoro-pyridin-2-yl)(4-(trifluoro-methoxy)-phenyl)methyl)-imidazo[1,2-a]pyridine-6-carboxamide;

(S)—N-((3-fluoro-pyridin-2-yl)(4-(trifluoro-methoxy)-phenyl)methyl)-2-oxoindoline-6-carboxamide;

(S)—N-((3-fluoro-pyridin-2-yl)(4-(trifluoro-methoxy)-phenyl)methyl)-2-oxoindoline-5-carboxamide;

(S)-6-oxo-N-((3-(prop-1-yn-1-yl)-pyridin-2-yl)(4-(trifluoromethyl)-phenyl)methyl)-1,6-dihydro-pyridine-3-carboxamide;

(S)—N-((3-(prop-1-yn-1-yl)pyridin-2-yl)(4-(trifluoro-methyl)phenyl)-methyl)quinoline-6-carboxamide;

(S)-1,3-dioxo-N-((4-(trifluoro-methyl)phenyl)-(3-(trifluoromethyl)pyridin-2-yl)methyl)-isoindoline-5-carboxamide;

(S)-4-methoxy-N-((3-(prop-1-yn-1-yl)pyridin-2-yl)(4-(trifluoromethyl)-phenyl)methyl)-benzamide;

(S)-6-methoxy-N-((3-(prop-1-yn-1-yl)pyridin-2-yl)(4-(trifluoromethyl)-phenyl)methyl)-nicotinamide;

(S)—N-((3-(prop-1-yn-1-yl)pyridin-2-yl)(4-(trifluoro-methyl)phenyl)-methyl)quinoline-7-carboxamide;

(S)—N-((3-(prop-1-yn-1-yl)pyridin-2-yl)(4-(trifluoro-methyl)phenyl)-methyl)-benzamide;

(S)-1,3-dioxo-2-(pyridin-2-yl)-N-((4-(trifluoro-methyl)phenyl)-(3-(trifluoro-methyl)pyridin-2-yl)methyl)-isoindoline-5-carboxamide;

(S)-2-bromo-4-(((4-(trifluoro-methyl)phenyl)-(3-(trifluoromethyl)pyridin-2-yl)methyl)-carbamoyl)-benzoic acid;

(S)—N-((3-(3-methyloxetan-3-yl)ethynyl)-pyridin-2-yl)(4-(trifluoromethyl)-phenyl)methyl)-quinoline-6-carboxamide;

(S)—N-((3-fluoro-4-(trifluoro-methoxy)-phenyl)(3-fluoro-pyridin-2-yl)-methyl)-6-oxo-1,6-dihydro-pyridine-3-carboxamide;

(S)—N-((3-fluoro-4-(trifluoro-methoxy)-phenyl)(3-fluoro-pyridin-2-yl)-methyl)-1-methyl-6-oxo-1,6-dihydro-pyridine-3-carboxamide;

(S)—N-((3-fluoro-pyridin-2-yl)(4-(trifluoromethyl)-phenyl)methyl)-2-oxo-1,2-dihydroquinoline-6-carboxamide;

(S)—N-((3-fluoro-pyridin-2-yl)(4-(trifluoromethyl)-phenyl)methyl)-4-hydro-xyquinoline-7-carboxamide;

(S)-4-hydroxy-N-((4-(trifluoro-methyl)phenyl)-(3-(trifluoro-methyl)pyridin-2-yl)methyl)-quinoline-7-carboxamide;

(S)—N-((3-fluoro-4-(trifluoro-methyl)phenyl)-(3-(trifluoro-methyl)pyridin-2-yl)methyl)-benzamide;
(S)—N-((3-fluoro-4-(trifluoro-methyl)phenyl)-(3-(trifluoro-methyl)pyridin-2-yl)methyl)-quinoxaline-6-carboxamide;
(S)-4-hydroxy-N-((4-(trifluoro-methyl)phenyl)-(3-(trifluoro-methyl)pyridin-2-yl)methyl)-quinoline-6-carboxamide;
(S)-4-chloro-N-((4-(trifluoro-methyl)phenyl)-(3-(trifluoro-methyl)pyridin-2-yl)methyl)-quinoline-7-carboxamide;
(S)—N-((3-fluoro-4-(trifluoro-methyl)phenyl)-(3-(trifluoro-methyl)pyridin-2-yl)methyl)-pyrazine-2-carboxamide;
(S)—N-((3-fluoro-4-(trifluoro-methyl)phenyl)-(3-(trifluoro-methyl)pyridin-2-yl)methyl)-picolinamide;
(S)-4-chloro-N-((3-fluoropyridin-2-yl)(4-(trifluoro-methyl)phenyl)-methyl)quinoline-6-carboxamide;
(S)—N-((3-fluoro-pyridin-2-yl)(4-(trifluoromethyl)-phenyl)methyl)-4-hydro-xyquinoline-6-carboxamide;
(S)—N-((4-ethylphenyl)(3-(trifluoromethyl)-pyridin-2-yl)-methyl)quinoline-7-carboxamide;
(S)-4-chloro-N-((4-(trifluoro-methyl)phenyl)-(3-(trifluoro-methyl)pyridin-2-yl)methyl)-quinoline-6-carboxamide;
(S)-3-iodo-N-((4-(trifluoromethyl)-phenyl)(3-(trifluoromethyl)-pyridin-2-yl)-methyl)-benzamide;
(S)-2-iodo-N-((4-(trifluoromethyl)-phenyl)(3-(trifluoromethyl)-pyridin-2-yl)-methyl)-benzamide;
(S)—N—((S)-(3-fluoro-4-(trifluoromethyl)-phenyl)(3-(trifluoromethyl)-pyridin-2-yl)-methyl)tetrahydrofuran-2-carboxamide;
(S)-4-chloro-N-((3-fluoropyridin-2-yl)(4-(trifluoro-methyl)phenyl)-methyl)quinoline-7-carboxamide;
(S)-4-(2-hydro-xypropan-2-yl)-N-((4-(trifluoro-methyl)phenyl)-(3-(trifluoro-methyl)pyridin-2-yl)methyl)-benzamide;
(S)-4-iodo-N-((4-(trifluoromethyl)-phenyl)(3-(trifluoromethyl)-pyridin-2-yl)-methyl)-benzamide;
(R)—N—((S)-(3-fluoro-4-(trifluoromethyl)-phenyl)(3-(trifluoromethyl)-pyridin-2-yl)-methyl)tetrahydrofuran-2-carboxamide;
(S)—N-((4-fluoro-phenyl)(3-(trifluoromethyl)-pyridin-2-yl)-methyl)-6-methoxynicotinamide;
(S)—N-((3-fluoro-pyridin-2-yl)(4-(trifluoromethyl)-phenyl)methyl)-2-oxo-1,2-dihydroquinoline-7-carboxamide;
(S)—N-((4-fluoro-phenyl)(3-(trifluoromethyl)-pyridin-2-yl)-methyl)-benzamide;
(S)-4-isopropyl-N-((4-(trifluoro-methyl)phenyl)-(3-(trifluoro-methyl)pyridin-2-yl)methyl)-benzamide;
(S)—N-((4-(trifluoromethyl)-phenyl)(3-(trifluoromethyl)-pyridin-2-yl)-methyl)-1,8-naphthyridine-2-carboxamide;
(S)—N-((3-fluoro-4-(trifluoro-methyl)phenyl)-(3-(trifluoro-methyl)pyridin-2-yl)methyl)-1,8-naphthyridine-2-carboxamide;
(S)—N-((3-fluoro-4-(trifluoro-methyl)phenyl)-(3-(trifluoro-methyl)pyridin-2-yl)methyl)-quinoline-6-carboxamide;
(S)—N-((3-fluoro-4-(trifluoro-methyl)phenyl)-(3-(trifluoro-methyl)pyridin-2-yl)methyl)-quinoline-7-carboxamide;
(S)—N-((4-(trifluoromethyl)-phenyl)(3-(trifluoromethyl)-pyridin-2-yl)-methyl)quinoline-7-carboxamide;
(S)—N-((4-(trifluoromethyl)-phenyl)(3-(trifluoromethyl)-pyridin-2-yl)-methyl)quinoline-6-carboxamide;
(S)-6-amino-N-((4-(trifluoro-methyl)phenyl)-(3-(trifluoro-methyl)pyridin-2-yl)methyl)-nicotinamide;
(S)-6-chloro-N-((4-(trifluoro-methyl)phenyl)-(3-(trifluoro-methyl)pyridin-2-yl)methyl)-nicotinamide;
(S)-2-amino-N-((4-(trifluoro-methyl)phenyl)-(3-(trifluoro-methyl)pyridin-2-yl)methyl)-thiazole-4-carboxamide;
(S)-4-amino-2-methyl-N-((4-(trifluoromethyl)-phenyl)(3-(trifluoromethyl)-pyridin-2-yl)-methyl)-pyrimidine-5-carboxamide;
(S)—N-((4-(trifluoromethyl)-phenyl)(3-(trifluoromethyl)-pyridin-2-yl)-methyl)-thiophene-2-carboxamide;
(S)-3-amino-N-((4-(trifluoro-methyl)phenyl)-(3-(trifluoro-methyl)pyridin-2-yl)methyl)-isonicotinamide;
(S)-methyl 4-(((4-(trifluoromethyl)-phenyl)(3-(trifluoromethyl)-pyridin-2-yl)-methyl)-carbamoyl)-benzoate;
(S)-4-(1H-tetrazol-5-yl)-N-((4-(trifluoro-methyl)phenyl)-(3-(trifluoro-methyl)pyridin-2-yl)methyl)-benzamide;
tert-butyl 3-(((S)-(4-(trifluoro-methyl)phenyl)-(3-(trifluoro-methyl)pyridin-2-yl)methyl)-carbamoyl)-piperidine-1-carboxylate;
(S)—N-((4-(trifluoromethyl)-phenyl)(3-(trifluoromethyl)-pyridin-2-yl)-methyl)-1H-pyrazole-4-carboxamide;
(S)-6-(dimethylamino)-N-((4-(trifluoro-methyl)phenyl)-(3-(trifluoro-methyl)pyridin-2-yl)methyl)-nicotinamide;
(S)-3-amino-N-((4-(trifluoro-methyl)phenyl)-(3-(trifluoro-methyl)pyridin-2-yl)methyl)-picolinamide;
(S)-3-(4-methylthiazol-5-yl)-N-((4-(trifluoromethyl)-phenyl)(3-(trifluoromethyl)-pyridin-2-yl)-methyl)-propanamide;
(S)-6-(ethylamino)-N-((4-(trifluoro-methyl)phenyl)-(3-(trifluoro-methyl)pyridin-2-yl)methyl)-nicotinamide;
(S)-1-methyl-N-((4-(trifluoro-methyl)phenyl)-(3-(trifluoro-methyl)pyridin-2-yl)methyl)-1H-imidazole-2-carboxamide;
(S)—N-((3-fluoro-pyridin-2-yl)(4-(trifluoromethyl)-phenyl)methyl)-2-methoxypyrimidine-5-carboxamide;
(S)—N-((4-(trifluoromethyl)-phenyl)(3-(trifluoromethyl)-pyridin-2-yl)-methyl)-pyrimidine-5-carboxamide;
(S)-6-acetamido-N-((4-(trifluoro-methyl)phenyl)-(3-(trifluoro-methyl)pyridin-2-yl)methyl)-nicotinamide;
(S)-5,7-dimethyl-N-((4-(trifluoro-methyl)phenyl)-(3-(trifluoro-methyl)pyridin-2-yl)methyl)-pyrazolo[1,5-a]pyrimidine-2-carboxamide;
(S)-6-oxo-N-((4-(trifluoromethyl)-phenyl)(3-(trifluoromethyl)-pyridin-2-yl)-methyl)-1,6-dihydro-pyridazine-3-carboxamide;
(S)-5,7-dimethyl-N-((4-(trifluoro-methyl)phenyl)-(3-(trifluoro-methyl)pyridin-2-yl)methyl)-[1,2,4]triazolo[1,5-a]pyrimidine-2-carboxamide;
(S)—N-((4-(trifluoromethyl)-phenyl)(3-(trifluoromethyl)-pyridin-2-yl)-methyl)-tetrahydro-2H-pyran-4-carboxamide;
(S)-2-(5-methyl-1H-pyrazol-1-yl)-N-((4-(trifluoro-methyl)phenyl)-(3-(trifluoro-methyl)pyridin-2-yl)methyl)-acetamide;
(S)-2-(2-oxooxazolidin-3-yl)-N-((4-(trifluoromethyl)-phenyl)(3-(trifluoromethyl)-pyridin-2-yl)-methyl)-acetamide;
(S)-3-(1H-imidazol-4-yl)-N-((4-(trifluoro-methyl)phenyl)-(3-(trifluoro-methyl)pyridin-2-yl)methyl)-propanamide;
(S)—N-((3-fluoro-4-(trifluoro-methyl)phenyl)-(3-(trifluoro-methyl)pyridin-2-yl)methyl)-2-isobutylquinoline-4-carboxamide;
2-(tetrahydrofuran-3-yl)-N—((S)-(4-(trifluoro-methyl)phenyl)-(3-(trifluoro-methyl)pyridin-2-yl)methyl)-acetamide;
(S)-2-(1H-imidazol-4-yl)-N-((4-(trifluoro-methyl)phenyl)-(3-(trifluoro-methyl)pyridin-2-yl)methyl)-acetamide;
(S)-3-amino-N-((4-(trifluoro-methyl)phenyl)-(3-(trifluoro-methyl)pyridin-2-yl)methyl)-1H-1,2,4-triazole-5-carboxamide;

(S)-2-(2-methyl-1H-imidazol-1-yl)-N-((4-(trifluoromethyl)-phenyl)(3-(trifluoromethyl)-pyridin-2-yl)-methyl)-acetamide;
(S)-2-(1H-imidazol-1-yl)-N-((4-(trifluoro-methyl)phenyl)-(3-(trifluoro-methyl)pyridin-2-yl)methyl)-acetamide;
2-acetamido-N—((S)-(4-(trifluoro-methyl)phenyl)-(3-(trifluoro-methyl)pyridin-2-yl)methyl)-propanamide;
5-oxo-N—((S)-(4-(trifluoromethyl)-phenyl)(3-(trifluoromethyl)-pyridin-2-yl)-methyl)-pyrrolidine-3-carboxamide;
(S)-2-(2-(trifluoro-methoxy)-phenyl)-N-((4-(trifluoromethyl)-phenyl)(3-(trifluoromethyl)-pyridin-2-yl)-methyl)-acetamide;
(S)-4-hydroxy-N-((4-(trifluoromethyl)phenyl)(3-(trifluoromethyl)pyridin-2-yl)methyl)benzamide;
(S)—N-((3-fluoro-pyridin-2-yl)(4-(trifluoromethyl)-phenyl)methyl)-1H-indazole-6-carboxamide;
(S)-4-cyano-N-((3-fluoropyridin-2-yl)(4-(trifluoro-methyl) phenyl)-methyl)-benzamide;
(S)-3-cyano-N-((4-(trifluoro-methyl)phenyl)-(3-(trifluoro-methyl)pyridin-2-yl)methyl)benzamide;
(S)—N-((3-fluoro-pyridin-2-yl)(4-(trifluoromethyl)-phenyl)methyl)-2-methoxybenzamide;
(S)—N-((3-fluoro-pyridin-2-yl)(4-(trifluoromethyl)-phenyl)methyl)-quinoxaline-6-carboxamide;
(S)-4-methoxy-N-((4-(trifluoro-methyl)phenyl)-(3-(trifluoro-methyl)pyridin-2-yl)methyl)-benzamide;
(S)—N-((3-fluoro-pyridin-2-yl)(4-(trifluoromethyl)-phenyl)methyl)-4-methoxybenzamide;
(S)—N-((3-fluoro-pyridin-2-yl)(4-(trifluoromethyl)-phenyl)methyl)-5-hydro-xypicolinamide;
(S)-4-(((4-(trifluoromethyl)-phenyl)(3-(trifluoromethyl)-pyridin-2-yl)-methyl)-carbamoyl)-phenyl acetate;
(S)—N-((4-(trifluoromethyl)-phenyl)(3-(trifluoromethyl)-pyridin-2-yl)-methyl)-1H-indazole-6-carboxamide;
(S)-2-methoxy-N-((4-(trifluoro-methyl)phenyl)-(3-(trifluoro-methyl)pyridin-2-yl)methyl)-benzamide;
(S)—N-((3-fluoro-pyridin-2-yl)(4-(trifluoromethyl)-phenyl)methyl)-2-oxo-2,3-dihydro-1H-benzo[d]imidazole-5-carboxamide;
(S)—N-((4-(trifluoromethyl)-phenyl)(3-(trifluoromethyl)-pyridin-2-yl)-methyl)-isonicotinamide;
(S)-3-(((4-(trifluoromethyl)-phenyl)(3-(trifluoromethyl)-pyridin-2-yl)-methyl)-carbamoyl)-benzoic acid;
(S)—N-((3-fluoro-pyridin-2-yl)(4-(trifluoromethyl)-phenyl)methyl)-benzamide;
(S)-4-cyano-N-((4-(trifluoro-methyl)phenyl)-(3-(trifluoro-methyl)pyridin-2-yl)methyl)-benzamide;
(S)-5-methyl-N-((4-(trifluoro-methyl)phenyl)-(3-(trifluoro-methyl)pyridin-2-yl)methyl)-nicotinamide;
(S)-4-fluoro-N-((4-(trifluoro-methyl)phenyl)-(3-(trifluoro-methyl)pyridin-2-yl)methyl)-benzamide;
(S)-3-cyano-N-((3-fluoropyridin-2-yl)(4-(trifluoro-methyl) phenyl)-methyl)-benzamide;
(S)-4-chloro-N-((4-(trifluoro-methyl)phenyl)-(3-(trifluoro-methyl)pyridin-2-yl)methyl)-benzamide;
(S)-3-(dimethylamino)-N-((4-(trifluoro-methyl)phenyl)-(3-(trifluoro-methyl)pyridin-2-yl)methyl)-benzamide;
(S)-3-fluoro-N-((3-fluoropyridin-2-yl)(4-(trifluoro-methyl) phenyl)-methyl)-benzamide;
(S)—N-((4-(trifluoromethyl)-phenyl)(3-(trifluoromethyl)-pyridin-2-yl)-methyl)-nicotinamide;
(S)-methyl 3-(((4-(trifluoromethyl)-phenyl)(3-(trifluoromethyl)-pyridin-2-yl)-methyl)-carbamoyl)-benzoate;
(S)-4-methyl-N-((4-(trifluoro-methyl)phenyl)-(3-(trifluoro-methyl)pyridin-2-yl)methyl)-oxazole-5-carboxamide;
(S)-3-methoxy-N-((4-(trifluoro-methyl)phenyl)-(3-(trifluoro-methyl)pyridin-2-yl)methyl)-benzamide;
(S)-1-methyl-N-((4-(trifluoro-methyl)phenyl)-(3-(trifluoro-methyl)pyridin-2-yl)methyl)-1H-pyrazole-3-carboxamide;
N-((3-fluoro-pyridin-2-yl)(4-(trifluoromethyl)-phenyl)methyl)-benzamide;
(S)—N-((3-fluoro-pyridin-2-yl)(4-(trifluoromethyl)-phenyl)methyl)-picolinamide;
(S)—N-((3-bromopyridin-2-yl)(4-(trifluoro-methyl)phenyl)-methyl)quinoline-7-carboxamide;
(S)-4-(dimethylamino)-N-((4-(trifluoro-methyl)phenyl)-(3-(trifluoro-methyl)pyridin-2-yl)methyl)-benzamide;
(S)-2-cyano-N-((4-(trifluoro-methyl)phenyl)-(3-(trifluoro-methyl)pyridin-2-yl)methyl)-benzamide;
(S)-5-bromo-6-chloro-N-((3-fluoropyridin-2-yl)(4-(trifluoro-methyl)phenyl)-methyl)-nicotinamide;
(S)—N-((4-(trifluoromethyl)-phenyl)(3-(trifluoromethyl)-pyridin-2-yl)-methyl)furan-3-carboxamide;
4-cyano-N-((3-fluoropyridin-2-yl)(4-(trifluoro-methyl)phenyl)-methyl)-benzamide;
(S)-6-oxo-N-(pyridin-2-yl(4-(trifluoromethyl)-phenyl)methyl)-1,6-dihydro-pyridine-3-carboxamide;
N-((3-fluoro-pyridin-2-yl)(4-(trifluoromethyl)-phenyl)methyl)-quinoxaline-6-carboxamide;
(S)—N-((3-fluoro-pyridin-2-yl)(4-(trifluoromethyl)-phenyl)methyl)-nicotinamide;
N-((3-fluoro-pyridin-2-yl)(4-(trifluoromethyl)-phenyl)methyl)-quinoline-7-carboxamide;
(S)-5-bromo-N-((4-(trifluoro-methyl)phenyl)-(3-(trifluoro-methyl)pyridin-2-yl)methyl)-picolinamide;
(S)-6-cyano-N-((4-(trifluoro-methyl)phenyl)-(3-(trifluoro-methyl)pyridin-2-yl)methyl)-nicotinamide;
(S)-3-(((3-fluoro-pyridin-2-yl)(4-(trifluoromethyl)-phenyl) methyl)-carbamoyl)-benzoic acid;
(S)-3-chloro-N-((4-(trifluoro-methyl)phenyl)-(3-(trifluoro-methyl)pyridin-2-yl)methyl)-benzamide;
3-fluoro-N-((3-fluoropyridin-2-yl)(4-(trifluoro-methyl)phenyl)-methyl)-benzamide;
(S)-5-methoxy-N-((4-(trifluoro-methyl)phenyl)-(3-(trifluoro-methyl)pyridin-2-yl)methyl)-picolinamide;
(S)-3-(trifluoro-methyl)-N-((4-(trifluoromethyl)-phenyl)(3-(trifluoromethyl)-pyridin-2-yl)-methyl)-benzamide;
(S)—N-((4-(trifluoromethyl)-phenyl)(3-(trifluoromethyl)-pyridin-2-yl)-methyl)-pyridazine-4-carboxamide;
(S)—N-((3-fluoro-pyridin-2-yl)(4-(trifluoromethyl)-phenyl)methyl)-4-(methylsulfonamido)benzamide;
N-((3-fluoro-pyridin-2-yl)(4-(trifluoromethyl)-phenyl)methyl)-3-methoxybenzamide;
(S)-1-methyl-N-((4-(trifluoro-methyl)phenyl)-(3-(trifluoro-methyl)pyridin-2-yl)methyl)-1H-indazole-3-carboxamide;
(S)—N-((3-fluoro-pyridin-2-yl)(4-(trifluoromethyl)-phenyl)methyl)-3-(methylsulfonyl)-benzamide;
(S)—N-((3-fluoro-pyridin-2-yl)(4-(trifluoromethyl)-phenyl)methyl)-4-(methylsulfonyl)-benzamide;
(S)-2-phenyl-N-((4-(trifluoro-methyl)phenyl)-(3-(trifluoro-methyl)pyridin-2-yl)methyl)-acetamide;
(S)-3-(trifluoro-methoxy)-N-((4-(trifluoromethyl)-phenyl) (3-(trifluoromethyl)-pyridin-2-yl)-methyl)-benzamide;
(S)—N-((4-(trifluoromethyl)-phenyl)(3-(trifluoromethyl)-pyridin-2-yl)-methyl)isoxazole-5-carboxamide;
N-((3-fluoro-pyridin-2-yl)(4-(trifluoromethyl)-phenyl)methyl)-4-methyloxazole-5-carboxamide;
(S)—N-((4-(trifluoromethyl)-phenyl)(3-(trifluoromethyl)-pyridin-2-yl)-methyl)-benzo[b]thiophene-2-carboxamide;
3-oxo-N—((S)-(4-(trifluoromethyl)-phenyl)(3-(trifluoromethyl)-pyridin-2-yl)-methyl)-cyclohexanecarboxamide;

(S)-3-methoxy-N-((4-(trifluoro-methyl)phenyl)-(3-(trifluoro-methyl)pyridin-2-yl)methyl)-propanamide;

N—((S)-(4-(trifluoromethyl)-phenyl)(3-(trifluoromethyl)-pyridin-2-yl)-methyl)tetrahydrofuran-3-carboxamide;

(S)-5-(((4-(trifluoromethyl)-phenyl)(3-(trifluoromethyl)-pyridin-2-yl)-methyl)-carbamoyl)-nicotinic acid;

(S)-3-fluoro-N-((4-(trifluoro-methyl)phenyl)-(3-(trifluoro-methyl)pyridin-2-yl)methyl)-benzamide;

(S)—N-((4-(trifluoromethyl)-phenyl)(3-(trifluoromethyl)-pyridin-2-yl)-methyl)-picolinamide;

(S)-tert-butyl 3-(2-oxo-2-(((4-(trifluoromethyl)-phenyl)(3-(trifluoromethyl)-pyridin-2-yl)-methyl)amino)-ethyl)azetidine-1-carboxylate;

(S)—N-((4-(trifluoromethyl)-phenyl)(3-(trifluoromethyl)-pyridin-2-yl)-methyl)quinoline-3-carboxamide;

(S)-4-(trifluoro-methoxy)-N-((4-(trifluoromethyl)-phenyl)(3-(trifluoromethyl)-pyridin-2-yl)-methyl)-benzamide;

N—((S)-(3-((R)-2,2-dimethylcyclopropyl)pyridin-2-yl)-(4-(trifluoro-methyl)phenyl)-methyl)quinoline-7-carboxamide;

N—((S)-(3-((R)-2,2-dimethylcyclopropyl)pyridin-2-yl)-(4-(trifluoro-methyl)phenyl)-methyl)quinoline-6-carboxamide;

(S)—N—((S)-(4-(trifluoromethyl)-phenyl)(3-(trifluoromethyl)-pyridin-2-yl)-methyl)tetrahydrofuran-2-carboxamide;

(S)—N—((S)-(3-allylpyridin-2-yl)-(4-(trifluoro-methyl)phenyl)-methyl)-2-phenylpropanamide;

(S)—N-((3-neopentylpyridin-2-yl)(4-(trifluoro-methyl)phenyl)methyl)quinoline-6-carboxamide;

3,3,3-trifluoro-2-methoxy-2-phenyl-N—((S)-(4-(trifluoromethyl)phenyl)(3-(trifluoromethyl)-pyridin-2-yl)-methyl)-propanamide;

(S)-2-(pyridin-3-yl)-N-((4-(trifluoromethyl)-phenyl)(3-(trifluoromethyl)-pyridin-2-yl)-methyl)-acetamide;

(S)—N-((4-(trifluoromethyl)-phenyl)(3-(trifluoromethyl)-pyridin-2-yl)-methyl)-benzo[d]thiazole-6-carboxamide;

(S)-2-methoxy-2-methyl-N-((4-(trifluoromethyl)-phenyl)(3-(trifluoromethyl)-pyridin-2-yl)-methyl)-propanamide;

(1s,4R)-4-(hydro-xymethyl)-N—((S)-(4-(trifluoro-methyl)phenyl)-(3-(trifluoro-methyl)pyridin-2-yl)methyl)-cyclohexanecarboxamide;

(S)-4-hydroxy-N-((4-(trifluoro-methyl)phenyl)-(3-(trifluoro-methyl)pyridin-2-yl)methyl)-cyclohexanecarboxamide;

(S)-2,2-dimethyl-3-oxo-3-(((4-(trifluoromethyl)-phenyl)(3-(trifluoromethyl)-pyridin-2-yl)-methyl)amino)-propanoic acid;

(S)-4-(((4-(trifluoromethyl)-phenyl)(3-(trifluoromethyl)-pyridin-2-yl)-methyl)-carbamoyl)-cyclohexanecarboxylic acid;

(S)-3-oxo-N-((4-(trifluoromethyl)-phenyl)(3-(trifluoromethyl)-pyridin-2-yl)-methyl)-2,3-dihydro-1H-indene-5-carboxamide;

(S)-3-benzoyl-N-((4-(trifluoro-methyl)phenyl)-(3-(trifluoro-methyl)pyridin-2-ylmethyl)-benzamide;

N-((3,4-dichloro-phenyl)(pyridin-2-ylmethyl)-isoquinoline-6-carboxamide;

(S)—N-((3-chloro-pyridin-2-yl)(4-(trifluoromethyl)-phenyl)methyl)-6-oxo-1,6-dihydropyridine-3-carboxamide;

(S)—N-((3-chloro-pyridin-2-yl)(4-(trifluoromethyl)-phenyl)methyl)-1-methyl-6-oxo-1,6-dihydro-pyridine-3-carboxamide;

(S)—N-((3,4-dichlorophenyl)-(3-fluoropyridin-2-yl)methyl)-6-oxo-1,6-dihydro-pyridine-3-carboxamide;

(S)—N-((3,4-dichlorophenyl)-(3-fluoropyridin-2-yl)methyl)-1-methyl-6-oxo-1,6-dihydro-pyridine-3-carboxamide;

(S)—N-((3-fluoro-pyridin-2-yl)(4-(trifluoro-methoxy)-phenyl)methyl)-1-methyl-6-oxo-1,6-dihydro-pyridine-3-carboxamide;

(S)—N-((3-fluoro-pyridin-2-yl)(4-(trifluoromethyl)-phenyl)methyl)-imidazo[1,2-a]pyridine-6-carboxamide;

(S)—N-((4-(trifluoromethyl)-phenyl)(3-(trifluoromethyl)-pyridin-2-yl)-methyl)-imidazo[1,2-a]pyridine-6-carboxamide;

(S)-1-ethyl-N-((3-fluoropyridin-2-yl)(4-(trifluoro-methoxy)-phenyl)methyl)-6-oxo-1,6-dihydropyridine-3-carboxamide;

(S)—N-((2-bromophenyl)(4-(trifluoromethyl)-phenyl)methyl)-quinoline-6-carboxamide;

(S)—N-((3-fluoro-4-(trifluoro-methyl)phenyl)-(2-(trifluoro-methyl)phenyl)-methyl)quinoline-6-carboxamide;

(S)—N-((2,6-difluorophenyl)-(4-(trifluoro-methyl)phenyl)-methyl)-6-oxo-1,6-dihydro-pyridine-3-carboxamide;

(S)—N-((4-(trifluoromethyl)-phenyl)(4-(trifluoromethyl)-pyridin-3-yl)-methyl)quinoline-6-carboxamide;

(S)-3-oxo-N-((4-(trifluoromethyl)phenyl)(3-(trifluoromethyl)pyridin-2-yl)methyl)isoindoline-5-carboxamide;

(S)-2-hydroxy-N-((4-(trifluoromethyl)phenyl)(3-(trifluoromethyl)pyridin-2-yl)methyl)pyrimidine-5-carboxamide;

(S)-6-oxo-N-((3-propylpyridin-2-yl)(4-(trifluoromethyl)phenyl)methyl)-1,6-dihydropyridine-3-carboxamide;

(S)-2-allyl-1,3-dioxo-N-((4-(trifluoromethyl)phenyl)(3-(trifluoromethyl)pyridin-2-yl)methyl)isoindoline-5-carboxamide;

(S)-1,3-dioxo-2-propyl-N-((4-(trifluoromethyl)phenyl)(3-(trifluoromethyl)pyridin-2-yl)methyl)isoindoline-5-carboxamide;

(S)-2-methyl-1,3-dioxo-N-((4-(trifluoromethyl)phenyl)(3-(trifluoromethyl)pyridin-2-yl)methyl)isoindoline-5-carboxamide;

(S)-1-oxo-N-((4-(trifluoromethyl)phenyl)(3-(trifluoromethyl)pyridin-2-yl)methyl)isoindoline-5-carboxamide;

(S)-6-(((3-fluoropyridin-2-yl)(4-(trifluoromethoxy)phenyl)methyl)carbamoyl)nicotinic acid;

(S)—N2-((3-fluoropyridin-2-yl)(4-(trifluoromethyl)phenyl)methyl)-N5-methylpyridine-2,5-dicarboxamide;

(S)—N-((4-(trifluoromethyl)phenyl)(3-(trifluoromethyl)pyridin-2-yl)methyl)-1,2,3,4-tetrahydroquinoline-7-carboxamide;

(S)-5-cyano-N-((4-(trifluoromethyl)phenyl)(3-(trifluoromethyl)pyridin-2-yl)methyl)picolinamide;

(S)—N-(pyridin-2-yl(4-(trifluoromethyl)phenyl)methyl)-1,2,3,4-tetrahydroquinoline-7-carboxamide;

(S)-5-cyano-N-((3-fluoropyridin-2-yl)(4-(trifluoromethyl)phenyl)methyl)-6-oxo-1,6-dihydropyridine-3-carboxamide;

(S)—N-((3-cyanopyridin-2-yl)(4-(trifluoromethyl)phenyl)methyl)quinoline-7-carboxamide;

(S)-2-((6-(((3-fluoropyridin-2-yl)(4-(trifluoromethyl)phenyl)methyl)carbamoyl)pyridin-3-yl)oxy)acetic acid;

(S)-6-(((3-fluoropyridin-2-yl)(4-(trifluoromethyl)phenyl)methyl)carbamoyl)nicotinic acid;

(S)-6-(((4-(trifluoromethyl)phenyl)(3-(trifluoromethyl)pyridin-2-yl)methyl)carbamoyl)nicotinic acid;

(S)—N2-((3-fluoropyridin-2-yl)(4-(trifluoromethyl)phenyl)methyl)pyridine-2,5-dicarboxamide;

(S)-4-(((4-(trifluoromethyl)phenyl)(3-(trifluoromethyl)pyridin-2-yl)methyl)carbamoyl)benzoic acid;

(S)-3-(pyridin-2-yl)-N-((4-(trifluoromethyl)phenyl)(3-(trifluoromethyl)pyridin-2-yl)methyl)propanamide;

(S)-5-(((4-(trifluoromethyl)phenyl)(3-(trifluoromethyl)pyridin-2-yl)methyl)carbamoyl)picolinic acid; or (S)—N-((3-(tert-butyl)pyridin-2-yl)(4-(trifluoromethyl)phenyl)methyl)quinoline-7-carboxamide; or the pharmaceutically-acceptable salt thereof, the tautomer thereof, the pharmaceutically-acceptable salt of the tautomer, or the mixture thereof.

77. The compound of embodiment 1, wherein the compound is (R)—N-((3-fluoropyridin-2-yl)(4-(trifluoromethyl)phenyl)methyl)-6-oxo-1,6-dihydropyridine-3-carboxamide;

(S)—N-((3-fluoro-4-(trifluoromethoxy)phenyl)(3-fluoropyridin-2-yl)methyl)-2-(pyridin-2-yl)acetamide;

(S)—N-((3-fluoro-4-(trifluoromethoxy)phenyl)(3-fluoropyridin-2-yl)methyl)-2-(pyridin-3-yl)acetamide;

(S)—N-((3-fluoro-4-(trifluoromethoxy)phenyl)(3-fluoropyridin-2-yl)methyl)-2-(pyridin-4-yl)acetamide;

(S)—N-((3,6-difluoropyridin-2-yl)(4-(trifluoromethyl)phenyl)methyl)-6-oxo-1,6-dihydropyridine-3-carboxamide;

(S)—N-((3-fluoro-4-(trifluoromethoxy)phenyl)(5-fluoropyridin-2-yl)methyl)-6-oxo-1,6-dihydropyridine-3-carboxamide;

(S)—N-((3-fluoro-4-(trifluoromethoxy)phenyl)(pyridin-2-yl)methyl)-6-oxo-1,6-dihydropyridine-3-carboxamide;

(S)—N-((3-fluoro-4-(trifluoromethoxy)phenyl)(pyridin-2-yl)methyl)-1-methyl-6-oxo-1,6-dihydropyridine-3-carboxamide;

(S)—N-((3-fluoro-4-(trifluoromethoxy)phenyl)(2-fluorophenyl)methyl)-6-oxo-1,6-dihydropyridine-3-carboxamide;

(S)—N-((3-fluoro-4-(trifluoromethoxy)phenyl)(2-fluorophenyl)methyl)-1-methyl-6-oxo-1,6-dihydropyridine-3-carboxamide;

(S)—N-((3-fluoro-4-(trifluoromethoxy)phenyl)(3-fluoropyridin-2-yl)methyl)-1-(2-hydroxyethyl)-6-oxo-1,6-dihydropyridine-3-carboxamide;

N—((S)-(3-fluoro-4-(trifluoromethoxy)phenyl)(3-fluoropyridin-2-yl)methyl)-1-((S)-2-hydroxypropyl)-6-oxo-1,6-dihydropyridine-3-carboxamide;

N—((S)-(3-fluoro-4-(trifluoromethoxy)phenyl)(3-fluoropyridin-2-yl)methyl)-1-((R)-2-hydroxypropyl)-6-oxo-1,6-dihydropyridine-3-carboxamide;

N—((S)-(3-fluoropyridin-2-yl)(4-(trifluoromethyl)phenyl)methyl)-1-((S)-2-hydroxypropyl)-6-oxo-1,6-dihydropyridine-3-carboxamide;

N—((S)-(3-fluoropyridin-2-yl)(4-(trifluoromethyl)phenyl)methyl)-1-((R)-2-hydroxypropyl)-6-oxo-1,6-dihydropyridine-3-carboxamide;

(S)—N-((3-fluoro-4-(trifluoromethoxy)phenyl)(3-fluoropyridin-2-yl)methyl)-1-(2-hydroxy-2-methylpropyl)-6-oxo-1,6-dihydropyridine-3-carboxamide;

(S)—N-((3-fluoropyridin-2-yl)(4-(trifluoromethyl)phenyl)methyl)-1-(2-hydroxy-2-methylpropyl)-6-oxo-1,6-dihydropyridine-3-carboxamide;

(S)—N-((3-fluoro-4-(trifluoromethoxy)phenyl)(3-fluoropyridin-2-yl)methyl)-1-(oxetan-3-yl)-6-oxo-1,6-dihydropyridine-3-carboxamide;

(S)—N-((3-fluoropyridin-2-yl)(4-(trifluoromethyl)phenyl)methyl)-1-(oxetan-3-yl)-6-oxo-1,6-dihydropyridine-3-carboxamide;

(S)—N-(phenyl(3-(trifluoromethyl)pyridin-2-yl)methyl)quinoline-7-carboxamide;

(S)—N-((3-fluoropyridin-2-yl)(4-(trifluoromethyl)phenyl)methyl)tetrazolo[1,5-a]pyridine-6-carboxamide;

(S)—N-((3-fluoropyridin-2-yl)(4-(trifluoromethyl)phenyl)methyl)tetrazolo[1,5-a]pyridine-7-carboxamide;

(S)—N-((3-fluoropyridin-2-yl)(4-(trifluoromethoxy)phenyl)methyl)tetrazolo[1,5-a]pyridine-6-carboxamide;

(S)—N-((3-fluoropyridin-2-yl)(4-(trifluoromethoxy)phenyl)methyl)tetrazolo[1,5-a]pyridine-7-carboxamide;

(S)—N-((4-(trifluoromethyl)phenyl)(3-(trifluoromethyl)pyridin-2-yl)methyl)tetrazolo[1,5-a]pyridine-6-carboxamide;

(S)—N-((4-(trifluoromethyl)phenyl)(3-(trifluoromethyl)pyridin-2-yl)methyl)tetrazolo[1,5-a]pyridine-7-carboxamide;

(S)—N-((3-methylpyridin-2-yl)(4-(trifluoromethyl)phenyl)methyl)-2-oxo-2,3-dihydrobenzo[d]oxazole-6-carboxamide;

(S)—N-((3-methylpyridin-2-yl)(4-(trifluoromethyl)phenyl)methyl)imidazo[1,2-a]pyridine-6-carboxamide;

(S)—N-((3-fluoropyridin-2-yl)(4-(trifluoromethyl)phenyl)methyl)-4-(5-oxo-2,5-dihydro-1,2,4-oxadiazol-3-yl)benzamide;

(S)—N-((3-fluoropyridin-2-yl)(4-(trifluoromethoxy)phenyl)methyl)-4-(5-oxo-2,5-dihydro-1,2,4-oxadiazol-3-yl)benzamide;

(S)—N-((3-fluoropyridin-2-yl)(4-(trifluoromethyl)phenyl)methyl)-6-oxo-1,6-dihydropyridazine-3-carboxamide;

(S)—N-((3-fluoropyridin-2-yl)(4-(trifluoromethyl)phenyl)methyl)-2-oxo-1,2,3,4-tetrahydroquinoline-6-carboxamide;

(S)—N-((3-fluoropyridin-2-yl)(4-(trifluoromethyl)phenyl)methyl)-5-oxo-4,5-dihydropyrazine-2-carboxamide;

(S)—N-((3-fluoropyridin-2-yl)(4-(trifluoromethyl)phenyl)methyl)-6,7-dihydro-5H-pyrazolo[5,1-b][1,3]oxazine-2-carboxamide;

(S)—N-((3-fluoropyridin-2-yl)(4-(trifluoromethyl)phenyl)methyl)-1,4,5,6-tetrahydrocyclopenta[c]pyrazole-3-carboxamide;

(S)—N-((3-fluoropyridin-2-yl)(4-(trifluoromethyl)phenyl)methyl)-4,5,6,7-tetrahydro-1H-indazole-3-carboxamide;

(S)—N-((3-methylpyridin-2-yl)(4-(trifluoromethyl)phenyl)methyl)-4-(5-oxo-2,5-dihydro-1,2,4-oxadiazol-3-yl)benzamide;

(S)—N-((3,5-dimethylphenyl)(3-fluoropyridin-2-yl)methyl)-6-oxo-1,6-dihydropyridine-3-carboxamide;

(S)—N-((3-fluoro-5-methylphenyl)(3-fluoropyridin-2-yl)methyl)-6-oxo-1,6-dihydropyridine-3-carboxamide;

(S)—N-((3-fluoro-5-methylphenyl)(3-fluoropyridin-2-yl)methyl)-1-methyl-6-oxo-1,6-dihydropyridine-3-carboxamide;

(S)—N-((3-fluoro-5-(trifluoromethyl)phenyl)(3-fluoropyridin-2-yl)methyl)-6-oxo-1,6-dihydropyridine-3-carboxamide;

(S)—N-((3-fluoro-5-(trifluoromethyl)phenyl)(3-fluoropyridin-2-yl)methyl)-1-methyl-6-oxo-1,6-dihydropyridine-3-carboxamide;

(S)—N-((3,5-difluorophenyl)(3-fluoropyridin-2-yl)methyl)-6-oxo-1,6-dihydropyridine-3-carboxamide;

(S)—N-((3,5-difluorophenyl)(3-fluoropyridin-2-yl)methyl)-1-methyl-6-oxo-1,6-dihydropyridine-3-carboxamide;

(S)—N-((3,4-difluorophenyl)(3-fluoropyridin-2-yl)methyl)-6-oxo-1,6-dihydropyridine-3-carboxamide;

(S)—N-((3,4-difluorophenyl)(3-fluoropyridin-2-yl)methyl)-1-methyl-6-oxo-1,6-dihydropyridine-3-carboxamide;

(S)—N-((3-fluoropyridin-2-yl)(3-methyl-5-(trifluoromethyl)phenyl)methyl)-6-oxo-1,6-dihydropyridine-3-carboxamide;

(S)—N-((3-fluoro-4-methylphenyl)(3-fluoropyridin-2-yl)methyl)-6-oxo-1,6-dihydropyridine-3-carboxamide;

(S)—N-((3-fluoro-4-methylphenyl)(3-fluoropyridin-2-yl)methyl)-1-methyl-6-oxo-1,6-dihydropyridine-3-carboxamide;
(S)—N-((3-fluoro-4-methoxyphenyl)(3-fluoropyridin-2-yl)methyl)-6-oxo-1,6-dihydropyridine-3-carboxamide;
(S)—N-((3-fluoro-4-methoxyphenyl)(3-fluoropyridin-2-yl)methyl)-1-methyl-6-oxo-1,6-dihydropyridine-3-carboxamide;
(S)—N-((4-fluoro-3-methylphenyl)(3-fluoropyridin-2-yl)methyl)-6-oxo-1,6-dihydropyridine-3-carboxamide;
(S)—N-((4-fluoro-3-methylphenyl)(3-fluoropyridin-2-yl)methyl)-1-methyl-6-oxo-1,6-dihydropyridine-3-carboxamide;
(S)—N-((4-fluorophenyl)(3-fluoropyridin-2-yl)methyl)-6-oxo-1,6-dihydropyridine-3-carboxamide;
(S)—N-((4-fluorophenyl)(3-fluoropyridin-2-yl)methyl)-1-methyl-6-oxo-1,6-dihydropyridine-3-carboxamide;
(S)—N-((3-fluoropyridin-2-yl)(4-methoxyphenyl)methyl)-6-oxo-1,6-dihydropyridine-3-carboxamide;
(S)—N-((3-fluoropyridin-2-yl)(4-methoxyphenyl)methyl)-1-methyl-6-oxo-1,6-dihydropyridine-3-carboxamide;
(S)—N-((4-chloro-3-fluorophenyl)(3-fluoropyridin-2-yl)methyl)-6-oxo-1,6-dihydropyridine-3-carboxamide;
(S)—N-((4-chloro-3-fluorophenyl)(3-fluoropyridin-2-yl)methyl)-1-methyl-6-oxo-1,6-dihydropyridine-3-carboxamide;
(S)—N-((3-fluoro-4-(trifluoromethoxy)phenyl)(3-fluoropyridin-2-yl)methyl)-2-oxoindoline-5-carboxamide;
(S)—N-((3-fluoro-4-(trifluoromethoxy)phenyl)(3-methylpyridin-2-yl)methyl)-6-oxo-1,6-dihydropyridine-3-carboxamide;
(S)—N-((3-fluoro-4-(trifluoromethoxy)phenyl)(3-methylpyridin-2-yl)methyl)-1-methyl-6-oxo-1,6-dihydropyridine-3-carboxamide;
(S)—N-((3-fluoro-4-(trifluoromethoxy)phenyl)(3-fluoropyridin-2-yl)methyl)-6-oxo-1,6-dihydropyridazine-3-carboxamide;
(S)—N-((3-fluoropyridin-2-yl)(4-(trifluoromethoxy)phenyl)methyl)-6-oxo-1,6-dihydropyridazine-3-carboxamide;
(S)—N-((3-fluoro-4-(trifluoromethoxy)phenyl)(3-fluoropyridin-2-yl)methyl)-2-oxo-1,2,3,4-tetrahydroquinoline-6-carboxamide;
(S)—N-((3-fluoropyridin-2-yl)(4-(trifluoromethoxy)phenyl)methyl)-2-oxo-1,2,3,4-tetrahydroquinoline-6-carboxamide;
(S)—N-((3-fluoro-4-(trifluoromethoxy)phenyl)(3-fluoropyridin-2-yl)methyl)-5-oxo-4,5-dihydropyrazine-2-carboxamide;
(S)—N-((3-fluoropyridin-2-yl)(4-(trifluoromethoxy)phenyl)methyl)-5-oxo-4,5-dihydropyrazine-2-carboxamide;
(S)—N-((3-fluoro-4-(trifluoromethoxy)phenyl)(3-fluoropyridin-2-yl)methyl)-6,7-dihydro-5H-pyrazolo[5,1-b][1,3]oxazine-2-carboxamide;
(S)—N-((3-fluoropyridin-2-yl)(4-(trifluoromethoxy)phenyl)methyl)-6,7-dihydro-5H-pyrazolo[5,1-b][1,3]oxazine-2-carboxamide;
(S)—N-((3-fluoro-4-(trifluoromethoxy)phenyl)(3-methylpyridin-2-yl)methyl)-3-oxo-3,4-dihydro-2H-benzo[b][1,4]oxazine-7-carboxamide;
(S)—N-((3-fluoro-4-(trifluoromethoxy)phenyl)(3-methylpyridin-2-yl)methyl)-2-oxo-2,3-dihydrobenzo[d]oxazole-5-carboxamide;
(S)—N-((3-methylpyridin-2-yl)(4-(trifluoromethoxy)phenyl)methyl)-6-oxo-1,6-dihydropyridine-3-carboxamide;
(S)-1-methyl-N-((3-methylpyridin-2-yl)(4-(trifluoromethoxy)phenyl)methyl)-6-oxo-1,6-dihydropyridine-3-carboxamide;
(S)-2-oxo-N-(pyridin-2-yl(4-(trifluoromethyl)phenyl)methyl)-2,3-dihydrobenzo[d]oxazole-5-carboxamide;
(S)-2-oxo-N-(pyridin-2-yl(4-(trifluoromethoxy)phenyl)methyl)-2,3-dihydrobenzo[d]oxazole-5-carboxamide;
(S)-6-oxo-N-((4-(trifluoromethyl)phenyl)(3-vinylpyridin-2-yl)methyl)-1,6-dihydropyridine-3-carboxamide;
(S)-1-ethyl-N-((3-fluoropyridin-2-yl)(4-(trifluoromethyl)phenyl)methyl)-6-oxo-1,6-dihydropyridine-3-carboxamide;
(S)—N-((3,4-dichlorophenyl)(3-fluoropyridin-2-yl)methyl)-1-ethyl-6-oxo-1,6-dihydropyridine-3-carboxamide;
(S)-1-ethyl-N-((3-fluoro-4-(trifluoromethoxy)phenyl)(3-fluoropyridin-2-yl)methyl)-6-oxo-1,6-dihydropyridine-3-carboxamide;
(S)—N-((3-fluoropyridin-2-yl)(4-(trifluoromethyl)phenyl)methyl)-1-isopropyl-6-oxo-1,6-dihydropyridine-3-carboxamide;
(S)-5-bromo-N-((3-fluoropyridin-2-yl)(4-(trifluoromethyl)phenyl)methyl)-6-oxo-1,6-dihydropyridine-3-carboxamide;
(S)—N-((3-fluoropyridin-2-yl)(4-(trifluoromethyl)phenyl)methyl)-1-methoxy-6-oxo-1,6-dihydropyridine-3-carboxamide;
(S)—N-((3-fluoropyridin-2-yl)(4-(trifluoromethyl)phenyl)methyl)-1-(2-hydroxyethyl)-6-oxo-1,6-dihydropyridine-3-carboxamide;
(S)-1-benzyl-N-((3-fluoropyridin-2-yl)(4-(trifluoromethyl)phenyl)methyl)-6-oxo-1,6-dihydropyridine-3-carboxamide;
(S)—N-((3-fluoropyridin-2-yl)(4-(trifluoromethyl)phenyl)methyl)-6-oxo-1-(2,2,2-trifluoroethyl)-1,6-dihydropyridine-3-carboxamide;
(S)—N-((3-fluoropyridin-2-yl)(4-(trifluoromethyl)phenyl)methyl)-5-methyl-6-oxo-1,6-dihydropyridine-3-carboxamide;
(S)—N-((3-fluoropyridin-2-yl)(4-(trifluoromethoxy)phenyl)methyl)thiophene-2-carboxamide;
(S)—N-((3-fluoropyridin-2-yl)(4-(trifluoromethyl)phenyl)methyl)thiophene-2-carboxamide;
N-((4-iodophenyl)(3-(trifluoromethyl)pyridin-2-yl)methyl)-6-oxo-1,6-dihydropyridine-3-carboxamide;
(S)-6-oxo-N-(pyridin-2-yl(4-(trifluoromethoxy)phenyl)methyl)-1,6-dihydropyridine-3-carboxamide;
(S)-1-methyl-6-oxo-N-(pyridin-2-yl(4-(trifluoromethoxy)phenyl)methyl)-1,6-dihydropyridine-3-carboxamide;
(S)—N-((3-fluoropyridin-2-yl)(p-tolyl)methyl)-6-oxo-1,6-dihydropyridine-3-carboxamide;
(S)—N-((3,4-dimethylphenyl)(3-fluoropyridin-2-yl)methyl)-6-oxo-1,6-dihydropyridine-3-carboxamide;
(S)—N-((3-fluoropyridin-2-yl)(3-methyl-4-(trifluoromethoxy)phenyl)methyl)-6-oxo-1,6-dihydropyridine-3-carboxamide;
(S)—N-((3-bromopyridin-2-yl)(3-fluoro-4-(trifluoromethoxy)phenyl)methyl)-6-oxo-1,6-dihydropyridine-3-carboxamide;
(S)—N-((3-fluoro-4-(trifluoromethoxy)phenyl)(3-(trifluoromethyl)pyridin-2-yl)methyl)-6-oxo-1,6-dihydropyridine-3-carboxamide;
(S)—N-((3-bromopyridin-2-yl)(3-fluoro-4-(trifluoromethoxy)phenyl)methyl)-2-oxo-2,3-dihydrobenzo[d]oxazole-5-carboxamide;
(S)—N-((3-fluoro-4-(trifluoromethoxy)phenyl)(3-(trifluoromethyl)pyridin-2-yl)methyl)-2-oxo-2,3-dihydrobenzo[d]oxazole-5-carboxamide;

(S)—N-((2-fluoro-4-(trifluoromethoxy)phenyl)(3-fluoropyridin-2-yl)methyl)-6-oxo-1,6-dihydropyridine-3-carboxamide 2,2,2-trifluoroacetate;

(S)—N-((3-fluoro-4-(trifluoromethoxy)phenyl)(3-fluoropyridin-2-yl)methyl)-1-methyl-1H-imidazole-2-carboxamide 2,2,2-trifluoroacetate;

(S)—N-((3-fluoro-4-(trifluoromethoxy)phenyl)(3-fluoropyridin-2-yl)methyl)-4-methyl-1H-imidazole-2-carboxamide 2,2,2-trifluoroacetate;

(S)—N-((3-fluoro-4-(trifluoromethoxy)phenyl)(3-fluoropyridin-2-yl)methyl)-5-hydroxypicolinamide 2,2,2-trifluoroacetate;

(S)-4-acetamido-N-((3-fluoro-4-(trifluoromethoxy)phenyl)(3-fluoropyridin-2-yl)methyl)-3-hydroxybenzamide;

(S)—N-((3-fluoro-4-(trifluoromethoxy)phenyl)(pyridin-2-yl)methyl)-2-oxo-2,3-dihydrobenzo[d]oxazole-6-carboxamide;

(S)—N-((3-fluoropyridin-2-yl)(4-(trifluoromethyl)phenyl)methyl)-1H-benzo[d]imidazole-5-carboxamide;

(S)—N-((3-fluoro-4-(trifluoromethoxy)phenyl)(pyridin-2-yl)methyl)-1H-benzo[d]imidazole-5-carboxamide;

(S)—N-((3-fluoropyridin-2-yl)(4-(trifluoromethyl)phenyl)methyl)-1-methyl-1H-benzo[d]imidazole-5-carboxamide;

(S)—N-((3-fluoropyridin-2-yl)(4-(trifluoromethyl)phenyl)methyl)-1-methyl-1H-benzo[d]imidazole-6-carboxamide;

(S)-1-(difluoromethyl)-N-((3-fluoropyridin-2-yl)(4-(trifluoromethyl)phenyl)methyl)-6-oxo-1,6-dihydropyridine-3-carboxamide;

(S)—N-((3-fluoropyridin-2-yl)(4-(trifluoromethyl)phenyl)methyl)-2-methyl-1H-benzo[d]imidazole-5-carboxamide;

(S)-methyl 6-(((3-fluoro-4-(trifluoromethoxy)phenyl)(3-fluoropyridin-2-yl)methyl)carbamoyl)nicotinate;

(S)-1-(difluoromethyl)-N-((3-fluoro-4-(trifluoromethoxy)phenyl)(3-fluoropyridin-2-yl)methyl)-6-oxo-1,6-dihydropyridine-3-carboxamide;

(S)-5-fluoro-N-((3-fluoro-4-(trifluoromethoxy)phenyl)(3-fluoropyridin-2-yl)methyl)-6-oxo-1,6-dihydropyridine-3-carboxamide;

(S)-5-chloro-N-((3-fluoro-4-(trifluoromethoxy)phenyl)(3-fluoropyridin-2-yl)methyl)-6-oxo-1,6-dihydropyridine-3-carboxamide;

(S)—N-((3-fluoro-4-(trifluoromethoxy)phenyl)(3-fluoropyridin-2-yl)methyl)-6-oxo-5-(trifluoromethyl)-1,6-dihydropyridine-3-carboxamide;

(S)—N-((3-fluoro-4-(trifluoromethoxy)phenyl)(3-fluoropyridin-2-yl)methyl)-5-methyl-6-oxo-1,6-dihydropyridine-3-carboxamide;

(S)—N-((3-fluoro-4-(trifluoromethoxy)phenyl)(3-fluoropyridin-2-yl)methyl)-5-methoxy-6-oxo-1,6-dihydropyridine-2-carboxamide;

(S)—N-((3-fluoro-4-(trifluoromethyl)phenyl)(3-fluoropyridin-2-yl)methyl)-6-oxo-1,6-dihydropyridine-3-carboxamide;

(S)-methyl 6-(((3-fluoro-4-(trifluoromethoxy)phenyl)(pyridin-2-yl)methyl)carbamoyl)nicotinate;

(S)—N-((3-fluoro-4-(trifluoromethoxy)phenyl)(3-fluoropyridin-2-yl)methyl)-1-((1-hydroxycyclopropyl)methyl)-6-oxo-1,6-dihydropyridine-3-carboxamide;

N—((S)-(3-fluoro-4-(trifluoromethoxy)phenyl)(3-fluoropyridin-2-yl)methyl)-6-oxo-1-((S)-3,3,3-trifluoro-2-hydroxypropyl)-1,6-dihydropyridine-3-carboxamide;

N—((S)-(3-fluoro-4-(trifluoromethoxy)phenyl)(3-fluoropyridin-2-yl)methyl)-6-oxo-1-((R)-3,3,3-trifluoro-2-hydroxypropyl)-1,6-dihydropyridine-3-carboxamide;

(S)—N-((3-fluoro-6-methylpyridin-2-yl)(4-(trifluoromethyl)phenyl)methyl)-6-oxo-1,6-dihydropyridine-3-carboxamide;

N-((3-fluoro-4-(trifluoromethoxy)phenyl)(4-fluorophenyl)methyl)-6-oxo-1,6-dihydropyridine-3-carboxamide;

N-((2,3-difluorophenyl)(3-fluoro-4-(trifluoromethoxy)phenyl)methyl)-6-oxo-1,6-dihydropyridine-3-carboxamide;

N-((2,4-difluorophenyl)(3-fluoro-4-(trifluoromethoxy)phenyl)methyl)-6-oxo-1,6-dihydropyridine-3-carboxamide;

N-((2,5-difluorophenyl)(3-fluoro-4-(trifluoromethoxy)phenyl)methyl)-6-oxo-1,6-dihydropyridine-3-carboxamide;

(S)-6-(((3-fluoro-4-(trifluoromethoxy)phenyl)(3-fluoropyridin-2-yl)methyl)carbamoyl)picolinic acid trifluoroacetate;

(S)—N-((3-fluoro-4-(trifluoromethoxy)phenyl)(3-fluoropyridin-2-yl)methyl)-2-oxo-1,2-dihydropyridine-3-carboxamide;

N-((3-fluoro-4-(trifluoromethoxy)phenyl)(3-fluorophenyl)methyl)-6-oxo-1,6-dihydropyridine-3-carboxamide;

N-((2,6-difluorophenyl)(3-fluoro-4-(trifluoromethoxy)phenyl)methyl)-6-oxo-1,6-dihydropyridine-3-carboxamide;

(R)—N-((3-fluoro-4-(trifluoromethoxy)phenyl)(3-fluoropyridin-2-yl)methyl)-6-oxo-1,6-dihydropyridine-3-carboxamide;

N-((3-fluoro-4-(trifluoromethoxy)phenyl)(6-methoxypyridin-2-yl)methyl)-6-oxo-1,6-dihydropyridine-3-carboxamide;

N-((3-fluoro-4-(trifluoromethoxy)phenyl)(5-methoxypyridin-2-yl)methyl)-6-oxo-1,6-dihydropyridine-3-carboxamide;

N-((3-fluoro-4-(trifluoromethoxy)phenyl)(4-methoxypyridin-2-yl)methyl)-6-oxo-1,6-dihydropyridine-3-carboxamide;

N-((3-fluoro-4-(trifluoromethoxy)phenyl)(4-methylpyridin-2-yl)methyl)-6-oxo-1,6-dihydropyridine-3-carboxamide;

N-((3-fluoro-4-(trifluoromethoxy)phenyl)(5-methylpyridin-2-yl)methyl)-6-oxo-1,6-dihydropyridine-3-carboxamide;

(S)—N-((3-fluoro-4-(trifluoromethoxy)phenyl)(3-fluoropyridin-2-yl)methyl)-2-oxo-2,3-dihydrooxazolo[4,5-b]pyridine-5-carboxamide;

(S)—N-((3-fluoro-4-(trifluoromethoxy)phenyl)(3-fluoropyridin-2-yl)methyl)-2-oxo-1,2-dihydrooxazolo[5,4-b]pyridine-5-carboxamide;

(S)—N-((3-fluoro-4-(trifluoromethoxy)phenyl)(3-fluoropyridin-2-yl)methyl)-2-oxo-2,3-dihydrooxazolo[4,5-b]pyridine-6-carboxamide;

(S)-2-(5-(((3-fluoro-4-(trifluoromethoxy)phenyl)(3-fluoropyridin-2-yl)methyl)carbamoyl)-2-oxopyridin-1(2H)-yl)acetic acid;

(S)-2-(5-(((3-fluoropyridin-2-yl)(4-(trifluoromethyl)phenyl)methyl)carbamoyl)-2-oxopyridin-1(2H)-yl)acetic acid;

(S)—N-((3-ethylpyridin-2-yl)(4-(trifluoromethyl)phenyl)methyl)-6-oxo-1,6-dihydropyridine-3-carboxamide;

(S)-2-amino-4-(((3-fluoropyridin-2-yl)(4-(trifluoromethyl)phenyl)methyl)carbamoyl)phenyl acetate;

(S)-4-(((3-fluoro-4-(trifluoromethoxy)phenyl)(3-fluoropyridin-2-yl)methyl)carbamoyl)benzoic acid;

(S)—N-((3-fluoro-4-(trifluoromethoxy)phenyl)(3-fluoropyridin-2-yl)methyl)imidazo[1,2-a]pyridine-6-carboxamide;

(S)-6-(((3-fluoro-4-(trifluoromethoxy)phenyl)(3-fluoropyridin-2-yl)methyl)carbamoyl)nicotinic acid;

(R)-6-(((3-fluoro-4-(trifluoromethoxy)phenyl)(3-fluoropyridin-2-yl)methyl)carbamoyl)nicotinic acid;

(S)—N-((3-fluoro-4-(trifluoromethoxy)phenyl)(3-fluoropyridin-2-yl)methyl)-1-hydroxy-4-methyl-2,3-dioxo-1,2,3,4-tetrahydroquinoxaline-6-carboxamide;

(S)—N-((3-fluoro-4-(trifluoromethoxy)phenyl)(3-fluoropyridin-2-yl)methyl)-2-oxo-1,2-dihydrooxazolo[5,4-c]pyridine-6-carboxamide; or (S)—N-((3-fluoro-4-(trifluoromethoxy)phenyl)(3-fluoropyridin-2-yl)methyl)-2-oxo-2,3-dihydrooxazolo[4,5-c]pyridine-6-carboxamide; or the pharmaceutically-acceptable salt thereof, the tautomer thereof, the pharmaceutically-acceptable salt of the tautomer, or the mixture thereof.

78. The compound or tautomer of any one of embodiments 1-3 or 5-77 in a neutral form.

79. The compound of any one of embodiments 1-3 or 5-77 in a neutral form.

80. The pharmaceutically-acceptably salt of the compound or the pharmaceutically acceptable salt of the tautomer of any one of embodiments 1-3 or 5-77.

81. The pharmaceutically-acceptably salt of the compound of any one of embodiments 1-3 or 5-77.

82. A pharmaceutical composition comprising the compound according to any one of embodiments 1-3 or 5-77 or the pharmaceutically-acceptable salt thereof, the tautomer thereof, the pharmaceutically-acceptable salt of the tautomer, or the mixture thereof, and a pharmaceutically-acceptable diluent or carrier.

83. A method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject, the method comprising administering the compound according to any one of embodiments 1-3 or 5-77 or the pharmaceutically-acceptable salt thereof, the tautomer thereof, the pharmaceutically-acceptable salt of the tautomer, or the mixture thereof to the subject.

84. The method of embodiment 83, wherein the subject is suffering from neuropathic pain.

85. The method of embodiment 83, wherein the subject is suffering from migraine pain.

86. The use of the compound according to any one of embodiments 1-3 or 5-77 or the pharmaceutically-acceptable salt thereof, the tautomer thereof, the pharmaceutically-acceptable salt of the tautomer, or the mixture thereof in the preparation of a medicament.

87. The use of the compound according to any one of embodiments 1-3 or 5-77 or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject.

88. The use of embodiment 87, wherein the use is for treating neuropathic pain.

89. The use of embodiment 87, wherein the use is for treating migraine.

90. The compound according to any one of embodiments 1-3 or 5-71 or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject.

91. The compound of embodiment 90 or the pharmaceutically-acceptable salt thereof, the tautomer thereof, the pharmaceutically-acceptable salt of the tautomer, or the mixture thereof for treating neuropathic pain in a subject.

92. The compound of embodiment 90 or the pharmaceutically-acceptable salt thereof, the tautomer thereof, the pharmaceutically-acceptable salt of the tautomer, or the mixture thereof for treating migraine in a subject.

EXAMPLES

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. All examples were purified to >90% purity as determined by high-performance liquid chromatography. Unless otherwise stated, reactions were run at room temperature.

The following abbreviations are used:

AcOH—Acetic acid
DABCO—1,4-Diazabicyclo[2.2.2]octane
DCM—Dichloromethane
DIPEA—Diisopropyl ethylamine
DMSO—Dimethyl sulfoxide
DMF—N,N-dimethylformamide
THF—Tetrahydrofuran
EDCI—1-Ethyl-3-(3-dimethylaminopropyl) carbodiimide
$Et_2O$—Diethyl ether
EtOAc—Ethyl acetate
EtOH—Ethyl alcohol
HATU—2-(7-Aza-1H-benzotriazole-1-yl)-1,1,3,3-tetramethyluronium hexafluorophosphate
MeCN—Acetonitrile
MeOH—Methyl alcohol
n-BuLi—n-Butyllithium
NMP—N-Methyl-2-pyrrolidinone also known as 1-methyl-2-pyrrolidinone
SFC—Supercritical fluid chromatography
TEA—Triethylamine
TFA—Trifluoroacetic acid
TLC—Thin Layer Chromatography
pTSA—para-Toluenesulfonic acid
h—Hour
min—Minute
rt—Toom temperature (22-25° C.)
mL Milliliters
μL Microliters
g Grams
μg Micrograms
mg Milligrams
μmoL Micromolars

General Method of Preparation

The compounds described herein are prepared using techniques known to one skilled in the art through the reaction sequences depicted in schemes 1-4 as well as by other methods. Furthermore, in the following schemes, where specific acids, bases, reagents, coupling agents, solvents, etc. are mentioned, it is understood that other suitable acids, bases, reagents, coupling agents, solvents, etc. may be used and are included within the scope of the present invention.

Diarylamines used for the synthesis of compounds of the present invention were prepared as described in Scheme 1. 2-Formylpyridines of the Formula (1) were treated with 2-methylpropane-2-sulfinamide and copper sulfate in DCM to give 2-methyl-N-(pyridin-2-ylmethylene)propane-2-sulfinamides of the Formula (2a). The compounds of Formula (2a) were treated with aryl or heteroaryl metal halides of Formula (3) at low temperature to give sulfinamides of the Formula (4). Hydrolysis of sulfinamides (4) with hydrochloric acid in MeOH gives diaryl amines of Formula (5a).

Scheme 1

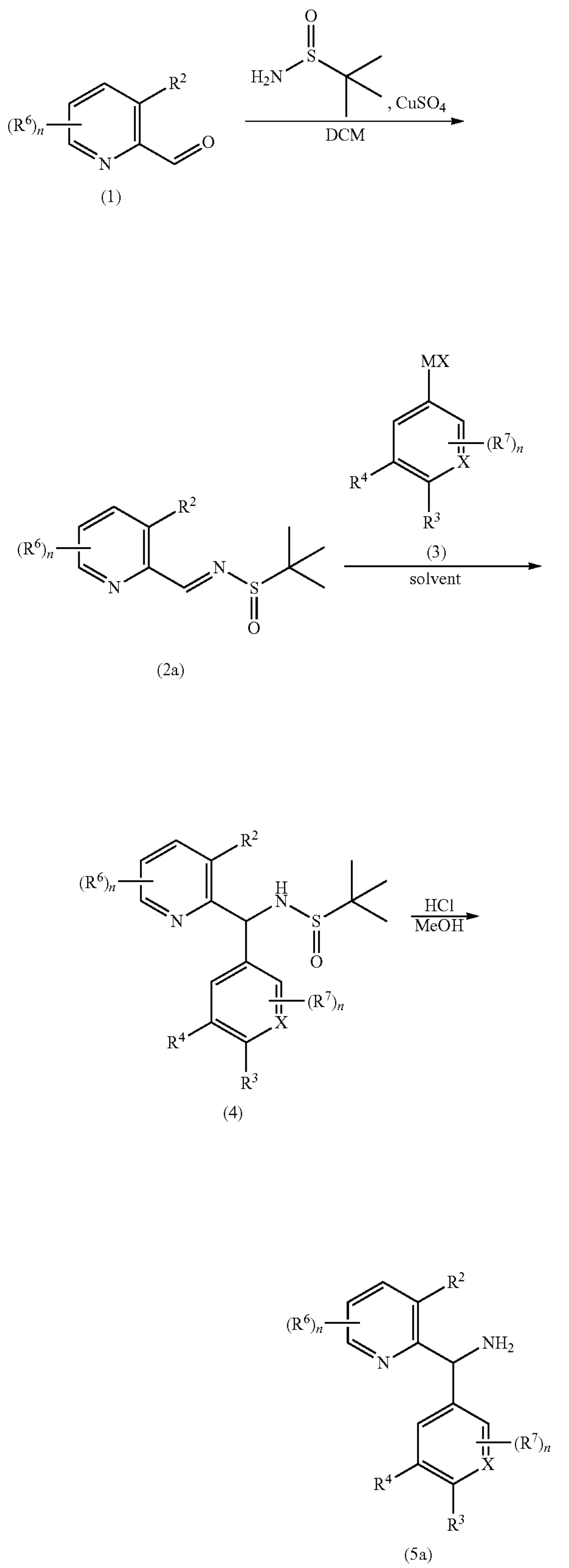

(1)
(2a)
(4)
(5a)

An alternative approach to diaryl amines of Formula (5a) is shown in Scheme 2. Aryl or heteroaryl aldehydes of the Formula (6) were treated with 2-methylpropane-2-sulfinamide and copper sulfate in DCM to give sulfinimines of the Formula (7). The compounds of Formula (7) were treated with aryl or heteroaryl metal halides of Formula (8) at low temperature to give sulfinamides of the Formula (4). Hydrolysis of sulfinamides (4) with hydrochloric acid in MeOH gives diaryl amines of Formula (5a).

Scheme 2

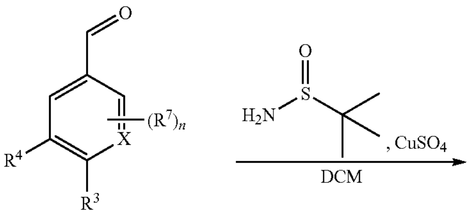

(6)

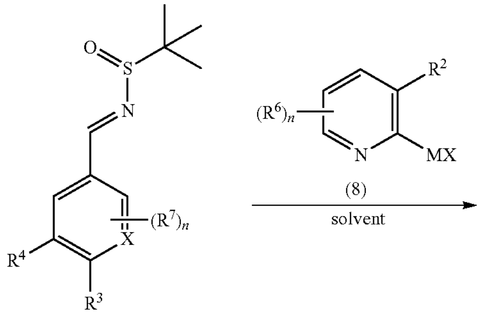

(7)

-continued

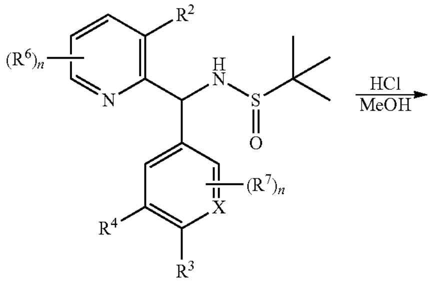

(4)

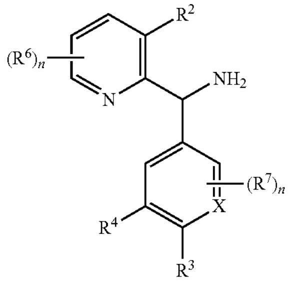

(5a)

The methods described in Scheme 1-2 can be adapted to a asymmetric syntheses using the appropriate (R)- or (S)-2-methylpropane-2-sulfinamides to give sulfinimines of the Formula (2b) or (2c). Subsequent aryl metal addition and hydrolysis gave chiral amines of Formula (5b) or (5c).

Scheme 3

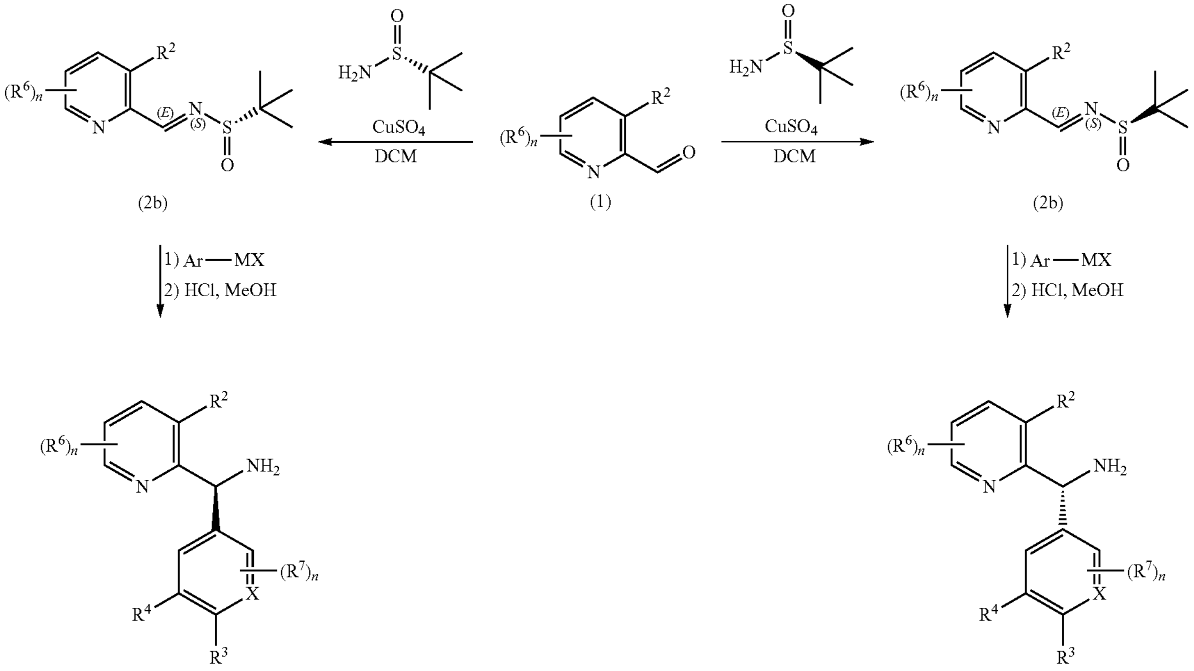

The coupling reaction of diarylamines of Formula (5a-c) with the various carboxylic acids of Formula (9) can be performed as shown in Scheme 4. The coupling reaction can be mediated by a suitable coupling agent such as HATU in the presence of a base in a suitable solvent to afford compounds of the present invention (Formula (I)).

Scheme 4

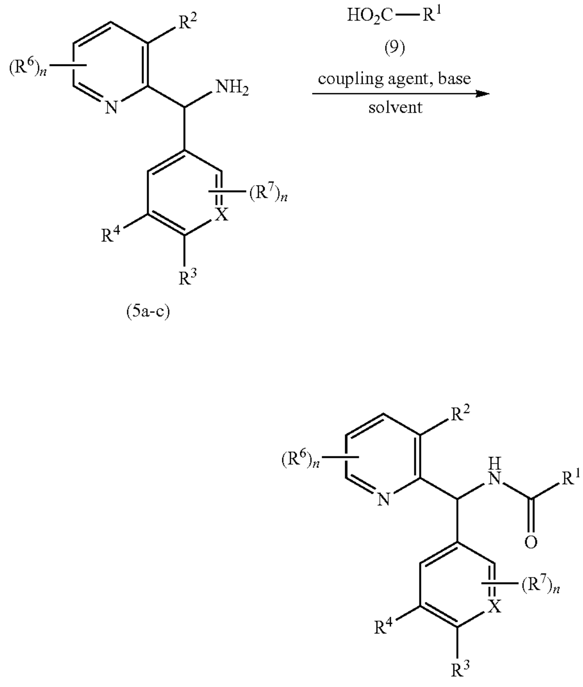

(5a-c)

(I)

Experimentals for Intermediates

Scheme 5

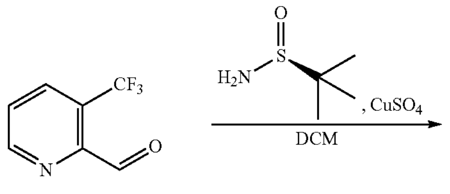

1a

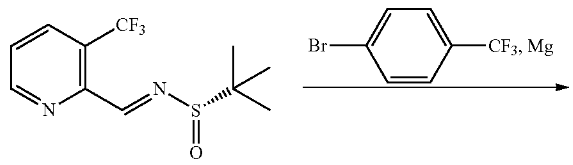

1b

-continued

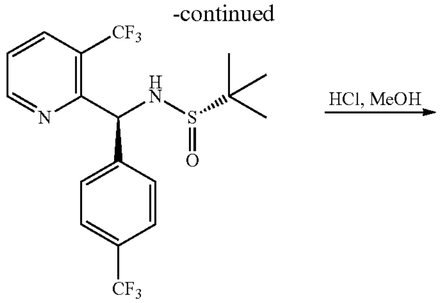

1c

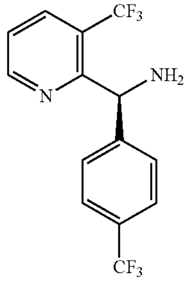

1d

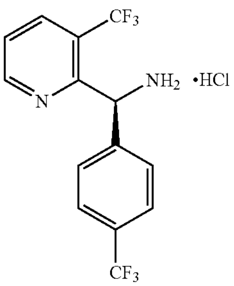

Intermediate 1: (S)-(4-(Trifluoromethyl)phenyl)(3-(trifluoromethyl)pyridin-2-yl)methanamine hydrochloride

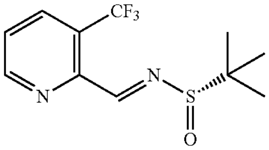 [SMILES: CC(C)(C)[S@](=O)/N=C/c1ncccc1C(F)(F)F]

Step 1. (S,E)-2-Methyl-N-((3-(trifluoromethyl)pyridin-2-yl)methylene)-propane-2-sulfinamide To a solution of 3-(trifluoromethyl)picolinaldehyde (Frontier Scientific, 9.80 g, 56.0 mmol) and DCM (50 mL) was added (S)-2-methylpropane-2-sulfinamide (AK Scientific, 10.3 g, 85.0 mmol) and copper(II) sulfate (35.3 g, 221 mmol). After 1.5 h at rt, the reaction was filtered through a pad of Celite® brand filter agent and rinsed with DCM. The filtrate was concentrated in vacuo to give a dark green oil. The oil thus obtained was loaded onto a silica gel column and eluted with 30% EtOAc in hexanes to give (S,E)-2-methyl-N-((3-(trifluoro-methyl)pyridin-2-yl)methylene)propane-2-sulfinamide, as a golden oil. $^1H$ NMR (δ ppm, $CDCl_3$, 300 MHz):

9.02 (d, J=4.3 Hz, 1H), 8.70 (d, J=1.3 Hz, 1H), 8.38 (d, J=7.7 Hz, 1H), 7.79 (dd, J=7.9 & 4.8 Hz, 1H), 1.18 (s, 9H). MS (ESI pos. ion) m/z: 279.1 (M+H).

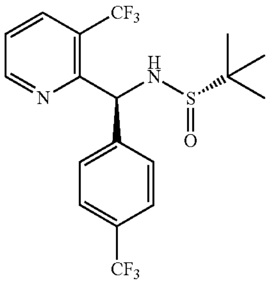 [SMILES: CC(C)(C)[S@](=O)N[C@@H](c1ccc(C(F)(F)F)cc1)c1ncccc1C(F)(F)F]

Step 2. (S)-2-Methyl-N—((S)-(4-(trifluoromethyl)phenyl)(3-(trifluoromethyl)-pyridin-2-yl)methyl)propane-2-sulfinamide To an oven-dried flask containing magnesium (3.46 g, 143 mmol) and $Et_2O$ (120 mL) was added diisobutylaluminum hydride (0.950 mL, 0.950 mmol) and 1 mL of 1-bromo-4-(trifluoromethyl)benzene (12.5 mL, 91 mmol) dropwise. The solution was stirred for ~20 min, during which time the reaction went from clear to a brownish tint. The reaction was placed in an ice bath and the remaining 1-bromo-4-(trifluoromethyl)benzene was added dropwise over 20 minutes. In a separate flask, a solution of (S,E)-2-methyl-N-((3-(trifluoromethyl)pyridin-2-yl)-methylene)propane-2-sulfinamide (13.22 g, 47.5 mmol) and THF (80 mL) was cooled to −78° C. for 10 min and the Grignard solution was added over 30 min. After 1 h, the reaction was quenched with saturated aqueous potassium sodium tartrate (10 mL). The reaction was then poured into $H_2O$ (150 mL). The entire solution was filtered through a pad of Celite® brand filter agent and rinsed with THF and EtOAc. The resulting filtrate was separated and the organics concentrated in vacuo to give the product as a dark orange oil. The oil thus obtained was adsorbed onto a plug of silica gel and chromatographed through a Redi-Sep® pre-packed silica gel column (120 g), eluting with 0% to 40% EtOAc in hexanes, to provide (S)-2-methyl-N—((S)-(4-(trifluoromethyl)phenyl)(3-(trifluoromethyl)pyridin-2-yl)methyl)propane-2-sulfinamide as a golden oil. $^1H$ NMR (δ ppm, DMSO-$d_6$, 600 MHz): δ 8.93 (d, J=4.8 Hz, 1H), 7.25 (d, J=7.8 Hz, 1H), 7.71-7.67 (m, 2H), 7.61-7.59 (m, 1H), 7.54 (d, J=8.4 Hz, 2H), 6.08 (d, J=9 Hz, 1H), 5.90 (d, J=9 Hz, 1H), 1.20 (s, 9H). MS (ESI pos. ion) m/z: 425.1 (M+H).

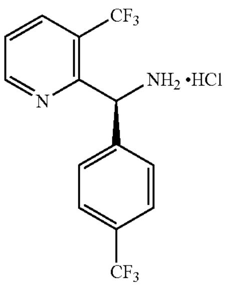 [SMILES: N[C@@H](c1ccc(C(F)(F)F)cc1)c1ncccc1C(F)(F)F ; Cl]

Step 3. (S)-(4-(Trifluoromethyl)phenyl)(3-(trifluoromethyl)pyridin-2-yl)-methanamine hydrochloride To a cooled (0° C.) stirring solution of ((S)-2-methyl-N—((S)-(4-(trifluoro-methyl)phenyl)(3-(trifluoromethyl)pyridin-2-yl)methyl)propane-2-sulfonamide (27 g, 63 mmol) in $Et_2O$ (270 mL) was added 4.0 M HCl in 1,4-dioxane (157 mL, 630 mmol, 10 equiv.) at 0° C., and the reaction mixture was stirred for 30 min at the same temperature. The reaction progress was monitored by TLC (50% EtOAc in petroleum ether). After completion of the reaction, the reaction mixture was concentrated under reduced pressure and triturated with $Et_2O$ to get a white solid which was filtered and dried to give (S)-(4-(trifluoromethyl)phenyl)(3-(trifluoromethyl)pyridin-2-yl)methanamine hydrochloride as a white solid. (δ ppm, DMSO-$d_6$, 600 MHz): δ 9.26 (s, 3H), 9.08 (d, J=4.2 Hz, 1H), 8.35 (d, J=7.8 Hz, 1H), 7.82-7.77 (m, 3H), 7.67 (d, J=8.4 Hz, 2H), 5.94 (s, 1H). MS (ESI pos. ion) m/z: 321.1 (M+H) for free base.

Scheme 6

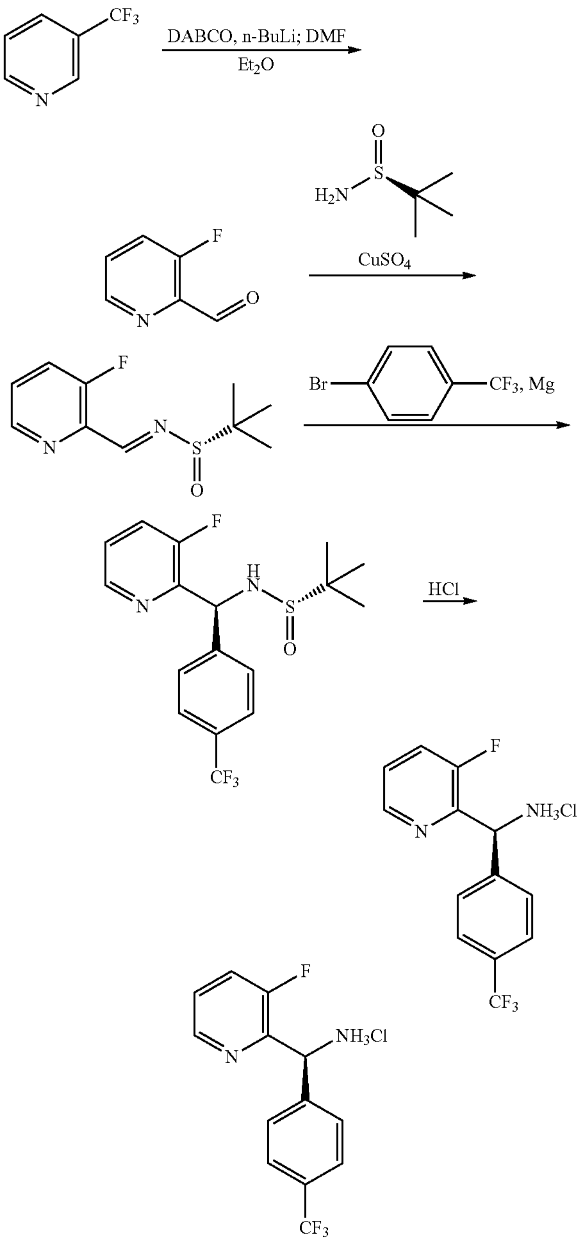

Intermediate 2: (S)-(4-(Trifluoromethyl)phenyl)(3-(trifluoromethyl)pyridin-2-yl)methanamine hydrochloride

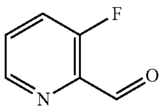

Step 1. 3-Fluoropicolinaldehyde

To a stirred solution of DABCO (262.4 g, 2342 mmol) in anhydrous $Et_2O$ (2.1 L) at −25° C. in a 10 L 3-neck round bottom flask was added n-BuLi (2.5 M in hexane, 938 mL, 2342 mmol). The mixture was stirred between −25° C. to −10° C. for 45 min. and then cooled to −70° C. To the above solution was added 3-fluoropyridine (206.7 g, 2129 mmol) dropwise, and the reaction was stirred between −70° C. to −60° C. for 1.5 h before DMF (344 mL, 4258 mmol) was added. The progress of the reaction was monitored by TLC (5% EtOAc in Petroleum ether). After 1 h stirring at −70° C., water (800 mL) was added, and the reaction was allowed to warm to rt. The layers were separated, and the aqueous layer was extracted with DCM (5×1 L). The combined organic layers were washed with brine and dried over sodium sulfate. After removal of solvent the initially obtained product was purified by silica gel chromatography using a gradient of EtOAc in hexane to give the title compound as pale yellow oil. $^1$H-NMR (400 MHz, $CDCl_3$): δ ppm 10.21 (s, 1H), 8.63 (t, J=2.2 Hz, 1H), 7.54-7.57 (m, 2H). MS (ESI pos. ion) m/z: 126.0 (M+H).

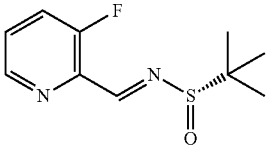

Step 2. (S,E)-N-((3-Fluoropyridin-2-yl)methylene)-2-methylpropane-2-sulfinamide

A mixture of 3-fluoropicolinaldehyde (300 g, 2400 mmol), copper sulfate (572 g, 3600 mmol) and (S)-2-methylpropane-2-sulfinamide (319 g, 2640 mmol) in DCM (3 L) in a 10 L 3-neck round bottom flask was stirred for 3 h at rt. The progress of the reaction was monitored by TLC (30% EtOAc in petroleum ether). After completion of reaction, the solid was filtered off and the filtrate was concentrated under vacuum. The initially obtained product was purified by column chromatography using silica (60-120 mesh) with 20% EtOAc in n-hexane as eluent to give the title compound sulfinamide as yellow oil. $^1$H-NMR (400 MHz, $CDCl_3$): δ ppm 8.89 (s, 1H), 8.64 (s, 1H), 7.55 (t, J=8.4 Hz, 1H), 7.46 (d, J=3.6 Hz, 1H), 1.29 (s, 9H). MS (ESI pos. ion) m/z: 155.0 (M-O and t-Bu).

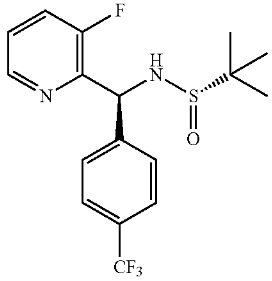 [SMILES: CC(C)(C)[S@](=O)N[C@@H](c1ccc(C(F)(F)F)cc1)c1ncccc1F]

Step-3. (S)—N—((S)-(3-Fluoropyridin-2-yl)(4-(trifluoromethyl)phenyl)methyl)-2-methylpropane-2-sulfinamide To a stirred suspension of magnesium (170 g, 2365 mmol) in THF (1.35 L), was added 4-bromobenzotrifluoride (532 g, 2365 mmol). Stirring was continued for 4 h (caution: slightly exothermic, cooled with a water bath if needed). The solution was cannulated to a stirred solution of (S, E)-N-((3-fluoropyridin-2-yl)methylene)-2-methylpropane-2-sulfinamide (270 g, 1182 mmol) in THF (1.3 L) at −78° C. dropwise. Stirring was continued for 1 h. The progress of the reaction was monitored by TLC (50% EtOAc in petroleum ether). After completion of the reaction, the reaction mixture was quenched with saturated aqueous $NH_4Cl$ (2.5 L), and the solution was extracted with $Et_2O$ (5×500 mL). The organic layers were combined, dried over $Na_2SO_4$, concentrated, and purified by column chromatography using silica (100-200 mesh) with 25-30% EtOAc in petroleum ether as eluent to give the title compound as a brown oil. $^1$H-NMR (400 MHz, $CDCl_3$): δ ppm 8.45 (d, J=3.6 Hz, 1H), 7.73-7.78 (m, 1H), 7.71 (d, J=8.4 Hz, 2H), 7.63 (m, 2H), 7.43-7.48 (m, 1H), 6.23 (d, J=6.8 Hz, 1H), 5.99 (d, J=6.8 Hz, 1H), 1.36 (s, 9H). MS (ESI pos. ion) m/z: 375.1 (M-O and t-Bu).

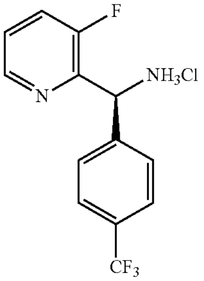

Step 4. (S)-(3-Fluoropyridin-2-yl)(4-(trifluoromethyl)phenyl)methanamine hydrochloride To a cooled (0° C.) stirring solution of (S)—N—((S)-(3-fluoropyridin-2-yl)(4-(trifluoromethyl)phenyl)methyl)-2-methylpropane-2-sulfinamide (108 g, 288.8 mmol) in DCM: EtOH (1:1, 1080 mL), was added saturated HCl in 1,4-dioxane (216 mL). Stirring was continued for 2 h at 0° C. The progress of the reaction was monitored by TLC (100% EtOAc). After completion of the reaction, the reaction mixture was concentrated and triturated with $Et_2O$ to give a white solid which was filtered and dried to give the title compound as a white solid. $^1$H-NMR (400 MHz, $CDCl_3$) δ ppm 9.23 (s, 3H), 8.60 (d, J=4.8 Hz, 1H), 7.87 (d, J=1.2 Hz, 1H), 7.84 (d, J=8.4 Hz, 2H), 7.72 (d, J=8.4 Hz, 2H), 7.59-7.63 (m, 1H), 6.09 (s, 1H). MS (ESI pos. ion) m/z: 270.1 (M+H).

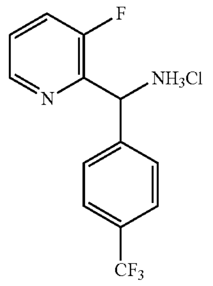

Intermediate 2a: (4-(Trifluoromethyl)phenyl)(3-(trifluoromethyl)pyridin-2-yl)methanamine hydrochloride Following the procedure detailed above for Intermediate 2, but replacing (S)-2-methylpropane-2-sulfinamide with racemic 2-methylpropane-2-sulfinamide in STEP 2 gave the title compound as a white solid.

General Procedure for Preparation of Diarylmethanamines (Intermediates 3-41)

Additional diarylmethanamies were prepared as described in Scheme 5, Steps 2-3 or Scheme 6, Steps 3-4; substituting the appropriate starting materials. Variations in methods applied in Step 2 of the various intermediate syntheses are elaborated below.

Method A:

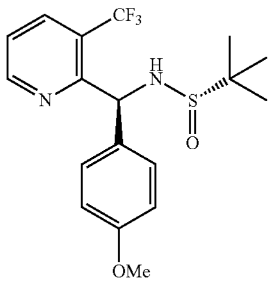 [SMILES: COc1ccc([C@H](N[S@@](=O)C(C)(C)C)c2ncccc2C(F)(F)F)cc1]

Intermediate 3: (S)—N—((S)-(4-Methoxyphenyl)(3-(trifluoromethyl)pyridin-2-yl)methyl)-2-methylpropane-2-sulfinamide Magnesium metal (0.095 g, 3.91 mmol) was activated using a crystal of iodine prior to addition of THF (1 mL). 1-Bromo-4-methoxybenzene (0.400 g, 2.139 mmol) was added, and the reaction was left without stirring for 5 minutes after which initiation was observed. Additional THF (15 mL) was added and the mixture was stirred for 2 hours. (S,E)-2-Methyl-N-((3-(trifluoromethyl)pyridin-2-yl)methylene)propane-2-sulfinamide (0.500 g, 1.797 mmol) was added, and the mixture was stirred for 10 minutes. The reaction was quenched by addition of saturated aqueous $NH_4Cl$ (10 mL). $H_2O$ (100 mL) and EtOAc (150 mL) were added, and the phases mixed and separated. The organic layer was dried with $MgSO_4$ and evaporated to dryness under reduced pressure. Purification using silica chromatography (hexane to EtOAc gradient) gave (S)—N—((S)-(4-methoxyphenyl)-(3-(trifluoromethyl)pyridin-2-yl)methyl)-2-methylpropane-2-sulfinamide.

The sulfinamide above was then subjected to the hydrolysis conditions similar to those described above in Scheme 5, Step 3 to give Intermediate 3 in Table 1 below.

Method B:

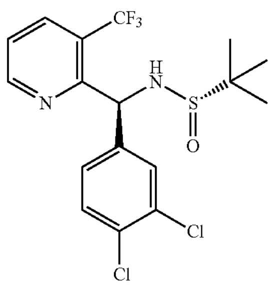 [SMILES: CC(C)(C)[S@](=O)N[C@@H](c1ccc(Cl)c(Cl)c1)c1ncccc1C(F)(F)F]

Intermediate 4: (S)—N—((S)-(3,4-Dichlorophenyl)(3-(trifluoromethyl)pyridin-2-yl)methyl)-2-methylpropane-2-sulfinamide (S,E)-2-Methyl-N-((3-(trifluoromethyl)pyridin-2-yl)methylene)propane-2-sulfinamide (0.493 g, 1.772 mmol) was dissolved in dry THF (10 mL) and cooled in an ice bath. 3,4-Dichlorophenylmagnesium bromide (Aldrich, 0.5 M solution in THF, 4.0 mL, 2.0 mmol) was added, and the reaction was stirred for 5 minutes. Saturated aqueous $NH_4Cl$ (10 mL), $H_2O$ (100 mL) and EtOAc (100 mL) were added and the phases were mixed and separated. The organic layer was dried with $MgSO_4$ and evaporated to dryness under reduced pressure. Purification using silica chromatography (hexane to EtOAc gradient) gave (S)—N—((S)-(3,4-dichloro-phenyl)(3-(trifluoromethyl)pyridin-2-yl)methyl)-2-methylpropane-2-sulfinamide.

The sulfinamide above was then subjected to the hydrolysis conditions similar to those described above in Scheme 5, Step 3 to give Intermediate 4 in Table 1 below.

Method C:

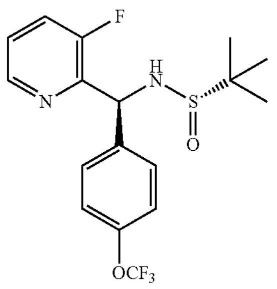

Intermediate 5: (S)—N—((S)-(3-Fluoropyridin-2-yl)(4-(trifluoromethoxy)-phenyl)methyl)-2-methylpropane-2-sulfinamide 1-Iodo-4-(trifluoromethoxy)benzene (1.00 g, 3.47 mmol) was dissolved in dry THF (10 mL) and cooled in an ice bath. Isopropylmagnesium chloride, lithium chloride complex (14% solution in THF, Aldrich, 3.07 mL, 2.82 mmol) was added, and the mixture was stirred for 10 min. A solution of (S,E)-N-((3-fluoropyridin-2-yl)methylene)-2-methylpropane-2-sulfinamide (0.643 g, 2.82 mmol) in dry THF (10 mL) was added and the reaction was stirred. After 50 minutes, the reaction was quenched by addition of saturated aqueous $NH_4Cl$ (10 mL). $H_2O$ (100 mL) and EtOAc (150 mL) were added, and the phases were mixed and separated. The organic layer was dried with $MgSO_4$ and evaporated to dryness under reduced pressure. Purification using silica chromatography (hexane to EtOAc gradient) gave the desired (S)—N—((S)-(3-fluoropyridin-2-yl)(4-(trifluoro-methoxy)phenyl)methyl)-2-methylpropane-2-sulfinamide.

The sulfinamide was then subjected to the hydrolysis conditions similar to those described above in Scheme 6, Step 4 to give Intermediate 5 in Table 1 below.

TABLE 1

Additional diarylmethanamines prepared analogous to Scheme 5 and 6 (Intermediates 3-41). Unless otherwise stated, all amines in this table are hydrochloride salts.

| Intermediate | Method | Aryl Halide or Grignard in Step 2 | Structure | Name | Mol. Formula (Mol. Wt.) |
|---|---|---|---|---|---|
| 3 | A | 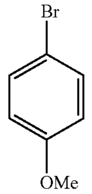 | 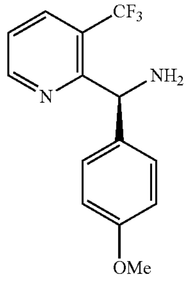 [SMILES: COc1ccc([C@H](N)c2ncccc2C(F)(F)F)cc1] | (S)-(4-methoxyphenyl)(3-(trifluoro-methyl)-pyridin-2-yl)-methanamine | $C_{14}H_{13}F_3N_2O$ (282.26) |
| 4 | B | 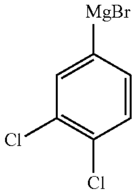 | 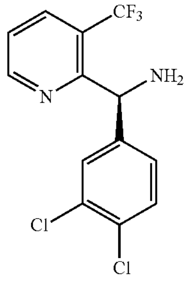 [SMILES: N[C@@H](c1ccc(Cl)c(Cl)c1)c1ncccc1C(F)(F)F] | (S)-(3,4-dichloro-phenyl)(3-methyl)-pyridin-2-yl)-methanamine | $C_{13}H_9Cl_2F_3N_2$ (321.13) |
| 5 | C | 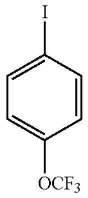 | 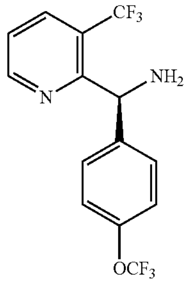 [SMILES: N[C@@H](c1ccc(OC(F)(F)F)cc1)c1ncccc1C(F)(F)F] | (S)-(4-(trifluoro-methoxy)-phenyl)(3-(trifluoro-methyl)-pyridin-2-yl)-methanamine | $C_{14}H_{10}F_6N_2O$ (336.23) |
| 6 | A | 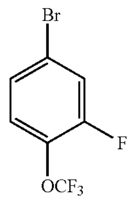 | 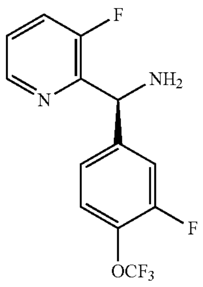 [SMILES: N[C@@H](c1ccc(OC(F)(F)F)c(F)c1)c1ncccc1F] | (S)-(3-fluoro-4-(trifluoro-methoxy)-phenyl)(3-fluoropyridin-2-yl)-methanamine | $C_{13}H_9F_5N_2O$ (304.22) |

TABLE 1-continued

Additional diarylmethanamines prepared analogous to Scheme 5 and 6 (Intermediates 3-41). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 6b[2] | A | 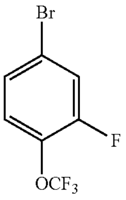 | 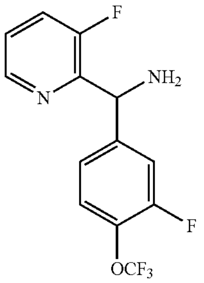 [SMILES: NC(c1ccc(OC(F)(F)F)c(F)c1)c1ncccc1F] | (3-fluoro-4-(trifluoro-methoxy)-phenyl)(3-fluoropyridin-2-yl)-methanamine | $C_{13}H_9F_5N_2O$ (304.22) |
| 7 | A | 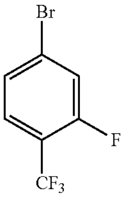 | 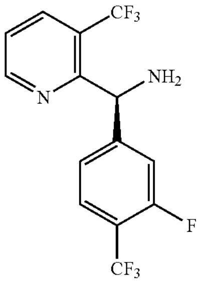 [SMILES: N[C@@H](c1ccc(C(F)(F)F)c(F)c1)c1ncccc1C(F)(F)F] | (S)-(3-fluoro-4-(trifluoro-methyl)-phenyl)(3-(trifluoro-methyl)-pyridin-2-yl)-methanamine | $C_{14}H_9F_7N_2$ (338.22) |
| 8 | C | 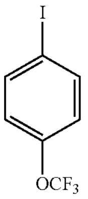 | 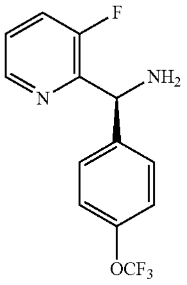 [SMILES: N[C@@H](c1ccc(OC(F)(F)F)cc1)c1ncccc1F] | (S)-(3-fluoro-pyridin-2-yl)-(4-(trifluoro-methoxy)-phenyl)-methanamine | $C_{14}H_{10}F_4N_2O$ (286.22) |
| 9 | C | 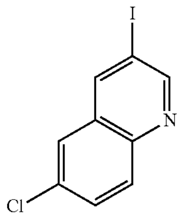 | 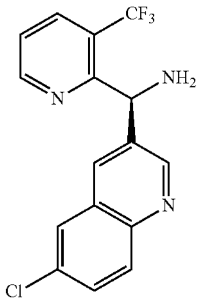 [SMILES: N[C@@H](c1cnc2ccc(Cl)cc2c1)c1ncccc1C(F)(F)F] | (S)-(6-chloro-quinolin-3-yl)-(3-(trifluoro-methyl)-pyridin-2-yl)-methanamine | $C_{16}H_{11}ClF_3N_3$ (337.73) |
| 10 | C | 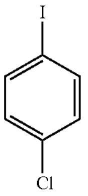 | 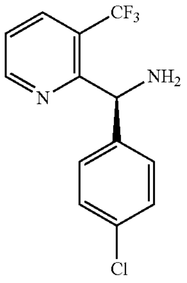 [SMILES: N[C@@H](c1ccc(Cl)cc1)c1ncccc1C(F)(F)F] | (S)-(4-chloro-phenyl)(3-(trifluoro-methyl)-pyridin-2-yl)-methanamine | $C_{13}H_{10}ClF_3N_2$ (286.68) |

TABLE 1-continued

Additional diarylmethanamines prepared analogous to Scheme 5 and 6 (Intermediates 3-41). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 11 | C | 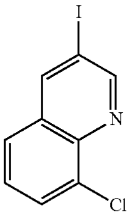 | 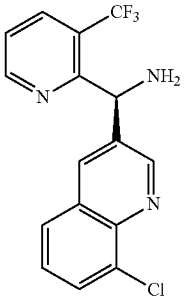 [SMILES: N[C@@H](c1cnc2c(Cl)cccc2c1)c1ncccc1C(F)(F)F] | (S)-(8-chloro-quinolin-3-yl)-(3-(trifluoro-methyl)-pyridin-2-yl)-methanamine | $C_{16}H_{11}ClF_3N_3$ (337.73) |
| 12 | C | 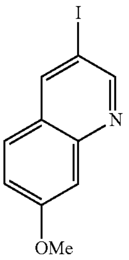 | 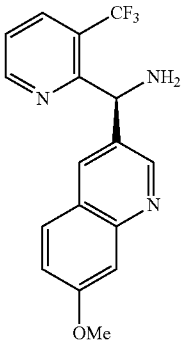 [SMILES: COc1ccc2cc([C@H](N)c3ncccc3C(F)(F)F)cnc2c1] | (S)-(7-methoxyquinolin-3-yl)(3-(trifluoro-methyl)-pyridin-2-yl)-methanamine | $C_{17}H_{14}F_3N_3O$ (333.31) |
| 13 | C | 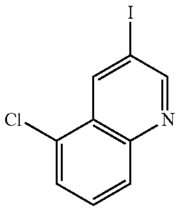 | 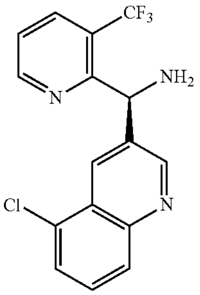 [SMILES: N[C@@H](c1cnc2cccc(Cl)c2c1)c1ncccc1C(F)(F)F] | (S)-(5-chloro-quinolin-3-yl)-(3-(trifluoro-methyl)-pyridin-2-yl)-methanamine | $C_{16}H_{11}ClF_3N_3$ (337.73) |
| 14 | C | 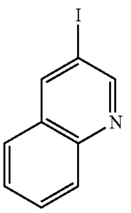 | 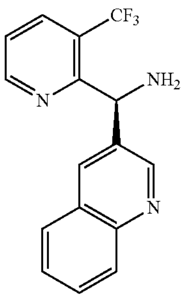 [SMILES: N[C@@H](c1cnc2ccccc2c1)c1ncccc1C(F)(F)F] | (S)-quinolin-3-yl(3-(trifluoro-methyl)-pyridin-2-yl)-methanamine | $C_{16}H_{12}F_3N_3$ (303.28) |

TABLE 1-continued

Additional diarylmethanamines prepared analogous to Scheme 5 and 6 (Intermediates 3-41). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 15 | A | 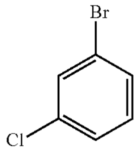 | 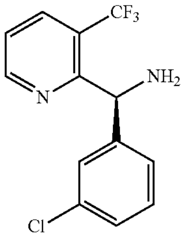 [SMILES: N[C@@H](c1cccc(Cl)c1)c1ncccc1C(F)(F)F] | (S)-(3-chloro-phenyl)(3-(trifluoro-methyl)-pyridin-2-yl)-methanamine | $C_{13}H_{10}ClF_3N_2$ (286.68) |
| 16 | B | 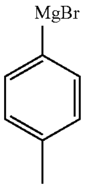 | 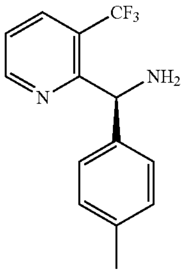 [SMILES: Cc1ccc([C@H](N)c2ncccc2C(F)(F)F)cc1] | (S)-p-tolyl(3-(trifluoro-methyl)-pyridin-2-yl)-methanamine | $C_{14}H_{13}F_3N_2$ (266.26) |
| 17 | A | 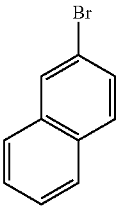 | 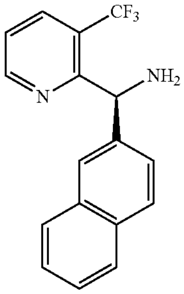 [SMILES: N[C@@H](c1ccc2ccccc2c1)c1ncccc1C(F)(F)F] | (S)-naphthalen-2-yl(3-(trifluoro-methyl)-pyridin-2-yl)-methanamine | $C_{17}H_{13}F_3N_2$ (302.29) |
| 18 | B | 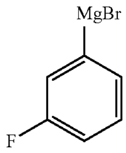 | 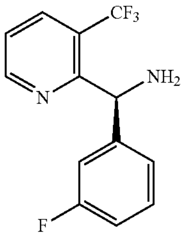 [SMILES: N[C@@H](c1cccc(F)c1)c1ncccc1C(F)(F)F] | (S)-(3-fluoro-phenyl)(3-(trifluoro-methyl)-pyridin-2-yl)-methanamine | $C_{13}H_{10}F_4N_2$ (270.23) |
| 19 | A | 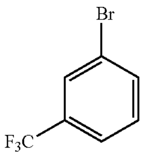 | 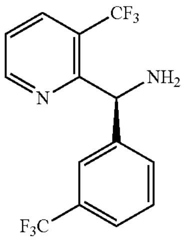 [SMILES: N[C@@H](c1cccc(C(F)(F)F)c1)c1ncccc1C(F)(F)F] | (S)-(3-(trifluoro-methyl)-phenyl)(3-(trifluoro-methyl)-pyridin-2-yl)-methanamine | $C_{14}H_{10}F_6N_2$ (320.23) |

TABLE 1-continued

Additional diarylmethanamines prepared analogous to Scheme 5 and 6 (Intermediates 3-41). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 20 | C | 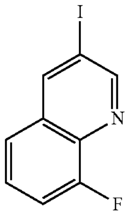 | 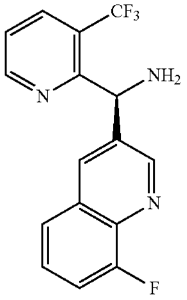 [SMILES: N[C@@H](c1cnc2c(F)cccc2c1)c1ncccc1C(F)(F)F] | (S)-(8-fluoro-quinolin-3-yl)-(3-(trifluoro-methyl)-pyridin-2-yl)-methanamine | $C_{16}H_{11}F_4N_3$ (321.27) |
| 21 | B | 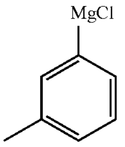 | 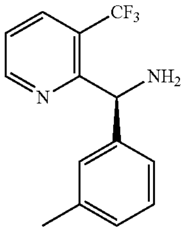 [SMILES: Cc1cccc([C@H](N)c2ncccc2C(F)(F)F)c1] | (S)-m-tolyl(3-(trifluoro-methyl)-pyridin-2-yl)-methanamine | $C_{14}H_{13}F_3N_2$ (266.26) |
| 22 | C | 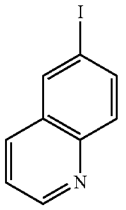 | 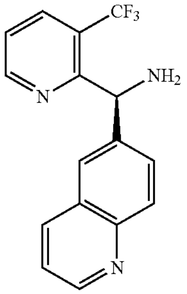 [SMILES: N[C@@H](c1ccc2ncccc2c1)c1ncccc1C(F)(F)F] | (S)-quinolin-6-yl(3-(trifluoro-methyl)-pyridin-2-yl)-methanamine | $C_{16}H_{12}F_3N_3$ (303.28) |
| 23 | C | 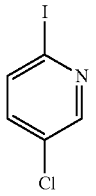 | 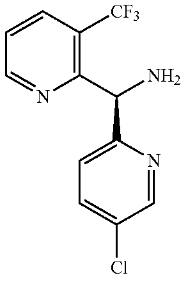 [SMILES: N[C@@H](c1ccc(Cl)cn1)c1ncccc1C(F)(F)F] | (S)-(5-chloro-pyridin-2-yl)-(3-(trifluoro-methyl)-pyridin-2-yl)-methanamine | $C_{12}H_9ClF_3N_3$ (287.67) |
| 24 | C | 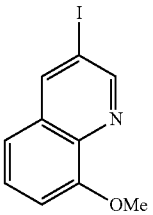 [SMILES: COc1cccc2cc(I)cnc12] | 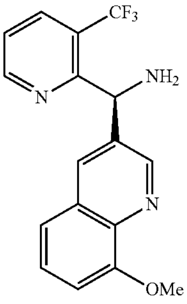 [SMILES: COc1cccc2cc([C@H](N)c3ncccc3C(F)(F)F)cnc12] | (S)-(8-methoxyquinolin-3-yl)(3-(trifluoro-methyl)-pyridin-2-yl)-methanamine | $C_{14}H_{10}F_6N_2$ (333.31) |

TABLE 1-continued

Additional diarylmethanamines prepared analogous to Scheme 5 and 6 (Intermediates 3-41). Unless otherwise stated, all amines in this table are hydrochloride salts.

| Intermediate | Method | Aryl Halide or Grignard in Step 2 | Structure | Name | Mol. Formula (Mol. Wt.) |
|---|---|---|---|---|---|
| 25 | B | 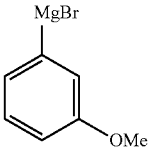 | 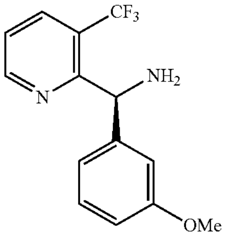 [SMILES: COc1cccc([C@H](N)c2ncccc2C(F)(F)F)c1] | (S)-(3-methoxyphenyl)(3-(trifluoro-methyl)-pyridin-2-yl)-methanamine | $C_{14}H_{13}F_3N_2O$ (282.26) |
| 26 | B | 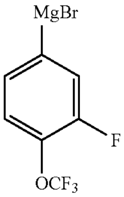 | 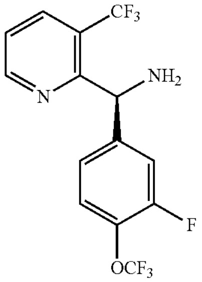 [SMILES: N[C@@H](c1ccc(OC(F)(F)F)c(F)c1)c1ncccc1C(F)(F)F] | (S)-(3-fluoro-4-(trifluoro-methoxy)-phenyl)(3-(trifluoro-methyl)-pyridin-2-yl)-methanamine | $C_{14}H_9F_7N_2O$ (354.22) |
| 27 | B | 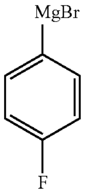 | 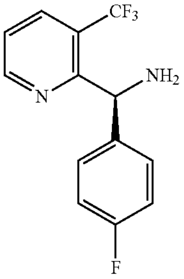 [SMILES: N[C@@H](c1ccc(F)cc1)c1ncccc1C(F)(F)F] | (S)-(4-fluoro-phenyl)(3-(trifluoro-methyl)-pyridin-2-yl)-methanamine | $C_{13}H_{10}F_4N_2$ (270.23) |
| 28 | B | 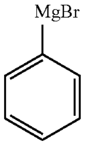 | 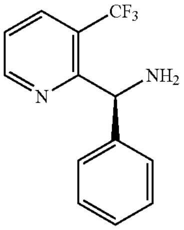 [SMILES: N[C@@H](c1ccccc1)c1ncccc1C(F)(F)F] | (S)-phenyl(3-(trifluoro-methyl)-pyridin-2-yl)-methanamine | $C_{13}H_{11}F_3N_2$ (252.24) |
| 29 | B | 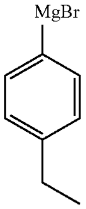 | 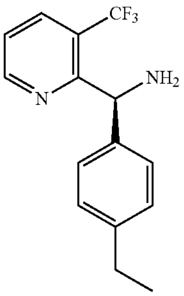 [SMILES: CCc1ccc([C@H](N)c2ncccc2C(F)(F)F)cc1] | (S)-(4-ethylphenyl)-(3-(trifluoro-methyl)-pyridin-2-yl)-methanamine | $C_{15}H_{15}F_3N_2$ (280.29) |

TABLE 1-continued

| Inter-mediate | Method | Aryl Halide or Grignard in Step 2 | Structure | Name | Mol. Formula (Mol. Wt.) |
|---|---|---|---|---|---|
| | | Additional diarylmethanamines prepared analogous to Scheme 5 and 6 (Intermediates 3-41). Unless otherwise stated, all amines in this table are hydrochloride salts. | | | |
| 30 | A | 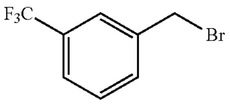 | 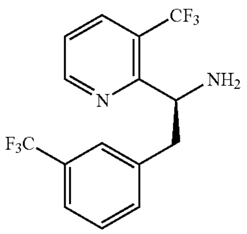 [SMILES: N[C@@H](Cc1cccc(C(F)(F)F)c1)c1ncccc1C(F)(F)F] | (S)-2-(3-(trifluoro-methyl)-phenyl)-1-(3-(trifluoro-methyl)-pyridin-2-yl)-ethanamine | $C_{15}H_{12}F_6N_2$ (334.26) |
| 31 | B | 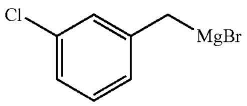 | 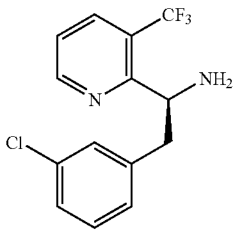 [SMILES: N[C@@H](Cc1cccc(Cl)c1)c1ncccc1C(F)(F)F] | (S)-2-(3-chlorophenyl)-1-(3-(trifluoro-methyl)-pyridin-2-yl)-ethanamine | $C_{14}H_{12}ClF_3N_2$ (300.71) |
| 32 | B | 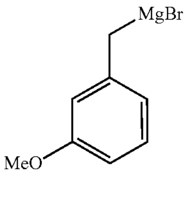 | 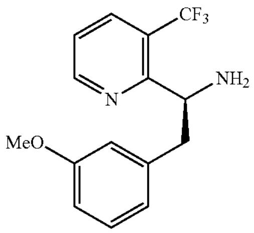 [SMILES: COc1cccc(C[C@H](N)c2ncccc2C(F)(F)F)c1] | (S)-2-(3-methoxyphenyl)-1-(3-(trifluoro-methyl)-pyridin-2-yl)-ethanamine | $C_{15}H_{15}F_3N_2O$ (296.29) |
| 33 | B | 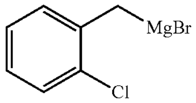 | 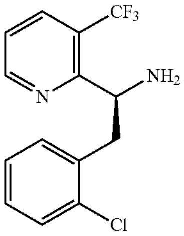 [SMILES: N[C@@H](Cc1ccccc1Cl)c1ncccc1C(F)(F)F] | (S)-2-(2-chlorophenyl)-1-(3-(trifluoro-methyl)-pyridin-2-yl)-ethanamine | $C_{14}H_{12}ClF_3N_2$ (300.71) |
| 34 | B | 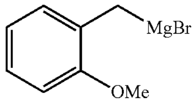 | 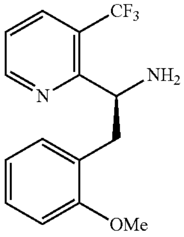 [SMILES: COc1ccccc1C[C@H](N)c1ncccc1C(F)(F)F] | (S)-2-(2-methoxyphenyl)-1-(3-(trifluoro-methyl)-pyridin-2-yl)-ethanamine | $C_{15}H_{15}F_3N_2O$ (296.29) |

TABLE 1-continued

Additional diarylmethanamines prepared analogous to Scheme 5 and 6 (Intermediates 3-41). Unless otherwise stated, all amines in this table are hydrochloride salts.

| Intermediate | Method | Aryl Halide or Grignard in Step 2 | Structure | Name | Mol. Formula (Mol. Wt.) |
|---|---|---|---|---|---|
| 35 | A | 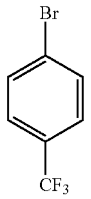 | 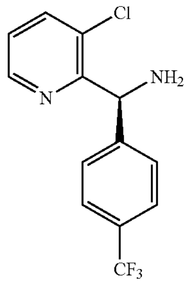 [SMILES: N[C@@H](c1ccc(C(F)(F)F)cc1)c1ncccc1Cl] | (S)-(3-chloropyridin-2-yl)-(4-(trifluoromethyl)-phenyl)-methanamine | $C_{13}H_{10}ClF_3N_2$ (286.68) |
| 36 | A | 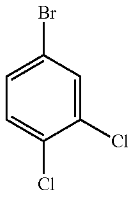 | 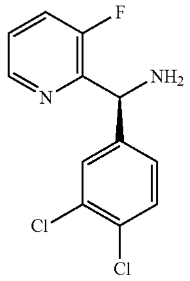 [SMILES: N[C@@H](c1ccc(Cl)c(Cl)c1)c1ncccc1F] | (S)-(3,4-dichlorophenyl)(3-fluoropyridin-2-yl)-methanamine | $C_{12}H_9Cl_2FN_2$ (271.12) |
| 37[1] | A | 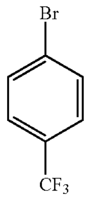 | 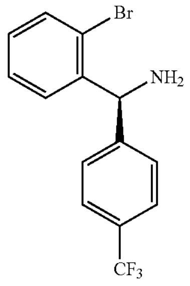 [SMILES: N[C@@H](c1ccc(C(F)(F)F)cc1)c1ccccc1Br] | (S)-(2-bromophenyl)(4-(trifluoromethyl)-phenyl)-methanamine | $C_{14}H_{11}BrF_3N$ (330.14) |
| 38[1] | A | 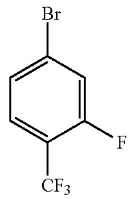 | 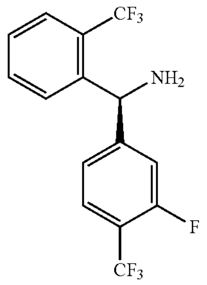 [SMILES: N[C@@H](c1ccc(C(F)(F)F)c(F)c1)c1ccccc1C(F)(F)F] | (S)-(3-fluoro-4-(trifluoromethyl)-phenyl)(2-(trifluoromethyl)-phenyl)-methanamine | $C_{15}H_{10}F_7N$ (337.24) |
| 39[1] | A | 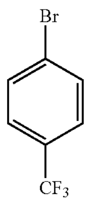 | 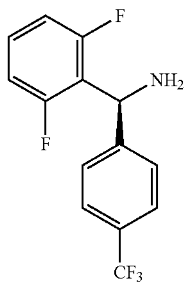 [SMILES: N[C@@H](c1ccc(C(F)(F)F)cc1)c1c(F)cccc1F] | (S)-(2,6-difluorophenyl)(4-(trifluoromethyl)-phenyl)-methanamine | $C_{14}H_{10}F_5N$ (287.23) |

TABLE 1-continued

Additional diarylmethanamines prepared analogous to Scheme 5 and 6 (Intermediates 3-41). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 40[2] | A | 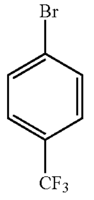 | 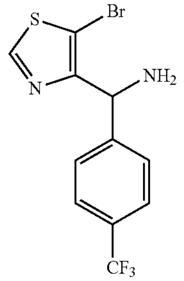 [SMILES: NC(c1ccc(C(F)(F)F)cc1)c1ncsc1Br] | (5-bromothiazol-4-yl)(4-(trifluoro-methyl)-phenyl)-methanamine | $C_{11}H_8BrF_3N_2S$ (337.16) |
| 41 | B | 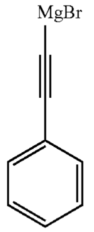 | 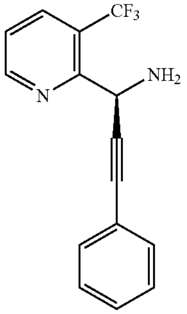 [SMILES: N[C@@H](C#Cc1ccccc1)c1ncccc1C(F)(F)F] | (S)-3-phenyl-1-(3-(trifluoro-methyl)-pyridin-2-yl)-prop-2-yn-1-amine | $C_{15}H_{11}F_3N_2$ (276.26) |

[1]These amines were prepared employing (R)-2-methylpropane-2-sulfinamide in the first step (Scheme 5). For reversal of stereochemistry observed in the Ellman sulfonylimine chemistry observed with 2-pyridyl substrates, see Kuduk, S. D.; DiPardo, R. M.; Chang, R. K.; Ng, C.; Bock, M. G. *Tetrahedron Lett.* 2004, 45, 6641-6643.

[2]Prepared employing racemic 2-methylpropane-2-sulfinamide in the first step (Scheme 5)

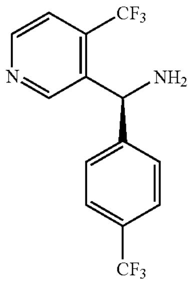 [SMILES: N[C@@H](c1ccc(C(F)(F)F)cc1)c1cnccc1C(F)(F)F]

Intermediate 42: (S)-(4-(Trifluoromethyl)phenyl)(4-(trifluoromethyl)pyridin-3-yl)methanamine

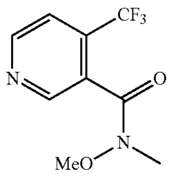 [SMILES: CON(C)C(=O)c1cnccc1C(F)(F)F]

Step 1: N-Methoxy-N-methyl-4-(trifluoromethyl)nicotinamide

To a solution of 4-(trifluoromethyl)nicotinic acid (2.11 g, 11.04 mmol) and N,O-dimethylhydroxylamine hydrochloride (1.077 g, 11.04 mmol) in DCM (20 mL) was added N-ethyl-N-isopropylpropan-2-amine (3.78 mL, 22.08 mmol), and HATU (4.20 g, 11.04 mmol). The reaction was stirred at rt under $N_2$ for 5 h. The reaction was then diluted with $H_2O$ (50 mL) and extracted with DCM (2×50 mL). The organic layers were combined, dried ($MgSO_4$), and concentrated to give the amide. Purification by ISCO (80 g $SiO_2$, 10-50% EtOAc/hexanes) gives N-methoxy-N-methyl-4-(trifluoromethyl)nicotinamide as a yellow oil.

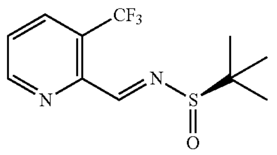 [SMILES: CC(C)(C)[S@@](=O)/N=C/c1ncccc1C(F)(F)F]

Step 2: (R)-2-Methyl-N-((4-(trifluoromethyl)pyridin-3-yl)methylene)propane-2-sulfinamide To a solution of N-methoxy-N-methyl-4-(trifluoromethyl) nicotinamide (1.50 g, 6.41 mmol) in THF (20 mL) at 0° C. was added diisopropylaluminum hydride (7.69 mL, 7.69 mmol) (1.0 M in hexanes). After addition, the reaction was immersed in an ice/water bath and stirred for 1 h. Additional diisopropylaluminum hydride (7.69 mL, 7.69 mmol) was added, and the reaction was stirred 1 h at 0° C. The reaction was quenched by slow addition of $H_2O$ (2 mL) followed by addition of saturated aqueous sodium potassium tartrate (100 mL). The reaction was diluted with $Et_2O$ and stirred at rt for 1 h. The organic layer was separated, and the aqueous layer was extracted with $Et_2O$. The combined organic layers were dried ($MgSO_4$), and the solution was concentrated to 10 mL in vacuo to give a solution of the aldehyde which was used in the next step without further purification.

To a the solution of 4-(trifluoromethyl)nicotinaldehyde from above was added DCM (10 mL), (R)-2-methylpropane-2-sulfinamide (1.553 g, 12.81 mmol; See Table 1, footnote 1) (AK Scientific) and copper sulfate (4.09 g, 25.6 mmol) (Aldrich, anhydrous). The suspension was stirred at rt under $N_2$ for 68 h. The suspension was then filtered through Celite® brand filter agent, and the solid was washed with DCM (2×20 mL). The filtrates were concentrated and purified by ISCO (40 g, $SiO_2$, 10-50% EtOAc/hexane) to give (R)-2-methyl-N-((4-(trifluoromethyl)pyridin-3-yl)methylene)propane-2-sulfinamide as a light yellow oil.

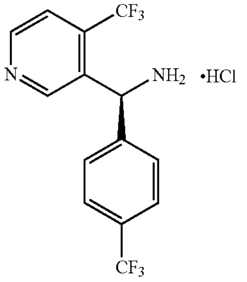 [SMILES: N[C@@H](c1ccc(C(F)(F)F)cc1)c1cnccc1C(F)(F)F ; Cl]

Step 3: (S)-(4-(Trifluoromethyl)phenyl)(4-(trifluoromethyl)pyridin-3-yl)-methanamine hydrochloride Following the procedure detailed above for Intermediate 2, steps 3-4 gave the title compound as a white solid.

Scheme 7

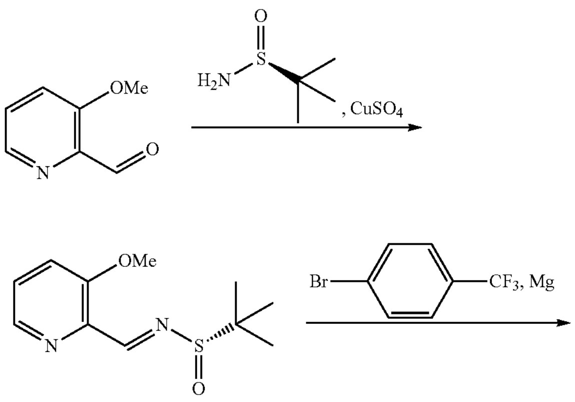

-continued

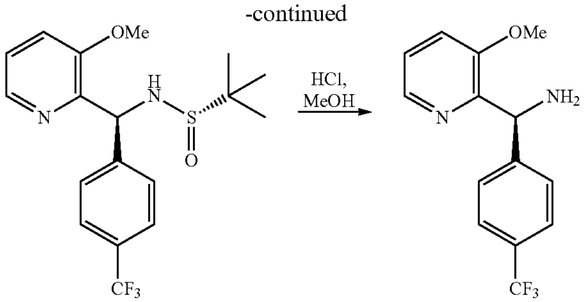

Intermediate 43: (S)-(3-Methoxypyridin-2-yl)(4-(trifluoromethyl)phenyl)-methanamine

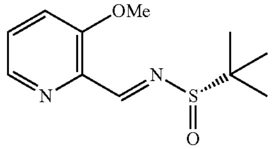 [SMILES: COc1cccnc1/C=N/[S@@](=O)C(C)(C)C]

Step 1. (S,E)-N-((3-Methoxypyridin-2-yl)methylene)-2-methylpropane-2-sulfinamide To a solution of 3-methoxy-pyridine-2-carbaldehyde (2.95 g, 21.51 mmol) in DCM (26 mL) was added (S)-2-methyl-propane-2-sulfinamide (5.3 g, 43.7 mmol) and copper(II) sulfate (6.95 g, 43.5 mmol). The suspension was stirred at rt under argon for 18 hours, filtered, and the solid washed with DCM (2×20 mL). The filtrates were concentrated, and the product thus obtained was purified by silica gel flash column chromatography (using a 80G ISCO cartridge) and eluted using hexanes/EtOAc gradient followed by DCM/MeOH to yield the desired product (S,E)-N-((3-methoxypyridin-2-yl)methylene)-2-methylpropane-2-sulfinamide as a light-yellow solid after drying under high vacuum.

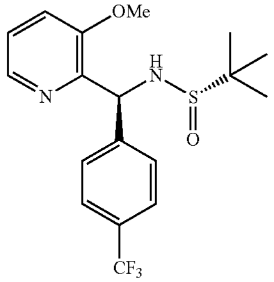

Step 2. (S)—N—((S)-(3-Methoxypyridin-2-yl)(4-(trifluoromethyl)phenyl)-methyl)-2-methylpropane-2-sulfinamide To a 150 mL round-bottomed flask containing magnesium turnings (0.370 g, 15.22 mmol) and $Et_2O$ (10 mL) was added diisobutylaluminum hydride, 1.0M solution in THF (0.095 mL, 0.095 mmol) followed by dropwise addition of 1-bromo-4-(trifluoromethyl)benzene (0.8 mL, 5.71 mmol). The solution was stirred for 2.0 hours during which it turned from turbid to dark brown color. The reaction mixture was cooled to −78° C. in a dry ice/acetone bath, then a solution of (S,E)-N-((3-methoxypyridin-2-yl)methylene)-2-methylpropane-2-sulfinamide (0.920 g, 3.83 mmol) in THF (10 mL) was added dropwise over 5 minutes. The reaction was stirred for 14 hours during which it warmed to rt. The reaction was then quenched with saturated aqueous $NH_4Cl$ (30 mL) and $H_2O$ (25 mL) and extracted with EtOAc (2×100 mL). The combined organic layers were dried over anhydrous sodium sulfate and concentrated to yield the initial product which was purified by silica gel flash column chromatography (using a 40G ISCO cartridge) and eluted using hexanes/EtOAc gradient to yield the desired product (S)—N—((S)-(3-methoxypyridin-2-yl)(4-(trifluoromethyl)phenyl)methyl)-2-methylpropane-2-sulfinamide as an yellow oil.

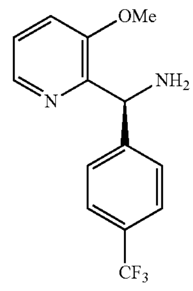 [SMILES: COc1cccnc1[C@@H](N)c1ccc(C(F)(F)F)cc1]

Step 3. (S)-(3-Methoxypyridin-2-yl)(4-(trifluoromethyl)phenyl)methanamine

A solution of (S)—N—((S)-(3-methoxypyridin-2-yl)(4-(trifluoromethyl)-phenyl)methyl)-2-methylpropane-2-sulfinamide (0.576 g, 1.491 mmol) in MeOH (6 mL) was treated with hydrochloric acid, 4.0 M solution in 1,4-dioxane (0.75 mL, 3.00 mmol) and stirred at rt for 2 h. The reaction was concentrated on the rotary evaporator resulting in a gummy residue which was taken up in EtOAc (100 mL), saturated aqueous $NaHCO_3$ (50 mL), and $H_2O$ (25 mL). The resulting mixture was transferred to a separatory funnel and after vigorous extraction, the organic layer was separated, dried over anhydrous sodium sulfate, and concentrated to yield the product (S)-(3-methoxypyridin-2-yl)(4-(trifluoromethyl)-phenyl)methanamine as a light-brown oil which was used without further purification in the next step.

Scheme 8

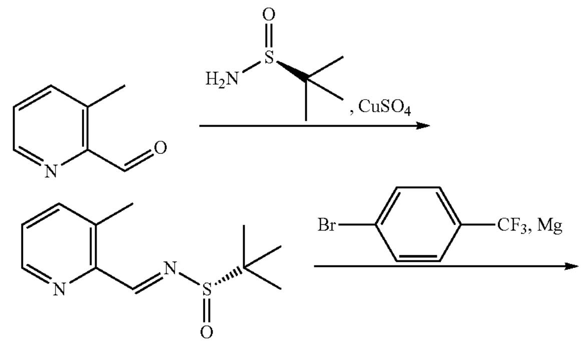

-continued

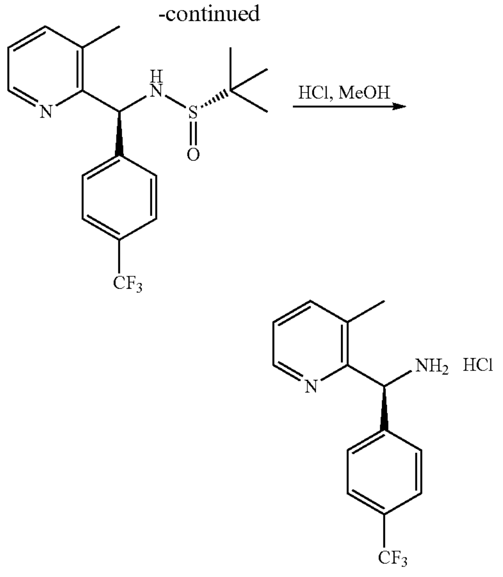

Intermediate 44: (S)-(3-Methylpyridin-2-yl)(4-(trifluoromethyl)phenyl)-methanamine hydrochloride

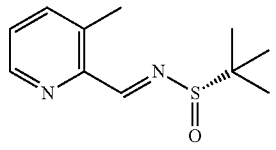

Step 1. (S,E)-2-Methyl-N-((3-methylpyridin-2-yl)methylene)propane-2-sulfinamide

To a solution of 3-methyl-2-pyridinecarboxaldehyde (3.243 g, 26.8 mmol) in DCM (18 mL) was added (S)-2-methylpropane-2-sulfinamide (6.55 g, 54.0 mmol) and copper(II) sulfate (8.72 g, 54.6 mmol). The suspension was stirred at rt for 17 hours, filtered, and the solid was washed with DCM (2×35 mL). The filtrates were concentrated, and the resulting product was purified by silica gel flash column chromatography (using a 80G ISCO cartridge) and eluted using DCM/MeOH gradient to yield the desired product (S,E)-2-methyl-N-((3-methylpyridin-2-yl)methylene)propane-2-sulfinamide as a yellow solid.

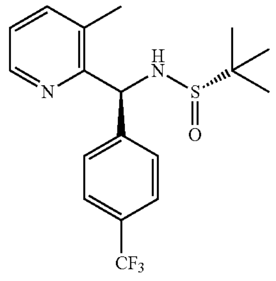 [SMILES: Cc1cccnc1[C@@H](N[S@@](=O)C(C)(C)C)c1ccc(C(F)(F)F)cc1]

Step 2. (S)-2-Methyl-N—((S)-(3-methylpyridin-2-yl)(4-(trifluoromethyl)-phenyl)methyl)propane-2-sulfinamide A 250 mL round-bottomed flask containing magnesium turnings (0.685 g, 28.2 mmol) and $Et_2O$ (25 mL) was added diisobutylaluminum hydride 1.0 M solution in hexanes (0.18 mL, 0.180 mmol) followed by dropwise addition of 4-bromobenzotrifluoride (2.0 mL, 14.28 mmol). The solution was stirred for 1.5 hours during which it turned from turbid to dark brown in color. The reaction mixture was cooled to −78° C. in a dry ice/acetone bath and then a solution of (S,E)-2-methyl-N-((3-methylpyridin-2-yl)methylene)propane-2-sulfinamide (2.15 g, 7.67 mmol) in THF (15 mL) was added dropwise over 5 minutes. The reaction was stirred for 5 hours during which it warmed to rt. The reaction was quenched with saturated aqueous $NH_4Cl$ (50 mL) and $H_2O$ (25 mL). The reaction mixture was extracted with EtOAc (2×100 mL). The combined organic layers were dried over anhydrous sodium sulfate and concentrated to yield the initial product which was purified by silica gel flash column chromatography (using a 80G ISCO cartridge) and eluted using hexanes/EtOAc gradient to yield the desired product (S)-2-methyl-N—((S)-(3-methylpyridin-2-yl)(4-(trifluoromethyl)phenyl)methyl)-propane-2-sulfinamide as an yellow solid

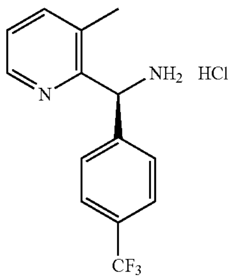 [SMILES: Cc1cccnc1[C@@H](N)c1ccc(C(F)(F)F)cc1 ; Cl]

Step 3. (S)-(3-Methylpyridin-2-yl)(4-(trifluoromethyl)phenyl)methanamine hydrochloride A solution of (S)-2-methyl-N—((S)-(3-methylpyridin-2-yl)(4-(trifluoro-methyl)phenyl)methyl)propane-2-sulfinamide (0.355 g, 0.958 mmol) in MeOH (10 mL) was treated with hydrogen chloride, 4.0 M solution in 1,4-dioxane (0.6 mL, 2.400 mmol) and stirred at rt. The reaction was concentrated on the rotary evaporator resulting in a gummy residue. The residue (S)-(3-methylpyridin-2-yl)-(4-(trifluoromethyl)phenyl)methanamine hydrochloride was used in the next steps without further purification.

Scheme 9

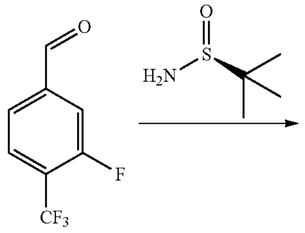

-continued

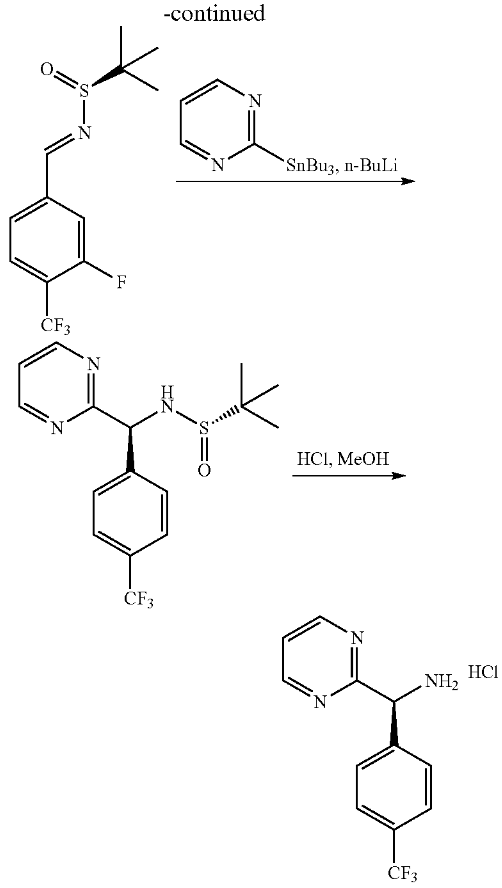

Intermediate 45: (S)-(3-Fluoro-4-(trifluoromethyl)phenyl)(3-(trifluoro-methyl)pyridin-2-yl)methanamine hydrochloride

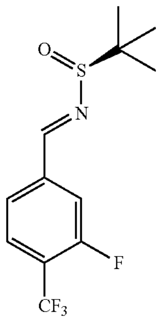 [SMILES: CC(C)(C)[S@](=O)/N=C/c1ccc(C(F)(F)F)c(F)c1]

Step 1. (S,E)-N-(3-Fluoro-4-(trifluoromethyl)benzylidene)-2-methylpropane-2-sulfinamide To a solution of 3-fluoro-4-(trifluoromethyl)benzaldehyde (5.7 g, 29.7 mmol) in DCM (60 mL) was added (S)-2-methylpropane-2-sulfinamide (7.19 g, 59.3 mmol) and copper (II) sulfate (18.94 g, 119 mmol). The suspension was stirred at rt under $N_2$ for 20 h. The suspension was then filtered through Celite® brand filter agent, and the solids were washed with DCM (2×20 mL). The filtrates were concentrated and purified by ISCO (120 g, $SiO_2$, 10-50% EtOAc/hexanes) to give (S,E)-N-(3-fluoro-4-(trifluoromethyl)benzylidene)-2-methylpropane-2-sulfinamide as a white solid.

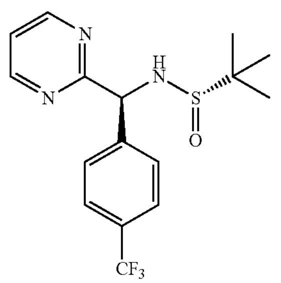 [SMILES: CC(C)(C)[S@](=O)N[C@@H](c1ccc(C(F)(F)F)cc1)c1ncccn1]

Step 2. (S)—N—((S)-(3-Fluoro-4-(trifluoromethyl)phenyl)(3-(trifluoromethyl)-pyridin-2-yl)methyl)-2-methylpropane-2-sulfinamide To a solution of 2-(tributylstannyl)pyrimidine (425 mg, 1.151 mmol) in THF (3 mL) at −78° C. was added n-butyllithium (0.720 mL, 1.151 mmol) (1.6 M in hexanes). The reaction was stirred at −78° C. for 1.5 h and then (S,E)-N-(3-fluoro-4-(trifluoromethyl)benzylidene)-2-methylpropane-2-sulfinamide (408 mg, 1.382 mmol) in THF (1 mL) was added. The cooling bath was then removed as the reaction was allowed to warm to rt and stirred for 1 h. LCMS showed 2 products with a ratio of 10:1. The reaction was quenched with saturated aqueous $NH_4Cl$ (5 mL) and $H_2O$ (5 mL). The reaction mixture was extracted with EtOAc (2×5 mL). The organic layers were combined, dried ($MgSO_4$), and concentrated to give the product. Purification by ISCO (12 g $SiO_2$, 20-80% EtOAc/hexanes) gave the major product, (S)—N—((S)-(3-fluoro-4-(trifluoromethyl)phenyl)-(pyrimidin-2-yl)methyl)-2-methylpropane-2-sulfinamide.

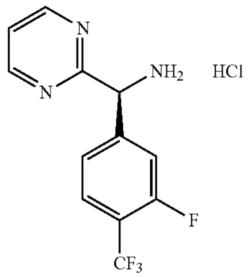 [SMILES: N[C@@H](c1ccc(C(F)(F)F)c(F)c1)c1ncccn1 ; Cl]

Step 3. (S)-(3-Fluoro-4-(trifluoromethyl)phenyl)(3-(trifluoromethyl)pyridin-2-yl)methanamine hydrochloride To a solution of (S)—N—((S)-(3-fluoro-4-(trifluoromethyl)phenyl)-(pyrimidin-2-yl)methyl)-2-methylpropane-2-sulfinamide (100 mg, 0.266 mmol) in MeOH (5 mL) was added hydrogen chloride (0.200 mL, 0.799 mmol) (4.0 M in 1,4-dioxane). The reaction was stirred for 2 h at rt under $N_2$ and then concentrated in vacuo to give the amine as the hydrochloride salt which was used in the next step without further purification.

Scheme 10

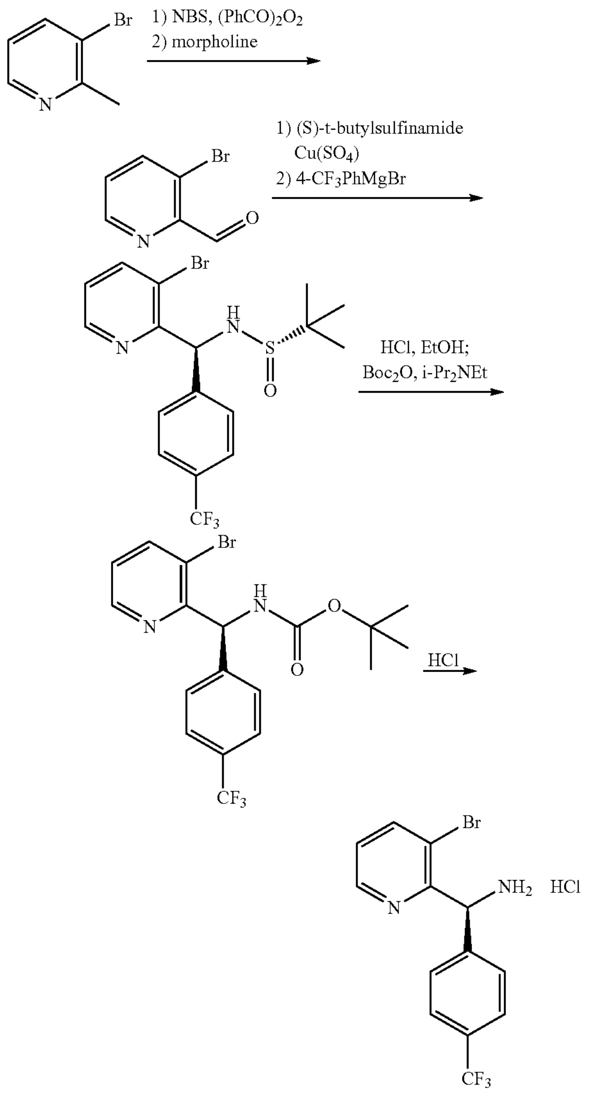

Intermediate 46: (S)-(3-(Prop-1-yn-1-yl)pyridin-2-yl)(4-(trifluoromethyl)-phenyl)methanamine hydrochloride

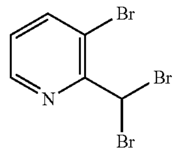

Step-1. 3-Bromo-2-dibromethyl-pyridine

To a solution of 3-bromo-picoline (25 g, 0.145 mol) in $CCl_4$ was added N-bromosuccinimide (51.66 g, 0.29 mol) and benzoylperoxide (2.5 g, 0.018 mol).

The mixture was then gradually heated to reflux and stirred for 30 h. The reaction mixture was then cooled to rt, the succinimide was removed by filtration, and the filtrate was concentrated under reduced pressure. The resulting product was purified by flash column chromatography using silica (100-200 mesh) with EtOAc: hexane (0.1:09) as eluent to furnish pure 3-Bromo-2-dibromomethyl-pyridine. $^1$H-NMR (400 MHz, $CDCl_3$): δ7.66-7.68 (d, 1H), 7.84-7.88 (d, 1H), 7.13-7.17 (t, 2H).

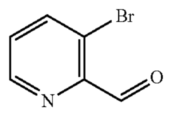

Step-2. 3-Bromo-pyridine-2-carbaldehyde

A suspension of 3-bromo-2-dibromomethyl-pyridine (10.0 g, 30.32 mmole) in morpholine (30.0 mL) was heated to 60° C. for 1 h. The reaction mixture was cooled to rt and diluted with EtOAc (200 mL). The pH was adjusted to 4.0 by adding citric acid (40.0 g). The reaction mixture was then extracted with EtOAc (3×200 mL) and the combined organic layers were dried over $Na_2SO_4$ and concentrated under reduced pressure. The residue was purified by column chromatography using silica (100-200 mesh) using 3% EtOAc in hexane as eluent to give 3-bromo-pyridine-2-carbaldehyde. $^1$H-NMR (400 MHz, $CDCl_3$): c 10.23 (s, 1H), 8.74-8.76 (d, 1H), 8.02-8.04 (d, 1H), 7.26-7.38 (t, 1H).

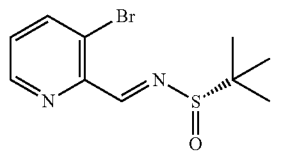

Step 3. (S,E)-N-((3-Bromopyridin-2-yl)methylene)-2-methylpropane-2-sulfinamide

A mixture of 3-bromo piconaldehyde (10 g, 53.8 mmol), copper sulfate (3.98 mL, 81 mmol) and (S)-2-methylpropane-2-sulfinamide (6.84 g, 56.4 mmol) in DCM (100 mL) was stirred at rt overnight. The solid was filtered off and the filtrate concentrated under vacuum. The residue was purified by column chromatography using silica (100-200 mesh) with 20% EtOAc in n-hexane as eluent to give (S,E)-N-((3-bromopyridin-2-yl)methylene)-2-methylpropane-2-sulfinamide as yellow oil. $^1$H-NMR (400 MHz, $CDCl_3$): δ9.0 (s, 1H), 8.74-8.76 (d, 1H), 7.9-8.04 (d, 1H), 7.26-7.38 (t, 1H), 5.2 (d, 1H), 1.3 (s, 9H).

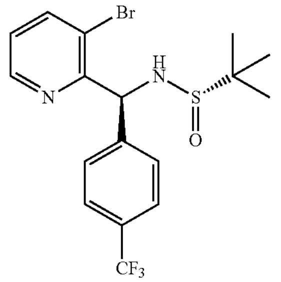

Step 4. (S)-2-Methyl-propane-2-sulfinic acid ((3-bromo-pyridin-2yl)-(4-trifluoromethyl-phenyl)-methyl)-amide To a stirred suspension of magnesium (2.143 g, 88 mmol) in THF (50 mL), was added 4-bromobenzotrifluoride (5.06 mL, 36.2 mmol). Stirring was continued for 4 h (caution: slightly exothermic, cooled with a water bath if needed). The resulting mixture was added to a stirred solution of (S,E)-N-((3-bromopyridin-2-yl)methylene)-2-methylpropane-2-sulfinamide (5.1 g, 17.64 mmol) in THF (100 mL) at −78° C. in a dropwise fashion. The mixture was stirred for another hour after addition and the reaction was then quenched with saturated aqueous $NH_4Cl$, extracted with $Et_2O$ (3×20 mL), dried over $Na_2SO_4$, concentrated, and purified by column chromatography using silica (100-200 mesh) with 5% EtOAc in hexane as eluent to give the title compound as a brown oil.

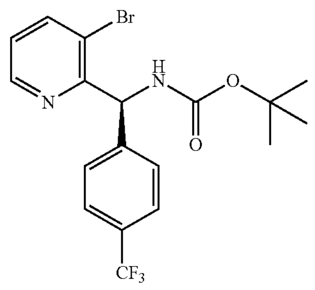 [SMILES: CC(C)(C)OC(=O)N[C@@H](c1ccc(C(F)(F)F)cc1)c1ncccc1Br]

Step 5. (S)-tert-Butyl((3-bromopyridin-2-yl)(4-(trifluoromethyl)phenyl)methyl)carbamate To a cooled (0° C.) stirred solution of (S)-2-methyl-propane-2-sulfinic acid ((3-bromo-pyridin-2yl)-(4-trifluoromethyl-phenyl)-methyl)-amide (5.0 g, 11.49 mmol) in DCM/EtOH (1/1, 60 mL) was added 4.0 M HCl in 1,4-dioxane (14.36 mL, 57.4 mmol). Stirring was continued for 2 h and then DIPEA (10.00 mL, 57.4 mmol) was added, followed by di-tert-butyl dicarbonate (4.00 mL, 17.23 mmol) added. The resulting mixture was stirred at rt overnight, diluted with $H_2O$, and extracted with DCM (3×100 mL). The combined organic layers were dried over $Na_2SO_4$ and concentrated under reduced pressure. The residue thus obtained was purified by silica gel (100-200 mesh) column chromatography using 5% EtOAc in hexane as eluent to give the title compound as a white solid. $^1$H-NMR (400 MHz, DMSO-$d_6$): δ8.5 (dd, 1H), 7.81 (dd, 1H), 7.52 (s, 4H), 7.2 (dd, 1H) 6.51 (d, 1H), 6.32 (d. 1H), 1.41 (s, 9H).

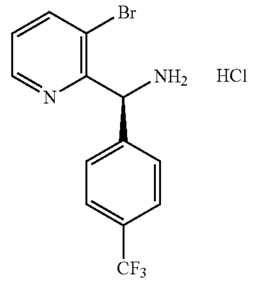 [SMILES: N[C@@H](c1ccc(C(F)(F)F)cc1)c1ncccc1Br ; Cl]

Step 6. (S)-(3-Bromopyridin-2-yl)(4-(trifluoromethyl)phenyl)methanamine hydrochloride To a solution of (S)-tert-butyl ((3-bromopyridin-2-yl)(4-(trifluoromethyl)-phenyl)methyl)carbamate (2.0 g, 4.64 mmol) in MeOH (10 mL) was added hydrogen chloride (3.48 mL, 13.91 mmol) (4.0 M in 1,4-dioxane). The reaction was stirred for 27 h at rt under $N_2$. The reaction was concentrated in vacuo to give the amine which was used without further purification in subsequent steps. MS (ESI pos. ion) m/z: 331.0, 332.9 (M+H).

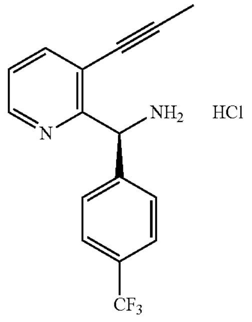 [SMILES: CC#Cc1cccnc1[C@@H](N)c1ccc(C(F)(F)F)cc1 ; Cl]

Intermediate 47: (S)-(3-(Prop-1-yn-1-yl)pyridin-2-yl)(4-(trifluoromethyl)-phenyl)methanamine hydrochloride

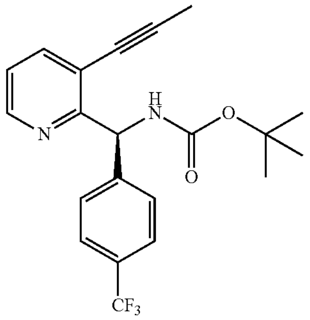 [SMILES: CC#Cc1cccnc1[C@@H](NC(=O)OC(C)(C)C)c1ccc(C(F)(F)F)cc1]

Step 1. (S)-tert-Butyl ((3-(prop-1-yn-1-yl)pyridin-2-yl)(4-(trifluoromethyl)-phenyl)methyl)carbamate To a microwave vial containing (S)-tert-butyl ((3-bromopyridin-2-yl)(4-(trifluoromethyl)phenyl)methyl)carbamate (500 mg, 1.159 mmol) and a stir bar was added 1,4-dioxane (6 mL). To this solution was added tetrakis(triphenylphosphine)palladium(0) (67.0 mg, 0.058 mmol, 0.05 eq) and tributyl(prop-1-yn-1-yl)stannane (458 mg, 1.391 mmol, 1.2 eq). The vial was capped and irradiated in a microwave at 120° C. for 20 min. The vial was allowed to cool, diluted with hexanes (5 mL) and loaded directly to a normal phase silica gel column (80 g ISCO, 0 to 40% EtOAc in hexanes) to provide (S)-tert-butyl ((3-(prop-1-yn-1-yl)-pyridin-2-yl)(4-(trifluoromethyl)phenyl)methyl)carbamate as a white solid.

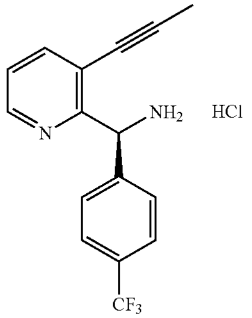 [SMILES: CC#Cc1cccnc1[C@@H](N)c1ccc(C(F)(F)F)cc1 ; Cl]

Step 2. (S)-(3-(Prop-1-yn-1-yl)pyridin-2-yl)(4-(trifluoromethyl)phenyl)-methanamine hydrochloride To a 500 mL round bottom flask containing (S)-tert-butyl ((3-(prop-1-yn-1-yl)pyridin-2-yl)(4-(trifluoromethyl)phenyl)methyl)carbamate (400 mg, 1.025 mmol) was added DCM (8 mL) and the mixture was stirred at 23° C. for 2 min. At this time, hydrogen chloride (4N in 1,4-dioxane) (37.4 mg, 1.025 mmol) (4 mL) was added via syringe. The reaction was stirred for 3 h then the volatiles were removed via rotoryevaporator. The solid was placed on high vacuum overnight to give (S)-(3-(prop-1-yn-1-yl)pyridin-2-yl)(4-(trifluoromethyl)phenyl)-methanamine hydrochloride as a white solid.

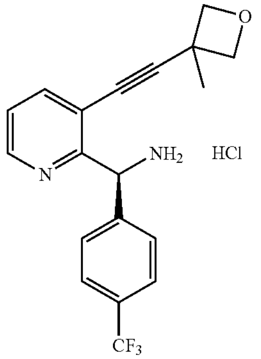 [SMILES: CC1(C#Cc2cccnc2[C@@H](N)c2ccc(C(F)(F)F)cc2)COC1 ; Cl]

Intermediate 48: (S)-(3-((3-Methyloxetan-3-yl)ethynyl)pyridin-2-yl)(4-(trifluoromethyl)phenyl)methanamine hydrochloride To a microwave flask containing trimethyl((3-methyloxetan-3-yl)-ethynyl)silane (0.585 g, 3.48 mmol) was added THF (7.73 mL) and the mixture was stirred at 23° C. for 2 min. At this time, (S)-tert-butyl ((3-bromopyridin-2-yl)-(4-trifluoromethyl)phenyl)methyl)carbamate (1.00 g, 2.319 mmol), tetrabutylammonium fluoride (0.909 g, 3.48 mmol), copper(I) iodide (0.022 g, 0.116 mmol) and lastly tetrakis (triphenylphosphine)palladium(0) (0.134 g, 0.116 mmol) were added to the flask. The flask was heated to 85° C. for 90 min. The flask was allowed to cool and then subjected to a EtOAc (100 mL) and $NaHCO_3$ (sat, 1M, 100 mL) work up. The aq layer was extracted with EtOAc (3×). The combined organics were washed with brine, dried with sodium sulfate, filtered and concentrated to give an oil (1.72 g). The oil thus obtained was subjected to silica gel chromatography (120 g ISCO, 20 to 35% EtOAc in hexanes) to give (S)-tert-butyl ((3-((3-methyloxetan-3-yl)ethynyl)pyridin-2-yl)(4-(trifluoromethyl)-phenyl)methyl)carbamate as a pale yellow oil.

(S)-tert-Butyl ((3-((3-methyloxetan-3-yl)ethynyl)pyridin-2-yl)(4-(trifluoro-methyl)phenyl)methyl)carbamate from above was prepared by following the procedure described for the preparation of Intermediate 47, Step 2 to give the title compound as a white solid.

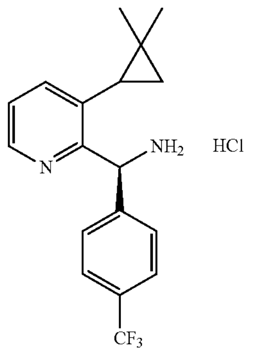 [SMILES: CC1(C)CC1c1cccnc1[C@@H](N)c1ccc(C(F)(F)F)cc1 ; Cl]

Intermediate 49: (1S)-(3-(2,2-Dimethylcyclopropyl) pyridin-2-yl)(4-(trifluoro-methyl)phenyl)methanamine hydrochloride A mixture of (S)-tert-butyl (3-bromopyridin-2-yl)(4-(trifluoromethyl)-phenyl)methylcarbamate (1.50 g, 3.48 mmol), potassium (2,2-dimethylcyclopropyl) trifluoroborate (0.857 g, 4.87 mmol), potassium phosphate (2.58 g, 12.17 mmol), dicyclohexyl(2',6'-dimethoxybiphenyl-2-yl)phosphine (0.314 g, 0.765 mmol), and palladium acetate (0.094 g, 0.417 mmol) in toluene/$H_2O$ (10:1, 11 mL) was heated at 100° C. for 24 h. The reaction mixture was cooled, diluted with $H_2O$, and extracted with EtOAc (3×). The combined extracts were dried over $MgSO_4$, concentrated and purified by ISCO (10% EtOAc/hexanes) to give a colorless oil which was dissolved in DCM (3 mL) and was treated with 4 mL of 4M HCl in 1,4-dioxane. The solution was stirred at rt overnight and concentrated to dryness to give the title compound as an off white solid. MS (ESI pos. ion) m/z: 321.0 (M+H).

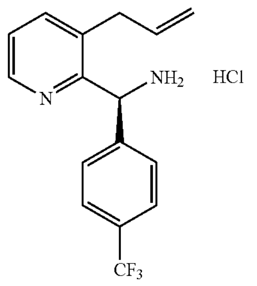 [SMILES: C=CCc1cccnc1[C@@H](N)c1ccc(C(F)(F)F)cc1 ; Cl]

Intermediate 50: (S)-(3-Allylpyridin-2-yl)(4-(trifluoromethyl)phenyl) methanamine hydrochloride A mixture of (S)-tert-butyl (3-bromopyridin-2-yl)(4-(trifluoromethyl)-phenyl)methylcarbamate (1.00 g, 2.319 mmol), allylboronic acid pinacol ester (0.507 mL, 3.01 mmol), cesium fluoride (0.171 mL, 4.64 mmol), and $(Ph_3P)_4Pd$ (0.536 g, 0.464 mmol) in 1,4-dioxane (10 mL) was heated by microwave at 125° C. for 30 min. The mixture was cooled, taken up in $H_2O$, extracted with $Et_2O$ (3×25 mL), the combined organic layers were dried over $MgSO_4$, concentrated and purified by ISCO (0-50% EtOAc/hexanes). The residue was dissolved in DCM (10 mL) was added HCl in 4M p-dioxane (4.64 mL, 18.55 mmol). Stirring was continued for 2 h, and the solution concentrated to the dryness to give the title compound as a white solid. MS (ESI pos. ion) m/z: 293.0 (M+H).

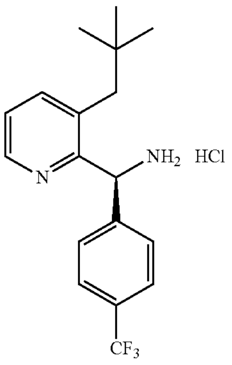 [SMILES: CC(C)(C)Cc1cccnc1[C@@H](N)c1ccc(C(F)(F)F)cc1 ; Cl]

Intermediate 51: (S)-(3-Neopentylpyridin-2-yl)(4-(trifluoromethyl)phenyl)-methanamine hydrochloride A mixture of (S)-tert-butyl (3-bromopyridin-2-yl)(4-(trifluoromethyl)-phenyl)methylcarbamate (0.500 g, 1.159 mmol), bis(tri-t-butylphosphine)-palladium (0) (0.119 g, 0.232 mmol), and neopentylzinc(II) bromide (4.75 mL, 2.377 mmol) in THF (5 mL) was stirred at 135° C. by microwave for 30 min. The reaction mixture was cooled, quenched with saturated aqueous $NH_4Cl$, and extracted with EtOAc (3×25 mL). The combined organic extracts were dried over $MgSO_4$, concentrated, and purified by ISCO (0-40% EtOAc/hexanes) to give the carbamate intermediate. The carbamate was dissolved in DCM (5 mL) and 4M HCl in 1,4-dioxane (2 mL) was added. The reaction mixture was stirred at rt overnight, and concentrated to dryness to give the title compound as a white solid. MS (ESI pos. ion) m/z: 323.0 (M+H).

Scheme 11

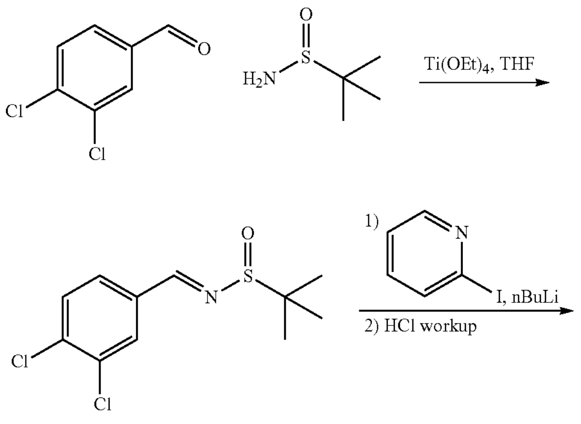

-continued

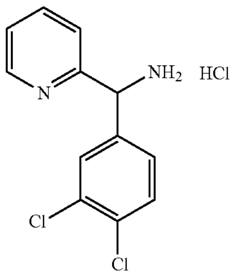

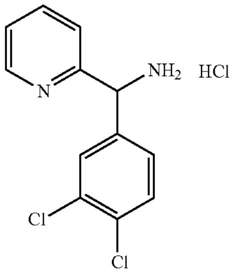

Intermediate 52: (S)-(3-Neopentylpyridin-2-yl)(4-(trifluoromethyl)phenyl)-methanamine hydrochloride

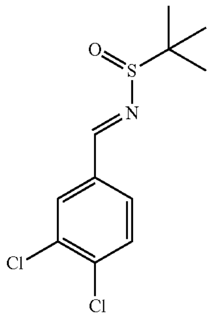 [SMILES: CC(C)(C)S(=O)/N=C/c1ccc(Cl)c(Cl)c1]

Step 1. (E)-N-(3,4-Dichlorobenzylidene)-2-methylpropane-2-sulfinamide

A 1-L round-bottomed flask was charged with 3,4-dichlorobenzaldehyde (25.0 g, 143 mmol), 2-methylpropane-2-sulfinamide (17.3 g, 143 mmol), and 200 mL of THF. To this was added $Ti(OEt)_4$ (65.2 g, 286 mmol) over 5 min. The reaction was stirred at rt for 5 h and then poured onto brine. The resulting white precipitate was removed by filtration, and the filter cake was washed with EtOAc. The filtrate was transferred to a separatory funnel and the layers were separated. The organic layers were combined and dried ($MgSO_4$), filtered, and concentrated to give (E)-N-(3,4-dichlorobenzylidene)-2-methylpropane-2-sulfinamide as a white solid.

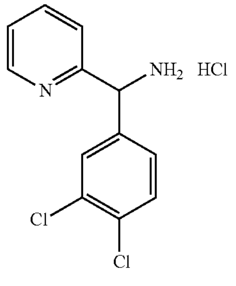 [SMILES: NC(c1ccc(Cl)c(Cl)c1)c1ccccn1 ; Cl]

Step 2. (S)-(3-Neopentylpyridin-2-yl)(4-(trifluoromethyl)phenyl)methanamine hydrochloride A 250-mL round-bottomed flask was charged with 2-iodopyridine (1.0 g, 4.88 mmol) and 50 mL of THF. The resulting mixture was cooled to −100° C. and then n-BuLi (2.5 M in hexanes, 5.3 mL, 13 mmol) was added at such a rate that the internal temp did not rise above −97° C. After 15 min at −100° C., (E)-N-(3,4-dichlorobenzylidene)-2-methylpropane-2-sulfinamide (1.36 g, 4.88 mmol) was added and stirring was continued for 1 h at −100° C. 30 mL of 1M HCl in ether was added, and the mixture was allowed to warm to rt. Once at rt, 5 mL of MeOH was added and the mixture was stirred for an additional 1 h. The resulting precipitate was collected by filtration to give (3,4-dichlorophenyl)(pyridin-2-yl)-methanamine hydrochloride as a white solid.

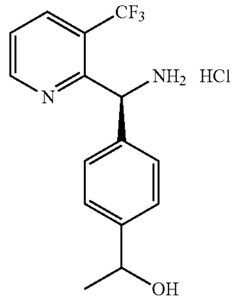 [SMILES: CC(O)c1ccc([C@H](N)c2ncccc2C(F)(F)F)cc1 ; Cl]

Intermediate 53: 1-(4-((S)-Amino(3-(trifluoromethyl)pyridin-2-yl)methyl)-phenyl)ethanol hydrochloride

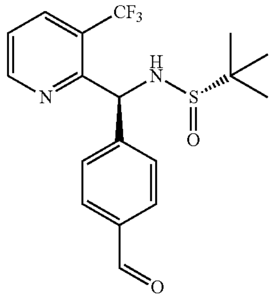 [SMILES: CC(C)(C)[S@](=O)N[C@@H](c1ccc(C=O)cc1)c1ncccc1C(F)(F)F]

Step 1. (S)—N—((S)-(4-Formylphenyl)(3-(trifluoromethyl)pyridin-2-yl)methyl)-2-methylpropane-2-sulfinamide Magnesium metal (0.200 g, 8.23 mmol) was activated using a crystal of iodine followed by the addition of THF (4 mL). 1-Bromo-4-(diethoxymethyl)-benzene (2.0 g, 7.72 mmol) was added and the mixture allowed to sit without stirring for 5 minutes. Gas evolution was observed and the colour of the iodine mostly disappeared. Stirring was then initiated and additional dry THF (20 mL) was added. After stirring for 2 hours, the mixture was allowed to settle. The supernatant was added to a solution of (S,E)-2-methyl-N-((3-(trifluoromethyl)-pyridin-2-yl)methylene)propane-2-sulfinamide (0.450 g, 1.617 mmol) in dry THF (10 mL). The resulting reaction mixture was stirred overnight. Saturated aqueous $NH_4Cl$ (10 mL) was added followed by $H_2O$ (80 mL) and EtOAc (100 mL). The phases were mixed and separated. The organic layer was dried with $MgSO_4$ and evaporated to dryness under reduced pressure. The acetal was further dried under high vacuum. The acetal was dissolved in EtOAc (50 mL) and treated with 50% TFA in $H_2O$ (50 mL). The solution was stirred vigorously for 20 minutes. Water (200 mL), EtOAc (100 mL), and $Et_2O$ (100 mL) were then added and the phases separated. The aqueous layer was removed, and the organic layer was washed with additional $H_2O$ (2×200 mL). The organic layer was then washed with saturated aqueous $NaHCO_3$ (3×100 mL, strong gas evolution) followed by $H_2O$ (100 mL) and finally brine (100 mL). The organic layer was dried with $MgSO_4$ and evaporated to dryness under reduced pressure. Purification using silica chromatography (hexane to EtOAc gradient) gave the desired (S)—N—((S)-(4-formylphenyl)(3-(trifluoromethyl)pyridin-2-yl)methyl)-2-methylpropane-2-sulfinamide as an oil.

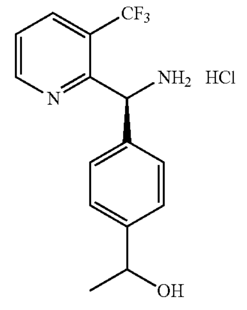 [SMILES: CC(O)c1ccc([C@H](N)c2ncccc2C(F)(F)F)cc1 ; Cl]

Step 2. 1-(4-((S)-Amino(3-(trifluoromethyl)pyridin-2-yl)methyl)phenyl)-ethanol hydrochloride (S)—N—((S)-(4-Formylphenyl)(3-(trifluoromethyl)pyridin-2-yl)methyl)-2-methylpropane-2-sulfinamide (0.200 g, 0.520 mmol) was dissolved in dry THF (30 mL) and cooled in an ice bath. Methylmagnesium bromide (3M in $Et_2O$, 0.50 mL, 1.50 mmol) was added dropwise and the reaction stirred. The resulting mixture was stirred for 1 h and then quenched by addition of saturated aqueous $NH_4Cl$ (10 mL). $H_2O$ (100 mL) and EtOAc (100 mL) were added, and the phases were mixed and separated. The organic layer was dried with $MgSO_4$ and evaporated to dryness under reduced pressure. Purification using silica chromatography (hexane to EtOAc gradient) gave impure material which was further purified using reverse phase HPLC to give the desired (S)—N-((1 S)-(4-(1-hydroxyethyl)phenyl)(3-(trifluoromethyl)pyridin-2-yl)methyl)-2-methylpropane-2-sulfinamide.

The sulfinamide was then subjected to the hydrolysis conditions similar to those described above in Scheme 6, Step 4 to give the title compound.

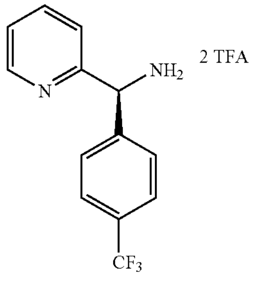 [SMILES: N[C@@H](c1ccc(C(F)(F)F)cc1)c1ccccn1 ; "2 TFA"]

Intermediate 54: (S)-Pyridin-2-yl(4-(trifluoromethyl)phenyl)methanamine bis(2,2,2-trifluoroacetate)

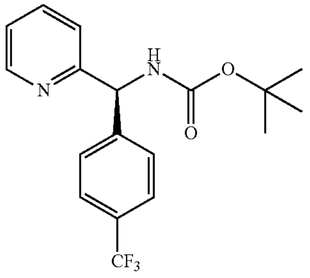 [SMILES: CC(C)(C)OC(=O)N[C@@H](c1ccc(C(F)(F)F)cc1)c1ccccn1]

Step 1. (S)-tert-Butyl (pyridin-2-yl(4-(trifluoromethyl)phenyl)methyl)-carbamate To a solution of (S)-tert-butyl ((3-bromopyridin-2-yl)(4-(trifluoromethyl)-phenyl)methyl)carbamate (2.24 g, 5.19 mmol) in MeOH (20 mL) was added palladium hydroxide, (20 wt % Pd (dry basis) on carbon, wet, degussa type) (0.365 g, 2.60 mmol). The resulting mixture was then stirred at rt under $H_2$ overnight. The mixture was filtered through Celite® brand filter agent and the solids were washed with a solution of MeOH/EtOAc (1:1, 3x20 mL). The combined filtrates were concentrated and dried to give the desired product as a yellow oil, which was used in the next step without further purification.

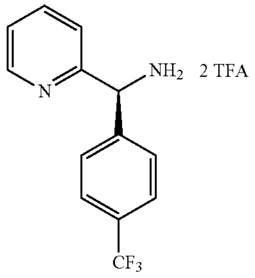 [SMILES: N[C@@H](c1ccc(C(F)(F)F)cc1)c1ccccn1 ; "2 TFA"]

Step 2. (S)-Pyridin-2-yl(4-(trifluoromethyl)phenyl)methanamine bis(2,2,2-trifluoroacetate)

To a solution of (S)-tert-butyl (pyridin-2-yl(4-(trifluoromethyl)phenyl)methyl)carbamate (1.83 g, 5.19 mmol) in DCM (12 mL) was added TFA (3.86 mL, 51.9 mmol). The resulting mixture was then stirred at rt for 1 h. The mixture was then concentrated and dried to give the title compound as a yellow oil which was used without further purification in the amide coupling step.

Scheme 12

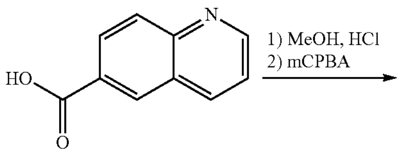

-continued

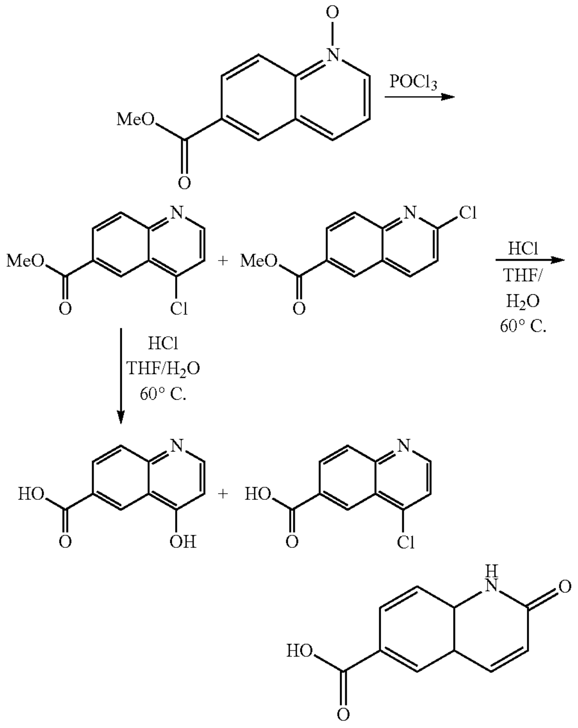

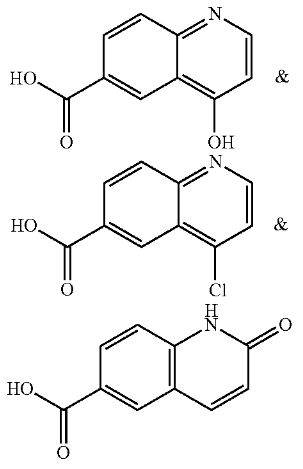

Intermediates 55-57: 4-Hydroxyquinoline-6-carboxylic acid (55), 4-chloroquinoline-6-carboxylic acid (56), and 2-oxo-1,2,4a,8a-tetrahydroquinoline-6-carboxylic acid (57)

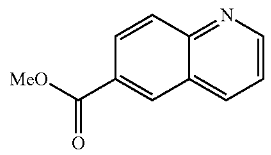 [SMILES: COC(=O)c1ccc2ncccc2c1]

Step 1. Methyl quinoline-6-carboxylate

To a solution of quinoline-6-carboxylic acid (1.00 g, 5.77 mmol) in MeOH (10 mL) was added hydrogen chloride (2.00 mL, 8.00 mmol) (4.0M in 1,4-dioxane). The reaction was stirred 18 h at rt, LCMS shows <10% conversion. Additional hydrogen chloride (2.00 mL, 8.00 mmol) was added and the reaction heated to 50° C. in an oil bath 36 h. The reaction was cooled to rt and concentrated in vacuo. The solid was dissolved in DCM and extracted with sat. aqueous $NaHCO_3$ (2×50 mL). The organic layer was dried ($MgSO_4$), and concentrated to give the product which was used without further purification in the next step.

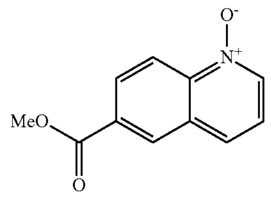 [SMILES: COC(=O)c1ccc2c(ccc[n+]2[O-])c1]

Step 2. 6-(Methoxycarbonyl)quinoline-N-oxide

To a solution of methyl quinoline-6-carboxylate from above in DCM (10 mL) was added 3-chlorobenzoperoxoic acid (1.991 g, 11.54 mmol). The reaction was stirred 21 h at rt. The mixture was then diluted with saturated aqueous $NaHCO_3$ (40 mL), and the mixture was extracted with DCM (2×30 mL). The organic layers were combined, washed with saturated aqueous NaCl (40 mL), dried ($MgSO_4$), and concentrated. The N-oxide was isolated as an orange solid which was used without purification in the next step.

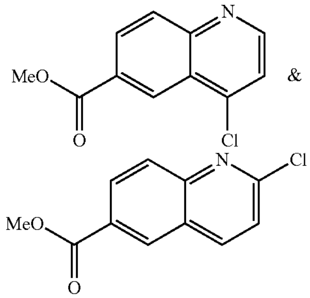

Step 3. Methyl 4-chloroquinoline-6-carboxylate and methyl 2-chloroquinoline-6-carboxylate To 6-(methoxycarbonyl)quinoline-N-oxide from the above step was added phosphoryl trichloride (5 mL, 54.6 mmol). The resulting mixture was then stirred at rt under $N_2$ for 2 h. The reaction was then slowly quenched by addition to an ice cold solution of saturated aqueous $NaHCO_3$ (50 mL) in an ice bath with rapid stirring. The aqueous solution was extracted with EtOAc (3×50 mL). The organic layers were combined, washed with saturated aqueous $NaHCO_3$ (25 mL), $H_2O$ (25 mL), dried ($MgSO_4$), and concentrated. Purification by ISCO (40 g $SiO_2$, 0-50% EtOAc/hexanes) gave as the major product, methyl 4-chloroquinoline-6-carboxylate (330 mg, 1.489 mmol, 25.8% yield over 3 steps) (m/z=221.9) as a white solid. Also isolated was the more polar, methyl 2-chloroquinoline-6-carboxylate with same mass (m/z=221.9).

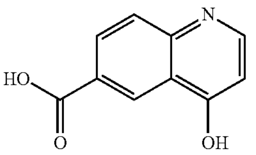

&

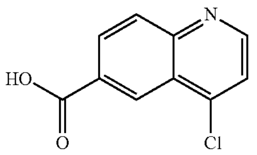

Step 4b.

2-Oxo-1,2,4a,8a-tetrahydroquinoline-6-carboxylic acid (57)

A solution of methyl 2-chloroquinoline-6-carboxylate (60 mg, 0.271 mmol) in THF/5 N aqueous HCl (1:1, 2 mL) was heated to 60° C. in a heating block. LCMS shows major product 86% peak area corresponding to title compound with hydrolysis of methyl ester (m/z=189.9). The reaction was concentrated and used in the subsequent amide coupling steps without further purification.

Scheme 13

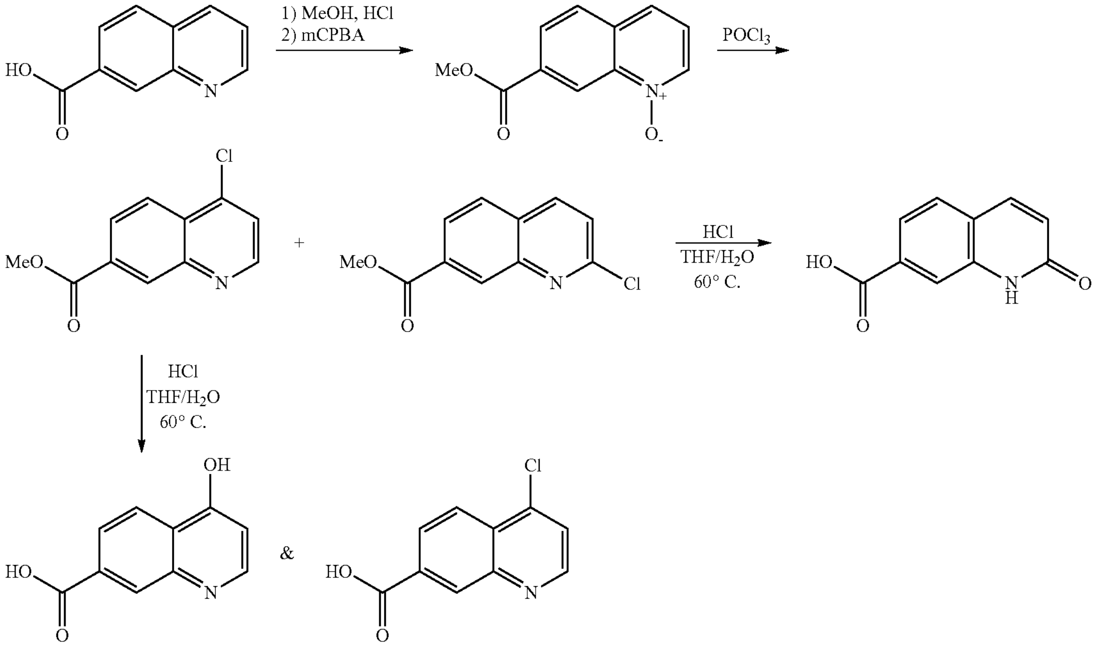

Step 4a. 4-Hydroxyquinoline-6-carboxylic acid (55) and 4-chloroquinoline-6-carboxylic acid (56)

A solution of methyl 4-chloroquinoline-6-carboxylate (110 mg, 0.496 mmol) in THF/5 N aqueous HCl (1:1, 2 mL) was heated to 60° C. in a heating block for 24 h. LCMS showed major product with a 56-70% peak area corresponding to 4-hydroxyquinoline-6-carboxylic acid with hydrolysis of methyl ester (M+H=189.9). Also present was a 18-34% peak area corresponding to 4-chloroquinoline-6-carboxylic acid. The reaction was concentrated and used in the subsequent amide coupling steps without further purification.

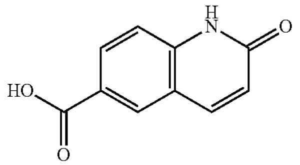 [SMILES: O=C(O)c1ccc2[nH]c(=O)ccc2c1]

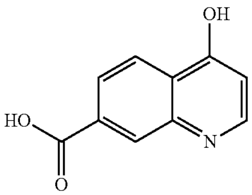

&

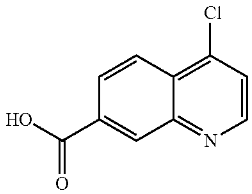

&

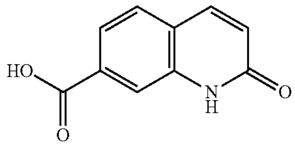

Intermediates 58-60: 4-Hydroxyquinoline-6-carboxylic acid, 4-chloroquinoline-6-carboxylic acid (58), 2-oxo-1,2,4a,8a-tetrahydroquinoline-6-carboxylic acid (59), and 2-oxo-1,2-dihydroquinoline-7-carboxylic acid (60)

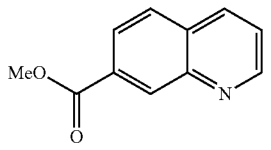 [SMILES: COC(=O)c1ccc2cccnc2c1]

Step 1. Methyl quinoline-7-carboxylate

To a solution of quinoline-7-carboxylic acid (1.00 g, 5.77 mmol) in MeOH (10 mL) was added hydrogen chloride (2.00 mL, 8.00 mmol) (4.0M in 1,4-dioxane). The reaction was stirred for 18 h at rt (LCMS showed <10% conversion to the desired product). Additional hydrogen chloride (2.00 mL, 8.00 mmol) was added, and the reaction mixture was heated to 50° C. in an oil bath for 36 h. The reaction was cooled to rt, and concentrated in vacuo. The solid was dissolved in DCM, and washed with saturated aqueous $NaHCO_3$ (2×50 mL). The organic layer was dried ($MgSO_4$) and concentrated to give the product, which was used without further purification in the next step.

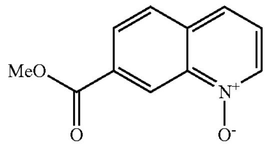 [SMILES: COC(=O)c1ccc2ccc[n+]([O-])c2c1]

Step 2. 7-(Methoxycarbonyl)quinoline-N-oxide

To a solution of the methyl quinoline-7-carboxylate from above in DCM (10 mL) was added 3-chlorobenzoperoxoic acid (1.991 g, 11.54 mmol). The reaction was stirred for 21 h at rt. The mixture was then diluted with saturated aqueous $NaHCO_3$ (40 mL) and the mixture was extracted with DCM (2×30 mL). The organic layers were combined, washed with saturated aqueous NaCl (40 mL), dried ($MgSO_4$), and concentrated. The N-oxide was isolated as an orange solid which was used without purification in the next step.

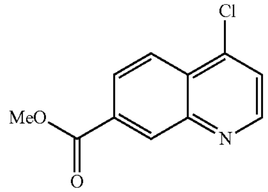

&

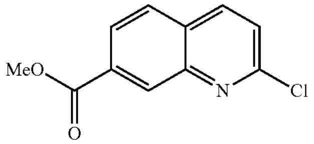

Step 3. Methyl 4-chloroquinoline-7-carboxylate and methyl 2-chloroquinoline-7-carboxylate To the N-oxide from above was added phosphoryl trichloride (10 mL, 109 mmol). The resulting reaction mixture was stirred at rt under $N_2$ or 2 h. The reaction was then quenched by slowly adding it to an ice cold solution of saturated aqueous $NaHCO_3$ (100 mL) in an ice bath with rapid stirring. The aqueous solution was extracted with EtOAc (3×50 mL), the organic layers combined, washed with saturated aqueous $NaHCO_3$ (25 mL), $H_2O$ (25 mL), dried ($MgSO_4$), and concentrated. Purification by ISCO (40 g $SiO_2$, 0-50% EtOAc/hexanes) gave methyl 4-chloroquinoline-7-carboxylate as a white solid and methyl 2-chloroquinoline-7-carboxylate as a white solid.

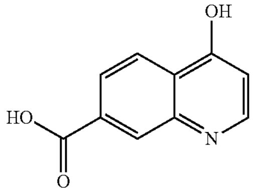

&

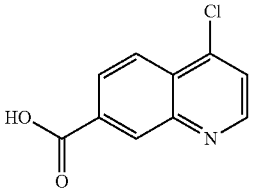

Step 4a. 4-Hydroxyquinoline-7-carboxylic acid (58) and 4-chloroquinoline-7-carboxylic acid (59)

A solution of methyl 4-chloroquinoline-7-carboxylate (110 mg, 0.496 mmol) in THF/5 N aqueous HCl (1:1, 2 mL) was heated to 60° C. in a heating block or 22 h. LCMS showed formation of product (40% peak area) with the mass of 4-hydroxyquinoline-7-carboxylic acid (m/z (M+H)=189.9). Additional product 20% peak area corresponding to the mass of 4-chloroquinoline-7-carboxylic acid (m/z (M+H)=207.9). The reaction was concentrated and used in the subsequent amide coupling steps without further purification.

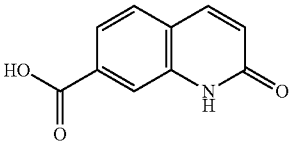 [SMILES: O=C(O)c1ccc2ccc(=O)[nH]c2c1]

Step 4b. 2-Oxo-1,2-dihydroquinoline-7-carboxylic acid (60)

A solution of methyl 2-chloroquinoline-7-carboxylate (150 mg, 0.677 mmol) in THF/5 N aqueous HCl (1:1, 2 mL) was heated to 60° C. in a heating block or 24 h. LCMS showed major product (47% peak area) corresponding to 2-oxo-1,2-dihydroquinoline-7-carboxylic acid (m/z (M+H)=189.9). The reaction was concentrated and used in the subsequent amide coupling steps without further purification.

EXAMPLES

General Amide Formation Procedure for Examples (1-261, 287-424)

To a solution of (S)-(4-(trifluoromethyl)phenyl)(3-(trifluoromethyl)pyridin-2-yl)methanamine (50 mg, 0.156 mmol), the corresponding carboxylic acid (0.156 mmol), and DIPEA (0.080 mL, 0.468 mmol) in DCM or DMF (1 mL) at rt is added an amide coupling reagent such as (HATU, TBTU, or EDCI) (0.156 mmol, 1.0 equiv.). The reaction was stirred 3 h at rt. The reaction was diluted with DMF (1 mL), filtered through a syringe filter, then purified by preparative reverse phase HPLC (gradient elution 10-100% MeCN/0.1% TFA in $H_2O$). The product containing fractions were then combined and the solvent removed by lyophilzation to provide the target compound as the TFA salt; or the product was dissolved in MeOH (1 mL) and washed through PL-$HCO_3$ MP-resin, the resin was further washed with MeOH (2×0.4 mL). The combined filtrates were then concentrated and dried in vacuo to give the title compounds as free bases; or the product containing fractions were concentrated, the solids dissolved in DCM and the organic layer extracted with saturated aqueous $NaHCO_3$, the organic layer was dried, and concentrated to provide the title compounds as free bases.

TABLE 2

Examples 1-261 prepared via amide formation analogous to Scheme 4

| Ex # | A-mine | Acid Structure | Product Structure | Product Name | MS M + H |
|---|---|---|---|---|---|
| 1 | 8 | 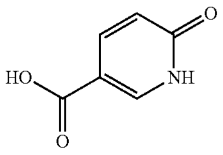 | 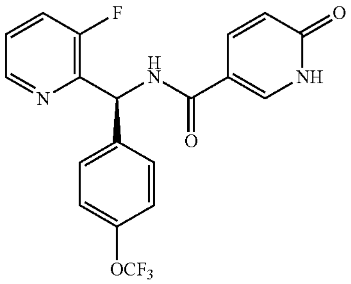 [SMILES: O=C(N[C@@H](c1ccc(OC(F)(F)F)cc1)c1ncccc1F)c1ccc(=O)[nH]c1] | (S)-N-((3-fluoro-pyridin-2-yl)(4-(trifluoro-methoxy)-phenyl)methyl)-6-oxo-1,6-dihydropyridine-3-carboxamide | 408.0 |
| 2 | 8 | 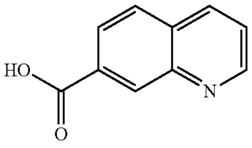 [SMILES: O=C(O)c1ccc2cccnc2c1] | 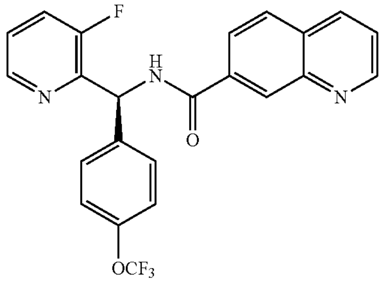 [SMILES: O=C(N[C@@H](c1ccc(OC(F)(F)F)cc1)c1ncccc1F)c1ccc2cccnc2c1] | (S)-N-((3-fluoro-pyridin-2-yl)(4-(trifluoro-methoxy)-phenyl)methyl)-quinoline-7-carboxamide | 442.0 |
| 3 | 4 | 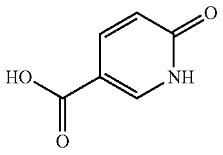 | 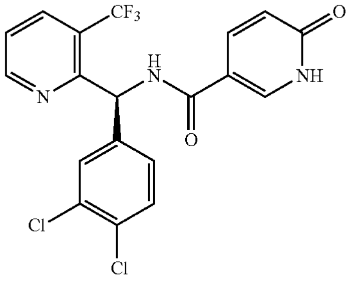 [SMILES: O=C(N[C@@H](c1ccc(Cl)c(Cl)c1)c1ncccc1C(F)(F)F)c1ccc(=O)[nH]c1] | (S)-N-((3,4-dichlorophenyl)-(3-(trifluoro-methyl)pyridin-2-yl)methyl)-6-hydroxy-nicotinamide | 442.0 |
| 4 | 9 | 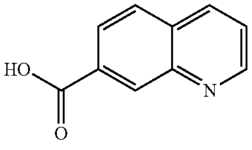 [SMILES: O=C(O)c1ccc2cccnc2c1] | 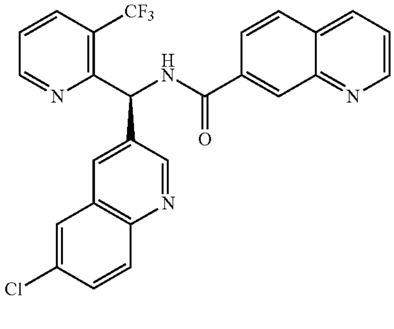 [SMILES: O=C(N[C@@H](c1cnc2ccc(Cl)cc2c1)c1ncccc1C(F)(F)F)c1ccc2cccnc2c1] | (S)-N-((6-chloro-quinolin-3-yl)(3-(trifluoromethyl)-pyridin-2-yl)-methyl)-quinoline-7-carboxamide | 493.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 5 | 5 | 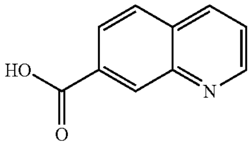 [SMILES: O=C(O)c1ccc2cccnc2c1] | 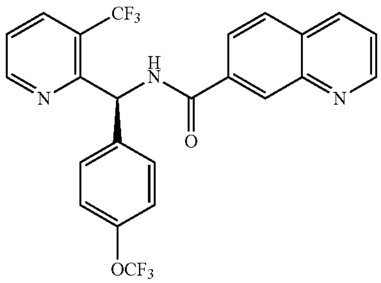 [SMILES: O=C(N[C@@H](c1ccc(OC(F)(F)F)cc1)c1ncccc1C(F)(F)F)c1ccc2cccnc2c1] | (S)-N-((4-(trifluoro-methoxy)-phenyl)(3-(trifluoromethyl)-pyridin-2-yl)-methyl)-quinoline-7-carboxamide | 492.0 |
| 6 | 10 | 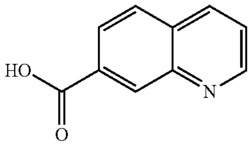 [SMILES: O=C(O)c1ccc2cccnc2c1] | 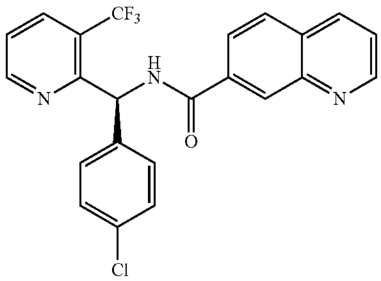 [SMILES: O=C(N[C@@H](c1ccc(Cl)cc1)c1ncccc1C(F)(F)F)c1ccc2cccnc2c1] | (S)-N-((4-chloro-phenyl)(3-(trifluoromethyl)-pyridin-2-yl)-methyl)-quinoline-7-carboxamide | 442.0 |
| 7 | 11 | 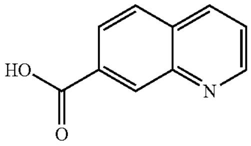 [SMILES: O=C(O)c1ccc2cccnc2c1] | 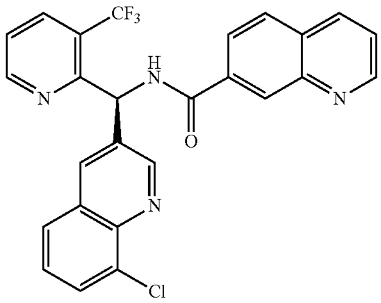 [SMILES: O=C(N[C@@H](c1cnc2c(Cl)cccc2c1)c1ncccc1C(F)(F)F)c1ccc2cccnc2c1] | (S)-N-((8-chloro-quinolin-3-yl)(3-(trifluoromethyl)-pyridin-2-yl)-methyl)-quinoline-7-carboxamide | 493.0 |
| 8 | 12 | 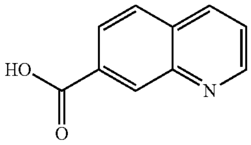 [SMILES: O=C(O)c1ccc2cccnc2c1] | 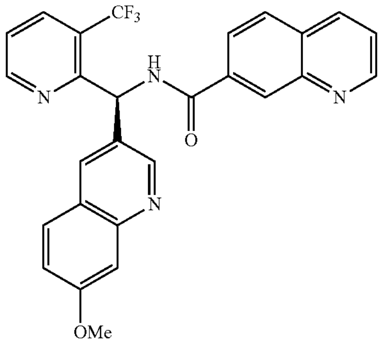 [SMILES: COc1ccc2cc([C@H](NC(=O)c3ccc4cccnc4c3)c3ncccc3C(F)(F)F)cnc2c1] | (S)-N-((7-methoxyquinolin-3-yl)(3-(trifluoro-methyl)pyridin-2 yl)methyl)-quinoline-7-carboxamide | 489.0 |
| 9 | 13 | 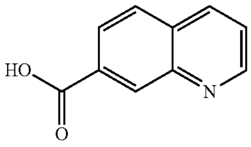 [SMILES: O=C(O)c1ccc2cccnc2c1] | 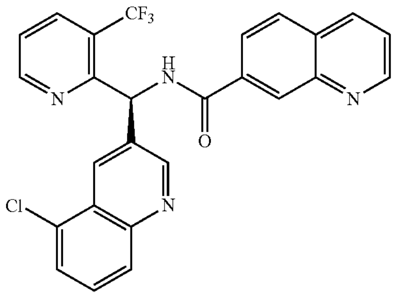 [SMILES: O=C(N[C@@H](c1cnc2cccc(Cl)c2c1)c1ncccc1C(F)(F)F)c1ccc2cccnc2c1] | (S)-N-((5-chloro-quinolin-3-yl)(3-(trifluoromethyl) pyridin-2-yl)-methyl)-quinoline-7-carboxamide | 493.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 10 | 4 | 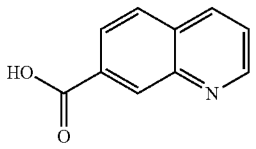 [SMILES: O=C(O)c1ccc2cccnc2c1] | 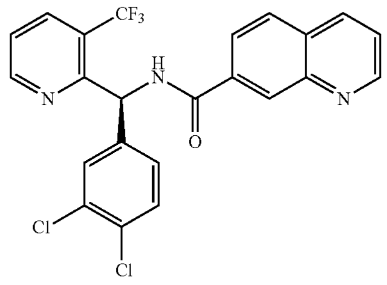 [SMILES: O=C(N[C@@H](c1ccc(Cl)c(Cl)c1)c1ncccc1C(F)(F)F)c1ccc2cccnc2c1] | (S)-N-((3,4-dichlorophenyl)-(3-(trifluoro-methyl)pyridin-2-yl)methyl)-quinoline-7-carboxamide | 475.9 |
| 11 | 9 | 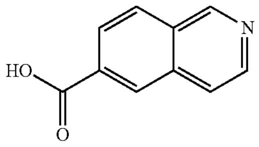 [SMILES: O=C(O)c1ccc2cnccc2c1] | 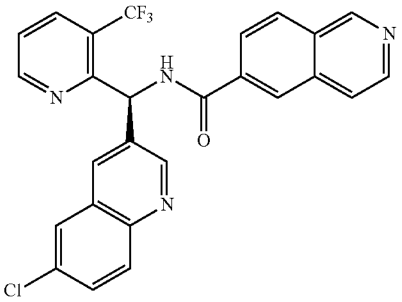 [SMILES: O=C(N[C@@H](c1cnc2ccc(Cl)cc2c1)c1ncccc1C(F)(F)F)c1ccc2cnccc2c1] | (S)-N-((6-chloro-quinolin-3-yl)(3-(trifluoromethyl)-pyridin-2-yl)-methyl)-isoquinoline-6-carboxamide | 493.0 |
| 12 | 14 | 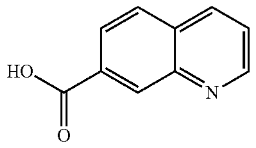 [SMILES: O=C(O)c1ccc2cccnc2c1] | 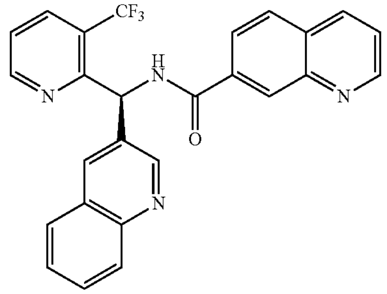 | (S)-N-(quinolin-3-yl(3-(trifluoro-methyl)pyridin-2-yl)methyl)-quinoline-7-carboxamide | 459.0 |
| 13 | 15 | 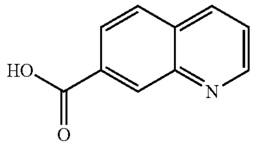 [SMILES: O=C(O)c1ccc2cccnc2c1] | 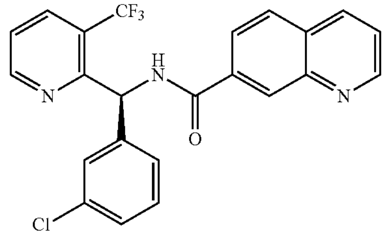 [SMILES: O=C(N[C@@H](c1cccc(Cl)c1)c1ncccc1C(F)(F)F)c1ccc2cccnc2c1] | (S)-N-((3-chloro-phenyl)(3-(trifluoromethyl)-pyridin-2-yl)-methyl)-quinoline-7-carboxamide | 442.0 |
| 14 | 16 | 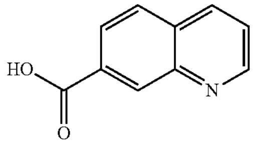 [SMILES: O=C(O)c1ccc2cccnc2c1] | 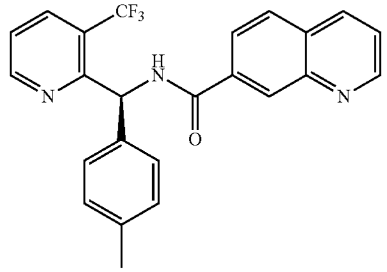 [SMILES: Cc1ccc([C@H](NC(=O)c2ccc3cccnc3c2)c2ncccc2C(F)(F)F)cc1] | (S)-N-(p-tolyl(3-(trifluoromethyl)pyridin-2-yl)-methyl)-quinoline-7-carboxamide | 422.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 15 | 17 | 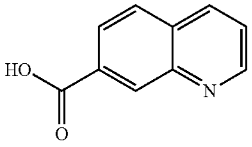 [SMILES: O=C(O)c1ccc2cccnc2c1] | 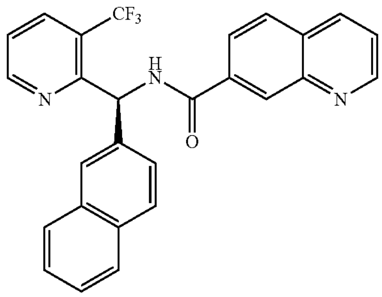 [SMILES: O=C(N[C@@H](c1ccc2ccccc2c1)c1ncccc1C(F)(F)F)c1ccc2cccnc2c1] | (S)-N-(naphthalen-2-yl(3-(trifluoro-methyl)pyridin-2-yl)methyl)-quinoline-7-carboxamide | 458.0 |
| 16 | 9 | 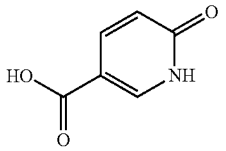 | 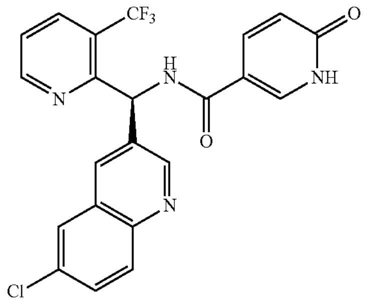 [SMILES: O=C(N[C@@H](c1cnc2ccc(Cl)cc2c1)c1ncccc1C(F)(F)F)c1ccc(=O)[nH]c1] | (S)-N-((6-chloro-quinolin-3-yl)(3-(trifluoromethyl)-pyridin-2-yl)-methyl)-6-hydroxy-nicotinamide | 458.9 |
| 17 | 18 | 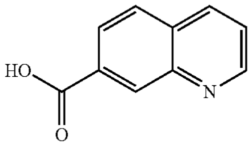 [SMILES: O=C(O)c1ccc2cccnc2c1] | 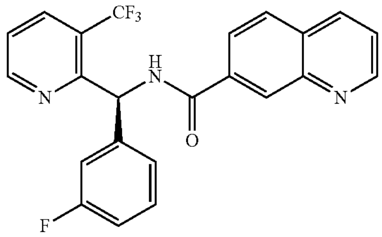 [SMILES: O=C(N[C@@H](c1cccc(F)c1)c1ncccc1C(F)(F)F)c1ccc2cccnc2c1] | (S)-N-((3-fluoro-phenyl)(3-(trifluoromethyl)-pyridin-2-yl)-methyl)-quinoline-7-carboxamide | 426.0 |
| 18 | 19 | 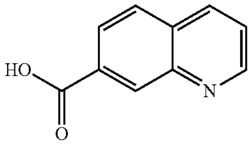 [SMILES: O=C(O)c1ccc2cccnc2c1] | 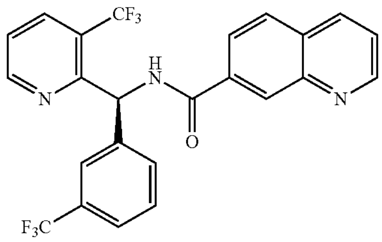 [SMILES: O=C(N[C@@H](c1cccc(C(F)(F)F)c1)c1ncccc1C(F)(F)F)c1ccc2cccnc2c1] | (S)-N-((3-(trifluoromethyl)-phenyl)(3-(trifluoromethyl)-pyridin-2-yl)-methyl)-quinoline-7-carboxamide | 476.0 |
| 19 | 3 | 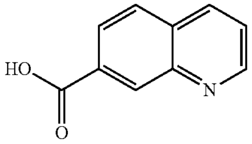 [SMILES: O=C(O)c1ccc2cccnc2c1] | 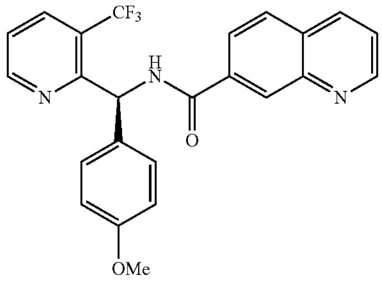 [SMILES: COc1ccc([C@H](NC(=O)c2ccc3cccnc3c2)c2ncccc2C(F)(F)F)cc1] | (S)-N-((4-methoxyphenyl)-(3-(trifluoro-methyl)pyridin-2-yl)methyl)-quinoline-7-carboxamide | 438.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 20 | 20 | 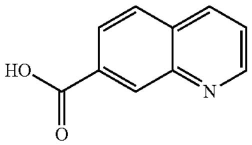 [SMILES: O=C(O)c1ccc2cccnc2c1] | 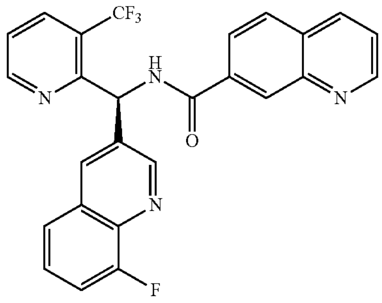 [SMILES: O=C(N[C@@H](c1cnc2c(F)cccc2c1)c1ncccc1C(F)(F)F)c1ccc2cccnc2c1] | (S)-N-((8-fluoro-quinolin-3-yl)(3-(trifluoromethyl)-pyridin-2-yl)-methyl)-quinoline-7-carboxamide | 477.0 |
| 21 | 21 | 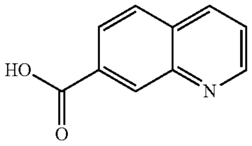 [SMILES: O=C(O)c1ccc2cccnc2c1] | 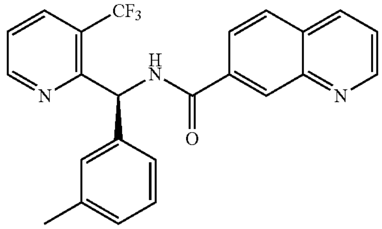 [SMILES: Cc1cccc([C@H](NC(=O)c2ccc3cccnc3c2)c2ncccc2C(F)(F)F)c1] | (S)-N-(m-tolyl(3-(trifluoromethyl)-pyridin-2-yl)-methyl)-quinoline-7-carboxamide | 422.0 |
| 22 | 22 | 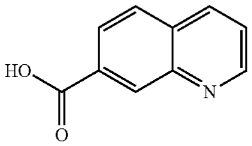 [SMILES: O=C(O)c1ccc2cccnc2c1] | 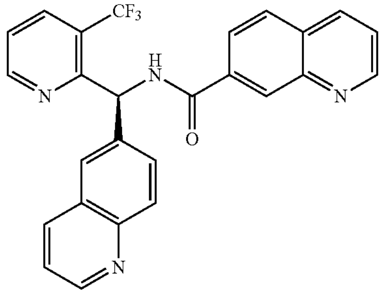 [SMILES: O=C(N[C@@H](c1ccc2ncccc2c1)c1ncccc1C(F)(F)F)c1ccc2cccnc2c1] | (S)-N-(quinolin-6-yl(3-(trifluoro-methyl)pyridin-2-yl)methyl)-quinoline-7-carboxamide | 458.9 |
| 23 | 24 | 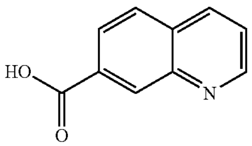 [SMILES: O=C(O)c1ccc2cccnc2c1] | 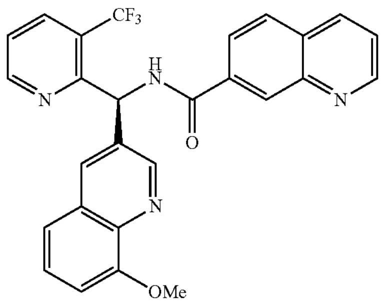 [SMILES: COc1cccc2cc([C@H](NC(=O)c3ccc4cccnc4c3)c3ncccc3C(F)(F)F)cnc12] | (S)-N-((8-methoxyquinolin-3-yl)(3-(trifluoro-methyl)pyridin-2-yl)methyl)-quinoline-7-carboxamide | 489.0 |
| 24 | 25 | 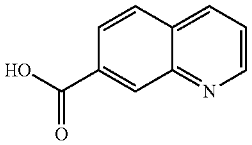 [SMILES: O=C(O)c1ccc2cccnc2c1] | 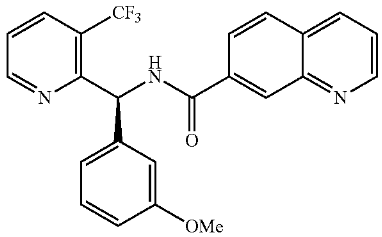 [SMILES: COc1cccc([C@H](NC(=O)c2ccc3cccnc3c2)c2ncccc2C(F)(F)F)c1] | (S)-N-((3-methoxyphenyl)-(3-(trifluoro-methyl)pyridin-2-yl)methyl)-quinoline-7-carboxamide | 438.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 25 | 26 | 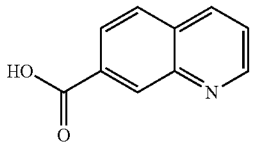 [SMILES: O=C(O)c1ccc2cccnc2c1] | 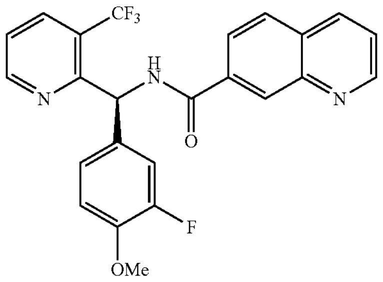 [SMILES: COc1ccc([C@H](NC(=O)c2ccc3cccnc3c2)c2ncccc2C(F)(F)F)cc1F] | (S)-N-((3-fluoro-4-methoxyphenyl)-(3-(trifluoro-methyl)pyridin-2-yl)methyl)-quinoline-7-carboxamide | 456.0 |
| 26 | 53 | 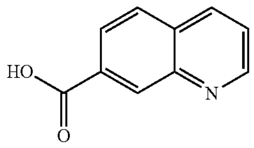 [SMILES: O=C(O)c1ccc2cccnc2c1] | 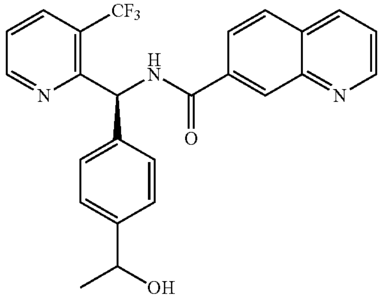 [SMILES: CC(O)c1ccc([C@H](NC(=O)c2ccc3cccnc3c2)c2ncccc2C(F)(F)F)cc1] | N-((1S)-(4-(1-hydroxyethyl)-phenyl)(3-(trifluoromethyl)-pyridin-2-yl)-methyl)-quinoline-7-carboxamide | 452.0 |
| 27 | 27 | 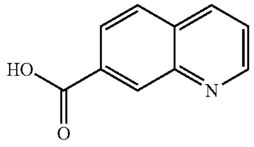 [SMILES: O=C(O)c1ccc2cccnc2c1] | 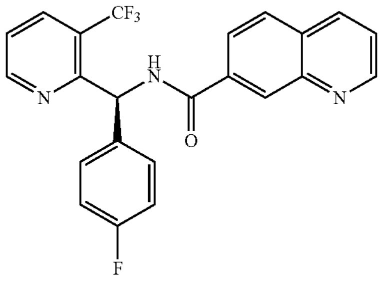 [SMILES: O=C(N[C@@H](c1ccc(F)cc1)c1ncccc1C(F)(F)F)c1ccc2cccnc2c1] | (S)-N-((4-fluoro-phenyl)(3-(trifluoromethyl)-pyridin-2-yl)-methyl)-quinoline-7-carboxamide | 426.0 |
| 28 | 43 | 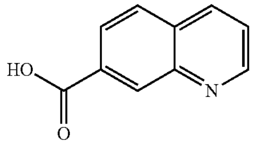 [SMILES: O=C(O)c1ccc2cccnc2c1] | 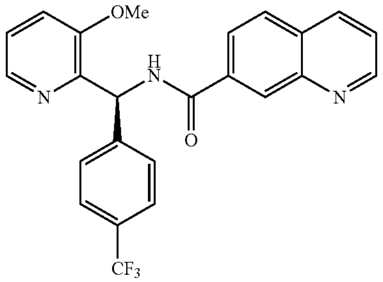 [SMILES: COc1cccnc1[C@@H](NC(=O)c1ccc2cccnc2c1)c1ccc(C(F)(F)F)cc1] | (S)-N-((3-methoxypyridin-2-yl)(4-(trifluoro-methyl)phenyl)-methyl)-quinoline-7-carboxamide | 438.2 |
| 29 | 1 | 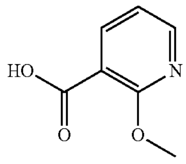 | 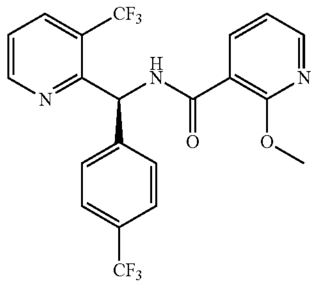 [SMILES: COc1ncccc1C(=O)N[C@@H](c1ccc(C(F)(F)F)cc1)c1ncccc1C(F)(F)F] | (S)-2-methoxy-N-((4-(trifluoro-methyl)phenyl)-(3-(trifluoro-methyl)pyridin-2-yl)methyl)-nicotinamide | 456.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 30 | 1 | 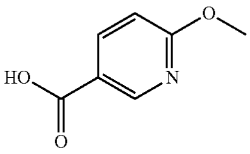 | 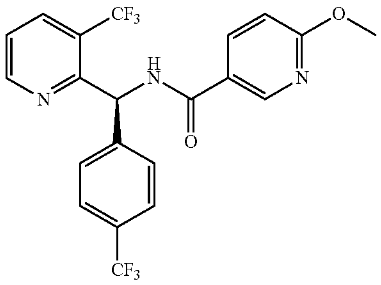 | (S)-6-methoxy-N-((4-(trifluoro-methyl)phenyl)-(3-(trifluoro-methyl)pyridin-2-yl)methyl)-nicotinamide | 456.0 |
| 31 | 1 | 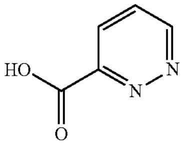 | 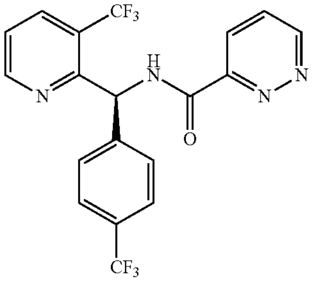 [SMILES: O=C(N[C@@H](c1ccc(C(F)(F)F)cc1)c1ncccc1C(F)(F)F)c1cccnn1] | (S)-N-((4-(trifluoromethyl)-phenyl)(3-(trifluoromethyl)-pyridin-2-yl)-methyl)-pyridazine-3-carboxamide | 427.1 |
| 32 | 1 | 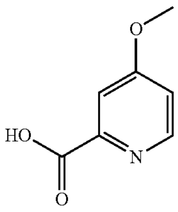 | 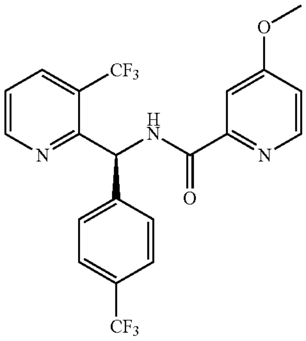 [SMILES: COc1ccnc(C(=O)N[C@@H](c2ccc(C(F)(F)F)cc2)c2ncccc2C(F)(F)F)c1] | (S)-4-methoxy-N-((4-(trifluoro-methyl)phenyl)-(3-(trifluoro-methyl)pyridin-2-yl)methyl)-picolinamide | 456.0 |
| 33 | 1 | 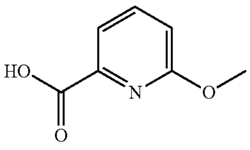 | 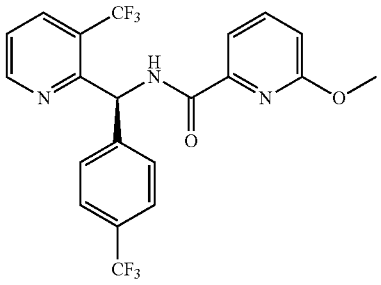 | (S)-6-methoxy-N-((4-(trifluoro-methyl)phenyl)-(3-(trifluoro-methyl)pyridin-2-yl)methyl)-picolinamide | 456.0 |
| 34 | 1 | 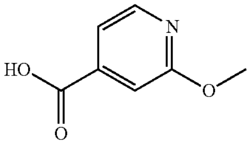 | 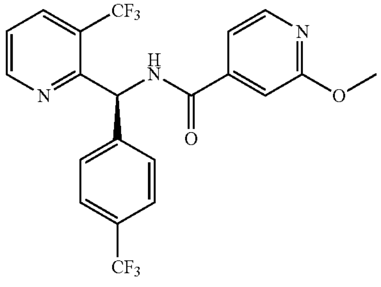 [SMILES: COc1cc(C(=O)N[C@@H](c2ccc(C(F)(F)F)cc2)c2ncccc2C(F)(F)F)ccn1] | (5)-2-methoxy-N-((4-(trifluoro-methyl)phenyl)-(3-(trifluoro-methyl)pyridin-2-yl)methyl)-isonicotinamide | 456.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 35 | 2a | 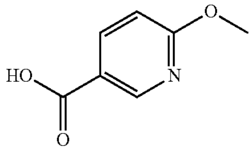 | 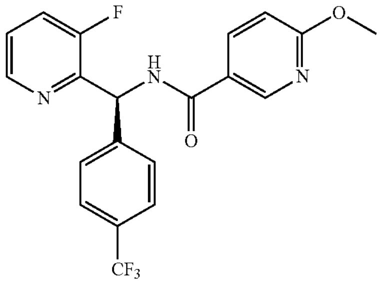 [SMILES: COc1ccc(C(=O)N[C@@H](c2ccc(C(F)(F)F)cc2)c2ncccc2F)cn1] | N-((3-fluoro-pyridin-2-yl)(4-(trifluoromethyl)-phenyl)methyl)-6-methoxy-nicotinamide | 406.1 |
| 36 | 2a | 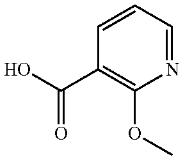 | 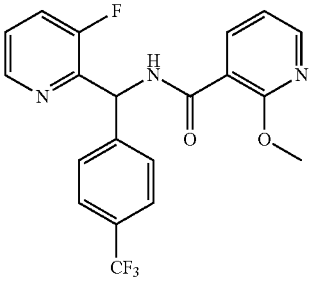 [SMILES: COc1ncccc1C(=O)NC(c1ccc(C(F)(F)F)cc1)c1ncccc1F] | N-((3-fluoro-pyridin-2-yl)(4-(trifluoromethyl)-phenyl)methyl)-2-methoxy-nicotinamide | 406.1 |
| 37 | 1 | 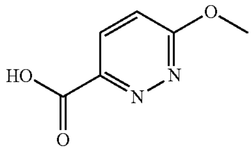 | 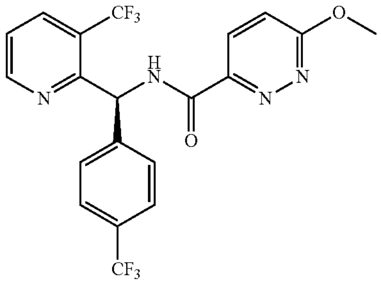 | (S)-6-methoxy-N-((4-(trifluoro-methyl)phenyl)-(3-(trifluoro-methyl)pyridin-2-yl)methyl)-pyridazine-3-carboxamide | 457.1 |
| 38 | 1 | 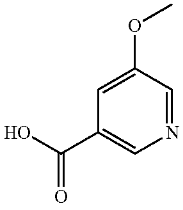 | 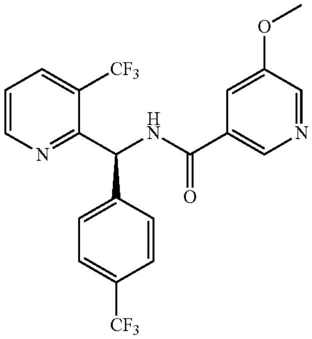 [SMILES: COc1cncc(C(=O)N[C@@H](c2ccc(C(F)(F)F)cc2)c2ncccc2C(F)(F)F)c1] | (S)-5-methoxy-N-((4-(trifluoro-methyl)phenyl)-(3-(trifluoro-methyl)pyridin-2-yl)methyl)-nicotinamide | 456.0 |
| 39 | 1 | 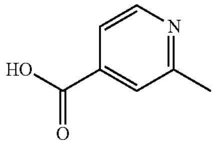 | 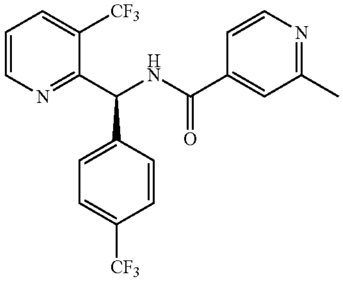 [SMILES: Cc1cc(C(=O)N[C@@H](c2ccc(C(F)(F)F)cc2)c2ncccc2C(F)(F)F)ccn1] | (S)-2-methyl-N-((4-(trifluoro-methyl)phenyl)-(3-(trifluoro-methyl)pyridin-2-yl)methyl)-isonicotinamide | 440.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 40 | 1 | 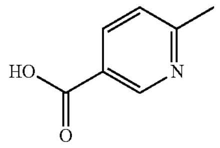 | 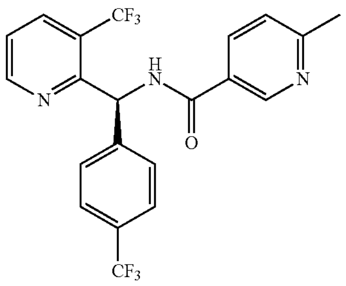 [SMILES: Cc1ccc(C(=O)N[C@@H](c2ccc(C(F)(F)F)cc2)c2ncccc2C(F)(F)F)cn1] | (S)-6-methyl-N-((4-(trifluoro-methyl)phenyl)-(3-(trifluoro-methyl)pyridin-2-yl)methyl)-nicotinamide | 440.1 |
| 41 | 1 | 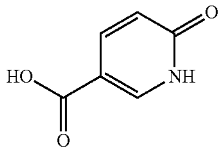 | 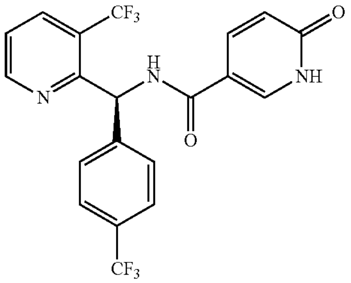 [SMILES: O=C(N[C@@H](c1ccc(C(F)(F)F)cc1)c1ncccc1C(F)(F)F)c1ccc(=O)[nH]c1] | (S)-6-oxo-N-((4-(trifluoromethyl)-phenyl)(3-(trifluoromethyl)-pyridin-2-yl)-methyl)-1,6-dihydropyridine-3-carboxamide | 442.1 |
| 42 | 1 | 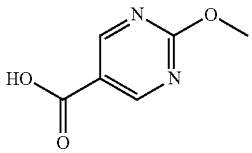 | 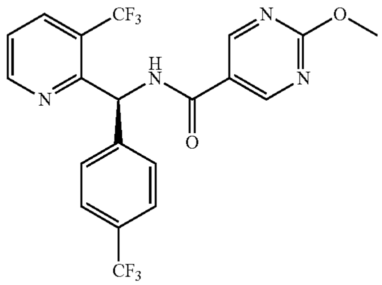 [SMILES: COc1ncc(C(=O)N[C@@H](c2ccc(C(F)(F)F)cc2)c2ncccc2C(F)(F)F)cn1] | (S)-2-methoxy-N-((4-(trifluoro-methyl)phenyl)-(3-(trifluoro-methyl)pyridin-2-yl)methyl)-pyrimidine-5-carboxamide | 457.1 |
| 43 | 1 | 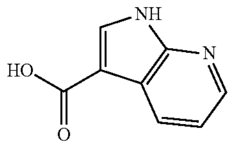 [SMILES: O=C(O)c1c[nH]c2ncccc12] | 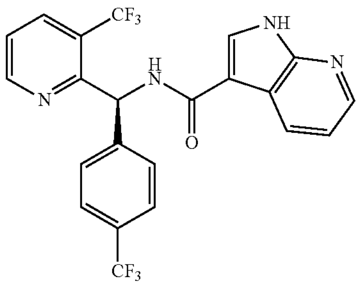 [SMILES: O=C(N[C@@H](c1ccc(C(F)(F)F)cc1)c1ncccc1C(F)(F)F)c1c[nH]c2ncccc12] | (S)-N-((4-(trifluoromethyl)-phenyl)(3-(trifluoromethyl)-pyridin-2-yl)-methyl)-1H-pyrrolo[2,3-b]pyridine-3-carboxamide | 465.0 |
| 44 | 1 | 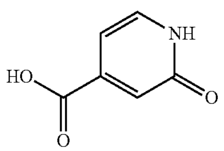 | 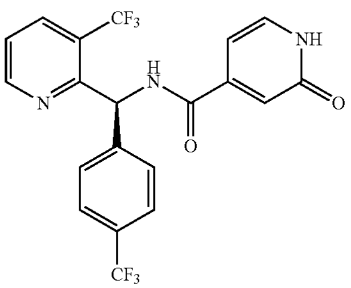 [SMILES: O=C(N[C@@H](c1ccc(C(F)(F)F)cc1)c1ncccc1C(F)(F)F)c1cc[nH]c(=O)c1] | (S)-2-hydroxy-N-((4-(trifluoro-methyl)phenyl)-(3-(trifluoro-methyl)pyridin-2-yl)methyl)-isonicotinamide | 442.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 45 | 1 | 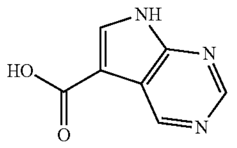 [SMILES: O=C(O)c1c[nH]c2ncncc12] | 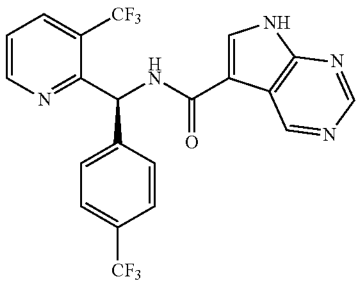 | (S)-N-((4-(trifluoromethyl)-phenyl)(3-(trifluoromethyl)-pyridin-2-yl)-methyl)-7H-pyrrolo[2,3-d]pyrimidine-5-carboxamide | 466.1 |
| 46 | 2 | 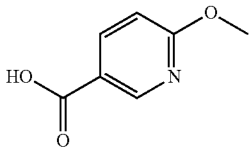 | 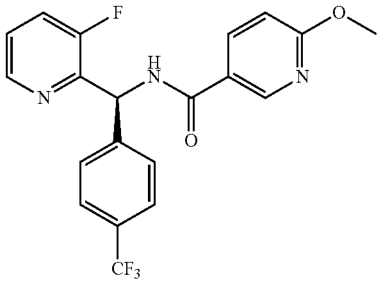 [SMILES: COc1ccc(C(=O)N[C@@H](c2ccc(C(F)(F)F)cc2)c2ncccc2F)cn1] | (S)-N-((3-fluoro-pyridin-2-yl)(4-(trifluoromethyl)-phenyl)methyl)-6-methoxy-nicotinamide | 406.1 |
| 47 | 2 | 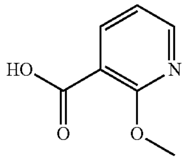 | 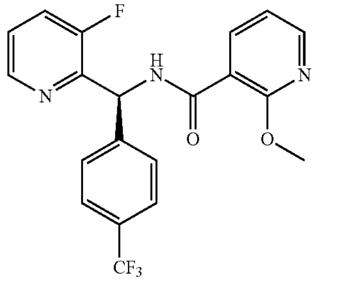 | (S)-N-((3-fluoro-pyridin-2-yl)(4-(trifluoromethyl)-phenyl)methyl)-2-methoxy-nicotinamide | 406.1 |
| 48 | 1 | 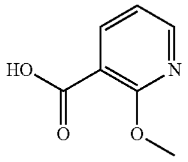 | 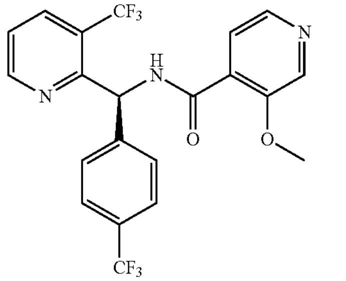 [SMILES: COc1cnccc1C(=O)N[C@@H](c1ccc(C(F)(F)F)cc1)c1ncccc1C(F)(F)F] | (S)-3-methoxy-N-((4-(trifluoro-methyl)phenyl)-(3-(trifluoro-methyl)pyridin-2-yl)methyl)-isonicotinamide | 456.0 |
| 49 | 1 | 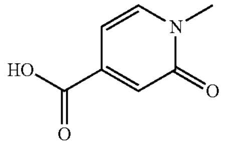 | 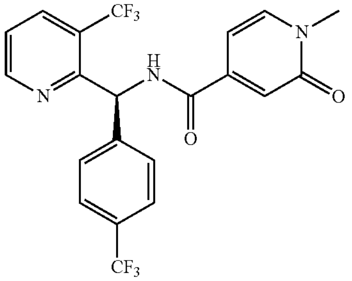 [SMILES: Cn1ccc(C(=O)N[C@@H](c2ccc(C(F)(F)F)cc2)c2ncccc2C(F)(F)F)cc1=O] | (S)-1-methyl-2-oxo-N-((4-(trifluoromethyl)-phenyl)(3-(trifluoromethyl)-pyridin-2-yl)-methyl)-1,2-dihydropyridine-4-carboxamide | 456.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 50 | 1 | 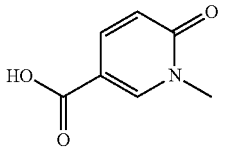 | 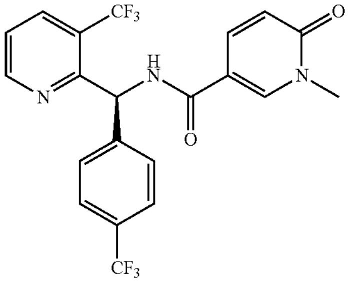 | (S)-1-methyl-6-oxo-N-((4-(trifluoromethyl)-phenyl)(3-(trifluoromethyl)-pyridin-2-yl)-methyl)-1,6-dihydropyridine-3-carboxamide | 456.0 |
| 51 | 2 | 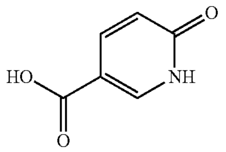 | 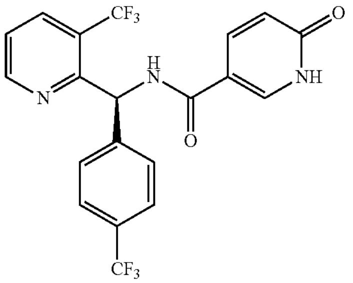 [SMILES: O=C(N[C@@H](c1ccc(C(F)(F)F)cc1)c1ncccc1C(F)(F)F)c1ccc(=O)[nH]c1] | (S)-N-((3-fluoro-pyridin-2-yl)(4-(trifluoromethyl)-phenyl)methyl)-6-oxo-1,6-dihydropyridme-3-carboxamide | 392.1 |
| 52 | 2 | 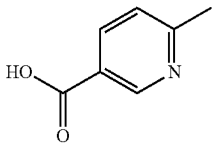 | 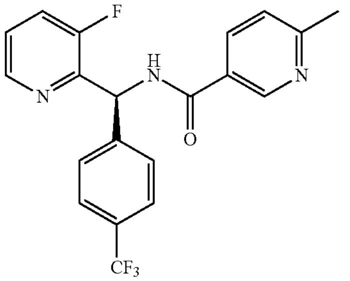 [SMILES: Cc1ccc(C(=O)N[C@@H](c2ccc(C(F)(F)F)cc2)c2ncccc2F)cn1] | (S)-N-((3-fluoro-pyridin-2-yl)(4-(trifluoromethyl)-phenyl)methyl)-6-methyl-nicotinamide | 390.2 |
| 53 | 2 | 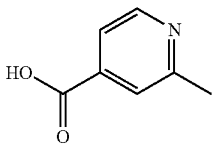 | 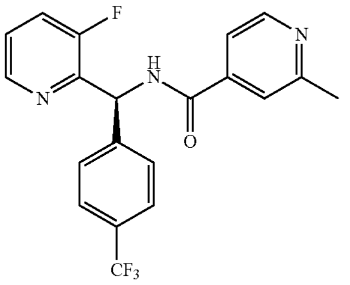 [SMILES: Cc1cc(C(=O)N[C@@H](c2ccc(C(F)(F)F)cc2)c2ncccc2F)ccn1] | (S)-N-((3-fluoro-pyridin-2-yl)(4-(trifluoromethyl)-phenyl)methyl)-2-methyl-isonicotinamide | 390.2 |
| 54 | 2 | 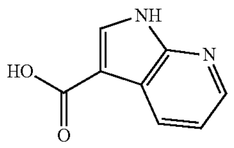 | 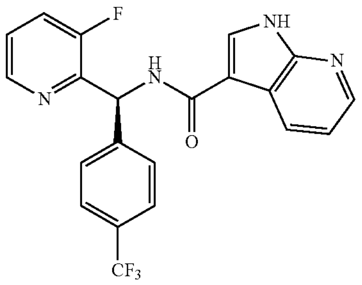 [SMILES: O=C(N[C@@H](c1ccc(C(F)(F)F)cc1)c1ncccc1F)c1c[nH]c2ncccc12] | (S)-N-((3-fluoro-pyridin-2-yl)(4-(trifluoromethyl)-phenyl)methyl)-1H-pyrrolo[2,3-b]pyridine-3-carboxamide | 415.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 55 | 1 | 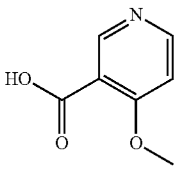 | 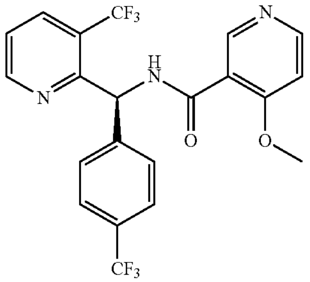 [SMILES: COc1ccncc1C(=O)N[C@@H](c1ccc(C(F)(F)F)cc1)c1ncccc1C(F)(F)F] | (S)-4-methoxy-N-((4-(trifluoro-methyl)phenyl)-(3-(trifluoro-methyl)pyridin-2-yl)methyl)-nicotinamide | 456.0 |
| 56 | 1 | 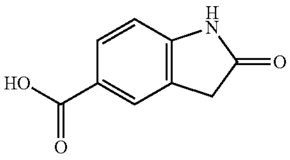 [SMILES: O=C1Cc2cc(C(=O)O)ccc2N1] | 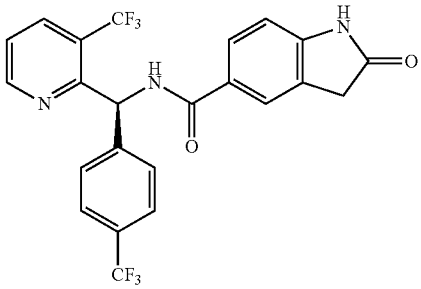 [SMILES: O=C1Cc2cc(C(=O)N[C@@H](c3ccc(C(F)(F)F)cc3)c3ncccc3C(F)(F)F)ccc2N1] | (S)-2-oxo-N-((4-(trifluoromethyl)-phenyl)(3-(trifluoromethyl)-pyridin-2-yl)-methyl)indoline-5-carboxamide | 480.0 |
| 57 | 1 | 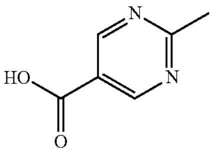 | 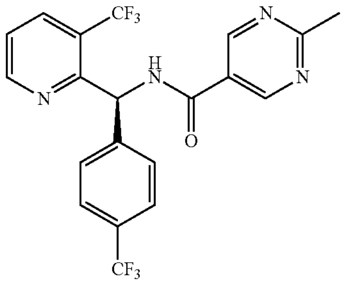 [SMILES: Cc1ncc(C(=O)N[C@@H](c2ccc(C(F)(F)F)cc2)c2ncccc2C(F)(F)F)cn1] | (S)-2-methyl-N-((4-(trifluoro-methyl)phenyl)-(3-(trifluoro-methyl)pyridin-2-yl)methyl)-pyrimidine-5-carboxamide | 441.0 |
| 58 | 1 | 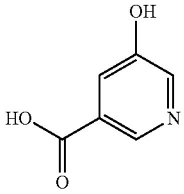 | 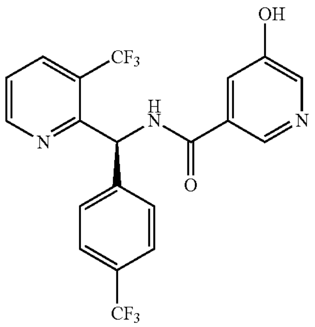 [SMILES: O=C(N[C@@H](c1ccc(C(F)(F)F)cc1)c1ncccc1C(F)(F)F)c1cncc(O)c1] | (S)-5-hydroxy-N-((4-(trifluoro-methyl)phenyl)-(3-(trifluoro-methyl)pyridin-2-yl)methyl)-nicotinamide | 442.1 |
| 59 | 1 | 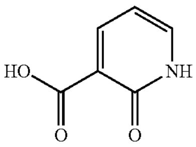 | 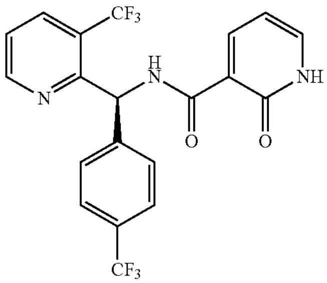 [SMILES: O=C(N[C@@H](c1ccc(C(F)(F)F)cc1)c1ncccc1C(F)(F)F)c1ccc[nH]c1=O] | (S)-2-oxo-N-((4-(trifluoromethyl)-phenyl)(3-(trifluoromethyl)-pyridin-2-yl)-methyl)-1,2-dihydropyridine-3-carboxamide | 442.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 60 | 1 | 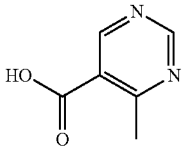 | 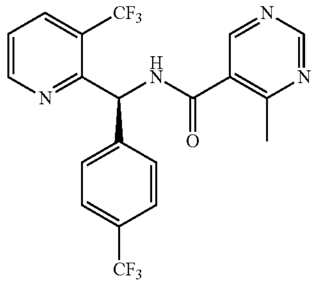 [SMILES: Cc1ncncc1C(=O)N[C@@H](c1ccc(C(F)(F)F)cc1)c1ncccc1C(F)(F)F] | (S)-4-methyl-N-((4-(trifluoro-methyl)phenyl)-(3-(trifluoro-methyl)pyridin-2-yl)methyl)-pyrimidine-5-carboxamide | 441.0 |
| 61 | 1 | 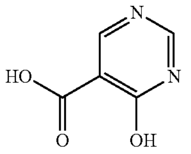 | 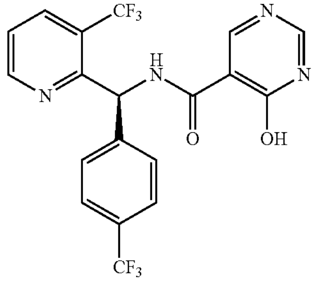 [SMILES: O=C(N[C@@H](c1ccc(C(F)(F)F)cc1)c1ncccc1C(F)(F)F)c1cncnc1O] | (S)-4-hydroxy-N-((4-(trifluoro-methyl)phenyl)-(3-(trifluoro-methyl)pyridin-2-yl)methyl)-pyrimidine-5-carboxamide | 443.1 |
| 62 | 1 | 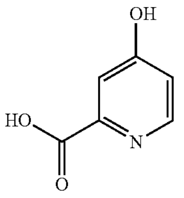 | 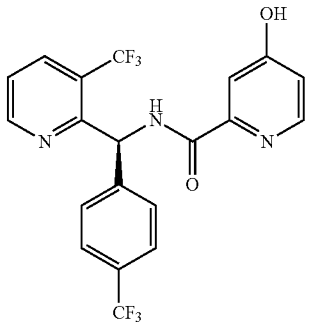 [SMILES: O=C(N[C@@H](c1ccc(C(F)(F)F)cc1)c1ncccc1C(F)(F)F)c1cc(O)ccn1] | (S)-4-hydroxy-N-((4-(trifluoro-methyl)phenyl)-(3-(trifluoro-methyl)pyridin-2-yl)methyl)-picolinamide | 442.1 |
| 63 | 1 | 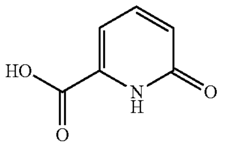 | 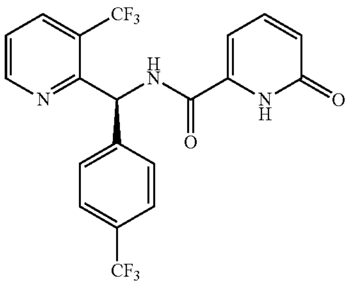 [SMILES: O=C(N[C@@H](c1ccc(C(F)(F)F)cc1)c1ncccc1C(F)(F)F)c1cccc(=O)[nH]1] | (S)-6-oxo-N-((4-(trifluoromethyl)-phenyl)(3-(trifluoromethyl)-pyridin-2-yl)-methyl)-1,6-dihydropyridine-2-carboxamide | 442.1 |
| 64 | 1 | 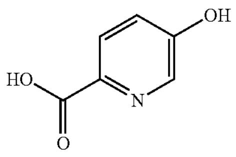 | 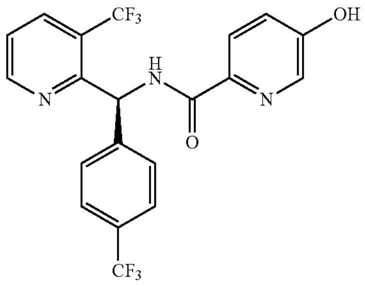 [SMILES: O=C(N[C@@H](c1ccc(C(F)(F)F)cc1)c1ncccc1C(F)(F)F)c1ccc(O)cn1] | (S)-5-hydroxy-N-((4-(trifluoro-methyl)phenyl)-(3-(trifluoro-methyl)pyridin-2-yl)methyl)-picolinamide | 442.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 65 | 1 | 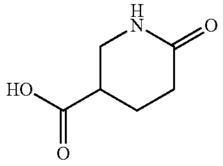 | 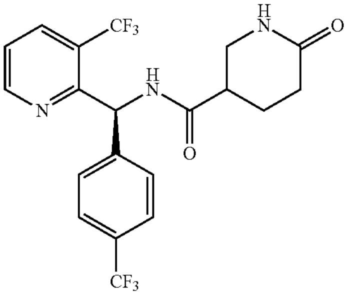 [SMILES: O=C1CCC(C(=O)N[C@@H](c2ccc(C(F)(F)F)cc2)c2ncccc2C(F)(F)F)CN1] | 6-oxo-N-((S)-(4-(trifluoromethyl)-phenyl)(3-(trifluoromethyl)-pyridin-2-yl)-methyl)-piperidine-3-carboxamide | 446.1 |
| 66 | 1 | 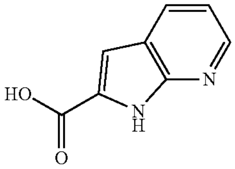 [SMILES: O=C(O)c1cc2cccnc2[nH]1] | 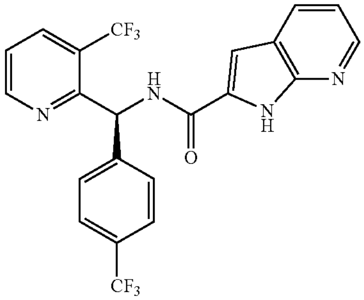 [SMILES: O=C(N[C@@H](c1ccc(C(F)(F)F)cc1)c1ncccc1C(F)(F)F)c1cc2cccnc2[nH]1] | (S)-N-((4-(trifluoromethyl)-phenyl)(3-(trifluoromethyl)-pyridin-2-yl)-methyl)-1H-pyrrolo[2,3-b]pyridine-2-carboxamide | 465.0 |
| 67 | 1 | 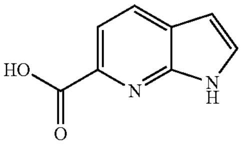 [SMILES: O=C(O)c1ccc2cc[nH]c2n1] | 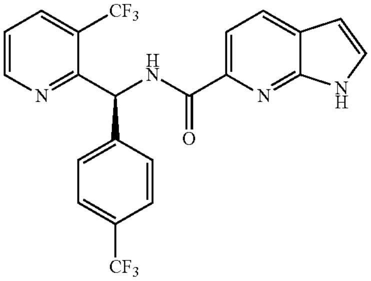 [SMILES: O=C(N[C@@H](c1ccc(C(F)(F)F)cc1)c1ncccc1C(F)(F)F)c1ccc2cc[nH]c2n1] | (S)-N-((4-(trifluoromethyl)phenyl)(3-(trifluoromethyl)pyridin-2-yl)-methyl)-1H-pyrrolo[2,3-b]pyridine-6-carboxamide | 465.0 |
| 68 | 2 | 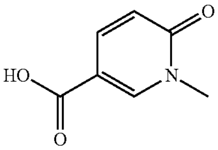 | 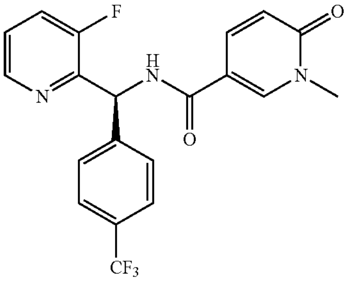 [SMILES: Cn1cc(C(=O)N[C@@H](c2ccc(C(F)(F)F)cc2)c2ncccc2F)ccc1=O] | (S)-N-((3-fluoro-pyridin-2-yl)(4-(trifluoromethyl)-phenyl)methyl)-1-methYl-6-oxo-1,6-dihydro-pyridine-3-carboxamide | 406.1 |
| 69 | 1 | 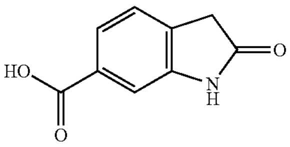 [SMILES: O=C1Cc2ccc(C(=O)O)cc2N1] | 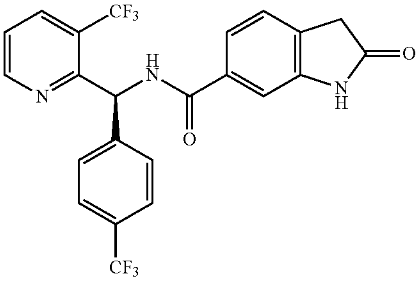 | (S)-2-oxo-N-((4-(trifluoromethyl)-phenyl)(3-(trifluoromethyl)-pyridin-2-yl)-methyl)indoline-6-carboxamide | 480.2 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 70 | 2 | 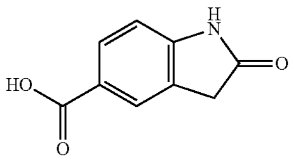 [SMILES: O=C1Cc2cc(C(=O)O)ccc2N1] | 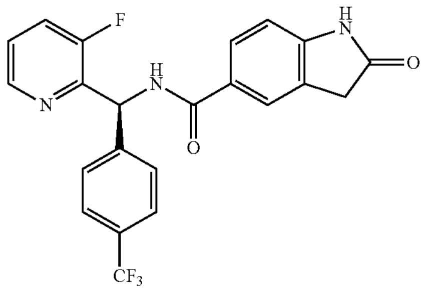 [SMILES: O=C1Cc2cc(C(=O)N[C@@H](c3ccc(C(F)(F)F)cc3)c3ncccc3F)ccc2N1] | (S)-N-((3-fluoro-pyridin-2-yl)(4-(trifluoromethyl)-phenyl)methyl)-2-oxoindoline-5-carboxamide | 430.1 |
| 71 | 2 | 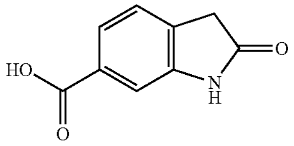 [SMILES: O=C1Cc2ccc(C(=O)O)cc2N1] | 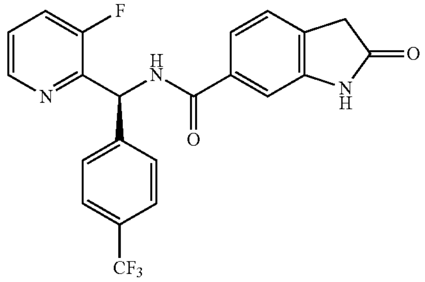 [SMILES: O=C1Cc2ccc(C(=O)N[C@@H](c3ccc(C(F)(F)F)cc3)c3ncccc3F)cc2N1] | (S)-N-((3-fluoro-pyridin-2-yl)(4-(trifluoromethyl)-phenyl)methyl)-2-oxoindoline-6-carboxamide | 430.1 |
| 72 | 2 | 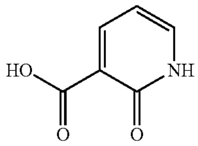 | 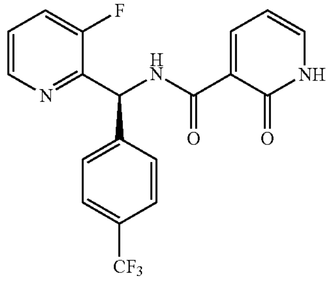 [SMILES: O=C(N[C@@H](c1ccc(C(F)(F)F)cc1)c1ncccc1F)c1ccc[nH]c1=O] | (S)-N-((3-fluoro-pyridin-2-yl)(4-(trifluoromethyl)-phenyl)methyl)-2-oxo-1,2-dihydropyndine-3-carboxamide | 392.1 |
| 73 | 2 | 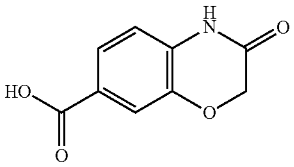 [SMILES: O=C1COc2cc(C(=O)O)ccc2N1] | 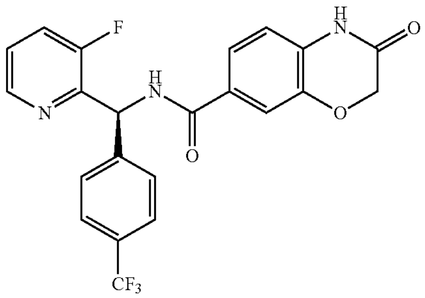 [SMILES: O=C1COc2cc(C(=O)N[C@@H](c3ccc(C(F)(F)F)cc3)c3ncccc3F)ccc2N1] | (S)-N-((3-fluoro-pyridin-2-yl)(4-(trifluoromethyl)-phenyl)methyl)-3-oxo-3,4-dihydro-2H-benzo[b][1,4]oxazine-7-carboxamide | 446.1 |
| 74 | 2 | 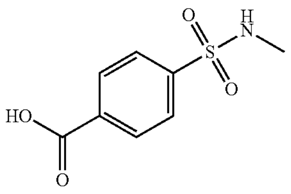 | 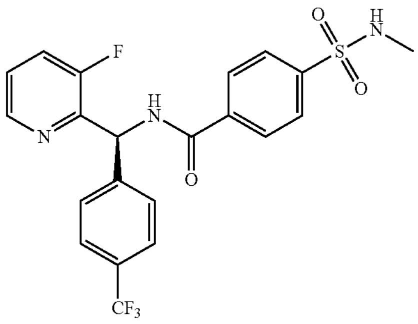 [SMILES: CNS(=O)(=O)c1ccc(C(=O)N[C@@H](c2ccc(C(F)(F)F)cc2)c2ncccc2F)cc1] | (S)-N-((3-fluoro-pyridin-2-yl)(4-(trifluoromethyl)-phenyl)methyl)-4-(N-methylsulfamoyl)benzamide | 468.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 75 | 2 | 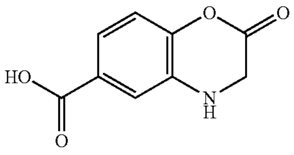 [SMILES: O=C1CNc2cc(C(=O)O)ccc2O1] | 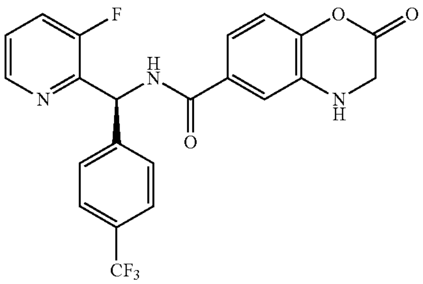 [SMILES: O=C1CNc2cc(C(=O)N[C@@H](c3ccc(C(F)(F)F)cc3)c3ncccc3F)ccc2O1] | (S)-N-((3-fluoro-pyridin-2-yl)(4-(trifluoromethyl)-phenyl)methyl)-2-oxo-3,4-dihydro-2H-benzo[b][1,4]oxazine-6-carboxamide | 446.1 |
| 76 | 2 | 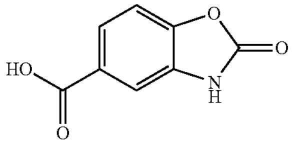 [SMILES: O=C(O)c1ccc2oc(=O)[nH]c2c1] | 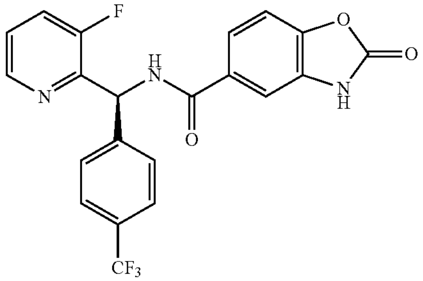 | (S)-N-((3-fluoro-pyridin-2-yl)(4-(trifluoromethyl)-phenyl)methyl)-2-oxo-2,3-dihydro-benzo[d]oxazole-5-carboxamide | 432.0 |
| 77 | 2 | 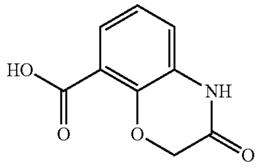 [SMILES: O=C1COc2c(cccc2C(=O)O)N1] | 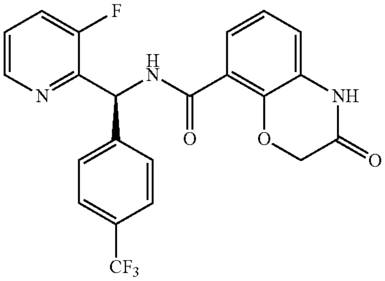 [SMILES: O=C1COc2c(cccc2C(=O)N[C@@H](c2ccc(C(F)(F)F)cc2)c2ncccc2F)N1] | (S)-N-((3-fluoro-pyridin-2-yl)(4-(trifluoromethyl)-phenyl)melhyl)-3-oxo-3,4-dihydro-2H-benzo[b][1,4]oxazine-8-carboxamide | 446.1 |
| 78 | 2 | 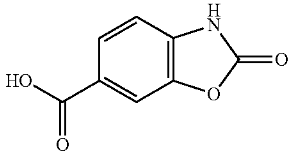 | 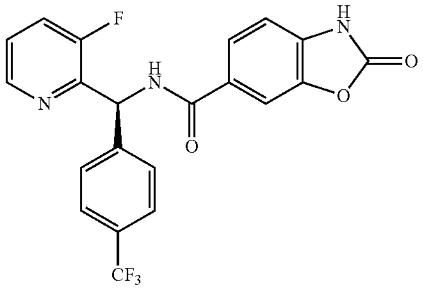 [SMILES: O=C(N[C@@H](c1ccc(C(F)(F)F)cc1)c1ncccc1F)c1ccc2[nH]c(=O)oc2c1] | (S)-N-((3-fluoro-pyridin-2-yl)(4-(trifluoromethyl)-phenyl)methyl)-2-oxo-2,3-dihydro-benzo[d]oxazole-6-carboxamide | 432.2 |
| 79 | 8 | 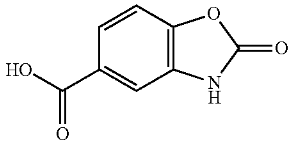 [SMILES: O=C(O)c1ccc2oc(=O)[nH]c2c1] | 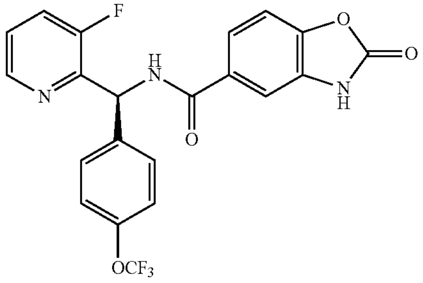 | (S)-N-((3-fluoro-pyridin-2-yl)(4-(trifluoro-methoxy)-phenyl)methyl)-2-oxo-2,3-dihydro-benzo[d]oxazole-5-carboxamide | 448.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 80 | 8 | 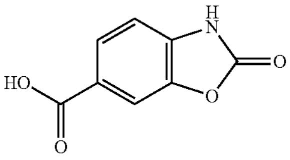 | 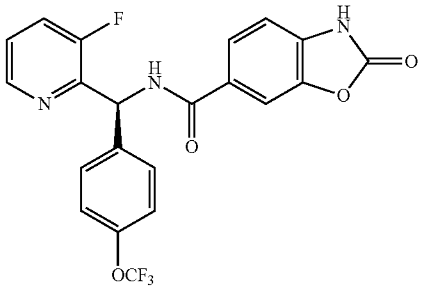 [SMILES: O=C(N[C@@H](c1ccc(OC(F)(F)F)cc1)c1ncccc1F)c1ccc2[nH]c(=O)oc2c1] | (S)-N-((3-fluoro-pyridin-2-yl)(4-(trifluoro-methoxy)-phenyl)methyl)-2-oxo-2,3-dihydro-benzo[d]oxazole-6-carboxamide | 448.1 |
| 81 | 8 | 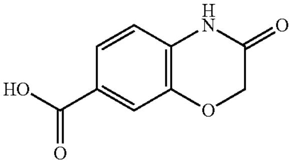 [SMILES: O=C1COc2cc(C(=O)O)ccc2N1] | 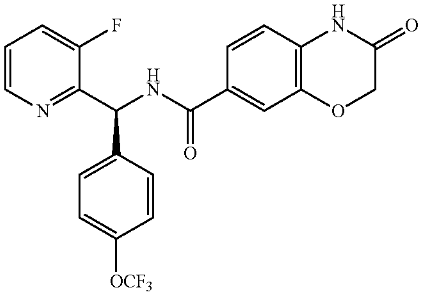 | (S)-N-((3-fluoro-pyridin-2-yl)(4-(trifluoro-methoxy)-phenyl)methyl)-3-oxo-3,4-dihydro-2H-benzo[b][1,4]oxazine-7-carboxamide | 462.0 |
| 82 | 44 | 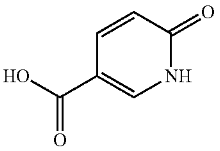 | 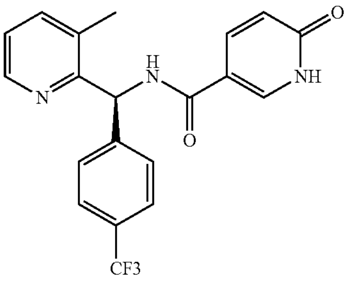 [SMILES: Cc1cccnc1[C@@H](NC(=O)c1ccc(=O)[nH]c1)c1ccc(C(F)(F)F)cc1] | (S)-N-((3-methylpyridin-2-yl)(4-(trifluoro-methyl)phenyl)-methyl)-6-oxo-1,6-dihydro-pyridine-3-carboxamide 2,2,2-trifluoroacetate | 388.1 |
| 83 | 44 | 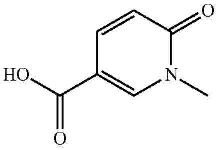 | 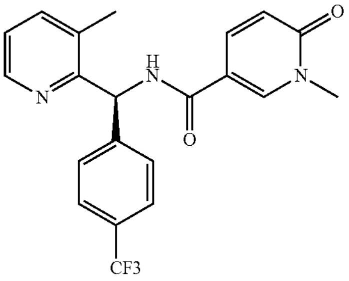 [SMILES: Cc1cccnc1[C@@H](NC(=O)c1ccc(=O)n(C)c1)c1ccc(C(F)(F)F)cc1] | (S)-1-methyl-N-((3-methylpyridin-2-yl)(4-(trifluoro-methyl)phenyl)-methyl)-6-oxo-1,6-dihydro-pyridine-3-carboxamide 2,2,2-trifluoroacetate | 402.2 |
| 84 | 44 | 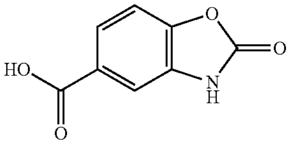 [SMILES: O=C(O)c1ccc2oc(=O)[nH]c2c1] | 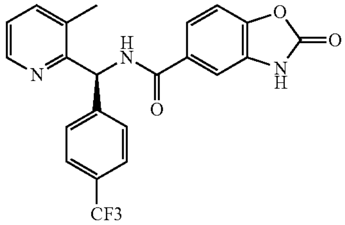 [SMILES: Cc1cccnc1[C@@H](NC(=O)c1ccc2oc(=O)[nH]c2c1)c1ccc(C(F)(F)F)cc1] | (S)-N-((3-methylpyridin-2-yl)(4-(trifluoro-methyl)phenyl)-methyl)-2-oxo-2,3-dihydro-benzo[d]oxazole-5-carboxamide | 428.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 85 | 44 | 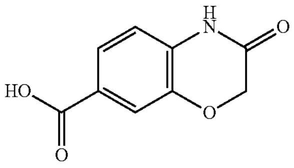 [SMILES: O=C1COc2cc(C(=O)O)ccc2N1] | 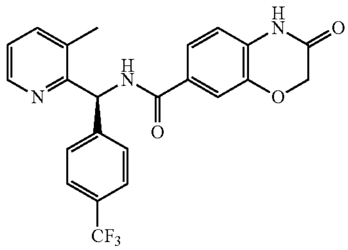 [SMILES: Cc1cccnc1[C@@H](NC(=O)c1ccc2c(c1)OCC(=O)N2)c1ccc(C(F)(F)F)cc1] | (S)-N-((3-methylpyridin-2-yl)(4-(trifluoro-methyl)phenyl)-methyl)-3-oxo-3,4-dihydro-2H-benzo[b][1,4] oxazine-7-carboxamide | 442.1 |
| 86 | 2 | 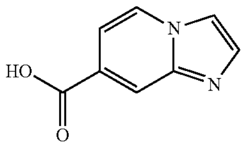 [SMILES: O=C(O)c1ccn2ccnc2c1] | 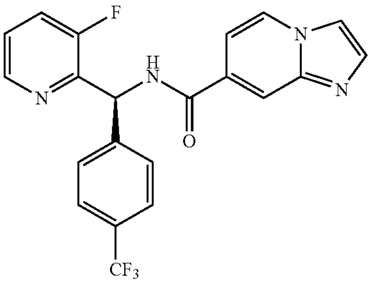 | (S)-N-((3-fluoro-pyridin-2-yl)(4-(trifluoromethyl)-phenyl)methyl)-imidazo[1,2-a]pyridine-7-carboxamide | 415.1 |
| 87 | 1 | 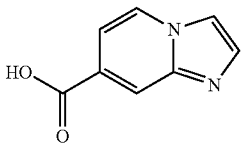 [SMILES: O=C(O)c1ccn2ccnc2c1] | 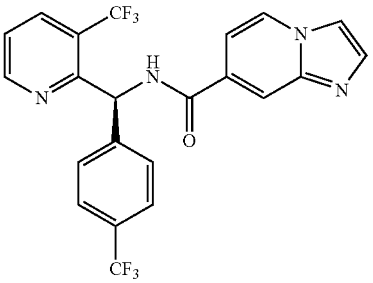 [SMILES: O=C(N[C@@H](c1ccc(C(F)(F)F)cc1)c1ncccc1C(F)(F)F)c1ccn2ccnc2c1] | (S)-N-((4-(trifluoromethyl)-phenyl)(3-(trifluoromethyl)-pyridin-2-yl)-methyl)-imidazo[1,2-a]pyridine-7-carboxamide | 465.0 |
| 88 | 8 | 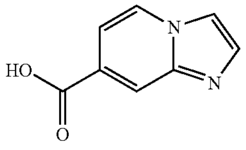 [SMILES: O=C(O)c1ccn2ccnc2c1] | 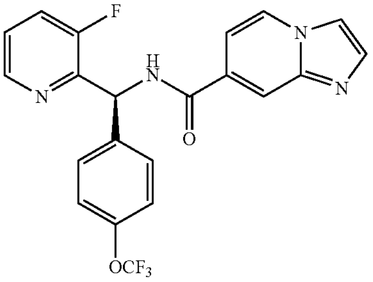 [SMILES: O=C(N[C@@H](c1ccc(OC(F)(F)F)cc1)c1ncccc1F)c1ccn2ccnc2c1] | (S)-N-((3-fluoro-pyridin-2-yl)(4-(trifluoro-methoxy)-phenyl)methyl)-imidazo[1,2-a]pyridine-7-carboxamide | 431.1 |
| 89 | 8 | 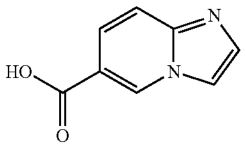 [SMILES: O=C(O)c1ccc2nccn2c1] | 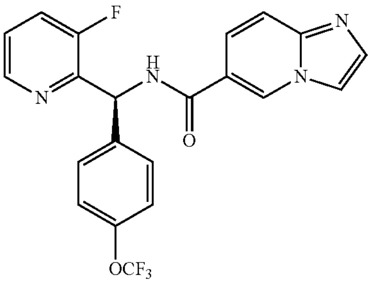 [SMILES: O=C(N[C@@H](c1ccc(OC(F)(F)F)cc1)c1ncccc1F)c1ccc2nccn2c1] | (S)-N-((3-fluoro-pyridin-2-yl)(4-(trifluoro-methoxy)-phenyl)methyl)-imidazo[1,2-a]pyridine-6-carboxamide 2,2,2-trifluoroacetate | 431.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 90 | 8 | 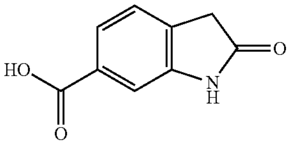 [SMILES: O=C1Cc2ccc(C(=O)O)cc2N1] | 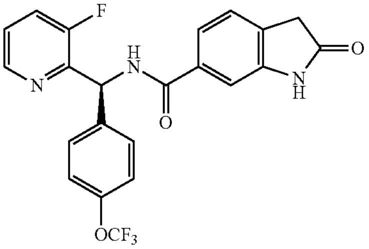 [SMILES: O=C1Cc2ccc(C(=O)N[C@@H](c3ccc(OC(F)(F)F)cc3)c3ncccc3F)cc2N1] | (S)-N-((3-fluoro-pyridin-2-yl)(4-(trifluoro-methoxy)-phenyl)methyl)-2-oxoindoline-6-carboxamide | 446.1 |
| 91 | 8 | 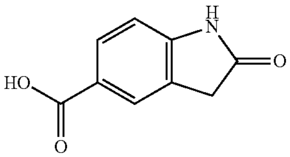 | 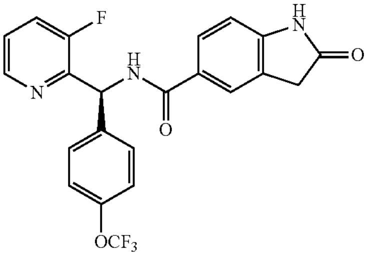 [SMILES: O=C1Cc2cc(C(=O)N[C@@H](c3ccc(OC(F)(F)F)cc3)c3ncccc3F)ccc2N1] | (S)-N-((3-fluoro-pyridin-2-yl)(4-(trifluoro-methoxy)-phenyl)methyl)-2-oxoindoline-5-carboxamide | 446.1 |
| 92 | 47 | 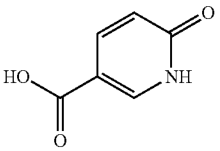 | 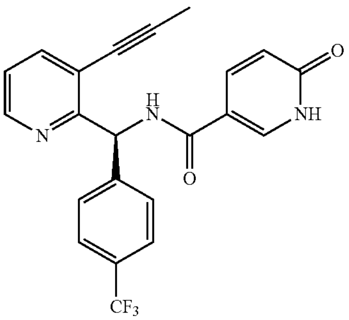 [SMILES: CC#Cc1cccnc1[C@@H](NC(=O)c1ccc(=O)[nH]c1)c1ccc(C(F)(F)F)cc1] | (S)-6-oxo-N-((3-(prop-1-yn-1-yl)-pyridin-2-yl)(4-(trifluoromethyl)-phenyl)methyl)-1,6-dihydro-pyridine-3-carboxamide | 412.1 |
| 93 | 47 | 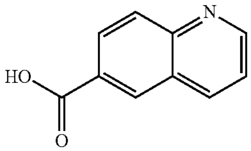 [SMILES: O=C(O)c1ccc2ncccc2c1] | 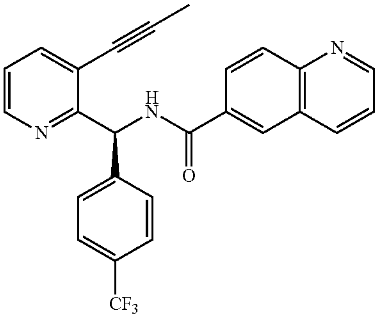 [SMILES: CC#Cc1cccnc1[C@@H](NC(=O)c1ccc2ncccc2c1)c1ccc(C(F)(F)F)cc1] | (S)-N-((3-(prop-1-yn-1-yl)-pyridin-2-yl)(4-(trifluoromethyl)-phenyl)methyl)-quinoline-6-carboxamide | 446.2 |
| 94 | 1 | 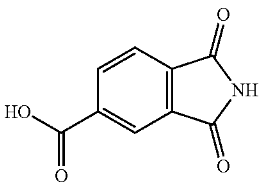 [SMILES: O=C(O)c1ccc2c(c1)C(=O)NC2=O] | 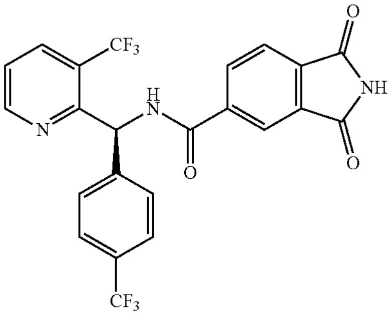 [SMILES: O=C(N[C@@H](c1ccc(C(F)(F)F)cc1)c1ncccc1C(F)(F)F)c1ccc2c(c1)C(=O)NC2=O] | (S)-1,3-dioxo-N-((4-(trifluoro-methyl)phenyl)-(3-(trifluoro-methyl)pyridin-2-yl)methyl)-isoindoline-5-carboxamide | 494.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 95 | 47 | 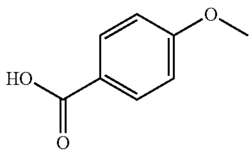 | 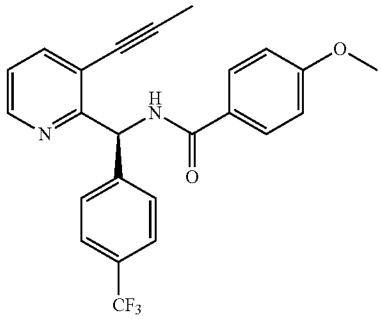 | (S)-4-methoxy-N-((3-(prop-1-yn-1-yl)pyridin-2-yl)(4-(trifluoro-methyl)phenyl)-methyl)-benzamide 2,2,2-trifluoroacetate | 425.2 |
| 96 | 47 | 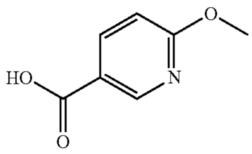 | 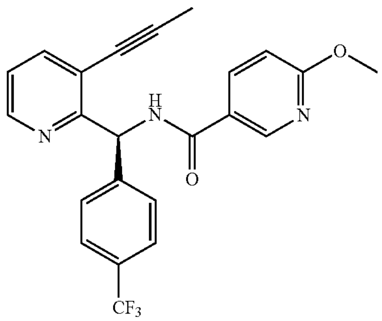 [SMILES: CC#Cc1cccnc1[C@@H](NC(=O)c1ccc(OC)cc1)c1ccc(C(F)(F)F)cc1] | (S)-6-methoxy-N-((3-(prop-1-yn-1-yl)pyridin-2-yl)(4-(trifluoro-methyl)phenyl)-methyl)-nicotinamide | 426.2 |
| 97 | 47 | 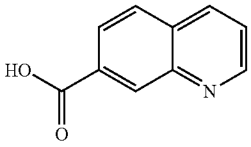 [SMILES: O=C(O)c1ccc2cccnc2c1] | 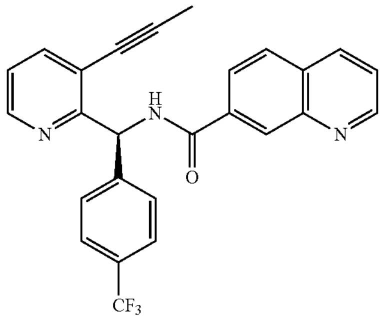 [SMILES: CC#Cc1cccnc1[C@@H](NC(=O)c1ccc2cccnc2c1)c1ccc(C(F)(F)F)cc1] | (S)-N-((3-(prop-1-yn-1-yl)-pyridin-2-yl)(4-(trifluoromethyl)-phenyl)methyl)-quinoline-7-carboxamide 2,2,2-trifluoroacetate | 446.2 |
| 98 | 47 | 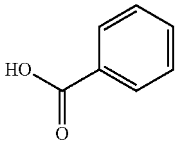 | 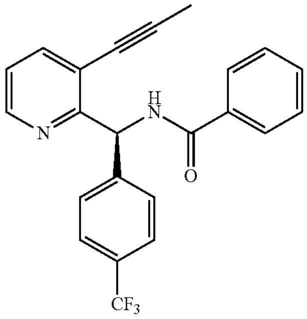 [SMILES: CC#Cc1cccnc1[C@@H](NC(=O)c1ccccc1)c1ccc(C(F)(F)F)cc1] | (S)-N-((3-(prop-1-yn-1-yl)-pyridin-2-yl)(4-(trifluoromethyl)-phenyl)methyl)-benzamide | 395.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 99 | 1 | 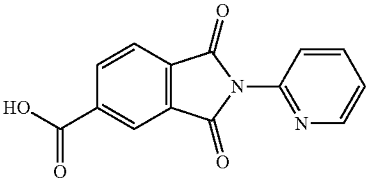 [SMILES: O=C(O)c1ccc2c(c1)C(=O)N(c1ccccn1)C2=O] | 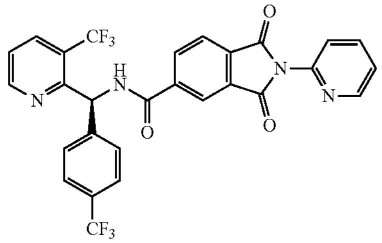 [SMILES: O=C(N[C@@H](c1ccc(C(F)(F)F)cc1)c1ncccc1C(F)(F)F)c1ccc2c(c1)C(=O)N(c1ccccn1)C2=O] | (S)-1,3-dioxo-2-(pyridin-2-yl)-N-((4-(trifluoro-methyl)phenyl)-(3-(trifluoro-methyl)pyridin-2-yl)methyl)-isoindoline-5-carboxamide 2,2,2-trifluoroacetate | 571.1 |
| 100 | 1 | 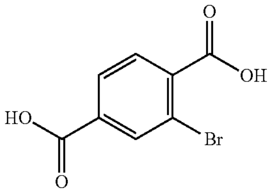 [SMILES: O=C(O)c1ccc(C(=O)O)c(Br)c1] | 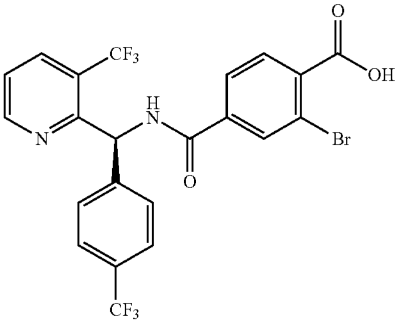 [SMILES: O=C(N[C@@H](c1ccc(C(F)(F)F)cc1)c1ncccc1C(F)(F)F)c1ccc(C(=O)O)c(Br)c1] | (S)-2-bromo-4-(((4-(trifluoro-methyl)phenyl)-(3-(trifluoro-methyl)pyridin-2-yl)methyl)-carbamoyl)-benzoic acid | 549.0 |
| 101 | 48 | 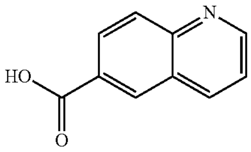 [SMILES: O=C(O)c1ccc2ncccc2c1] | 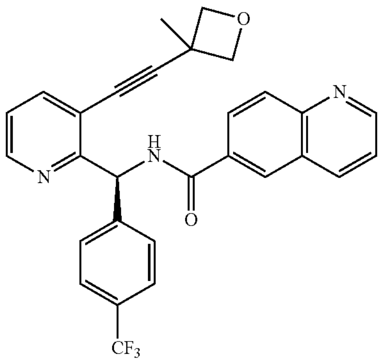 [SMILES: CC1(C#Cc2cccnc2[C@@H](NC(=O)c2ccc3ncccc3c2)c2ccc(C(F)(F)F)cc2)COC1] | (S)-N-((3-((3-methyloxetan-3-yl)ethynyl)-pyridin-2-yl)(4-(trifluoromethyl)-phenyl)methyl)-quinoline-6-carboxamide 2,2,2-trifluoroacetate | 502.2 |
| 102 | 6 | 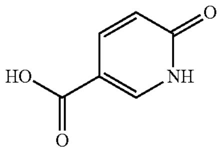 | 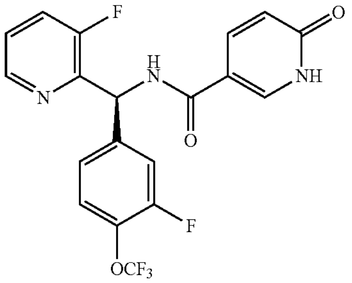 [SMILES: O=C(N[C@@H](c1ccc(OC(F)(F)F)c(F)c1)c1ncccc1F)c1ccc(=O)[nH]c1] | (S)-N-((3-fluoro-4-(trifluoro-phenyl)(3-fluoro-pyridin-2-yl)-methyl)-6-oxo-1,6-dihydro-pyridine-3-carboxamide 2,2,2-trifluoroacetate | 425.9 |
| 103 | 6 | 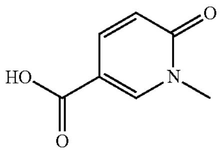 | 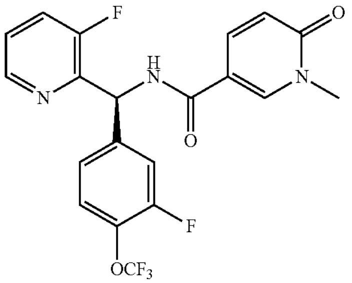 [SMILES: Cn1cc(C(=O)N[C@@H](c2ccc(OC(F)(F)F)c(F)c2)c2ncccc2F)ccc1=O] | (S)-N-((3-fluoro-4-(trifluoro-methoxy)-phenyl)(3-fluoro-pyridin-2-yl)-methyl)-1-methyl-6-oxo-1,6-dihydro-pyridine-3-carboxamide | 439.9 |

TABLE 2-continued

| Examples 1-261 prepared via amide formation analogous to Scheme 4 | | | | | |
|---|---|---|---|---|---|
| Ex # | A-mine | Acid Structure | Product Structure | Product Name | MS M + H |
| 104 | 2 | 57 | 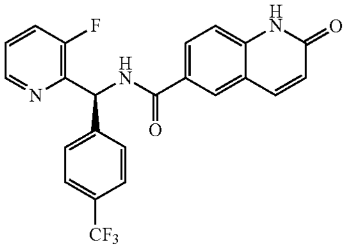 [SMILES: O=C(N[C@@H](c1ccc(C(F)(F)F)cc1)c1ncccc1F)c1ccc2[nH]c(=O)ccc2c1] | (S)-N-((3-fluoro-pyridin-2-yl)(4-(trifluoromethyl)-phenyl)methyl)-2-oxo-1,2-dihydro-quinoline-6-carboxamide | 441.8 |
| 105 | 2 | 58 | 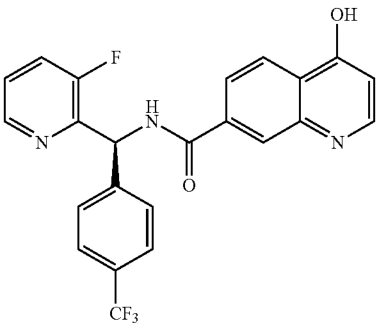 [SMILES: O=C(N[C@@H](c1ccc(C(F)(F)F)cc1)c1ncccc1F)c1ccc2c(O)ccnc2c1] | (S)-N-((3-fluoro-pyridin-2-yl)(4-(trifluoromethyl)-phenyl)methyl)-4-hydroxy-quinoline-7-carboxamide 2,2,2-trifluoroacetate | 441.8 |
| 106 | 1 | 58 | 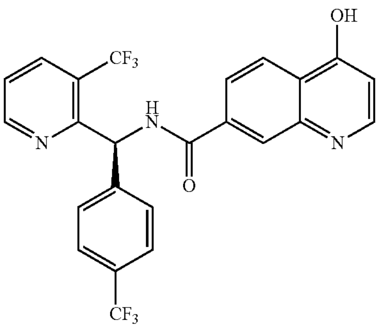 [SMILES: O=C(N[C@@H](c1ccc(C(F)(F)F)cc1)c1ncccc1C(F)(F)F)c1ccc2c(O)ccnc2c1] | (S)-4-hydroxy-N-((4-(trifluoro-meyhyl)phenyl)-(3-(trifluoro-yl)methyl)-quinoline-7-carboxamide 2,2,2-trifluoroacetate | 491.6 |
| 107 | 7 | 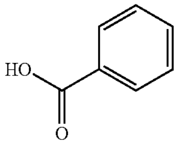 | 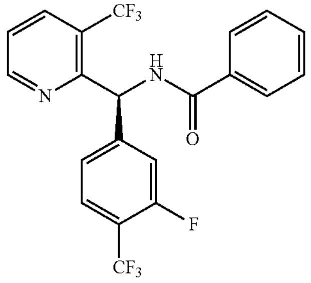 [SMILES: O=C(N[C@@H](c1ccc(C(F)(F)F)c(F)c1)c1ncccc1C(F)(F)F)c1ccccc1] | (S)-N-((3-fluoro-4-(trifluoro-methyl)phenyl)-(3-(trifluoro-methyl)pyridin-2-yl)methyl)-benzamide | 443.0 |
| 108 | 7 | 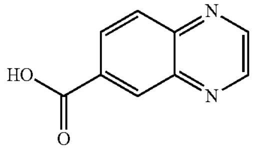 [SMILES: O=C(O)c1ccc2nccnc2c1] | 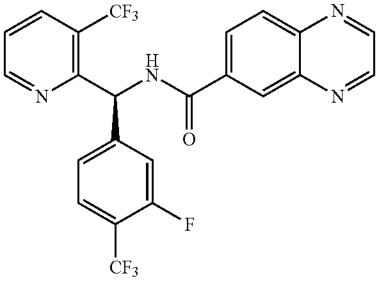 | (S)-N-((3-fluoro-4-(trifluoro-methyl)phenyl)-(3-(trifluoro-methyl)pyridin-2-yl)methyl)-quinoxaline-6-carboxamide | 494.9 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 109 | 1 | 55 | 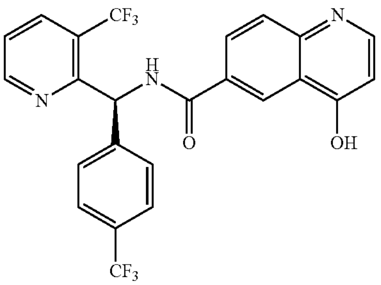 | (S)-4-hydroxy-N-((4-(trifluoro-methyl)phenyl)-(3-(trifluoro-methyl)pyridin-2-yl)methyl)-quinoline-6-carboxamide 2,2,2-trifluoroacetate | 491.6 |
| 110 | 1 | 59 | 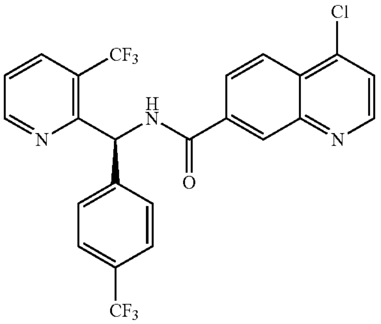 [SMILES: O=C(N[C@@H](c1ccc(C(F)(F)F)cc1)c1ncccc1C(F)(F)F)c1ccc2c(Cl)ccnc2c1] | (S)-4-chloro-N-((4-(trifluoro-methyl)phenyl)-(3-(trifluoro-methyl)pyridin-2-yl)methyl)-quinoline-7-carboxamide 2,2,2-trifluoroacetate | 509.6 |
| 111 | 7 | 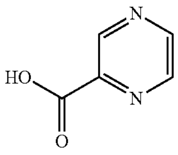 | 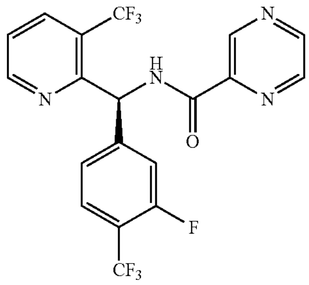 | (S)-N-((3-fluoro-4-(trifluoro-methyl)phenyl)-methyl)pyridin-2-yl)methyl)-pyrazine-2-carboxamide | 445.0 |
| 112 | 7 | 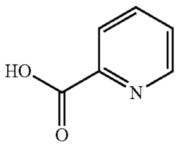 | 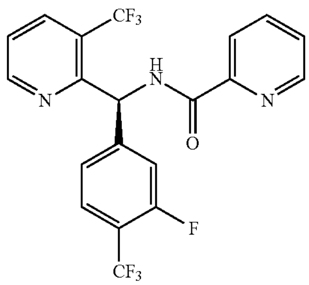 [SMILES: O=C(N[C@@H](c1ccc(C(F)(F)F)c(F)c1)c1ncccc1C(F)(F)F)c1ccccn1] | (S)-N-((3-fluoro-4-(trifluoro-methyl)phenyl)-(3-(trifluoro-methyl)pyridin-2-yl)methyl)-picolinamide | 443.9 |
| 113 | 2 | 56 | 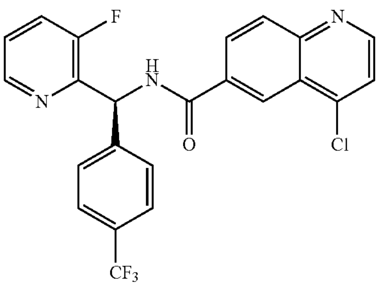 [SMILES: O=C(N[C@@H](c1ccc(C(F)(F)F)cc1)c1ncccc1F)c1ccc2nccc(O)c2c1] | (S)-4-chloro-N-((3-fluoropyridin-2-yl)(4-(trifluoro-methyl)phenyl)-methyl)-quinoline-6-carboxamide 2,2,2-trifluoroacetate | 459.6 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 114 | 2 | 55 | 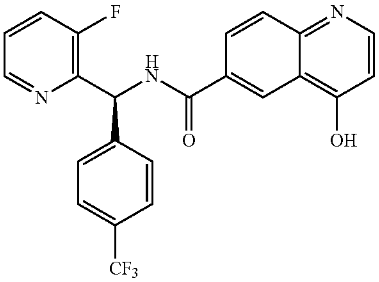 | (S)-N-((3-fluoro-pyridin-2-yl)(4-(trifluoromethyl)-phenyl)methyl)-4-hydroxy-quinoline-6-carboxamide 2,2,2-trifluoroacetate | 441.8 |
| 115 | 29 | 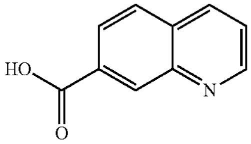 [SMILES: O=C(O)c1ccc2cccnc2c1] | 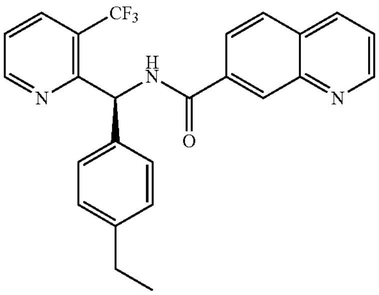 [SMILES: CCc1ccc([C@H](NC(=O)c2ccc3cccnc3c2)c2ncccc2C(F)(F)F)cc1] | (S)-N-((4-ethylphenyl)(3-(trifluoromethyl)-pyridin-2-yl)-methyl)-quinoline-7-carboxamide | 436.1 |
| 116 | 1 | 56 | 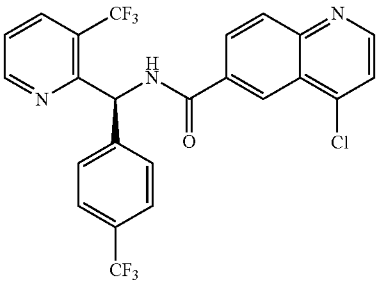 | (S)-4-chloro-N-((4-(trifluoro-methyl)phenyl)-(3-(trifluoro-methyl)pyridin-2-yl)methyl)-carboxamide 2,2,2-trifluoroacetate | 509.6 |
| 117 | 1 | 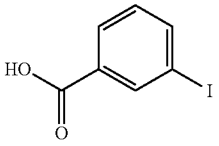 | 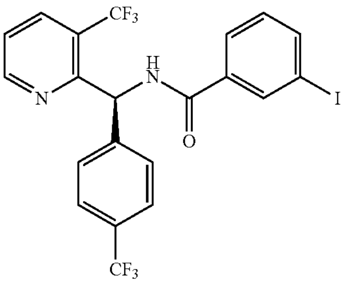 [SMILES: O=C(N[C@@H](c1ccc(C(F)(F)F)cc1)c1ncccc1C(F)(F)F)c1cccc(I)c1] | (S)-3-iodo-N-((4-(trifluoromethyl)-phenyl)(3-(trifluoromethyl)-pyridin-2-yl)-methyl)-benzamide | 550.5 |
| 118 | 1 | 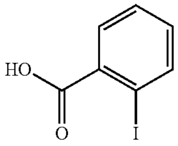 | 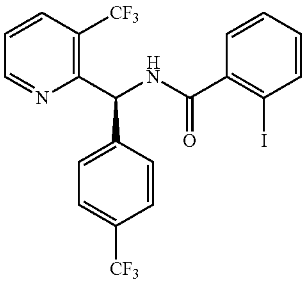 [SMILES: O=C(N[C@@H](c1ccc(C(F)(F)F)cc1)c1ncccc1C(F)(F)F)c1ccccc1I] | (S)-2-iodo-N-((4 (trifluoromethyl) phenyl)(3-(trifluoromethyl) pyridin-2-yl)-methyl)-benzamide | 550.5 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 119 | 7 | 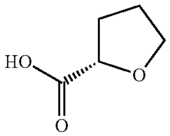 | 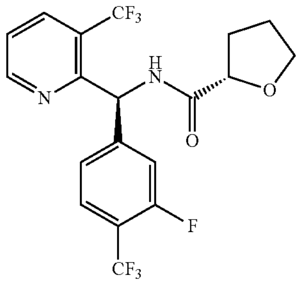 [SMILES: O=C(N[C@@H](c1ccc(C(F)(F)F)c(F)c1)c1ncccc1C(F)(F)F)[C@@H]1CCCO1] | (S)-N-((S)-(3-fluoro-4-(trifluoromethyl)-phenyl)(3-(trifluoromethyl)-pyridin-2-yl)-methyl)THF-2-carboxamide | 437.0 |
| 120 | 2 | 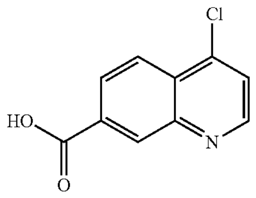 [SMILES: O=C(O)c1ccc2c(Cl)ccnc2c1] | 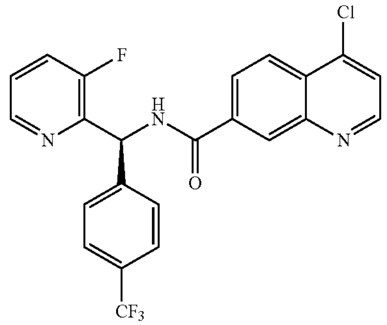 [SMILES: O=C(N[C@@H](c1ccc(C(F)(F)F)cc1)c1ncccc1F)c1ccc2c(Cl)ccnc2c1] | (S)-4-chloro-N-((3-fluoropyridin-2-yl)(4-(trifluoro-methyhphenyl)-methyl)-quinoline-7-carboxamide 2,2,2-trifluoroacetate | 459.6 |
| 121 | 1 | 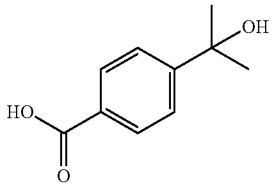 | 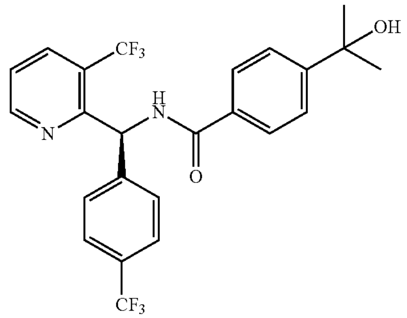 [SMILES: CC(C)(O)c1ccc(C(=O)N[C@@H](c2ccc(C(F)(F)F)cc2)c2ncccc2C(F)(F)F)cc1] | (S)-4-(2-hydroxy-propan-2-yl)-N-((4-(trifluoro-methyl)phenyl)-(3-(trifluoro-methyl)pyridin-2-yl)methyl)-benzamide | 483.0 |
| 122 | 1 | 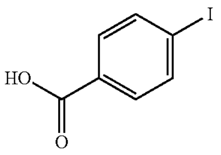 | 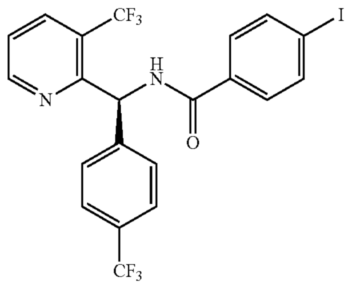 [SMILES: O=C(N[C@@H](c1ccc(C(F)(F)F)cc1)c1ncccc1C(F)(F)F)c1ccc(I)cc1] | (S)-4-iodo-N-((4-(trifluoromethyl)-phenyl)(3-(trifluoromethyl)-pyridin-2-yl)-methyl)-benzamide | 550.5 |
| 123 | 7 | 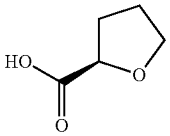 | 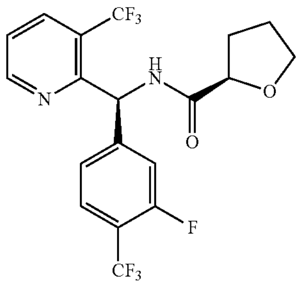 [SMILES: O=C(N[C@@H](c1ccc(C(F)(F)F)c(F)c1)c1ncccc1C(F)(F)F)[C@H]1CCCO1] | (R)-N-((S)-(3-fluoro-4-(trifluoromethyl) phenyl)(3-(trifluoromethyl) pyridin-2-yl)-methyl)THF-2-carboxamide | 437.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 124 | 27 | 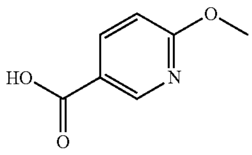 | 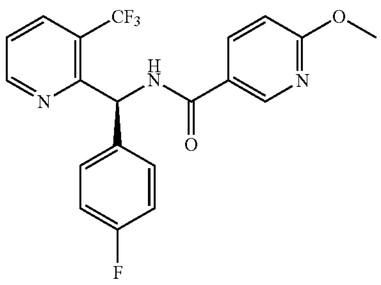 [SMILES: COc1ccc(C(=O)N[C@@H](c2ccc(F)cc2)c2ncccc2C(F)(F)F)cn1] | (S)-N-((4-fluoro-phenyl)(3-(trifluoromethyl)-pyridin-2-yl)-methyl)-6-methoxy-nicotinamide | 406.1 |
| 125 | 2 | 60 | 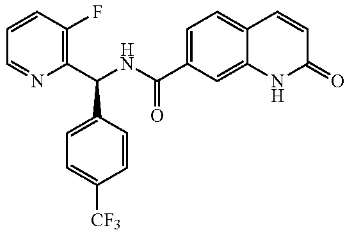 [SMILES: O=C(N[C@@H](c1ccc(C(F)(F)F)cc1)c1ncccc1F)c1ccc2ccc(=O)[nH]c2c1] | (S)-N-((3-fluoro-pyridin-2-yl)(4-(trifluoromethyl)-phenyl)methyl)-2-oxo-1,2-dihydro-quinoline-7-carboxamide | 441.8 |
| 126 | 27 | 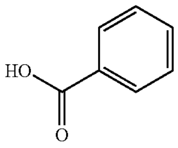 | 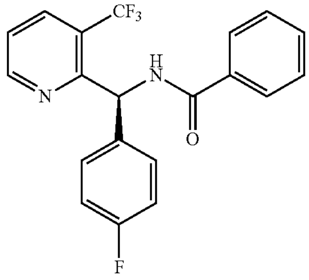 [SMILES: O=C(N[C@@H](c1ccc(F)cc1)c1ncccc1C(F)(F)F)c1ccccc1] | (S)-N-((4-fluoro-phenyl)(3-(trifluoromethyl)-pyridin-2-yl)-methyl)-benzamide | 375.1 |
| 127 | 1 | 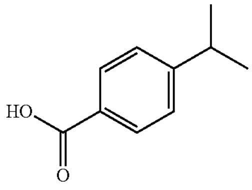 | 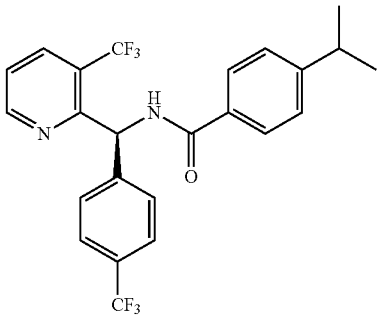 [SMILES: CC(C)c1ccc(C(=O)N[C@@H](c2ccc(C(F)(F)F)cc2)c2ncccc2C(F)(F)F)cc1] | (S)-4-isopropyl-N-((4-(trifluoro-methyl)phenyl)-(3-(trifluoro-methyl)pyridin-2-yl)methyl)-benzamide | 485.0 |
| 128 | 1 | 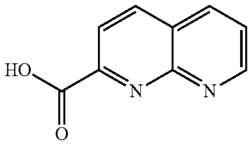 [SMILES: O=C(O)c1ccc2cccnc2n1] | 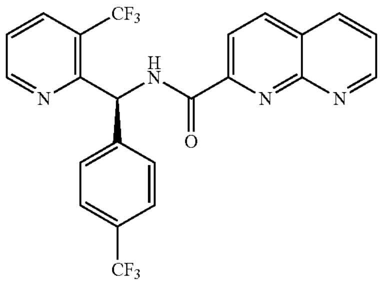 [SMILES: O=C(N[C@@H](c1ccc(C(F)(F)F)cc1)c1ncccc1C(F)(F)F)c1ccc2cccnc2n1] | (S)-N-((4-(trifluoromethyl)-phenyl)(3-(trifluoromethyl)-pyridin-2-yl)-methyl)-1,8-naphthyridine-2-carboxamide 2,2,2-trifluoroacetate | 476.9 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 129 | 7 | 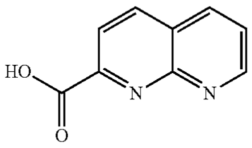 [SMILES: O=C(O)c1ccc2cccnc2n1] | 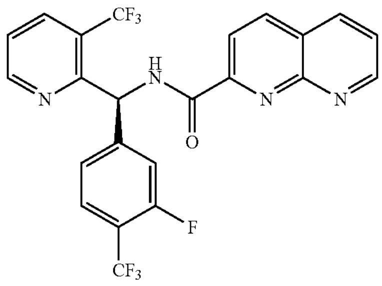 [SMILES: O=C(N[C@@H](c1ccc(C(F)(F)F)c(F)c1)c1ncccc1C(F)(F)F)c1ccc2cccnc2n1] | (S)-N-((3-fluoro-4-(trifluoro-methyl)phenyl)-(3-(trifluoro-methyl)pyridin-2-yl)methyl)-1,8-naphthyridine-2-carboxamide 2,2,2-trifluoroacetate | 494.9 |
| 130 | 7 | 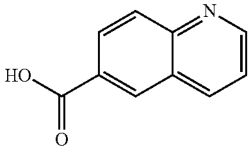 [SMILES: O=C(O)c1ccc2ncccc2c1] | 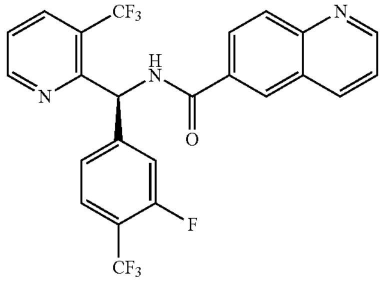 [SMILES: O=C(N[C@@H](c1ccc(C(F)(F)F)c(F)c1)c1ncccc1C(F)(F)F)c1ccc2ncccc2c1] | (S)-N-((3-fluoro-4-(trifluoro-methyl)phenyl)-(3-(trifluoro-methyl)pyridin-2-yl)methyl)-quinoline-6-carboxamide bis (2,2,2-trifluoroacetate) | 494.0 |
| 131 | 7 | 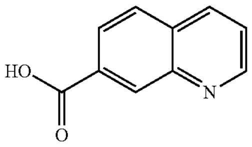 [SMILES: O=C(O)c1ccc2cccnc2c1] | 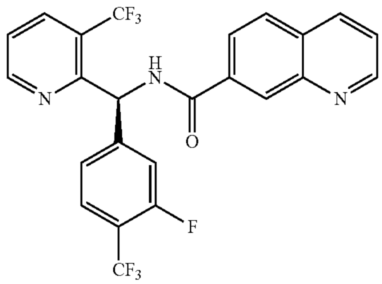 [SMILES: O=C(N[C@@H](c1ccc(C(F)(F)F)c(F)c1)c1ncccc1C(F)(F)F)c1ccc2cccnc2c1] | (S)-N-((3-fluoro-4-(trifluoro-methyl)phenyl)-(3-(trifluoro-methyl)pyridin-2-yl)methyl)-quinoline-7-carboxamide | 494.0 |
| 132 | 1 | 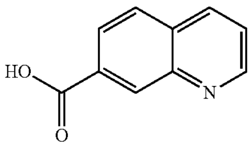 [SMILES: O=C(O)c1ccc2cccnc2c1] | 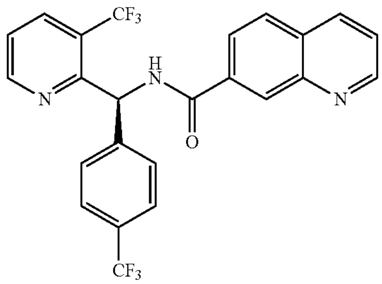 [SMILES: O=C(N[C@@H](c1ccc(C(F)(F)F)cc1)c1ncccc1C(F)(F)F)c1ccc2cccnc2c1] | (S)-N-((4-(trifluoromethyl)-phenyl)(3-(trifluoromethyl)-pyridin-2-yl)-methyl)-quinoline-7-carboxamide | 476.0 |
| 133 | 1 | 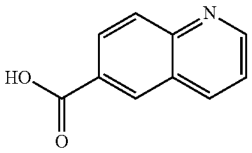 [SMILES: O=C(O)c1ccc2ncccc2c1] | 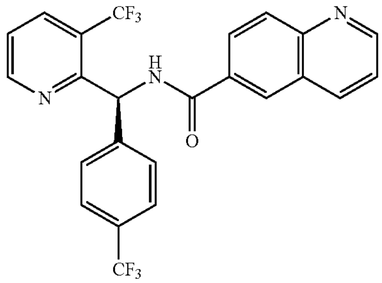 [SMILES: O=C(N[C@@H](c1ccc(C(F)(F)F)cc1)c1ncccc1C(F)(F)F)c1ccc2ncccc2c1] | (S)-N-((4-(trifluoromethyl)-phenyl)(3-(trifluoromethyl)-pyridin-2-yl)-methyl)-quinoline-6-carboxamide | 476.0 |

TABLE 2-continued

| Ex # | A-mine | Acid Structure | Product Structure | Product Name | MS M + H |
|---|---|---|---|---|---|
| Examples 1-261 prepared via amide formation analogous to Scheme 4 | | | | | |
| 134 | 1 | 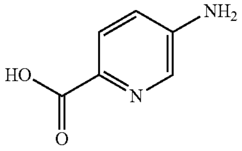 | 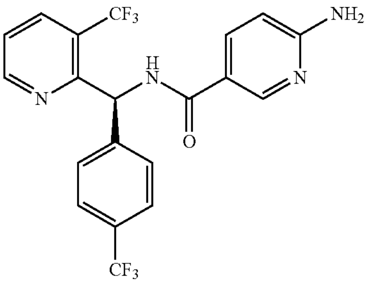 [SMILES: Nc1ccc(C(=O)N[C@@H](c2ccc(C(F)(F)F)cc2)c2ncccc2C(F)(F)F)cn1] | (S)-6-amino-N-((4-(trifluoro-methyl)phenyl)-(3-(trifluoro-methyl)pyridin-2-yl)methyl)-nicotinamide | 441.0 |
| 135 | 1 | 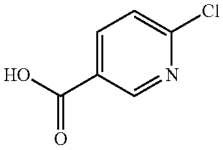 | 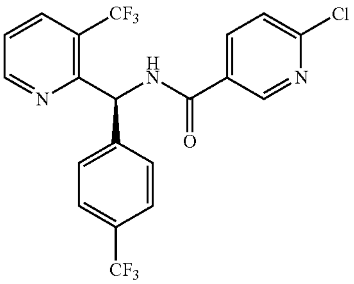 [SMILES: O=C(N[C@@H](c1ccc(C(F)(F)F)cc1)c1ncccc1C(F)(F)F)c1ccc(Cl)nc1] | (S)-6-chloro-N-((4-(trifluoro-methyl)phenyl)-(3-(trifluoro-methyl)pyridin-2-yl)methyl)-nicotinamide | 460.0 |
| 136 | 1 | 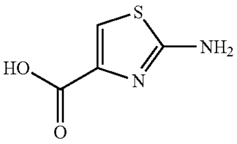 | 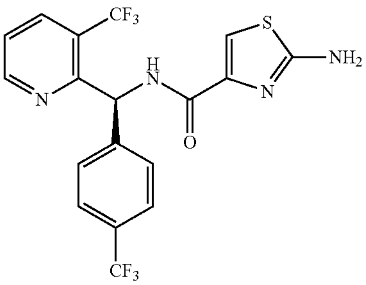 [SMILES: Nc1nc(C(=O)N[C@@H](c2ccc(C(F)(F)F)cc2)c2ncccc2C(F)(F)F)cs1] | (S)-2-amino-N-((4-(trifluoro-methyl)phenyl)-(3-(trifluoro-methyl)pyridin-2-yl)methyl)-thiazole-4-carboxamide 2,2,2-trifluoroacetate | 446.9 |
| 137 | 1 | 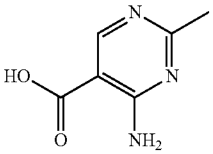 | 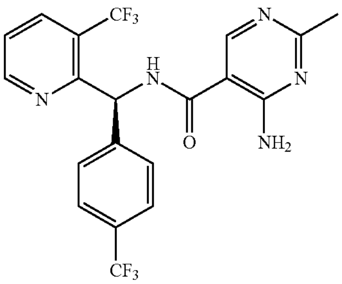 [SMILES: Cc1ncc(C(=O)N[C@@H](c2ccc(C(F)(F)F)cc2)c2ncccc2C(F)(F)F)c(N)n1] | (S)-4-amino-2-methyl-N-((4-(trifluoromethyl)-phenyl)(3-(trifluoromethyl)-pyridin-2-yl)-methyl)-pyrimidine-5-carboxamide | 456.0 |
| 138 | 1 | 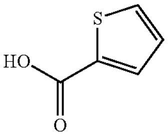 | 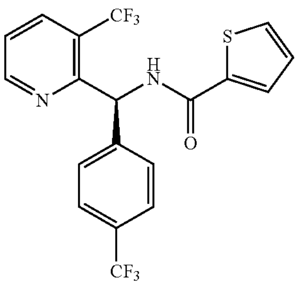 [SMILES: O=C(N[C@@H](c1ccc(C(F)(F)F)cc1)c1ncccc1C(F)(F)F)c1cccs1] | (S)-N-((4-(trifluoromethyl)-phenyl)(3-(trifluoromethyl)-pyridin-2-yl)-methyl)-thiophene-2-carboxamide | 430.9 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 139 | 1 | 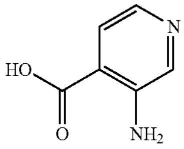 | 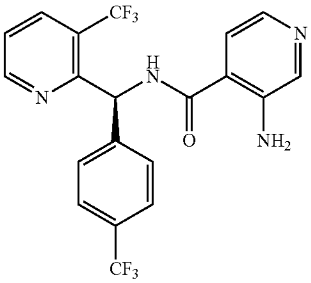 [SMILES: Nc1cnccc1C(=O)N[C@@H](c1ccc(C(F)(F)F)cc1)c1ncccc1C(F)(F)F] | (S)-3-amino-N-((4-(trifluoro-methyl)phenyl)-(3-(trifluoro-methyl)pyridin-2-yl)methyl)-isonicotinamide | 441.0 |
| 140 | 1 | 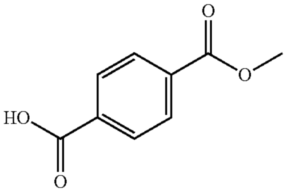 | 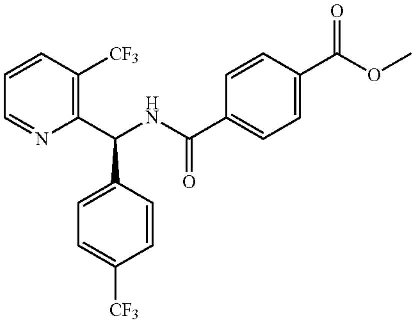 [SMILES: COC(=O)c1ccc(C(=O)N[C@@H](c2ccc(C(F)(F)F)cc2)c2ncccc2C(F)(F)F)cc1] | (S)-methyl 4-(((4-(trifluoro-methyl)phenyl)-(3-(trifluoro-methyl)pyridin-2-yl)methyl)-carbamoyl)-benzoate | 482.9 |
| 141 | 1 | 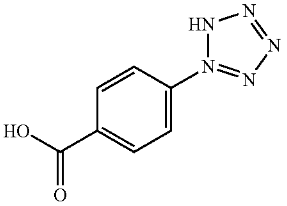 | 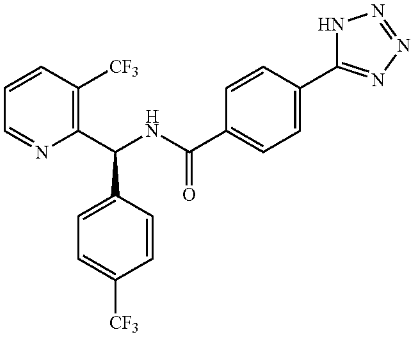 [SMILES: O=C(N[C@@H](c1ccc(C(F)(F)F)cc1)c1ncccc1C(F)(F)F)c1ccc(-c2nnn[nH]2)cc1] | (S)-4-(1H-tetrazol-5-yl)-N-((4-(trifluoro-methyl)phenyl)-(3-(trifluoro-methyl)pyridin-2-yl)methyl)-benzamide | 493.0 |
| 142 | 1 | 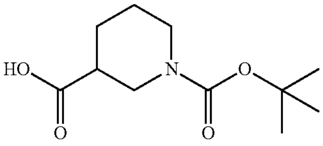 [SMILES: CC(C)(C)OC(=O)N1CCCC(C(=O)O)C1] | 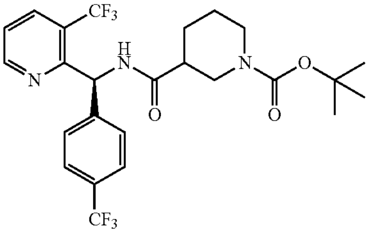 [SMILES: CC(C)(C)OC(=O)N1CCCC(C(=O)N[C@@H](c2ccc(C(F)(F)F)cc2)c2ncccc2C(F)(F)F)C1] | tert-butyl 3-(((S)-(4-(trifluoro-methyl)phenyl)-(3-(trifluoro-methyl)pyridin-2-yl)methyl)-carbamoyl)-piperidine-1-carboxylate | 554.0 (M + Na) |
| 143 | 1 | 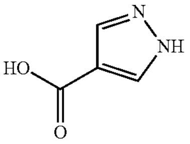 | 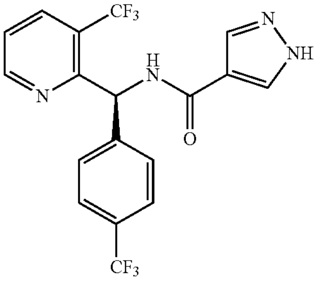 [SMILES: O=C(N[C@@H](c1ccc(C(F)(F)F)cc1)c1ncccc1C(F)(F)F)c1cn[nH]c1] | (S)-N-((4-(trifluoromethyl)-phenyl)(3-(trifluoromethyl)-pyridin-2-yl)-methyl)-1H-pyrazole-4-carboxamide | 415.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 144 | 1 | 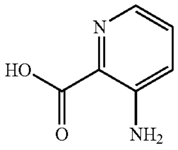 | 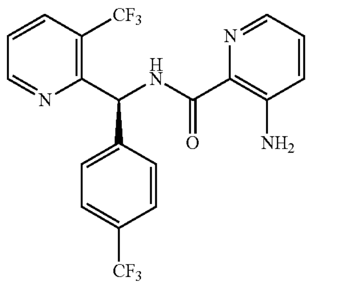 [SMILES: Nc1cccnc1C(=O)N[C@@H](c1ccc(C(F)(F)F)cc1)c1ncccc1C(F)(F)F] | (S)-3-amino-N-((4-(trifluoro-methyl)phenyl)-(3-(trifluoro-methyl)pyridin-2-yl)methyl)-picolinamide | 441.0 |
| 145 | 1 | 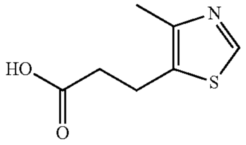 | 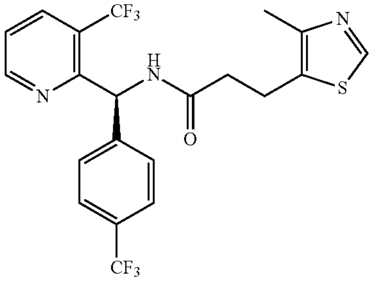 [SMILES: Cc1ncsc1CCC(=O)N[C@@H](c1ccc(C(F)(F)F)cc1)c1ncccc1C(F)(F)F] | (S)-3-(4-methylthiazol-5-yl)-N-((4-(trifluoromethyl)-phenyl)(3-(trifluoromethyl)-pyridin-2-yl)-methyl)-propanamide | 474.0 |
| 146 | 1 | 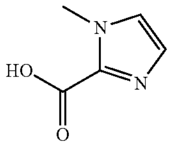 | 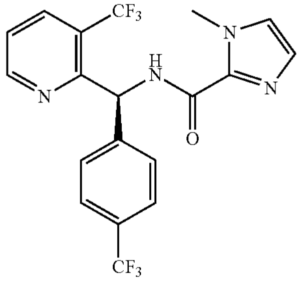 [SMILES: Cn1ccnc1C(=O)N[C@@H](c1ccc(C(F)(F)F)cc1)c1ncccc1C(F)(F)F] | (S)-1-methyl-N-((4-(trifluoro-methyl)phenyl)-(3-(trifluoro-methyl)pyridin-2-yl)methyl)-1H-imidazole-2-carboxamide | 429.0 |
| 147 | 1 | 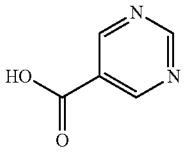 | 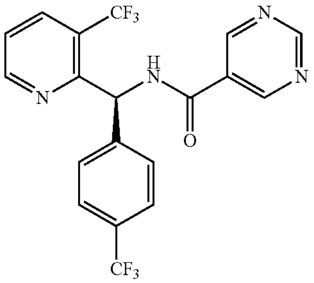 [SMILES: O=C(N[C@@H](c1ccc(C(F)(F)F)cc1)c1ncccc1C(F)(F)F)c1cncnc1] | (S)-N-((4-(trifluoromethyl)-phenyl)(3-(trifluoromethyl)-pyridin-2-yl)-methyl)-pyrimidine-5-carboxamide | 427.0 |
| 148 | 1 | 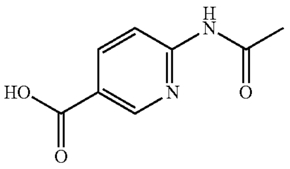 | 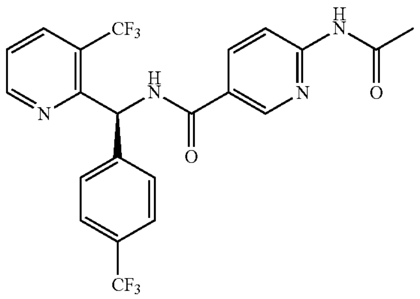 [SMILES: CC(=O)Nc1ccc(C(=O)N[C@@H](c2ccc(C(F)(F)F)cc2)c2ncccc2C(F)(F)F)cn1] | (S)-6-acetamido-N-((4-(trifluoro-methyhphenyl)-(3-(trifluoro-methyl)pyridin-2-yl)methyl)-nicotinamide 2,2,2-trifluoroacetate | 482.9 |

TABLE 2-continued

| Ex # | A-mine | Acid Structure | Product Structure | Product Name | MS M + H |
|---|---|---|---|---|---|
| | | Examples 1-261 prepared via amide formation analogous to Scheme 4 | | | |
| 149 | 1 | 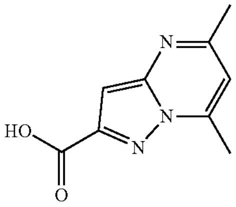 | 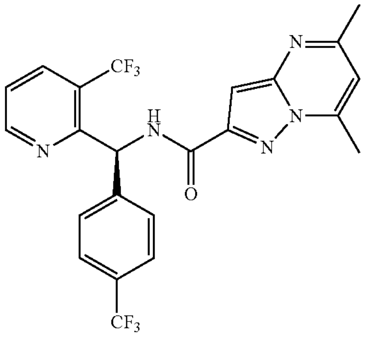 [SMILES: Cc1cc(C)n2nc(C(=O)N[C@@H](c3ccc(C(F)(F)F)cc3)c3ncccc3C(F)(F)F)cc2n1] | (S)-5,7-dimethyl-N-((4-(trifluoro-methyl)phenyl)-(3-(trifluoro-methyl)pyridin-2-yl)methyl)-pyrazolo[1,5-a]pyrimidine-2-carboxamide | 494.0 |
| 150 | 1 | 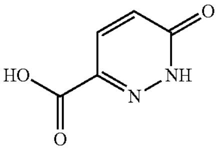 | 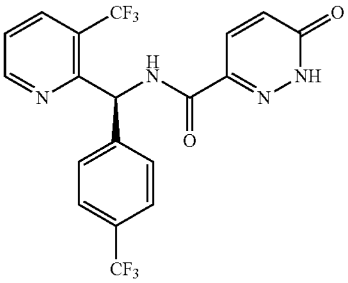 [SMILES: O=C(N[C@@H](c1ccc(C(F)(F)F)cc1)c1ncccc1C(F)(F)F)c1ccc(=O)[nH]n1] | (S)-6-oxo-N-((4-(trifluoromethyl)-phenyl)(3-(trifluoromethyl)-pyridin-2-yl)-methyl)-1,6-dihydro-pyridazine-3-carboxamide | 443.0 |
| 151 | 1 | 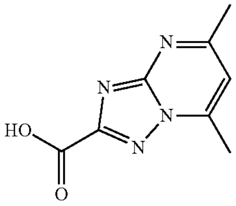 | 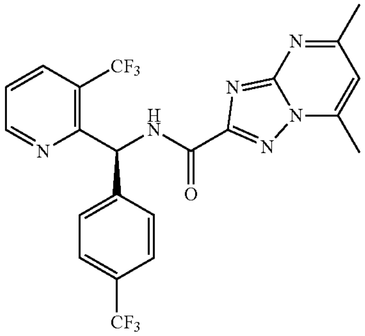 [SMILES: Cc1cc(C)n2nc(C(=O)N[C@@H](c3ccc(C(F)(F)F)cc3)c3ncccc3C(F)(F)F)nc2n1] | (S)-5,7-dimethyl-N-((4-(trifluoro-methyl)phenyl)-(3-(trifluoro-methyl)pyridin-2-yl)methyl)-[1,2,4]triazolo[1,5-a]pyrimidine-2-carboxamide 2,2,2-trifluoroacetate | 495.0 |
| 152 | 1 | 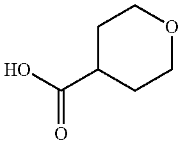 | 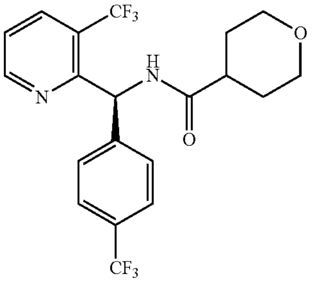 [SMILES: O=C(N[C@@H](c1ccc(C(F)(F)F)cc1)c1ncccc1C(F)(F)F)C1CCOCC1] | (S)-N-((4-(trifluoromethyl)-phenyl)(3-(trifluoromethyl)-pyridin-2-yl)-methyl)-tetrahydro-2H-pyran-4-carboxamide | 433.0 |

TABLE 2-continued

| Ex # | A-mine | Acid Structure | Product Structure | Product Name | MS M + H |
|---|---|---|---|---|---|
| Examples 1-261 prepared via amide formation analogous to Scheme 4 | | | | | |
| 153 | 1 | 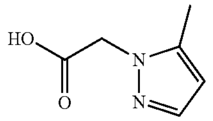 | 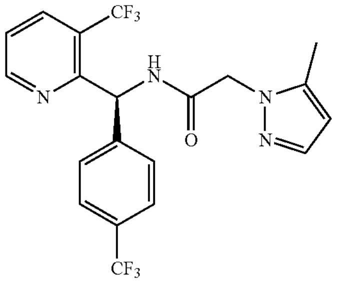 [SMILES: Cc1ccnn1CC(=O)N[C@@H](c1ccc(C(F)(F)F)cc1)c1ncccc1C(F)(F)F] | (S)-2-(5-methyl-1H-pyrazol-1-yl)-N-((4-(trifluoro-methyl)phenyl)-(3-(trifluoro-methyl)pyridin-2-yl)methyl)-acetamide | 443.0 |
| 154 | 1 | 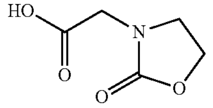 | 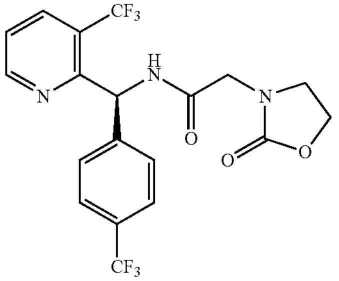 [SMILES: O=C(CN1CCOC1=O)N[C@@H](c1ccc(C(F)(F)F)cc1)c1ncccc1C(F)(F)F] | (S)-2-(2-oxooxazolidin-3-yl)-N-((4-(trifluoromethyl)-phenyl)(3-(trifluoromethyl)-pyridin-2-yl)-methyl)acetamide | 448.0 |
| 155 | 1 | 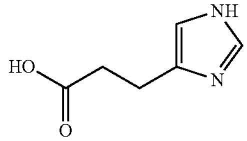 | 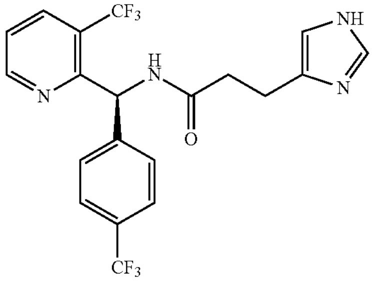 [SMILES: O=C(CCc1c[nH]cn1)N[C@@H](c1ccc(C(F)(F)F)cc1)c1ncccc1C(F)(F)F] | (S)-3-(1H-imidazol-4-yl)-N-((4-(trifluoro-methyl)phenyl)-(3-(trifluoro-methyl)pyridin-2-yl)methyl)-propanamide 2,2,2-trifluoroacetate | 443.0 |
| 156 | 7 | 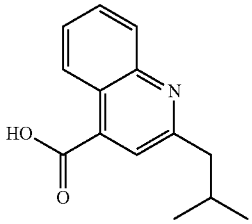 [SMILES: CC(C)Cc1cc(C(=O)O)c2ccccc2n1] | 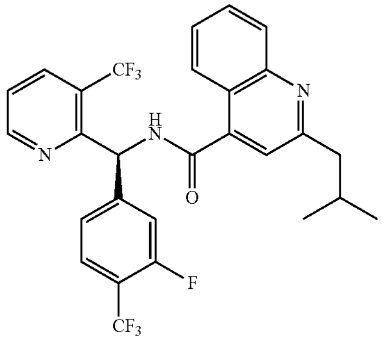 [SMILES: CC(C)Cc1cc(C(=O)N[C@@H](c2ccc(C(F)(F)F)c(F)c2)c2ncccc2C(F)(F)F)c2ccccc2n1] | (S)-N-((3-fluoro-4-(trifluoro-methyl)phenyl)-(3-(trifluoro-methyl)pyridin-2-yl)methyl)-2-isobutylquinoline-4-carboxamide bis (2,2,2-trifluoroacetate) | 550.0 |
| 157 | 1 | 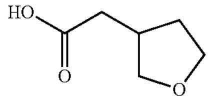 | 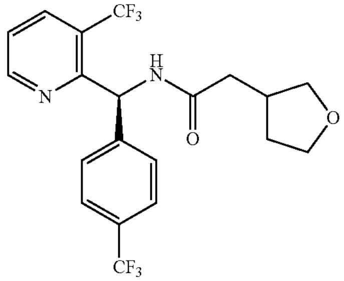 [SMILES: O=C(CC1CCOC1)N[C@@H](c1ccc(C(F)(F)F)cc1)c1ncccc1C(F)(F)F] | 2-(THF-3-yl)-N-((S)-(4-(trifluoro-methyl)phenyl)-(3-(trifluoro-methyl)pyridin-2-yl)methyl)-acetamide | 433.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 158 | 1 | 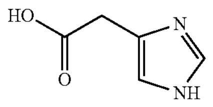 | 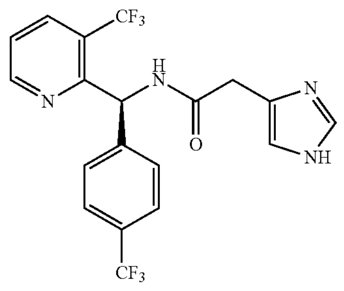 [SMILES: O=C(Cc1c[nH]cn1)N[C@@H](c1ccc(C(F)(F)F)cc1)c1ncccc1C(F)(F)F] | (S)-2-(1H-imidazol-4-yl)-N-((4-(trifluoro-methyl)phenyl)-(3-(trifluoro-methyl)pyridin-2-yl)methyl)-acetamide | 429.0 |
| 159 | 1 | 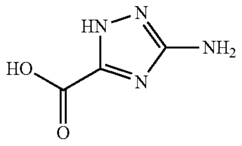 | 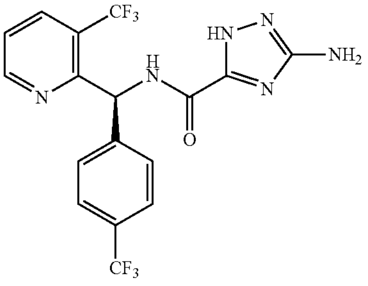 [SMILES: Nc1n[nH]c(C(=O)N[C@@H](c2ccc(C(F)(F)F)cc2)c2ncccc2C(F)(F)F)n1] | (S)-3-amino-N-((4-(trifluoro-methyl)phenyl)-(3-(trifluoro-methyl)pyridin-2-yl)methyl)-1H-1,2,4-triazole-5-carboxamide | 431.0 |
| 160 | 1 | 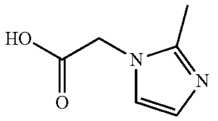 | 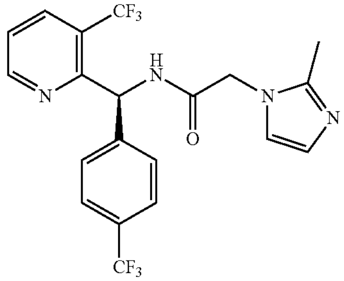 [SMILES: Cc1nccn1CC(=O)N[C@@H](c1ccc(C(F)(F)F)cc1)c1ncccc1C(F)(F)F] | (S)-2-(2-methyl-1H-imidazol-1-yl)-N-((4-(trifluoromethyl)-phenyl)(3-(trifluoromethyl)-pyridin-2-yl)-methyl)acetamide | 443.0 |
| 161 | 1 | 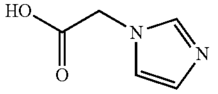 | 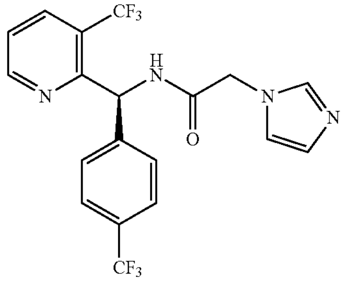 [SMILES: O=C(Cn1ccnc1)N[C@@H](c1ccc(C(F)(F)F)cc1)c1ncccc1C(F)(F)F] | (S)-2-(1H-imidazol-1-yl)-N-((4-(trifluoro-methyl)phenyl)-(3-(trifluoro-methyl)pyridin-2-yl)methyl)-acetamide 2,2,2-trifluoroacetate | 428.9 |
| 162 | 1 | 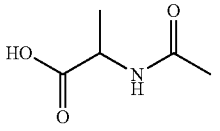 | 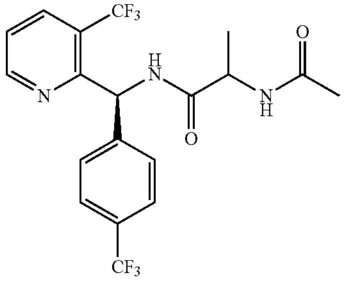 [SMILES: CC(=O)NC(C)C(=O)N[C@@H](c1ccc(C(F)(F)F)cc1)c1ncccc1C(F)(F)F] | 2-acetamido-N-((S)-(4-(trifluoro-methyl)phenyl)-(3-(trifluoro-methyl)pyridin-2-yl)methyl)-propanamide | 434.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 163 | 1 | 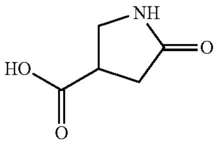 | 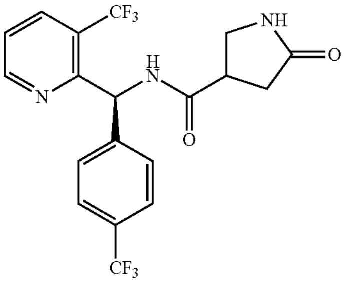 [SMILES: O=C1CC(C(=O)N[C@@H](c2ccc(C(F)(F)F)cc2)c2ncccc2C(F)(F)F)CN1] | 5-oxo-N-((S)-(4-(trifluoromethyl)-phenyl)(3-(trifluoromethyl)-pyridin-2-yl)-methyl)-pyrrolidine-3-carboxamide | 432.0 |
| 164 | 1 | 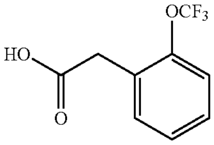 [SMILES: O=C(O)Cc1ccccc1OC(F)(F)F] | 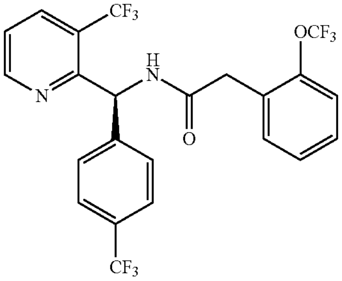 [SMILES: O=C(Cc1ccccc1OC(F)(F)F)N[C@@H](c1ccc(C(F)(F)F)cc1)c1ncccc1C(F)(F)F] | (S)-2-(2-(trifluoro-methoxy)-phenyl)-N-((4-(trifluoromethyl)-phenyl)(3-(trifluoromethyl)-pyridin-2-yl)-methyl)acetamide | 523.0 |
| 165 | 1 | 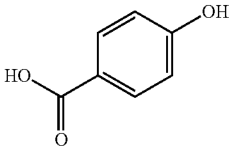 | 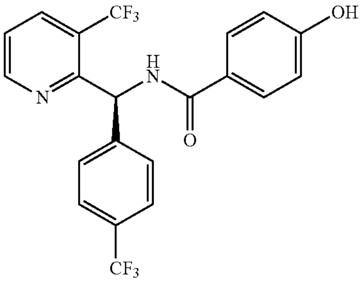 | (S)-4-hydroxy-N-((4-(trifluoro-methyl)phenyl)-(3-(trifluoro-methyl)pyridin-2- | 441.0 |
| 166 | 2 | 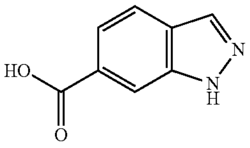 [SMILES: O=C(O)c1ccc2cn[nH]c2c1] | 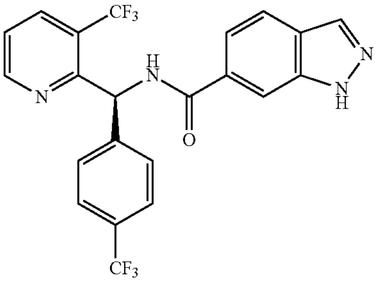 [SMILES: O=C(N[C@@H](c1ccc(C(F)(F)F)cc1)c1ncccc1C(F)(F)F)c1ccc2cn[nH]c2c1] | (S)-N-((3-fluoro-pyridin-2-yl)(4-(trifluoromethyl)-phenyl)methyl)-1H-indazole-6-carboxamide | 415.1 |
| 167 | 2 | 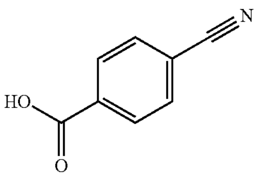 [SMILES: N#Cc1ccc(C(=O)O)cc1] | 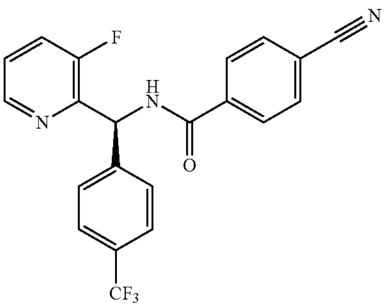 [SMILES: N#Cc1ccc(C(=O)N[C@@H](c2ccc(C(F)(F)F)cc2)c2ncccc2F)cc1] | (S)-4-cyano-N-((3-fluoropyridin-2-yl)(4-(trifluoro-methyl)phenyl)-methyl)-benzamide | 400.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 168 | 1 | 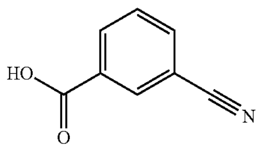 [SMILES: N#Cc1cccc(C(=O)O)c1] | 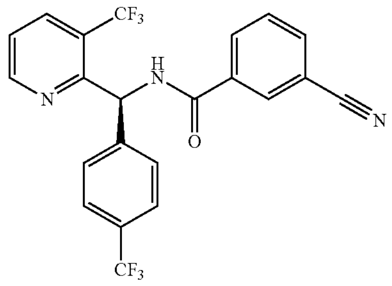 [SMILES: N#Cc1cccc(C(=O)N[C@@H](c2ccc(C(F)(F)F)cc2)c2ncccc2C(F)(F)F)c1] | (S)-3-cyano-N-((4-(trifluoro-methyl)phenyl)-(3-(trifluoro-methyl)pyridin-2-yl)methyl)be | 450.0 |
| 169 | 2 | 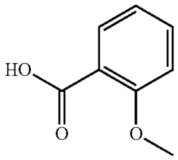 | 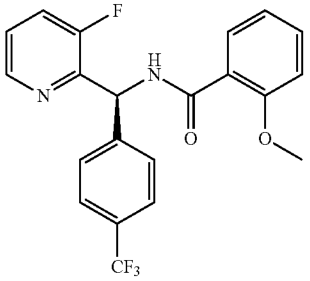 [SMILES: COc1ccccc1C(=O)N[C@@H](c1ccc(C(F)(F)F)cc1)c1ncccc1F] | (S)-N-((3-fluoro-pyridin-2-yl)(4-(trifluoromethyl)-phenyl)methyl)-2-methoxy-benzamide | 405.2 |
| 170 | 2 | 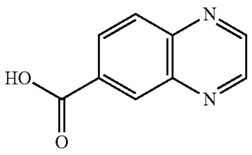 [SMILES: O=C(O)c1ccc2nccnc2c1] | 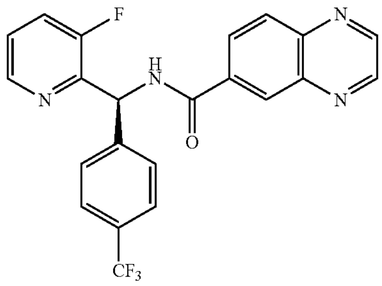 | (S)-N-((3-fluoro-pyridin-2-yl)(4-(trifluoromethyl)-phenyl)methyl)-quinoxaline-6-carboxamide | 427.1 |
| 171 | 1 | 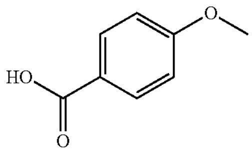 | 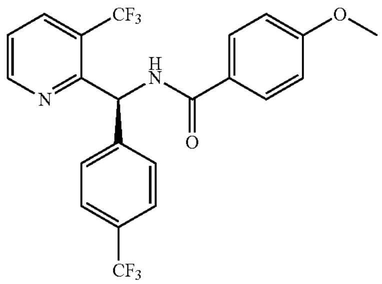 [SMILES: COc1ccc(C(=O)N[C@@H](c2ccc(C(F)(F)F)cc2)c2ncccc2C(F)(F)F)cc1] | (S)-4-methoxy-N-((4-(trifluoro-methyl)phenyl)-(3-(trifluoro-methyl)pyridin-2-yl)methyl)-benzamide | 455.1 |
| 172 | 2 | 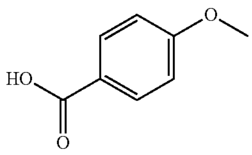 | 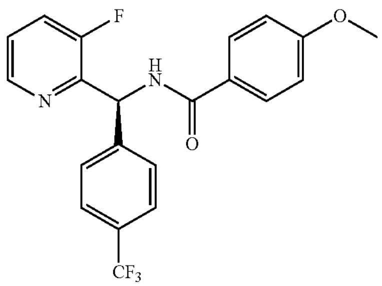 | (S)-N-((3-fluoro-pyridin-2-yl)(4-(trifluoromethyl)-phenyl)methyl)-4-methoxy-benzamide | 405.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 173 | 2 | 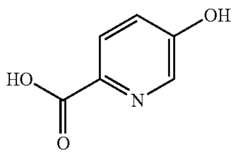 | 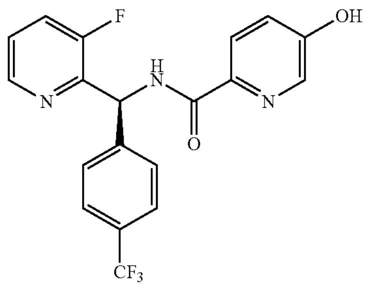 [SMILES: O=C(N[C@@H](c1ccc(C(F)(F)F)cc1)c1ncccc1F)c1ccc(O)cn1] | (S)-N-((3-fluoro-pyridin-2-yl)(4-(trifluoromethyl)-phenyl)methyl)-5-hydroxy-picolinamide | 392.1 |
| 174 | 1 | 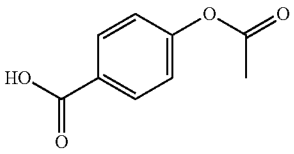 | 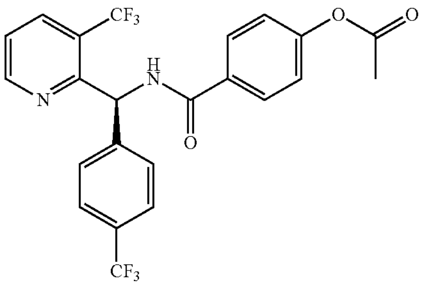 [SMILES: CC(=O)Oc1ccc(C(=O)N[C@@H](c2ccc(C(F)(F)F)cc2)c2ncccc2C(F)(F)F)cc1] | (S)-4-(((4-(trifluoromethyl)-phenyl)(3-(trifluoromethyl)-pyridin-2-yl)-methyl)-carbamoyl)-phenyl acetate | 483.0 |
| 175 | 1 | 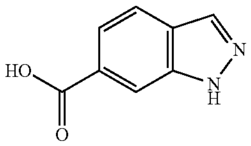 [SMILES: O=C(O)c1ccc2cn[nH]c2c1] | 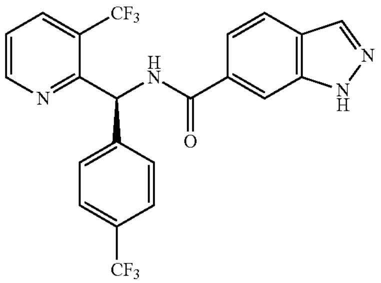 [SMILES: O=C(N[C@@H](c1ccc(C(F)(F)F)cc1)c1ncccc1C(F)(F)F)c1ccc2cn[nH]c2c1] | (S)-N-((4-(trifluoromethyl)-phenyl)(3-(trifluoromethyl)-pyridin-2-yl)-methyl)-1H-indazole-6-carboxamide | 465.0 |
| 176 | 1 | 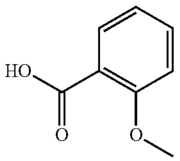 | 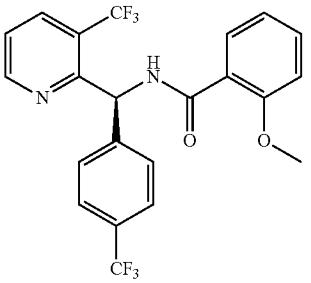 [SMILES: COc1ccccc1C(=O)N[C@@H](c1ccc(C(F)(F)F)cc1)c1ncccc1C(F)(F)F] | (S)-2-methoxy-N-((4-(trifluoro-methyl)phenyl)-(3-(trifluoro-methyl)pyridin-2-yl)methyl)-benzamide | 455.1 |
| 177 | 2 | 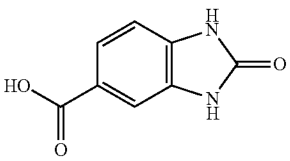 [SMILES: O=C(O)c1ccc2[nH]c(=O)[nH]c2c1] | 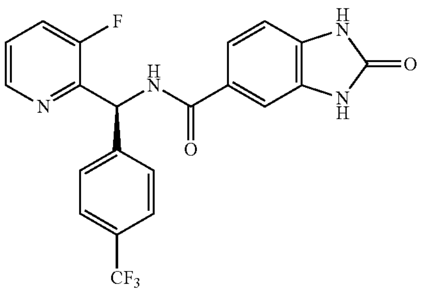 [SMILES: O=C(N[C@@H](c1ccc(C(F)(F)F)cc1)c1ncccc1F)c1ccc2[nH]c(=O)[nH]c2c1] | (S)-N-((3-fluoro-pyridin-2-yl)(4-(trifluoromethyl)-phenyl)methyl)-2-oxo-2,3-dihydro-1H-benzo[d]imidazole-5-carboxamide | 431.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 178 | 1 | 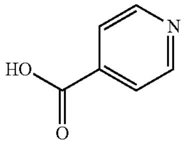 | 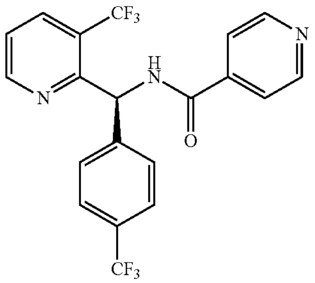 | (S)-N-((4-(trifluoromethyl)-phenyl)(3-(trifluoromethyl)-pyridin-2-yl)-methyl)-isonicotinamide | 426.0 |
| 179 | 1 | 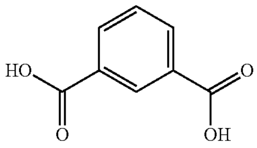 [SMILES: O=C(O)c1cccc(C(=O)O)c1] | 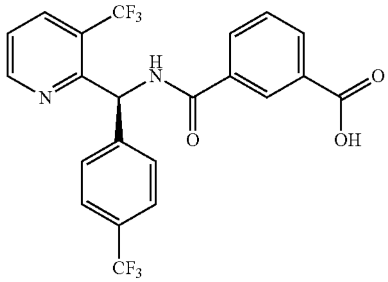 [SMILES: O=C(O)c1cccc(C(=O)N[C@@H](c2ccc(C(F)(F)F)cc2)c2ncccc2C(F)(F)F)c1] | (S)-3-(((4-(trifluoromethyl)-phenyl)(3-(tritluoromethyl)-pyridin-2-yl)-methyl)-carbamoyl)-benzoic acid | 469.1 |
| 180 | 2 | 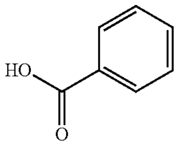 | 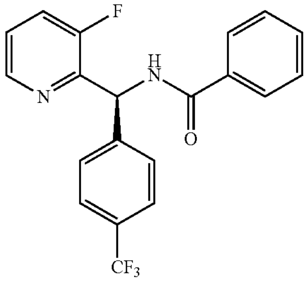 | (S)-N-((3-fluoro-pyridin-2-yl)(4-(trifluoromethyl)-phenyl)methyl)-benzamide | 375.2 |
| 181 | 1 | 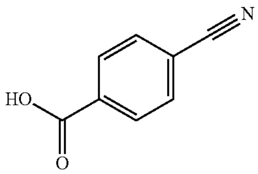 [SMILES: N#Cc1ccc(C(=O)O)cc1] | 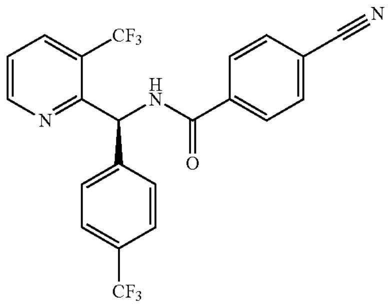 [SMILES: N#Cc1ccc(C(=O)N[C@@H](c2ccc(C(F)(F)F)cc2)c2ncccc2C(F)(F)F)cc1] | (S)-4-cyano-N-((4-(trifluoro-methyl)phenyl)-(3-(trifluoro-methyl)pyridin-2-yl)methyl)-benzamide | 450.0 |
| 182 | 1 | 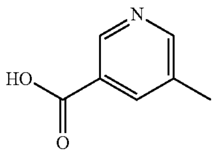 | 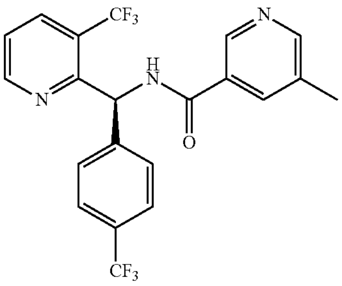 [SMILES: Cc1cncc(C(=O)N[C@@H](c2ccc(C(F)(F)F)cc2)c2ncccc2C(F)(F)F)c1] | (S)-5-methyl-N-((4-(trifluoro-methyl)phenyl)-(3-(trifluoro-methyl)pyridin-2-yl)methyl)-nicotinamide 2,2,2-trifluoroacetate | 440.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 183 | 1 | 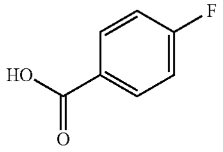 | 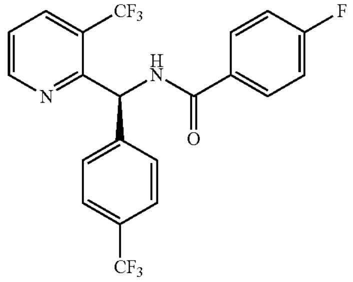 [SMILES: O=C(N[C@@H](c1ccc(C(F)(F)F)cc1)c1ncccc1C(F)(F)F)c1ccc(F)cc1] | (S)-4-fluoro-N-((4-(trifluoro-methyl)phenyl)-(3-(trifluoro-methyl)pyridin-2-yl)methyl)-benzamide | 443.1 |
| 184 | 2 | 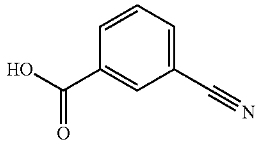 [SMILES: N#Cc1cccc(C(=O)O)c1] | 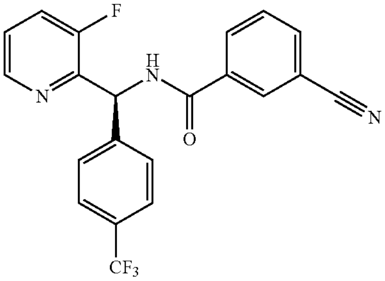 [SMILES: N#Cc1cccc(C(=O)N[C@@H](c2ccc(C(F)(F)F)cc2)c2ncccc2F)c1] | (S)-3-cyano-N-((3-fluoropyridin-2-yl)(4-(trifluoro-methyl)phenyl)-methyl)-benzamide | 400.1 |
| 185 | 1 | 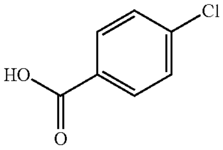 | 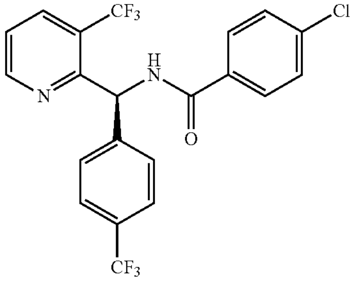 [SMILES: O=C(N[C@@H](c1ccc(C(F)(F)F)cc1)c1ncccc1C(F)(F)F)c1ccc(Cl)cc1] | (S)-4-chloro-N-((4-(trifluoro-methyl)phenyl)-(3-(trifluoro-methyl)pyridin-2-yl)methyl)-benzamide | 459.0 |
| 186 | 1 | 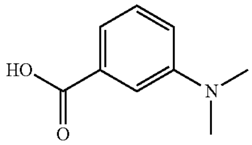 | 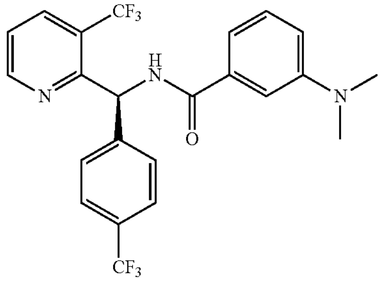 [SMILES: CN(C)c1cccc(C(=O)N[C@@H](c2ccc(C(F)(F)F)cc2)c2ncccc2C(F)(F)F)c1] | (S)-3-(dimethylamino)-N-((4-(trifluoro-methyl)phenyl)-(3-(trifluoro-methyl)pyridin-2-yl)methyl)-benzamide | 468.2 |
| 187 | 2 | 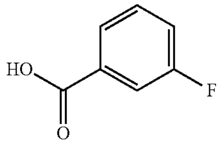 | 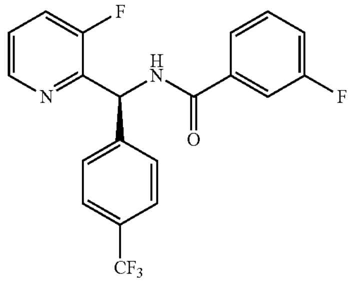 | (S)-3-fluoro-N-((3-fluoropyridin-2-yl)(4-(trifluoro-methyl)phenyl)-methyl)-benzamide | 393.0 |

TABLE 2-continued

| Examples 1-261 prepared via amide formation analogous to Scheme 4 | | | | | |
|---|---|---|---|---|---|
| Ex # | A-mine | Acid Structure | Product Structure | Product Name | MS M + H |
| 188 | 1 | 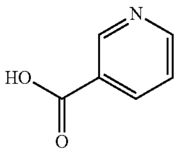 | 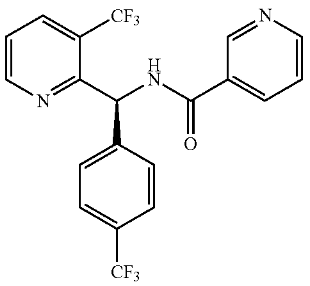 | (S)-N-((4-(trifluoromethyl)-phenyl)(3-(trifluoromethyl)-pyridin-2-yl)-methyl)-nicotinamide | 426.0 |
| 189 | 1 | 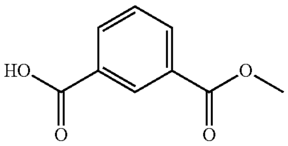 | 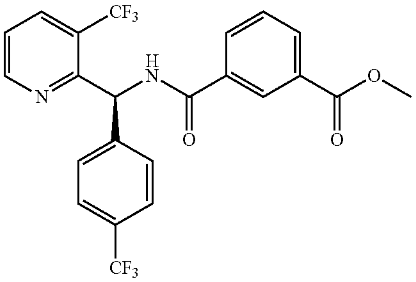 [SMILES: COC(=O)c1cccc(C(=O)N[C@@H](c2ccc(C(F)(F)F)cc2)c2ncccc2C(F)(F)F)c1] | (S)-methyl 3-(((4-(trifluoro-methyl)phenyl)-(3-(trifluoro-methyl)pyridin-2-yl)methyl)-carbamoyl)-benzoate | 483.0 |
| 190 | 1 | 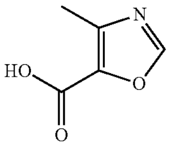 | 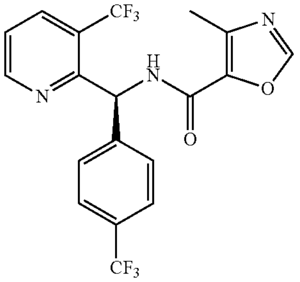 [SMILES: Cc1ncoc1C(=O)N[C@@H](c1ccc(C(F)(F)F)cc1)c1ncccc1C(F)(F)F] | (S)-4-methyl-N-((4-(trifluoro-methyl)phenyl)-(3-(trifluoro-methyl)pyridin-2-yl)methyl)-oxazole-5-carboxamide | 430.1 |
| 191 | 1 | 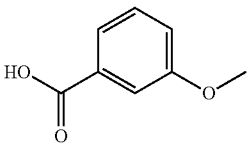 | 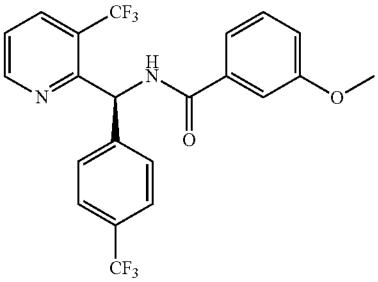 | (S)-3-methoxy-N-((4-(trifluoro-methyl)phenyl)-(3-(trifluoro-methyl)pyridin-2-yl)methyl)-benzamide | 455.1 |
| 192 | 1 | 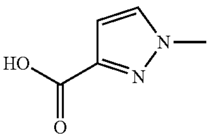 | 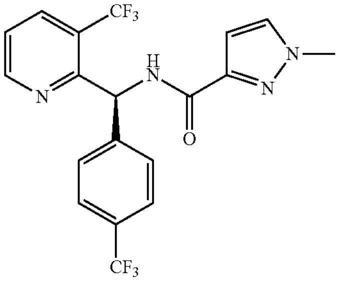 [SMILES: Cn1ccc(C(=O)N[C@@H](c2ccc(C(F)(F)F)cc2)c2ncccc2C(F)(F)F)n1] | (S)-1-methyl-N-((4-(trifluoro-methyl)phenyl)-(3-(trifluoro-methyl)pyridin-2-yl)methyl)-1H-pyrazole-3-carboxamide | 429.2 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 193 | 2a | 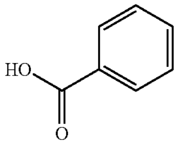 | 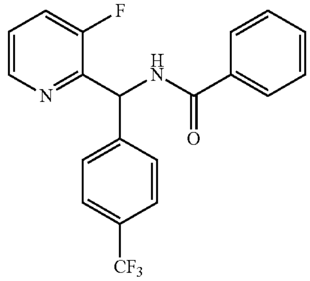 [SMILES: O=C(NC(c1ccc(C(F)(F)F)cc1)c1ncccc1F)c1ccccc1] | N-((3-fluoro-pyridin-2-yl)(4-(trifluoromethyl)-phenyl)methyl)-benzamide | 375.0 |
| 194 | 2 | 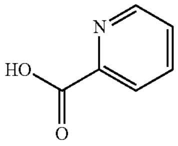 | 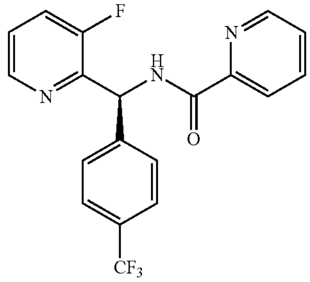 [SMILES: O=C(N[C@@H](c1ccc(C(F)(F)F)cc1)c1ncccc1F)c1ccccn1] | (S)-N-((3-fluoro-pyridin-2-yl)(4-(trifluoromethyl)-phenyl)methyl)-picolinamide | 376.1 |
| 195 | 44 | 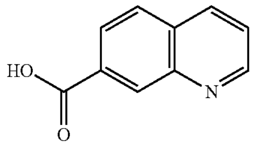 [SMILES: O=C(O)c1ccc2cccnc2c1] | 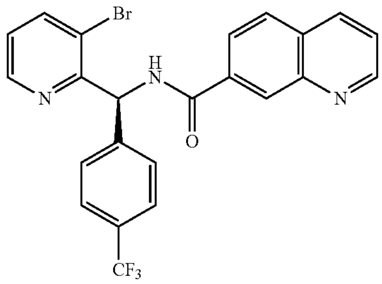 [SMILES: O=C(N[C@@H](c1ccc(C(F)(F)F)cc1)c1ncccc1Br)c1ccc2cccnc2c1] | (S)-N-((3-bromopyridin-2-yl)(4-(trifluoro-methyl)phenyl)-methyl)-quinoline-7-carboxamide | 486.0, 488.0 |
| 196 | 1 | 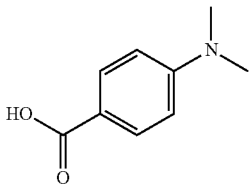 | 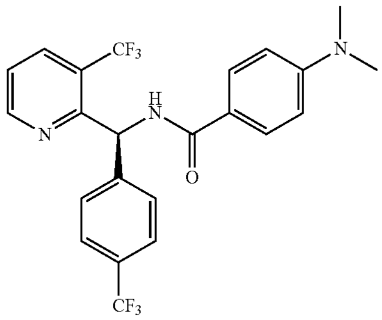 [SMILES: CN(C)c1ccc(C(=O)N[C@@H](c2ccc(C(F)(F)F)cc2)c2ncccc2C(F)(F)F)cc1] | (S)-4-(dimethylamino)-N-((4-(trifluoro-methyl)phenyl)-(3-(trifluoro-methyl)pyridin-2-yl)methyl)-benzamide | 468.1 |
| 197 | 1 | 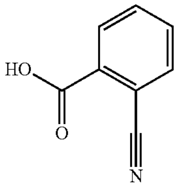 [SMILES: N#Cc1ccccc1C(=O)O] | 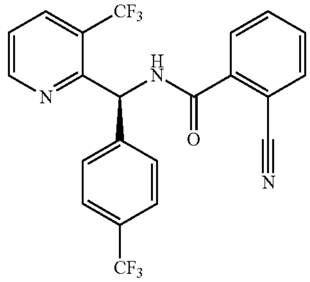 [SMILES: N#Cc1ccccc1C(=O)N[C@@H](c1ccc(C(F)(F)F)cc1)c1ncccc1C(F)(F)F] | (S)-2-cyano-N-((4-(trifluoro-methyl)phenyl)-(3-(trifluoro-methyl)pyridin-2-yl)methyl)-benzamide | 450.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 198 | 2 | 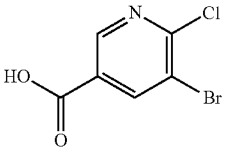 [SMILES: O=C(O)c1cnc(Cl)c(Br)c1] | 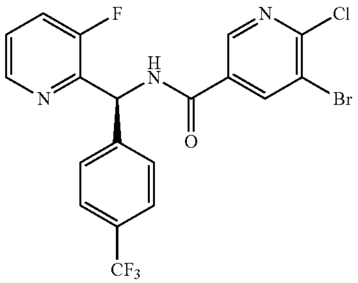 [SMILES: O=C(N[C@@H](c1ccc(C(F)(F)F)cc1)c1ncccc1F)c1cnc(Cl)c(Br)c1] | (S)-5-bromo-6-chloro-N-((3-fluoropyridin-2-yl)(4-(trifluoro-methyl)phenyl)-methyl)-nicotinamide | 488.0, 490.0 |
| 199 | 1 | 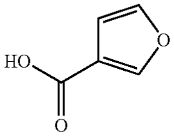 | 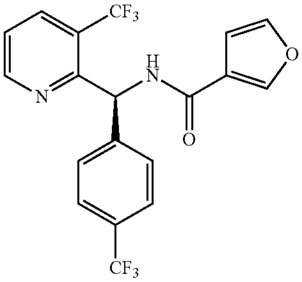 [SMILES: O=C(N[C@@H](c1ccc(C(F)(F)F)cc1)c1ncccc1C(F)(F)F)c1ccoc1] | (S)-N-((4-(trifluoromethyl)-phenyl)(3-(trifluoromethyl)-pyridin-2-yl)-methyl)furan-3-carboxamide | 415.1 |
| 200 | 2a | 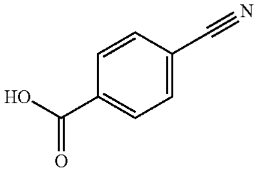 [SMILES: N#Cc1ccc(C(=O)O)cc1] | 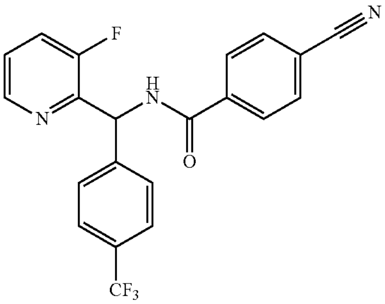 [SMILES: N#Cc1ccc(C(=O)NC(c2ccc(C(F)(F)F)cc2)c2ncccc2F)cc1] | 4-cyano-N-((3-fluoropyridin-2-yl)(4-(trifluoro-methyl)phenyl)-methyl)-benzamide | 400.1 |
| 201 | 54 | 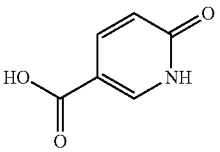 | 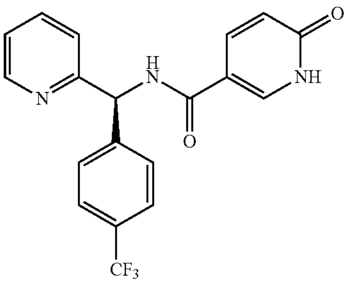 [SMILES: O=C(N[C@@H](c1ccc(C(F)(F)F)cc1)c1ccccn1)c1ccc(=O)[nH]c1] | (S)-6-oxo-N-(pyridin-2-yl(4-(trifluoromethyl)-phenyl)methyl)-1,6-dihydro-pyridine-3-carboxamide 2,2,2-trifluoroacetate | 374.1 |
| 202 | 2a | 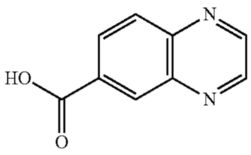 [SMILES: O=C(O)c1ccc2nccnc2c1] | 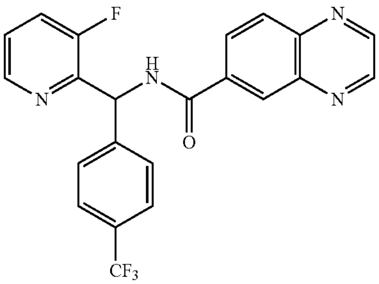 [SMILES: O=C(NC(c1ccc(C(F)(F)F)cc1)c1ncccc1F)c1ccc2nccnc2c1] | N-((3-fluoro-pyridin-2-yl)(4-(trifluoromethyl)-phenyl)methyl)-quinoxaline-6-carboxamide | 427.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 203 | 2 | 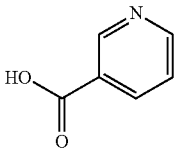 | 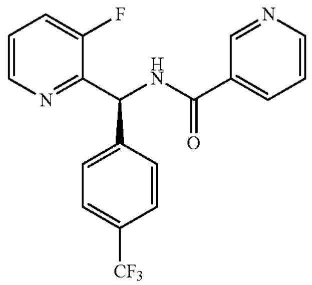 [SMILES: O=C(N[C@@H](c1ccc(C(F)(F)F)cc1)c1ncccc1F)c1cccnc1] | (S)-N-((3-fluoro-pyridin-2-yl)(4-(trifluoromethyl)-phenyl)methyl)-nicotinamide | 376.1 |
| 204 | 2a | 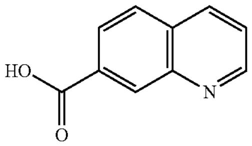 [SMILES: O=C(O)c1ccc2cccnc2c1] | 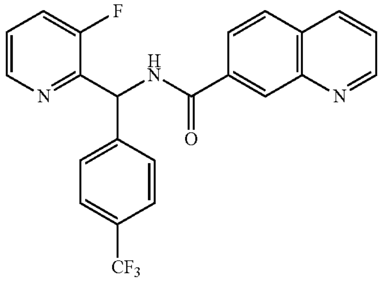 [SMILES: O=C(NC(c1ccc(C(F)(F)F)cc1)c1ncccc1F)c1ccc2cccnc2c1] | N-((3-fluoro-pyridin-2-yl)(4-(trifluoromethyl)-phenyl)methyl)-quinoline-7-carboxamide | 426.2 |
| 205 | 1 | 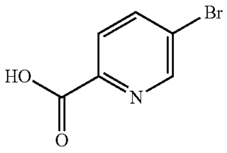 | 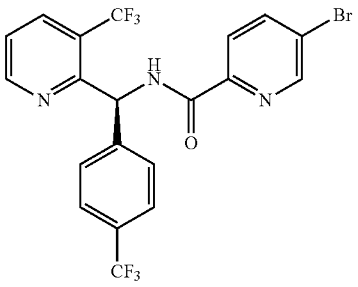 [SMILES: O=C(N[C@@H](c1ccc(C(F)(F)F)cc1)c1ncccc1C(F)(F)F)c1ccc(Br)cn1] | (S)-5-bromo-N-((4-(trifluoro-methyl)phenyl)-(3-(trifluoro-methyl)pyridin-2-yl)methyl)-picolinamide | 505.0, 507.0 |
| 206 | 1 | 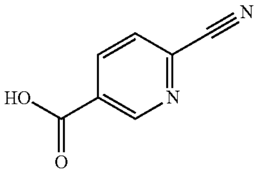 [SMILES: N#Cc1ccc(C(=O)O)cn1] | 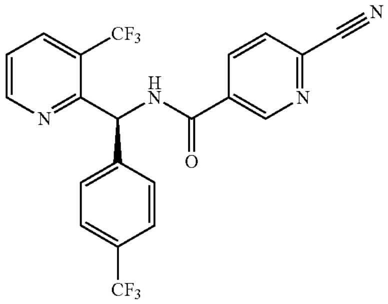 [SMILES: N#Cc1ccc(C(=O)N[C@@H](c2ccc(C(F)(F)F)cc2)c2ncccc2C(F)(F)F)cn1] | (S)-6-cyano-N-((4-(trifluoro-methyl)phenyl)-(3-(trifluoro-methyl)pyridin-2-yl)methyl)-nicotinamide | 451.1 |
| 207 | 1 | 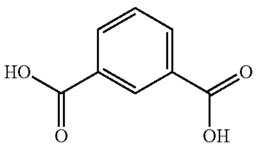 [SMILES: O=C(O)c1cccc(C(=O)O)c1] | 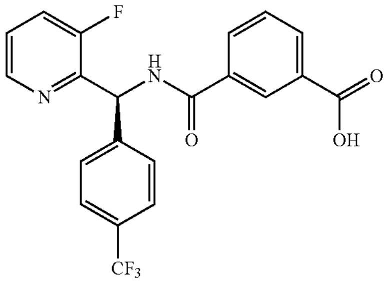 [SMILES: O=C(O)c1cccc(C(=O)N[C@@H](c2ccc(C(F)(F)F)cc2)c2ncccc2F)c1] | (S)-3-(((3-fluoro-pyridin-2-yl)(4-(trifluoromethyl)-phenyl)methyl)-carbamoyl)-benzoic acid | 419.1 |

TABLE 2-continued

| Ex # | A-mine | Acid Structure | Product Structure | Product Name | MS M + H |
|---|---|---|---|---|---|
| Examples 1-261 prepared via amide formation analogous to Scheme 4 | | | | | |
| 208 | 1 | 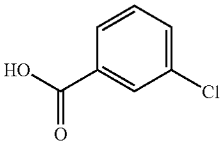 | 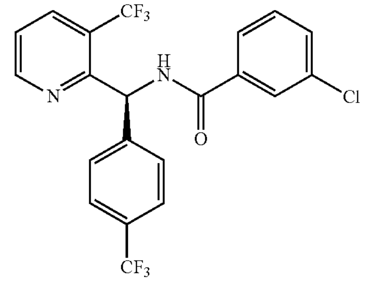 [SMILES: O=C(N[C@@H](c1ccc(C(F)(F)F)cc1)c1ncccc1C(F)(F)F)c1cccc(Cl)c1] | (S)-3-chloro-N-((4-(trifluoro-methyl)phenyl)-(3-(trifluoro-methyl)pyridin-2-yl)methyl)-benzamide | 460.1 |
| 209 | 2a | 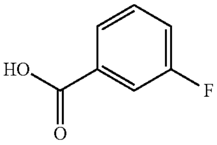 | 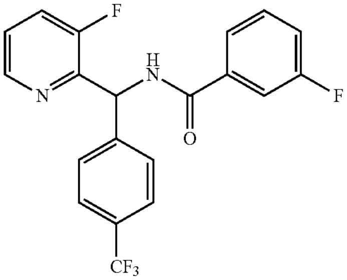 [SMILES: O=C(NC(c1ccc(C(F)(F)F)cc1)c1ncccc1F)c1cccc(F)c1] | 3-fluoro-N-((3-fluoropyridin-2-yl)(4-(trifluoro-methyl)phenyl)-methyl)-benzamide | 393.0 |
| 210 | 1 | 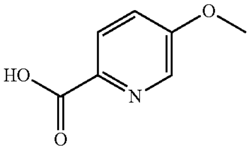 | 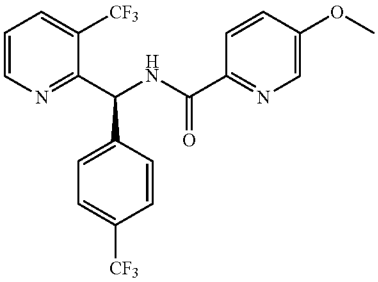 [SMILES: COc1ccc(C(=O)N[C@@H](c2ccc(C(F)(F)F)cc2)c2ncccc2C(F)(F)F)nc1] | (S)-5-methoxy-N-((4-(trifluoro-methyl)phenyl)-(3-(trifluoro-methyl)pyridin-2-yl)methyl)-picolinamide | 456.0 |
| 211 | 1 | 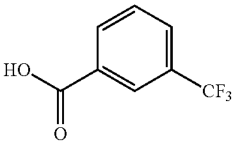 [SMILES: O=C(O)c1cccc(C(F)(F)F)c1] | 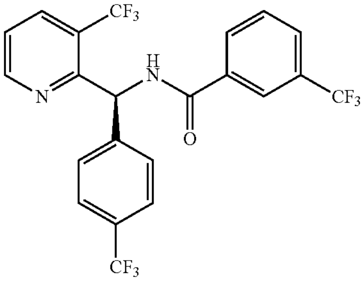 [SMILES: O=C(N[C@@H](c1ccc(C(F)(F)F)cc1)c1ncccc1C(F)(F)F)c1cccc(C(F)(F)F)c1] | (S)-3-(trifluoro-methyl)-N-((4-(trifluoromethyl)-phenyl)(3-(trifluoromethyl)-pyridin-2-yl)-methyl)-benzamide | 493.1 |
| 212 | 1 | 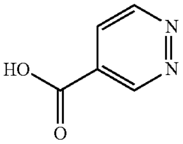 | 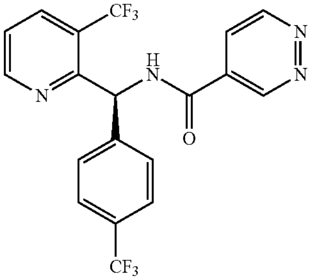 [SMILES: O=C(N[C@@H](c1ccc(C(F)(F)F)cc1)c1ncccc1C(F)(F)F)c1ccnnc1] | (S)-N-((4-(trifluoromethyl)-phenyl)(3-(trifluoromethyl)-pyridin-2-yl)-methyl)-pyridazine-4-carboxamide | 427.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 213 | 2 | 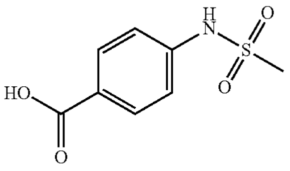 | 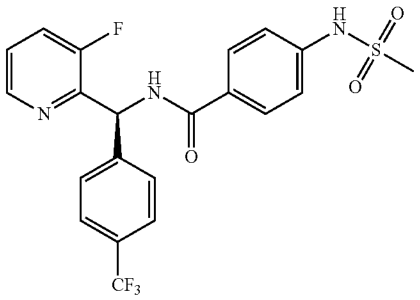 [SMILES: CS(=O)(=O)Nc1ccc(C(=O)N[C@@H](c2ccc(C(F)(F)F)cc2)c2ncccc2F)cc1] | (S)-N-((3-fluoro-pyridin-2-yl)(4-(trifluoromethyl)-phenyl)methyl)-4-(methyl-sulfonamido) benzamide | 468.0 |
| 214 | 2a | 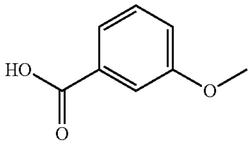 | 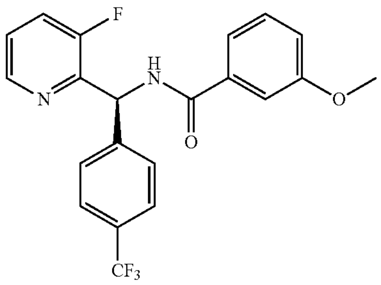 [SMILES: COc1cccc(C(=O)N[C@@H](c2ccc(C(F)(F)F)cc2)c2ncccc2F)c1] | N-((3-fluoro-pyridin-2-yl)(4-(trifluoromethyl)-phenyl)methyl)-3-methoxy-benzamide | 405.0 |
| 215 | 1 | 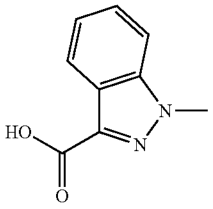 | 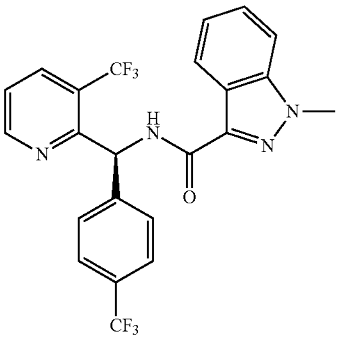 [SMILES: Cn1nc(C(=O)N[C@@H](c2ccc(C(F)(F)F)cc2)c2ncccc2C(F)(F)F)c2ccccc21] | (S)-1-methyl-N-((4-(trifluoro-methyl)phenyl)-(3-(trifluoro-methyl)pyridin-2-yl)methyl)-1H-indazole-3-carboxamide | 479.1 |
| 216 | 2 | 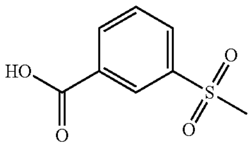 | 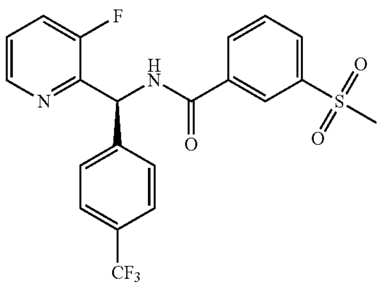 [SMILES: CS(=O)(=O)c1cccc(C(=O)N[C@@H](c2ccc(C(F)(F)F)cc2)c2ncccc2F)c1] | (S)-N-((3-fluoro-pyridin-2-yl)(4-(trifluoromethyl)-phenyl)methyl)-3-(methylsulfonyl)-benzamide | 453.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 217 | 2 | 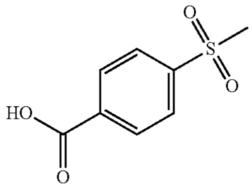 | 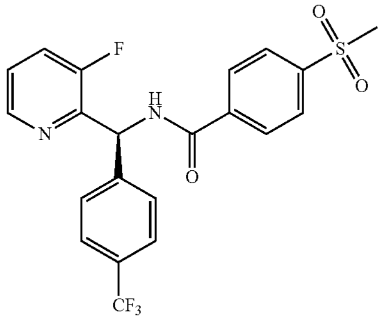 [SMILES: CS(=O)(=O)c1ccc(C(=O)N[C@@H](c2ccc(C(F)(F)F)cc2)c2ncccc2F)cc1] | (S)-N-((3-fluoro-pyridin-2-yl)(4-(trifluoromethyl)-phenyl)methyl)-4-(methylsulfonyl)-benzamide | 453.0 |
| 218 | 1 | 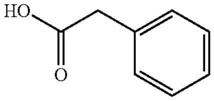 | 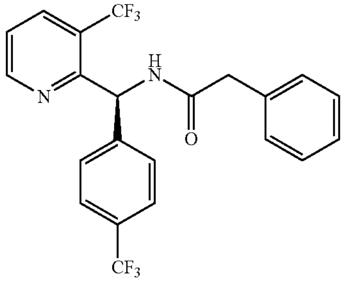 [SMILES: O=C(Cc1ccccc1)N[C@@H](c1ccc(C(F)(F)F)cc1)c1ncccc1C(F)(F)F] | (S)-2-phenyl-N-((4-(trifluoro-methyl)phenyl)-(3-(trifluoro-methyl)pyridin-2-yl)methyl)-acetamide | 439.1 |
| 219 | 1 | 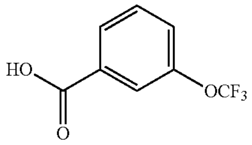 [SMILES: O=C(O)c1cccc(OC(F)(F)F)c1] | 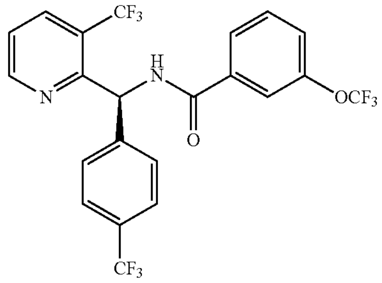 [SMILES: O=C(N[C@@H](c1ccc(C(F)(F)F)cc1)c1ncccc1C(F)(F)F)c1cccc(OC(F)(F)F)c1] | (S)-3-(trifluoro-methoxy)-N-((4-(trifluoromethyl)-phenyl)(3-(trifluoromethyl)-pyridin-2-yl)-methyl)-benzamide | 509.1 |
| 220 | 1 | 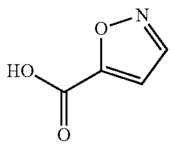 | 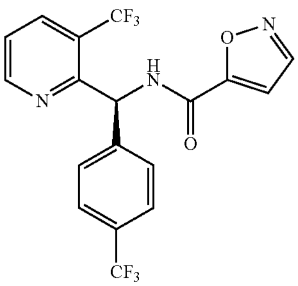 [SMILES: O=C(N[C@@H](c1ccc(C(F)(F)F)cc1)c1ncccc1C(F)(F)F)c1ccno1] | (S)-N-((4-(trifluoromethyl)-phenyl)(3-(trifluoromethyl)-pyridin-2-yl)-methyl)-isoxazole-5-carboxamide | 416.1 |
| 221 | 2a | 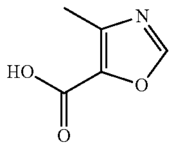 | 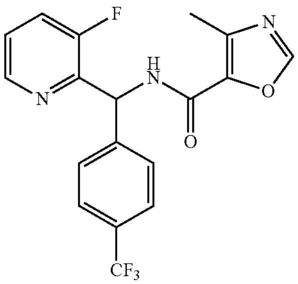 [SMILES: Cc1ncoc1C(=O)NC(c1ccc(C(F)(F)F)cc1)c1ncccc1F] | N-((3-fluoro-pyridin-2-yl)(4-(trifluoromethyl)-phenyl)methyl)-4-methyloxazole-5-carboxamide | 380.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 222 | 1 | 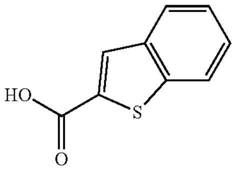 [SMILES: O=C(O)c1cc2ccccc2s1] | 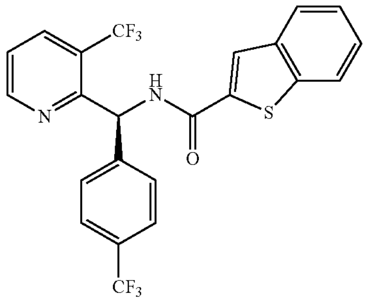 [SMILES: O=C(N[C@@H](c1ccc(C(F)(F)F)cc1)c1ncccc1C(F)(F)F)c1cc2ccccc2s1] | (S)-N-((4-(trifluoromethyl)-phenyl)(3-(trifluoromethyl)-pyridin-2-yl)-methyl)-benzo[b]thiophene-2-carboxamide | 481.1 |
| 223 | 1 | 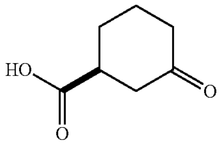 | 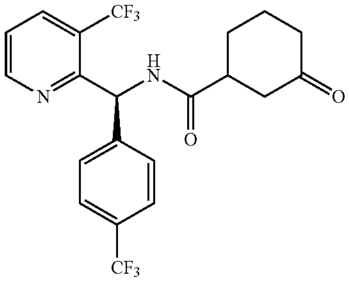 [SMILES: O=C1CCCC(C(=O)N[C@@H](c2ccc(C(F)(F)F)cc2)c2ncccc2C(F)(F)F)C1] | 3-oxo-N-((S)-(4-(trifluoromethyl)-phenyl)(3-(trifluoromethyl)-pyridin-2-yl)-methyl)-cyclohexane-carboxamide | 445.1 |
| 224 | 1 | 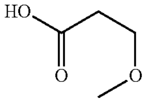 | 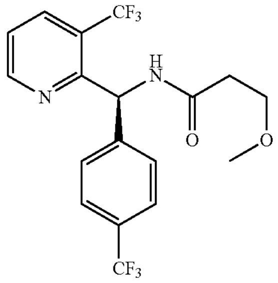 [SMILES: COCCC(=O)N[C@@H](c1ccc(C(F)(F)F)cc1)c1ncccc1C(F)(F)F] | (S)-3-methoxy-N-((4-(trifluoro-methyl)phenyl)-(3-(trifluoro-methyl)pyridin-2-yl)methyl)-propanamide | 407.1 |
| 225 | 1 | 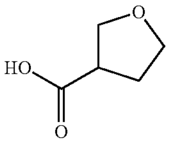 | 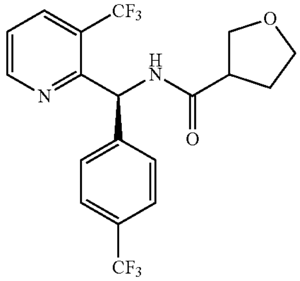 [SMILES: O=C(N[C@@H](c1ccc(C(F)(F)F)cc1)c1ncccc1C(F)(F)F)C1CCOC1] | N-((S)-(4-(trifluoromethyl)-phenyl)(3-(trifluoromethyl)-pyridin-2-yl)-melhyl)THF-3-carboxamide | 419.1 |
| 226 | 1 | 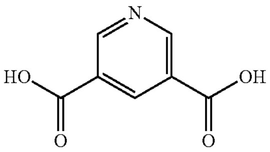 [SMILES: O=C(O)c1cncc(C(=O)O)c1] | 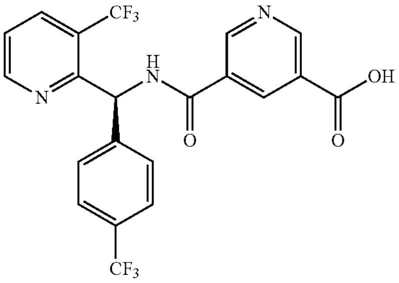 [SMILES: O=C(O)c1cncc(C(=O)N[C@@H](c2ccc(C(F)(F)F)cc2)c2ncccc2C(F)(F)F)c1] | (S)-5-(((4-(trifluoromethyl)-phenyl)(3-(trifluoromethyl)-pyridin-2-yl)-methyl)-carbamoyl)-nicotinic acid | 470.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 227 | 1 | 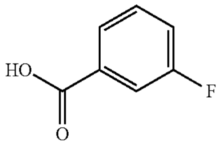 | 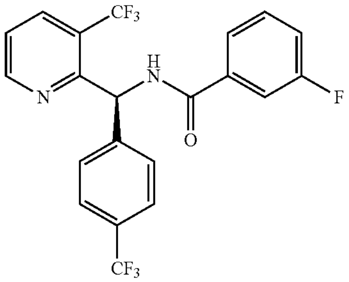 [SMILES: O=C(N[C@@H](c1ccc(C(F)(F)F)cc1)c1ncccc1C(F)(F)F)c1cccc(F)c1] | (S)-3-fluoro-N-((4-(trifluoro-methyl)phenyl)-(3-(trifluoro-methyl)pyridin-2-yl)methyl)-benzamide | 443.1 |
| 228 | 1 | 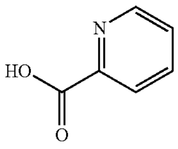 | 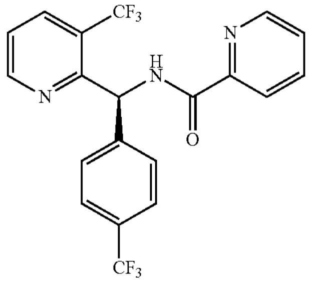 [SMILES: O=C(N[C@@H](c1ccc(C(F)(F)F)cc1)c1ncccc1C(F)(F)F)c1ccccn1] | (S)-N-((4-(trifluoromethyl)-phenyl)(3-(trifluoromethyl)-pyridin-2-yl)-methyl)-picolinamide | 426.0 |
| 229 | 1 | 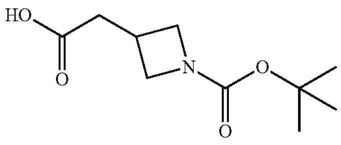 | 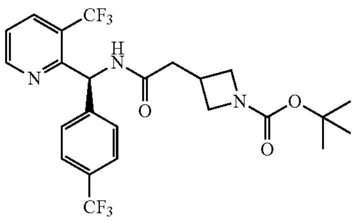 [SMILES: CC(C)(C)OC(=O)N1CC(CC(=O)N[C@@H](c2ccc(C(F)(F)F)cc2)c2ncccc2C(F)(F)F)C1] | (S)-tert-butyl 3-(2-oxo-2-(((4-(trifluoromethyl)-phenyl)(3-(trifluoromethyl)-pyridin-2-yl)-methyl)amino)-ethyl)acetidine-1-carboxylate | 462.0 (M − tBu) |
| 230 | 1 | 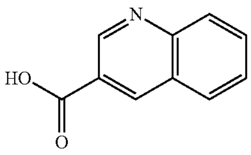 [SMILES: O=C(O)c1cnc2ccccc2c1] | 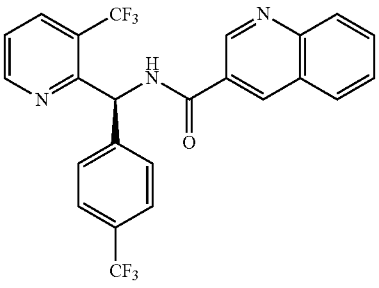 [SMILES: O=C(N[C@@H](c1ccc(C(F)(F)F)cc1)c1ncccc1C(F)(F)F)c1cnc2ccccc2c1] | (S)-N-((4-(trifluoromethyl)-phenyl)(3-(trifluoromethyl)-pyridin-2-yl)-methyl)-quinoline-3-carboxamide | 476.1 |
| 231 | 1 | 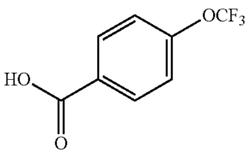 [SMILES: O=C(O)c1ccc(OC(F)(F)F)cc1] | 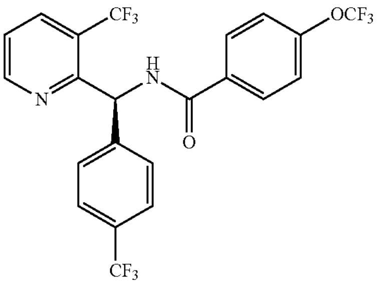 [SMILES: O=C(N[C@@H](c1ccc(C(F)(F)F)cc1)c1ncccc1C(F)(F)F)c1ccc(OC(F)(F)F)cc1] | (S)-4-(trifluoro-methoxy)-N-((4-(trifluoromethyl)-phenyl)(3-(trifluoromethyl)-pyridin-2-yl)-methyl)-benzamide | 509.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 232 | 49 | 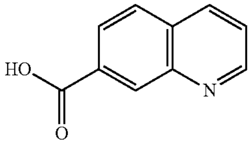 [SMILES: O=C(O)c1ccc2cccnc2c1] | 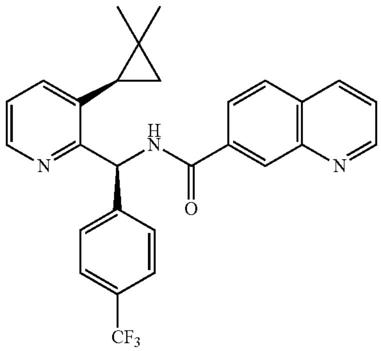 [SMILES: CC1(C)C[C@H]1c1cccnc1[C@@H](NC(=O)c1ccc2cccnc2c1)c1ccc(C(F)(F)F)cc1] | N-((S)-(3-((R)-2,2-dimethyl-cyclopropyl) pyridin-2-yl)-(4-(trifluoro-methyl)phenyl)-methyl)-quinoline-7-carboxamide | 476.0 |
| 233 | 49 | 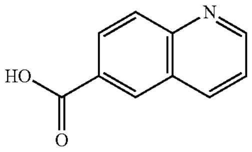 [SMILES: O=C(O)c1ccc2ncccc2c1] | 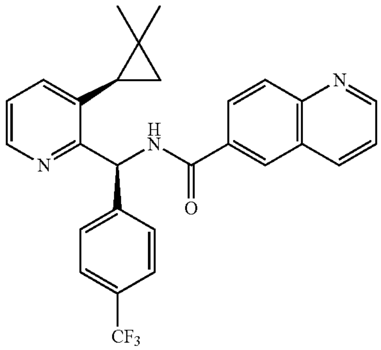 [SMILES: CC1(C)C[C@H]1c1cccnc1[C@@H](NC(=O)c1ccc2ncccc2c1)c1ccc(C(F)(F)F)cc1] | N-((S)-(3-((R)-2,2-dimethyl-cyclopropyl) pyridin-2-yl)-(4-(trifluoro-methyl)phenyl)-methyl)-quinoline-6-carboxamide | 476.0 |
| 234 | 1 | 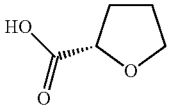 | 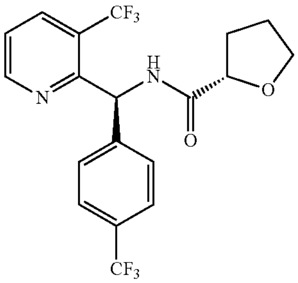 [SMILES: O=C(N[C@@H](c1ccc(C(F)(F)F)cc1)c1ncccc1C(F)(F)F)[C@@H]1CCCO1] | (S)-N-((S)-(4-(trifluoromethyl)-phenyl)(3-(trifluoromethyl)-pyridin-2-yl)-methyl)THF-2-carboxamide | 419.0 |
| 235 | 50 | 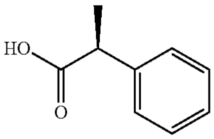 | 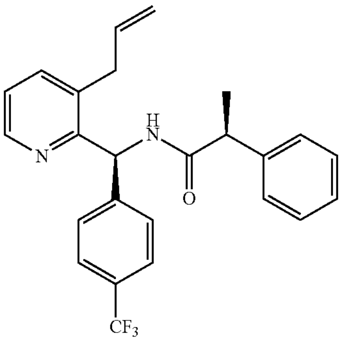 [SMILES: C=CCc1cccnc1[C@@H](NC(=O)[C@@H](C)c1ccccc1)c1ccc(C(F)(F)F)cc1] | (S)-N-((S)-(3-allylpyridin-2-yl)(4-(trifluoro-methyl)phenyl)-methyl)-2-phenyl-propanamide | 425.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 236 | 51 | 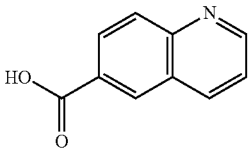 [SMILES: O=C(O)c1ccc2ncccc2c1] | 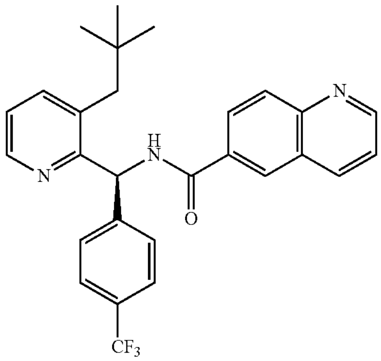 [SMILES: CC(C)(C)Cc1cccnc1[C@@H](NC(=O)c1ccc2ncccc2c1)c1ccc(C(F)(F)F)cc1] | (S)-N-((3-neopentylpyridin-2-yl)(4-(trifluoro-methyl)phenyl) methyl)-quinoline-6-carboxamide | 478.0 |
| 237 | 1 | 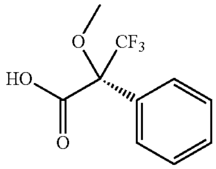 [SMILES: CO[C@@](C(=O)O)(c1ccccc1)C(F)(F)F] | 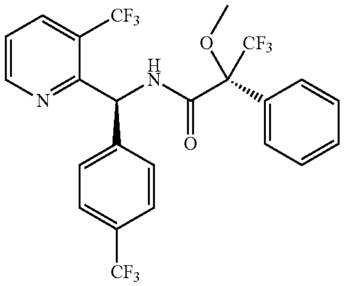 [SMILES: CO[C@@](C(=O)N[C@@H](c1ccc(C(F)(F)F)cc1)c1ncccc1C(F)(F)F)(c1ccccc1)C(F)(F)F] | 3,3,3-trifluoro-2-methoxy-2-phenyl-N-((S)-(4-(trifluoromethyl) phenyl)) 3-(trifluoromethyl)-pyridin-2-yl)-methyl)-propanamide | 537.0 |
| 238 | 1 | 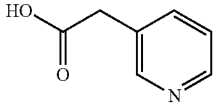 | 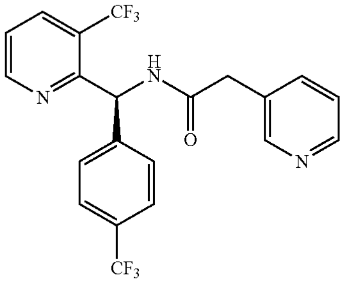 [SMILES: O=C(Cc1cccnc1)N[C@@H](c1ccc(C(F)(F)F)cc1)c1ncccc1C(F)(F)F] | (S)-2-(pyridin-3-yl)-N-((4-(trifluoromethyl)-phenyl)(3-(trifluoromethyl)-pyridin-2-yl)-methyl)acetamide | 440.0 |
| 239 | 1 | 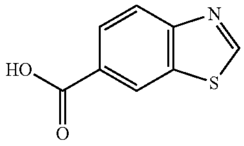 | 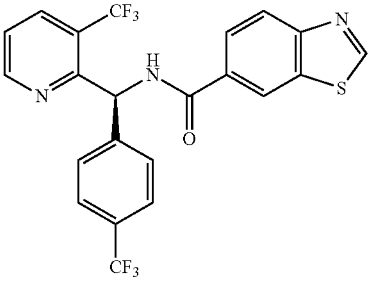 [SMILES: O=C(N[C@@H](c1ccc(C(F)(F)F)cc1)c1ncccc1C(F)(F)F)c1ccc2ncsc2c1] | (S)-N-((4-(trifluoromethyl)-phenyl)(3-(trifluoromethyl)-pyridin-2-yl)-methyl)-benzo[d]thiazole-6-carboxamide | 481.9 |
| 240 | 1 | 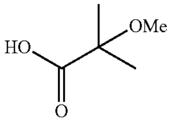 | 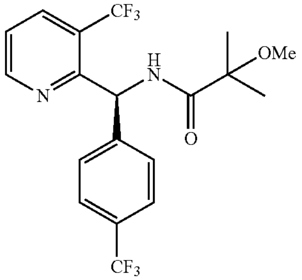 [SMILES: COC(C)(C)C(=O)N[C@@H](c1ccc(C(F)(F)F)cc1)c1ncccc1C(F)(F)F] | (S)-2-methoxy-2-methyl-N-((4-(trifluoromethyl)-phenyl)(3-(trifluoromethyl)-pyridin-2-yl)-methyl)-propanamide | 421.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 241 | 1 | 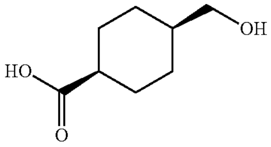 [SMILES: O=C(O)[C@H]1CC[C@@H](CO)CC1] | 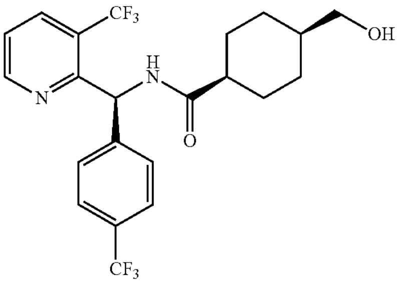 [SMILES: O=C(N[C@@H](c1ccc(C(F)(F)F)cc1)c1ncccc1C(F)(F)F)[C@H]1CC[C@@H](CO)CC1] | (1s,4R)-4-(hydroxy-methyl)-N-((S)-(4-(trifluoro-methyl)phenyl)-(3-(trifluoro-methyl)pyridin-2-yl)methyl)-cyclohexane-carboxamide | 461.0 |
| 242 | 1 | 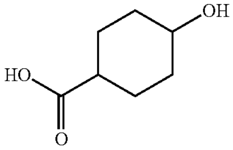 | 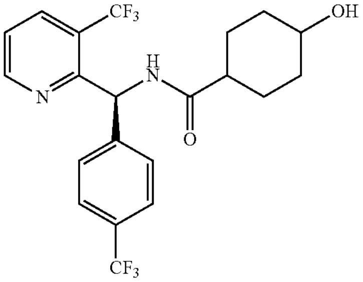 [SMILES: O=C(N[C@@H](c1ccc(C(F)(F)F)cc1)c1ncccc1C(F)(F)F)C1CCC(O)CC1] | (S)-4-hydroxy-N-((4-(trifluoro-methyl)phenyl)-(3-(trifluoro-methyl)pyridin-2-yl)methyl)-cyclohexane-carboxamide | 447.0 |
| 243 | 1 | 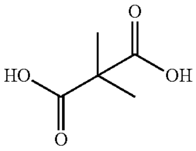 | 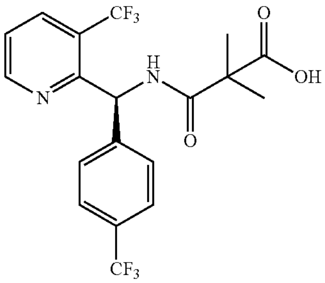 [SMILES: CC(C)(C(=O)O)C(=O)N[C@@H](c1ccc(C(F)(F)F)cc1)c1ncccc1C(F)(F)F] | (S)-2,2-dimethyl-3-oxo-3-(((4-(trifluoromethyl)-phenyl)(3-(trifluoromethyl)-pyridin-2-yl)-methyl)amino)-propanoic acid | 434.9 |
| 244 | 1 | 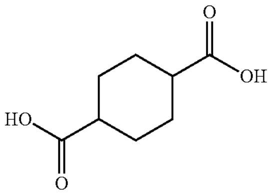 [SMILES: O=C(O)C1CCC(C(=O)O)CC1] | 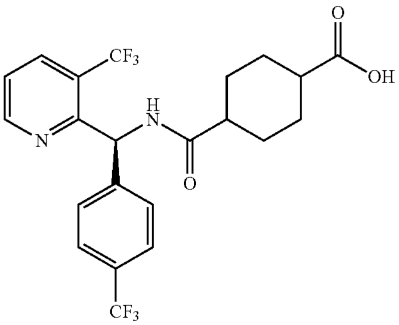 [SMILES: O=C(O)C1CCC(C(=O)N[C@@H](c2ccc(C(F)(F)F)cc2)c2ncccc2C(F)(F)F)CC1] | (S)-4-(((4-(trifluoromethyl)-phenyl)(3-(trifluoromethyl)-pyridin-2-yl)-methyl)-carbamoyl)-cyclohexane-carboxylic acid | 475.0 |
| 245 | 1 | 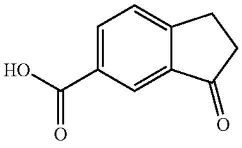 [SMILES: O=C(O)c1ccc2c(c1)C(=O)CC2] | 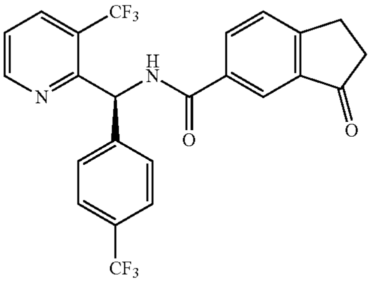 [SMILES: O=C(N[C@@H](c1ccc(C(F)(F)F)cc1)c1ncccc1C(F)(F)F)c1ccc2c(c1)C(=O)CC2] | (S)-3-oxo-N-((4-(trifluoromethyl)-phenyl)(3-(trifluoromethyl)-pyridin-2-yl)-methyl)-2,3-dihydro-1H-indene-5-carboxamide | 479.0 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 246 | 1 | 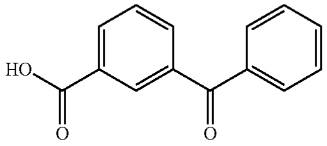 [SMILES: O=C(O)c1cccc(C(=O)c2ccccc2)c1] | 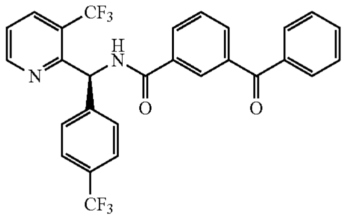 [SMILES: O=C(N[C@@H](c1ccc(C(F)(F)F)cc1)c1ncccc1C(F)(F)F)c1cccc(C(=O)c2ccccc2)c1] | (S)-3-benzoyl-N-((4-(trifluoro-methyl)phenyl)-(3-(trifluoro-methyl)pyridin-2-yl)methyl)-benzamide 2,2,2-trifluoroacetate | 529.0 |
| 247 | 52 | 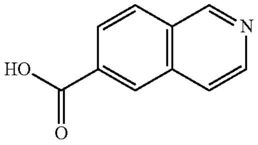 [SMILES: O=C(O)c1ccc2cnccc2c1] | 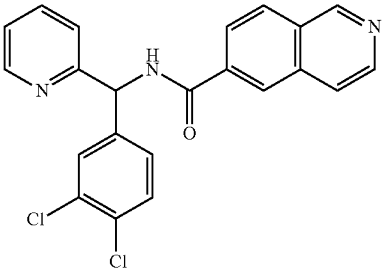 [SMILES: O=C(NC(c1ccc(Cl)c(Cl)c1)c1ccccn1)c1ccc2cnccc2c1] | N-((3,4-dichloro-phenyl)(pyridin-2-yl)methyl)-isoquinoline-6-carboxamide bis-hydrochloride | 409.0, 410.0 |
| 248 | 35 | 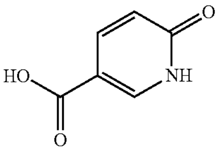 | 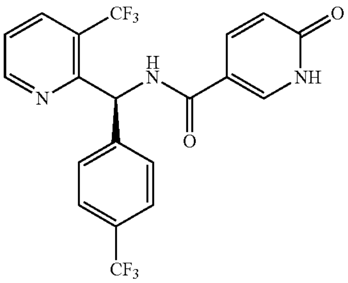 | (S)-N-((3-chloro-pyridin-2-yl)(4-(trifluoromethyl)-phenyl)methyl)-6-oxo-1,6-dihydropyridine-3-carboxamide 2,2,2-trifluoroacetate | 407.7 |
| 249 | 35 | 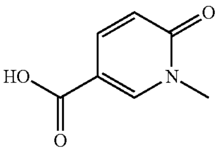 | 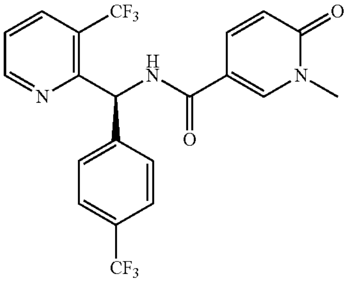 [SMILES: Cn1cc(C(=O)N[C@@H](c2ccc(C(F)(F)F)cc2)c2ncccc2C(F)(F)F)ccc1=O] | (S)-N-((3-chloro-pyridin-2-yl)(4-(trifluoromethyl)-phenyl)methyl)-1-methyl-6-oxo-1,6-dihydro-pyridine-3-carboxamide 2,2,2-trifluoroacetate | 421.9 |
| 250 | 36 | 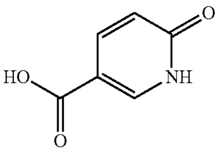 | 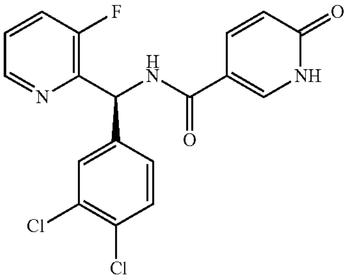 [SMILES: O=C(N[C@@H](c1ccc(Cl)c(Cl)c1)c1ncccc1F)c1ccc(=O)[nH]c1] | (S)-N-((3,4-dichlorophenyl)-(3-fluoropyridin-2-yl)methyl)-6-oxo-1,6-dihydro-pyridine-3-carboxamide 2,2,2-trifluoroacetate | 391.7 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 251 | 36 | 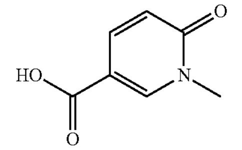 | 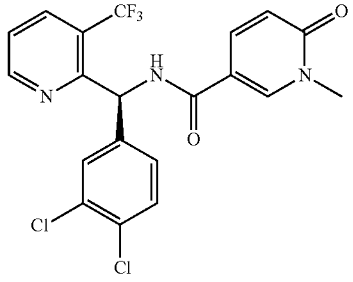 [SMILES: Cn1cc(C(=O)N[C@@H](c2ccc(Cl)c(Cl)c2)c2ncccc2C(F)(F)F)ccc1=O] | (S)-N-((3,4-dichlorophenyl)-(3-fluoropyridin-2-yl)methyl)-1-methyl-6-oxo-1,6-dihydro-pyridine-3-carboxamide 2,2,2-trifluoroacetate | 450.8 |
| 252 | 8 | 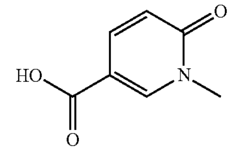 | 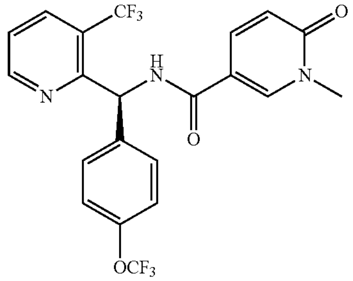 [SMILES: Cn1cc(C(=O)N[C@@H](c2ccc(OC(F)(F)F)cc2)c2ncccc2C(F)(F)F)ccc1=O] | (S)-N-((3-fluoro-pyridin-2-yl)(4-(trifluoro-methoxy)-phenyl)methyl)-1-methyl-6-oxo-1,6-dihydro-pyridine-3-carboxamide 2,2,2-trifluoroacetate | 422.1 |
| 253 | 2 | 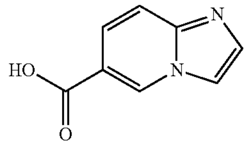 [SMILES: O=C(O)c1ccc2nccn2c1] | 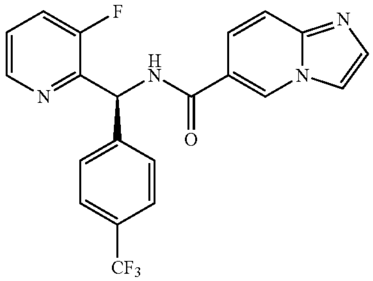 [SMILES: O=C(N[C@@H](c1ccc(C(F)(F)F)cc1)c1ncccc1F)c1ccc2nccn2c1] | (S)-N-((3-fluoro-pyridin-2-yl)(4-(trifluoromethyl)-phenyl)methyl)-imidazo[1,2-a]pyridine-6-carboxamide 2,2,2-trifluoroacetate | 415.2 |
| 254 | 1 | 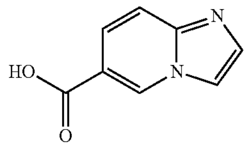 [SMILES: O=C(O)c1ccc2nccn2c1] | 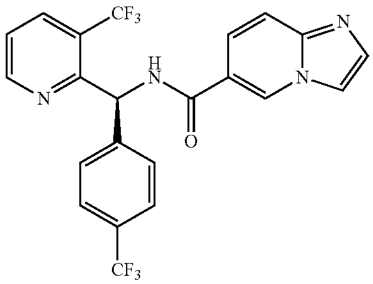 [SMILES: O=C(N[C@@H](c1ccc(C(F)(F)F)cc1)c1ncccc1C(F)(F)F)c1ccc2nccn2c1] | (S)-N-((4-(trifluoromethyl)-phenyl)(3-(trifluoromethyl)-pyridin-2-yl)-methyl)-imidazo[1,2-a]pyridine-6-carboxamide 2,2,2-trifluoroacetate | 465.1 |
| 255 | 8 | 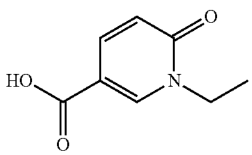 | 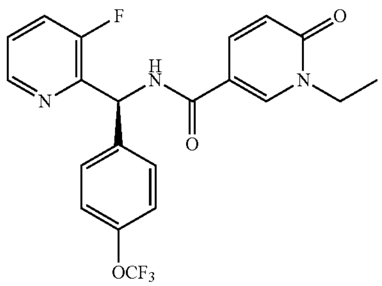 | (S)-1-ethyl-N-((3-fluoropyridin-2-yl)(4-(trifluoro-methoxy)-phenyl)methyl)-6-oxo-1,6-dihydropyridine-3-carboxamide | 436.1 |

TABLE 2-continued

Examples 1-261 prepared via amide formation analogous to Scheme 4

| Ex # | A-mine | Acid Structure | Product Structure | Product Name | MS M + H |
|---|---|---|---|---|---|
| 256 | 37 | 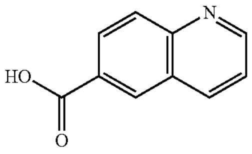 [SMILES: O=C(O)c1ccc2ncccc2c1] | 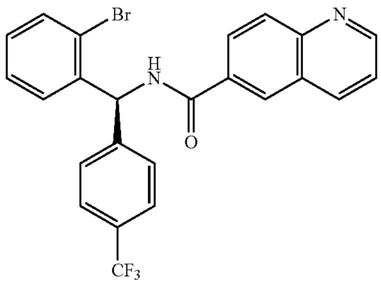 [SMILES: O=C(N[C@@H](c1ccc(C(F)(F)F)cc1)c1ccccc1Br)c1ccc2ncccc2c1] | (S)-N-((2-bromophenyl)(4-(trifluoromethyl)-phenyl)methyl)-quinoline-6-carboxamide 2,2,2-trifluoroacetate | 484.9, 486.9 |
| 257 | 38 | 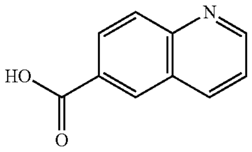 [SMILES: O=C(O)c1ccc2ncccc2c1] | 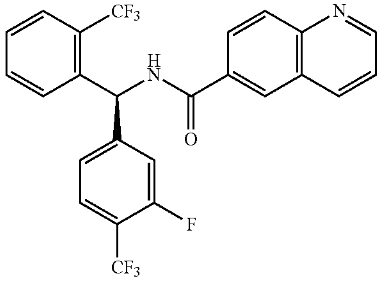 | (S)-N-((3-fluoro-4-(trifluoro-methyl)phenyl)-(2-(trifluoro-methyl)phenyl)-methyl)-quinoline-6-carboxamide | 493.0 |
| 258 | 39 | 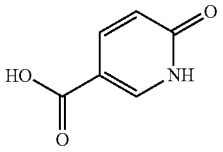 | 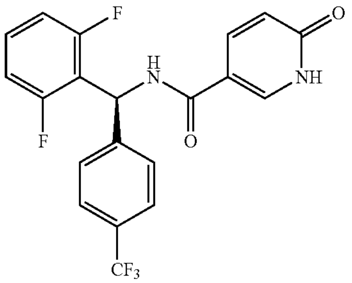 [SMILES: O=C(N[C@@H](c1ccc(C(F)(F)F)cc1)c1c(F)cccc1F)c1ccc(=O)[nH]c1] | (S)-N-((2,6-difluorophenyl)-(4-(trifluoro-methyl)phenyl)-methyl)-6-oxo-1,6-dihydro-pyridine-3-carboxamide | 408.8 |
| 259 | 40 | 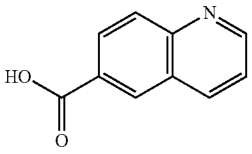 [SMILES: O=C(O)c1ccc2ncccc2c1] | 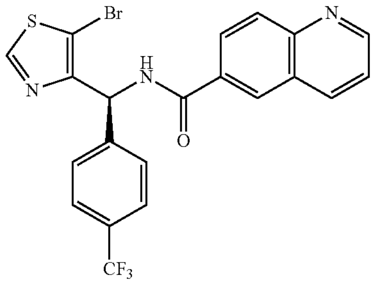 [SMILES: O=C(N[C@@H](c1ccc(C(F)(F)F)cc1)c1ncsc1Br)c1ccc2ncccc2c1] | (S)-N-((5-bromothiazol-4-yl)(4-(trifluoro-methyl)phenyl)-methyl)-quinoline-6-carboxamide 2,2,2-trifluoroacetate | 491.8 493.9 |
| 260 | 42 | 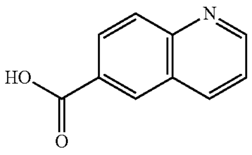 | 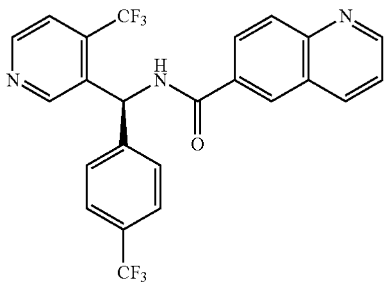 [SMILES: O=C(N[C@@H](c1ccc(C(F)(F)F)cc1)c1cnccc1C(F)(F)F)c1ccc2ncccc2c1] | (S)-N-((4-(trifluoromethyl)-phenyl)(4-(trifluoromethyl)-pyridin-3-yl)-methyl)-quinoline-6-carboxamide bis (2,2,2-trifluoroacetate) | 476.0 |

TABLE 2-continued

| Examples 1-261 prepared via amide formation analogous to Scheme 4 | | | | | |
|---|---|---|---|---|---|
| Ex # | A-mine | Acid Structure | Product Structure | Product Name | MS M + H |
| 261 | 41 | 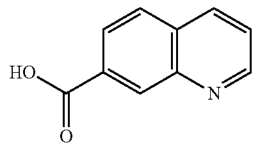 [SMILES: O=C(O)c1ccc2cccnc2c1] | 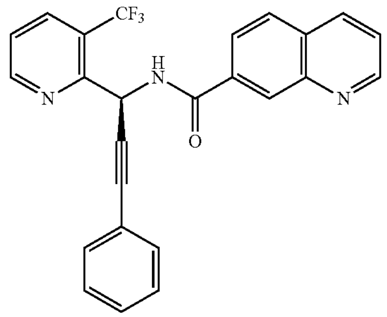 [SMILES: O=C(N[C@@H](C#Cc1ccccc1)c1ncccc1C(F)(F)F)c1ccc2cccnc2c1] | (S)-N-(3-phenyl-1-(3-(trifluoro-methyl)pyridin-2-yl)prop-2-yn-1-yl)quinoline-7-carboxamide | 432.0 |

Additional Examples

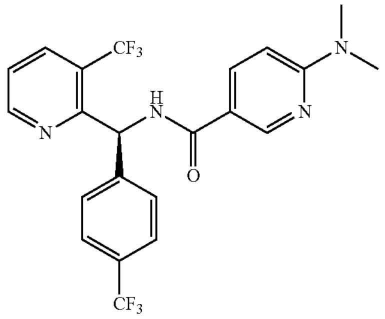 [SMILES: CN(C)c1ccc(C(=O)N[C@@H](c2ccc(C(F)(F)F)cc2)c2ncccc2C(F)(F)F)cn1]

Example 262

(S)-6-(Dimethylamino)-N-((4-(trifluoromethyl)phenyl)(3-(trifluoromethyl)pyridin-2-yl)methyl)nicotinamide A glass microwave reaction vessel was charged with (S)-6-chloro-N-((4-(trifluoromethyl)phenyl)(3-(trifluoromethyl)pyridin-2-yl)methyl)nicotinamide (50 mg, 0.109 mmol, example 135), DMF (1 mL), and 2 M diethylamine in THF (0.054 mL, 0.109 mmol). The reaction mixture was stirred and heated in a Biotage Initiator at 100° C. for 30 minutes. This was repeated at 150° C. for 30 minutes at a time until LC-MS indicated complete consumption of starting material. The reaction product was purified by reverse-phase preparative HPLC (Shimadzu) on a Phenomenex Gemini column (5 micron, C18, 110 Å, Axia, 100×30 mm) eluting at 45 mL/min with a linear gradient of 20% to 70% MeCN (0.1% TFA) in water (0.1% TFA) over 20 minutes. The desired fractions were poured into 10% $Na_2CO_3$ and extracted with DCM (3×5 mL). The combined DCM layers were washed with brine, dried over $MgSO_4$, and concentrated in vacuo to give the title compound as a white solid. $^1H$ NMR ($CDCl_3$, 300 MHz) 6 ppm 8.86 (d, J=3.8 Hz, 1H), 8.66 (d, J=2.2 Hz, 1H), 8.02 (d, J=7.9 Hz, 2H), 7.92 (dd, J=9.1, 2.5 Hz, 1H), 7.54 (s, 4H), 7.45 (dd, J=7.7, 4.4 Hz, 1H), 6.87 (d, J=7.9 Hz, 1H), 6.49 (d, J=9.2 Hz, 1H), 3.14 (s, 6H) MS (ESI pos. ion) m/z: 469.0 (M+H).

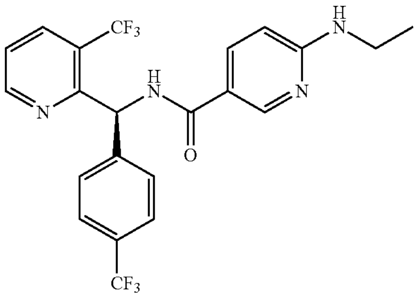 [SMILES: CCNc1ccc(C(=O)N[C@@H](c2ccc(C(F)(F)F)cc2)c2ncccc2C(F)(F)F)cn1]

Example 263

(S)-6-(Ethylamino)-N-((4-(trifluoromethyl)phenyl)(3-(trifluoromethyl)pyridin-2-yl)methyl)nicotinamide A glass microwave reaction vessel was charged with (S)-6-chloro-N-((4-(trifluoromethyl)phenyl)(3-(trifluoromethyl)pyridin-2-yl)methyl)nicotinamide (50 mg, 0.109 mmol, example 135), THF (1 mL), and 2 M ethylamine in THF (0.054 mL, 0.109 mmol). The reaction mixture was stirred and heated in a Biotage Initiator at 100° C. for 30 minutes. This was repeated at 150° C. for 30 minutes at a time until LC-MS indicated complete consumption of starting material. The reaction product was purified by reverse-phase preparative HPLC (Shimadzu) on a Phenomenex Gemini column (5 micron, C18, 110 Å, Axia, 100×30 mm) eluting at 45 mL/min with a linear gradient of 20% to 70% MeCN (0.1% TFA) in water (0.1% TFA) over 20 minutes to give (S)-6-(ethylamino)-N-((4-(trifluoromethyl)phenyl)(3-(trifluoromethyl)pyridin-2-yl)methyl)nicotinamide 2,2,2-trifluoroacetate as a white solid after lyopholization. $^1H$ NMR ($CDCl_3$, 300 MHz) δ ppm 10.41 (br. s., 1H), 8.93 (d, J=4.1 Hz, 1H), 8.12-8.39 (m, 3H), 8.05 (d, J=7.7 Hz, 1H), 7.41-7.63 (m, 5H), 6.71-6.86 (m, 2H), 3.25-3.49 (m, 2H), 1.37 (t, J=7.3 Hz, 3H) MS (ESI pos. ion) m/z: 469.0 (M+H).

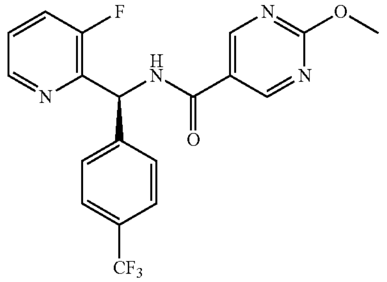 [SMILES: COc1ncc(C(=O)N[C@@H](c2ccc(C(F)(F)F)cc2)c2ncccc2F)cn1]

Example 264

(S)—N-((3-Fluoropyridin-2-yl)(4-(trifluoromethyl) phenyl)methyl)-2-methoxypyrimidine-5-carboxamide To a solution of 2-methoxypyrimidine-5-carboxylic acid (80 mg, 0.519 mmol), DIPEA (0.25 mL, 1.435 mmol) in toluene (3 mL) was added DPPA (0.19 mL, 0.882 mmol). The reaction was stirred at 80° C. for 2 hours. (S)-(3-fluoropyridin-2-yl)(4-(trifluoromethyl)phenyl)methanamine dihydrochloride (167 mg, 0.487 mmol) was then added as a solid in one portion. After 24 hours, the reaction was concentrated in vacuo and the residue was adsorbed onto a plug of silica gel and chromatographed through a Redi-Sep® pre-packed silica gel column (12 g), eluting with 0% to 80% EtOAc in hexane, to provide the title compound as an off-white solid. $^1$H NMR (DMSO-d6, 400 MHz) δ ppm 9.02 (d, J=4.7 Hz, 1H), 8.97 (d, J=8.6 Hz, 1H), 8.30 (d, J=7.8 Hz, 1H), 7.63-7.77 (m, 3H), 7.54 (d, J=8.2 Hz, 2H), 7.39 (s, 1H), 7.01 (s, 1H), 6.66 (d, J=8.6 Hz, 1H), 3.93 (s, 3H) MS (ESI pos. ion) m/z: 407.0 (M+H).

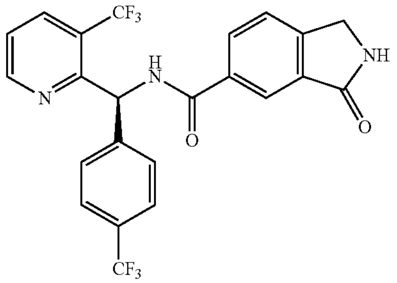 [SMILES: O=C(N[C@@H](c1ccc(C(F)(F)F)cc1)c1ncccc1C(F)(F)F)c1ccc2c(c1)C(=O)NC2]

Example 265

(S)-3-Oxo-N-((4-(trifluoromethyl)phenyl)(3-(trifluoromethyl)-pyridin-2-yl)methyl)isoindoline-5-carboxamide To a 25 mL round bottom flask containing (S)-(4-(trifluoromethyl)-phenyl)(3-(trifluoromethyl)pyridin-2-yl)methanamine hydrochloride (Intermediate 1) (120 mg, 0.336 mmol) was added toluene (3 mL). The resulting mixture was stirred at rt for 2 min. At this time, sodium carbonate (143 mg, 1.346 mmol), 4,5-bis(diphenylphosphino)-9,9-dimethylxanthene (3.89 mg, 6.73 mol), palladium (II) acetate (1.5 mg, 6.7 mol) and 6-bromo-2,3-dihydro-isoindol-1-one (71.3 mg, 0.336 mmol) were added to the flask. The reaction vessel was flushed with argon and then left under 1.0 atm of carbon monoxide gas (from a lecture bottle, in hood). The flask was heated to 85° C. overnight, filtered though Celite® brand filter agent, and eluted with EtOAc. Purification by reverse phase HPLC, and concentration of the containing fractions gave (S)-3-oxo-N-((4-(trifluoromethyl)-phenyl)(3-(trifluoromethyl)pyridin-2-yl)methyl)isoindoline-5-carboxamide as a yellow foamy solid. $^1$H NMR (300 MHz, $CDCl_3$): δ ppm 8.92 (d, J=4.5 Hz, 1H), 8.40 (d, J=7.7 Hz, 1H), 7.60-7.56 (m, 5H), 7.46-7.48 (m, 2H), 6.90 (d, J=7.6 Hz, 1H), 4.54 (s, 2H). MS (ESI pos. ion) m/z: 480.1 (M+H).

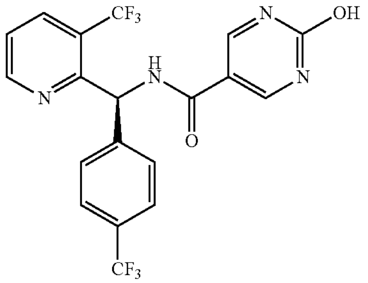 [SMILES: O=C(N[C@@H](c1ccc(C(F)(F)F)cc1)c1ncccc1C(F)(F)F)c1cnc(O)nc1]

Example 266

(S)-2-Hydroxy-N-((4-(trifluoromethyl)phenyl)(3-(trifluoro-methyl)pyridin-2-yl)methyl)pyrimidine-5-carboxamide A 25 mL round-bottomed flask containing a suspension of (S)-2-methoxy-N-((4-(trifluoromethyl)phenyl)(3-(trifluoromethyl)pyridin-2-yl)methyl)pyrimidine-5-carboxamide (Example 44) (0.094 g, 0.206 mmol) and sodium iodide, anhydrous (0.129 g, 0.861 mmol) in anhydrous MeCN (3.5 mL) was treated with chlorotrimethylsilane, redistilled (0.130 mL, 1.028 mmol). The resulting suspension was stirred at rt for 17.5 h. The reaction was concentrated on the rotary evaporator resulting in a gummy residue which was taken up in DCM (55 mL), $H_2O$ (25 mL), and 10% aqueous sodium thiosulfate (20 mL). The resulting mixture was transferred to a separatory funnel and after vigorous extraction the organic layer was separated, dried over anhydrous sodium sulfate, and concentrated to yield the product. The product thus obtained was dissolved in DMSO/MeOH(1/1) (3.5 mL) and loaded on a Gibson HPLC system for purification using a MeCN/$H_2O$/0.1% TFA gradient and Phenomenex™ Gemini Axia-5μ C-18 column (150×30 mm). The solvent was removed from the pure fractions in the Genevac™ and the resulting product was dissolved in MeOH (3 mL), concentrated in the Genevac™, and dried under high vacuum to yield (S)-2-hydroxy-N-((4-(trifluoromethyl)phenyl)(3-(trifluoromethyl)pyridin-2-yl)-methyl)pyrimidine-5-carboxamide as an amorphous white solid. $^1$H NMR (400 MHz, DMSO-$d_6$) δ ppm 9.30 (d, J=7.6 Hz, 1H), 8.93 (d, J=3.9 Hz, 1H), 8.80 (s, 2H), 8.27 (dd, J=8.0, 1.2 Hz, 1H), 7.75-7.70 (m, 2H), 7.64 (dd, J=7.9, 5.0 Hz, 1H), 7.56-7.50 (m, 2H), 6.76 (d, J=7.6 Hz, 1H). MS (ESI pos. ion) m/z: 443.1 (M+H).

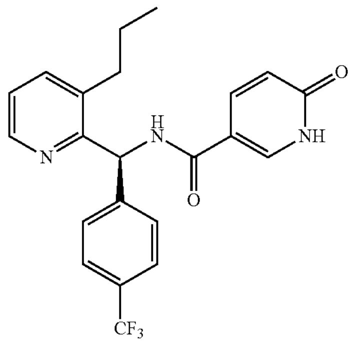 [SMILES: CCCc1cccnc1[C@@H](NC(=O)c1ccc(=O)[nH]c1)c1ccc(C(F)(F)F)cc1]

Example 267

(S)-6-Oxo-N-((3-propylpyridin-2-yl)(4-(trifluoromethyl)-phenyl)methyl)-1,6-dihydropyridine-3-carboxamide To a 250 mL round bottom flask containing (S)-6-oxo-N-((3-(prop-1-yn-1-yl)pyridin-2-yl)(4-(trifluoromethyl)phenyl)methyl)-1,6-dihydropyridine-3-carboxamide (Example 94) (50 mg, 0.122 mmol), were added EtOAc (50 mL) and MeOH (10 mL). The resulting mixture then stirred at 23° C. for 2 min. At this time, Pd/C (10%, 50 mg) was added and hydrogen was bubbled through the reaction vessel for 15 min, and the reaction was stirred under 1.0 atm hydrogen for 3 h, filtered through a pad of Celite™, eluted with EtOAc (150 mL), and concentrated to give (S)-tert-butyl ((3-(prop-1-yn-1-yl)pyridin-2-yl)(4-(trifluoro-methyl)phenyl)methyl)carbamate as a foamy white solid. $^1H$ NMR (300 MHz, $CDCl_3$) δ ppm 13.03 (br. s., 1H), 8.68 (d, J=6.9 Hz, 1H), 8.53 (dd, J=1.5, 4.7 Hz, 1H), 8.09 (d, J=2.3 Hz, 1H), 7.95 (dd, J=2.6, 9.6 Hz, 1H), 7.62-7.41 (m, 5H), 7.33-7.20 (m, 1H), 6.60 (d, J=9.5 Hz, 1H), 6.52 (d, J=6.9 Hz, 1H), 2.73-2.57 (m, 1H), 2.56-2.39 (m, 1H), 1.87 (br. s., 1H), 1.68-1.48 (m, 1H), 1.47-1.30 (m, 1H), 0.92 (t, J=7.3 Hz, 3H). MS (ESI pos. ion) m/z: 416.2 (M+H).

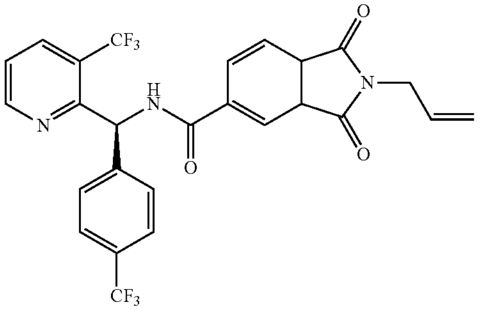 [SMILES: C=CCN1C(=O)C2C=CC(C(=O)N[C@@H](c3ccc(C(F)(F)F)cc3)c3ncccc3C(F)(F)F)=CC2C1=O]

Example 268

(S)-2-Allyl-1,3-dioxo-N-((4-(trifluoromethyl)phenyl)(3-(trifluoromethyl)pyridin-2-yl)methyl)isoindoline-5-carboxamide To a 25 mL pear-shaped flask was added solid 1,3-dioxo-1,3-dihydroisobenzofuran-5-carboxylic acid (200 mg, 1.041 mmol) and allylamine (234 μL, 3.12 mmol, 3 eq) via syringe. Toluene (2 mL) and AcOH (1 mL) were added via syringes and the flask was refluxed for 12 h. The flask was allowed to cool and then subjected to a DCM (75 mL) and HCl (1N, 50 mL) work up. The aqueous layer was extracted with DCM (3×25 mL). The combined organic layers were washed with brine, dried with sodium sulfate, filtered and concentrated. The residue thus obtained was azeotropically dried with toluene (2×, 5 mL) and heptane (2×5 mL). The resulting reside was placed on a high vacuum for 3 to give 2-allyl-1,3-dioxoisoindoline-5-carboxylic acid.

2-Allyl-1,3-dioxoisoindoline-5-carboxylic acid was then coupled with Intermediate 1 using the general methods described above for the amide coupling reaction (Table 2) to provide the title compound, (S)-2-allyl-1,3-dioxo-N-((4-(trifluoromethyl)phenyl)(3-(trifluoromethyl)pyridin-2-yl)methyl)isoindoline-5-carboxamide as a white solid. $^1H$ NMR (300 MHz, $CDCl_3$) δ ppm 8.93 (d, J=3.9 Hz, 1H), 8.44 (d, J=7.6 Hz, 1H), 8.30-8.21 (m, 2H), 8.11-8.02 (m, 1H), 7.98-7.89 (m, 1H), 7.64-7.46 (m, 5H), 6.88 (d, J=7.6 Hz, 1H), 5.99-5.75 (m, 1H), 5.34-5.15 (m, 2H), 4.31 (d, J=5.7 Hz, 2H). MS (ESI pos. ion) m/z: 534.1 (M+H).

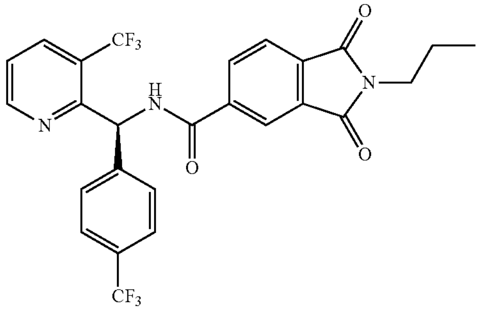 [SMILES: CCCN1C(=O)c2ccc(C(=O)N[C@@H](c3ccc(C(F)(F)F)cc3)c3ncccc3C(F)(F)F)cc2C1=O]

Example 269

(S)-1,3-Dioxo-2-propyl-N-((4-(trifluoromethyl)phenyl)(3-(trifluoromethyl)pyridin-2-yl)methyl)isoindoline-5-carboxamide To a 50 mL round bottom flask containing (S)-2-allyl-1,3-dioxo-N-((4-(trifluoromethyl)phenyl)(3-(trifluoromethyl)pyridin-2-yl)methyl)isoindoline-5-carboxamide (Example 276) (160 mg, 0.300 mmol) was added EtOAc (15 mL). The resulting mixture was stirred at 23° C. for 2 min. At this time, Pd/C (10%, 50 mg) was added and hydrogen was bubbled through the mixture for 10 min. The reaction mixture was then left under 1 atm of hydrogen for 1 h. The solid was filtered off on a pad of Celite™ and eluted with EtOAc (75 mL). The solvent was evaporated to give (S)-1,3-dioxo-2-propyl-N-((4-(trifluoromethyl)phenyl)(3-(trifluoromethyl)pyridin-2-yl)methyl)isoindoline-5-carboxamide as a white solid. $^1H$ NMR (300 MHz, $CDCl_3$) δ ppm 8.93 (d, J=4.1 Hz, 1H), 8.42 (d, J=7.6 Hz, 1H), 8.30-8.19 (m, 2H), 8.11-8.01 (m, 1H), 7.91 (d, J=7.7 Hz, 1H), 7.64-7.45 (m, 5H), 6.88 (d, J=7.6 Hz, 1H), 3.68 (t, J=1.0 Hz, 2H), 1.72 (sxt, J=7.4 Hz, 2H), 0.95 (t, J=7.5 Hz, 3H). MS (ESI pos. ion) m/z: 536.2 (M+H).

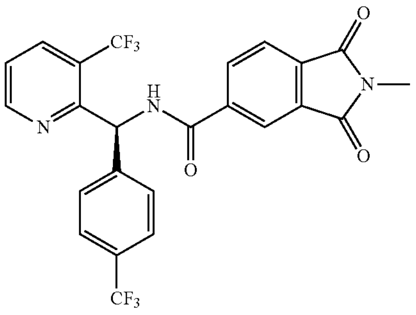 [SMILES: CN1C(=O)c2ccc(C(=O)N[C@@H](c3ccc(C(F)(F)F)cc3)c3ncccc3C(F)(F)F)cc2C1=O]

Example 270

(S)-2-Methyl-1,3-dioxo-N-((4-(trifluoromethyl)phenyl)(3-(trifluoromethyl)pyridin-2-yl)methyl)isoindoline-5-carboxamide To a microwave vial was added 1,3-dioxo-1,3-dihydroisobenzofuran-5-carboxylic acid (200 mg, 1.041 mmol), THF (2 mL) and methylamine (2.0M THF, 2.0 mL). The flask was irradiated in a microwave at 100° C. for 5 min. At this time, AcOH (glacial, 0.4 mL) and an additional portion of methylamine (2.0M THF, 2.0 mL) were added, and the flask was placed in a the microwave at 100° C. for 2 h. The flask was allowed to cool and then azeotropically dried (toluene, 3×5 mL). The flask was placed under a high vacuum for 12 h to provide 2-methyl-1,3-dioxoisoindoline-5-carboxylic acid which was used directly in the amide coupling reaction without further purification.

2-Allyl-1,3-dioxoisoindoline-5-carboxylic acid was then coupled with Intermediate 1 using the general methods described above for the amide coupling reaction (Table 2) to provide the title compound, (S)-2-methyl-1,3-dioxo-N-((4-(trifluoromethyl)phenyl)(3-(trifluoromethyl)pyridin-2-yl)methyl)isoindoline-5-carboxamide as a white solid. $^{1}$H NMR (300 MHz, $CDCl_3$) δ ppm 8.95 (d, J=4.7 Hz, 1H), 8.44 (d, J=7.5 Hz, 1H), 8.31-8.20 (m, 2H), 8.08 (d, J=8.2 Hz, 1H), 7.93 (d, J=7.6 Hz, 1H), 7.65-7.42 (m, 5H), 6.88 (d, J=7.6 Hz, 1H), 3.22 (s, 3H). MS (ESI pos. ion) m/z: 508.1 (M+H).

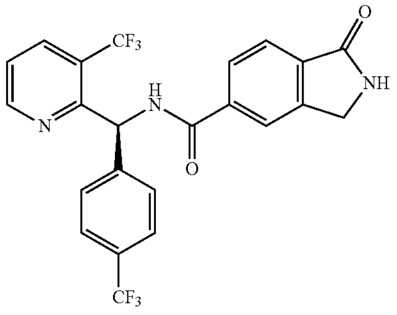 [SMILES: O=C(N[C@@H](c1ccc(C(F)(F)F)cc1)c1ncccc1C(F)(F)F)c1ccc2c(c1)CNC2=O]

Example 271

(S)-1-Oxo-N-((4-(trifluoromethyl)phenyl)(3-(trifluoromethyl)-pyridin-2-yl)methyl)isoindoline-5-carboxamide

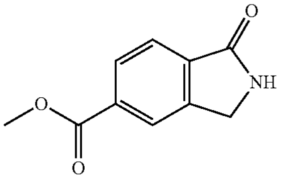

Step 1. Methyl 1-oxoisoindoline-5-carboxylate

To a 25 mL round bottom flask containing 5-bromo-2,3-dihydro-isoindol-1-one (500 mg, 2.36 mmol), was added TEA. The resulting mixture was then stirred at 23° C. for 2 min. At this time, MeOH (954 L, 23.58 mmol), 4,5-bis(diphenylphosphino)-9,9-dimethylxanthene (54.6 mg, 0.094 mmol) (Xantphos) and palladium(II) acetate (10.59 mg, 0.047 mmol) were added to the flask. The reaction mixture was then flushed with argon and then with carbon monoxide. The flask was fitted with a rubber septa and a balloon of carbon monoxide was inserted through septa. The flask was stirred at 70° C. overnight under carbon monoxide, allowed to cool, diluted with EtOAc (50 mL) and filtered through Celite™ eluting with EtOAc (300 mL). The solid remaining on the Celite™ pad was washed with DCM (200 mL) and DCM/MeOH (10:1)(150 mL) and the filtrates concentrated to give a pale green solid (800 mg). A portion of this material was taken on to the next reaction with no further purification.

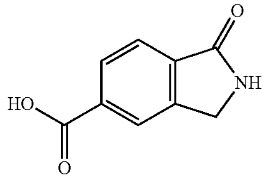 [SMILES: O=C(O)c1ccc2c(c1)CNC2=O]

Step 2. 1-Oxoisoindoline-5-carboxylic acid

To a 100 mL round bottom flask containing methyl 1-oxoisoindoline-5-carboxylate (200 mg, 1.046 mmol) was added THF (6 mL) and $H_2O$ (2 mL) the mixture was stirred at 23° C. for 2 min. At this time, lithium hydroxide monohydrate (87 μL, 3.14 mmol) was added and the flask was gently heated on aluminum block for 5 min. The solid went into solution and LC/MS showed product formation. The contents of the reaction were poured into HCl (1 M, 15 mL) and extracted with DCM (15 mL). An emulsion formed, the layers separated, and a white solid formed at the boundary of the layers and stuck to the separatory funnel. This material was collected, dissolved in MeOH, and concentrated. After drying under high vacuum for 2 h, the 1-oxoisoindoline-5-carboxylic acid thus obtained was taken on directly to the next reaction without further purification.

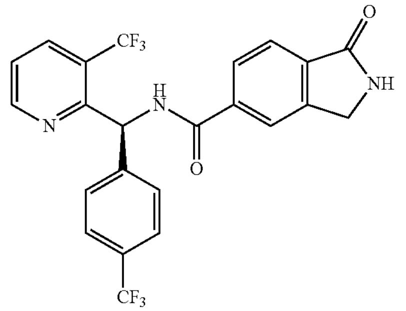 [SMILES: O=C(N[C@@H](c1ccc(C(F)(F)F)cc1)c1ncccc1C(F)(F)F)c1ccc2c(c1)CNC2=O]

Step 3. (S)-1-Oxo-N-((4-(trifluoromethyl)phenyl)(3-(trifluoromethyl)pyridin-2-yl)methyl)isoindoline-5-carboxamide 1-Oxoisoindoline-5-carboxylic acid was then coupled with Intermediate 1 using the general methods described above for the amide coupling reaction (Table 2) to provide the title compound, (S)-1-oxo-N-((4-(trifluoromethyl)phenyl)(3-(trifluoromethyl)pyridin-2-yl)methyl)isoindoline-5-carboxamide, as a white solid. $^1$H NMR (400 MHz, $CDCl_3$) δ ppm 8.92 (d, J=4.7 Hz, 1H), 8.36 (d, J=7.4 Hz, 1H), 8.09-7.99 (m, 2H), 7.97-7.88 (m, 2H), 7.65-7.53 (m, 5H), 7.51 (dd, J=4.9, 7.8 Hz, 1H), 6.90 (d, J=7.6 Hz, 1H), 4.54 (s, 2H). MS (ESI pos. ion) m/z: 480.2 (M+H).

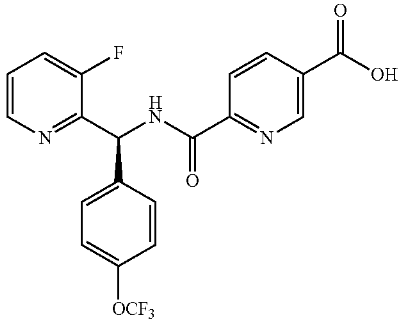 [SMILES: O=C(O)c1ccc(C(=O)N[C@@H](c2ccc(OC(F)(F)F)cc2)c2ncccc2F)nc1]

Example 272

(S)-6-(((3-Fluoropyridin-2-yl)(4-(trifluoromethoxy)phenyl)-methyl)carbamoyl)nicotinic acid To a 150 mL round bottom flask containing (S)-methyl 6-(((3-fluoro-pyridin-2-yl)(4-(trifluoromethoxy)phenyl)methyl)carbamoyl)nicotinate (250 mg, 0.556 mmol) (prepared using the general coupling procedure Table 2 with Intermediate 1 and 5-((methylperoxy)carbonyl)picolinic acid) were added THF (6 mL) and $H_2O$ (2 mL). The resulting mixture was stirred at 23° C. for 2 min. At this time, lithium hydroxide monohydrate (61.8 μL, 2.23 mmol) was added and the reaction was stirred for 3 h. The bulk of the solvent was evaporated to give a foamy solid that oiled out. The residue was dissolved in AcOH (8 mL). The solution was purified by reverse phase HPLC and the product-containing fractions concentrated to give the title compound as a white solid. $^1$H NMR (300 MHz, $CDCl_3$) δ ppm 9.65 (d, J=7.3 Hz, 1H), 9.21 (s, 1H), 8.61 (d, J=4.1 Hz, 1H), 8.42 (d, J=7.3 Hz, 1H), 8.24 (d, J=8.0 Hz, 1H), 7.63-7.42 (m, 3H), 7.39 (dd, J=4.2, 8.3 Hz, 1H), 7.20 (d, J=7.9 Hz, 2H), 6.74 (d, J=6.7 Hz, 1H). MS (ESI pos. ion) m/z: 436.2 (M+H).

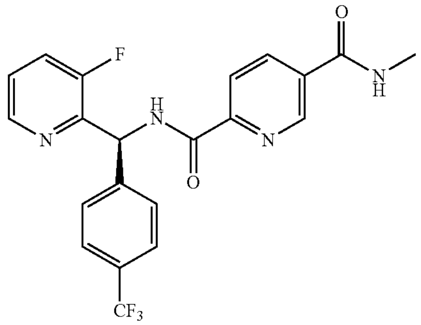 [SMILES: CNC(=O)c1ccc(C(=O)N[C@@H](c2ccc(C(F)(F)F)cc2)c2ncccc2F)nc1]

Example 273

(S)—$N^2$-((3-Fluoropyridin-2-yl)(4-(trifluoromethyl)phenyl)-methyl)-$N^5$-methylpyridine-2,5-dicarboxamide 2,2,2-trifluoroacetate To a 50 mL round bottom flask containing (S)-6-(((3-fluoropyridin-2-yl)-(4-(trifluoromethyl)phenyl)methyl)carbamoyl)nicotinic acid (Example 280) (86 mg, 0.205 mmol) was added DMF (3 mL). The resulting mixture was stirred at 23° C. for 2 min. At this time, DIPEA (143 μL, 0.820 mmol), methylamine (2.0 M in THF, 103 μL, 0.205 mmol) and then HATU (78 mg, 0.205 mmol) were added to the flask. The reaction was stirred for 1 h and then directly purified by reverse phase HPLC. The pure fractions were concentrated to give the title compound as a white solid. $^1$H NMR (300 MHz, $CDCl_3$) δ ppm 9.85 (d, J=7.2 Hz, 1H), 9.00 (s, 1H), 8.55 (d, J=4.4 Hz, 1H), 8.20 (s, 2H), 7.60 (s, 4H), 7.52 (t, J=8.7 Hz, 1H), 7.45-7.34 (m, 1H), 6.74 (d, J=7.3 Hz, 1H), 6.55 (br. s., 1H), 3.07 (d, J=4.5 Hz, 3H). MS (ESI pos. ion) m/z: 433.1 (M+H).

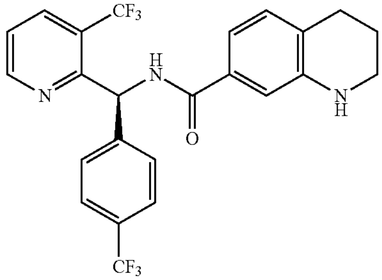 [SMILES: O=C(N[C@@H](c1ccc(C(F)(F)F)cc1)c1ncccc1C(F)(F)F)c1ccc2c(c1)NCCC2]

Example 274

(S)—N-((4-(Trifluoromethyl)phenyl)(3-(trifluoromethyl)pyridin-2-yl)methyl)-1,2,3,4-tetrahydroquinoline-7-carboxamide To a solution of (S)—N-((4-(trifluoromethyl)phenyl)(3-(trifluoromethyl)-pyridin-2-yl)methyl)quinoline-7-carboxamide (Example 132) (0.500 g, 1.052 mmol) in MeOH (6 mL) was added palladium hydroxide, (20 wt % Pd (dry basis) on carbon, wet, degussa type) (0.148 g, 1.052 mmol). The resulting mixture was then stirred at rt under $H_2$ overnight. The resulting mixture was filtered through Celite® brand filter agent and the Celite® filter agent was washed with MeOH (2×3 mL). The combined filtrates were concentrated and the mixture was dissolved in DMSO (3 mL). The mixture was purified by preparative HPLC (0%-100% MeCN 0.1% TFA/$H_2O$ 0.1% TFA) to give the desired product, which was dissolved in MeOH (2 mL). The solution was washed through PL_$HCO_3$ MP-SPE resin and the resin was washed with MeOH (2×2 mL). The combined filtrates were concentrated and dried in vacuo to give the title compound as a yellow solid. $^1$H NMR (400 MHz, MeOH) δ ppm 8.94 (d, J=4.1 Hz, 1H), 8.22 (dd, J=8.0, 1.0 Hz, 1H), 7.50-7.70 (m, 5H), 6.94-7.02 (m, 3H), 6.90 (s, 1H), 3.24-3.31 (m, 2H), 2.78 (t, J=6.4 Hz, 2H), 1.86-1.99 (m, 2H). MS (ESI pos. ion) m/z: 480.2 (M+H).

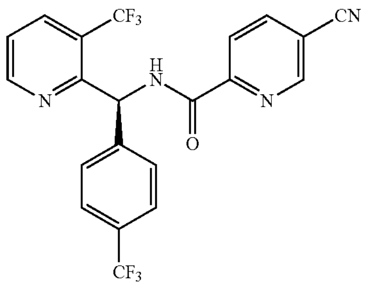 [SMILES: N#Cc1ccc(C(=O)N[C@@H](c2ccc(C(F)(F)F)cc2)c2ncccc2C(F)(F)F)nc1]

Example 275

(S)-5-Cyano-N-((4-(trifluoromethyl)phenyl)(3-(trifluoro-methyl)pyridin-2-yl)methyl)picolinamide To a solution of (S)-5-bromo-N-((4-(trifluoromethyl)phenyl)(3-(trifluoro-methyl)pyridin-2-yl)methyl)picolinamide (Example 205) (0.100 g, 0.198 mmol) in DMF (1.3 mL) was added zinc cyanide (0.050 mL, 0.793 mmol) and tetrakis (triphenylphosphine)palladium(0) (0.023 g, 0.020 mmol). The resulting mixture was subjected to a microwave irradiation at 140° C. for 20 min. The mixture was then purified by preparative HPLC (0%-100% MeCN 0.1% TFA/$H_2O$ 0.1% TFA) to give the title compound as a white solid. $^1$H NMR (400 MHz, MeOH) δ ppm 8.95-9.06 (m, 2H), 8.39 (dd, J=8.1, 2.1 Hz, 1H), 8.21-8.32 (m, 2H), 7.57-7.70 (m, 5H), 6.89 (s, 1H). MS (ESI pos. ion) m/z: 451.1 (M+H).

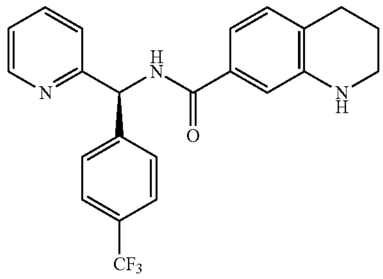 [SMILES: O=C(N[C@@H](c1ccc(C(F)(F)F)cc1)c1ccccn1)c1ccc2c(c1)NCCC2]

Example 276

(S)—N-(Pyridin-2-yl(4-(trifluoromethyl)phenyl) methyl)-1,2,3,4-tetrahydroquinoline-7-carboxamide To a solution of (S)—N-((3-bromopyridin-2-yl)(4-(trifluoromethyl)phenyl)-methyl)quinoline-7-carboxamide (Example 195) (0.130 g, 0.267 mmol) in MeOH (0.8 mL) and EtOAc (0.800 mL) was added palladium hydroxide, (20 wt % Pd (dry basis) on carbon, wet) (0.019 g, 0.134 mmol). The resulting mixture was then stirred at rt under $H_2$ (balloon) overnight. The mixture was then filtered through Celite® brand filter agent and the Celite® filter agent was washed with MeOH (2×3 mL). The combined filtrates were concentrated, and the residue was dissolved in MeOH (1 mL). The solution was purified by preparative HPLC (0%-100% MeCN 0.1% TFA/$H_2O$ 0.1% TFA) to give the desired product, which was dissolved in MeOH (1 mL). The solution was washed through PL_$HCO_3$ MP-SPE and the resin was washed with MeOH (2×1 mL). The combined filtrates were concentrated and dried in vacuo to give the title compound as a yellow solid. $^1$H NMR (400 MHz, MeOH) δ ppm 8.59 (d, J=4.7 Hz, 1H), 7.84 (td, J=7.7, 1.6 Hz, 1H), 7.61-7.68 (m, 2H), 7.54-7.60 (m, 2H), 7.49 (d, J=7.8 Hz, 1H), 7.36 (dd, J=7.5, 5.0 Hz, 1H), 6.93-7.07 (m, 3H), 6.44 (s, 1H), 3.25-3.30 (m, 2H), 2.78 (t, J=6.4 Hz, 2H), 1.91 (dt, J=11.6, 6.0 Hz, 2H). MS (ESI pos. ion) m/z: 412.1 (M+H).

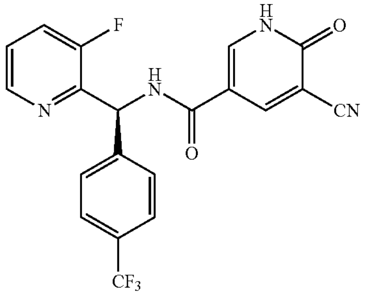 [SMILES: N#Cc1cc(C(=O)N[C@@H](c2ccc(C(F)(F)F)cc2)c2ncccc2F)c[nH]c1=O]

Example 277

(S)-5-Cyano-N-((3-fluoropyridin-2-yl)(4-(trifluoromethyl)-phenyl)methyl)-6-oxo-1,6-dihydropyridine-3-carboxamide

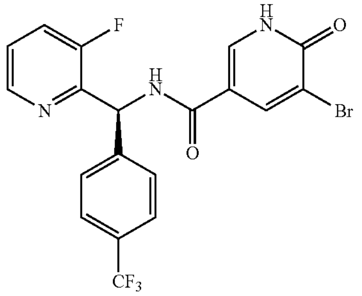 [SMILES: O=C(N[C@@H](c1ccc(C(F)(F)F)cc1)c1ncccc1F)c1c[nH]c(=O)c(Br)c1]

Step 1. (S)-5-Bromo-N-((3-fluoropyridin-2-yl)(4-(trifluoromethyl)phenyl)-methyl)-6-oxo-1,6-dihydro-pyridine-3-carboxamide To a solution of HATU (0.332 g, 0.874 mmol) in DCM (2 mL) was added 5-bromo-6-hydroxynicotinic acid (0.191 g, 0.874 mmol) and DIPEA (0.406 mL, 2.331 mmol). The resulting mixture was then stirred at rt for 5 min, then (S)-(3-fluoropyridin-2-yl)(4-(trifluoromethyl)phenyl)methanamine hydrochloride (Intermediate 2) (0.200 g, 0.583 mmol) was added. The mixture was then stirred at rt overnight. The mixture was purified by silica gel column chromatography using an ISCO instrument (0%-100% EtOAc/hexane) to give the title compound as a brown oil.

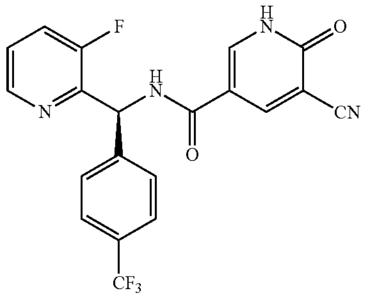 [SMILES: N#Cc1cc(C(=O)N[C@@H](c2ccc(C(F)(F)F)cc2)c2ncccc2F)c[nH]c1=O]

Step 2. (S)-5-Cyano-N-((3-fluoropyridin-2-yl)(4-(trifluoromethyl)phenyl)-methyl)-6-oxo-1,6-dihydro-pyridine-3-carboxamide To a solution of (S)-5-bromo-N-((3-fluoropyridin-2-yl)(4-(trifluoro-methyl)phenyl)methyl)-6-oxo-1,6-dihydropyridine-3-carboxamide (0.080 g, 0.170 mmol) in DMF (0.5 mL) was added zinc(II) cyanide (0.043 mL, 0.681 mmol) and tetrakis(triphenylphosphine)palladium(0) (0.020 g, 0.017 mmol). The resulting mixture was then subjected to a microwave irradiation at 130° C. for 30 min. Then, the mixture was purified by preparative HPLC (0%-100% MeCN 0.1% TFA/$H_2O$ 0.1% TFA) to give the title compound as a white solid. $^1$H NMR (400 MHz, MeOH) δ ppm 8.63 (d, J=2.5 Hz, 1H), 8.51 (d, J=4.7 Hz, 1H), 8.42 (d, J=2.5 Hz, 1H), 7.55-7.73 (m, 6H), 7.47 (dt, J=8.5, 4.4 Hz, 1H), 6.75 (s, 1H). MS (ESI pos. ion) m/z: 417.0 (M+H).

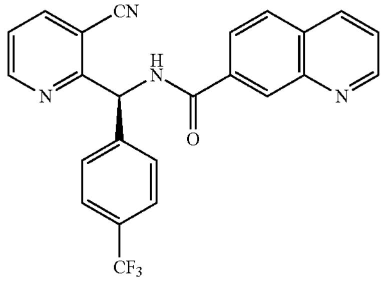

Example 278

(S)—N-((3-Cyanopyridin-2-yl)(4-(trifluoromethyl)phenyl)-methyl)quinoline-7-carboxamide To a microwave vial were added (S)—N-((3-bromopyridin-2-yl)(4-(trifluoromethyl)phenyl)methyl)quinoline-7-carboxamide (Example 195) (0.100 g, 0.206 mmol), zinc cyanide (0.026 mL, 0.411 mmol), tetrakis(triphenylphosphine)-palladium(0) (0.024 g, 0.021 mmol), and DMF (1.3 mL). The resulting mixture was then subjected to microwave irradiation at 130° C. for 30 min. EtOAc (10 mL) and $H_2O$ (10 mL) were then added, and the resulting mixture was stirred at rt for 5 min. The organic layer was collected, dried over $MgSO_4$ and concentrated. The residue was then purified by preparative HPLC (0%-100% MeCN 0.1% TFA/$H_2O$ 0.1% TFA) to give the desired product, which was dissolved in MeOH (1 mL). The solution was washed through PL_$HCO_3$ MP-SPE resin and the resin was washed with MeOH (2×1 mL). The combined filtrates were concentrated and dried in vacuo to give the title compound as a yellow solid. $^1$H NMR (400 MHz, MeOH) δ ppm 8.98 (dd, J=4.1, 1.6 Hz, 1H), 8.93 (dd, J=4.9, 1.6 Hz, 1H), 8.60 (s, 1H), 8.46 (d, J=8.4 Hz, 1H), 8.25 (dd, J=7.8, 1.6 Hz, 1H), 8.08 (s, 2H), 7.70-7.81 (m, 4H), 7.66 (dd, J=8.4, 4.3 Hz, 1H), 7.58 (dd, J=7.8, 4.9 Hz, 1H), 6.91 (s, 1H). MS (ESI pos. ion) m/z: 433.1 (M+H).

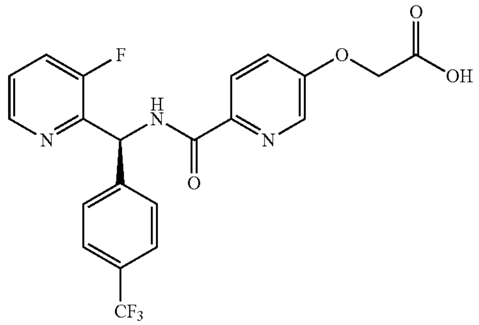 [SMILES: O=C(O)COc1ccc(C(=O)N[C@@H](c2ccc(C(F)(F)F)cc2)c2ncccc2F)nc1]

Example 279

(S)-2-((6-(((3-Fluoropyridin-2-yl)(4-(trifluoromethyl)phenyl)-methyl)carbamoyl)pyridin-3-yl)oxy) acetic acid To a solution of (S)—N-((3-fluoropyridin-2-yl)(4-(trifluoromethyl)phenyl)-methyl)-5-hydroxypicolinamide (Example 173) (0.145 g, 0.371 mmol) in DCM (2 mL) and DMF (0.2 mL) were added bromoacetic acid t-butyl ester (0.072 mL, 0.445 mmol) and cesium carbonate (0.241 g, 0.741 mmol). The resulting mixture was then stirred at rt for 2 h. Then, the mixture was filtered and the solid was washed with DCM (1×1 mL) and MeOH (1×1 mL). The combined filtrates were concentrated and dried to give the desired product, which was used without further purification in the next step.

To a solution of the (S)-tert-butyl 2-((6-(((3-fluoropyridin-2-yl)(4-(trifluoromethyl)phenyl)methyl)carbamoyl)pyridin-3-yl)oxy)acetate from above in DCM (0.5 mL), was added TFA (0.550 mL, 7.40 mmol). The resulting mixture was then stirred at rt for 1 h. The mixture was then concentrated and MeOH (1 mL) was added. The mixture was purified by preparative HPLC (0%-100% MeCN 0.1% TFA/$H_2O$ 0.1% TFA) to give the title compound as a white solid. $^1$H NMR (400 MHz, MeOH) δ ppm 8.55 (d, J=4.7 Hz, 1H), 8.42 (d, J=2.5 Hz, 1H), 8.08 (d, J=8.8 Hz, 1H), 7.59-7.72 (m, 5H), 7.42-7.55 (m, 2H), 6.68 (d, J=1.6 Hz, 1H), 4.89 (s, 2H). MS (ESI pos. ion) m/z: 450.2 (M+H).

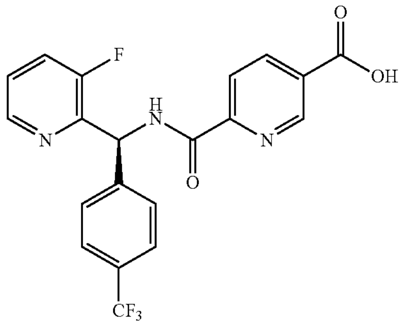 [SMILES: O=C(O)c1ccc(C(=O)N[C@@H](c2ccc(C(F)(F)F)cc2)c2ncccc2F)nc1]

Example 280

(S)-6-(((3-Fluoropyridin-2-yl)(4-(trifluoromethyl) phenyl)-methyl)carbamoyl)nicotinic acid To a solution of 5-(methoxycarbonyl)picolinic acid (101 mg, 0.558 mmol) in DCM (4 mL) was added HATU (217 mg, 0.571 mmol) and DIPEA (0.20 mL, 1.148 mmol). After stirring for 30 min at rt, the reaction was treated with (S)-(3-fluoropyridin-2-yl)(4-(trifluoromethyl)phenyl)methanamine hydrochloride (Intermediate 2) (125 mg, 0.364 mmol). After 16 h, the reaction was concentrated in vacuo and then taken up in THF (3 mL), MeOH (1 mL), and 1M LiOH (1 mL). The resulting mixture was stirred at rt for 2 h. The reaction mixture was concentrated in vacuo, acidified with 1N HCl and extracted with EtOAc (3×5 mL). The combined EtOAc layers were concentrated in vacuo and chromatographed through a Redi-Sep® pre-packed silica gel column (4 g), eluting with 0% to 100% EtOAc in hexane, to provide the title compound as an off-white solid. $^1$H NMR ($CDCl_3$: $CD_3OD$, 300 MHz) δ ppm 9.21 (d, J=1.5 Hz, 1H), 8.47 (d, J=4.7 Hz, 1H), 8.39 (dd, J=8.0, 1.9 Hz, 1H), 8.14 (d, J=8.0 Hz, 1H), 7.56 (d, J=8.5 Hz, 2H), 7.50 (d, J=8.6 Hz, 2H), 7.42 (t, J=9.5 Hz, 1H), 7.27-7.32 (m, 1H), 6.63 (s, 1H). MS (ESI pos. ion) m/z: 419.9 (M+H).

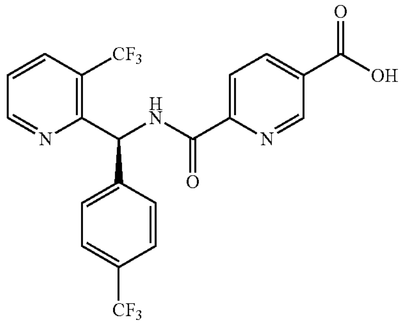 [SMILES: O=C(O)c1ccc(C(=O)N[C@@H](c2ccc(C(F)(F)F)cc2)c2ncccc2C(F)(F)F)nc1]

Example 281

(S)-6-(((4-(Trifluoromethyl)phenyl)(3-(trifluoromethyl)-pyridin-2-yl)methyl)carbamoyl)nicotinic acid To a solution of 5-(methoxycarbonyl)picolinic acid (70.7 mg, 0.390 mmol) and DIPEA (0.20 mL, 1.148 mmol) in DMF (2 mL) were added HATU (223 mg, 0.586 mmol) and (S)-(4-(trifluoromethyl)phenyl)(3-(trifluoromethyl)pyridin-2-yl)-methanamine hydrochloride (Intermediate 1) (125 mg, 0.390 mmol). The resulting mixture was stirred at rt 16 h. The mixture was then diluted with THF (10 mL), MeOH (3 mL), and 1M LiOH (2 mL). After a further 16 h, the reaction was concentrated in vacuo, taken up in a minimum of DMF and purified by reverse-phase preparative HPLC (Shimadzu) on a Phenomenex Gemini™ column (5 micron, C18, 110 Å, Axia, 100×30 mm) eluting at 45 mL/min with a linear gradient of 20% to 90% MeCN (0.1% TFA) in $H_2O$ (0.1% TFA) over 10 minutes to give the title compound as a white solid after lyopholization. $^1$H NMR ($CDCl_3$, 300 MHz) δ ppm 9.74 (d, J=8.2 Hz, 1H), 9.25 (s, 1H), 8.97 (d, J=4.0 Hz, 1H), 8.47 (dd, J=8.0, 2.1 Hz, 1H), 8.26 (d, J=8.8 Hz, 1H), 8.04 (d, J=8.0 Hz, 1H), 7.61 (d, J=8.5 Hz, 2H), 7.55 (d, J=8.5 Hz, 2H), 7.46 (dd, J=7.5, 5.0 Hz, 1H), 6.88 (d, J=8.2 Hz, 1H). MS (ESI pos. ion) m/z: 469.9 (M+H).

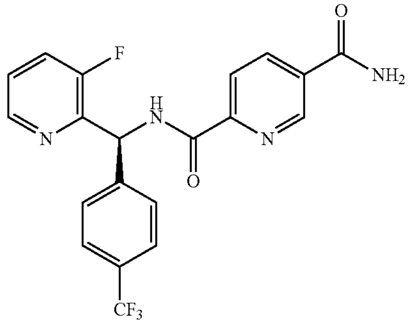 [SMILES: NC(=O)c1ccc(C(=O)N[C@@H](c2ccc(C(F)(F)F)cc2)c2ncccc2F)nc1]

Example 282

(S)—$N^2$-((3-Fluoropyridin-2-yl)(4-(trifluoromethyl) phenyl)-methyl)pyridine-2,5-dicarboxamide To a solution of 5-cyanopicolinic acid (93 mg, 0.628 mmol) in DCM (6 mL) were added DIPEA (0.3 mL, 1.722 mmol) and HATU (247 mg, 0.650 mmol). The solution was stirred at rt. After 20 minutes, the reaction was treated with (S)-(3-fluoropyridin-2-yl)(4-(trifluoromethyl)phenyl) methanamine hydrochloride (Intermediate 2) (115 mg, 0.426 mmol). After stirring for 16 h, the reaction was poured into $H_2O$ (20 mL). The aqueous layer was back-extracted with DCM (10 mL). The combined DCM layers were concentrated in vacuo and taken up in 3 mL of concentrated sulfuric acid. The mixture was stirred at rt for 4 hours and then was poured into 75 g of ice. After stirring for 1 hour, the reaction was filtered, and the solids were rinsed with $H_2O$. The solids were then taken up in EtOAc (30 mL) and washed with saturated aqueous $NaHCO_3$. The EtOAc layer was concentrated in vacuo to give the title compound as an off-white solid. $^1$H NMR ($CDCl_3$, 300 MHz) δ ppm 9.93 (d, J=7.5 Hz, 1H), 9.07 (s, 1H), 8.53 (d, J=4.7 Hz, 1H), 8.23-8.27 (m, 2H), 7.61 (d, J=8.3 Hz, 2H), 7.55 (d, J=8.3 Hz, 2H), 7.42 (td, J=8.2, 1.3 Hz, 1H), 7.27-7.35 (m, 1H), 6.69 (dd, J=7.8, 1.9 Hz, 1H), 5.92 (br s, 2H). MS (ESI pos. ion) m/z: 419.9 (M+H).

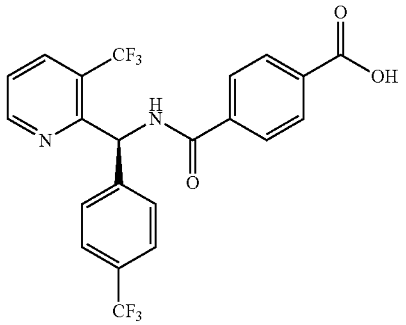 [SMILES: O=C(O)c1ccc(C(=O)N[C@@H](c2ccc(C(F)(F)F)cc2)c2ncccc2C(F)(F)F)cc1]

Example 283

(S)-4-(((4-(Trifluoromethyl)phenyl)(3-(trifluoromethyl)-pyridin-2-yl)methyl)carbamoyl)benzoic acid To a solution of (S)-methyl 4-(((4-(trifluoromethyl)phenyl)(3-(trifluoro-methyl)pyridin-2-yl)methyl)carbamoyl) benzoate (135 mg, 0.280 mmol, Example 140) and THF (7 mL):MeOH (3 mL) was added 1M LiOH (1 mL, 1.000 mmol). After 2 h, the reaction was concentrated in vacuo. The off-white solid was taken up in a minimum of DCM and eluted through a Redi-Sep® pre-packed silica gel column (4 g) with EtOAc to provide the title compound as a white solid. $^1$H NMR ($CD_3OD$, 300 MHz) δ ppm 8.91 (d, J=4.8 Hz, 1H), 8.18 (d, J=7.9 Hz, 1H), 8.03 (d, J=8.3 Hz, 2H), 7.85 (d, J=8.2 Hz, 2H), 7.53-7.66 (m, 5H), 6.93 (s, 1H). MS (ESI pos. ion) m/z: 469.0 (M+H).

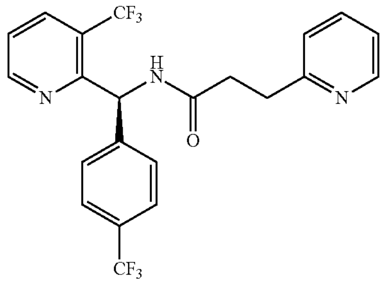 [SMILES: O=C(CCc1ccccn1)N[C@@H](c1ccc(C(F)(F)F)cc1)c1ncccc1C(F)(F)F]

Example 284

(S)-3-(Pyridin-2-yl)-N-((4-(trifluoromethyl)phenyl)(3-(trifluoromethyl)pyridin-2-yl)methyl)propanamide To a solution of 3-(pyridin-2-yl)propanoic acid (89 mg, 0.586 mmol, Oakwood) and DCM (4 mL) were added CDI (95 mg, 0.586 mmol) and DIPEA (0.20 mL, 1.148 mmol). After 0.5 hours, the reaction was treated with a solution of (S)-(4-(trifluoromethyl)phenyl)(3-(trifluoromethyl)pyridin-2-yl)methanamine hydrochloride (Intermediate 1) (125 mg, 0.390 mmol) in DCM (1.5 mL). The solution was stirred at rt. After 4 days, the resulting product was adsorbed onto a plug of silica gel and chromatographed through a Redi-Sep® pre-packed silica gel column (4 g), eluting with 0% to 60% EtOAc in hexane, to provide the title compound as a colorless oil. $^1$H NMR ($CDCl_3$, 300 MHz) δ ppm 8.79 (d, J=3.8 Hz, 1H), 8.45 (d, J=4.8 Hz, 1H), 7.96 (d, J=7.9 Hz, 1H), 7.78 (d, J=7.9 Hz, 1H), 7.44-7.52 (m, 3H), 7.34-7.43 (m, 3H), 7.03-7.12 (m, 2H), 6.63 (d, J=8.0 Hz, 1H), 3.11 (td, J=6.7 & 2.5 Hz, 2H), 2.74 (td, J=7.2 & 2.5 Hz, 2H). MS (ESI pos. ion) m/z: 454.0 (M+H).

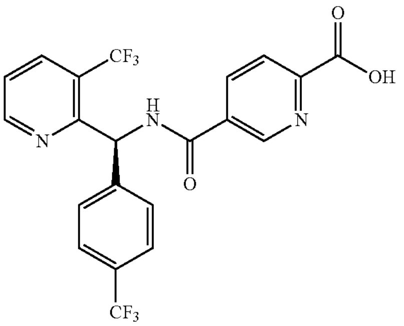 [SMILES: O=C(N[C@@H](c1ccc(C(F)(F)F)cc1)c1ncccc1C(F)(F)F)c1ccc(C(=O)O)nc1]

Example 285

(S)-5-(((4-(Trifluoromethyl)phenyl)(3-(trifluoromethyl)-pyridin-2-yl)methyl)carbamoyl)picolinic acid 2,2,2-trifluoroacetate To a solution of 6-(methoxycarbonyl)nicotinic acid (58.4 mg, 0.322 mmol) and DIPEA (0.20 mL, 1.148 mmol) in DMF (2 mL) were added HATU (178 mg, 0.468 mmol) and (S)-(4-(trifluoromethyl)phenyl)(3-(trifluoromethyl)pyridin-2-yl)-methanamine hydrochloride (Intermediate 1) (100 mg, 0.312 mmol). The solution was stirred at rt for 2 h. The solution was then diluted with THF (10 mL), MeOH (3 mL), and 1M LiOH (2 mL). After a further 16 h, the reaction was concentrated in vacuo, taken up in a minimum of DMF and purified by reverse-phase preparative HPLC (Shimadzu) on a Phenomenex Gemini™ column (5 micron, C18, 110 Å, Axia, 100×30 mm) eluting at 45 mL/min with a linear gradient of 20% to 90% MeCN (0.1% TFA) in $H_2O$ (0.1% TFA) over 10 minutes to the title compound as a yellow solid. $^1$H NMR ($CDCl_3$, 300 MHz) δ ppm 9.14 (s, 1H), 8.94 (d, J=4.4 Hz, 1H), 8.64 (d, J=7.2 Hz, 1H), 8.41 (d, J=8.0 Hz, 1H), 8.25 (d, J=7.9 Hz, 1H), 8.13 (d, J=7.9 Hz, 1H), 7.46-7.63 (m, 5H), 6.88 (d, J=7.0 Hz, 1H). MS (ESI pos. ion) m/z: 469.9 (M+H).

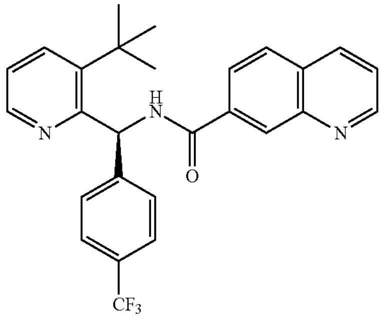 [SMILES: CC(C)(C)c1cccnc1[C@@H](NC(=O)c1ccc2cccnc2c1)c1ccc(C(F)(F)F)cc1]

Example 286

(S)—N-((3-(tert-Butyl)pyridin-2-yl)(4-(trifluoromethyl)phenyl)-methyl)quinoline-7-carboxamide 2,2,2-trifluoroacetate To a −78° C. solution of(S)—N-((3-bromopyridin-2-yl)(4-(trifluoromethyl)-phenyl)methyl)quinoline-7-carboxamide (97 mg, 0.199 mmol, Example 195) and THF (5 mL) was added tert-butyllithium (1.7M in pentane, 0.35 mL, 0.595 mmol) dropwise. After 30 seconds, the reaction was treated with acetone. After 1 min, LC-MS shows a new peak with m/z=466 (MH+), ~20% conversion. The reaction was treated with more tert-butyllithium (0.1 mL) and allowed to slowly warm to rt. Another reaction was setup at the same scale and as described above. The reactions were combined and concentrated in vacuo. The residue was taken up in MeOH (3 mL) and purified by reverse-phase preparative HPLC (Shimadzu) on a Phenomenex Gemini™ column (10 micron, C18, 110 Å, Axia, 100×50 mm) eluting at 90 mL/min with a linear gradient of 20% to 90% MeCN (0.1% TFA) in $H_2O$ (0.1% TFA) over 10 minutes to give the title compound as an off-white solid after lyophilization. $^1H$ NMR ($CDCl_3$, 300 MHz) δ ppm 9.85 (s, 1H), 9.44 (d, J=7.3 Hz, 1H), 8.79 (d, J=4.2 Hz, 1H), 8.64 (d, J=8.8 Hz, 1H), 8.37 (d, J=8.5 Hz, 1H), 8.05 (d, J=8.5 Hz, 1H), 7.98 (t, J=7.3 Hz, 1H), 7.86 (d, J=8.8 Hz, 1H), 7.69-7.82 (m, 3H), 7.61 (d, J=8.2 Hz, 1H), 7.45-7.53 (m, 1H), 6.76 (d, J=7.3 Hz, 1H), 1.67 (s, 9H). MS (ESI pos. ion) m/z: 464.0 (M+H).

TABLE 3

Additional diarylmethanamines prepared analogous to Scheme 5 and 6 (Intermediates 61-97). Unless otherwise stated, all amines in this table are hydrochloride salts.

| Intermediate | Method | Aryl Halide or Grignard in Step 2 | Structure | Name | Mol. Formula (Mol. Wt.) |
|---|---|---|---|---|---|
| 61 | A | 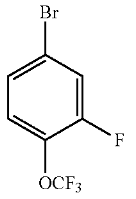 | 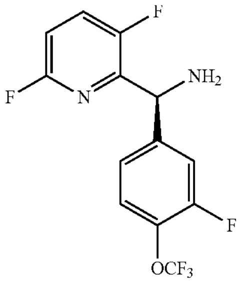 [SMILES: N[C@@H](c1ccc(OC(F)(F)F)c(F)c1)c1nc(F)ccc1F] | (S)-(3,6-difluoropyridin-2-yl)(3-fluoro-4-(trifluoro-methoxy)phenyl) methanamine | $C_{13}H_8F_6N_2O$ (322.21) |
| 62 | A | 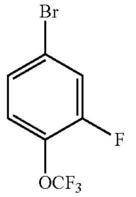 | 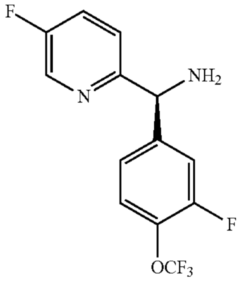 [SMILES: N[C@@H](c1ccc(OC(F)(F)F)c(F)c1)c1ccc(F)cn1] | (S)-(3-fluoro-4-(trifluoromethoxy) phenyl)(5-fluoropyridin-2-yl)methanamine | $C_{13}H_9F_5N_2O$ (304.22) |
| 63 | A | 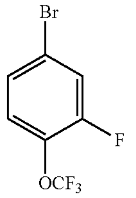 | 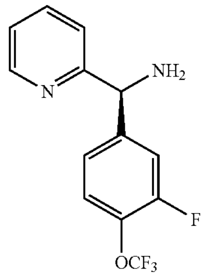 [SMILES: N[C@@H](c1ccc(OC(F)(F)F)c(F)c1)c1ccccn1] | (S)-(3-fluoro-4-(trifluoromethoxy) phenyl)(pyridin-2-yl)methanamine | $C_{13}H_{10}F_4N_2O$ (286.22) |
| 64[1] | A | 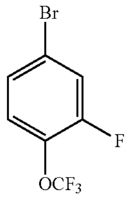 | 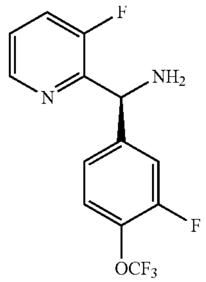 [SMILES: N[C@@H](c1ccc(OC(F)(F)F)c(F)c1)c1ncccc1F] | (S)-(3-fluoro-4-(trifluoromethoxy) phenyl)(2-fluorophenyl) methanamine | $C_{14}H_{10}F_5NO$ (303.23) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 65 | C | 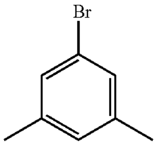 | 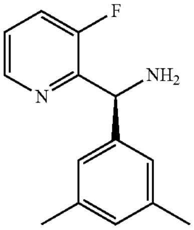 [SMILES: Cc1cc(C)cc([C@H](N)c2ncccc2F)c1] | (S)-(3,5-dimethylphenyl)(3-fluoropyridin-2-yl)methanamine | $C_{14}H_{15}FN_2$ (230.28) |
| 66 | C | 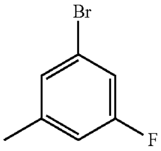 | 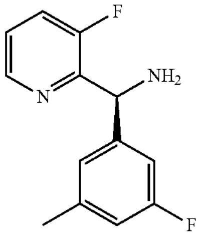 [SMILES: Cc1cc(F)cc([C@H](N)c2ncccc2F)c1] | (S)-(3-fluoro-5-methylphenyl)(3-fluoropyridin-2-yl)methanamine | $C_{13}H_{12}F_2N_2$ (234.24) |
| 67 | C | 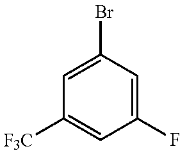 | 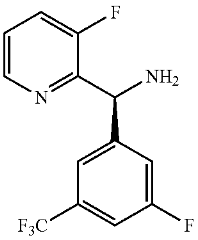 [SMILES: N[C@@H](c1cc(F)cc(C(F)(F)F)c1)c1ncccc1F] | (S)-(3-fluoro-5-(trifluoromethyl)phenyl)(3-fluoropyridin-2-yl)methanamine | $C_{13}H_9F_5N_2$ (288.22) |
| 68 | C | 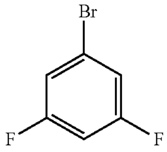 | 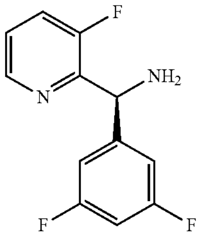 [SMILES: N[C@@H](c1cc(F)cc(F)c1)c1ncccc1F] | (S)-(3,5-difluorophenyl)(3-fluoropyridin-2-yl)methanamine | $C_{12}H_9F_3N_2$ (238.21) |
| 69 | C | 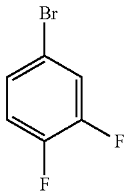 | 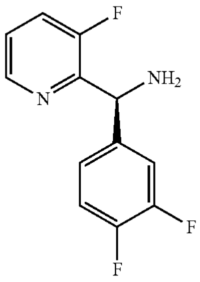 [SMILES: N[C@@H](c1ccc(F)c(F)c1)c1ncccc1F] | (S)-(3,4-difluorophenyl)(3-fluoropyridin-2-yl)methanamine | $C_{12}H_9F_3N_2$ (238.21) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 70 | C | 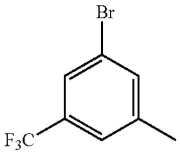 | 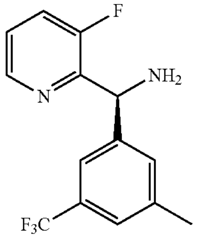 [SMILES: Cc1cc([C@H](N)c2ncccc2F)cc(C(F)(F)F)c1] | (S)-(3-fluoropyridin-2-yl)(3-methyl-5-(trifluoromethyl)phenyl)methanamine | $C_{14}H_{12}F_4N_2$ (284.25) |
| 71 | A | 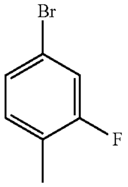 | 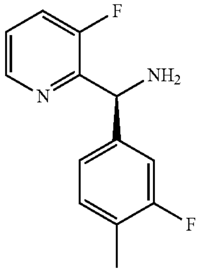 [SMILES: Cc1ccc([C@H](N)c2ncccc2F)cc1F] | (S)-(3-fluoro-4-methylphenyl)(3-fluoropyridin-2-yl)methanamine | $C_{13}H_{12}F_2N_2$ (234.24) |
| 72 | A | 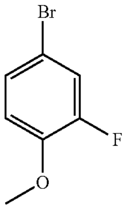 | 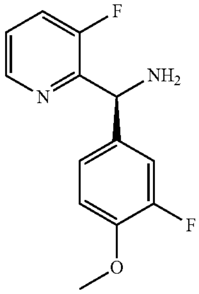 [SMILES: COc1ccc([C@H](N)c2ncccc2F)cc1F] | (S)-(3-fluoro-4-methoxyphenyl)(3-fluoropyridin-2-yl)methanamine | $C_{13}H_{12}F_2N_2O$ (250.24) |
| 73 | B | 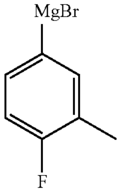 | 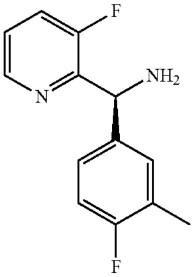 [SMILES: Cc1cc([C@H](N)c2ncccc2F)ccc1F] | (S)-(4-fluoro-3-methylphenyl)(3-fluoropyridin-2-yl)methanamine | $C_{13}H_{12}F_2N_2$ (234.24) |
| 74 | B | 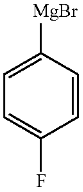 | 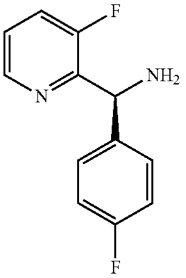 [SMILES: N[C@@H](c1ccc(F)cc1)c1ncccc1F] | (S)-(4-fluorophenyl)(3-fluoropyridin-2-yl)methanamine | $C_{12}H_{10}F_2N_2$ (220.22) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 75 | B | 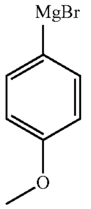 | 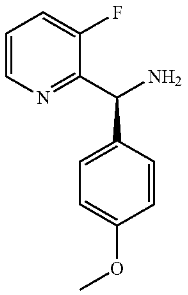 [SMILES: COc1ccc([C@H](N)c2ncccc2F)cc1] | (S)-(3-fluoropyridin-2-yl)(4-methoxyphenyl) methanamine | $C_{13}H_{13}FN_2O$ (232.25) |
| 76 | B | 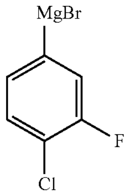 | 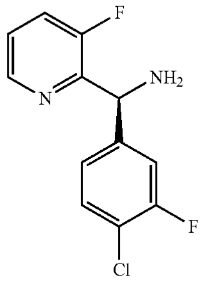 [SMILES: N[C@@H](c1ccc(Cl)c(F)c1)c1ncccc1F] | (S)-(4-chloro-3-fluorophenyl)(3-fluoropyridin-2-yl)methanamine | $C_{12}H_9ClF_2N_2$ (254.66) |
| 77 | A | 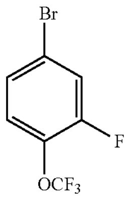 | 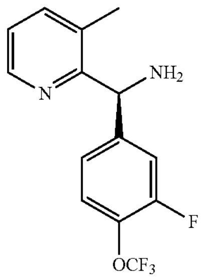 [SMILES: Cc1cccnc1[C@@H](N)c1ccc(OC(F)(F)F)c(F)c1] | (S)-(3-fluoro-4-(trifluoromethoxy) phenyl)(3-methylpyridin-2-yl)methanamine | $C_{14}H_{12}F_4N_2O$ (300.25) |
| 78 | A | 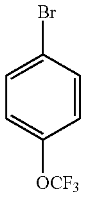 | 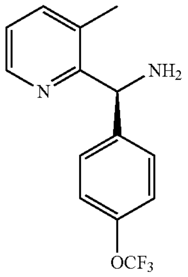 [SMILES: Cc1cccnc1[C@@H](N)c1ccc(OC(F)(F)F)cc1] | (S)-(3-methylpyridin-2-yl)(4-(trifluoromethoxy) phenyl) methanamine | $C_{14}H_{13}F_3N_2O$ (282.26) |
| 79 | A | 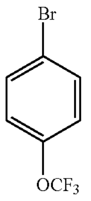 | 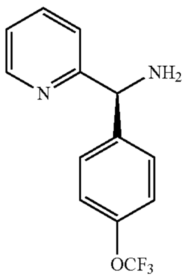 [SMILES: N[C@@H](c1ccc(OC(F)(F)F)cc1)c1ccccn1] | (S)-pyridin-2-yl(4-(trifluoromethoxy) phenyl) methanamine | $C_{13}H_{11}F_3N_2O$ (268.23) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 80 | A | 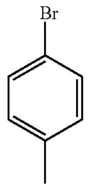 | 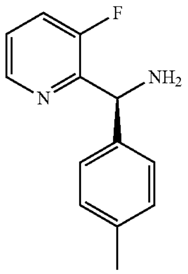 [SMILES: Cc1ccc([C@H](N)c2ncccc2F)cc1] | (S)-(3-fluoropyridin-2-yl)(p-tolyl) methanamine | $C_{13}H_{13}FN_2$ (216.25) |
| 81 | A | 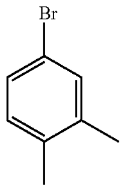 | 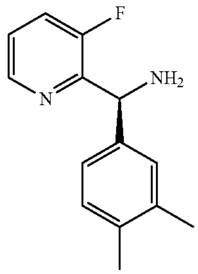 [SMILES: Cc1ccc([C@H](N)c2ncccc2F)cc1C] | (S)-(3,4-dimethylphenyl) (3-fluoropyridin-2-yl)methanamine | $C_{14}H_{15}FN_2$ (230.28) |
| 82 | A | 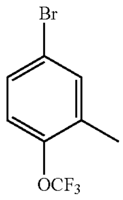 | 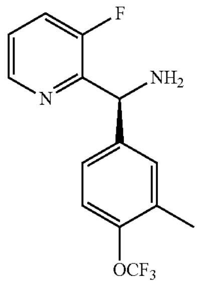 [SMILES: Cc1cc([C@H](N)c2ncccc2F)ccc1OC(F)(F)F] | (S)-(3-fluoropyridin-2-yl)(3-methyl-4-(trifluoromethoxy) phenyl) methanamine | $C_{14}H_{12}F_4N_2O$ (300.25) |
| 83 | A | 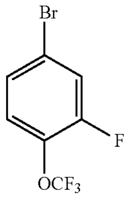 | 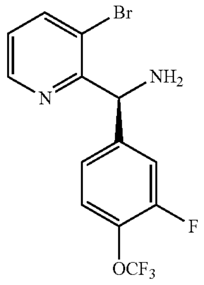 [SMILES: N[C@@H](c1ccc(OC(F)(F)F)c(F)c1)c1ncccc1Br] | (S)-(3-bromopyridin-2-yl)(3-fluoro-4-(trifluoromethoxy) phenyl) methanamine | $C_{13}H_9BrF_4N_2O$ (365.12) |
| 84 | A | 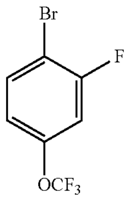 | 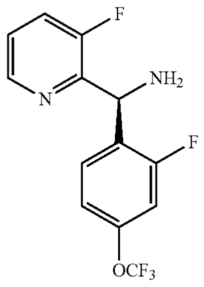 [SMILES: N[C@@H](c1ccc(OC(F)(F)F)cc1F)c1ncccc1F] | (S)-(2-fluoro-4-(trifluoromethoxy) phenyl)(3-fluoropyridin-2-yl)methanamine | $C_{13}H_9F_5N_2O$ (304.22) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 85 | A | 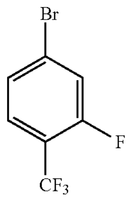 | 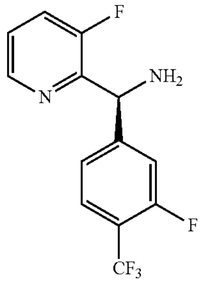 [SMILES: N[C@@H](c1ccc(C(F)(F)F)c(F)c1)c1ncccc1F] | (S)-(3-fluoro-4-(trifluoromethyl) phenyl)(3-fluoropyridin-2-yl)methanamine | $C_{13}H_9F_5N_2$ (288.22) |
| 86 | A | 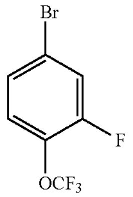 | 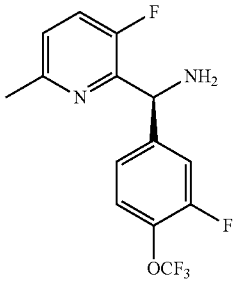 [SMILES: Cc1ccc(F)c([C@@H](N)c2ccc(OC(F)(F)F)c(F)c2)n1] | (S)-(3-fluoro-4-(trifluoromethoxy) phenyl)(3-fluoro-6-methylpyridin-2-yl)methanamine | $C_{14}H_{11}F_5N_2O$ (318.24) |
| 87[2] | A | 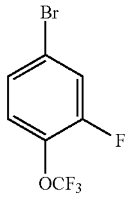 | 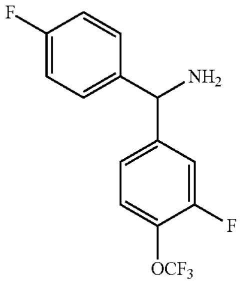 [SMILES: NC(c1ccc(F)cc1)c1ccc(OC(F)(F)F)c(F)c1] | (3-fluoro-4-(trifluoromethoxy) phenyl)(4-fluorophenyl) methanamine | $C_{14}H_{10}F_5NO$ (303.23) |
| 88[2] | A | 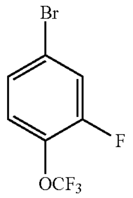 | 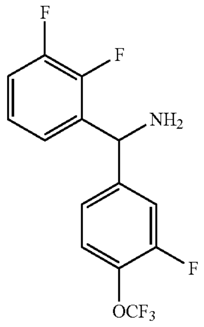 [SMILES: NC(c1ccc(OC(F)(F)F)c(F)c1)c1cccc(F)c1F] | (2,3-difluorophenyl) (3-fluoro-4-(trifluoromethoxy) phenyl) methanamine | $C_{14}H_9F_5NO$ (321.22) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 89[2] | A | 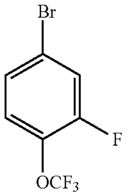 | 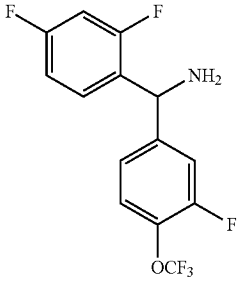 [SMILES: NC(c1ccc(OC(F)(F)F)c(F)c1)c1ccc(F)cc1F] | (2,5-difluorophenyl)(3-fluoro-4-(trifluoromethoxy)phenyl)methanamine | $C_{14}H_9F_6NO$ (321.22) |
| 90[2] | A | 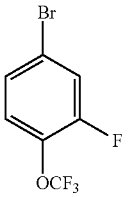 | 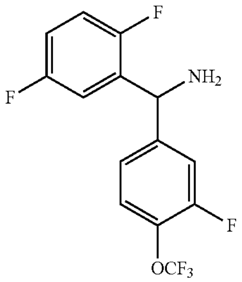 [SMILES: NC(c1ccc(OC(F)(F)F)c(F)c1)c1cc(F)ccc1F] | (2,5-difluorophenyl)(3-fluoro-4-(trifluoromethoxy)phenyl)methanamine | $C_{14}H_9F_6NO$ (321.22) |
| 91[2] | A | 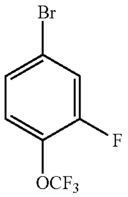 | 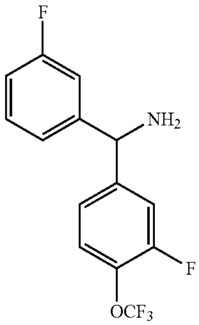 [SMILES: NC(c1cccc(F)c1)c1ccc(OC(F)(F)F)c(F)c1] | (3-fluoro-4-(trifluoromethoxy)phenyl)(3-fluorophenyl)methanamine | $C_{14}H_{10}F_5NO$ (303.23) |
| 92[2] | A | 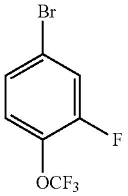 | 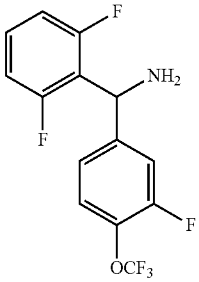 [SMILES: NC(c1ccc(OC(F)(F)F)c(F)c1)c1c(F)cccc1F] | (2,6-difluorophenyl)(3-fluoro-4-(trifluoromethoxy)phenyl)methanamine | $C_{14}H_9F_6NO$ (321.22) |
| 93[2] | A | 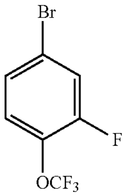 | 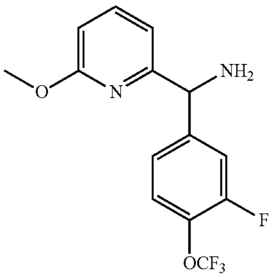 [SMILES: COc1cccc(C(N)c2ccc(OC(F)(F)F)c(F)c2)n1] | (3-fluoro-4-(trifluoromethoxy)phenyl)(6-methoxypyridin-2-yl)methanamine | $C_{14}H_{12}F_4N_2O_2$ (316.25) |

TABLE 3-continued

Additional diarylmethanamines prepared analogous to Scheme 5 and 6 (Intermediates 61-97). Unless otherwise stated, all amines in this table are hydrochloride salts.

| Inter-mediate | Method | Aryl Halide or Grignard in Step 2 | Structure | Name | Mol. Formula (Mol. Wt.) |
|---|---|---|---|---|---|
| 94[2] | A | 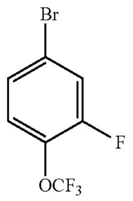 | 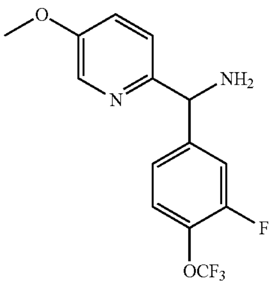 [SMILES: COc1ccc(C(N)c2ccc(OC(F)(F)F)c(F)c2)nc1] | (3-fluoro-4-(trifluoromethoxy) phenyl)(5-methoxypyridin-2-yl)methanamine | $C_{14}H_{12}F_4N_2O_2$ (316.25) |
| 95[2] | A | 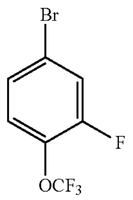 | 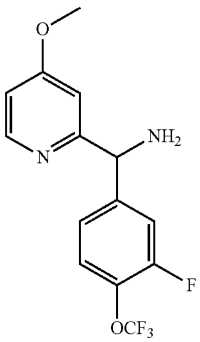 [SMILES: COc1ccnc(C(N)c2ccc(OC(F)(F)F)c(F)c2)c1] | (3-fluoro-4-(trifluoromethoxy) phenyl)(4-methoxypyridin-2-yl)methanamine | $C_{14}H_{12}F_4N_2O_2$ (316.25) |
| 96[2] | A | 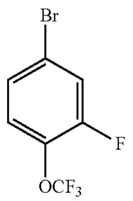 | 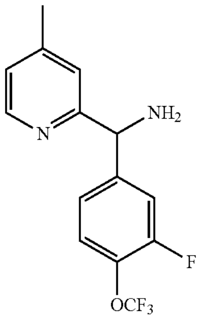 [SMILES: Cc1ccnc(C(N)c2ccc(OC(F)(F)F)c(F)c2)c1] | (3-fluoro-4-(trifluoromethoxy) phenyl)(4-methylpyridin-2-yl)methanamine | $C_{14}H_{12}F_4N_2O$ (300.25) |
| 97[2] | A | 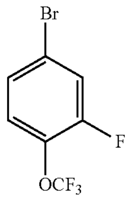 | 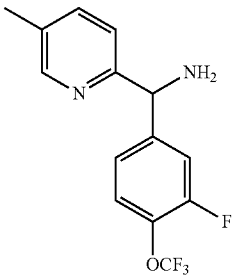 [SMILES: Cc1ccc(C(N)c2ccc(OC(F)(F)F)c(F)c2)nc1] | (3-fluoro-4-(trifluoromethoxy) phenyl)(5-methylpyridin-2-yl)methanamine | $C_{14}H_{12}F_4N_2O$ (300.25) |

[1]Prepared employing (R)-2-methylpropane-2-sulfinamide in the first step (Scheme 5). For reversal of stereochemistry observed in the Ellman sulfonylimine chemistry observed with 2-pyridyl substrates, see Kuduk, S.D.; DiPardo, R. M.; Chang, R. K.; Ng, C.; Bock, M. G. *Tetrahedron Lett.* 2004, 45, 6641-6643.

[2]Prepared employing racemic 2-methylpropane-2-sulfinamide in the first step (Scheme 5)

Scheme 14

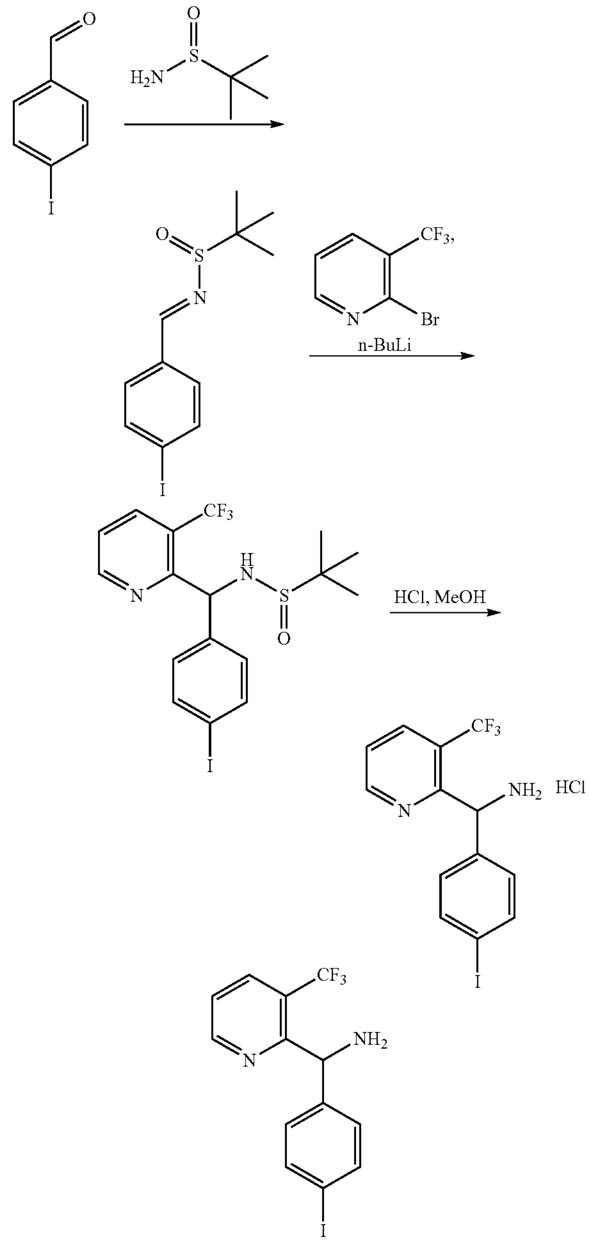

Intermediate 98: (4-Iodophenyl)(3-(trifluoromethyl)pyridin-2-yl)methanamine hydrochloride

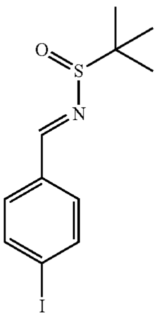

Step 1. (E)-N-(4-Iodobenzylidene)-2-methylpropane-2-sulfinamide

To a solution of 4-(iodo)benzaldehyde (2.00 g, 8.62 mmol) (BioNet Research) in DCM (20 mL) was added 2-methylpropane-2-sulfinamide (2.09 g, 17.2 mmol) (AK Scientific) and copper (II) sulfate (2.75 g, 17.2 mmol) (Fluka). The suspension was stirred at rt under $N_2$ for 17 h. The suspension was then filtered through Celite® brand filter agent, and the solids were washed with DCM (2×20 mL). The filtrates were concentrated and purified by ISCO (80 g, $SiO_2$, 0-100% EtOAc/hexanes) to give the title compound as a yellow solid.

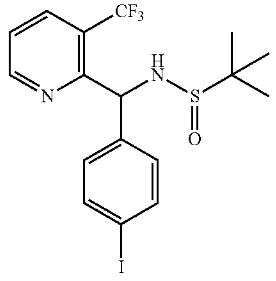 [SMILES: CC(C)(C)S(=O)NC(c1ccc(I)cc1)c1ncccc1C(F)(F)F]

Step 2. N-((4-Iodophenyl)(3-(trifluoromethyl)pyridin-2-yl)methyl)-2-methylpropane-2-sulfinamide To a solution of 2-bromo-3-(trifluoromethyl)pyridine (750 mg, 3.32 mmol) (prepared as described in Schlosser, M. et al. *Eur. J. Org. Chem.* 2003, 1559) in THF (5.0 mL) at −78° C. was added n-butyllithium (3.94 mL, 6.31 mmol, 1.6 M in n-hexane). The resulting mixture was then stirred for 15 min. N-(4-iodobenzylidene)-2-methylpropane-2-sulfinamide (556 mg, 1.66 mmol) in THF (5 mL) was added, and the reaction was allowed to warm to rt and stirred for 4 h. The reaction was quenched with saturated aqueous $NH_4Cl$ (10 mL) and stirred rapidly for 1 h. The aqueous layer was extracted with EtOAc (2×10 mL) and the combined organic layers were dried ($MgSO_4$) and concentrated. The product thus obtained was taken into the next step without further purification.

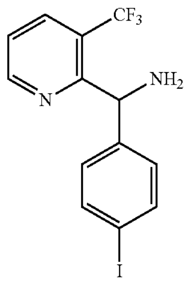 [SMILES: NC(c1ccc(I)cc1)c1ncccc1C(F)(F)F]

Step 3. (4-Iodophenyl)(3-(trifluoromethyl)pyridin-2-yl)methanamine

To a solution of N-((4-iodophenyl)(3-(trifluoromethyl)pyridin-2-yl)methyl)-2-methylpropane-2-sulfinamide in MeOH (5 mL) was added HCl (2.0 mL, 8.0 mmol) (4.0 M in 1,4-dioxane). The reaction was stirred at rt under $N_2$ for 18 h. The reaction was then concentrated, and the residue was purified by reverse-phase preparative HPLC (Shimadzu) on a Phenomenex Gemini™ column (5 micron, C18, 110 Å, Axia, 100×30 mm) eluting at 45 mL/min with a linear gradient of 10% to 100% MeCN (0.1% TFA) in $H_2O$ (0.1% TFA) over 20 minutes. The product-containing fractions were combined, concentrated, dissolved in DCM (5 mL) and extracted with saturated aqueous $NaHCO_3$ (2×5 mL). The organic layer was dried and concentrated to give (4-iodophenyl)(3-(trifluoromethyl)-pyridin-2-yl)methanamine as a clear oil.

Scheme 15

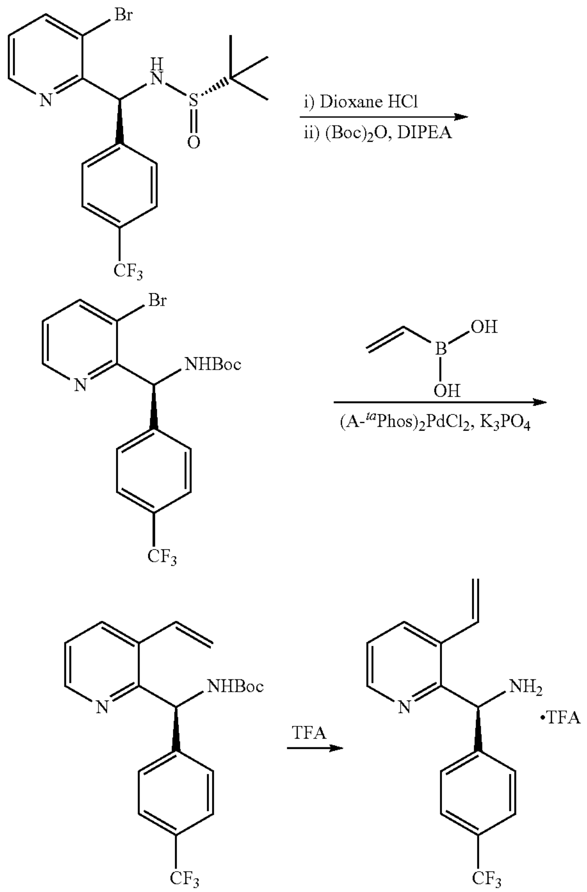

Intermediate 99: (S)-(4-(Trifluoromethyl)phenyl)(3-vinylpyridin-2-yl)methanamine 2,2,2-trifluoroacetate

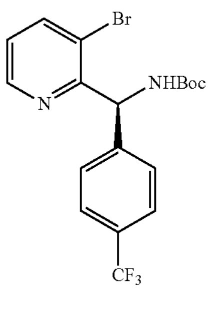 [SMILES: CC(C)(C)OC(=O)N[C@@H](c1ccc(C(F)(F)F)cc1)c1ncccc1Br]

STEP 1. (S)-tert-Butyl ((3-bromopyridin-2-yl)(4-(trifluoromethyl)phenyl)methyl)carbamate To a stirring solution of (S)—N—((S)-(3-bromopyridin-2-yl)(4-(trifluoromethyl)phenyl)methyl)-2-methylpropane-2-sulfinamide (Intermediate 40, Step 4, 0.6 g, 1.38 mmol) in 1,4-dioxane (6 mL) at 0° C. was added HCl (4.0 M in dioxane solution, 12 mL, 27.6 mmol). The resulting mixture was warmed to room temperature and stirred for 1 h. The reaction progress was monitored by TLC (20% EtOAc in petroleum ether). After completion, Boc anhydride (0.76 g, 3.4 mmol) and DIPEA (0.28 g, 2 mmol) in 1,4-dioxane (5 mL) were added to the reaction mixture, and the mixture was stirred at room temperature for 1 h. The reaction progress was monitored by TLC (20% EtOAc in petroleum ether). After completion of reaction, water (25 mL) was added to the reaction mixture, and the product was extracted with DCM (3×25 mL). The combined organic layers were dried over anhydrous sodium sulfate and purified by column chromatography using silica (100-200 mesh) with 15-30% EtOAc in petroleum ether as an eluent to afford the title compound as a white solid. MS (ESI pos. ion) m/z: 431.0 (M-100).

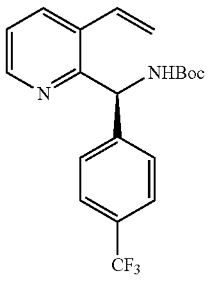 [SMILES: C=Cc1cccnc1[C@@H](NC(=O)OC(C)(C)C)c1ccc(C(F)(F)F)cc1]

STEP 2. (S)-tert-Butyl ((4-(trifluoromethyl)phenyl)(3-vinylpyridin-2-yl)methyl)carbamate To a mixture of (S)-tert-butyl ((3-bromopyridin-2-yl)(4-(trifluoromethyl)-phenyl)methyl)carbamate (0.4 g, 0.93 mmol) in water (2 mL) and EtOH (8 mL) were added $K_3PO_4$ (0.3 g, 1.3 mmol), vinyl boronic acid (4 mL, 9.3 mmol) and $A^{-ta}Phos)_2PdCl_2$ (Guram, A. S. et al. *Org. Lett.* 2006, 8, 1787; 0.13 g, 0.01 mmol). The resulting mixture was stirred at 120° C. for 1 h. Reaction progress was monitored by TLC (20% EtOAc in petroleum ether). After completion of reaction, water (50 mL) was added to the reaction mixture, and the product was extracted with DCM (3×25 mL). The combined organic layers were separated, dried over anhydrous sodium sulfate, and purified by column chromatography using silica (100-200 mesh) and using 15-30% EtOAc in petroleum ether as an eluent. In this manner, (S)-tert-butyl ((4-(trifluoromethyl)phenyl)(3-vinylpyridin-2-yl)methyl)carbamate was obtained as an off-white solid. MS (ESI pos. ion) m/z: 378.9 (M+1).

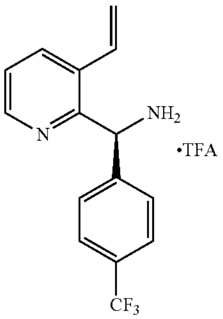 [SMILES: C=Cc1cccnc1[C@@H](N)c1ccc(C(F)(F)F)cc1]

STEP 3. (S)-(4-(Trifluoromethyl)phenyl)(3-vinylpyridin-2-yl)methanamine 2,2,2-trifluoroacetate To a 50 mL round bottom flask containing (S)-tert-butyl ((4-(trifluoromethyl)phenyl)(3-vinylpyridin-2-yl)methyl) carbamate (97 mg, 0.256 mmol) was added DCM (3 mL). The resulting mixture was then stirred at 23° C. for 2 min. At this time, TFA was added (3 mL) and the reaction was stirred for 3 h. The solvent was removed, and the material was immediately used with no further purification. MS (ESI pos. ion) m/z: 279.1 (M+1).

Scheme 16

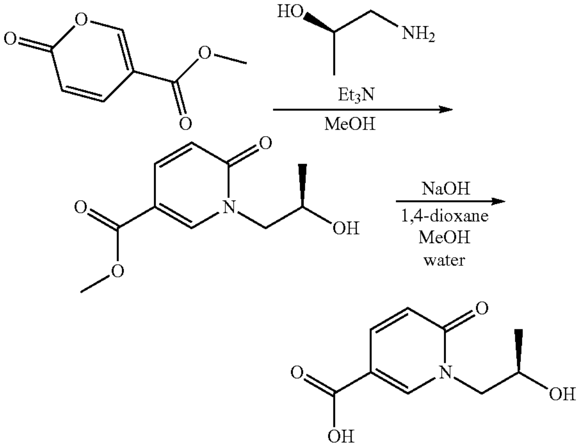

Intermediate 100: (R)-1-(2-Hydroxypropyl)-6-oxo-1,6-dihydropyridine-3-carboxylic acid

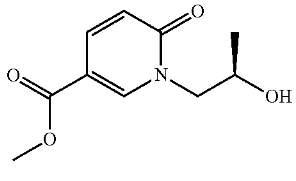

STEP 1. (R)-Methyl 1-(2-hydroxypropyl)-6-oxo-1,6-dihydropyridine-3-carboxylate

A solution of methyl coumalate (500 mg, 3.24 mmol) in MeOH (10 mL) was treated with (R)-(−)-1-amino-2-propanol (0.319 mL, 4.06 mmol) and TEA (0.790 mL, 5.68 mmol). The reaction was stirred at 23° C. under nitrogen. After 1 h, the reaction was concentrated and purified by silica gel chromatography (eluent: 55-95% EtOAc/hexane), affording (R)-methyl 1-(2-hydroxypropyl)-6-oxo-1,6-dihydropyridine-3-carboxylate as a white solid. MS (ESI pos. ion) m/z: 212.1 (M+1).

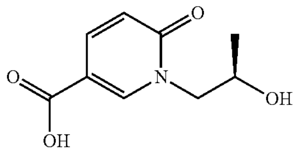

STEP 2. (R)-1-(2-Hydroxypropyl)-6-oxo-1,6-dihydropyridine-3-carboxylic acid

A solution of (R)-methyl 1-(2-hydroxypropyl)-6-oxo-1,6-dihydropyridine-3-carboxylate (508 mg, 2.405 mmol) in 1,4-dioxane (12 mL) and MeOH (4.00 mL) was treated with aqueous sodium hydroxide, 5.0 M (0.962 mL, 4.81 mmol).

The reaction was stirred at 23° C. After 20 h, the reaction was neutralized to pH=6.0 with 2 N HCl, and concentrated in vacuo. The residue was azeotroped with toluene (3×10 mL), suspended in a 1:1 MeOH:DCM solution (25 mL), and the white NaCl residue was removed by filtration. The filtrate was concentrated, affording (R)-1-(2-hydroxypropyl)-6-oxo-1,6-dihydropyridine-3-carboxylic acid as a white solid. MS (ESI pos. ion) m/z: 198.1 (M+1).

TABLE 4

Additional carboxylic acids prepared from methyl coumalate analogous to Scheme 16 (Intermediates 101-110)

| Intermediate | Amine in Step 1 | Structure | Name | Mol. Formula (Mol. Wt.) |
|---|---|---|---|---|
| 101 | 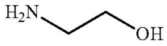 | 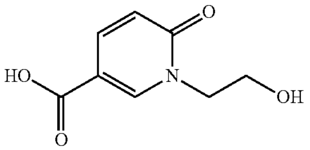 [SMILES: O=C(O)c1ccc(=O)n(CCO)c1] | 1-(2-hydroxyethyl)-6-oxo-1,6-dihydropyridine-3-carboxylic acid | $C_8H_9NO_4$ (183.16) |

TABLE 4-continued

Additional carboxylic acids prepared from methyl coumalate analogous to Scheme 16 (Intermediates 101-110)

| Intermediate | Amine in Step 1 | Structure | Name | Mol. Formula (Mol. Wt.) |
|---|---|---|---|---|
| 102 | 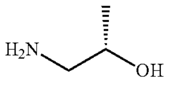 | 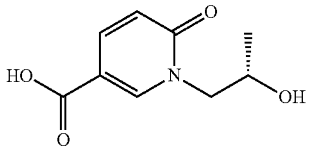 | (S)-1-(2-hydroxypropyl)-6-oxo-1,6-dihydropyridine-3-carboxylic acid | $C_9H_{11}NO_4$ (197.19) |
| 103 | 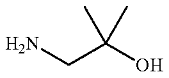 | 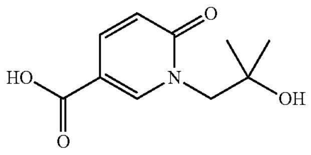 | 1-(2-hydroxy-2-methylpropyl)-6-oxo-1,6-dihydropyridine-3-carboxylic acid | $C_{10}H_{13}NO_4$ (211.21) |
| 104 | 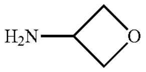 | 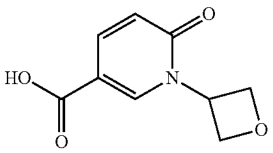 [SMILES: O=C(O)c1ccc(=O)n(C2COC2)c1] | 1-(oxetan-3-yl)-6-oxo-1,6-dihydropyridine-3-carboxylic acid | $C_9H_9NO_4$ (195.17) |
| 105 | 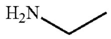 | 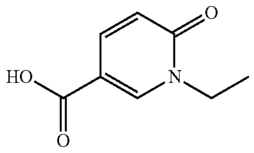 | 1-ethyl-6-oxo-1,6-dihydropyridine-3-carboxylic acid | $C_8H_9NO_3$ (167.16) |
| 106 | 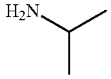 | 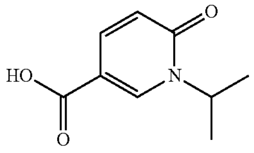 | 1-isopropyl-6-oxo-1,6-dihydropyridine-3-carboxylic acid | $C_9H_{11}NO_3$ (181.19) |
| 107 | 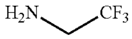 | 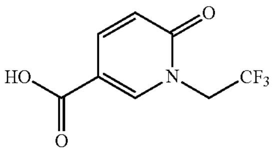 [SMILES: O=C(O)c1ccc(=O)n(CC(F)(F)F)c1] | 6-oxo-1-(2,2,2-trifluoroethyl)-1,6-dihydropyridine-3-carboxylic acid | $C_8H_6F_3NO_3$ (211.13) |
| 108 | 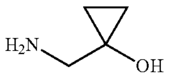 | 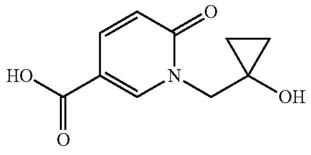 [SMILES: O=C(O)c1ccc(=O)n(CC2(O)CC2)c1] | 1-((1-hydroxycyclopropyl)methyl)-6-oxo-1,6-dihydropyridine-3-carboxylic acid | $C_{10}H_{11}NO_4$ (209.20) |
| 109 | 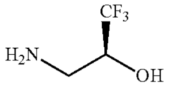 | 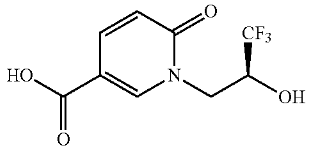 [SMILES: O=C(O)c1ccc(=O)n(C[C@H](O)C(F)(F)F)c1] | (S)-6-oxo-1-(3,3,3-trifluoro-2-hydroxypropyl)-1,6-dihydropyridine-3-carboxylic acid | $C_9H_8F_3NO_4$ (251.16) |
| 110 | 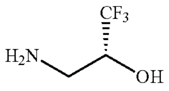 | 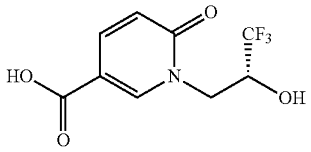 [SMILES: O=C(O)c1ccc(=O)n(C[C@@H](O)C(F)(F)F)c1] | (R)-6-oxo-1-(3,3,3-trifluoro-2-hydroxypropyl)-1,6-dihydropyridine-3-carboxylic acid | $C_9H_8F_3NO_4$ (251.16) |

Scheme 17

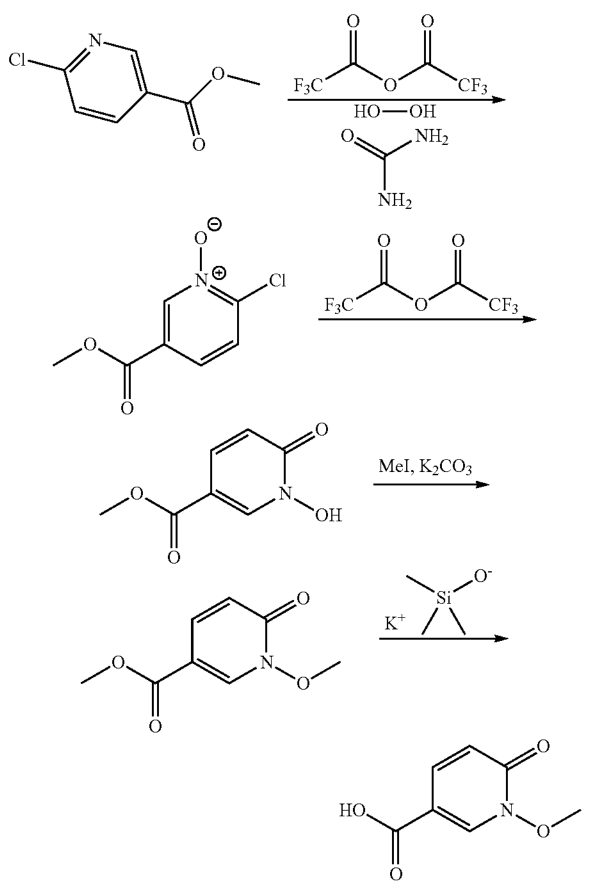

Intermediate 111: 1-Methoxy-6-oxo-1,6-dihydropyridine-3-carboxylic acid

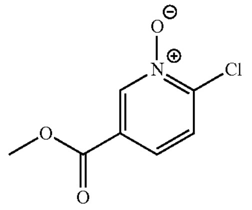

STEP 1. 2-Chloro-5-(methoxycarbonyl)pyridine 1-oxide

To a 500 mL round bottom flask containing methyl 6-chloronicotinate (4.50 g, 26.2 mmol) was added MeCN (100 mL). The resulting mixture was then stirred at 0° C. for 10 min. At this time, urea hydrogen peroxide (4.93 g, 52.5 mmol) solid was added before the dropwise addition of trifluoroacetic anhydride (7.41 mL, 52.5 mmol). The reaction was stirred for 30 min and then the ice bath was removed. The reaction was then stirred for 3 h and then the bulk of MeCN was removed by rotary evaporation. The residue was dissolved in EtOAc (150 mL) and washed with sodium thiosulfate (aqueous, 0.5 M, 2×100 mL), water (100 mL), brine (100 mL), dried with sodium sulfate and concentrated to a tan solid. The solid thus obtained was dissolved in DCM (150 mL) and MeOH (30 mL). The solid residue was removed by filtration, and the filtrate was concentrated affording 2-chloro-5-(methoxycarbonyl)pyridine 1-oxide as a tan solid.

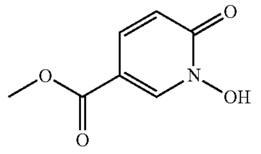

STEP 2. Methyl 1-hydroxy-6-oxo-1,6-dihydropyridine-3-carboxylate

To a 250 mL round bottom flask containing 2-chloro-5-(methoxycarbonyl)pyridine 1-oxide (2.45 g, 13.06 mmol) was added MeCN (10 mL). The resulting mixture was stirred at 23° C. for 5 min. At this time, trifluoroacetic anhydride (20 mL) was added and the reaction was stirred 1 h. Solid $NaHCO_3$ (25 g) was added to the flask followed by MeOH (100 mL). The solid was filtered awau and the filtrate was concentrated and subjected to silica gel chromatography (80 g ISCO column, 0-5% MeOH in $CHCl_3$) to give methyl 1-hydroxy-6-oxo-1,6-dihydropyridine-3-carboxylate as a yellow solid.

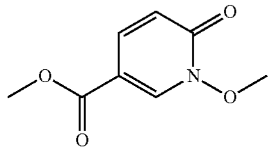

STEP 3. Methyl 1-methoxy-6-oxo-1,6-dihydropyridine-3-carboxylate

To a solution of methyl 1-hydroxy-6-oxo-1,6-dihydropyridine-3-carboxylate (0.75 g, 4.43 mmol) in 5 mL DMF at 23° C., were added potassium carbonate (1.8 g, 13.3 mmol) and MeI (1.5 g, 11 mmol). The resulting mixture was stirred overnight and then MeOH (6 mL) was added and the resulting mixture was stirred for 2 h. The volatiles were removed under vacuum, and the resulting residue was dissolved in EtOAc (75 mL), washed with water (2×50 mL), brine (50 mL), dried ($MgSO_4$), and concentrated to give methyl 1-methoxy-6-oxo-1,6-dihydropyridine-3-carboxylate as a brown oil.

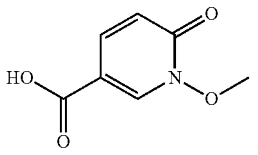

STEP 4. 1-Methoxy-6-oxo-1,6-dihydropyridine-3-carboxylic acid

A solution of methyl 1-methoxy-6-oxo-1,6-dihydropyridine-3-carboxylate (64 mg, 0.349 mmol) and potassium trimethylsilanolate (90 mg, 0.699 mmol) in THF (6 mL) was stirred at 23° C. for 20 min. MeOH (5 mL) was added, and the mixture was filtered. The filtrate was concentrated affording 1-methoxy-6-oxo-1,6-dihydropyridine-3-carboxylic acid as a white solid.

Scheme 18

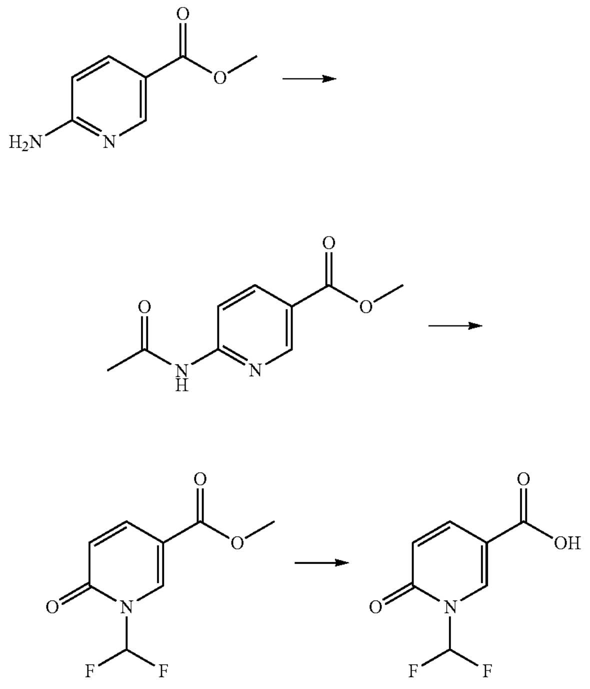

Intermediate 112: 1-(Difluoromethyl)-6-oxo-1,6-dihydropyridine-3-carboxylic acid

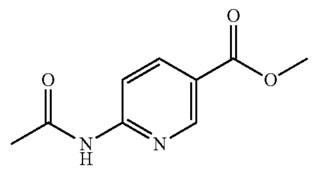

STEP 1. Methy 6-acetamidonicotinate

To a mixture of methyl 6-aminopyridine-3-carboxylate (3 g, 19.72 mmol, Aldrich) in 1,4-ioxane (50 mL) was added acetic anhydride (3.72 mL, 39.4 mmol, Aldrich). The resulting mixture was then heated at 85° C. for 3 h and at 100° C. for an additional 3 h. The mixture was then cooled to rt and diluted with EtOAc (400 mL). The mixture was then washed with saturated $NaHCO_3$ solution (2x200 mL), brine (150 mL), dried over $MgSO_4$, and concentrated in vacuo to afford the title compound as a white solid, which was used in the next step without purification. MS (ESI, positive ion) m/z: 195 (M+H).

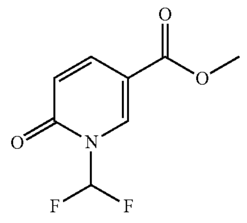

STEP 2. Methyl 1-(difluoromethyl)-6-oxo-1,6-dihydropyridine-3-carboxylate

A mixture of methyl 6-acetamidonicotinate (1.93 g, 9.94 mmol), sodium chlorodifluoroacetate (1.818 g, 11.93 mmol, Alfa Aesar Avocado Lancaster) and 18-crown-6 (0.525 g, 1.988 mmol, Aldrich) in MeCN (40 mL) was heated to 90° C. (reflux) under nitrogen. After 5 h, a solution of $KHSO_4$ (1% in $H_2O$, 10 mL) was added and the mixture was refluxed for 21 h. The mixture was then cooled to room temperature and concentrated. The mixture was diluted with EtOAc (250 mL), washed with 10% aqueous hydrochloric acid (100 mL), and then with saturated aqueous $NaHCO_3$ (100 mL), and finally with brine (100 mL). The mixture was dried ($MgSO_4$) and concentrated in vacuo. The residue was dissolved in DCM (5 mL), and the solution was purified by silica gel flash column chromatography (5-30% EtOAc/hexane) to afford the title compound as a white solid. MS (ESI, positive ion) m/z: 204 (M+H).

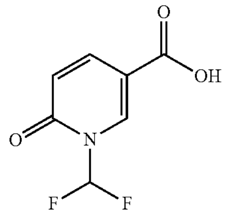 [SMILES: O=C(O)c1ccc(=O)n(C(F)F)c1]

STEP 3. 1-(Difluoromethyl)-6-oxo-1,6-dihydropyridine-3-carboxylic acid

To a solution of methyl 1-(difluoromethyl)-6-oxo-1,6-dihydropyridine-3-carboxylate (0.500 g, 2.461 mmol) in MeOH (12 mL) and water (4 mL) was added lithium hydroxide hydrate (0.207 g, 4.92 mmol, Aldrich). The resulting mixture was then stirred at room temperature for 4 h. Solvent (MeOH) was removed in vacuok, and the remaining aqueous solution was adjusted to pH=5-6 by addition of concentrated HCl. The mixture was then extracted with EtOAc (3x10 mL). The combined organic layers were dried ($MgSO_4$), and the solvent removed to give the title compound as a yellow solid. MS (ESI, positive ion) m/z: 190 (M+H).

Scheme 19

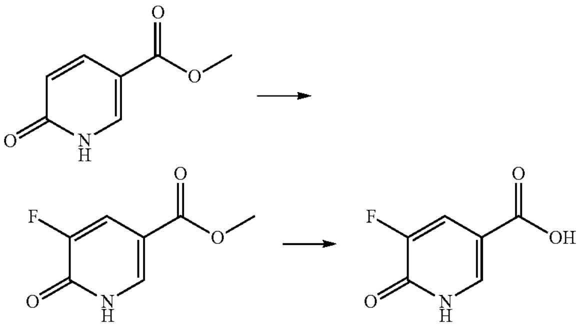

Intermediate 113: 5-Fluoro-6-oxo-1,6-dihydropyridine-3-carboxylic acid

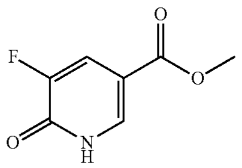

STEP 1. Methyl 5-fluoro-6-oxo-1,6-dihydropyridine-3-carboxylate

To a solution of methyl 6-oxo-1,6-dihydro-3-pyridinecarboxylate (2.00 g, 13.06 mmol, Bionet Research) in MeCN (40 mL) was added SelectFluor® (4.63 g, 13.06 mmol, Aldrich). The resulting mixture was then heated at 65° C. for 18 h. Then, the mixture was cooled to rt and water (20 mL) was added. The solvent, (MeCN) was removed and the remaining aqueous solution was extracted with EtOAc (2×20 mL). The combined organic extracts were dried ($MgSO_4$) and concentrated in vacuo. The residue was dissolved in MeOH (100 mL) and silica gel was added. The mixture was concentrated and dried in vacuo. Purification by silica gel flash column chromatography (0%-100% EtOAc/hexane) gave the title compound as a white solid. MS (ESI, positive ion) m/z: 172 (M+H).

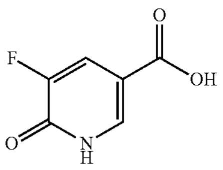 [SMILES: O=C(O)c1c[nH]c(=O)c(F)c1]

STEP 2. 5-Fluoro-6-oxo-1,6-dihydropyridine-3-carboxylic acid

To a solution of methyl 5-fluoro-6-oxo-1,6-dihydropyridine-3-carboxylate (0.876 g, 5.12 mmol) in MeOH (33 mL) and water (11 mL), was added lithium hydroxide hydrate (1.074 g, 25.6 mmol). The resulting mixture was then stirred at rt for 5 h. The mixture was concentrated and the pH was adjusted to pH=5 using concentrated HCl. The mixture was then concentrated and dried in vacuo. The resulting residue was dissolved in MeOH (20 mL) and silica gel was added. The mixture was concentrated and dried. The solid mixture was then purified by silica gel flash column chromatography (30%-100% EtOAc/hexane, then 0%-100% MeOH/DCM) to give the title compound as an off-white solid. MS (ESI, positive ion) m/z: 158 (M+H).

Scheme 20

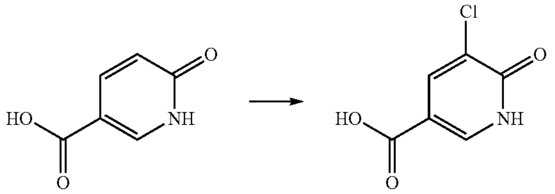

Intermediate 114: 5-Chloro-6-oxo-1,6-dihydropyridine-3-carboxylic acid

To a solution of 6-hydroxy nicotinic acid (0.500 g, 3.59 mmol, TCI) in MeCN (20 mL), was added N-chlorosuccinimide (0.436 mL, 5.39 mmol, Aldrich). The resulting mixture was then heated at 80° C. for 72 h. A white precipitate was present. The mixture was filtered and the white solid was washed with EtOAc (2×1 mL) and dried in vacuo to afford the title compound as a white solid. MS (ESI, positive ion) m/z: 174,176 (M+H).

Scheme 21

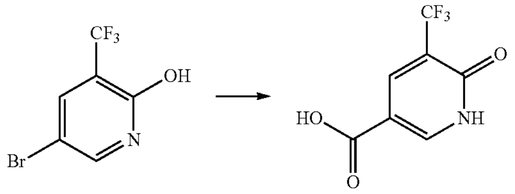

Intermediate 115: 6-Oxo-5-(trifluoromethyl)-1,6-dihydropyridine-3-carboxylic acid To a solution of 5-bromo-3-(trifluoromethyl)pyridin-2-ol (0.960 g, 3.97 mmol, Aldrich) in THF (20 mL) at −78° C. under $N_2$ was slowly added n-butyllithium solution, 1.6 M in hexane (5.45 mL, 8.73 mmol). After addition, the mixture was stirred at −78° C. for 30 min. Then, dry ice was added and the mixture was stirred at −78° C. for 30 min and at rt for 30 min. Water (20 mL) was then added slowly, and the mixture was stirred at rt for 15 min. The aqueous phase was collected and acidified (pH=5-6) using concentrated HCl. The mixture was extracted with EtOAc (3×15 mL). The combined organic layers were dried ($MgSO_4$), concentrated, and dried in vacuo to give the title compound as a yellow solid. MS (ESI, positive ion) m/z: 208 (M+H).

Scheme 22

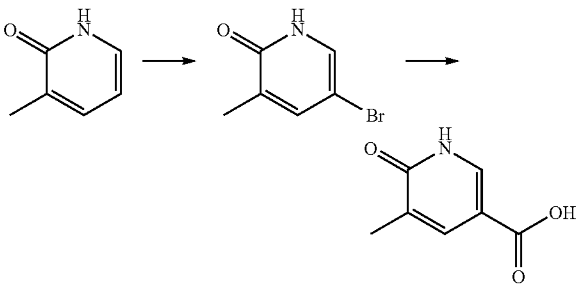

Intermediate 116:
5-Methyl-6-oxo-1,6-dihydropyridine-3-carboxylic acid

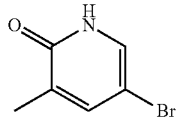

STEP 1. 5-Bromo-3-methylpyridin-2(1H)-one

To a solution of 2-hydroxy-3-methylpyridine (0.500 g, 4.58 mmol, Acros Organics) in DCM (15 mL) was slowly added bromine (0.282 mL, 5.50 mmol). After addition, the mixture was stirred at rt for 18 h. The mixture was cooled to 0° C. and was quenched with saturated aqueous $NaHCO_3$ (5 mL). The mixture was then extracted with EtOAc (3×20 mL). The combined organic layer were dried over $MgSO_4$ and concentrated. The residue was then dissolved in MeOH (20 mL) and silica gel was added. The mixture was concentrated and dried in vacuo. The resulting mixture was then purified by silica gel flash column chromatography (solid loading, 0%-100% EtOAc/hexane) to afford the title compound as a light pink solid. MS (ESI, positive ion) m/z: 188,190 (M+H).

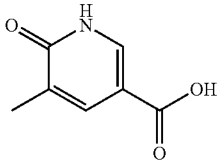

STEP 2.
5-Methyl-6-oxo-1,6-dihydropyridine-3-carboxylic acid

To a solution of 5-bromo-3-methylpyridin-2(1H)-one (0.400 g, 2.127 mmol) in THF (9 mL) at −78° C. under $N_2$ was slowly added n-butyllithium solution, 1.6 M in hexane (5.32 mL, 8.51 mmol). After addition, the mixture was stirred at −78° C. for 20 min. The mixture was then quenched with dry ice and allowed to warm to 0° C. and stirred for 60 min. The mixture was then immersed in a 0° C. bath and the pH was adjusted to pH=5-6 using concentrated HCl. The mixture was concentrated and dried in vacuo to give the title compound as a light brown solid. MS (ESI, positive ion) m/z: 154 (M+H).

Scheme 23

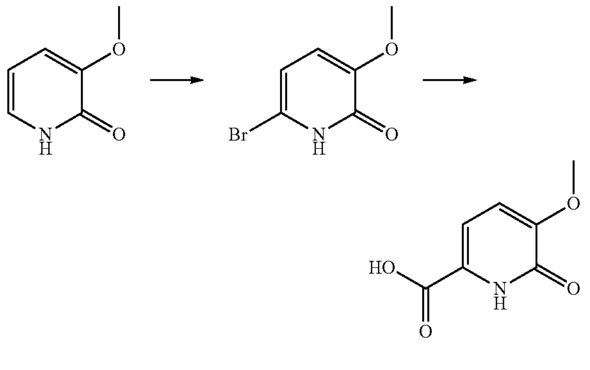

Intermediate 117:
5-Methoxy-6-oxo-1,6-dihydropyridine-2-carboxylic acid

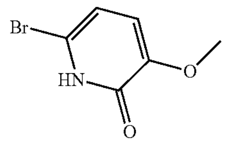

STEP 1. 6-Bromo-3-methoxypyridin-2(1H)-one

To a solution of 3-methoxy-2(1 h)-pyridone (1.00 g, 7.99 mmol, AstaTech, Inc) in DCM (26 mL) at 0° C. was slowly added bromine (0.819 mL, 15.98 mmol). After addition, the mixture was stirred at rt for 18 h. The mixture was then cooled to 0° C. and saturated aqueous $NaHCO_3$ (4 mL) was slowly added. The mixture was then stirred at rt for 30 min. The organic layer was collected and the aqueous layer was extracted with EtOAc (1×20 mL). The combined organic layers were dried over $MgSO_4$ and concentrated in vacuo. The residue was then dissolved in MeOH (20 mL) and silica gel was added. The mixture was concentrated and dried in vacuo. The solid mixture was purified by silica gel flash column chromatography (solid loading, 0%-100% EtOAc/hexane) to give the title compound as a tan solid. MS (ESI, positive ion) m/z: 204,206 (M+H).

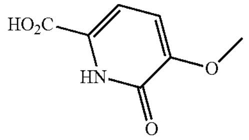

STEP 2.
5-Methoxy-6-oxo-1,6-dihydropyridine-2-carboxylic acid

To a solution of 6-bromo-3-methoxypyridin-2(1H)-one (0.200 g, 0.980 mmol) in THF (3.5 mL) under $N_2$ at −78° C.

was added n-butyllithium solution, 1.6 M in hexanes (2.5 mL, 3.9 mmol) slowly. After addition, the mixture was stirred at −78° C. for 20 min. Then, the mixture was quenched with dry ice at −78° C. The mixture was then stirred at 0° C. for 1 h. The resulting mixture was adjusted to pH=5-6 using concentrated HCl. The mixture was stirred at rt for 15 min. Then, the aqueous layer was collected, concentrated, and dried in vacuo. Then, a solution of DCM/MeOH (1:1, 20 mL) was added to the residue, and the mixture was stirred at rt for 10 min. The mixture was filtered and filtrate was collected, dried over $MgSO_4$, concentrated, and dried in vacuo to afford the title compound as a light brown solid. MS (ESI, positive ion) m/z: 170 (M+H).

TABLE 5

Examples 287-424 prepared via amide formation analogous to Scheme 4

| Ex # | Amine | Acid Structure | Product Structure | Product Name | MS M + H |
|---|---|---|---|---|---|
| 287[1] | 2b | 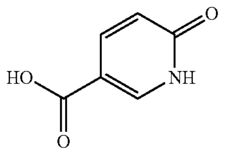 | 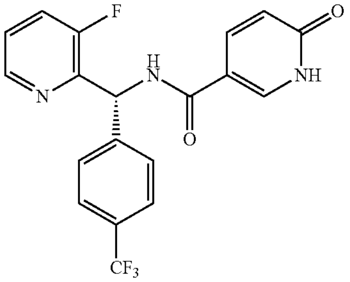 [SMILES: O=C(N[C@H](c1ccc(C(F)(F)F)cc1)c1ncccc1F)c1ccc(=O)[nH]c1] | (R)-N-((3-fluoropyridin-2-yl)(4-(trifluoromethyl)phenyl)methyl)-6-oxo-1,6-dihydropyridine-3-carboxamide | 392.1 |
| 288 | 6 | 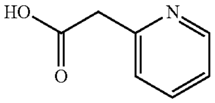 | 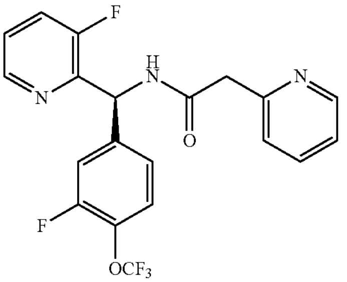 [SMILES: O=C(Cc1ccccn1)N[C@@H](c1ccc(OC(F)(F)F)c(F)c1)c1ncccc1F] | (S)-N-((3-fluoro-4-(trifluoromethoxy)phenyl)(3-fluoropyridin-2-yl)methyl)-2-(pyridin-2-yl)acetamide | 424.1 |
| 289 | 6 | 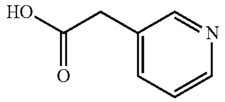 | 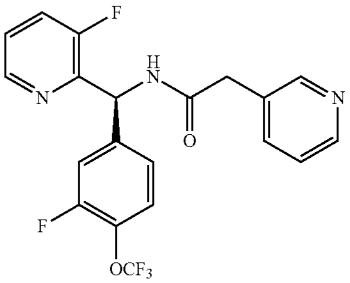 [SMILES: O=C(Cc1cccnc1)N[C@@H](c1ccc(OC(F)(F)F)c(F)c1)c1ncccc1F] | (S)-N-((3-fluoro-4-(trifluoromethoxy)phenyl)(3-fluoropyridin-2-yl)methyl)-2-(pyridin-3-yl)acetamide | 424.1 |
| 290 | 6 | 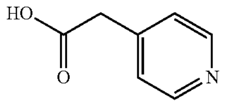 | 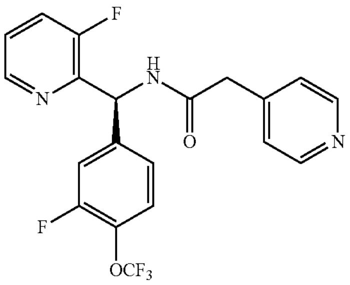 [SMILES: O=C(Cc1ccncc1)N[C@@H](c1ccc(OC(F)(F)F)c(F)c1)c1ncccc1F] | (S)-N-((3-fluoro-4-(trifluoromethoxy)phenyl)(3-fluoropyridin-2-yl)methyl)-2-(pyridin-4-yl)acetamide | 424.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 291 | 61 | 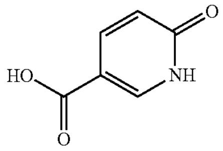 | 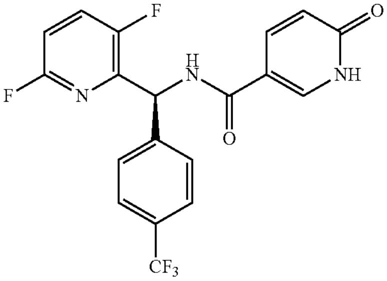 [SMILES: O=C(N[C@@H](c1ccc(C(F)(F)F)cc1)c1nc(F)ccc1F)c1ccc(=O)[nH]c1] | (S)-N-((3,6-difluoropyridin-2-yl)(4 (trifluoromethyl) phenyl)methyl)-6-oxo-1,6-dihydropyridine-3-carboxamide | 410.1 |
| 292 | 62 | 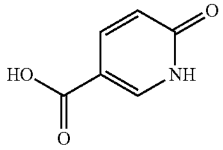 | 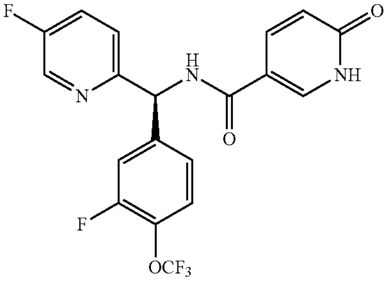 [SMILES: O=C(N[C@@H](c1ccc(OC(F)(F)F)c(F)c1)c1ccc(F)cn1)c1ccc(=O)[nH]c1] | (S)-N-((3-fluoro-4-(trifluoromethoxy) phenyl)(5-fluoropyridin-2-yl)methyl)-6-oxo-1,6-dihydropyridine-3-carboxamide | 426.0 |
| 293 | 63 | 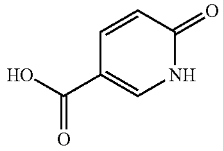 | 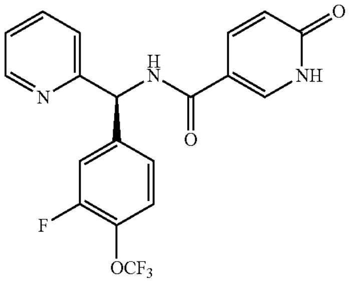 [SMILES: O=C(N[C@@H](c1ccc(OC(F)(F)F)c(F)c1)c1ccccn1)c1ccc(=O)[nH]c1] | (S)-N-((3-fluoro-4-(trifluoromethoxy) phenyl)(pyridin-2-yl)methyl)-6-oxo-1,6-dihydropyridine-3-carboxamide | 408.0 |
| 294 | 63 | 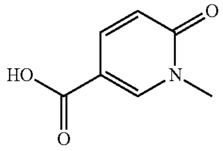 | 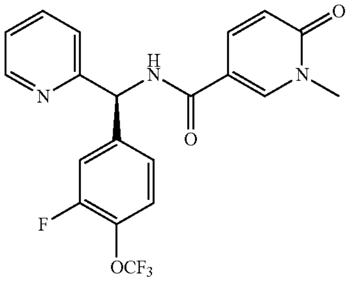 [SMILES: Cn1cc(C(=O)N[C@@H](c2ccc(OC(F)(F)F)c(F)c2)c2ccccn2)ccc1=O] | (S)-N-((3-fluoro-4-(trifluoromethoxy) phenyl)(pyridin-2-yl)methyl)-1-methyl-6-oxo-1,6-dihydropyridine-3-carboxamide | 422.1 |
| 295 | 64 | 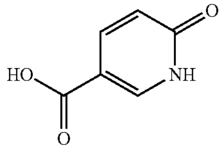 | 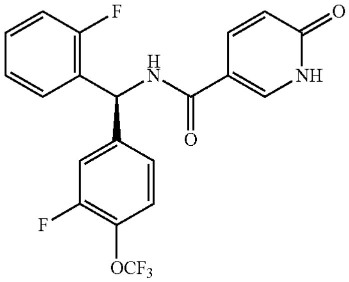 [SMILES: O=C(N[C@@H](c1ccc(OC(F)(F)F)c(F)c1)c1ccccc1F)c1ccc(=O)[nH]c1] | (S)-N-((3-fluoro-4-(trifluoromethoxy) phenyl)(2-fluorophenyl) methyl)-6-oxo-1,6-dihydropyridine-3-carboxamide | 425.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 296 | 64 | 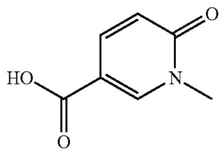 | 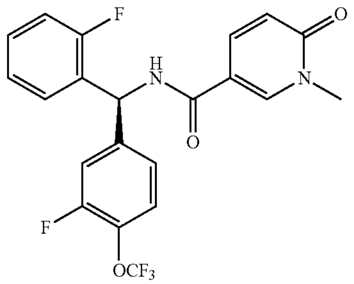 [SMILES: Cn1cc(C(=O)N[C@@H](c2ccc(OC(F)(F)F)c(F)c2)c2ccccc2F)ccc1=O] | (S)-N-((3-fluoro-4-(trifluoromethoxy)phenyl)(2-fluorophenyl)methyl)-1-methyl-6-oxo-1,6-dihydropyridine-3-carboxamide | 439.1 |
| 297 | 6 | 101 | 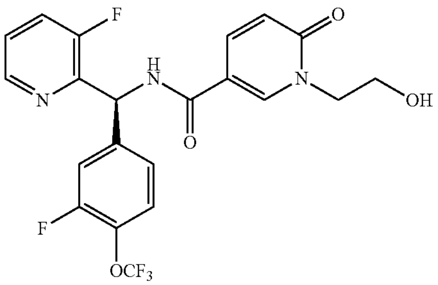 [SMILES: O=C(N[C@@H](c1ccc(OC(F)(F)F)c(F)c1)c1ncccc1F)c1ccc(=O)n(CCO)c1] | (S)-N-((3-fluoro-4-(trifluoromethoxy)phenyl)(3-fluoropyridin-2-yl)methyl)-1-(2-hydroxyethyl)-6-oxo-1,6-dihydropyridine-3-carboxamide | 470.1 |
| 298 | 6 | 102 | 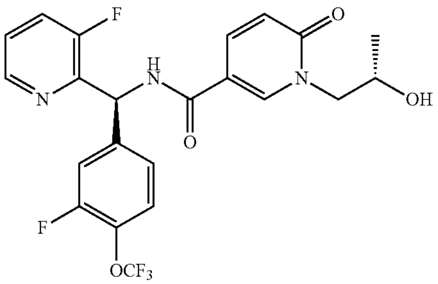 [SMILES: C[C@H](O)Cn1cc(C(=O)N[C@@H](c2ccc(OC(F)(F)F)c(F)c2)c2ncccc2F)ccc1=O] | N-((S)-(3-fluoro-4-(trifluoromethoxy)phenyl)(3-fluoropyridin-2-yl)methyl)-1-((S)-2-hydroxypropyl)-6-oxo-1,6-dihydropyridine-3-carboxamide | 484.1 |
| 299 | 6 | 100 | 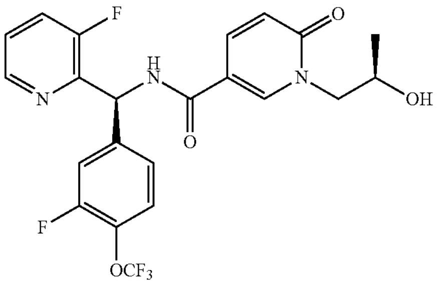 [SMILES: C[C@@H](O)Cn1cc(C(=O)N[C@@H](c2ccc(OC(F)(F)F)c(F)c2)c2ncccc2F)ccc1=O] | N-((S)-(3-fluoro-4-(trifluoromethoxy)phenyl)(3-fluoropyridin-2-yl)methyl)-1-((R)-2-hydroxypropyl)-6-oxo-1,6-dihydropyridine-3-carboxamide | 484.1 |
| 300 | 2 | 102 | 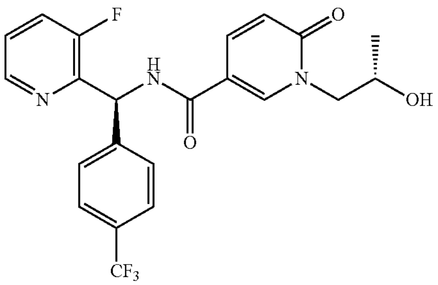 [SMILES: C[C@H](O)Cn1cc(C(=O)N[C@@H](c2ccc(C(F)(F)F)cc2)c2ncccc2F)ccc1=O] | N-((S)-(3-fluoropyridin-2-yl)(4-trifluoromethyl)phenyl)methyl)-1-((S)-2-hydroxypropyl)-6-oxo-1,6-dihydropyridine-3-carboxamide | 450.1 |

TABLE 5-continued

| Ex # | Amine | Acid Structure | Product Structure | Product Name | MS M + H |
|---|---|---|---|---|---|
| | | | Examples 287-424 prepared via amide formation analogous to Scheme 4 | | |
| 301 | 2 | 100 | 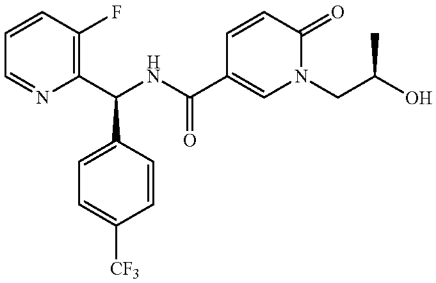 [SMILES: C[C@@H](O)Cn1cc(C(=O)N[C@@H](c2ccc(C(F)(F)F)cc2)c2ncccc2F)ccc1=O] | N-((S)-(3-fluoropyridin-2-yl)(4-(trifluoromethyl)phenyl)methyl)-1-((R)-2-hydroxypropyl)-6-oxo-1,6-dihydropyridine-3-carboxamide | 450.1 |
| 302 | 6 | 103 | 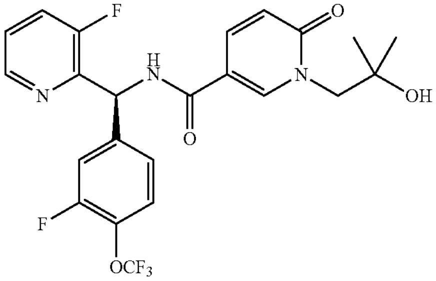 [SMILES: CC(C)(O)Cn1cc(C(=O)N[C@@H](c2ccc(OC(F)(F)F)c(F)c2)c2ncccc2F)ccc1=O] | (S)-N-((3-fluoro-4-(trifluoromethoxy)phenyl)(3-fluoropyridin-2-yl)methyl)-1-(2-hydroxy-2-methylpropyl)-6-oxo-1,6-dihydropyridine-3-carboxamide | 498.2 |
| 303 | 2 | 103 | 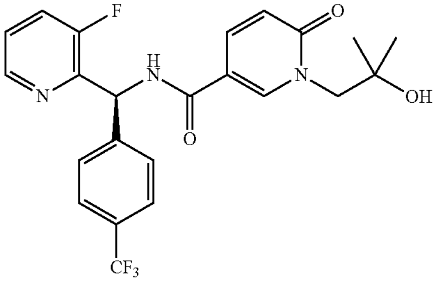 [SMILES: CC(C)(O)Cn1cc(C(=O)N[C@@H](c2ccc(C(F)(F)F)cc2)c2ncccc2F)ccc1=O] | (S)-N-((3-fluoropyridin-2-yl)(4-(trifluoromethyl)phenyl)methyl)-1-(2-hydroxy-2-methylpropyl)-6-oxo-1,6-dihydropyridine-3-carboxamide | 464.1 |
| 304 | 6 | 104 | 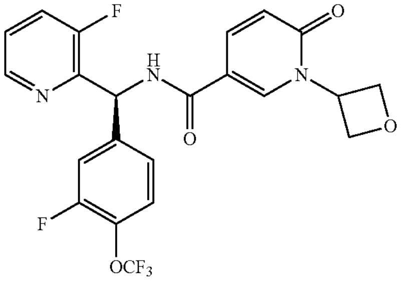 [SMILES: O=C(N[C@@H](c1ccc(OC(F)(F)F)c(F)c1)c1ncccc1F)c1ccc(=O)n(C2COC2)c1] | (S)-N-((3-fluoro-4-(trifluoromethoxy)phenyl)(3-fluoropyridin-2-yl)methyl)-1-(oxetan-3-yl)-6-oxo-1,6-dihydropyridine-3-carboxamide | 482.1 |
| 305 | 2 | 104 | 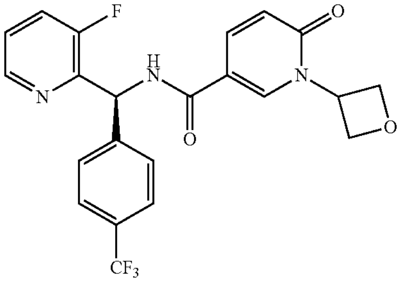 [SMILES: O=C(N[C@@H](c1ccc(C(F)(F)F)cc1)c1ncccc1F)c1ccc(=O)n(C2COC2)c1] | (S)-N-((3-fluoropyridin-2-yl)(4-(trifluoromethyl)phenyl)methyl)-1-(oxetan-3-yl)-6-oxo-1,6-dihydropyridine-3-carboxamide | 448.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 306 | 28 | 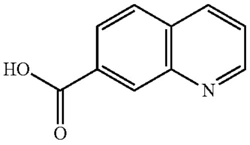 [SMILES: O=C(O)c1ccc2cccnc2c1] | 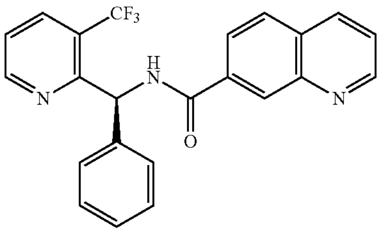 [SMILES: O=C(N[C@@H](c1ccccc1)c1ncccc1C(F)(F)F)c1ccc2cccnc2c1] | (S)-N-(phenyl(3-(trifluoromethyl)pyridin-2-yl)methyl)quinoline-7-carboxamide | 408.0 |
| 307 | 2 | 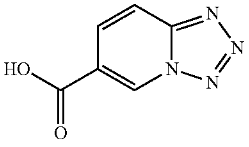 [SMILES: O=C(O)c1ccc2nnnn2c1] | 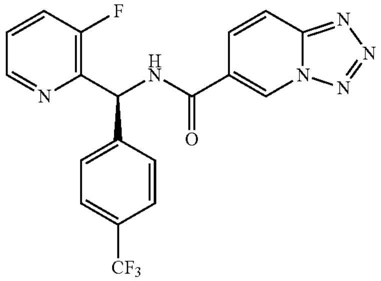 [SMILES: O=C(N[C@@H](c1ccc(C(F)(F)F)cc1)c1ncccc1F)c1ccc2nnnn2c1] | (S)-N-((3-fluoropyridin-2-yl)(4-(trifluoromethyl)phenyl)methyl)tetrazolo[1,5-a]pyridine-6-carboxamide | 417.2 |
| 308 | 2 | 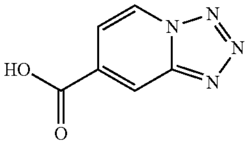 [SMILES: O=C(O)c1ccn2nnnc2c1] | 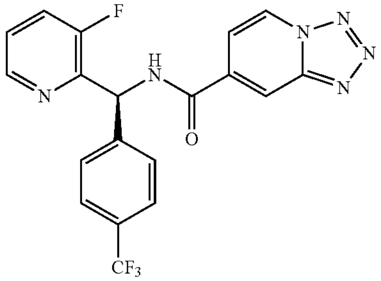 [SMILES: O=C(N[C@@H](c1ccc(C(F)(F)F)cc1)c1ncccc1F)c1ccn2nnnc2c1] | (S)-N-((3-fluoropyridin-2-yl)(4-(trifluoromethyl)phenyl)methyl)tetrazolo[1,5-a]pyridine-7-carboxamide | 417.2 |
| 309 | 8 | 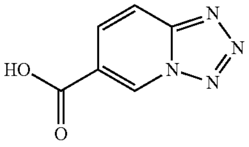 [SMILES: O=C(O)c1ccc2nnnn2c1] | 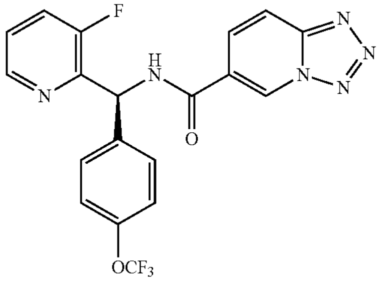 [SMILES: O=C(N[C@@H](c1ccc(OC(F)(F)F)cc1)c1ncccc1F)c1ccc2nnnn2c1] | (S)-N-((3-fluoropyridin-2-yl)(4-(trifluoromethoxy)phenyl)methyl)tetrazolo[1,5-a]pyridine-6-carboxamide | 433.1 |
| 310 | 8 | 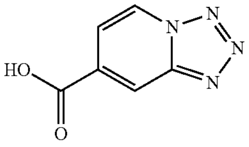 [SMILES: O=C(O)c1ccn2nnnc2c1] | 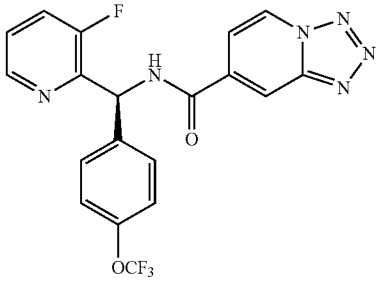 [SMILES: O=C(N[C@@H](c1ccc(OC(F)(F)F)cc1)c1ncccc1F)c1ccn2nnnc2c1] | (S)-N-((3-fluoropyridin-2-yl)(4-(trifluoromethoxy)phenyl)methyl)tetrazolo[1,5-a]pyridine-7-carboxamide | 433.1 |

TABLE 5-continued

| Examples 287-424 prepared via amide formation analogous to Scheme 4 | | | | | |
|---|---|---|---|---|---|
| Ex # | Amine | Acid Structure | Product Structure | Product Name | MS M + H |
| 311 | 1 | 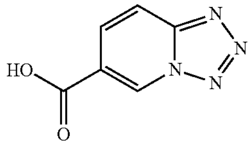 [SMILES: O=C(O)c1ccc2nnnn2c1] | 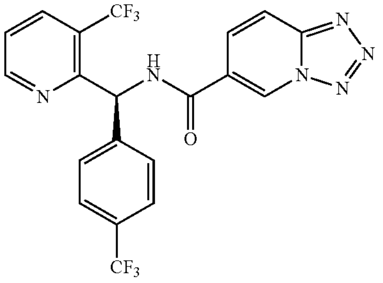 [SMILES: O=C(N[C@@H](c1ccc(C(F)(F)F)cc1)c1ncccc1C(F)(F)F)c1ccc2nnnn2c1] | (S)-N-((4-(trifluoromethyl)phenyl)(3-(trifluoromethyl)pyridin-2-yl)methyl)tetrazolo[1,5-a]pyridine-6-carboxamide | 467.1 |
| 312 | 1 | 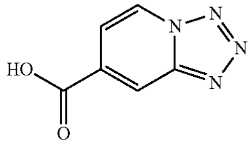 [SMILES: O=C(O)c1ccn2nnnc2c1] | 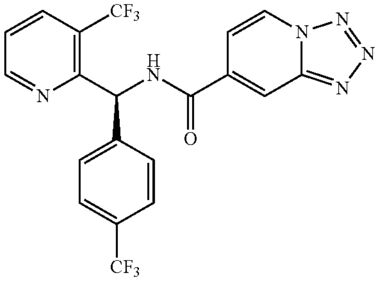 [SMILES: O=C(N[C@@H](c1ccc(C(F)(F)F)cc1)c1ncccc1C(F)(F)F)c1ccn2nnnc2c1] | (S)-N-((4-(trifluoromethyl)phenyl)(3-(trifluoromethyl)pyridin-2-yl)methyl)tetrazolo[1,5-a]pyridine-7-carboxamide | 467.1 |
| 313 | 44 | 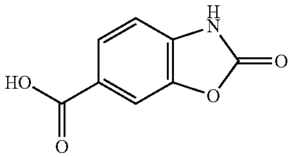 [SMILES: O=C(O)c1ccc2[nH]c(=O)oc2c1] | 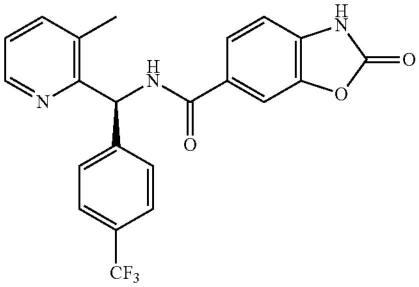 [SMILES: Cc1cccnc1[C@@H](NC(=O)c1ccc2[nH]c(=O)oc2c1)c1ccc(C(F)(F)F)cc1] | (S)-N-((3-methylpyridin-2-yl)(4-(trifluoromethyl)phenyl)methyl)-2-oxo-2,3-dihydrobenzo[d]oxazole-6-carboxamide | 428.1 |
| 314 | 44 | 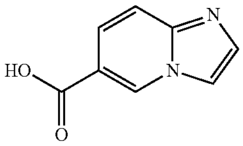 [SMILES: O=C(O)c1ccc2nccn2c1] | 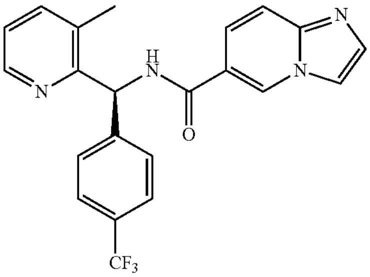 [SMILES: Cc1cccnc1[C@@H](NC(=O)c1ccc2nccn2c1)c1ccc(C(F)(F)F)cc1] | (S)-N-((3-methylpyridin-2-yl)(4-(trifluoromethyl)phenyl)methyl)imidazo[1,2-a]pyridine-6-carboxamide | 411.2 |
| 315 | 2 | 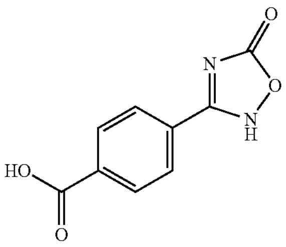 [SMILES: O=C(O)c1ccc(-c2nc(=O)o[nH]2)cc1] | 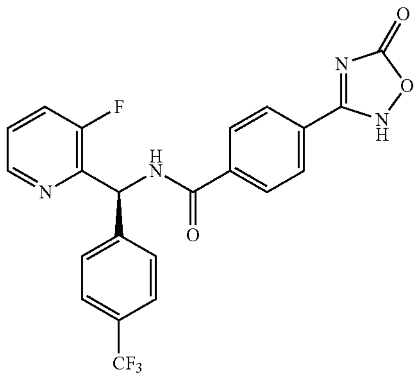 [SMILES: O=C(N[C@@H](c1ccc(C(F)(F)F)cc1)c1ncccc1F)c1ccc(-c2nc(=O)o[nH]2)cc1] | (S)-N-((3-fluoropyridin-2-yl)(4-(trifluoromethyl)phenyl)methyl)-4-(5-oxo-2,5-dihydro-1,2,4-oxadiazol-3-yl)benzamide | 459.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 316 | 8 | 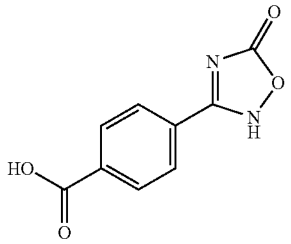 [SMILES: O=C(O)c1ccc(-c2nc(=O)o[nH]2)cc1] | 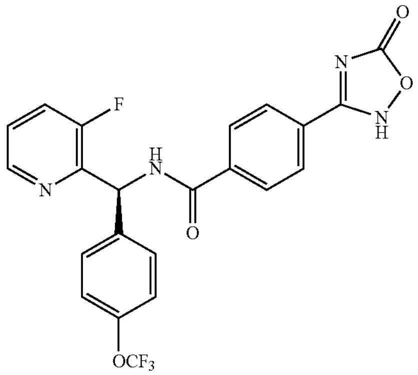 [SMILES: O=C(N[C@@H](c1ccc(OC(F)(F)F)cc1)c1ncccc1F)c1ccc(-c2nc(=O)o[nH]2)cc1] | (S)-N-((3-fluoropyridin-2-yl)(4-(trifluoromethoxy)phenyl)methyl)-4-(5-oxo-1,2,4-oxadiazol-3-yl)benzamide | 475.1 |
| 317 | 2 | 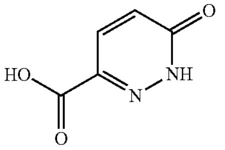 | 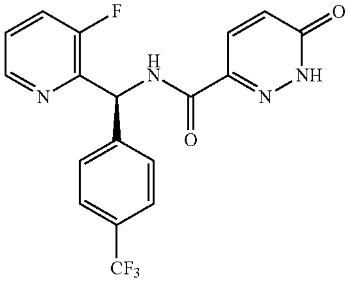 [SMILES: O=C(N[C@@H](c1ccc(C(F)(F)F)cc1)c1ncccc1F)c1ccc(=O)[nH]n1] | (S)-N-((3-fluoropyridin-2-yl)(4-(trifluoromethyl)phenyl)methyl)-6-oxo-1,6-dihydropyridazine-3-carboxamide | 393.2 |
| 318 | 2 | 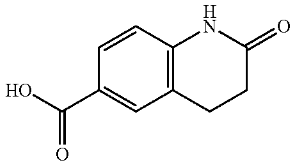 [SMILES: O=C1CCc2cc(C(=O)O)ccc2N1] | 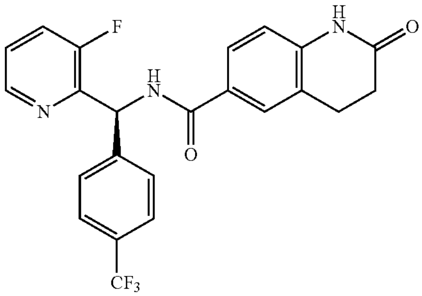 [SMILES: O=C1CCc2cc(C(=O)N[C@@H](c3ccc(C(F)(F)F)cc3)c3ncccc3F)ccc2N1] | (S)-N-((3-fluoropyridin-2-yl)(4-(trifluoromethyl)phenyl)methyl)-2-oxo-1,2,3,4-tetrahydroquinoline-6-carboxamide | 444.2 |
| 319 | 2 | 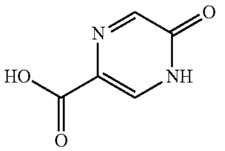 | 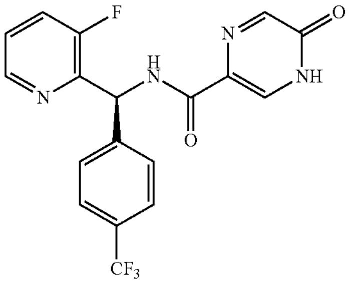 [SMILES: O=C(N[C@@H](c1ccc(C(F)(F)F)cc1)c1ncccc1F)c1c[nH]c(=O)cn1] | (S)-N-((3-fluoropyridin-2-yl)(4-(trifluoromethyl)phenyl)methyl)-5-oxo-4,5-dihydropyrazine-2-carboxamide | 393.2 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 320 | 2 | 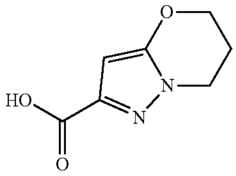 [SMILES: O=C(O)c1cc2n(n1)CCCO2] | 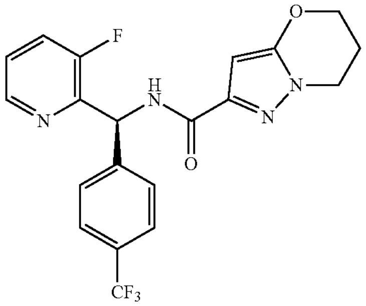 [SMILES: O=C(N[C@@H](c1ccc(C(F)(F)F)cc1)c1ncccc1F)c1cc2n(n1)CCCO2] | (S)-N-((3-fluoropyridin-2-yl)(4-(trifluoromethyl)phenyl)methyl)-6,7-dihydro-5H-pyrazolo[5,1-b][1,3]oxazine-2-carboxamide | 421.1 |
| 321 | 2 | 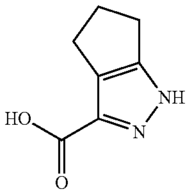 | 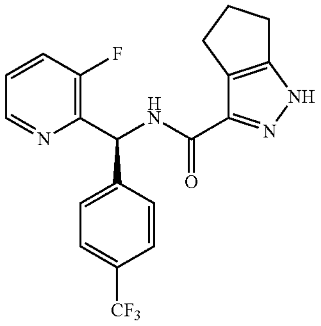 [SMILES: O=C(N[C@@H](c1ccc(C(F)(F)F)cc1)c1ncccc1F)c1n[nH]c2c1CCC2] | (S)-N-((3-fluoropyridin-2-yl)(4-(trifluoromethyl)phenyl)methyl)-1,4,5,6-tetrahydrocyclopenta[c]pyrazole-3-carboxamide | 405.2 |
| 322 | 2 | 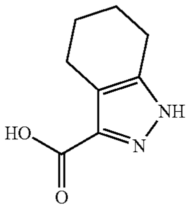 | 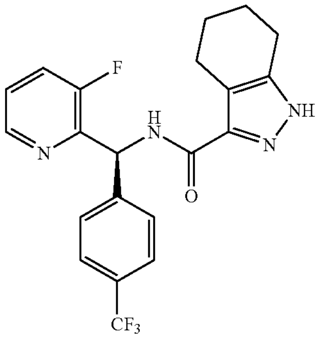 [SMILES: O=C(N[C@@H](c1ccc(C(F)(F)F)cc1)c1ncccc1F)c1n[nH]c2c1CCCC2] | (S)-N-((3-fluoropyridin-2-yl)(4-(trifluoromethyl)phenyl)methyl)-4,5,6,7-tetrahydro-1H-indazole-3-carboxamide | 419.1 |
| 323 | 44 | 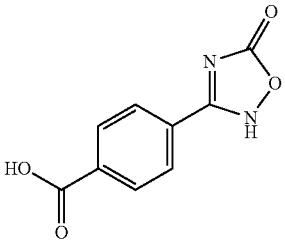 [SMILES: O=C(O)c1ccc(-c2nc(=O)o[nH]2)cc1] | 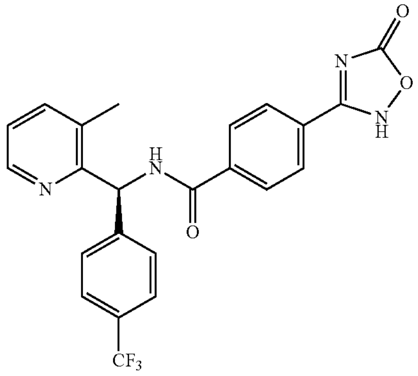 [SMILES: Cc1cccnc1[C@@H](NC(=O)c1ccc(-c2nc(=O)o[nH]2)cc1)c1ccc(C(F)(F)F)cc1] | (S)-N-((3-methylpyridin-2-yl)(4-(trifluoromethyl)phenyl)methyl)-4-(5-oxo-2,5-dihydro-1,2,4-oxadiazol-3-yl)benzamide | 455.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 324 | 65 | 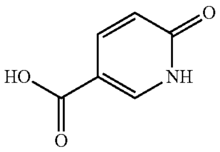 | 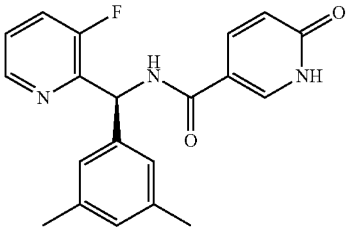 [SMILES: Cc1cc(C)cc([C@H](NC(=O)c2ccc(=O)[nH]c2)c2ncccc2F)c1] | (S)-N-((3,5-dimethylphenyl)(3-fluoropyridin-2-yl)methyl)-6-oxo-1,6-dihydropyridine-3-carboxamide | 352.1 |
| 325 | 66 | 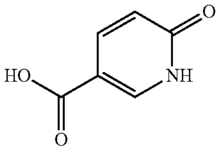 | 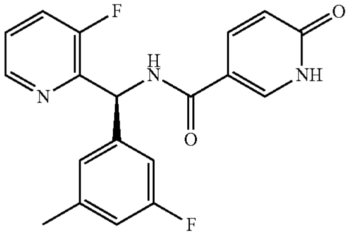 | (S)-N-((3-fluoro-5-methylphenyl)(3-fluoropyridin-2-yl)methyl)-6-oxo-1,6-dihydropyridine-3-carboxamide | 356.1 |
| 326 | 66 | 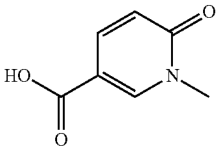 | 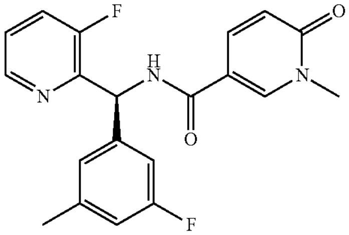 [SMILES: Cc1cc(F)cc([C@H](NC(=O)c2ccc(=O)n(C)c2)c2ncccc2F)c1] | (S)-N-((3-fluoro-5-methylphenyl)(3-fluoropyridin-2-yl)methyl)-1-methyl-6-oxo-1,6-dihydropyridine-3-carboxamide | 370.1 |
| 327 | 67 | 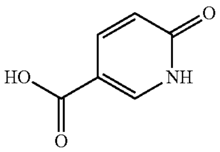 | 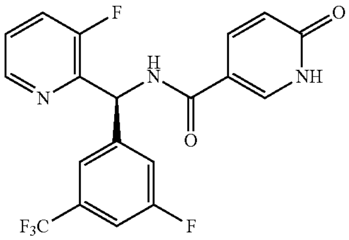 | (S)-N-((3-fluoro-5-(trifluoromethyl)phenyl)(3-fluoropyridin-2-yl)methyl)-6-oxo-1,6-dihydropyridine-3-carboxamide | 410.1 |
| 328 | 67 | 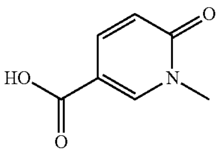 | 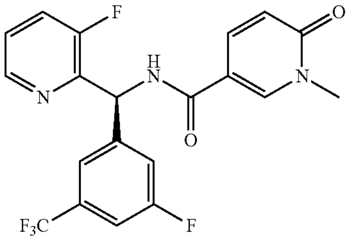 [SMILES: Cn1cc(C(=O)N[C@@H](c2cc(F)cc(C(F)(F)F)c2)c2ncccc2F)ccc1=O] | (S)-N-((3-fluoro-5-(trifluoromethyl)phenyl)(3-fluoropyridin-2-yl)methyl)-1-methyl-6-oxo-1,6-dihydropyridine-3-carboxamide | 424.1 |
| 329 | 68 | 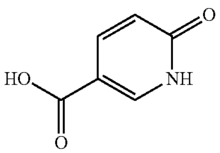 | 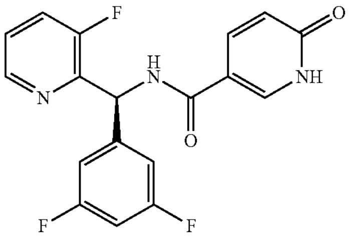 [SMILES: O=C(N[C@@H](c1cc(F)cc(F)c1)c1ncccc1F)c1ccc(=O)[nH]c1] | (S)-N-((3,5-difluorophenyl)(3-fluoropyridin-2-yl)methyl)-6-oxo-1,6-dihydropyridine-3-carboxamide | 360.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 330 | 68 | 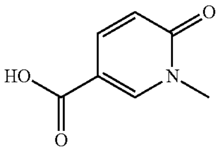 | 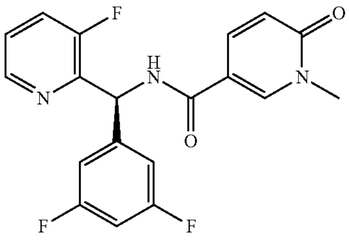 [SMILES: Cn1cc(C(=O)N[C@@H](c2cc(F)cc(F)c2)c2ncccc2F)ccc1=O] | (S)-N-((3,5-difluorophenyl)(3-fluoropyridin-2-yl)methyl)-1-methyl-6-oxo-1,6-dihydropyridine-3-carboxamide | 374.1 |
| 331 | 69 | 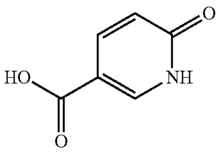 | 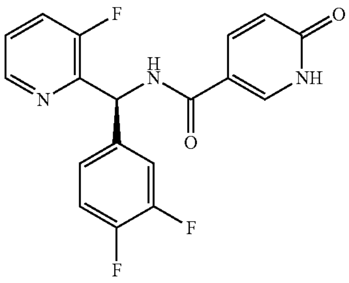 [SMILES: O=C(N[C@@H](c1ccc(F)c(F)c1)c1ncccc1F)c1ccc(=O)[nH]c1] | (S)-N-((3,4-difluorophenyl)(3-fluoropyridin-2-yl)methyl)-6-oxo-1,6-dihydropyridine-3-carboxamide | 360.0 |
| 332 | 69 | 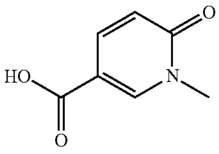 | 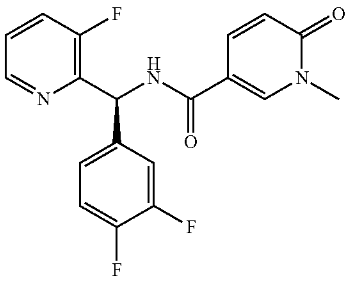 [SMILES: Cn1cc(C(=O)N[C@@H](c2ccc(F)c(F)c2)c2ncccc2F)ccc1=O] | (S)-N-((3,4-difluorophenyl)(3-fluoropyridin-2-yl)methyl)-1-methyl-6-oxo-1,6-dihydropyridine-3-carboxamide | 374.0 |
| 333 | 70 | 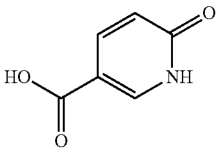 | 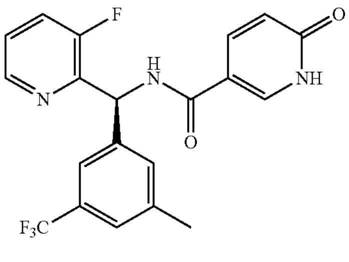 [SMILES: Cc1cc([C@H](NC(=O)c2ccc(=O)[nH]c2)c2ncccc2F)cc(C(F)(F)F)c1] | (S)-N-((3-fluoropyridin-2-yl)(3-methyl-5-(trifluoromethyl)phenyl)methyl)-6-oxo-1,6-dihydropyridine-3-carboxamide | 406.1 |
| 334 | 71 | 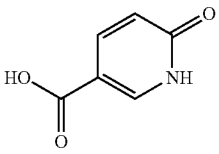 | 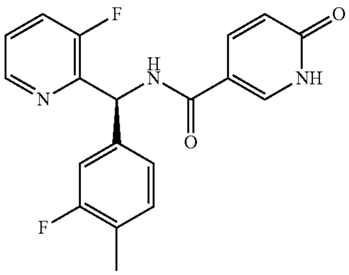 [SMILES: Cc1ccc([C@H](NC(=O)c2ccc(=O)[nH]c2)c2ncccc2F)cc1F] | (S)-N-((3-fluoro-4-methylphenyl)(3-fluoropyridin-2-yl)methyl)-6-oxo-1,6-dihydropyridine-3-carboxamide | 356.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 335 | 71 | 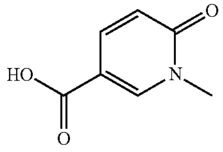 | 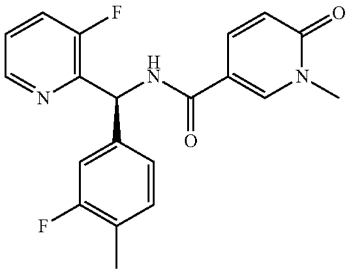 [SMILES: Cc1ccc([C@H](NC(=O)c2ccc(=O)n(C)c2)c2ncccc2F)cc1F] | (S)-N-((3-fluoro-4-methylphenyl)(3-fluoropyridin-2-yl)methyl)-1-methyl-6-oxo-1,6-dihydropyridine-3-carboxamide | 370.1 |
| 336 | 72 | 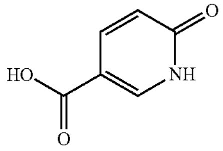 | 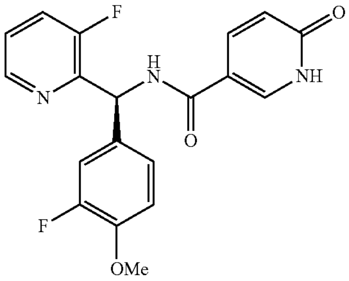 [SMILES: COc1ccc([C@H](NC(=O)c2ccc(=O)[nH]c2)c2ncccc2F)cc1F] | (S)-N-((3-fluoro-4-methoxyphenyl)(3-fluoropyridin-2-yl)methyl)-6-oxo-1,6-dihydropyridine-3-carboxamide | 372.0 |
| 337 | 72 | 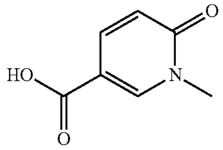 | 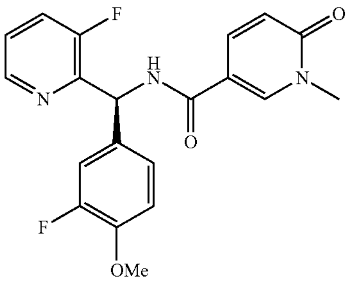 [SMILES: COc1ccc([C@H](NC(=O)c2ccc(=O)n(C)c2)c2ncccc2F)cc1F] | (S)-N-((3-fluoro-4-methoxyphenyl)(3-fluoropyridin-2-yl)methyl)-1-methyl-6-oxo-1,6-dihydropyridine-3-carboxamide | 386.0 |
| 338 | 73 | 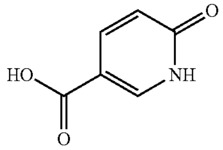 | 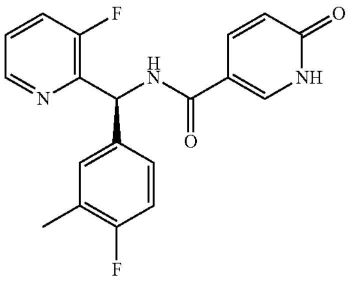 [SMILES: Cc1cc([C@H](NC(=O)c2ccc(=O)[nH]c2)c2ncccc2F)ccc1F] | (S)-N-((4-fluoro-3-methylphenyl)(3-fluoropyridin-2-yl)methyl)-6-oxo-1,6-dihydropyridine-3-carboxamide | 356.0 |
| 339 | 73 | 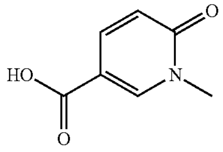 | 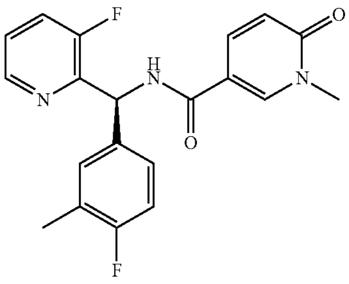 [SMILES: Cc1cc([C@H](NC(=O)c2ccc(=O)n(C)c2)c2ncccc2F)ccc1F] | (S)-N-((4-fluoro-3-methylphenyl)(3-fluoropyridin-2-yl)methyl)-1-methyl-6-oxo-1,6-dihydropyridine-3-carboxamide | 370.1 |

TABLE 5-continued

| Examples 287-424 prepared via amide formation analogous to Scheme 4 | | | | | |
|---|---|---|---|---|---|
| Ex # | Amine | Acid Structure | Product Structure | Product Name | MS M + H |
| 340 | 74 | 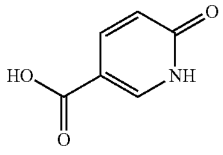 | 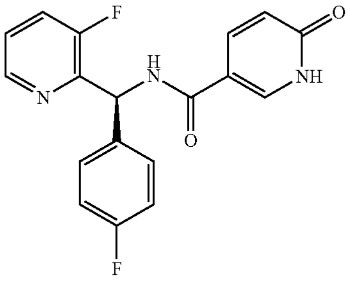 [SMILES: O=C(N[C@@H](c1ccc(F)cc1)c1ncccc1F)c1ccc(=O)[nH]c1] | (S)-N-((4-fluorophenyl)(3-fluoropyridin-2-yl)methyl)-6-oxo-1,6-dihydropyridine-3-carboxamide | 342.0 |
| 341 | 74 | 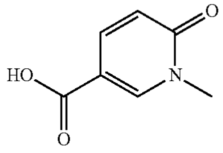 | 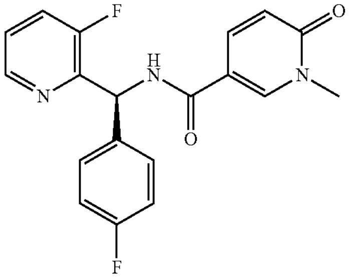 [SMILES: Cn1cc(C(=O)N[C@@H](c2ccc(F)cc2)c2ncccc2F)ccc1=O] | (S)-N-((4-fluorophenyl)(3-fluoropyridin-2-yl)methyl)-1-methyl-6-oxo-1,6-dihydropyridine-3-carboxamide | 356.0 |
| 342 | 75 | 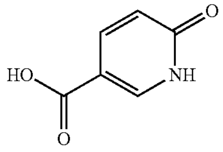 | 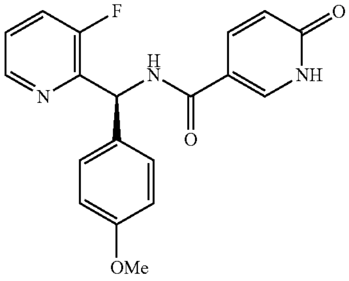 [SMILES: COc1ccc([C@H](NC(=O)c2ccc(=O)[nH]c2)c2ncccc2F)cc1] | (S)-N-((3-fluoropyridin-2-yl)(4-methoxyphenyl)methyl)-6-oxo-1,6-dihydropyridine-3-carboxamide | 354.0 |
| 343 | 75 | 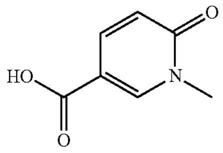 | 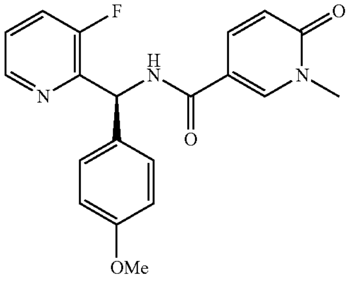 [SMILES: COc1ccc([C@H](NC(=O)c2ccc(=O)n(C)c2)c2ncccc2F)cc1] | (S)-N-((3-fluoropyridin-2-yl)(4-methoxyphenyl)methyl)-1-methyl-6-oxo-1,6-dihydropyridine-3-carboxamide | 368.0 |
| 344 | 76 | 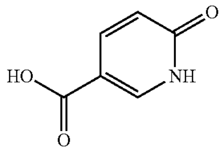 | 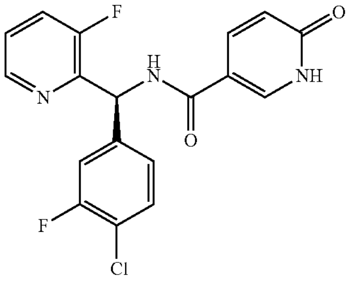 [SMILES: O=C(N[C@@H](c1ccc(Cl)c(F)c1)c1ncccc1F)c1ccc(=O)[nH]c1] | (S)-N-((4-chloro-3-fluorophenyl)(3-fluoropyridin-2-yl)methyl)-6-oxo-1,6-dihydropyridine-3-carboxamide | 376.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 345 | 76 | 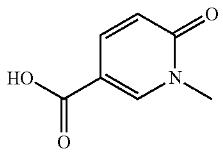 | 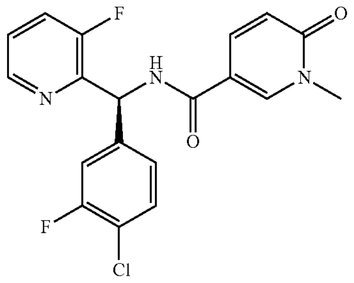 [SMILES: Cn1cc(C(=O)N[C@@H](c2ccc(Cl)c(F)c2)c2ncccc2F)ccc1=O] | (S)-N-((4-chloro-3-fluorophenyl)(3-fluoropyridin-2-yl)methyl)-1-methyl-6-oxo-1,6-dihydropyridine-3-carboxamide | 390.0 |
| 346 | 6 | 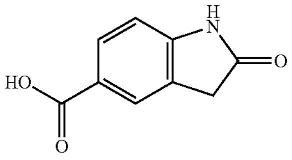 [SMILES: O=C1Cc2cc(C(=O)O)ccc2N1] | 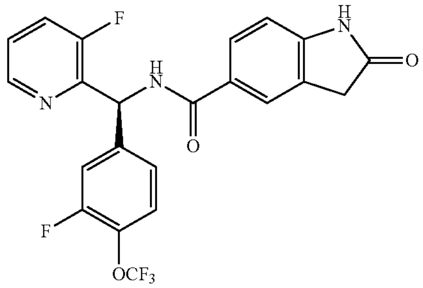 [SMILES: O=C1Cc2cc(C(=O)N[C@@H](c3ccc(OC(F)(F)F)c(F)c3)c3ncccc3F)ccc2N1] | (S)-N-((3-fluoro-4-(trifluoromethoxy)phenyl)(3-fluoropyridin-2-yl)methyl)-2-oxoindoline-5-carboxamide | 464.0 |
| 347 | 77 | 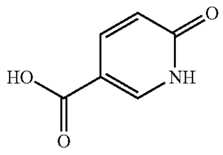 | 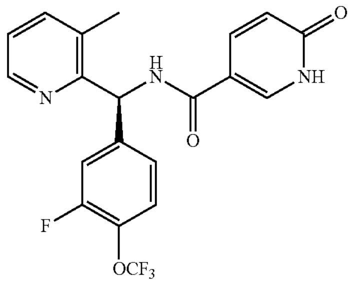 | (S)-N-((3-fluoro-4-(trifluoromethoxy)phenyl)(3-methylpyridin-2-yl)methyl)-6-oxo-1,6-dihydropyridine-3-carboxamide | 422.0 |
| 348 | 77 | 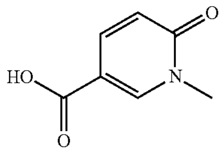 | 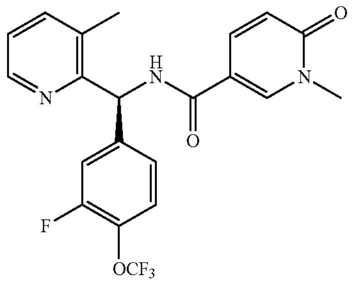 | (S)-N-((3-fluoro-4-(trifluoromethoxy)phenyl)(3-methylpyridin-2-yl)methyl)-1-methyl-6-oxo-1,6-dihydropyridine-3-carboxamide | 436.0 |
| 349 | 6 | 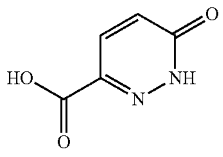 | 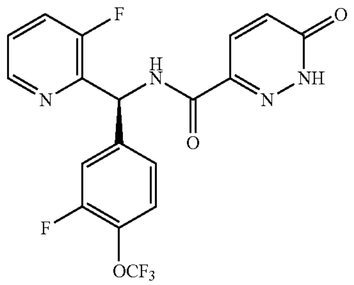 | (S)-N-((3-fluoro-4-(trifluoromethoxy)phenyl)(3-fluoropydin-2-yl)methyl)-6-oxo-1,6-dihydropyridazine-3-carboxamide | 427.0 |

TABLE 5-continued

Examples 287-424 prepared via amide formation analogous to Scheme 4

| Ex # | Amine | Acid Structure | Product Structure | Product Name | MS M + H |
| --- | --- | --- | --- | --- | --- |
| 350 | 8 | 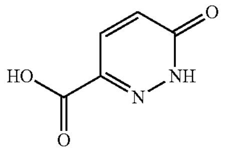 | 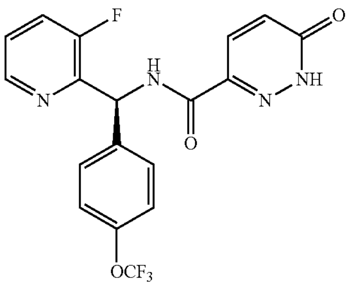 | (S)-N-((3-fluoropyridin-2-yl)(4-(trifluoromethoxy)phenyl)methyl)-6-oxo-1,6-dihydropyridazine-3-carboxamide | 409.0 |
| 351 | 6 | 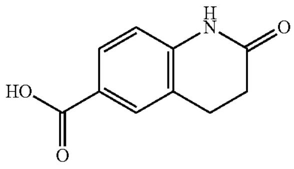 [SMILES: O=C1CCc2cc(C(=O)O)ccc2N1] | 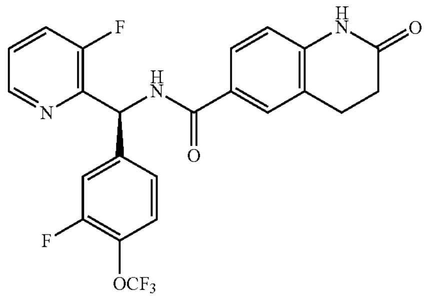 [SMILES: O=C1CCc2cc(C(=O)N[C@@H](c3ccc(OC(F)(F)F)c(F)c3)c3ncccc3F)ccc2N1] | (S)-N-((3-fluoro-4-(trifluoromethoxy)phenyl)(3-fluoropyridin-2-yl)methyl)-2-oxo-1,2,3,4-tetrahydroquinoline-6-carboxamide | 478.0 |
| 352 | 8 | 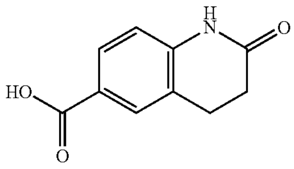 | 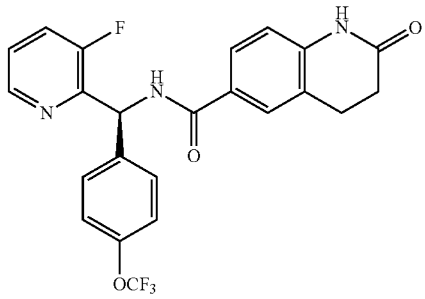 | (S)-N-((3-fluoropyridin-2-yl)(4-(trifluoromethoxy)phenyl)methyl)-2-oxo-1,2,3,4-tetrahydroquinoline-6-carboxamide | 460.0 |
| 353 | 6 | 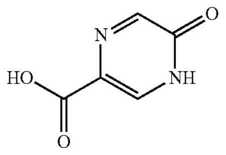 | 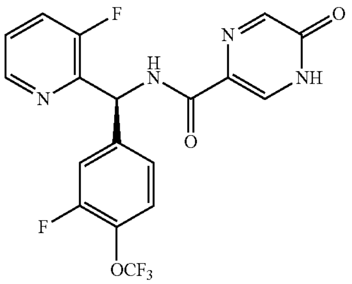 | (S)-N-((3-fluoro-4-(trifluoromethoxy)phenyl)(3-fluoropyridin-2-yl)methyl)-5-oxo-4,5-dihydropyrazine-2-carboxamide | 427.0 |
| 354 | 8 | 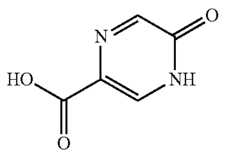 | 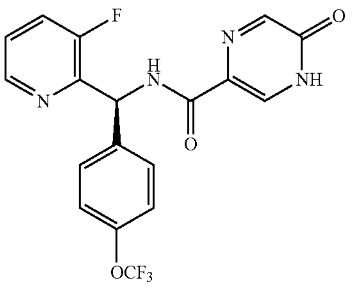 | (S)-N-((3-fluoropyridin-2-yl)(4-(trifluoromethoxy)phenyl)methyl)-5-oxo-4,5-dihydropyrazine-2-carboxamide | 409.0 |

TABLE 5-continued

| Examples 287-424 prepared via amide formation analogous to Scheme 4 | | | | | |
|---|---|---|---|---|---|
| Ex # | Amine | Acid Structure | Product Structure | Product Name | MS M + H |
| 355 | 6 | 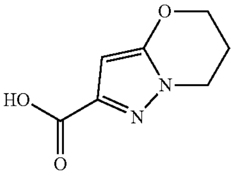 [SMILES: O=C(O)c1cc2n(n1)CCCO2] | 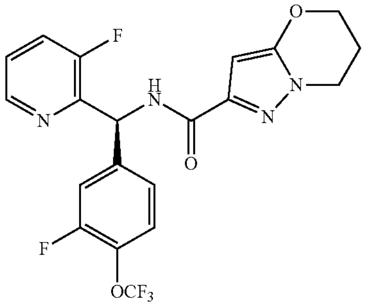 [SMILES: O=C(N[C@@H](c1ccc(OC(F)(F)F)c(F)c1)c1ncccc1F)c1cc2n(n1)CCCO2] | (S)-N-((3-fluoro-4-(trifluoromethoxy)phenyl)(3-fluoropyridin-2-yl)methyl)-6,7-dihydro-5H-pyrazolo[5,1-b][1,3]oxazine-2-carboxamide | 455.0 |
| 356 | 8 | 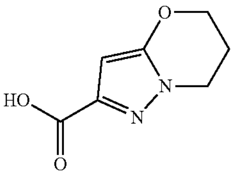 [SMILES: O=C(O)c1cc2n(n1)CCCO2] | 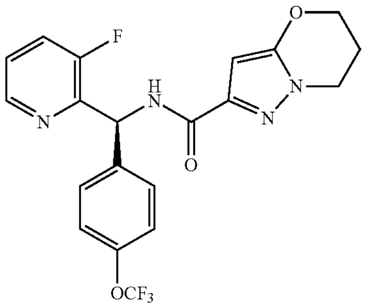 [SMILES: O=C(N[C@@H](c1ccc(OC(F)(F)F)cc1)c1ncccc1F)c1cc2n(n1)CCCO2] | (S)-N-((3-fluoropyridin-2-yl)(4-(trifluoromethoxy)phenyl)methyl)-6,7-dihydro-5H-pyrazolo[5,1-b][1,3]oxazine-2-carboxamide | 437.0 |
| 357 | 77 | 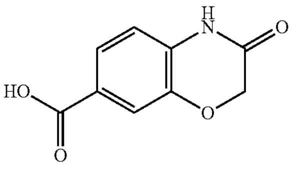 [SMILES: O=C1COc2cc(C(=O)O)ccc2N1] | 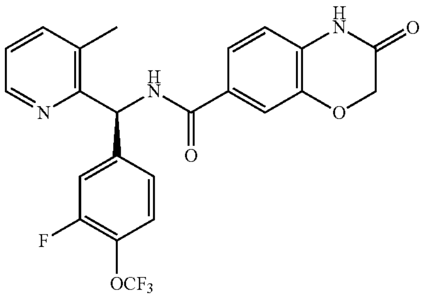 [SMILES: Cc1cccnc1[C@@H](NC(=O)c1ccc2c(c1)OCC(=O)N2)c1ccc(OC(F)(F)F)c(F)c1] | (S)-N-((3-fluoro-4-(trifluoromethoxy)phenyl)(3-methylpyridin-2-yl)methyl)-3-oxo-3,4-dihydro-2H-benzo[b][1,4]oxazine-7-carboxamide | 476.0 |
| 358 | 77 | 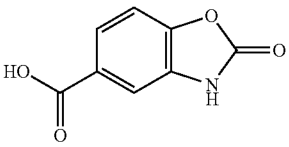 [SMILES: O=C(O)c1ccc2oc(=O)[nH]c2c1] | 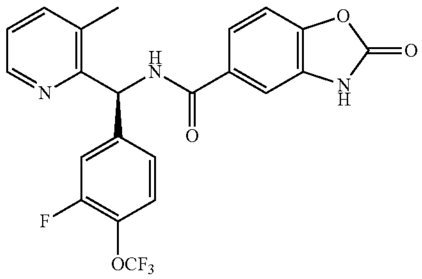 [SMILES: Cc1cccnc1[C@@H](NC(=O)c1ccc2oc(=O)[nH]c2c1)c1ccc(OC(F)(F)F)c(F)c1] | (S)-N-((3-fluoro-4-(trifluoromethoxy)phenyl)(3-methylpyridin-2-yl)methyl)-2-oxo-2,3-dihydrobenzo[d]oxazole-5-carboxamide | 462.0 |
| 359 | 78 | 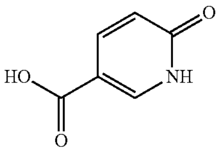 | 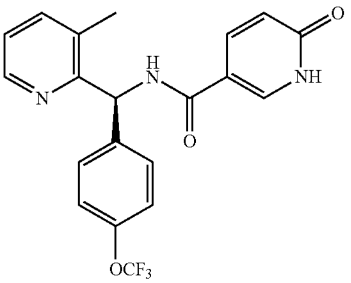 | (S)-N-((3-methylpyridin-2-yl)(4-(trifluoromethoxy)phenyl)methyl)-6-oxo-1,6-dihydropyridine-3-carboxamide | 404.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 360 | 78 | 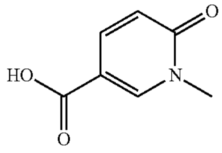 | 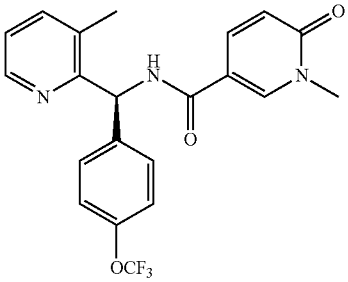 [SMILES: Cc1cccnc1[C@@H](NC(=O)c1ccc(=O)n(C)c1)c1ccc(OC(F)(F)F)cc1] | (S)-1-methyl-N-((3-methylpyridin-2-yl)(4-(trifluoromethoxy)phenyl)methyl)-6-oxo-1,6-dihydropyridine-3-carboxamide | 418.1 |
| 361 | 54 | 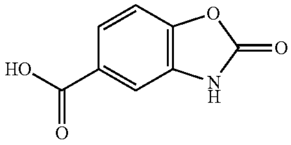 [SMILES: O=C(O)c1ccc2oc(=O)[nH]c2c1] | 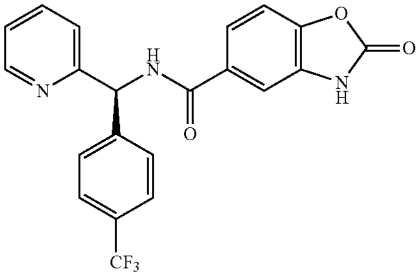 [SMILES: O=C(N[C@@H](c1ccc(C(F)(F)F)cc1)c1ccccn1)c1ccc2oc(=O)[nH]c2c1] | (S)-2-oxo-N-(pyridin-2-yl(4-(trifluoromethyl)phenyl)methyl)-2,3-dihydrobenzo[d]oxazole-5-carboxamide | 414.0 |
| 362 | 79 | 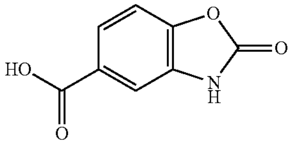 [SMILES: O=C(O)c1ccc2oc(=O)[nH]c2c1] | 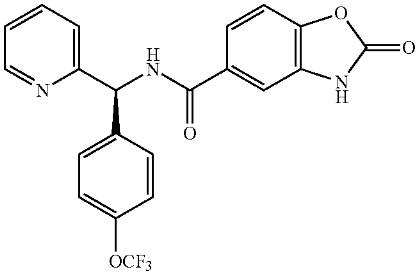 [SMILES: O=C(N[C@@H](c1ccc(OC(F)(F)F)cc1)c1ccccn1)c1ccc2oc(=O)[nH]c2c1] | (S)-2-oxo-N-(pyridin-2-yl(4-(trifluoromethoxy)phenyl)methyl)-2,3-dihydrobenzo[d]oxazole-5-carboxamide | 430.0 |
| 363 | 99 | 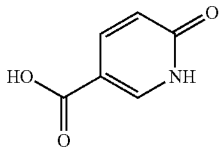 | 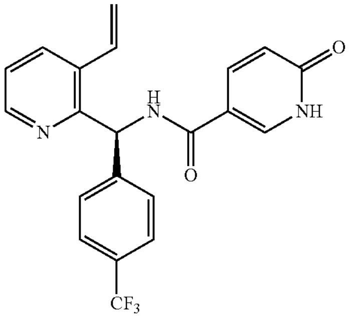 [SMILES: C=Cc1cccnc1[C@@H](NC(=O)c1ccc(=O)[nH]c1)c1ccc(C(F)(F)F)cc1] | (S)-6-oxo-N-((4-(trifluoromethyl)phenyl)(3-vinylpyridin-2-yl)methyl)-1,6-dihydropyridine-3-carboxamide | 400.1 |
| 364 | 2 | 105 | 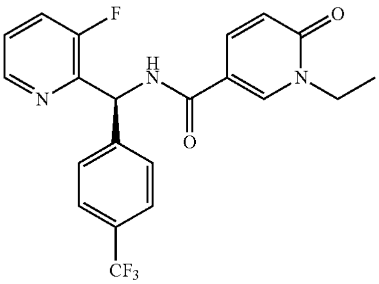 | (S)-1-ethyl-N-((3-fluoropyridin-2-yl)(4-(trifluoromethyl)phenyl)methyl)-6-oxo-1,6-dihydropyridine-3-carboxamide | 420.2 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 365 | 36 | 105 | 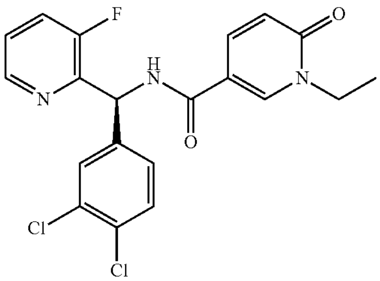 [SMILES: CCn1cc(C(=O)N[C@@H](c2ccc(Cl)c(Cl)c2)c2ncccc2F)ccc1=O] | (S)-N-((3,4-dichlorophenyl)(3-fluoropyridin-2-yl)methyl)-1-ethyl-6-oxo-1,6-dihydropyridine-3-carboxamide | 420.1 |
| 366 | 6 | 105 | 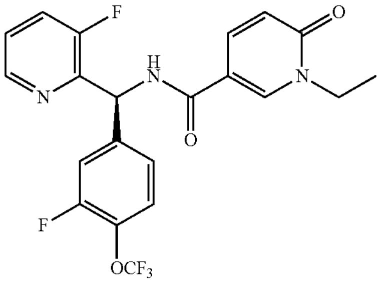 [SMILES: CCn1cc(C(=O)N[C@@H](c2ccc(OC(F)(F)F)c(F)c2)c2ncccc2F)ccc1=O] | (S)-1-ethyl-N-((3-fluoro-4-(trifluoromethoxy)phenyl)(3-fluoropyridin-2-yl)methyl)-6-oxo-1,6-dihydropyridine-3-carboxamide | 454.1 |
| 367 | 2 | 106 | 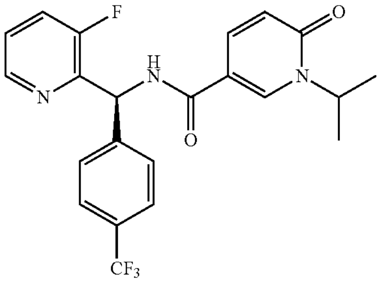 [SMILES: CC(C)n1cc(C(=O)N[C@@H](c2ccc(C(F)(F)F)cc2)c2ncccc2F)ccc1=O] | (S)-N-((3-fluoropyridin-2-yl)(4-(trifluoromethyl)phenyl)methyl)-1-isopropyl-6-oxo-1,6-dihydropyridine-3-carboxamide | 434.1 |
| 368 | 2 | 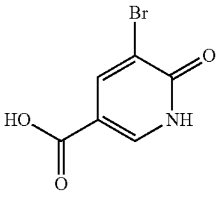 [SMILES: O=C(O)c1c[nH]c(=O)c(Br)c1] | 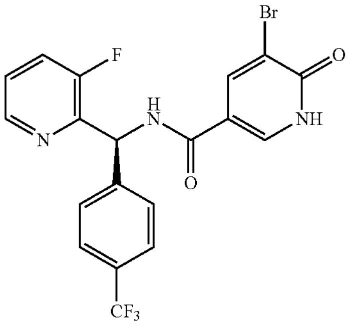 [SMILES: O=C(N[C@@H](c1ccc(C(F)(F)F)cc1)c1ncccc1F)c1c[nH]c(=O)c(Br)c1] | (S)-5-bromo-N-((3-fluoropyridin-2-yl)(4-(trifluoromethyl)phenyl)methyl)-6-oxo-1,6-dihydropyridine-3-carboxamide | 470 |
| 369 | 2 | 111 | 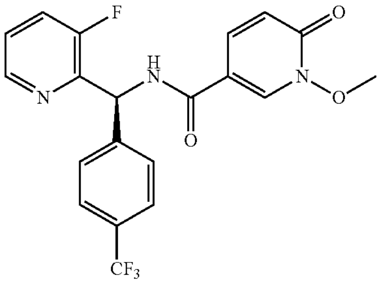 [SMILES: COn1cc(C(=O)N[C@@H](c2ccc(C(F)(F)F)cc2)c2ncccc2F)ccc1=O] | (S)-N-((3-fluoropyridin-2-yl)(4-(trifluoromethyl)phenyl)methyl)-1-methoxy-6-oxo-1,6-dihydropyridine-3-carboxamide | 422.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 370 | 2 | 101 | 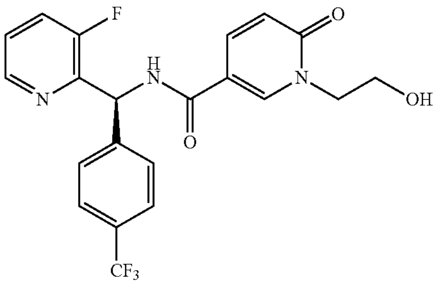 [SMILES: O=C(N[C@@H](c1ccc(C(F)(F)F)cc1)c1ncccc1F)c1ccc(=O)n(CCO)c1] | (S)-N-((3-fluoropyridin-2-yl)(4-(trifluoromethyl)phenyl)methyl)-1-(2-hydroxyethyl)-6-oxo-1,6-dihydropyridine-3-carboxamide | 436.2 |
| 371 | 2 | 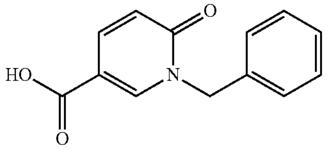 [SMILES: O=C(O)c1ccc(=O)n(Cc2ccccc2)c1] | 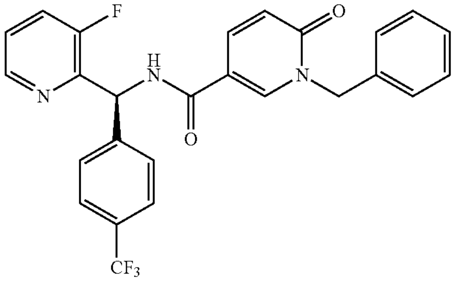 [SMILES: O=C(N[C@@H](c1ccc(C(F)(F)F)cc1)c1ncccc1F)c1ccc(=O)n(Cc2ccccc2)c1] | (S)-1-benzyl-N-((3-fluoropyridin-2-yl)(4-(trifluoromethyl)phenyl)methyl)-6-oxo-1,6-dihydropyridine-3-carboxamide | 482.2 |
| 372 | 2 | 107 | 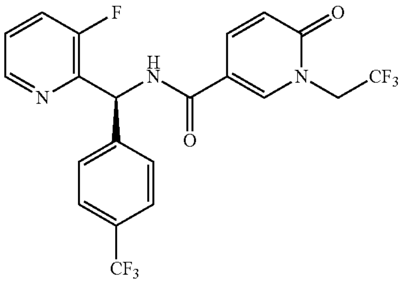 [SMILES: O=C(N[C@@H](c1ccc(C(F)(F)F)cc1)c1ncccc1F)c1ccc(=O)n(CC(F)(F)F)c1] | (S)-N-((3-fluoropyridin-2-yl)(4-(trifluoromethyl)phenyl)methyl)-6-oxo-1-(2,2,2-trifluoroethyl)-1,6-dihydropyridine-3-carboxamide | 474.1 |
| 373 | 2 | 116 | 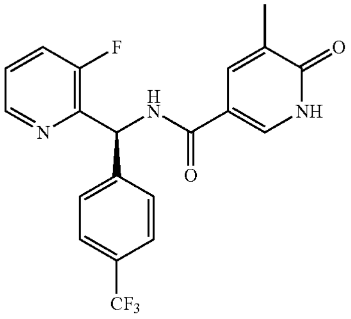 [SMILES: Cc1cc(C(=O)N[C@@H](c2ccc(C(F)(F)F)cc2)c2ncccc2F)c[nH]c1=O] | (S)-N-((3-fluoropyridin-2-yl)(4-(trifluoromethyl)phenyl)methyl)-5-methyl-6-oxo-1,6-dihydropyridine-3-carboxamide | 406.1 |
| 374 | 8 | 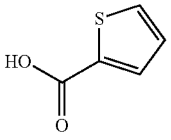 | 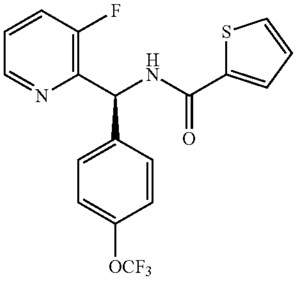 [SMILES: O=C(N[C@@H](c1ccc(OC(F)(F)F)cc1)c1ncccc1F)c1cccs1] | (S)-N-((3-fluoropyridin-2-yl)(4-(trifluoromethoxy)phenyl)methyl)thiophene-2-carboxamide | 397.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 375 | 2 | 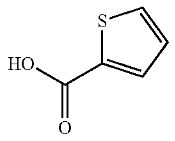 | 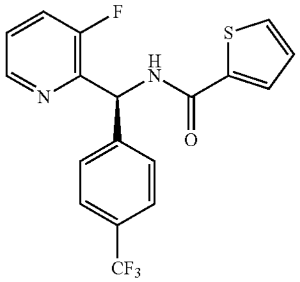 [SMILES: O=C(N[C@@H](c1ccc(C(F)(F)F)cc1)c1ncccc1F)c1cccs1] | (S)-N-((3-fluoropyridin-2-yl)(4-(trifluoromethyl)phenyl)methyl)thiophene-2-carboxamide | 381.1 |
| 376 | 98 | 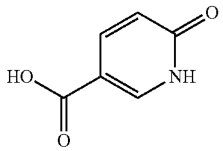 | 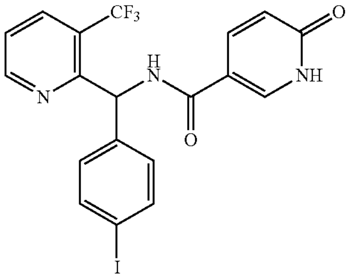 [SMILES: O=C(NC(c1ccc(I)cc1)c1ncccc1C(F)(F)F)c1ccc(=O)[nH]c1] | N-((4-iodophenyl)(3-(trifluoromethyl)pyridin-2-yl)methyl)-6-oxo-1,6-dihydropyridine-3-carboxamide | 499.5 |
| 377 | 79 | 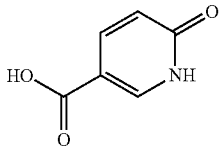 | 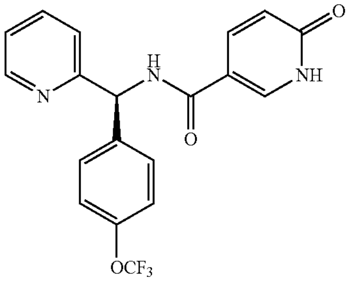 [SMILES: O=C(N[C@@H](c1ccc(OC(F)(F)F)cc1)c1ccccn1)c1ccc(=O)[nH]c1] | (S)-6-oxo-N-(pyridin-2-yl(4-(trifluoromethoxy)phenyl)methyl)-1,6-dihydropyridine-3-carboxamide | 389.7 |
| 378 | 79 | 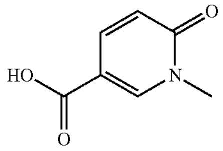 | 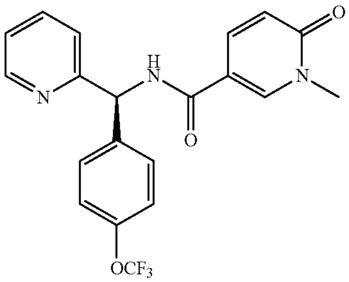 [SMILES: Cn1cc(C(=O)N[C@@H](c2ccc(OC(F)(F)F)cc2)c2ccccn2)ccc1=O] | (S)-1-methyl-6-oxo-N-(pyridin-2-yl(4-(trifluoromethoxy)phenyl)methyl)-1,6-dihydropyridine-3-carboxamide | 403.9 |
| 379 | 80 | 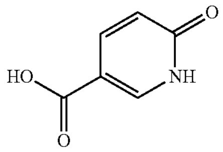 | 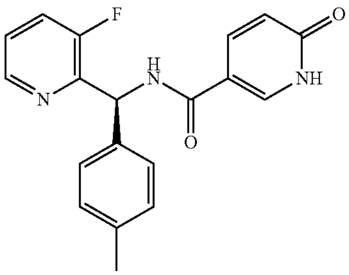 [SMILES: Cc1ccc([C@H](NC(=O)c2ccc(=O)[nH]c2)c2ncccc2F)cc1] | (S)-N-((3-fluoropyridin-2-yl)(p-tolyl)methyl)-6-oxo-1,6-dihydropyridine-3-carboxamide | 337.9 |

TABLE 5-continued

Examples 287-424 prepared via amide formation analogous to Scheme 4

| Ex # | Amine | Acid Structure | Product Structure | Product Name | MS M + H |
| --- | --- | --- | --- | --- | --- |
| 380 | 81 | 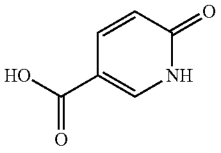 | 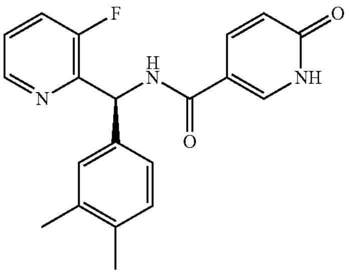 [SMILES: Cc1ccc([C@H](NC(=O)c2ccc(=O)[nH]c2)c2ncccc2F)cc1C] | (S)-N-((3,4-dimethylphenyl)(3-fluoropyridin-2-yl)methyl)-6-oxo-1,6-dihydropyridine-3-carboxamide | 351.8 |
| 381 | 82 | 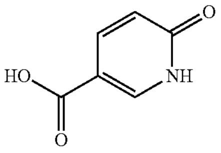 | 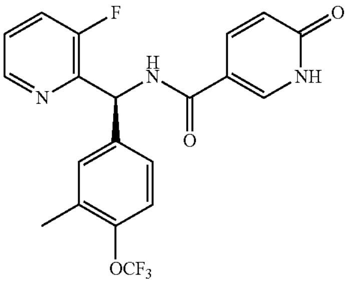 [SMILES: Cc1cc([C@H](NC(=O)c2ccc(=O)[nH]c2)c2ncccc2F)ccc1OC(F)(F)F] | (S)-N-((3-fluoropyridin-2-yl)(3-methyl-4-(trifluoromethoxy)phenyl)methyl)-6-oxo-1,6-dihydropyridine-3-carboxamide | 421.9 |
| 382 | 83 | 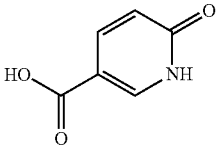 | 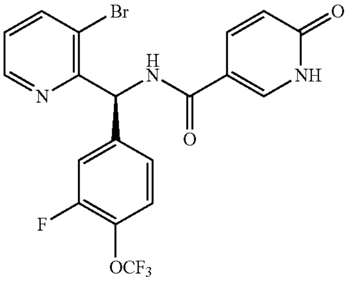 [SMILES: O=C(N[C@@H](c1ccc(OC(F)(F)F)c(F)c1)c1ncccc1Br)c1ccc(=O)[nH]c1] | (S)-N-((3-bromopyridin-2-yl)(3-fluoro-4-(trifluoromethoxy)phenyl)methyl)-6-oxo-1,6-dihydropyridine-3-carboxamide | 486.0 488.0 |
| 383 | 26 | 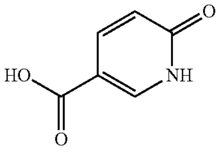 | 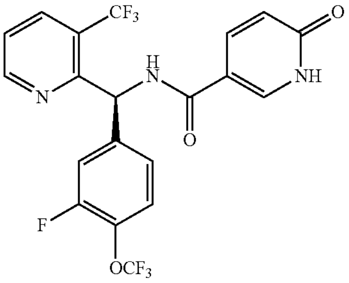 [SMILES: O=C(N[C@@H](c1ccc(OC(F)(F)F)c(F)c1)c1ncccc1C(F)(F)F)c1ccc(=O)[nH]c1] | (S)-N-((3-fluoro-4-(trifluoromethoxy)phenyl)(3-(trifluoromethyl)pyridin-2-yl)methyl)-6-oxo-1,6-dihydropyridine-3-carboxamide | 476.0 |
| 384 | 83 | 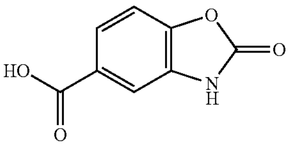 [SMILES: O=C(O)c1ccc2oc(=O)[nH]c2c1] | 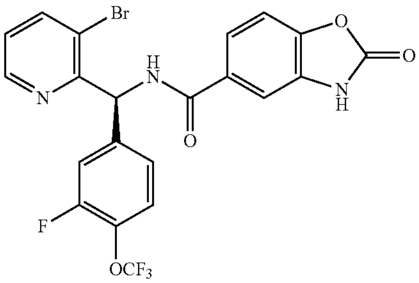 [SMILES: O=C(N[C@@H](c1ccc(OC(F)(F)F)c(F)c1)c1ncccc1Br)c1ccc2oc(=O)[nH]c2c1] | (S)-N-((3-bromopyridin-2-yl)(3-fluoro-4-(trifluoromethoxy)phenyl)methyl)-2-oxo-2,3-dihydrobenzo[d]oxazole-5-carboxamide | 526.0 528.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 385 | 26 | 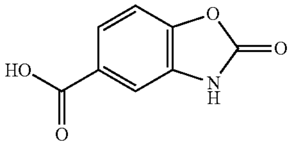 [SMILES: O=C(O)c1ccc2oc(=O)[nH]c2c1] | 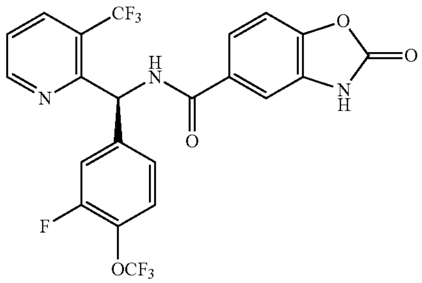 [SMILES: O=C(N[C@@H](c1ccc(OC(F)(F)F)c(F)c1)c1ncccc1C(F)(F)F)c1ccc2oc(=O)[nH]c2c1] | (S)-N-((3-fluoro-4-(trifluoromethoxy)phenyl)(3-(trifluoromethyl)pyridin-2-yl)methyl)-2-oxo-2,3-dihydrobenzo[d]oxazole-5-carboxamide | 516.0 |
| 386 | 84 | 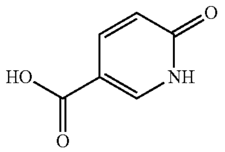 | 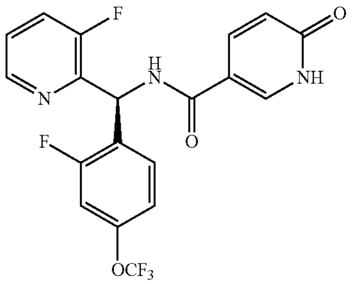 [SMILES: O=C(N[C@@H](c1ccc(OC(F)(F)F)cc1F)c1ncccc1F)c1ccc(=O)[nH]c1] | (S)-N-((2-fluoro-4-(trifluoromethoxy)phenyl)(3-fluoropyridin-2-yl)methyl)-6-oxo-1,6-dihydropyridine-3-carboxamide 2,2,2-trifluoroacetate | 426.0 |
| 387 | 6 | 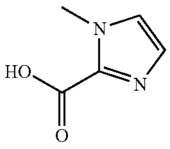 | 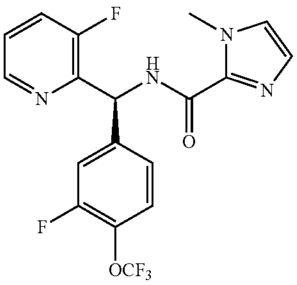 [SMILES: Cn1ccnc1C(=O)N[C@@H](c1ccc(OC(F)(F)F)c(F)c1)c1ncccc1F] | (S)-N-((3-fluoro-4-(trifluoromethoxy)phenyl)(3-fluoropyridin-2-yl)methyl)-1-methyl-1H-imidazole-2-carboxamide 2,2,2-trifluoroacetate | 413.0 |
| 388 | 6 | 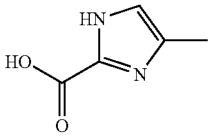 | 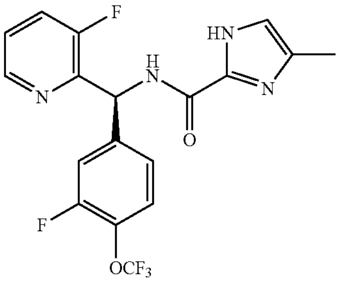 [SMILES: Cc1c[nH]c(C(=O)N[C@@H](c2ccc(OC(F)(F)F)c(F)c2)c2ncccc2F)n1] | (S)-N-((3-fluoro-4-(trifluoromethoxy)phenyl)(3-fluoropyridin-2-yl)methyl)-4-methyl-1H-imidazole-2-carboxamide 2,2,2-trifluoroacetate | 413.0 |
| 389 | 6 | 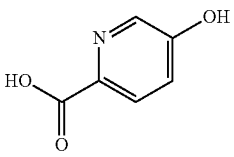 | 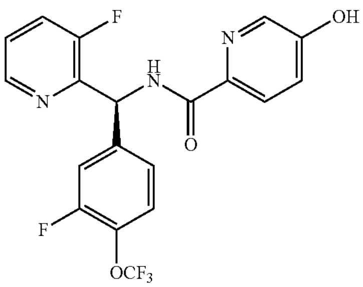 [SMILES: O=C(N[C@@H](c1ccc(OC(F)(F)F)c(F)c1)c1ncccc1F)c1ccc(O)cn1] | (S)-N-((3-fluoro-4-(trifluoromethoxy)phenyl)(3-fluoropyridin-2-yl)methyl)-5-hydroxypicolinamide 2,2,2-trifluoroacetate | 426.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 390 | 6 | 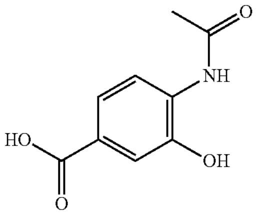 | 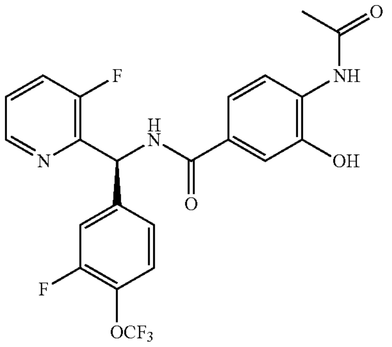 [SMILES: CC(=O)Nc1ccc(C(=O)N[C@@H](c2ccc(OC(F)(F)F)c(F)c2)c2ncccc2F)cc1O] | (S)-4-acetamido-N-((3-fluoro-4-(trifluoromethoxy)phenyl)(3-fluoropyridin-2-yl)methyl)-3-hydroxybenzamide | 482.0 |
| 391 | 63 | 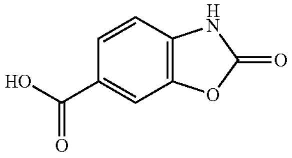 [SMILES: O=C(O)c1ccc2[nH]c(=O)oc2c1] | 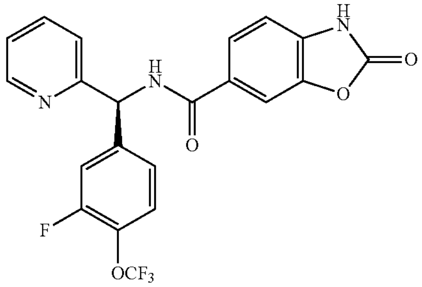 [SMILES: O=C(N[C@@H](c1ccc(OC(F)(F)F)c(F)c1)c1ccccn1)c1ccc2[nH]c(=O)oc2c1] | (S)-N-((3-fluoro-4-(trifluoromethoxy)phenyl)(pyridin-2-yl)methyl)-2-oxo-2,3-dihydrobenzo[d]oxazole-6-carboxamide | 448.0 |
| 392 | 2 | 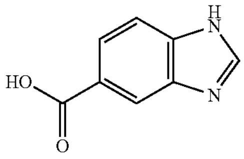 [SMILES: O=C(O)c1ccc2[nH]cnc2c1] | 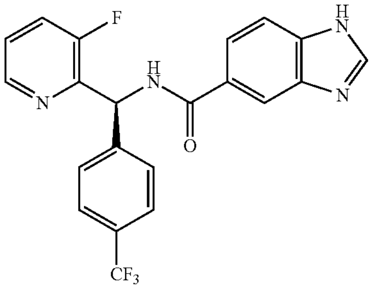 [SMILES: O=C(N[C@@H](c1ccc(C(F)(F)F)cc1)c1ncccc1F)c1ccc2[nH]cnc2c1] | (S)-N-((3-fluoropyridin-2-yl)(4-(trifluoromethyl)phenyl)methyl)-1H-benzo[d]imidazole-5-carboxamide | 415.1 |
| 393 | 63 | 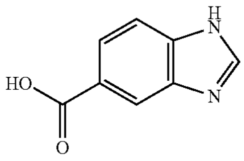 [SMILES: O=C(O)c1ccc2[nH]cnc2c1] | 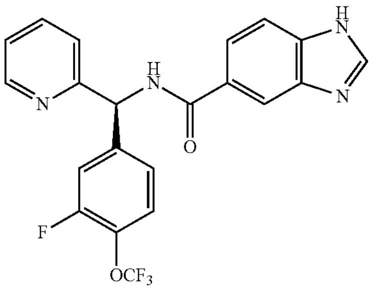 [SMILES: O=C(N[C@@H](c1ccc(OC(F)(F)F)c(F)c1)c1ccccn1)c1ccc2[nH]cnc2c1] | (S)-N-((3-fluoro-4-(trifluoromethoxy)phenyl)(pyridin-2-yl)methyl)-1H-benzo[d]imidazole-5-carboxamide | 431.0 |
| 394 | 2 | 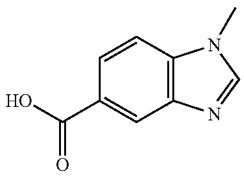 | 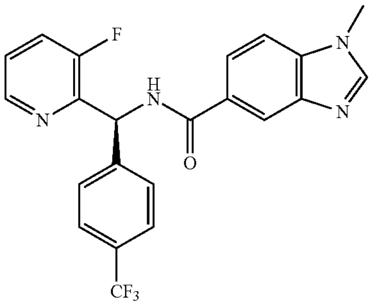 [SMILES: Cn1cnc2cc(C(=O)N[C@@H](c3ccc(C(F)(F)F)cc3)c3ncccc3F)ccc21] | (S)-N-((3-fluoropyridin-2-yl)(4-(trifluoromethyl)phenyl)methyl)-1-methyl-1H-benzo[d]imidazole-5-carboxamide | 429.0 |

TABLE 5-continued

| Ex # | Amine | Acid Structure | Product Structure | Product Name | MS M + H |
|---|---|---|---|---|---|
| | | Examples 287-424 prepared via amide formation analogous to Scheme 4 | | | |
| 395 | 2 | 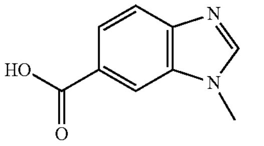 | 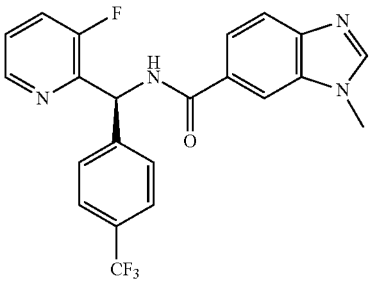 [SMILES: Cn1cnc2ccc(C(=O)N[C@@H](c3ccc(C(F)(F)F)cc3)c3ncccc3F)cc21] | (S)-N-((3-fluoropyridin-2-yl)(4-(trifluoromethyl)phenyl)methyl)-1-methyl-1H-benzo[d]imidazole-6-carboxamide | 429.0 |
| 396 | 2 | 112 | 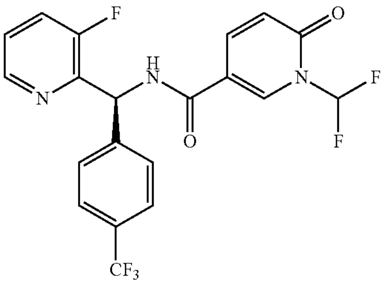 [SMILES: O=C(N[C@@H](c1ccc(C(F)(F)F)cc1)c1ncccc1F)c1ccc(=O)n(C(F)F)c1] | (S)-1-(difluoromethyl)-N-((3-fluoropyridin-2-yl)(4-(trifluoromethyl)phenyl)methyl)-6-oxo-1,6-dihydropyridine-3-carboxamide | 442.0 |
| 397 | 2 | 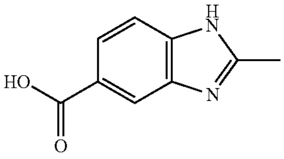 | 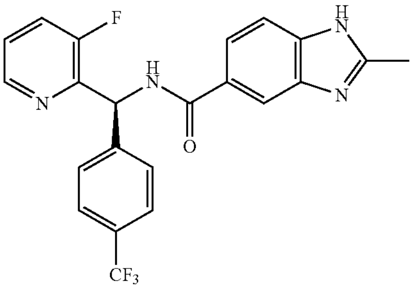 [SMILES: Cc1nc2cc(C(=O)N[C@@H](c3ccc(C(F)(F)F)cc3)c3ncccc3F)ccc2[nH]1] | (S)-N-((3-fluoropyridin-2-yl)(4-(trifluoromethyl)phenyl)methyl)-2-methyl-1H-benzo[d]imidazole-5-carboxamide | 429.2 |
| 398 | 6 | 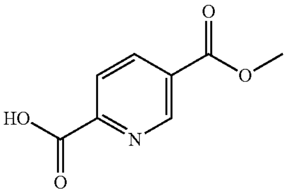 | 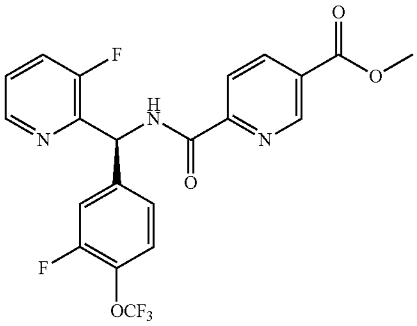 [SMILES: COC(=O)c1ccc(C(=O)N[C@@H](c2ccc(OC(F)(F)F)c(F)c2)c2ncccc2F)nc1] | (S)-methyl 6-(((3-fluoro-4-(trifluoromethoxy)phenyl)(3-fluoropyridin-2-yl)methyl)carbamoyl)nicotinate | 468.0 |
| 399 | 6 | 112 | 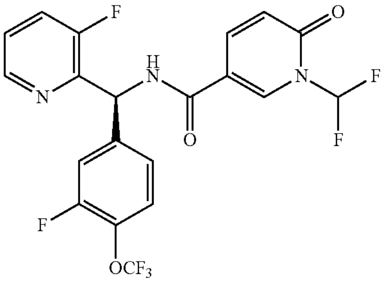 [SMILES: O=C(N[C@@H](c1ccc(OC(F)(F)F)c(F)c1)c1ncccc1F)c1ccc(=O)n(C(F)F)c1] | (S)-1-(difluoromethyl)-N-((3-fluoro-4-(trifluoromethoxy)phenyl)(3-fluoropyridin-2-yl)methyl)-6-oxo-1,6-dihydropyridine-3-carboxamide | 476.0 |

TABLE 5-continued

| Ex # | Amine | Acid Structure | Product Structure | Product Name | MS M + H |
|---|---|---|---|---|---|
| Examples 287-424 prepared via amide formation analogous to Scheme 4 | | | | | |
| 400 | 6 | 113 | 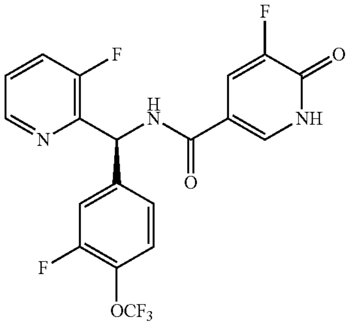 [SMILES: O=C(N[C@@H](c1ccc(OC(F)(F)F)c(F)c1)c1ncccc1F)c1c[nH]c(=O)c(F)c1] | (S)-5-fluoro-N-((3-fluoro-4-(trifluoromethoxy)phenyl)(3-fluoropyridin-2-yl)methyl)-6-oxo-1,6-dihydropyridine-3-carboxamide | 444.0 |
| 401 | 6 | 114 | 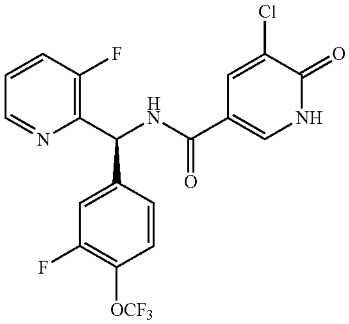 [SMILES: O=C(N[C@@H](c1ccc(OC(F)(F)F)c(F)c1)c1ncccc1F)c1c[nH]c(=O)c(Cl)c1] | (S)-5-chloro-N-((3-fluoro-4-(trifluoromethoxy)phenyl)(3-fluoropyridin-2-yl)methyl)-6-oxo-1,6-dihydropyridine-3-carboxamide | 460.0 462.0 |
| 402 | 6 | 115 | 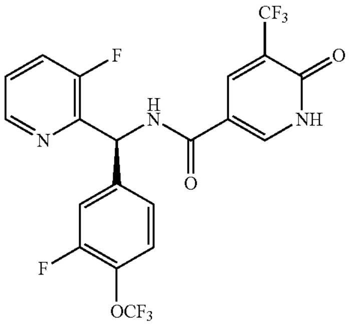 [SMILES: O=C(N[C@@H](c1ccc(OC(F)(F)F)c(F)c1)c1ncccc1F)c1c[nH]c(=O)c(C(F)(F)F)c1] | (S)-N-((3-fluoro-4-(trifluoromethoxy)phenyl)(3-fluoropyridin-2-yl)methyl)-6-oxo-5-(trifluoromethyl)-1,6-dihydropyridine-3-carboxamide | 494.0 |
| 403 | 6 | 116 | 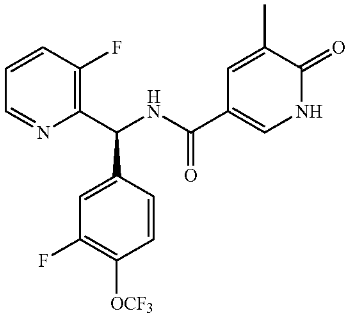 [SMILES: Cc1cc(C(=O)N[C@@H](c2ccc(OC(F)(F)F)c(F)c2)c2ncccc2F)c[nH]c1=O] | (S)-N-((3-fluoro-4-(trifluoromethoxy)phenyl)(3-fluoropyridin-2-yl)methyl)-5-methyl-6-oxo-1,6-dihydropyridine-3-carboxamide | 440.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 404 | 6 | 117 | 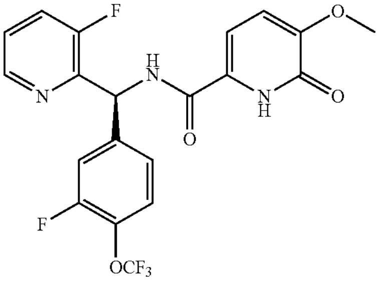 [SMILES: COc1ccc(C(=O)N[C@@H](c2ccc(OC(F)(F)F)c(F)c2)c2ncccc2F)[nH]c1=O] | (S)-N-((3-fluoro-4-(trifluoromethoxy)phenyl)(3-fluoropyridin-2-yl)methyl)-5-methoxy-6-oxo-1,6-dihydropyridine-2-carboxamide | 456.0 |
| 405 | 85 | 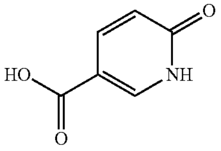 | 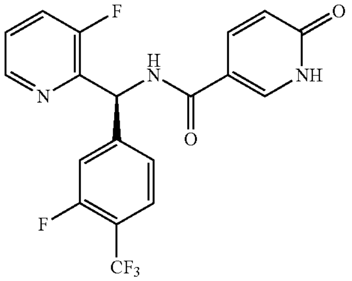 [SMILES: O=C(N[C@@H](c1ccc(C(F)(F)F)c(F)c1)c1ncccc1F)c1ccc(=O)[nH]c1] | (S)-N-((3-fluoro-4-(trifluoromethyl)phenyl)(3-fluoropyridin-2-yl)methyl)-6-oxo-1,6-dihydropyridine-3-carboxamide | 410.0 |
| 406 | 63 | 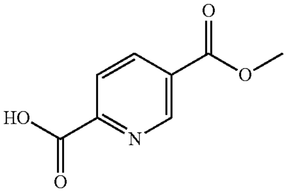 | 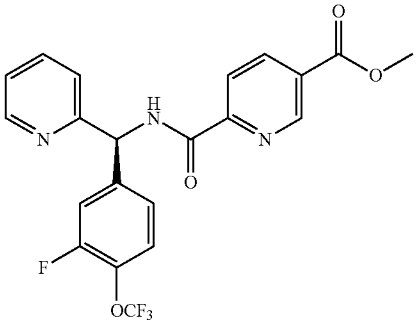 [SMILES: COC(=O)c1ccc(C(=O)N[C@@H](c2ccc(OC(F)(F)F)c(F)c2)c2ccccn2)nc1] | (S)-methyl 6-(((3-fluoro-4-(trifluoromethoxy)phenyl)(pyridin-2-yl)methyl)carbamoyl)nicotinate | 450.0 |
| 407 | 6 | 108 | 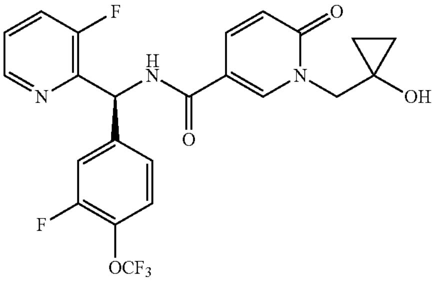 [SMILES: O=C(N[C@@H](c1ccc(OC(F)(F)F)c(F)c1)c1ncccc1F)c1ccc(=O)n(CC2(O)CC2)c1] | (S)-N-((3-fluoro-4-(trifluoromethoxy)phenyl)(3-fluoropyridin-2-yl)methyl)-1-((1-hydroxycyclopropyl)methyl)-6-oxo-1,6-dihydropyridine-3-carboxamide | 496.1 |
| 408 | 6 | 109 | 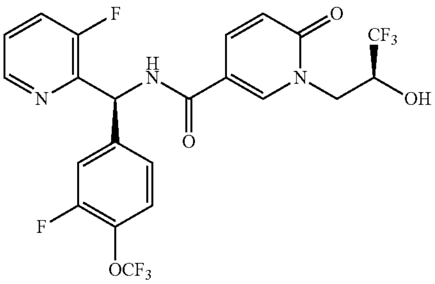 [SMILES: O=C(N[C@@H](c1ccc(OC(F)(F)F)c(F)c1)c1ncccc1F)c1ccc(=O)n(C[C@H](O)C(F)(F)F)c1] | N-((S)-(3-fluoro-4-(trifluoromethoxy)phenyl)(3-fluoropyridin-2-yl)methyl)-6-oxo-1-((S)-3,3,3-trifluoro-2-hydroxypropyl)-1,6-dihydropyridine-3-carboxamide | 538.1 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 409 | 6 | 110 | 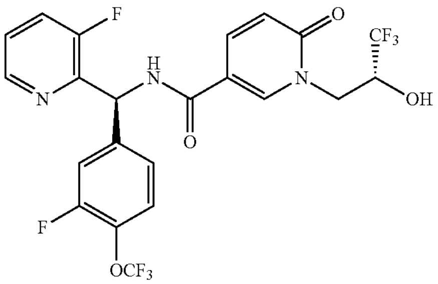 [SMILES: O=C(N[C@@H](c1ccc(OC(F)(F)F)c(F)c1)c1ncccc1F)c1ccc(=O)n(C[C@@H](O)C(F)(F)F)c1] | N-((S)-(3-fluoro-4-(trifluoromethoxy)phenyl)(3-fluoropyridin-2-yl)methyl)-6-oxo-1-((R)-3,3,3-trifluoro-2-hydroxypropyl)-1,6-dihydropyridine-3-carboxamide | 538.1 |
| 410 | 86 | 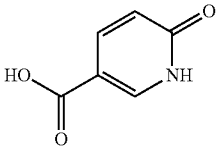 | 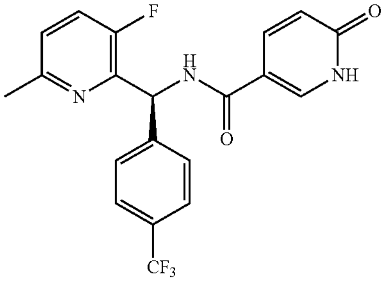 [SMILES: Cc1ccc(F)c([C@@H](NC(=O)c2ccc(=O)[nH]c2)c2ccc(C(F)(F)F)cc2)n1] | (S)-N-((3-fluoro-6-methylpyridin-2-yl)(4-(trifluoromethyl)phenyl)methyl)-6-oxo-1,6-dihydropyridine-3-carboxamide | 406.1 |
| 411 | 87 | 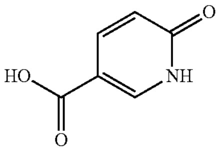 | 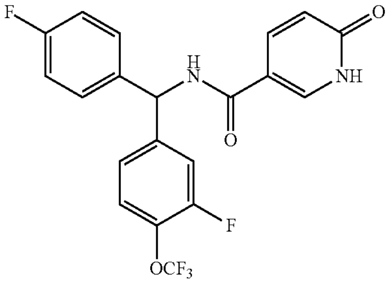 [SMILES: O=C(NC(c1ccc(F)cc1)c1ccc(OC(F)(F)F)c(F)c1)c1ccc(=O)[nH]c1] | N-((3-fluoro-4-(trifluoromethoxy)phenyl)(4-fluorophenyl)methyl)-6-oxo-1,6-dihydropyridine-3-carboxamide | 425.0 |
| 412 | 88 | 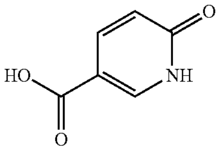 | 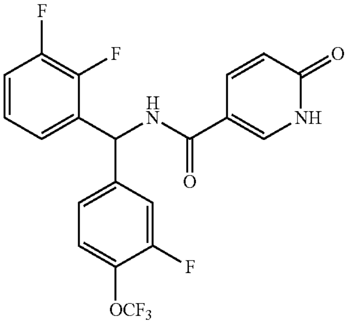 [SMILES: O=C(NC(c1ccc(OC(F)(F)F)c(F)c1)c1cccc(F)c1F)c1ccc(=O)[nH]c1] | N-((2,3-difluorophenyl)(3-fluoro-4-(trifluoromethoxy)phenyl)methyl)-6-oxo-1,6-dihydropyridine-3-carboxamide | 442.8 |
| 413 | 89 | 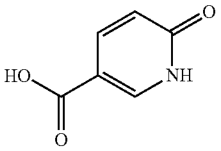 | 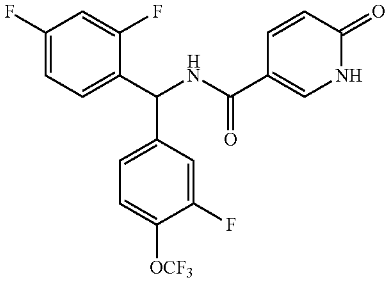 [SMILES: O=C(NC(c1ccc(OC(F)(F)F)c(F)c1)c1ccc(F)cc1F)c1ccc(=O)[nH]c1] | N-((2,4-difluorophenyl)(3-fluoro-4-(trifluoromethoxy)phenyl)methyl)-6-oxo-1,6-dihydropyridine-3-carboxamide | 442.8 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 414 | 90 | 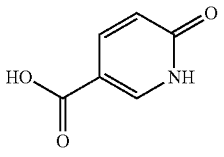 | 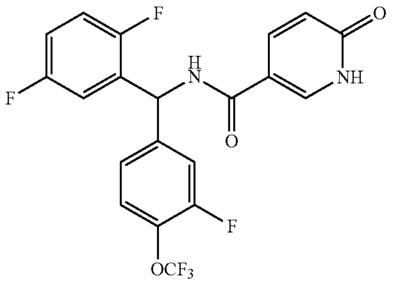 [SMILES: O=C(NC(c1ccc(OC(F)(F)F)c(F)c1)c1cc(F)ccc1F)c1ccc(=O)[nH]c1] | N-((2,5-difluorophenyl)(3-fluoro-4-(trifluoromethoxy)phenyl)methyl)-6-oxo-1,6-dihydropyridine-3-carboxamide | 443.5 |
| 415 | 6 | 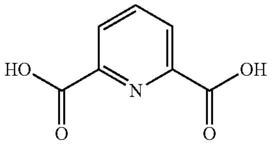 [SMILES: O=C(O)c1cccc(C(=O)O)n1] | 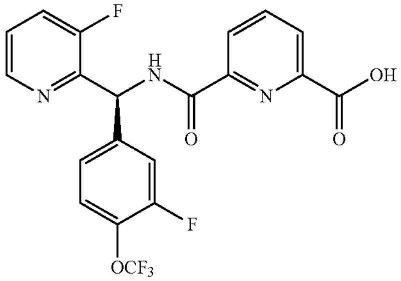 [SMILES: O=C(O)c1cccc(C(=O)N[C@@H](c2ccc(OC(F)(F)F)c(F)c2)c2ncccc2F)n1] | (S)-6-(((3-fluoro-4-(trifluoromethoxy)phenyl)(3-fluoropyridin-2-yl)methyl)carbamoyl)picolinic acid trifluoroacetate | 454.1 |
| 416 | 6 | 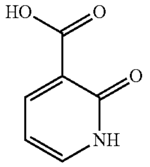 | 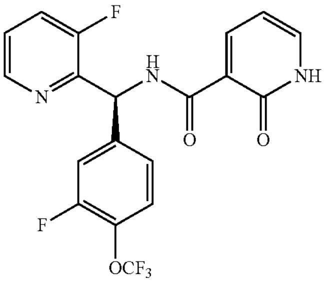 [SMILES: O=C(N[C@@H](c1ccc(OC(F)(F)F)c(F)c1)c1ncccc1F)c1ccc[nH]c1=O] | (S)-N-((3-fluoro-4-(trifluoromethoxy)phenyl)(3-fluoropyridin-2-yl)methyl)-2-oxo-1,2-dihydropyridine-3-carboxamide | 426.0 |
| 417 | 91 | 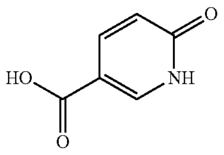 | 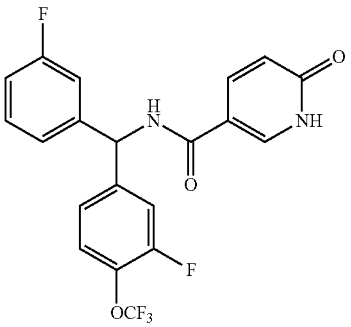 [SMILES: O=C(NC(c1cccc(F)c1)c1ccc(OC(F)(F)F)c(F)c1)c1ccc(=O)[nH]c1] | N-((3-fluoro-4-(trifluoromethoxy)phenyl)(3-fluorophenyl)methyl)-6-oxo-1,6-dihydropyridine-3-carboxamide | 425.2 |
| 418 | 92 | 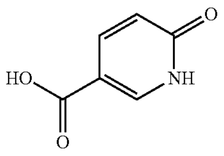 | 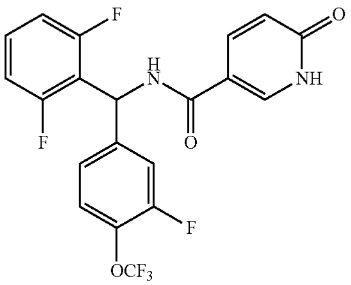 [SMILES: O=C(NC(c1ccc(OC(F)(F)F)c(F)c1)c1c(F)cccc1F)c1ccc(=O)[nH]c1] | N-((2,6-difluorophenyl)(3-fluoro-4-(trifluoromethoxy)phenyl)methyl)-6-oxo-1,6-dihydropyridine-3-carboxamide | 442.8 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 419[2] | 6b | 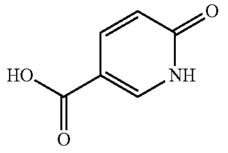 | 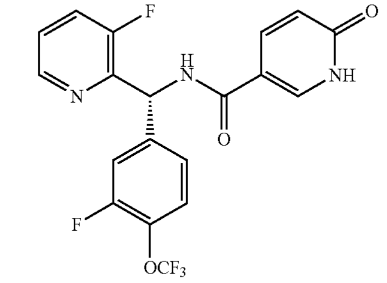 [SMILES: O=C(N[C@H](c1ccc(OC(F)(F)F)c(F)c1)c1ncccc1F)c1ccc(=O)[nH]c1] | (R)-N-((3-fluoro-4-(trifluoromethoxy)phenyl)(3-fluoropyridin-2-yl)methyl)-6-oxo-1,6-dihydropyridine-3-carboxamide | 425.9 |
| 420 | 93 | 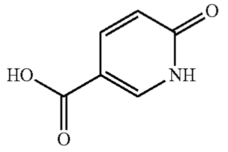 | 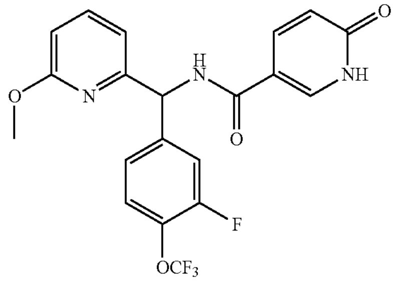 [SMILES: COc1cccc(C(NC(=O)c2ccc(=O)[nH]c2)c2ccc(OC(F)(F)F)c(F)c2)n1] | N-((3-fluoro-4-(trifluoromethoxy)phenyl)(6-methoxypyridin-2-yl)methyl)-6-oxo-1,6-dihydropyridine-3-carboxamide | 438.1 |
| 421 | 94 | 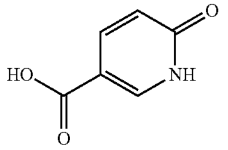 | 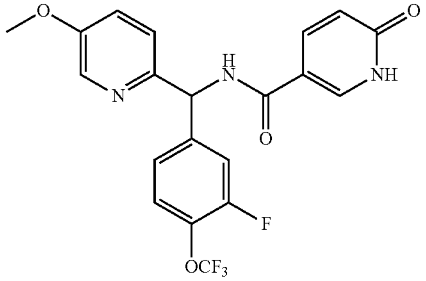 [SMILES: COc1ccc(C(NC(=O)c2ccc(=O)[nH]c2)c2ccc(OC(F)(F)F)c(F)c2)nc1] | N-((3-fluoro-4-(trifluoromethoxy)phenyl(5-methoxypyridin-2-yl)methyl)-6-oxo-1,6-dihydropyridine-3-carboxamide | 438.3 |
| 422 | 95 | 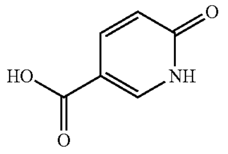 | 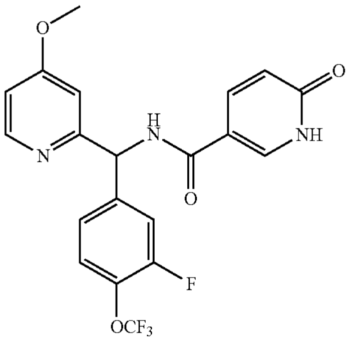 [SMILES: COc1ccnc(C(NC(=O)c2ccc(=O)[nH]c2)c2ccc(OC(F)(F)F)c(F)c2)c1] | N-((3-fluoro-4-(trifluoromethoxy)phenyl)(4-methoxypyridin-2-yl)methyl)-6-oxo-1,6-dihydropyridine-3-carboxamide | 438.5 |
| 423 | 96 | 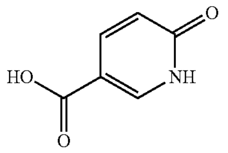 | 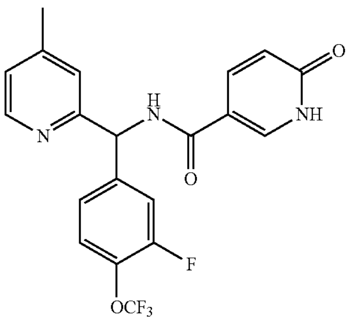 [SMILES: Cc1ccnc(C(NC(=O)c2ccc(=O)[nH]c2)c2ccc(OC(F)(F)F)c(F)c2)c1] | N-((3-fluoro-4-(trifluoromethoxy)phenyl)(4-methylpyridin-2-yl)methyl)-6-oxo-1,6-dihydropyridine-3-carboxamide | 422.0 |

TABLE 5-continued

Examples 287-424 prepared via amide formation analogous to Scheme 4

| Ex # | Amine | Acid Structure | Product Structure | Product Name | MS M + H |
|---|---|---|---|---|---|
| 424 | 97 | 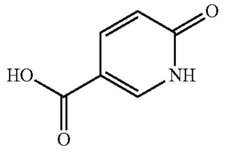 | 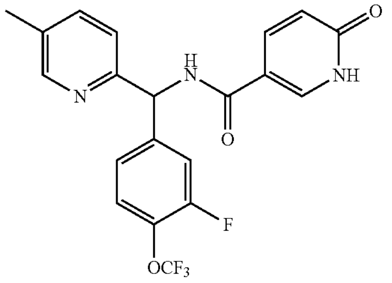 [SMILES: Cc1ccc(C(NC(=O)c2ccc(=O)[nH]c2)c2ccc(OC(F)(F)F)c(F)c2)nc1] | N-((3-fluoro-4-(trifluoromethoxy) phenyl)(5-methylpyridin-2-yl)methyl)-6-oxo-1,6-dihydropyridine-3-carboxamide | 422.0 |

[1]Purified via preparative SFC [using a Chiralpak AS-H column (250 × 21 mm, 10 μm); mobile phase 88:12 liquid $CO_2$:MeOH at a flow rate of 65 mL/min] resulting in Peak 1 and 2 fractions with enantiomeric excess >99%. Peak 1 correlates with the (S) enantiomer example 51, peak 2 was assigned as the (R) enantiomer.

[2]Purified via preparative SFC [using a Chiralpak AS-H column (150 × 21 mm, 5 μm); mobile phase 88:12 liquid $CO_2$:MeOH (20 mM $NH_3$) at a flow rate of 75 mL/min] resulting in Peak 1 and 2 fractions with enantiomeric excess >99%. Peak 1 correlates with the (S) enantiomer example 102, peak 2 was assigned as the (R) enantiomer.

Additional Examples

Scheme 24

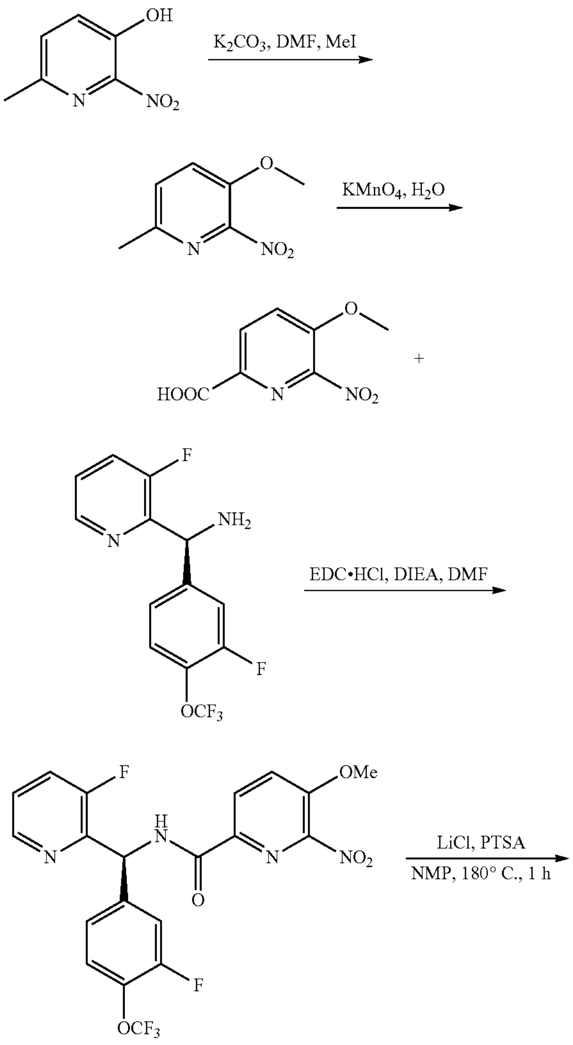

-continued

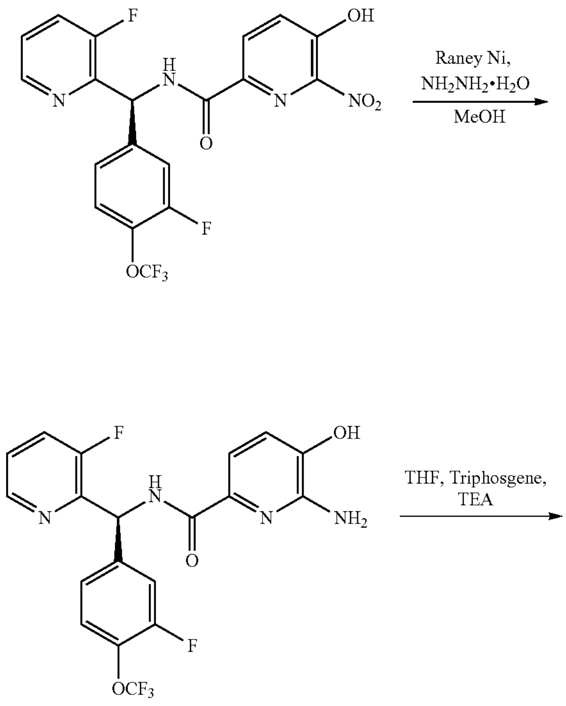

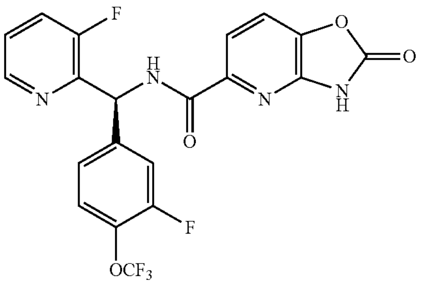

Example 425

(S)—N((3-Fluoro-4-(trifluoromethoxy)phenyl)(3-fluoropyridin-2-yl)methyl)-2-oxo-2,3-dihydrooxazolo[4,5-b]pyridine-5-carboxamide

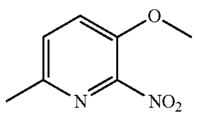

To a stirred mixture of 6-methyl-2-nitropyridin-3-ol (5 g, 0.032 mol, Sigma Aldrich) in DMF (50.0 mL) was added $K_2CO_3$ (6.72 g, 0.048 mol, S.d. fine chemicals, India). The reaction mixture was stirred for 30 min at room temperature. MeI (9 mL, 0.14 mol, Spectrochem, India) was then added at room temperature, and the reaction mixture was stirred overnight. After completion of the reaction (monitored by TLC, 30% EtOAc in hexane), the reaction mixture was quenched with ice water, following which the solid product precipitated. The solid was collected by filtration and washed with n-hexane to give the title compound. $^1$H-NMR (400 MHz, DMSO-$d_6$): δ 7.88 (d, J=8.4 Hz, 1H), 7.64 (d, J=8.8 Hz, 1H), 3.92 (s, 3H), 2.44 (s, 3H). MS (ESI, positive ion) m/z: 169 (M+H).

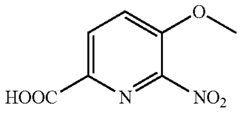

Step 2. 5-Methoxy-6-nitropicolinic acid

To a suspension of 3-methoxy-6-methyl-2-nitropyridine (7 g, 0.041 mol) in water (140.0 mL) was added $KMnO_4$ (32.88 g, 0.208 mol, S.d. fine chemicals, India) at 80° C. The reaction mixture was stirred for 16 h at 100° C. After completion of the reaction (monitored by TLC, 50% EtOAc in hexane), the reaction mixture was filtered and the solids were washed with water. The filtrate was acidified and extracted with EtOAc (500 mL×2). The organic layers were then dried over sodium sulfate and concentrated under reduced pressure to afford the title compound as an off white solid. $^1$H-NMR (400 MHz, DMSO-$d_6$): δ 13.6 (br. s., 1H), 8.39 (d, J=8.8 Hz, 1H), 8.09 (d, J=8.8 Hz, 1H), 4.06 (s, 3H). MS (ESI, positive ion) m/z: 199 (M+H).

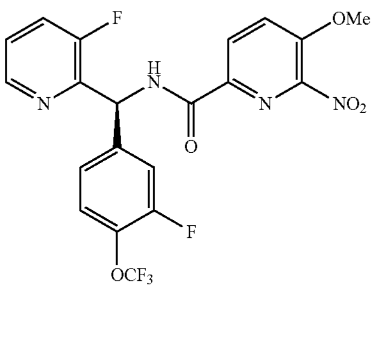 [SMILES: COc1ccc(C(=O)N[C@@H](c2ccc(OC(F)(F)F)c(F)c2)c2ncccc2F)nc1[N+](=O)[O-]]

Step 3. (S)—N-((3-Fluoro-4-(trifluoromethoxy)phenyl) (3-fluoropyridin-2-yl)methyl)-5-methoxy-6-nitropicolinamide To a stirred solution of 5-methoxy-6-nitropicolinic acid (200 mg, 0.001 mol) in DMF was added EDCI.HCl (231.6 mg, 0.0012 mol, Molekula, India) followed by HOBt (164.7 mg, 0.0012 mol, Spectrochem, India), DIPEA (521.87 mg, 0.0040 mol, Spectrochem, India) and (S)-(3-fluoro-4-(trifluoromethoxy) phenyl) (3-fluoropyridin-2-yl) methanamine hydrochloride (349.83 mg, 0.0010 mmol, Intermediate 6) at 0° C. The reaction mixture was stirred at room temperature overnight. After completion of the reaction (monitored by TLC, 50% EtOAc in hexane), water (20 mL) was added to the reaction mixture, and the aqueous solution was extracted with EtOAc (20 mL×2). The combined organic layers were washed with water (100 mL×2). The organic layer was dried and concentrated providing a residue which was purified by silica gel (60-120 mesh) column chromatography eluting with 40-50% EtOAc in petroleum ether to give the title compound as a solid. $^1$H-NMR (400 MHz, DMSO-$d_6$): δ 9.46 (d, J=7.6 Hz, 1H), 8.53 (d, J=4.4 Hz, 1H), 8.34 (d, J=8.4 Hz, 1H), 8.12 (d, J=8.8 Hz, 1H), 7.83 (t, J=9.6 Hz, 1H), 7.58-7.55 (m, 3H), 7.35 (d, J=8.4 Hz, 1H), 6.57 (d, J=7.2 Hz, 1H), 4.04 (s, 3H). MS (ESI, positive ion) m/z: 485 (M+H).

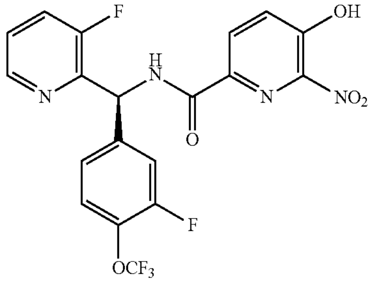 [SMILES: O=C(N[C@@H](c1ccc(OC(F)(F)F)c(F)c1)c1ncccc1F)c1ccc(O)c([N+](=O)[O-])n1]

Step 4. (S)—N-((3-Fluoro-4-(trifluoromethoxy)phenyl)(3-fluoropyridin-2-yl)methyl)-5-hydroxy-6-nitropicolinamide To a stirred solution of (S)—N-((3-fluoro-4-(trifluoromethoxy)phenyl) (3-fluoropyridin-2-yl)methyl)-5-methoxy-6-nitropicolinamide (700 mg, 0.0011 mol) in NMP (7.0 mL) was added LiCl (183.79 mg, 0.0043 mol, Sigma Aldrich, India) followed by pTSA (746.63 mg, 0.0043 mol, Sigma Aldrich, India) at room temperature. The reaction mixture was stirred at 180° C. for 2 h. After completion of the reaction (monitored by TLC, 100% EtOAc), the reaction mixture was cooled to room temperature and water (50 mL) was added and the aqueous solution was extracted with EtOAc (25 mL×2). The organic extracts were washed with water (25 mL×2) and brine (25 mL) and dried over anhydrous sodium sulfate and concentrated. The resulting material was purified by silica gel (60-120 mesh) column chromatography eluting with 60-70% EtOAc in petroleum ether to give the title compound as an off-white solid. $^1$H-NMR (400 MHz, DMSO-$d_6$): δ 12.77 (br. s., 1H), 9.43 (d, J=7.2 Hz, 1H), 8.57 (d, J=4.4 Hz, 1H), 8.24 (d, J=8.4 Hz, 1H), 7.86-7.79 (m, 2H), 7.59-7.54 (m, 3H), 7.37 (d, J=8.4 Hz, 1H), 6.57 (d, J=7.2 Hz, 1H). MS (ESI, positive ion) m/z: 471 (M+H).

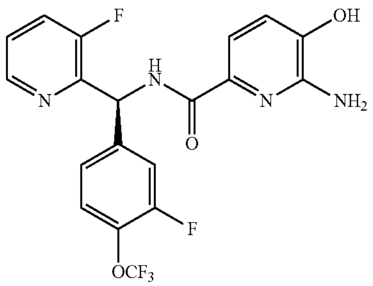 [SMILES: Nc1nc(C(=O)N[C@@H](c2ccc(OC(F)(F)F)c(F)c2)c2ncccc2F)ccc1O]

Step 5. (S)-6-Amino-N-((3-fluoro-4-(trifluoromethoxy)phenyl)(3-fluoropyridin-2-yl)methyl)-5-hydroxypicolinamide To a stirred suspension of Raney Nickel (0.2 g, Monarch, India) in MeOH (10 mL), was added (S)—N-((3-fluoro-4-(trifluoromethoxy)phenyl)(3-fluoropyridin-2-yl)methyl)-5-hydroxy-6-nitropicolinamide (200 mg, 0.0004252 mol) at room temperature. The temperature was raised to 56° C. and hydrazine hydrate (0.2 mL, Spectrochem, India) was added very slowly over 5 min (exothermic reaction). The reaction mixture was then stirred for 10 min at the same temperature. After completion of the reaction, monitored by TLC (TLC eluent: 50% EtOAc in petroleum ether, uv active), the mixture was cooled to room temperature, filtered through Celite® brand filter agent and concentrated under high vacuum to remove excess hydrazine hydrate. The resulting product was triturated with petroleum ether to give the title compound as a grey solid. $^{1}$H-NMR (400 MHz, DMSO-$d_6$): δ 9.23 (d, J=8 Hz, 1H), 8.57 (d, J=4.4 Hz, 1H), 7.87 (t, J=8.8 Hz, 1H), 7.61-7.54 (m, 2H), 7.47 (d, J=11.6 Hz, 1H), 7.31 (d, J=8.4 Hz, 1H), 7.19 (d, J=8 Hz, 1H), 6.86 (d, J=8 Hz, 1H), 6.57 (d, J=8 Hz, 1H), 5.53 (br. s., 2H). MS (ESI, positive ion) m/z: 441 (M+H).

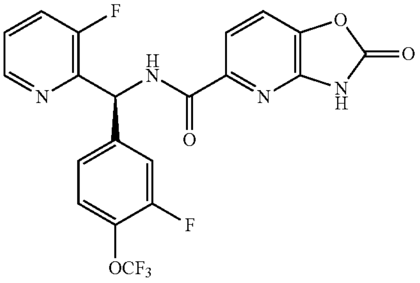 [SMILES: O=C(N[C@@H](c1ccc(OC(F)(F)F)c(F)c1)c1ncccc1F)c1ccc2oc(=O)[nH]c2n1]

Step 6. (S)—N-((3-Fluoro-4-(trifluoromethoxy)phenyl)(3-fluoropyridin-2-yl)methyl)-2-oxo-2,3-dihydrooxazolo[4,5-b]pyridine-5-carboxamide To a solution of (S)-6-amino-N-((3-fluoro-4-(trifluoromethoxy)phenyl)(3-fluoropyridin-2-yl)methyl)-5-hydroxypicolinamide (300 mg, 0.681 mmol) in THF (10 mL) was added TEA (689.4 mg, 0.00068 mmol, S.d fine, India) and triphosgene (242 mg, 0.0008 mmol, Sigma Aldrich, India) at 0° C. The reaction mixture was stirred for 2 h at room temperature. After completion of the reaction, monitored by TLC (TLC eluent: 50% EtOAc in petroleum ether), the reaction mixture was quenched with sat'd $NaHCO_3$ solution and extracted with EtOAc (3×20 mL). The combined organic layers were washed with brine, dried over anhydrous sodium sulfate, concentrated and purified by silica gel (60-120 mesh) column chromatography eluting with 80-100% EtOAc in petroleum ether to afford the title compound as an off white solid. $^{1}$H-NMR (400 MHz, DMSO-$d_6$): δ 12.8 (br. s., 1H), 9.46 (d, J=7.2 Hz, 1H), 8.55 (d, J=4.4 Hz, 1H), 7.83-7.77 (m, 3H), 7.57-7.49 (m, 3H), 7.33 (d, J=8.4 Hz, 1H), 6.55 (d, J=6.8 Hz, 1H). MS (ESI, positive ion) m/z: 467.2 (M+H).

Scheme 25

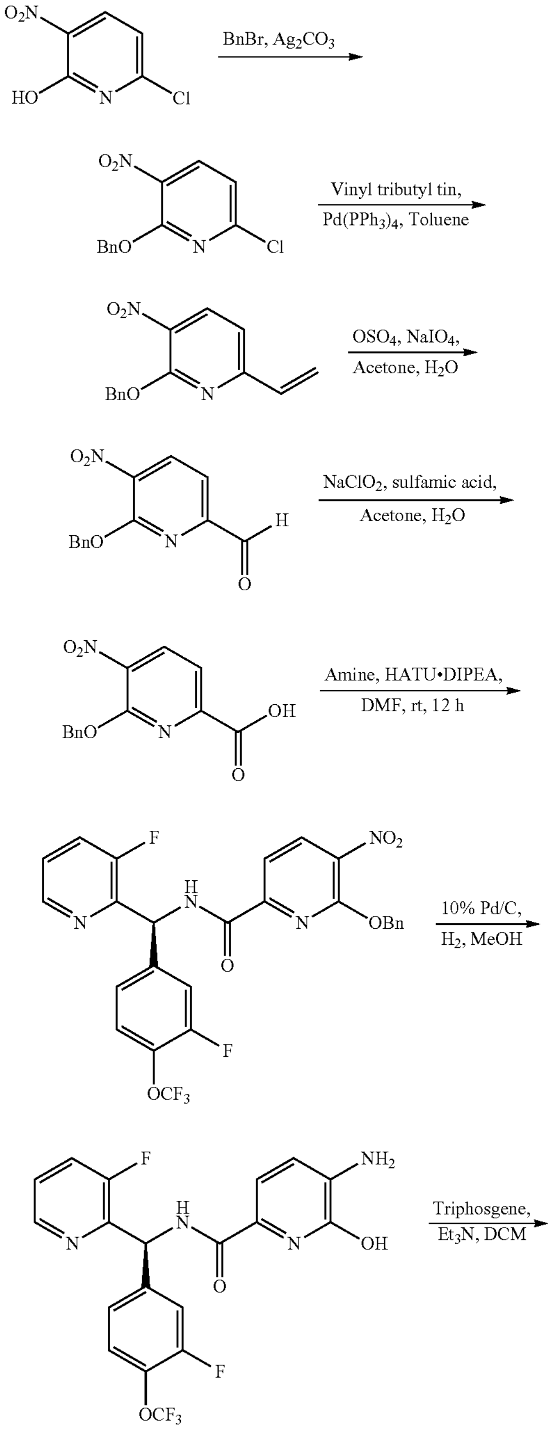

-continued

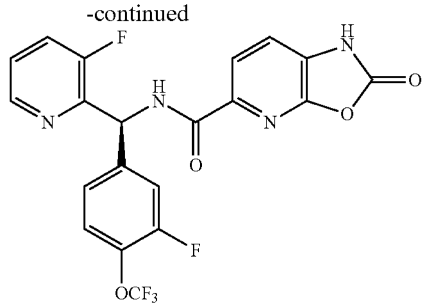

Example 426

(S)—N-((3-fluoro-4-(trifluoromethoxy)phenyl)(3-fluoropyridin-2-yl)methyl)-2-oxo-1,2-dihydrooxazolo[5,4-b]pyridine-5-carboxamide

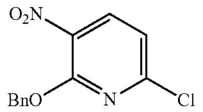 [SMILES: O=[N+]([O-])c1ccc(Cl)nc1OCc1ccccc1]

Step 1. 2-(Benzyloxy)-6-chloro-3-nitropyridine

To a stirred mixture of 6-chloro-3-nitropyridin-2-ol (5 g, 0.0286 mol, Combi Blocks) in toluene (50.0 mL) in a 250 mL sealed tube, were added $Ag_2CO_3$ (11.84 g, 0.041 mol, Aldrich) and benzyl bromide (5.8 g, 0.033 mol) in one lot. The reaction mixture was capped, and the mixture was stirred for 12 h at 110° C. temperature. After completion of the reaction (monitored by TLC, 10% EtOAc in hexane), the reaction mixture was quenched with water (50 mL) and extracted with EtOAc (50 mL×3). The organic layers were combined, dried over anhydrous sodium sulfate, and concentrated under reduced pressure to give a brown solid which was further purified column chromatography, silica gel (60-120 mesh) using 2-6% EtOAc in petroleum ether as an eluent to obtain the title compound as a white solid. $^1$H NMR (400 MHz, $CDCl_3$) δ: 8.30 (d, J=8.1 Hz, 1H), 7.54 (d, J=6.9 Hz, 2H), 7.42-7.26 (m, 3H), 7.09 (t, J=8.4 Hz, 1H), 5.58 (s, 2H).

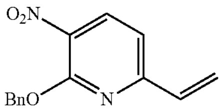 [SMILES: C=Cc1ccc([N+](=O)[O-])c(OCc2ccccc2)n1]

Step 2. 2-(Benzyloxy)-3-nitro-6-vinylpyridine

To a stirred mixture of (2-(benzyloxy)-6-chloro-3-nitropyridine (3.2 g, 0.0123 mol) in toluene (32.5 mL) in a 250 mL sealed tube, were added $Pd(PPh_3)_4$ (426 mg, 0.000369 mol, Aldrich) and vinyl tributyltin (3.90 g, 0.0123 mol). The tube was purged with the argon gas for 10 min, capped and stirred for 12 h at 110° C. After completion of the reaction (monitored by TLC, 10% EtOAc in hexane), the reaction mixture was quenched with water (20 mL) and extracted with EtOAc (50 mL×3). The organic layers were combined, dried over anhydrous sodium sulfate, and purified by column chromatography, silica gel (60-120 mesh) using 5-7% EtOAc in petroleum ether as an eluent to afford the title compound as a white solid. $^1$H NMR (400 MHz, DMSO-$d_6$) δ: 8.47 (d, J=8.1 Hz, 1H), 7.52 (d, J=6.9 Hz, 1H), 7.43-7.27 (m, 3H), 7.20 (br. s., 2H), 6.92-6.83 (m, 1H), 6.49 (dd, J=17.4, 1.5 Hz, 1H), 5.74 (dd, J=10.5, 1.5 Hz, 1H), 5.59 (s, 2H). MS (ESI, positive ion) m/z: 257 (M+H).

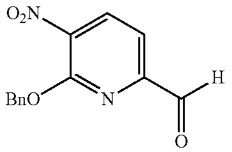 [SMILES: O=Cc1ccc([N+](=O)[O-])c(OCc2ccccc2)n1]

Step 3. 6-(Benzyloxy)-5-nitropicolinaldehyde

To a cooled (0° C.) stirred mixture of (2-(benzyloxy)-3-nitro-6-vinylpyridine (0.5 g, 0.0019 mol) in acetone:water (1:1, 5 mL), was added $OsO_4$ (16.39 mg, 0.000064 mol, Aldrich) and $NaIO_4$ (1.67 g, 0.0078 mol, Aldrich). The reaction mixture was stirred for 4 h at room temperature. After completion of the reaction (monitored by TLC, 10% EtOAc in hexane), the reaction mixture was quenched with water (10 mL) and extracted with EtOAc (5 mL×3). The organic layers were combined, dried over anhydrous sodium sulfate and purified by column chromatography, silica gel (60-120 mesh) using 5-7% EtOAc in petroleum ether as an eluent to afford the title compound. $^1$H NMR (400 MHz, $CDCl_3$) δ: 10.00 (s, 1H), 8.38 (d, J=6 Hz, 1H), 7.69 (d, J=6 Hz, 1H), 7.54 (d, J=5.7 Hz, 2H), 7.41-7.37 (m, 3H), 5.69 (s, 2H).

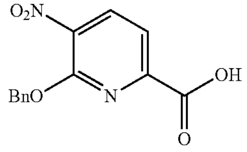 [SMILES: O=C(O)c1ccc([N+](=O)[O-])c(OCc2ccccc2)n1]

Step 4. 6-(Benzyloxy)-5-nitropicolinic acid

To a cooled (0° C.) stirred mixture of 6-(benzyloxy)-5-nitropicolinaldehyde (0.5 g, 0.0019 mol) in acetone:water (1:1, 5 mL), was added sulphamic acid (280 mg, 0.00029 mol, Aldrich) and $NaClO_2$ (260 mg, 0.00029 mol, Aldrich). The reaction mixture was stirred for 2 h at the same temperature. After completion of the reaction (monitored by TLC, 10% EtOAc in hexane), the reaction mixture was quenched with water (2 mL) and extracted with EtOAc (20 mL×3). The organic layers were combined, dried over anhydrous sodium sulfate, and purified by column chromatography, silica gel (60-120 mesh) using 5-9% EtOAc in petroleum ether as an eluent to give the title compound. $^1$H NMR (400 MHz, $CDCl_3$) δ: 13.80 (br. s., 1H), 8.45 (d, J=8.1 Hz, 1H), 7.96 (d, J=8.1 Hz, 1H), 7.51 (d, J=7.2 Hz, 2H), 7.44-7.36 (m, 3H), 5.62 (s, 2H).

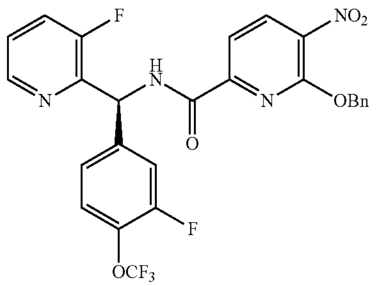 [SMILES: O=C(N[C@@H](c1ccc(OC(F)(F)F)c(F)c1)c1ncccc1F)c1ccc([N+](=O)[O-])c(OCc2ccccc2)n1]

Step 5. (S)-6-(Benzyloxy)-N-((3-fluoro-4-(trifluoromethoxy)phenyl)(3-fluoropyridin-2-yl)methyl)-5-nitropicolinamide To a stirred solution of 6-(benzyloxy)-5-nitropicolinic acid (500 mg, 0.0018 mol) in DMF (10 mL), were added (S)-(3-fluoro-4-(trifluoromethoxy)phenyl)(3-fluoropyridin-2-yl) methanamine hydrochloride (620 mg, 0.0018 mol, Intermediate 6), HATU (1 g, 0.0029 mol) and DIPEA (700 mg, 0.0054 mol). The reaction mixture was then stirred for 12 h at room temperature. Progress was monitored by TLC (100% EtOAc). After completion of reaction, water (100 mL) was added and product was extracted with EtOAc (50 mL×3) and concentrated to obtain the product which was purified by column chromatography, silica gel (100-200 mesh), using 80-100% EtOAc in petroleum ether as the eluent to afford the title compound $^1$H NMR (400 MHz, DMSO-$d_6$) δ: 9.75 (d, J=7.6 Hz, 1H), 8.61-8.56 (m, 2H), 7.79 (d, J=8.4 Hz, 2H), 7.59-7.54 (m, 5H), 7.35-7.32 (m, 4H), 6.60 (d, 1H), 5.77 (s, 2H).

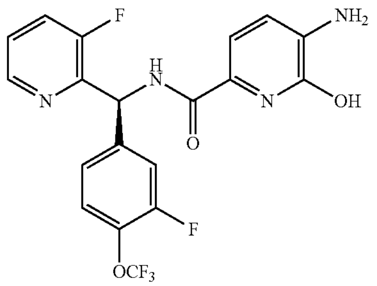 [SMILES: Nc1ccc(C(=O)N[C@@H](c2ccc(OC(F)(F)F)c(F)c2)c2ncccc2F)nc1O]

Step 6. (S)-5-Amino-N-((3-fluoro-4-(trifluoromethoxy)phenyl)(3-fluoropyridin-2-yl)methyl)-6-hydroxypicolinamide To a stirred mixture of (S)-6-(benzyloxy)-N-((3-fluoro-4-(trifluoromethoxy)phenyl)(3-fluoropyridin-2-yl)methyl)-5-nitropicolinamide (800 mg, 0.0014 mol) in THF (8 mL), was added 10% Pd/C (800 mg, Aldrich). The reaction mixture was stirred under hydrogen atmosphere in the form of hydrogen bladder (~20-22 PSI) for 12 h at room temperature. After completion of the reaction (monitored by TLC, 100% EtOAc), the reaction mixture was filtered through Celite® brand filter agent, the filtrate dried over anhydrous sodium sulfate and concentrated under reduced pressure to afford the title compound. $^1$H NMR (400 MHz, DMSO-$d_6$) δ: 11.00 (s, 1H), 9.13 (d, J=6 Hz, 1H), 8.46 (d, J=4 Hz, 1H), 7.79 (t, J=9.2 Hz, 1H), 7.57-7.46 (m, 3H), 7.33 (d, J=8.4 Hz, 1H), 7.08 (br.

s., 1H), 6.62 (d, J=7.6 Hz, 1H), 6.40 (br. s., 1H), 5.83 (br. s., 2H). MS (ESI, positive ion) m/z: 440.9 (M+H).

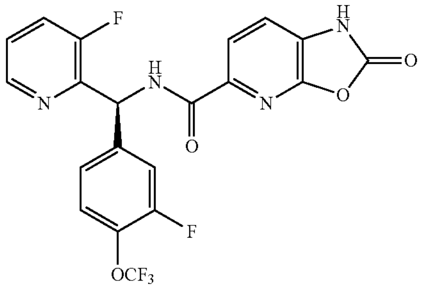 [SMILES: O=C(N[C@@H](c1ccc(OC(F)(F)F)c(F)c1)c1ncccc1F)c1ccc2[nH]c(=O)oc2n1]

Step 7. (S)—N-((3-Fluoro-4-(trifluoromethoxy)phenyl)(3-fluoropyridin-2-yl)methyl)-2-oxo-1,2-dihydrooxazolo[5,4-b]pyridine-5-carboxamide To a cooled (−78° C.), stirred mixture of (S)-5-amino-N-((3-fluoro-4-(trifluoromethoxy)phenyl)(3-fluoropyridin-2-yl)methyl)-6-hydroxypicolinamide (400 mg, 0.00098 mol) in THF (4 mL) was added TEA (1.31 mL, 0.0090 mol, Spectrochem, India) and triphosgene (323 mg, 0.0010 mol, Spectrochem, India) in one lot and the reaction mixture was stirred for 2 h at the same temperature. The reaction was slowly warmed to room temperature overnight. After completion of the reaction (monitored by TLC, 50% EtOAc in hexane), the reaction mixture was quenched with water (2 mL) and extracted with EtOAc (2 mL×3). The combined organic layers were dried over anhydrous sodium sulfate and purified by column chromatography, silica (60-120 mesh) using 50-60% EtOAc in petroleum ether as an eluent, and subsequently purified further using Prep TLC plates, mobile phase 50% EtOAc in hexane to give the title compound. $^1$H NMR (400 MHz, DMSO-$d_6$) δ: 12.40 (s, 1H), 9.53 (d, J=7.2 Hz, 1H), 8.59 (d, J=4.4 Hz, 1H), 7.90-7.80 (m, 2H), 7.61-7.53 (m, 4H), 7.35 (d, J=8.8 Hz, 1H), 6.54 (d, J=7.2 Hz, 1H). MS (ESI, positive ion) m/z: 467.1 (M+H).

Scheme 26

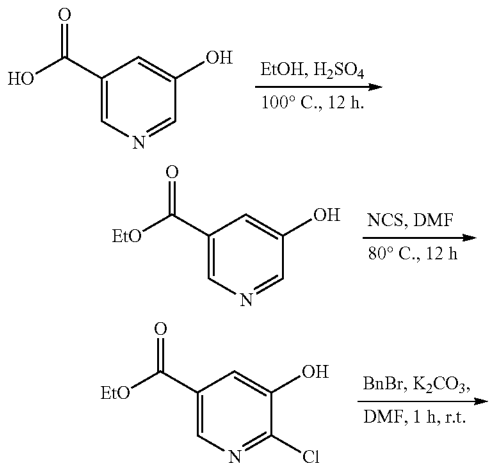

-continued

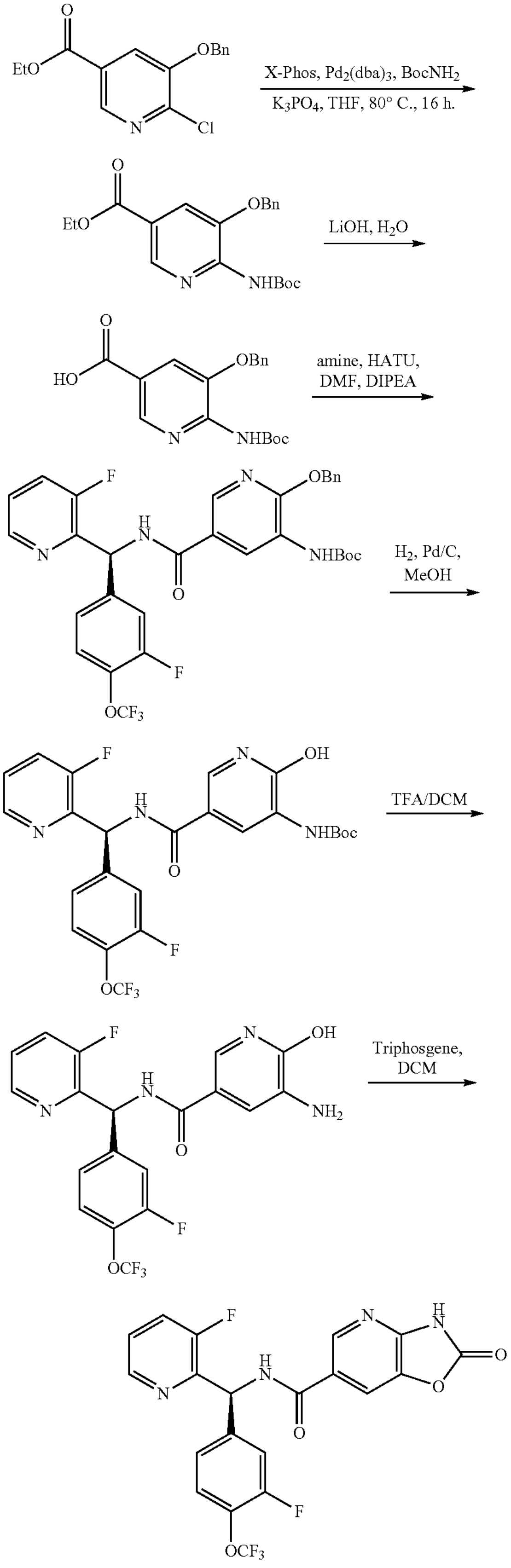

Example 427

(S)—N-((3-Fluoro-4-(trifluoromethoxy)phenyl)(3-fluoropyridin-2-yl)methyl)-2-oxo-2,3-dihydrooxazolo[4,5-b]pyridine-6-carboxamide

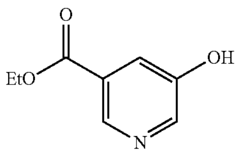 [SMILES: CCOC(=O)c1cncc(O)c1]

Step 1. Ethyl 5-hydroxynicotinate

To a stirred mixture of 5-hydroxynicotinic acid (25 g, 0.1797 mol, Combi Blocks) in EtOH (500 mL) was added a catalytic amount of conc. $H_2SO_4$. The resulting reaction mixture was stirred for 12 h at 110° C. After completion of the reaction (monitored by TLC, 10% MeOH in $CHCl_3$), EtOH was removed under reduced pressure and the reaction mixture was quenched with sat'd $NaHCO_3$ solution (50 mL) and extracted with EtOAc (50 mL×3). The combined organic layers were dried over anhydrous sodium sulfate and concentrated under reduced pressure to afford the title compound as a solid. $^1H$ NMR (400 MHz, $CDCl_3$) δ: 11.00 (br.s., 1H), 8.74 (s, 1H), 8.42 (d, J=2.1 Hz, 1H), 7.90 (t, J=3.9 Hz, 1H), 4.43 (q, J=7.2 Hz, 2H), 1.43 (t, J=6.9 Hz, 3H). MS (ESI, positive ion) m/z: 168 (M+H).

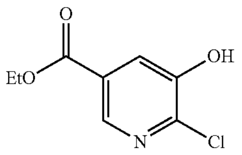 [SMILES: CCOC(=O)c1cnc(Cl)c(O)c1]

Step 2. Ethyl 6-chloro-5-hydroxynicotinate

To a stirred mixture of ethyl 5-hydroxynicotinate (20 g, 0.119 mol, in DMF (200.0 mL) was added NCS (19.18 g, 0.143 mol, Aldrich). The reaction mixture was stirred for 2 h at 80° C. After completion of the reaction (monitored by TLC, 30% EtOAc in hexane), the reaction mixture was quenched with sat'd $NaHCO_3$ solution (50 mL) and extracted with EtOAc (500 mL×3). The combined organic layers were dried over anhydrous sodium sulfate, and purified by column chromatography, silica gel (100-200 mesh), using 10-15% EtOAc in petroleum ether as the eluent to give the title compound as a solid. $^1H$ NMR (400 MHz, $CDCl_3$) δ: 8.61 (d, J=2.1 Hz, 1H), 7.92 (d, J=1.8 Hz, 1H), 5.94 (br. s., 1H), 4.53 (q, J=6.9 Hz, 2H), 1.43 (t, J=7.2 Hz, 3H). MS (ESI, positive ion) m/z: 202.1 (M+H).

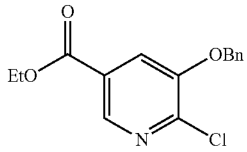 [SMILES: CCOC(=O)c1cnc(Cl)c(OCc2ccccc2)c1]

Step 3. Ethyl 5-(benzyloxy)-6-chloronicotinate

To a stirred mixture of ethyl 6-chloro-5-hydroxynicotinate (2 g, 0.01 mol) in Toluene (50.0 mL) were added $K_2CO_3$ (2.76 g, 0.02 mol, Rankem, India) and benzyl bromide (2 g, 0.0012 mol). The reaction mixture was stirred for 2 h at room temperature. After completion of the reaction (monitored by TLC, 20% EtOAc in hexane), the reaction mixture was quenched with water (50 mL), extracted with EtOAc (50 mL×3). The combined organic layers were dried over anhydrous sodium sulfate and purified by column chromatography, silica gel (60-120 mesh) using 12-16% EtOAc in petroleum ether as the eluent to give the title compound. MS (ESI, positive ion) m/z: 292.2 (M+H).

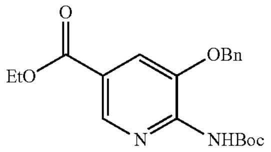 [SMILES: CCOC(=O)c1cnc(NC(=O)OC(C)(C)C)c(OCc2ccccc2)c1]

Step 4. Ethyl 5-(benzyloxy)-6-((tert-butoxycarbonyl) amino)nicotinate

To a stirred mixture of ethyl 5-(benzyloxy)-6-chloronicotinate (2.1 g, 0.00719 mol) in THF (21 mL) in a 250 mL sealed tube, were added $Pd_2(dba)_3$ (395 mg, 0.00043 mol, Aldrich), $NH_2Boc$ (1.68 g, 0.0143 mol, Aldrich), X-phos (500 mg, 0.0010 mol, Aldrich) and $K_3PO_4$ (4.5 g, 0.0010 mol). The vessel was purged with argon gas for 10 min. The reaction mixture was then stirred for 12 h at 80° C. After completion of the reaction (monitored by TLC, 30% EtOAc in hexane), the reaction mixture was quenched with water (50 mL) and extracted with EtOAc (50 mL×3). The combined organic layers were dried over anhydrous sodium sulfate, and purified by column chromatography, silica gel (60-120 mesh) using 23-30% EtOAc in petroleum ether as the eluent to give the title compound. $^1H$ NMR (400 MHz, DMSO-$d_6$) δ: 9.22 (s, 1H), 8.46 (d, J=1.8 Hz, 1H), 7.81 (d, J=1.8 Hz, 1H), 7.53 (d, J=6.6 Hz, 2H) 7.42-7.33 (m, 3H), 5.22 (s, 2H), 4.36 (q, J=6.9 Hz, 2H), 1.44 (s, 9H), 1.36 (t, 3H).

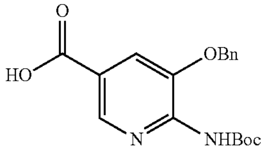 [SMILES: CC(C)(C)OC(=O)Nc1ncc(C(=O)O)cc1OCc1ccccc1]

Step 5. 5-(Benzyloxy)-6-((tert-butoxycarbonyl) amino)nicotinic acid

To a cooled (0° C.) stirred mixture of ethyl 5-(benzyloxy)-6-((tert-butoxycarbonyl) amino) nicotinate (1.2 g, 0.0032 mol) in EtOH: water (1:1, 12 mL), was added LiOH (154 mg, 0.0064 mol, Aldrich). The reaction mixture was stirred for 2 h at room temperature. After completion of the reaction (monitored by TLC, 100% EtOAc), the reaction mixture was quenched with 1N HCl at 0° C. temperature and extracted with EtOAc (2 mL×3). The combined organic layers were dried over anhydrous sodium sulfate and concentrated under reduced pressure to give the title compound. $^1H$ NMR (400 MHz, DMSO-$d_6$) δ: 13.24 (s, 1H), 9.18 (s, 1H), 8.45 (d, J=1.2 Hz, 1H), 7.80 (d, J=1.5, Hz, 1H), 7.53 (d, J=5.4 Hz, 2H), 7.41-7.34 (m, 2H), 5.24 (s, 2H), 1.38 (s, 9H).

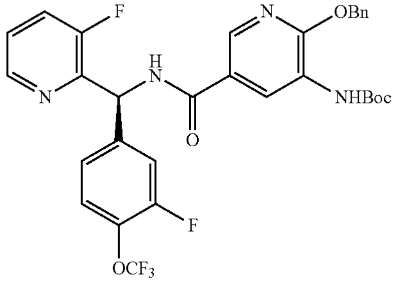 [SMILES: CC(C)(C)OC(=O)Nc1cc(C(=O)N[C@@H](c2ccc(OC(F)(F)F)c(F)c2)c2ncccc2F)cnc1OCc1ccccc1]

Step 6. (S)-tert-Butyl (2-(benzyloxy)-5-(((3-fluoro-4-(trifluoromethoxy)phenyl)(3-fluoropyridin-2-yl)methyl)carbamoyl)pyridin-3-yl)carbamate To a stirred solution of 5-(benzyloxy)-6-((tert-butoxycarbonyl)amino)nicotinic acid (800 mg, 0.0023 mol) in DMF (10 mL), were added (S)-(3-fluoro-4-(trifluoromethoxy)phenyl)(3-fluoropyridin-2-yl)methanamine hydrochloride (790 mg, 0.0023 mol, Intermediate 6), HATU (1.325 g, 0.0034 mol) and DIPEA (900 mg, 0.0069 mol). The reaction mixture was then stirred for 12 h at rt. Reaction progress was monitored by TLC (100% EtOAc). After completion of the reaction, water (8 mL) was added, and the aqueous solution was extracted with EtOAc (5 mL×3) and concentrated to provide the product. The product thus obtained was purified by column chromatography, silica gel (100-200 mesh), using 80-100% EtOAc in petroleum ether as the eluent to give the title compound. $^1H$ NMR (400 MHz, DMSO-$d_6$) δ: 9.52 (d, J=7.6 Hz, 1H), 9.10 (s, 1H), 8.47 (t, 7.5 Hz, 2H), 7.93 (d, J=1.8 Hz, 1H), 7.82 (dd, 0.9, 9.6 Hz, 1H), 7.63-7.46 (m, 4H), 7.40-7.33 (m, 4H), 6.75 (d, J=7.8 Hz, 1H), 5.20 (s, 2H), 1.40 (s, 9H).

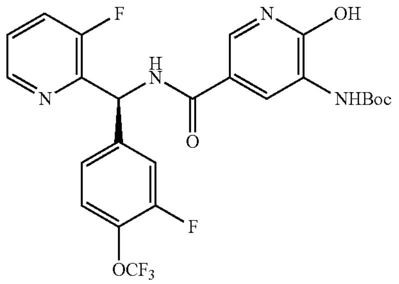 [SMILES: CC(C)(C)OC(=O)Nc1cc(C(=O)N[C@@H](c2ccc(OC(F)(F)F)c(F)c2)c2ncccc2F)cnc1O]

Step 7. ((S)-tert-Butyl (5-(((3-fluoro-4-(trifluoromethoxy)phenyl)(3-fluoropyridin-2-yl)methyl) carbamoyl)-2-hydroxypyridin-3-yl)carbamate To a stirred mixture of (S)-tert-butyl (2-(benzyloxy)-5-(((3-fluoro-4-(trifluoromethoxy)phenyl)(3-fluoropyridin-2- yl)methyl)carbamoyl)pyridine)-carbamate (800 mg, 0.0012 mol) in THF (8 mL) was added 10% Pd/C (800 mg, Aldrich). The reaction mixture was stirred under a hydrogen atmosphere in the form of a hydrogen bladder (~20-22 PSI) for 12 h at room temperature. After completion of the reaction (monitored by TLC, 100% EtOAc), the reaction mixture was filtered through Celite® brand filter agent. The filtrate was dried over anhydrous sodium sulfate and concentrated under reduced pressure to afford the title compound. $^{1}$H NMR (400 MHz, DMSO-$d_6$) δ: 10.40 (br. s., 1H), 9.42 (d, J=7.8 Hz, 1H), 9.01 (s, 1H), 8.45 (d, J=4.8 Hz, 1H), 8.35 (d, J=1.8 Hz, 1H), 7.95 (s, 1H), 7.80 (t, 9.6 Hz, 1H), 7.61-7.45 (m, 4H), 7.37 (d, 8.4 Hz, 1H), 1.44 (s, 9H). MS (ESI, positive ion) m/z: 541 (M+H).

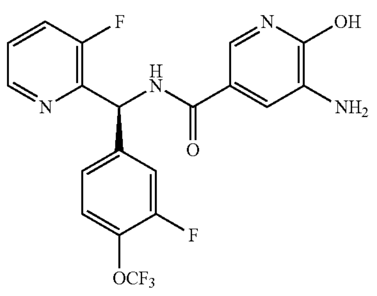 [SMILES: Nc1cc(C(=O)N[C@@H](c2ccc(OC(F)(F)F)c(F)c2)c2ncccc2F)cnc1O]

Step 8. (S)-5-Amino-N-((3-fluoro-4-(trifluoromethoxy)phenyl)(3-fluoropyridin-2-yl)methyl)-6-hydroxynicotinamide To a stirred mixture of ((S)-tert-butyl (5-(((3-fluoro-4-(trifluoromethoxy)phenyl)(3-fluoropyridin-2-yl)methyl)carbamoyl)-2-hydroxypyridin-3-yl)carbamate (600 mg, 0.0011 mol), in DCM (6 mL) was added TFA (1.2 mL, 0.143 mol, Aldrich). The resulting mixture was then stirred for 2 h at room temperature. After completion of the reaction (monitored by TLC, 30% EtOAc in hexane), the reaction mixture was quenched with sat'd $NaHCO_3$ solution (50 mL) and extracted with EtOAc (50 mL×3). The combined organic layers were dried over anhydrous sodium sulfate and concentrated under reduced pressure to afford the title compound. $^{1}$H NMR (400 MHz, DMSO-$d_6$) δ: 9.78 (s., 1H), 9.00 (d, J=7.8 Hz, 1H), 8.44 (d, J=4.8 Hz, 1H), 8.13 (d, J=1.8 Hz, 1H), 7.79 (dd, J=1.2, 9.9 Hz, 1H), 7.60-7.43 (m, 3H), 7.35 (d, 8.7 Hz, 1H), 7.26 (d, J=1.8 Hz, 1H), 6.66 (d, J=7.8 Hz, 1H), 6.18 (br.s., 2H). MS (ESI, positive ion) m/z: 441.1 (M+H).

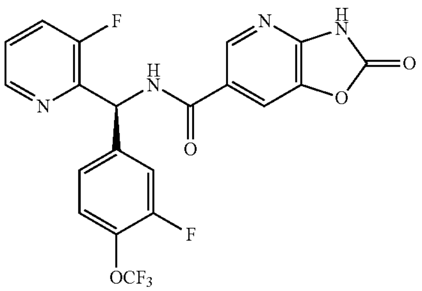 [SMILES: O=C(N[C@@H](c1ccc(OC(F)(F)F)c(F)c1)c1ncccc1F)c1cnc2[nH]c(=O)oc2c1]

Step 9. (S)—N-((3-Fluoro-4-(trifluoromethoxy)phenyl)(3-fluoropyridin-2-yl)methyl)-2-oxo-2,3-dihydrooxazolo[4,5-b]pyridine-6-carboxamide To a cooled (−78° C.) stirred mixture of (S)-5-amino-N-((3-fluoro-4-(trifluoromethoxy)phenyl) (3-fluoropyridin-2-yl)methyl)-6-hydroxynicotinamide (400 mg, 0.00098 mol) in THF (4 mL), were added TEA (1.31 mL, 0.0090 mol, Spectrochem, India) and triphosgene (323 mg, 0.0010 mol, Spectrochem, India). The reaction mixture was stirred for 2 h at the same temperature. The reaction was then slowly warmed to room temperature overnight. After completion of the reaction (monitored by TLC, 50% EtOAc in hexane), the reaction mixture was quenched with water (2 mL) and extracted with EtOAc (2 mL×3). The combined organic layers were dried over anhydrous sodium sulfate, and purified by column chromatography, silica gel (60-120 mesh) using 50-60% EtOAc in petroleum ether as an eluent, and purified again using Prep TLC plates, mobile phase 50% EtOAc in hexane to afford the title compound. $^{1}$H NMR (400 MHz, $CD_3OD$) δ: 8.58 (s., 1H), 8.48 (d, J=4.8 Hz, 1H), 7.89 (s, 1H), 7.65 (t, J=9.6 Hz, 1H), 7.46-7.32 (m, 4H), 6.68 (s, 2H). MS (ESI, positive ion) m/z: 467 (M+H).

Scheme 27

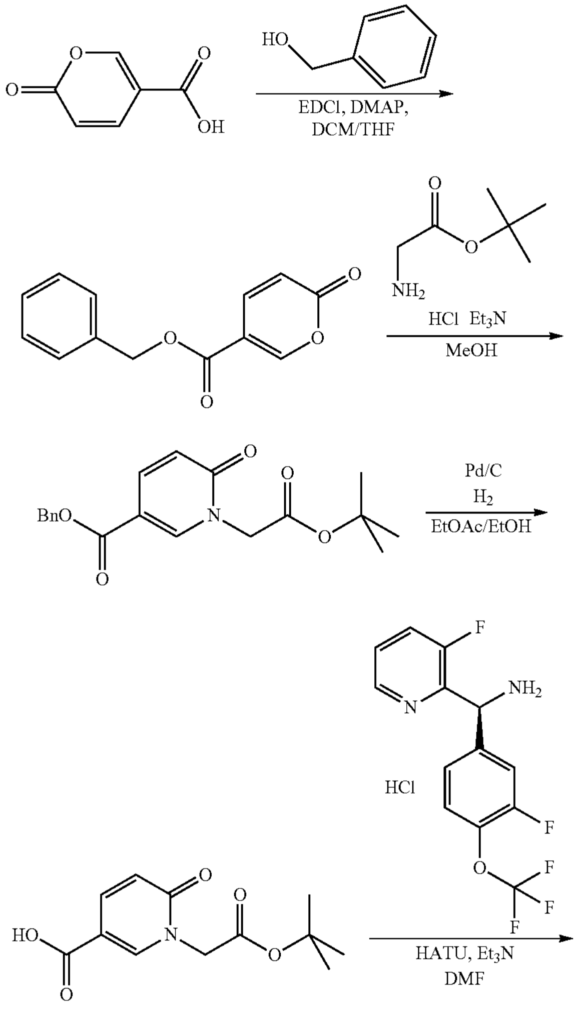

-continued

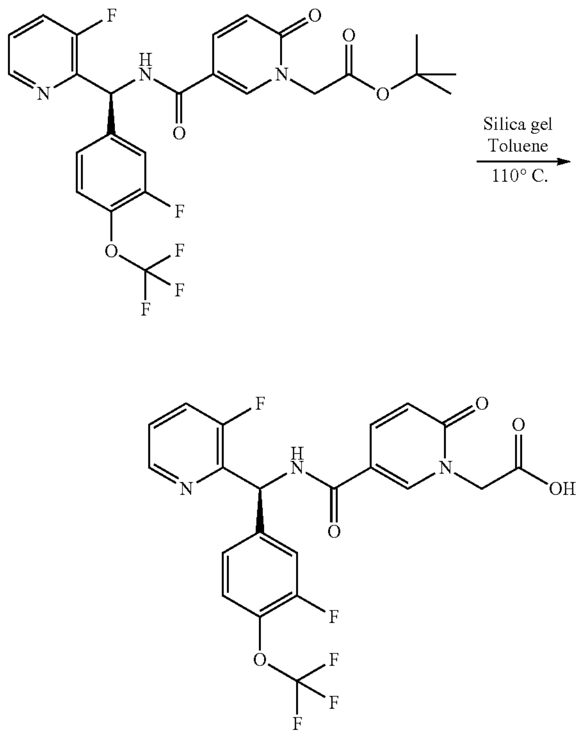

Example 428

(S)-2-(5-(((3-Fluoro-4-(trifluoromethoxy)phenyl)(3-fluoropyridin-2-yl)methyl)carbamoyl)-2-oxopyridin-1(2H)-yl)acetic acid

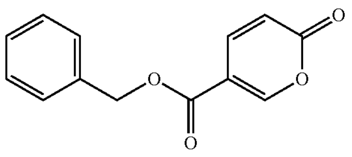 [SMILES: O=C(OCc1ccccc1)c1ccc(=O)oc1]

Step 1. Benzyl 2-oxo-2H-pyran-5-carboxylate

A solution of coumalic acid (1.2 g, 8.57 mmol) in DCM (20 mL) and THF (20 mL) was treated with 4-dimethylaminopyridine (0.105 g, 0.857 mmol). The reaction was stirred under nitrogen at 23° C. After 15 min, benzyl alcohol (0.886 mL, 8.57 mmol) and 1-(3-dimethylaminopropyl)-3-ethylcarbodiimide hydrochloride (1.642 g, 8.57 mmol) were added, and the stirring was continued. After 5 h, the solution was diluted with DCM (200 mL) and the mixture was washed with water (150 mL), dried over $MgSO_4$, concentrated in vacuo and purified by silica gel chromatography (eluent: 5-25% EtOAc/hexane), affording the title compound as a white solid. $^1H$ NMR (400 MHz, $CDCl_3$) δ ppm 8.32 (s, 1H), 7.80 (dd, J=9.78, 2.15 Hz, 1H), 7.33-7.48 (m, 5H), 6.33 (d, J=9.78 Hz, 1H), 5.31 (s, 2H). MS (ESI, positive ion) m/z: 231.1 (M+H).

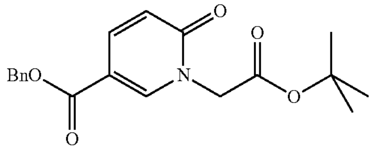 [SMILES: CC(C)(C)OC(=O)Cn1cc(C(=O)OCc2ccccc2)ccc1=O]

Step 2. Benzyl 1-(2-(tert-butoxy)-2-oxoethyl)-6-oxo-1,6-dihydropyridine-3-carboxylate A solution of benzyl 2-oxo-2H-pyran-5-carboxylate (906 mg, 3.94 mmol) and glycine tert butyl ester hydrochloride (726 mg, 4.33 mmol) in MeOH (20 mL) was treated with TEA (1.642 mL, 11.81 mmol). The reaction was stirred at 23° C. under nitrogen. After 1 h, the solution was concentrated in vacuo and purified by silica gel chromatography (eluent: 10-50% EtOAc/hexane), affording the title compound as a light yellow oil. $^1H$ NMR (400 MHz, $CDCl_3$) δ ppm 8.11 (d, J=2.35 Hz, 1H), 7.90 (dd, J=9.59, 2.54 Hz, 1H), 7.31-7.54 (m, 5H), 6.55 (d, J=9.59 Hz, 1H), 5.30 (s, 2H), 4.56 (s, 2H), 1.48 (s, 9H). MS (ESI, positive ion) m/z: 366.0 (M+H).

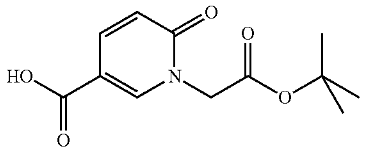 [SMILES: CC(C)(C)OC(=O)Cn1cc(C(=O)O)ccc1=O]

Step 3. 1-(2-(tert-Butoxy)-2-oxoethyl)-6-oxo-1,6-dihydropyridine-3-carboxylic acid A solution of benzyl 1-(2-(tert-butoxy)-2-oxoethyl)-6-oxo-1,6-dihydropyridine-3-carboxylate (924 mg, 2.69 mmol) in EtOAc (20 mL) and EtOH (5 mL) was treated with palladium 10 wt. % on activated carbon (143 mg, 0.135 mmol) under nitrogen. The reaction vessel was purged through 3 vacuum-hydrogen cycles, and was stirred under a hydrogen balloon at 23° C. After 45 min, the reaction was filtered through Celite® brand filter agent, the filter cake washed with MeOH (100 mL), the filtrates were combined and concentrated, affording the title compound as a white solid. $^1H$ NMR (400 MHz, DMSO-$d_6$) δ ppm 12.02-13.68 (br. s., 1H), 8.49 (br. s., 1H), 7.83 (d, J=9.39 Hz, 1H), 6.44 (d, J=9.19 Hz, 1H), 4.68 (br. s., 2H), 1.41 (s, 9H). MS (ESI, positive ion) m/z: 276.0 (M+H).

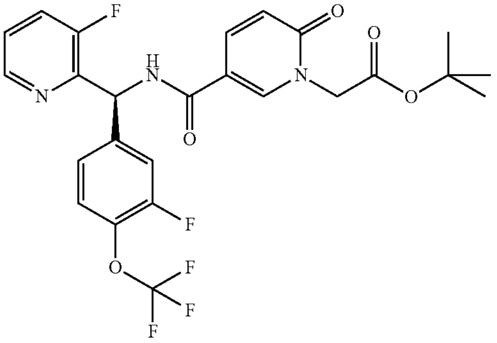 [SMILES: CC(C)(C)OC(=O)Cn1cc(C(=O)N[C@@H](c2ccc(OC(F)(F)F)c(F)c2)c2ncccc2F)ccc1=O]

Step 4. (S)-tert-Butyl 2-(5-(((3-fluoro-4-(trifluoromethoxy)phenyl)(3-fluoropyridin-2-yl)methyl)carbamoyl)-2-oxopyridin-1(2H)-yl)acetate A solution of (S)-(3-fluoro-4-(trifluoromethoxy)phenyl)(3-fluoropyridin-2-yl)methanamine hydrochloride (400 mg, 1.174 mmol, Intermediate 6), 1-(2-(tert-butoxy)-2-oxoethyl)-6-oxo-1,6-dihydropyridine-3-carboxylic acid (327 mg, 1.292 mmol) and HATU (491 mg, 1.292 mmol) in DMF (10 mL) was treated with TEA (0.490 mL, 3.52 mmol). The reaction was then stirred at 23° C. under nitrogen. After 17 h, the solution was diluted with EtOAc (100 mL) and washed with brine (100 mL), dried over $MgSO_4$, concentrated in vacuo and purified by silica gel chromatography (eluent: 5-30% EtOAc/DCM), affording the title compound as a colorless oil. The compound was taken forward to the next step. MS (ESI, positive ion) m/z: 540.2 (M+H).

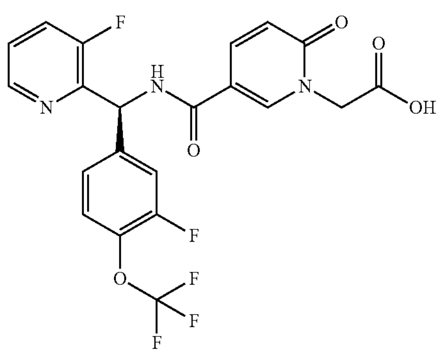 [SMILES: O=C(O)Cn1cc(C(=O)N[C@@H](c2ccc(OC(F)(F)F)c(F)c2)c2ncccc2F)ccc1=O]

Step 5. (S)-2-(5-(((3-Fluoro-4-(trifluoromethoxy)phenyl)(3-fluoropyridin-2-yl)methyl)carbamoyl)-2-oxopyridin-1(2H)-yl)acetic acid A mixture of (S)-tert-butyl 2-(5-(((3-fluoro-4-(trifluoromethoxy)phenyl)(3-fluoropyridin-2-yl)methyl)carbamoyl)-2-oxopyridin-1(2H)-yl)acetate (633 mg, 1.173 mmol) and silica gel 60 (70.5 mg, 1.173 mmol) in toluene (10 mL) was heated to 110° C. After 3 h, the reaction was cooled to 23° C. and filtered. The residue was washed with 10% MeOH/DCM (100 mL), and the filtrates were combined and concentrated affording the title compound as a tan solid. $^1H$ NMR (400 MHz, DMSO-$d_6$) δ ppm 9.08 (d, J=7.8 Hz, 1H), 8.44 (br. s., 2H), 7.87-8.02 (m, 1H), 7.76 (s, 1H), 7.42-7.63 (m, 3H), 7.34 (d, J=8.4 Hz, 1H), 6.66 (d, J=7.4 Hz, 1H), 6.41 (d, J=9.6 Hz, 1H), 4.57 (d, J=3.7 Hz, 2H). MS (ESI, positive ion) m/z: 484.1 (M+H).

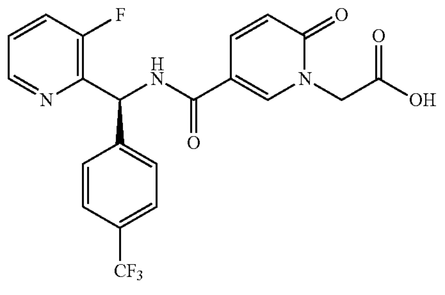 [SMILES: O=C(O)Cn1cc(C(=O)N[C@@H](c2ccc(C(F)(F)F)cc2)c2ncccc2F)ccc1=O]

Example 429

(S)-2-(5-(((3-Fluoropyridin-2-yl)(4-(trifluoromethyl)phenyl)methyl)carbamoyl)-2-oxopyridin-1(2H)-yl)acetic acid This compound was prepared by the same method as Example 428 employing amine intermediate 2 in Step 4. $^1H$ NMR (400 MHz, DMSO-$d_6$) δ ppm 9.10 (d, J=7.6 Hz, 1H), 8.45 (br. s., 2H), 7.94 (dd, J=9.4, 2.3 Hz, 1H), 7.67-7.83 (m, 3H), 7.61 (d, J=8.0 Hz, 2H), 7.47 (dt, J=8.5, 4.3 Hz, 1H), 6.71 (d, J=7.6 Hz, 1H), 6.40 (d, J=9.6 Hz, 1H), 4.54 (d, J=4.1 Hz, 2H). MS (ESI, positive ion) m/z: 450.0 (M+H).

Scheme 28

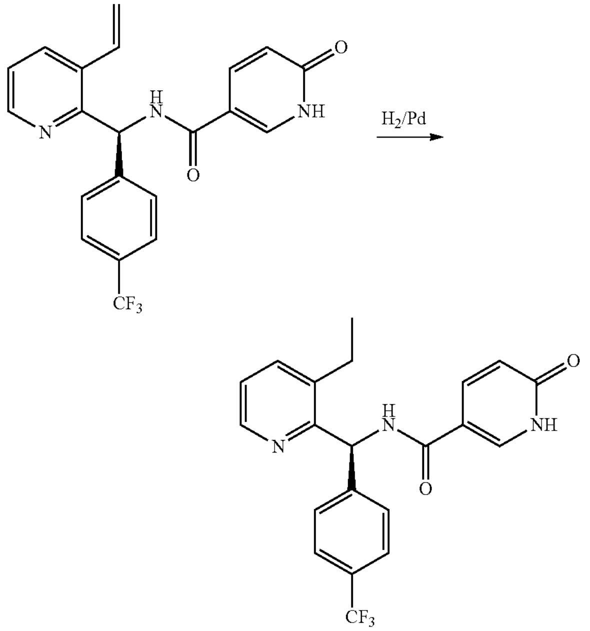

Example 430

(S)—N-((3-Ethylpyridin-2-yl)(4-(trifluoromethyl)phenyl)methyl)-6-oxo-1,6-dihydropyridine-3-carboxamide To a 100 mL round bottom flask containing (S)-6-oxo-N-((4-(trifluoromethyl)phenyl)(3-vinylpyridin-2-yl)methyl)-1,6-dihydropyridine-3-carboxamide (40 mg, 0.100 mmol, Example 363) was added EtOAc (20 mL). The resulting mixture was then stirred at 23° C. for 2 min. At this time, Pd/C (10%, 20 mg) was added before a balloon of hydrogen was bubbled through the mixture. The reaction was stirred for 2 h under hydrogen (1 atm) and was then filtered though a plug of Celite® brand filter agent and eluted with EtOAc (50 mL). The solvent was removed, and the material was placed on high vacuum for 1 h to give the title compound as a white solid. $^1H$ NMR (400 MHz, $CDCl_3$) δ ppm 8.67 (d, J=6.9 Hz, 1H), 8.53 (d, J=4.7 Hz, 1H), 8.07 (d, J=2.2 Hz, 1H), 7.94 (dd, J=9.6, 2.4 Hz, 1H), 7.36-7.67 (m, 5H), 7.27-7.36 (m, 1H), 6.60 (d, J=9.5 Hz, 1H), 6.50 (d, J=6.7 Hz, 1H), 2.63-2.82 (m, 1H), 2.36-2.62 (m, 1H), 1.11 (t, J=7.5 Hz, 3H). MS (ESI, positive ion) m/z: 402.1 (M+H).

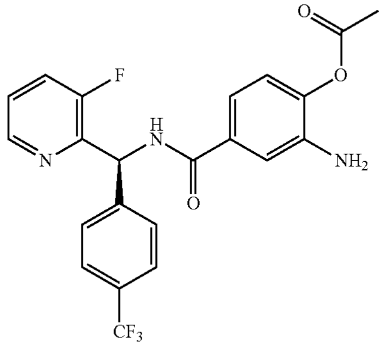 [SMILES: CC(=O)Oc1ccc(C(=O)N[C@@H](c2ccc(C(F)(F)F)cc2)c2ncccc2F)cc1N]

Example 431

(S)-2-Amino-4-(((3-fluoropyridin-2-yl)(4-(trifluoromethyl)phenyl)methyl)carbamoyl)phenyl acetate

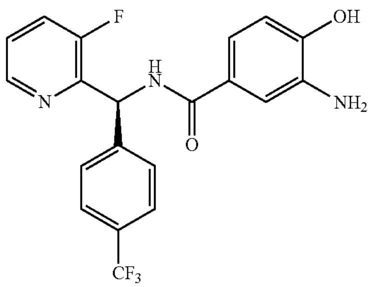 [SMILES: Nc1cc(C(=O)N[C@@H](c2ccc(C(F)(F)F)cc2)c2ncccc2F)ccc1O]

Step 1. (S)—N-((3-Fluoropyridin-2-yl)(4-(trifluoromethyl)phenyl)methyl)-4-hydroxy-3-nitrobenzamide To a solution of 4-hydroxy-3-nitrobenzoic acid (285 mg, 1.556 mmol) and DMF (5 mL), were added DIPEA (0.69 mL, 3.96 mmol) and HATU (612 mg, 1.611 mmol). After stirring for 45 min, (S)-(3-fluoropyridin-2-yl)(4-(trifluoromethyl)phenyl)methanamine hydrochloride (380 mg, 1.239 mmol, Intermediate 2) was added in one portion. The reaction was stirred at room temperature for 5 h and was then diluted with water (50 mL). The aqueous solution was extracted with EtOAc (3×20 mL). The combined EtOAc layers were concentrated in vacuo and adsorbed onto a plug of silica gel and chromatographed through a Redi-Sep® pre-packed silica gel column (12 g), eluting with 0 to 75% EtOAc in hexane, to provide the title compound as a yellow solid. MS (ESI pos. ion) m/z: 436.1 (M+H).

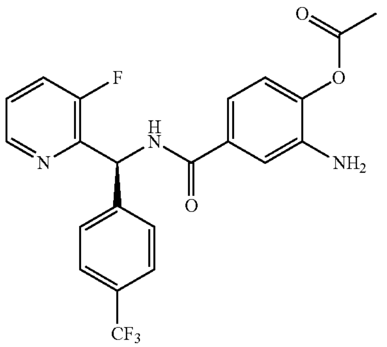 [SMILES: CC(=O)Oc1ccc(C(=O)N[C@@H](c2ccc(C(F)(F)F)cc2)c2ncccc2F)cc1N]

Step 2. (S)-4-(((3-Fluoropyridin-2-yl)(4-(trifluoromethyl)phenyl)methyl)carbamoyl)-2-nitrophenyl acetate To a solution of (S)—N-((3-fluoropyridin-2-yl)(4-(trifluoromethyl)phenyl)methyl)-4-hydroxy-3-nitrobenzamide (83 mg, 0.191 mmol) and DCM (5 mL) were added acetic anhydride (0.2 mL, 2.120 mmol) and DIPEA (0.15 mL, 0.861 mmol). After stirring for 45 min, the reaction was quenched with water and after stirring for 3 days, the aqueous solution was filtered to give the title compound as a yellow solid. The resulting product was used in the next step without further purification. MS (ESI pos. ion) m/z: 478.1 (M+H).

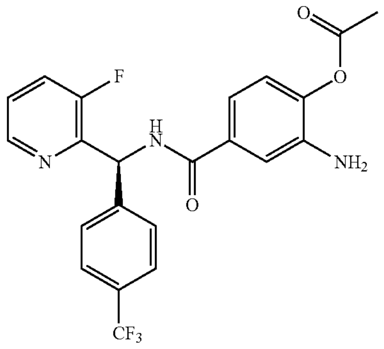 [SMILES: CC(=O)Oc1ccc(C(=O)N[C@@H](c2ccc(C(F)(F)F)cc2)c2ncccc2F)cc1N]

Step 3. (S)-2-Amino-4-(((3-fluoropyridin-2-yl)(4-(trifluoromethyl)phenyl)methyl)carbamoyl)phenyl acetate To a round bottom flask purged with $N_2$ was added 10% Pd/C (20.29 mg, 0.019 mmol) and under a $N_2$ atmosphere (S)-4-(((3-fluoropyridin-2-yl)(4-(trifluoromethyl)phenyl)methyl)carbamoyl)-2-nitrophenyl acetate (91 mg, 0.191 mmol) in EtOAc (10 mL) was added. The solution was purged for a further 2 min, then capped with a balloon of $H_2$. After 5 h, the reaction was filtered through a pad of Celite® brand filter agent and the Celite® brand filter agent rinsed with EtOAc. The filtrate was concentrated in vacuo and adsorbed onto a plug of silica gel and chromatographed through a Redi-Sep® pre-packed silica gel column (4 g), eluting with 0 to 75% EtOAc in hexane, to provide the title compound as a white solid. $^1$H NMR (300 MHz, $CDCl_3$) δ ppm 9.85 (s, 1H), 8.35-8.54 (m, 2H), 8.19 (s, 1H), 7.66 (d, J=2.2 Hz, 1H), 7.59 (dd, J=8.5, 2.0 Hz, 1H), 7.55 (s, 4H), 7.38-7.47 (m, 1H), 7.32 (dt, J=8.4, 4.3 Hz, 1H), 7.04 (d, J=8.3 Hz, 1H), 6.62 (dd, J=6.9, 2.0 Hz, 1H), 2.20 (s, 3H). MS (ESI pos. ion) m/z: 448.1 (M+H).

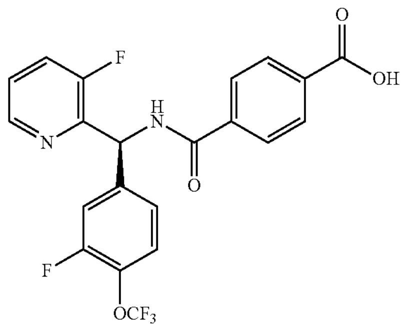 [SMILES: O=C(O)c1ccc(C(=O)N[C@@H](c2ccc(OC(F)(F)F)c(F)c2)c2ncccc2F)cc1]

Example 432

(S)-4-(((3-Fluoro-4-(trifluoromethoxy)phenyl)(3-fluoropyridin-2-yl)methyl)carbamoyl)benzoic acid

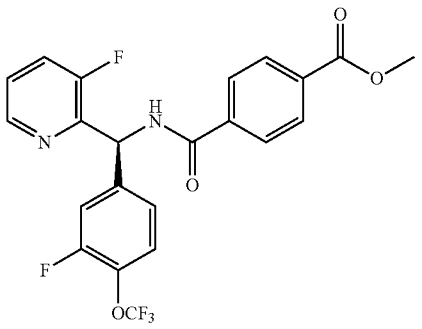 [SMILES: COC(=O)c1ccc(C(=O)N[C@@H](c2ccc(OC(F)(F)F)c(F)c2)c2ncccc2F)cc1]

Step 1. (S)-Methyl 4-(((3-fluoro-4-(trifluoromethoxy)phenyl)(3-fluoropyridin-2-yl)methyl)carbamoyl)benzoate To a solution of (S)-(3-fluoro-4-(trifluoromethoxy)phenyl)(3-fluoropyridin-2-yl)methanamine hydrochloride (100 mg, 0.294 mmol, Intermediate 6), 4-(methoxycarbonyl)benzoic acid (52.9 mg, 0.294 mmol), and DMF (2 mL) were added TEA (0.123 mL, 0.881 mmol) and 50% propylphosphonic anhydride in EtOAc (0.175 mL, 0.587 mmol). The solution was stirred at room temperature. After 2 h, the reaction was diluted with water (30 mL), stirred for 30 min, and then filtered. The solids were washed with water and dried in the funnel to give the title compound as a white solid. MS (ESI pos. ion) m/z: 467.0 (M+H).

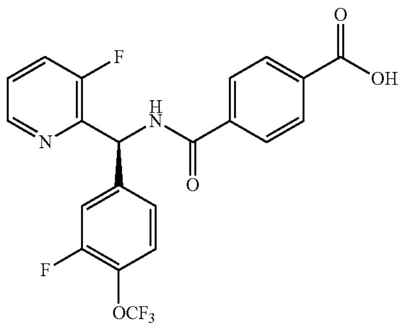 [SMILES: O=C(O)c1ccc(C(=O)N[C@@H](c2ccc(OC(F)(F)F)c(F)c2)c2ncccc2F)cc1]

Step 2. (S)-4-(((3-Fluoro-4-(trifluoromethoxy)phenyl)(3-fluoropyridin-2-yl)methyl)carbamoyl)benzoic acid To a solution of (S)-methyl 4-(((3-fluoro-4-(trifluoromethoxy)phenyl)(3-fluoropyridin-2-yl)methyl)carbamoyl)benzoate (105 mg, 0.225 mmol) and THF (2 mL):MeOH (1 mL) was added 1M LiOH (1 mL). The solution was stirred at room temperature. After 16 h, the reaction was diluted with water. The aqueous solution was acidified with 1 N HCl to a pH of 7 and extracted with EtOAc (3×15 mL). The combined EtOAc layers were dried over $MgSO_4$ and concentrated in vacuo to give the title compound as a white solid. $^1$H NMR (300 MHz, MeOH-d4) δ ppm 8.49 (d, J=4.7 Hz, 1H), 8.06-8.15 (m, J=8.5 Hz, 2H), 7.89-8.00 (m, J=8.5 Hz, 2H), 7.64 (t, J=9.1 Hz, 1H), 7.31-7.51 (m, 4H), 6.70 (s, 1H). MS (ESI pos. ion) m/z: 453.0 (M+H).

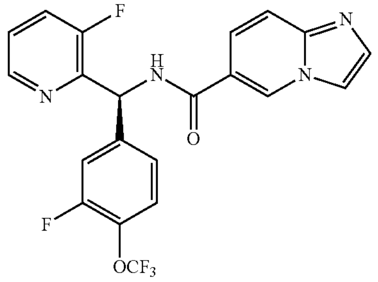 [SMILES: O=C(N[C@@H](c1ccc(OC(F)(F)F)c(F)c1)c1ncccc1F)c1ccc2nccn2c1]

Example 433

(S)—N-((3-Fluoro-4-(trifluoromethoxy)phenyl)(3-fluoropyridin-2-yl)methyl)imidazo[1,2-a]pyridine-6-carboxamide To a solution of (S)-(3-fluoro-4-(trifluoromethoxy)phenyl)(3-fluoropyridin-2-yl)methanamine hydrochloride (81 mg, 0.238 mmol, Intermediate 6) and EtOAc (3 mL) was added 50% propylphosphonic anhydride in EtOAc (0.28 mL, 0.470 mmol), imidazo[1,2-a]pyridine-6-carboxylic acid (47 mg, 0.290 mmol) and DIPEA (0.12 mL, 0.689 mmol). The solution was stirred at room temperature. After 16 h, the reaction product was adsorbed onto a plug of silica gel and chromatographed through a Redi-Sep® pre-packed silica gel column (4 g), eluting with 0 to 100% EtOAc in hexane, to provide the title compound as a white solid. $^1$H NMR (300 MHz, MeOH-d4) δ ppm 9.06-9.16 (m, 1H), 8.44-8.55 (m, 1H), 7.96 (s, 1H), 7.76 (dd, J=9.5, 1.8 Hz, 1H), 7.56-7.71 (m, 3H), 7.42-7.51 (m, 2H), 7.32-7.42 (m, 2H), 6.68-6.76 (m, 1H). MS (ESI pos. ion) m/z: 449.0 (M+H).

Scheme 29

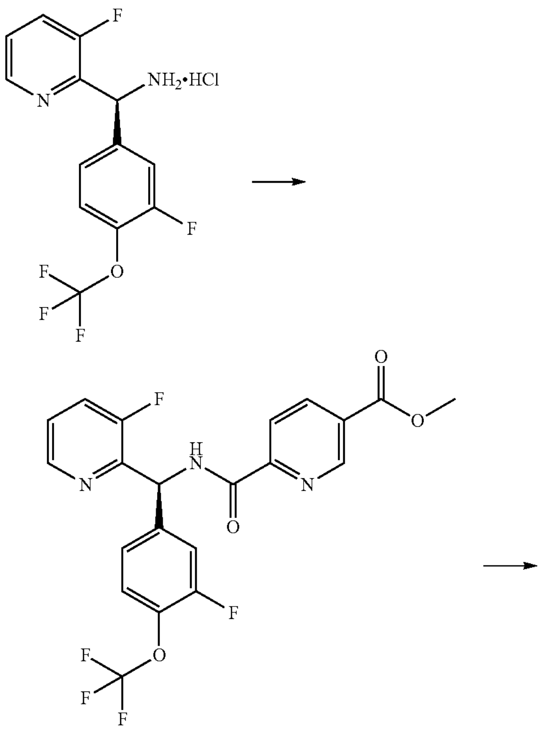

-continued

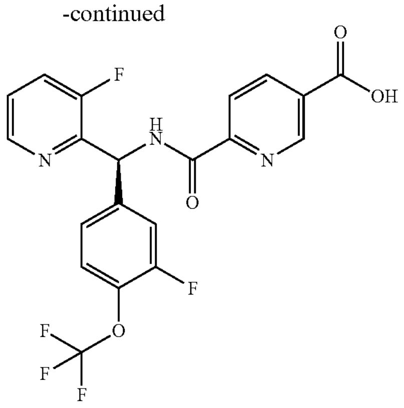

Example 434

(S)-6-(((3-Fluoro-4-(trifluoromethoxy)phenyl)(3-fluoropyridin-2-yl)methyl)carbamoyl)nicotinic acid

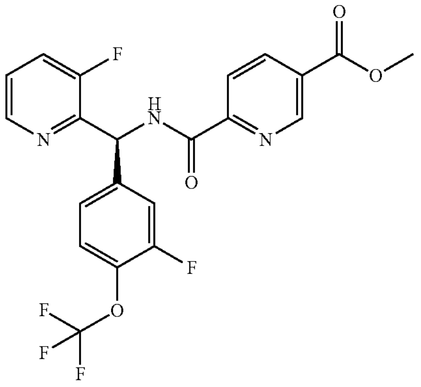 [SMILES: COC(=O)c1ccc(C(=O)N[C@@H](c2ccc(OC(F)(F)F)c(F)c2)c2ncccc2F)nc1]

Step 1. (S)-Methyl 6-(((3-fluoro-4-(trifluoromethoxy)phenyl)(3-fluoropyridin-2-yl)methyl)carbamoyl)nicotinate To a solution of (S)-(3-fluoro-4-(trifluoromethoxy)phenyl)(3-fluoropyridin-2-yl)methanamine hydrochloride (17.0 g, 49.9 mmol, Intermediate 6) in DMF (166 mL, Aldrich) was added 5-(methoxycarbonyl)pyridine-2-carboxylic acid (9.94 g, 54.9 mmol, Oakwood Products, Inc.), HATU (20.87 g, 54.9 mmol, Accela ChemBio, Inc.), and DIPEA (18.23 mL, 105 mmol, EMD Biosciences, Inc.). The resulting mixture was then stirred at room temperature for 18 h. Water (400 mL) was then added and the mixture was extracted with EtOAc (2×200 mL). The combined organic extracts were dried over $MgSO_4$ and concentrated in vacuo. The residue was then dissolved in MeOH (500 mL) and silica gel was added. The mixture was concentrated and dried in vacuo. The solid mixture was purified by silica gel flash column chromatography using ISCO instrument (solid loading, 0-100% EtOAc/hexane) to give the title compound as a white solid. MS (ESI, positive ion) m/z: 468 (M+H).

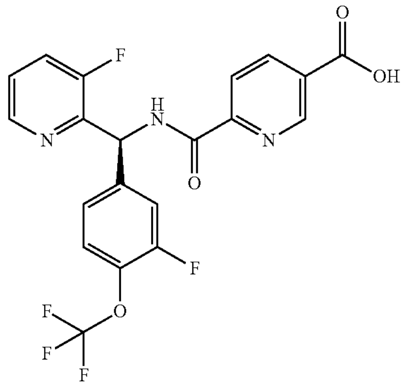 [SMILES: O=C(O)c1ccc(C(=O)N[C@@H](c2ccc(OC(F)(F)F)c(F)c2)c2ncccc2F)nc1]

Step 2. (S)-6-(((3-Fluoro-4-(trifluoromethoxy)phenyl)(3-fluoropyridin-2-yl)methyl)carbamoyl)nicotinic acid To a solution of (S)-methyl 6-(((3-fluoro-4-(trifluoromethoxy)phenyl)(3-fluoropyridin-2-yl)methyl)carbamoyl)nicotinate (11.5 g, 24.61 mmol) in MeOH (140 mL, Aldrich) was added lithium hydroxide hydrate (2.065 g, 49.2 mmol, Aldrich). The mixture was stirred at room temperature for 5 min followed by the addition of THF (5 mL, Aldrich) and the mixture was stirred at room temperature for 1 h. The mixture was concentrated in vacuo, cooled to 0° C. and was adjusted to pH=6-7 with concentrated HCl. EtOAc (300 mL) was added to the adjusted pH mixture, and the resulting mixture was stirred at room temperature for 15 min. The organic layer was collected and the aqueous phase was extracted with EtOAc (1×200 mL). The combined organic layers were dried over $MgSO_4$ and concentrated in vacuo. The residue was then dissolved in MeOH (400 mL) and silica gel was added. The mixture was concentrated and dried in vacuo. The solid mixture was then purified by silica gel flash column chromatography using ISCO instrument (solid loading, 40% EtOAc/hexane, then 10% MeOH in EtOAc) to give the title compound as a white solid. $^1H$ NMR (400 MHz, DMSO-$d_6$) δ ppm 13.75 (br. s., 1H), 9.85 (d, J=7.4 Hz, 1H), 9.18 (d, J=1.4 Hz, 1H), 8.58 (d, J=4.7 Hz, 1H), 8.48 (dd, J=8.1, 2.1 Hz, 1H), 8.16 (d, J=8.0 Hz, 1H), 7.83 (t, J=9.3 Hz, 1H), 7.50-7.61 (m, 3H), 7.36 (d, J=8.4 Hz, 1H), 6.58 (d, J=7.2 Hz, 1H). MS (ESI, positive ion) m/z: 454.0 (M+H)

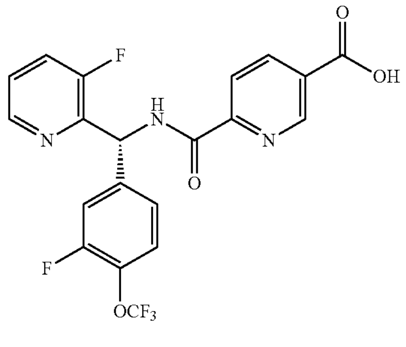 [SMILES: O=C(O)c1ccc(C(=O)N[C@H](c2ccc(OC(F)(F)F)c(F)c2)c2ncccc2F)nc1]

Example 435

(R)-6-(((3-Fluoro-4-(trifluoromethoxy)phenyl)(3-fluoropyridin-2-yl)methyl)carbamoyl)nicotinic acid This compound was prepared using the same procedure as example 434, except the use of Intermediate 6b in Step 1. The compound was purified via preparative SFC [using a Chiralpak AS-H column (250×21 mm, 5 μm); mobile phase 92:8 liquid $CO_2$: EtOH with 0.2% diethylamine at a flow rate of 70 mL/min] resulting in Peak 1 and 2 fractions with enantiomeric excess >99%. Peak 2 correlates with the (S) enantiomer (example 434), peak 1 was assigned as the (R) enantiomer. $^1$H NMR (400 MHz, DMSO-$d_6$) δ ppm 9.78 (d, J=7.6 Hz, 1H), 9.05 (s, 1H), 8.59 (d, J=4.7 Hz, 1H), 8.31 (dd, J=7.9, 1.7 Hz, 1H), 8.00 (d, J=7.8 Hz, 1H), 7.82 (t, J=9.2 Hz, 1H), 7.49-7.61 (m, 3H), 7.35 (d, J=8.6 Hz, 1H), 6.57 (d, J=7.0 Hz, 1H). MS (ESI, positive ion) m/z: 454.1 (M+H)

Scheme 30

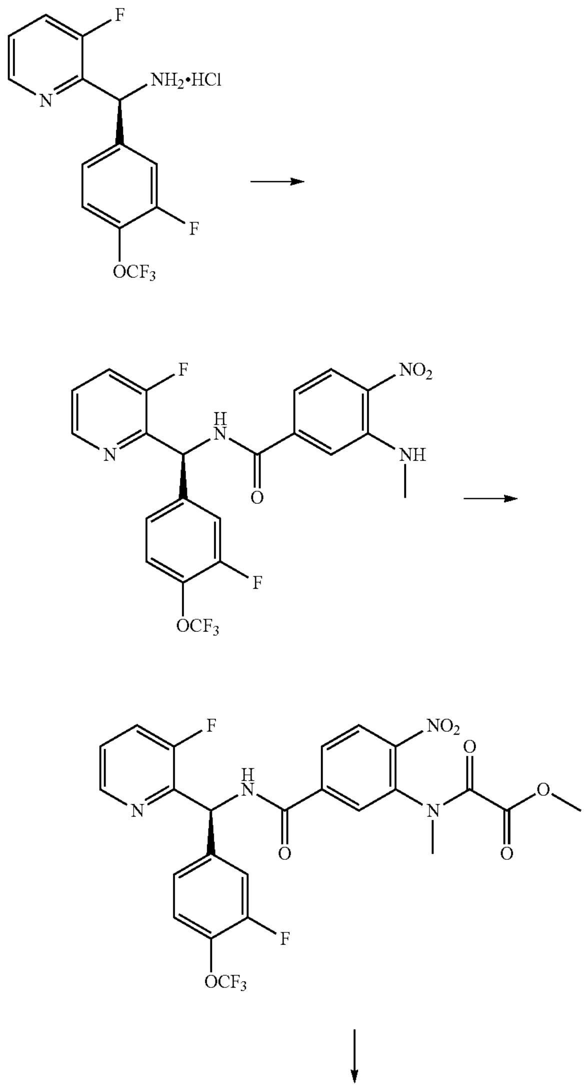

-continued

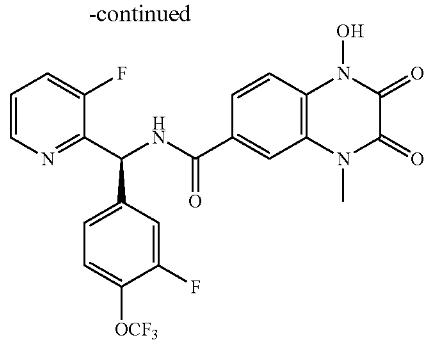

Example 436

(S)—N-((3-Fluoro-4-(trifluoromethoxy)phenyl)(3-fluoropyridin-2-yl)methyl)-1-hydroxy-4-methyl-2,3-dioxo-1,2,3,4-tetrahydroquinoxaline-6-carboxamide

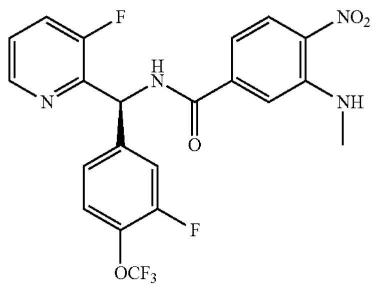 [SMILES: CNc1cc(C(=O)N[C@@H](c2ccc(OC(F)(F)F)c(F)c2)c2ncccc2F)ccc1[N+](=O)[O-]]

Step 1. (S)—N-((3-Fluoro-4-(trifluoromethoxy)phenyl)(3-fluoropyridin-2-yl)methyl)-3-(methylamino)-4-nitrobenzamide To a solution of (S)-(3-fluoro-4-(trifluoromethoxy)phenyl)(3-fluoropyridin-2-yl)methanamine hydrochloride (1.0 g, 2.94 mmol, intermediate 6) in DMF (20 mL, Aldrich) was added 3-fluoro-4-nitrobenzenecarboxylic acid (0.543 g, 2.94 mmol, Bionet Research (A Trading Division of Key Organics Ltd)), HATU (1.228 g, 3.23 mmol, Oakwood Products, Inc.), and DIPEA (1.123 mL, 6.46 mmol, EMD Biosciences, Inc.). The resulting mixture was then stirred at room temperature for 1 h. The mixture was transferred to a pressure tube, and methylamine, 2.0M solution in THF (7.34 mL, 14.68 mmol, Aldrich) and DIPEA (1.123 mL, 6.46 mmol, EMD Biosciences, Inc.) were added. The resulting mixture was heated at 55° C. for 18 h, then cooled to room temperature. Water (150 mL) was added and the mixture was extracted with EtOAc (2×150 mL). The combined organic extracts were dried over $MgSO_4$ and concentrated in vacuo. The residue was dissolved in DCM and the solution mixture was purified by silica gel flash column chromatography using ISCO instrument (0-100% EtOAc/hexane) to give the title compound as a yellow solid. MS (ESI, positive ion) m/z: 483 (M+H).

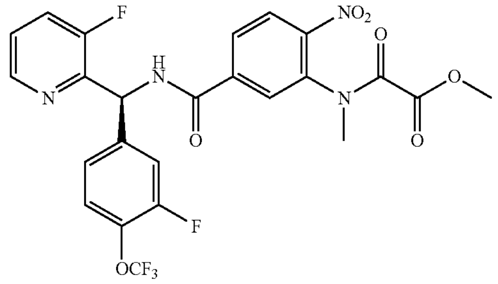 [SMILES: COC(=O)C(=O)N(C)c1cc(C(=O)N[C@@H](c2ccc(OC(F)(F)F)c(F)c2)c2ncccc2F)ccc1[N+](=O)[O-]]

Step 2. (S)-Methyl 2-((5-(((3-fluoro-4-(trifluoromethoxy)phenyl)(3-fluoropyridin-2-yl)methyl)carbamoyl)-2-nitrophenyl)(methyl)amino)-2-oxoacetate To a solution of (S)—N-((3-fluoro-4-(trifluoromethoxy)phenyl)(3-fluoropyridin-2-yl)methyl)-3-(methylamino)-4-nitrobenzamide (1.28 g, 2.65 mmol) and DIPEA (0.462 mL, 2.65 mmol, EMD Biosciences, Inc.) in DCM (7 mL, Aldrich) at 0° C. was added methyl chloro oxoacetate (0.268 mL, 2.92 mmol, Aldrich) in a drop-wise fashion. The resulting mixture was stirred at 0° C. for 2 h. Water (20 mL) was added, and the mixture was stirred at room temperature for 5 min. The organic layer was collected, and the aqueous layer was extracted with EtOAc (1×20 mL). The combined organic layers were dried over $MgSO_4$ and concentrated in vacuo. The residue was dissolved in DCM, and the mixture was purified by silica gel column chromatography using ISCO instrument (35-100% EtOAc/hexane) to give the title compound as a yellow solid. MS (ESI, positive ion) m/z: 569 (M+H).

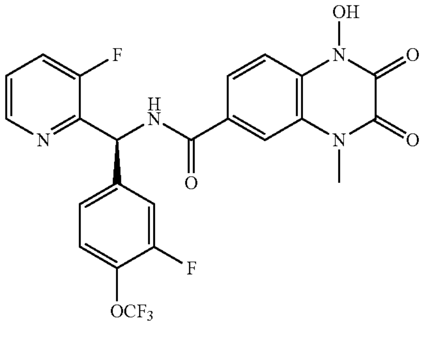 [SMILES: Cn1c(=O)c(=O)n(O)c2ccc(C(=O)N[C@@H](c3ccc(OC(F)(F)F)c(F)c3)c3ncccc3F)cc21]

Step 3. (S)—N-((3-Fluoro-4-(trifluoromethoxy)phenyl)(3-fluoropyridin-2-yl)methyl)-1-hydroxy-4-methyl-2,3-dioxo-1,2,3,4-tetrahydroquinoxaline-6-carboxamide To a solution of (S)-methyl 2-((5-(((3-fluoro-4-(trifluoromethoxy)phenyl)(3-fluoropyridin-2-yl)methyl)carbamoyl)-2-nitrophenyl)(methyl)amino)-2-oxoacetate (0.500 g, 0.880 mmol) in MeOH (3 mL, Aldrich), was added palladium, 10 wt. % (dry basis) on activate carbon, wet, degussa type (0.047 g, 0.440 mmol, Aldrich). The resulting mixture was stirred at room temperature under hydrogen (balloon) for 4 h. The mixture was filtered through celite and the celite was washed with MeOH (2×10 mL). The combined filtrates were concentrated in vacuo. Dioxane (3.00 mL, Aldrich) and water (1 mL) were added, followed by potassium phosphate (0.560 g, 2.64 mmol, Strem Chemical). The mixture was heated at 90° C. for 18 h. The mixture was then cooled to room temperature and filtered. The solid was washed with water (2×30 mL) and dried in vacuo to afford the title compound as a yellow solid. $^1$H NMR (400 MHz, DMSO-$d_6$) δ ppm 9.37 (d, J=7.8 Hz, 1H), 8.47 (d, J=4.5 Hz, 1H), 7.93 (br. s., 1H), 7.74-7.84 (m, 3H), 7.55-7.67 (m, 2H), 7.50 (dt, J=8.5, 4.3 Hz, 1H), 7.40 (d, J=8.4 Hz, 1H), 6.78 (d, J=7.8 Hz, 1H), 3.52-3.66 (m, 3H). MS (ESI, positive ion) m/z: 523 (M+H).

Scheme 31

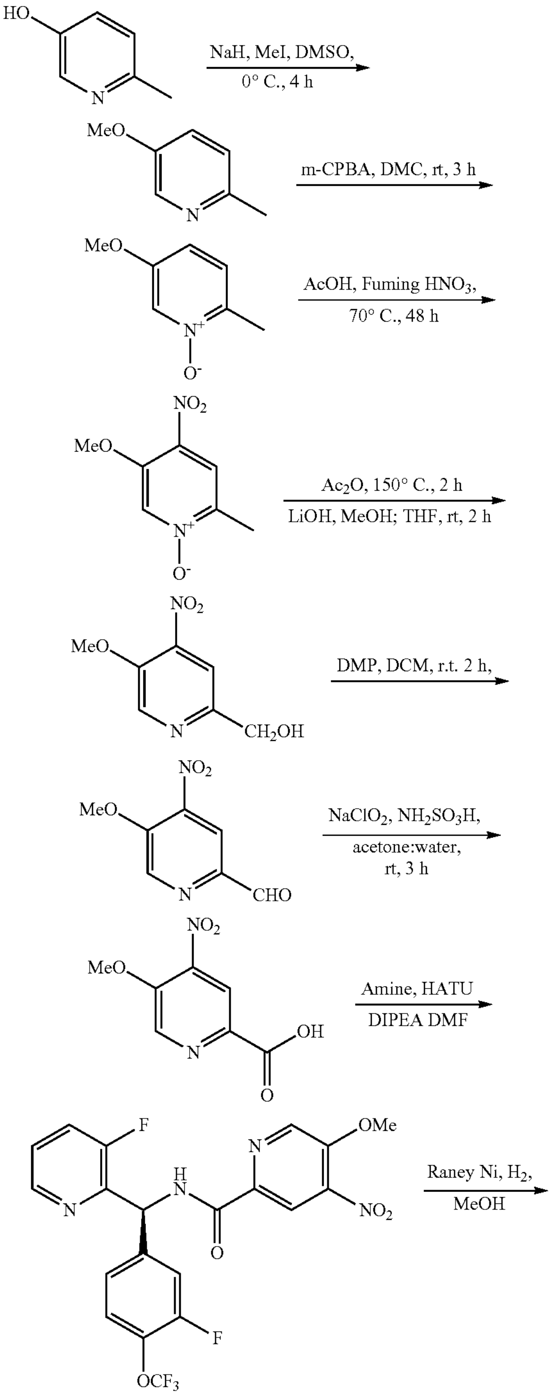

-continued

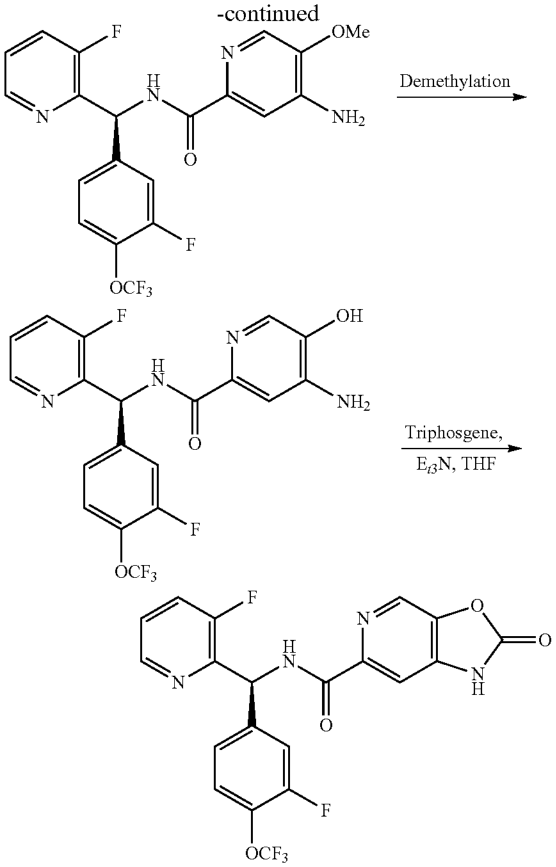

Example 437

(S)—N-((3-Fluoro-4-(trifluoromethoxy)phenyl)(3-fluoropyridin-2-yl)methyl)-2-oxo-1,2-dihydrooxazolo[5,4-c]pyridine-6-carboxamide

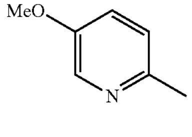

Step 1. 5-Methoxy-2-methylpyridine

To a stirred solution of 60% NaH (in mineral oil) (18.27 g, 0.458 mol, Aldrich, India) in DMSO (66 mL, Spectrochem., India) at 0° C., was added 6-methylpyridin-3-ol (25.0 g, 0.229 mol) dissolved in DMSO (100 mL) drop wise over a period of 15 min. After complete addition, the reaction mixture was stirred at 0° C. for 40 min. Methyl iodide (29.5 mL, 0.458 mol, Spectrochem, India) was added and the reaction mixture was stirred at rt for 2 h. The reaction with water and $Et_2O$ (1:1, 200 mL). The organic layer was separated and aqueous layer was back extracted with $Et_2O$ (75 mL×3). The organic layers were combined, dried over anhydrous sodium sulfate and concentrated to give the title compound as a dark brown gummy oil. $^1H$ NMR (400 MHz, $CDCl_3$) δ ppm 8.19 (d, J=2.8 Hz, 1H), 7.12-7.05 (m, 2H), 3.83 (s, 3H), 2.49 (s, 3H). MS (ESI, positive ion) m/z: 124.0 (M+H).

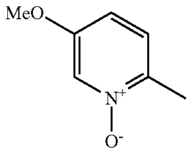

Step 2. 5-Methoxy-2-methylpyridine 1-oxide

To a stirred solution of 5-methoxy-2-methylpyridine (15 g, 0.121 mol) in DCM (200 mL) was added 3-chloro peroxybenzoic acid (23.14 g, 0.134 mol, Aldrich). The reaction was stirred at rt for 3 h. Reaction progress was monitored by TLC (50% EtOAc in petroleum ether). After completion of reaction, the reaction mixture was concentrated under reduced pressure providing the product as a yellow oil. The oil was dissolved in EtOAc (50 mL) and passed through a silica gel plug (60-120 mesh) and the plug eluted with 10% MeOH in $CHCl_3$ to give the title compound as a colorless liquid. $^1H$ NMR (400 MHz, DMSO-$d_6$) δ ppm 8.08 (d, J=2.4 Hz, 1H), 7.37 (d, J=8.7 Hz, 1H), 6.98 (dd, J=2.7 and 8.7 Hz, 1H), 3.78 (s, 3H), 2.26 (s, 3H). MS (ESI, positive ion) m/z: 140.0 (M+H).

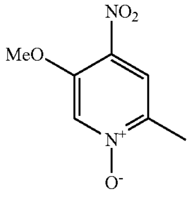

Step 3. 5-Methoxy-2-methyl-4-nitropyridine 1-oxide

To fuming nitric acid (20 mL, Spectrochem, India) was added (5-methoxy-2-methylpyridine 1-oxide (14 g, 0.100 mol) in one lot and the reaction was stirred at rt for 2 h. Reaction progress was monitored by TLC (50% EtOAc in pet ether.). After completion of the reaction, the reaction mixture was poured in to ice water (100 mL) and neutralized with 40% NaOH solution (PH~7-7.5) to get a yellow precipitate. The precipitate was stirred for 5-10 min, then filtered and dried to give the title compound as a yellow solid. $^1H$ NMR (400 MHz, DMSO-$d_6$) δ ppm 8.51 (s, 1H), 8.21 (s, 1H), 3.95 (s, 3H), 2.31 (s, 3H). MS (ESI, positive ion) m/z: 184.8 (M+H).

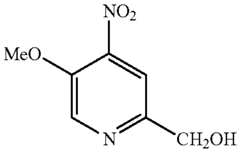 [SMILES: COc1cnc(CO)cc1[N+](=O)[O-]]

Step 4. (5-Methoxy-4-nitropyridin-2-yl) methanol

5-Methoxy-2-methyl-4-nitropyridine 1-oxide (7 g, 0.038 mol) was dissolved in acetic anhydride (70 mL, Sdfine, India) and the resulting solution was stirred for 3 h at 150° C. The reaction mixture was concentrated and $Et_2O$ (250 mL) was added to the residue and it was neutralized with sat'd $NaHCO_3$ (100 mL). The organic layer was separated and dried over anhydrous sodium sulfate, concentrated to afford a pale yellow solid which was dissolved in MeOH and THF (100 mL) and treated with LiOH (2.73 g, 0.113 mol). The reaction mixture was stirred for 2 h at rt. The progress of the reaction was monitored by TLC (5% MeOH in $CHCl_3$). After completion of acetate hydrolysis, sat $NH_4Cl$ (20 mL) was added and the product was extracted with EtOAc. The organic layer was dried over anhydrous sodium sulfate and concentrated under reduced pressure to afford the title compound as an off white solid. $^1H$ NMR (400 MHz, DMSO-$d_6$) δ ppm 8.71 (s, 1H), 7.81 (s, 1H), 5.62 (t, J=5.7 Hz, 1H), 4.59 (d, J=6 Hz, 2H), 4.04 (s, 3H). MS (ESI, positive ion) m/z: 185.1 (M+H).

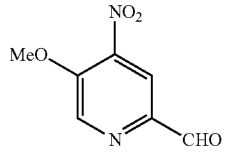 [SMILES: COc1cnc(C=O)cc1[N+](=O)[O-]]

Step 5. 5-Methoxy-4-nitropicolinaldehyde

To a stirred solution of (5-methoxy-4-nitropyridin-2-yl) methanol (4 g, 0.021 mol) in DCM (30 mL), was added Dess-Martin Periodinane (18.43 g, 0.043 mol, Spectrochem, India) and reaction was stirred for 3 h at rt. The reaction progress was monitored by TLC (50% EtOAc in petroleum ether). After completion of the reaction, sat'd $NaHCO_3$ (20 mL) was added and the product was extracted with DCM (3×25 mL). The combined organic layers were dried over anhydrous sodium sulfate and concentrated to give the title compound as a pale yellow solid. $^1H$ NMR (400 MHz, DMSO-$d_6$) δ ppm 9.95 (s, 1H), 9.02 (s, 1H), 8.36 (s, 1H), 4.19 (s, 3H). MS (ESI, positive ion) m/z: 182.9 (M+H).

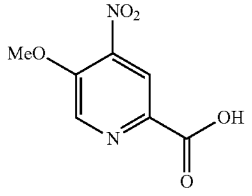 [SMILES: COc1cnc(C(=O)O)cc1[N+](=O)[O-]]

Step 6. 5-Methoxy-4-nitropicolinic acid

To a stirred solution of 5-methoxy-4-nitropicolinaldehyde (4 g, 0.02 mol) in acetone and water (1:1,100 mL) was added sodium chlorite (5.9 g, 0.065 mol, spectrochem, india) and sulfamic acid (6.3 g, 0.065 mol, Rankem, India) and the reaction mixture was stirred for 1 h at rt. Reaction progress was monitored by TLC (50% EtOAc in petroleum ether). After completion, the reaction mixture was concentrated to get a white precipitate which was filtered and dried to afford the title compound as a white solid. $^1H$ NMR (400 MHz, DMSO-$d_6$) δ ppm 13.6 (brs, 1H) 8.90 (s, 1H), 8.41 (s, 1H), 4.15 (s, 3H). MS (ESI, positive ion) m/z: 197.8 (M+H).

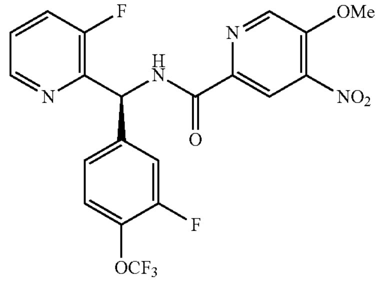

Step 7. (S)—N-((3-Fluoro-4-(trifluoromethoxy)phenyl)(3-fluoropyridin-2-yl)methyl)-5-methoxy-4-nitropicolinamide To a stirred solution of 5-methoxy-4-nitropicolinic acid (1 g, 0.005 mol) in DMF (10 mL) were added (S)-(3-fluoro-4-(trifluoromethoxy)phenyl)(3-fluoropyridin-2-yl)methanamine hydrochloride (1.8 g, 0.0055 mol, Intermediate 6), HATU (2.8 g, 0.0075 mol, molekula, India) and DIPEA (2.4 g, 0.02 mol, Aldrich). The reaction mixture was stirred for 12 h at rt. The reaction progress was monitored by TLC (50% EtOAc in pet ether). After completion of reaction, water (10 mL) was added and product was extracted with EtOAc (50 mL×3) and concentrated to get initial product. The product thus obtained was purified by column chromatography, silica gel (60-120 mesh), using 80-100% EtOAc in petroleum ether as the eluent to give the title compound. $^1H$ NMR (400 MHz, DMSO-$d_6$) δ ppm 9.74 (d, J=7.6 Hz, 1H), 8.94 (s, 1H), 8.56 (d, J=4.8 Hz, 1H), 8.38 (s, 1H), 7.82 (t, J=8.8 Hz, 1H), 7.57-7.53 (m, 3H), 7.35 (d, J=8.8 Hz, 1H), 6.55 (d, J=7.2 Hz, 1H), 4.16 (s, 3H). MS (ESI, positive ion) m/z: 485.1 (M+H).

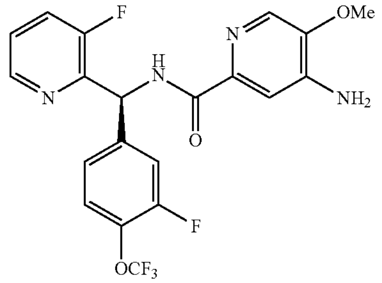 [SMILES: COc1cnc(C(=O)N[C@@H](c2ccc(OC(F)(F)F)c(F)c2)c2ncccc2F)cc1[N+](=O)[O-]]

Step 8. (S)-4-Amino-N-((3-fluoro-4-(trifluoromethoxy)phenyl) (3-fluoropyridin-2-yl)methyl)-5-methoxypicolinamide To a stirred suspension of Raney Nickel (0.4 g, Monarch, India) in MeOH (10 mL) was added (S)—N-((3-fluoro-4-(trifluoromethoxy)phenyl)(3-fluoropyridin-2-yl)methyl)-5-methoxy-4-nitropicolinamide (700 mg, 0.0014 mol) at rt. The reaction mixture was stirred under a hydrogen balloon for 2 h. After completion of the reaction, monitored by TLC (TLC eluent: 50% EtOAc in petroleum ether), the reaction mixture was filtered through Celite® brand filter agent and concentrated. The resulting product was triturated with petroleum ether to give the title compound as a white solid. MS (ESI, positive ion) m/z: 455.2 (M+H).

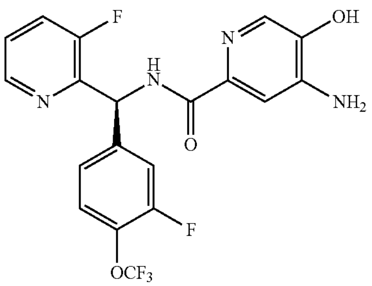

Step 9. (S)-4-Amino-N-((3-fluoro-4-(trifluoromethoxy)phenyl)(3-fluoropyridin-2-yl)methyl)-5-hydroxypicolinamide To a stirred solution of (S)-4-amino-N-((3-fluoro-4-(trifluoromethoxy)phenyl) (3-fluoropyridin-2-yl)methyl)-5-methoxypicolinamide (600 mg, 0.0013 mol) in NMP (10 mL) was added LiCl (168 mg, 0.0039 mol, Aldrich) followed by pTSA (754 mg, 0.0039 mol, Aldrich) at rt. The reaction mixture was stirred at 180° C. for 2 h. After completion of the reaction (monitored by TLC, 50% EtOAc in petroleum ether), the reaction mixture was cooled to room temperature and sat'd $NaHCO_3$ (50 mL) was added and the aqueous solution was extracted with EtOAc (25 mL×2). The combined organic layers were washed with water (25 mL×2), saturated NaCl (25 mL) and dried over anhydrous sodium sulfate. The product thus obtained was purified by silica gel (60-120 mesh) column chromatography eluting with 60-70% EtOAc in petroleum ether to give the title compound as an off-white solid. $^1H$ NMR (400 MHz, DMSO-$d_6$) δ ppm 9.90 (s, 1H), 9.51 (d, J=8 Hz, 1H), 8.55 (d, J=4.8 Hz, 1H), 7.82-7.78 (m, 2H), 7.56-7.50 (m, 2H), 7.46 (d, J=1.6 Hz, 10.4 Hz, 1H), 7.30 (d, J=12.8, 2H), 6.48 (d, J=4.4 Hz, 1H), 5.78 (s, 2H). MS (ESI, positive ion) m/z: 441.3 (M+H).

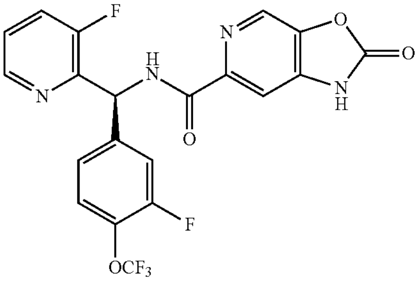 [SMILES: O=C(N[C@@H](c1ccc(OC(F)(F)F)c(F)c1)c1ncccc1F)c1cc2[nH]c(=O)oc2cn1]

Step 10. (S)—N-((3-Fluoro-4-(trifluoromethoxy)phenyl)(3-fluoropyridin-2-yl)methyl)-2-oxo-1,2-dihydrooxazolo[5,4-c]pyridine-6-carboxamide To a cooled (−78° C.) stirred mixture of (S)-4-amino-N-((3-fluoro-4-(trifluoromethoxy)phenyl)(3-fluoropyridin-2-yl)methyl)-5-hydroxypicolinamide (200 mg, 0.00045 mol) in THF (5 mL) were added TEA (0.31 mL, 0.002 mol, Spectrochem, India) and triphosgene (270 mg, 0.0009 mol, Spectrochem, India) in one lot and the reaction mixture was stirred for 2 h at the same temperature, warmed to rt and stirred for 12 h. After completion of the reaction (monitored by TLC, 50% EtOAc in hexane), the reaction mixture was quenched with sat'd $NaHCO_3$ (5 mL), extracted with EtOAc (10 mL×3). The organic layers were combined and dried over anhydrous sodium sulfate and concentrated. The product thus obtained was purified by column chromatography, silica gel (60-120 mesh) using 50-60% EtOAc in petroleum ether as the eluent, and further purified using Prep TLC plates, mobile phase 50% EtOAc in hexanes to give the title compound. $^1H$ NMR (400 MHz, DMSO-$d_6$) δ ppm 9.76 (d, J=7.6 Hz, 1H), 8.60 (s, 1H), 8.58 (d, J=4.8 Hz, 1H), 7.82 (t, J=8.8 Hz, 1H), 7.70 (s, 1H), 7.56-7.50 (m, 3H), 7.34 (d, J=8.4 Hz, 1H), 6.53 (d, J=6.8 Hz, 1H). MS (ESI, positive ion) m/z: 468.0 (M+H).

Scheme 32

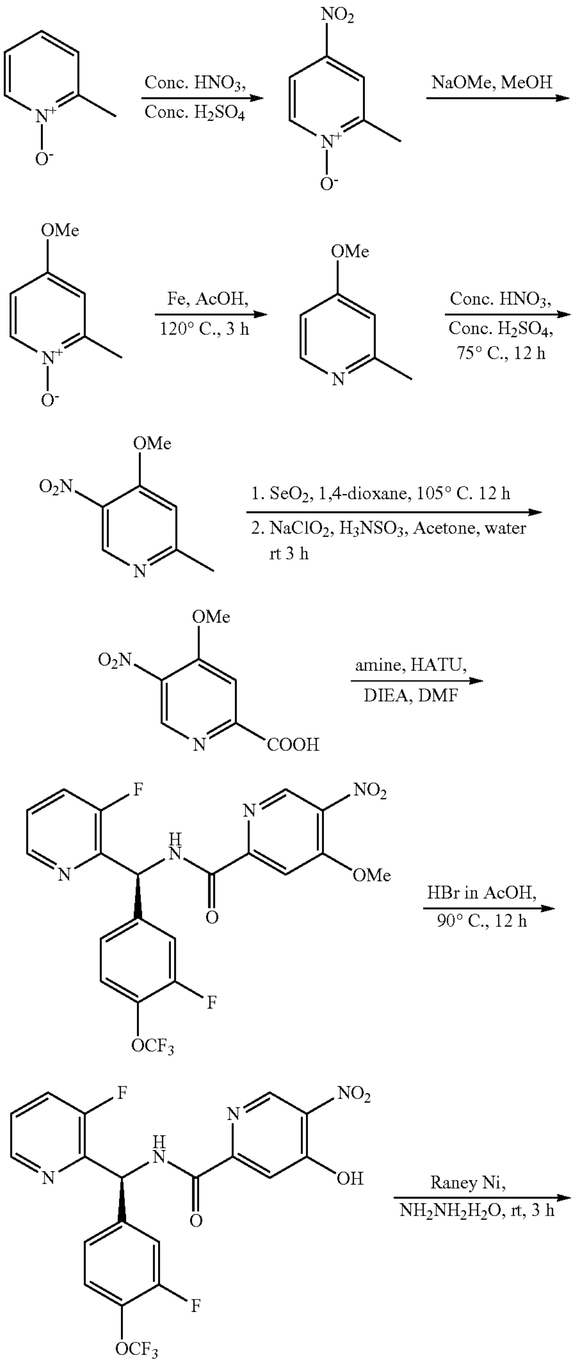

-continued

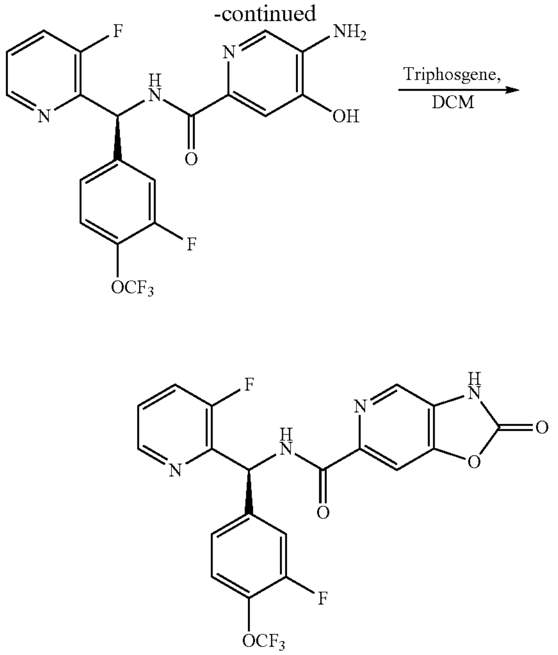

Example 438

(S)—N-((3-Fluoro-4-(trifluoromethoxy)phenyl)(3-fluoropyridin-2-yl)methyl)-2-oxo-2,3-dihydrooxazolo[4,5-c]pyridine-6-carboxamide

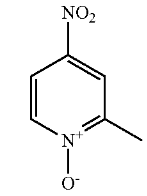

Step 1. 2-Methyl-4-nitropyridine 1-oxide

A 25 mL round bottom flask was charged with conc. $H_2SO_4$ (1 mL) and cooled to 0° C. 2-Methylpyridine 1-oxide (0.4 g, 0.003 mol, Aldrich) was added in one portion, followed by the addition of fuming $HNO_3$ (1 mL, spectrochem, india) in a drop-wise fashion. The reaction was stirred at rt for 30 min and a further 12 h at 70° C. Reaction progress was monitored by TLC (50% EtOAc in petroleum ether). After completion of the reaction, EtOAc (10 mL) was added to the reaction mixture after cooling to 0° C. and the reaction was neutralized to pH-8-9 with 40% NaOH solution, and extracted with EtOAc (2×10 mL). The combined organic layers were dried over anhydrous sodium sulfate, filtered and concentrated to give the title compound as a yellow solid. $^1H$ NMR (400 MHz, DMSO-$d_6$) δ ppm 8.82 (d, J=5.4 Hz, 1H), 8.03 (d, J=1.8 Hz, 1H), 7.92 (dd, J=1.8, 5.1 Hz, 1H), 2.64 (s, 3H).

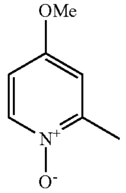

Step 2. 4-Methoxy-2-methylpyridine 1-oxide

To a stirred solution of 2-methyl-4-nitropyridine 1-oxide (24 g, 0.155 mol) in MeOH (100 mL). Sodium methoxide (10 g, 0.187 mol, Aldrich) was added, and the reaction mixture was stirred for 2 h at 80° C. Reaction progress was monitored by TLC (50% EtOAc in petroleum ether). The reaction mixture was concentrated and water (50 mL) was added and the aqueous solution was extracted with EtOAc (4×50 mL). The combined organic layers were dried over sodium sulfate, filtered and concentrated to afford the title compound as a brown liquid. $^1H$ NMR (400 MHz, DMSO-$d_6$) δ ppm 8.14 (d, J=7.2 Hz, 1H), 7.14 (d, J=3.3 Hz, 1H), 6.91 (dd, J=3.6, 7.2 Hz, 1H), 3.80 (s, 3H), 2.32 (s, 3H).

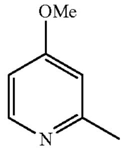

Step 3. 4-Methoxy-2-methylpyridine

To a stirred solution of 4-methoxy-2-methylpyridine 1-oxide (20 g, 0.143 mol) in AcOH (200 mL, sdfine, India), was added Fe (16 g, 0.287 mol, sdfine, India) and the reaction mixture was stirred for 2 h at 120° C. The reaction mixture was concentrated and neutralized with sat'd $NaHCO_3$. EtOAc was added to the mixture and it was filtered through Celite® brand filter agent. The organic layer was separated and the aqueous layer was extracted with EtOAc (3×150 mL). The combined organic layers were dried over sodium sulfate, filtered and concentrated to give the title compound as a brown liquid. $^1H$ NMR (400 MHz, DMSO-$d_6$) δ ppm 8.33 (d, J=6 Hz, 1H), 6.68-6.64 (m, 2H), 3.84 (s, 3H), 2.52 (s, 3H). MS (ESI, positive ion) m/z: 124.0 (M+H).

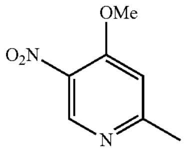

Step 4. 4-Methoxy-2-methyl-5-nitropyridine

To a stirred solution of 4-methoxy-2-methylpyridine (25 g, 0.148 mol) in conc. $H_2SO_4$ (17 mL, S. D. Fine, India), a mixture of $H_2SO_4$ (17 mL, S.D. Fine, India) and 65% $HNO_3$ (22 mL, Rankem, India) was added in a drop-wise fashion at 0° C. over 30 min. The resulting solution was heated at 65° C.

for 12 h. After completion, the reaction mixture was poured in to ice water and neutralized (PH-8) with 40% NaOH solution to give a yellow precipitate. The precipitate was further stirred and filtered, dried to give a mixture of 3-nitro (major product) and the desired 5-nitro isomers. The product was isolated by column chromatography, silica gel (230-400), eluting with 15% EtOAc in petroleum ether to give the title compound as yellow needles. $^{1}$H NMR (400 MHz, DMSO-$d_6$) δ: 8.86 (s, 1H), 7.33 (s, 1H), 3.99 (s, 3H), 2.52 (s, 3H). MS (ESI, positive ion) m/z: 169.0 (M+H).

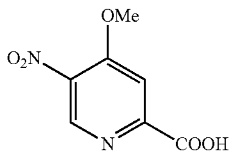 [SMILES: COc1cc(C(=O)O)ncc1[N+](=O)[O-]]

Step 5. 4-Methoxy-5-nitropicolinic acid

To a stirred solution of 4-methoxy-2-methyl-5-nitropyridine (2 g, 0.011 mol) in 1,4-dioxane (20 mL), was added $SeO_2$ (3.2 g, 0.047 mol, Aldrich), and the reaction mixture was stirred for 12 h at 105° C. The progress of reaction was monitored by TLC (30% EtOAc in hexane). After completion, the reaction mixture was cooled to rt and filtered. The filtrate was concentrated to afford the aldehyde intermediate which was dissolved in acetone and water (1:1, 5 mL) and treated with sodium chlorite (3.2 g, 0.035 mol, Aldrich) and sulfamic acid (3.4 g, 0.035 mol, Aldrich). The reaction mixture was stirred for 1 h at rt. The reaction progress was monitored by TLC (50% EtOAc in petroleum ether). After completion, the reaction mixture was concentrated to give a white precipitate, which was filtered and dried to afford the title compound as a white solid. $^{1}$H NMR (400 MHz, DMSO-$d_6$) δ ppm 13.9 (br s, 1H), 9.06 (s, 1H), 7.92 (s, 1H), 4.10 (s, 3H). MS (ESI, positive ion) m/z: 197.0 (M+H).

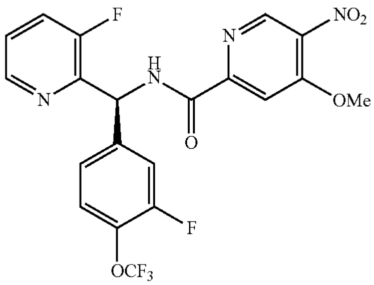 [SMILES: COc1cc(C(=O)N[C@@H](c2ccc(OC(F)(F)F)c(F)c2)c2ncccc2F)ncc1[N+](=O)[O-]]

Step 6. (S)—N-((3-Fluoro-4-(trifluoromethoxy)phenyl)(3-fluoropyridin-2-yl)methyl)-4-methoxy-5-nitropicolinamide To a stirred solution of 4-methoxy-5-nitropicolinic acid (1 g, 0.005 mol) in DMF (10 mL) were added (S)-(3-fluoro-4-(trifluoromethoxy)phenyl)(3-fluoropyridin-2-yl)methanamine hydrochloride (1.8 g, 0.0055 mol, Intermediate 6), HATU (2.8 g, 0.0075 mol, Molicula, India) and DIPEA (2.4 g, 0.02 mol, Aldrich). The reaction mixture was stirred for 12 h at rt. The reaction progress was monitored by TLC (50% EtOAc in petroleum ether). After completion of the reaction, water (100 mL) was added and aqueous solution was extracted with EtOAc (50 mL×3) and concentrated to give the product. The product thus obtained was purified by column chromatography, silica gel (60-120 mesh), using 80-100% EtOAc in petroleum ether as the eluent to give the title compound. $^{1}$H NMR (400 Mhz, DMSO-$d_6$) δ ppm 9.89 (d, J=7.2 Hz, 1H), 9.13 (s, 1H), 8.57 (d, J=4.5 Hz, 1H), 7.92 (s, 1H), 7.82 (t, J=8.7 Hz, 1H), 7.56 (t, J=4.8 Hz, 3H), 7.36 (d, J=8.4 Hz, 1H), 6.54 (d, J=6.3 Hz, 1H), 4.11 (s, 3H). MS (ESI, positive ion) m/z: 485.0 (M+H).

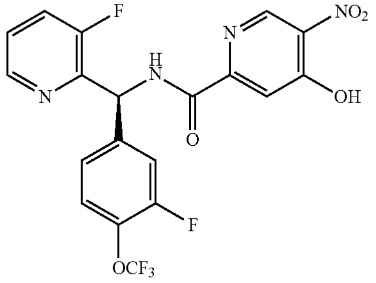

Step 7. (S)—N-((3-Fluoro-4-(trifluoromethoxy)phenyl)(3-fluoropyridin-2-yl)methyl)-4-hydroxy-5-nitropicolinamide To a solution of 30% HBr in AcOH (10 mL, Spectrochem, India) was added (S)—N-((3-fluoro-4-(trifluoromethoxy)phenyl)(3-fluoropyridin-2-yl)methyl)-4-methoxy-5-nitropicolinamide (1 g, 0.002 mol), and the resulting reaction mixture was stirred for 12 h at 90° C. The reaction progress was monitored by TLC (50% EtOAc in petroleum ether). After completion of the reaction, the reaction mixture was concentrated and neutralized with sat'd $NaHCO_3$ solution (pH~7-7.5) and the aqueous solution was extracted with EtOAc (3×10 mL). The combined organic layers were dried over anhydrous sodium sulfate, and concentrated to afford the title compound as a pale yellow solid. $^{1}$H NMR (DMSO-$d_6$) δ: 9.84 (d, J=7.5 Hz, 1H), 8.77 (s, 1H), 8.53 (d, J=4.5 Hz, 1H), 7.83-7.70 (m, 1H), 7.57-7.49 (m, 3H), 7.38-7.31 (m, 2H), 6.56 (d, J=7.5 Hz, 1H). MS (ESI, positive ion) m/z: 471.4 (M+H).

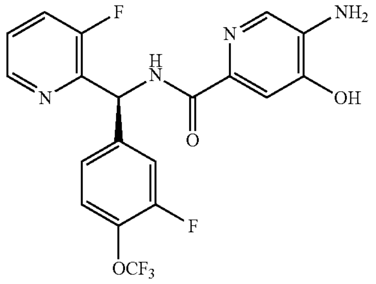 [SMILES: Nc1cnc(C(=O)N[C@@H](c2ccc(OC(F)(F)F)c(F)c2)c2ncccc2F)cc1O]

Step 8. ((S)-5-Amino-N-((3-fluoro-4-(trifluoromethoxy)phenyl) (3-fluoropyridin-2-yl)methyl)-4-hydroxypicolinamide To a stirred solution of (S)—N-((3-fluoro-4-(trifluoromethoxy)phenyl)(3-fluoropyridin-2-yl)methyl)-4-hydroxy-5-nitropicolinamide (0.35 g, 0.0007 mol) in MeOH (10 mL) was added Raney Ni (0.3 g, Monarch), followed by hydrazine hydrate (2 mL, Aldrich) added in a drop-wise fashion at rt. The reaction mixture was stirred for 3 h. After completion of the reaction (monitored by TLC, 50% EtOAc in hexane), the reaction mixture was filtered through Celite® brand filter agent and concentrated providing a residue. The residue was triturated with $Et_2O$, filtered dried under vacuum to give the title compound as a brown solid. $^1H$ NMR ($DMSO-d_6$) δ: 9.41 (d, J=7.5 Hz, 1H), 8.55 (d, J=4.2 Hz, 1H), 7.83-7.78 (m, 2H), 7.54-7.44 (m, 3H), 7.27 (d, J=9.9 Hz, 2H), 6.46 (d, J=6.9 Hz, 1H), 5.29 (s, 2H).

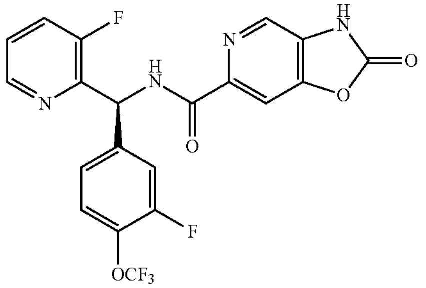 [SMILES: O=C(N[C@@H](c1ccc(OC(F)(F)F)c(F)c1)c1ncccc1F)c1cc2oc(=O)[nH]c2cn1]

Step 9. (S)—N-((3-Fluoro-4-(trifluoromethoxy)phenyl)(3-fluoropyridin-2-yl)methyl)-2-oxo-2,3-dihydrooxazolo[4,5-c]pyridine-6-carboxamide To a cooled (−78° C.) and stirred mixture of ((S)-5-amino-N-((3-fluoro-4-(trifluoromethoxy)phenyl) (3-fluoropyridin-2-yl)methyl)-4-hydroxypicolinamide (200 mg, 0.00045 mol) in THF (5 mL) was added TEA (0.31 mL, 0.002 mol, Spectrochem, India) and triphosgene (270 mg, 0.0009 mol, Spectrochem, India). The reaction mixture was stirred for 2 h at same temperature, slowly warmed to rt and stirred overnight. After completion of the reaction (monitored by TLC, 50% EtOAc in hexane), the reaction mixture was quenched with sat'd $NaHCO_3$ (5 mL), extracted with EtOAc (10 mL×3). The combined organic layers were dried over anhydrous sodium sulfate, concentrated and purified by column chromatography, silica gel (60-120 mesh) using 50-60% EtOAc in petroleum ether as the eluent, followed by further purification using Prep TLC plates, mobile phase 50% EtOAc in hexanes to give the title compound. $^1H$ NMR (400 MHz, $DMSO-d_6$) δ ppm 9.79 (d, J=7.2 Hz, 1H), 9.00 (s, 1H), 8.53 (d, J=4.4 Hz, 1H), 8.41 (s, 1H), 8.08 (s, 1H), 7.44-7.35 (m, 1H), 7.35-7.31 (m, 3H), 7.26-7.21 (m, 1H), 6.64 (d, J=7.6 Hz, 1H). MS (ESI, positive ion) m/z: 467.2 (M+H).

TABLE 6

$^1H$ NMR Data of Examples 1-261 and 287-424.

| Ex. # | Freq., Solvent | $^1$HNMR Data (δ ppm) |
|---|---|---|
| 1 | 400 MHz $d_4$-MeOH | 8.38-8.52 (m, 1H), 8.14 (d, J = 2.2 Hz, 1H), 8.04 (dd, J = 9.6, 2.5 Hz, 1H), 7.59 (ddd, J = 9.7, 8.5, 1.2 Hz, 1H), 7.44-7.53 (m, J = 8.8 Hz, 2H), 7.41 (dt, J = 8.5, 4.4 Hz, 1H), 7.15-7.26 (m, J = 8.0 Hz, 2H), 6.66 (s, 1H), 6.44-6.57 (m, 1H) |
| 2 | 400 MHz $CDCl_3$ | 8.97 (dd, J = 4.2, 1.5 Hz, 1H), 8.89 (d, J = 7.0 Hz, 1H), 8.62 (s, 1H), 8.45-8.52 (m, 1H), 8.25 (d, J = 8.2 Hz, 1H), 8.09 (dd, J = 8.5, 1.7 Hz, 1H), 7.93 (d, J = 8.4 Hz, 1H), 7.49-7.58 (m, 3H), 7.46 (td, J = 8.6, 1.2 Hz, 1H), 7.28-7.39 (m, 1H), 7.17 (d, J = 8.6 Hz, 2H), 6.68-6.75 (m, 1H) |
| 3 | 400 MHz $d_4$-MeOH | 8.92 (d, J = 4.1 Hz, 1H), 8.18 (dd, J = 8.0, 1.0 Hz, 1H), 8.14 (d, J = 2.5 Hz, 1H), 8.03 (dd, J = 9.6, 2.7 Hz, 1H), 7.58 (dd, J = 7.8, 4.9 Hz, 1H), 7.54 (d, J = 2.2 Hz, 1H), 7.45 (d, J = 8.2 Hz, 1H), 7.29 (dd, J = 8.4, 2.2 Hz, 1H), 6.78 (s, 1H), 6.52 (d, J = 9.6 Hz, 1H), 4.86 (br s, 2H) |
| 4 | 400 MHz $CDCl_3$ | 9.06-9.11 (m, 1H), 8.94-9.00 (m, 2H), 8.70 (d, J = 7.4 Hz, 1H), 8.56 (s, 1H), 8.12-8.20 (m, 2H), 8.02-8.10 (m, 2H), 7.97 (d, J = 9.0 Hz, 1H), 7.88 (d, J = 8.4 Hz, 1H), 7.77 (d, J = 1.8 Hz, 1H), 7.59 (dd, J = 9.0, 2.2 Hz, 1H), 7.44-7.53 (m, 2H), 7.06 (d, J = 7.4 Hz, 1H) |
| 5 | 400 MHz $CDCl_3$ | 8.97 (dd, J = 4.2, 1.7 Hz, 1H), 8.87-8.92 (m, 1H), 8.49-8.56 (m, 2H), 8.21 (dd, J = 8.2, 0.8 Hz, 1H), 8.08 (dd, J = 8.5, 1.7 Hz, 1H), 8.03 (dd, J = 8.2, 0.6 Hz, 1H), 7.90 (d, J = 8.6 Hz, 1H), 7.43-7.52 (m, 2H), 7.21-7.26 (m, 1H), 7.18 (dd, J = 12.2, 2.1 Hz, 1H), 6.90 (t, J = 8.6 Hz, 1H), 6.83 (d, J = 7.8 Hz, 1H) |
| 6 | 400 MHz $CDCl_3$ | 8.91 (d, J = 2.2 Hz, 1H), 8.85 (d, J = 4.7 Hz, 1H), 8.59 (d, J = 7.8 Hz, 1H), 8.48 (s, 1H), 8.17 (d, J = 8.2 Hz, 1H), 7.96-8.04 (m, 2H), 7.86 (d, J = 8.6 Hz, 1H), 7.40-7.50 (m, 2H), 7.34-7.40 (m, 2H), 7.21-7.27 (m, 2H), 6.83 (d, J = 7.8 Hz, 1H) |
| 7 | 400 MHz $CDCl_3$ | 9.17 (s, 1H), 8.97 (dd, J = 9.7, 4.4 Hz, 2H), 8.71 (d, J = 7.2 Hz, 1H), 8.56 (s, 1H), 8.33 (s, 1H), 8.19 (d, J = 8.2 Hz, 1H), 8.03-8.11 (m, 2H), 7.89 (d, J = 8.6 Hz, 1H), 7.79 (d, J = 7.4 Hz, 1H), 7.75 (d, J = 8.2 Hz, 1H), 7.40-7.54 (m, 3H), 7.08 (d, J = 7.4 Hz, 1H) |
| 8 | 400 MHz $CDCl_3$ | 8.92-9.03 (m, 3H), 8.67 (d, J = 7.4 Hz, 1H), 8.56 (s, 1H), 8.14-8.23 (m, 2H), 8.01-8.10 (m, 2H), 7.88 (d, J = 8.4 Hz, 1H), 7.67 (d, J = 9.0 Hz, 1H), 7.43-7.53 (m, 2H), 7.39 (br. s, 1H), 7.17 (dd, J = 9.0, 2.0 Hz, 1H), 7.04 (d, J = 7.4 Hz, 1H), 3.92 (s, 3H) |
| 9 | 400 MHz $CDCl_3$ | 9.19 (d, J = 1.8 Hz, 1H), 8.95-9.03 (m, 2H), 8.71 (d, J = 7.4 Hz, 1H), 8.62 (s, 1H), 8.58 (s, 1H), 8.19 (d, J = 8.0 Hz, 1H), 8.04-8.12 (m, 2H), 7.94-8.03 (m, 1H), 7.89 (d, J = 8.6 Hz, 1H), 7.59 (s, 1H), 7.57 (d, J = 1.4 Hz, 1H), 7.44-7.54 (m, 2H), 7.12 (d, J = 7.6 Hz, 1H) |

TABLE 6-continued

| $^1H$ NMR Data of Examples 1-261 and 287-424. | | |
|---|---|---|
| Ex. # | Freq., Solvent | $^1$HNMR Data (δ ppm) |
| 10 | 400 MHz $d_4$-MeOH | 8.90-8.97 (m, 2H), 8.72 (d, J = 7.4 Hz, 1H), 8.52 (s, 1H), 8.25 (d, J = 8.2 Hz, 1H), 8.02-8.10 (m, 2H), 7.93 (d, J = 8.6 Hz, 1H), 7.48-7.58 (m, 3H), 7.33-7.42 (m, 2H), 6.85 (d, J = 7.8 Hz, 1H) |
| 11 | 400 MHz $CDCl_3$ | 9.19 (s, 1H), 8.92 (d, J = 2.0 Hz, 1H), 8.87 (d, J = 4.7 Hz, 1H), 8.33-8.43 (m, 2H), 8.18 (d, J = 1.4 Hz, 1H), 8.13 (d, J = 8.0 Hz, 1H), 8.07 (d, J = 8.6 Hz, 1H), 7.98 (dd, J = 8.8, 1.4 Hz, 1H), 7.78-7.91 (m, 3H), 7.60 (dd, J = 9.0, 2.3 Hz, 1H), 7.52 (dd, J = 7.7, 5.0 Hz, 1H), 6.98-7.02 (m, 1H) |
| 12 | 400 MHz $CDCl_3$ | 9.09 (d, J = 1.8 Hz, 1H), 8.92-9.00 (m, 2H), 8.70 (d, J = 7.6 Hz, 1H), 8.56 (s, 1H), 8.25 (s, 1H), 8.17 (d, J = 8.2 Hz, 1H), 8.02-8.10 (m, 3H), 7.87 (d, J = 8.4 Hz, 1H), 7.79 (d, J = 8.2 Hz, 1H), 7.67 (t, J = 7.6 Hz, 1H), 7.43-7.55 (m, 3H), 7.08 (d, J = 7.6 Hz, 1H) |
| 13 | 400 MHz $CDCl_3$ | 8.89-8.96 (m, 2H), 8.72 (d, J = 7.8 Hz, 1H), 8.53 (s, 1H), 8.26 (d, J = 8.2 Hz, 1H), 8.01-8.11 (m, 2H), 7.93 (d, J = 8.4 Hz, 1H), 7.47-7.57 (m, 2H), 7.44 (s, 1H), 7.33-7.40 (m, 1H), 7.21-7.28 (m, 2H), 6.89 (d, J = 7.8 Hz, 1H) |
| 14 | 400 MHz $CDCl_3$ | 8.95 (dd, J = 4.2, 1.7 Hz, 1H), 8.87 (d, J = 4.1 Hz, 1H), 8.53 (s, 1H), 8.44 (d, J = 7.8 Hz, 1H), 8.16 (dd, J = 8.2, 0.8 Hz, 1H), 8.07 (dd, J = 8.5, 1.7 Hz, 1H), 7.98 (dd, J = 8.0, 1.0 Hz, 1H), 7.85 (d, J = 8.4 Hz, 1H), 7.44 (dd, J = 8.3, 4.2 Hz, 1H), 7.33-7.42 (m, 3H), 7.05-7.16 (m, 2H), 6.89 (d, J = 7.8 Hz, 1H), 2.28 (s, 3H) |
| 15 | 400 MHz $CDCl_3$ | 8.94-8.99 (m, J = 4.3, 1.6 Hz, 1H), 8.92 (d, J = 4.7 Hz, 1H), 8.61 (d, J = 7.8 Hz, 1H), 8.56 (s, 1H), 8.17 (d, J = 8.2 Hz, 1H), 8.08 (dd, J = 8.5, 1.7 Hz, 1H), 8.02 (d, J = 7.8 Hz, 1H), 7.74-7.90 (m, 5H), 7.65 (dd, J = 8.6, 1.4 Hz, 1H), 7.38-7.49 (m, 4H), 7.09 (d, J = 8.0 Hz, 1H) |
| 16 | 400 MHz $CDCl_3$ | 12.90 (br. s., 1H), 8.96-9.03 (m, 1H), 8.93 (d, J = 4.5 Hz, 1H), 8.21 (d, J = 7.6 Hz, 1H), 8.00-8.12 (m, 3H), 7.96 (d, J = 9.0 Hz, 1H), 7.88 (dd, J = 9.6, 2.2 Hz, 1H), 7.74 (d, J = 2.0 Hz, 1H), 7.59 (dd, J = 9.0, 2.2 Hz, 1H), 7.51 (dd, J = 7.7, 5.0 Hz, 1H), 6.92 (d, J = 7.4 Hz, 1H), 6.56 (d, J = 9.6 Hz, 1H) |
| 17 | 400 MHz $CDCl_3$ | 8.97 (dd, J = 4.1, 1.4 Hz, 1H), 8.90 (d, J = 4.5 Hz, 1H), 8.54 (s, 1H), 8.47 (d, J = 7.8 Hz, 1H), 8.19 (d, J = 8.0 Hz, 1H), 8.09 (dd, J = 8.5, 1.5 Hz, 1H), 8.03 (d, J = 7.8 Hz, 1H), 7.89 (d, J = 8.6 Hz, 1H), 7.46 (td, J = 8.3, 4.6 Hz, 2H), 7.24-7.32 (m, 2H), 7.16 (d, J = 9.8 Hz, 1H), 6.85-6.99 (m, 2H) |
| 18 | 400 MHz $CDCl_3$ | 8.98 (dd, J = 4.2, 1.5 Hz, 1H), 8.92 (d, J = 4.5 Hz, 1H), 8.50-8.58 (m, 2H), 8.20 (d, J = 8.2 Hz, 1H), 8.09 (dd, J = 8.4, 1.6 Hz, 1H), 8.04 (d, J = 7.8 Hz, 1H), 7.90 (d, J = 8.4 Hz, 1H), 7.69-7.78 (m, 2H), 7.39-7.55 (m, 4H), 6.94 (d, J = 7.6 Hz, 1H) |
| 19 | 400 MHz $CDCl_3$ | 8.93 (d, J = 3.3 Hz, 1H), 8.86 (d, J = 4.3 Hz, 1H), 8.46-8.58 (m, 2H), 8.13 (d, J = 8.2 Hz, 1H), 8.06 (d, J = 8.4 Hz, 1H), 7.97 (d, J = 8.2 Hz, 1H), 7.83 (d, J = 8.6 Hz, 1H), 7.34-7.48 (m, 4H), 6.79-6.92 (m, 3H), 3.73 (s, 3H) |
| 20 | 400 MHz $CDCl_3$ | 9.12 (d, J = 1.8 Hz, 1H), 8.95-9.00 (m, 2H), 8.71 (d, J = 7.4 Hz, 1H), 8.57 (s, 1H), 8.31 (s, 1H), 8.20 (d, J = 8.0 Hz, 1H), 8.03-8.10 (m, 2H), 7.89 (d, J = 8.6 Hz, 1H), 7.60 (d, J = 8.2 Hz, 1H), 7.40-7.55 (m, 3H), 7.35 (ddd, J = 10.2, 7.7, 0.9 Hz, 1H), 7.07 (d, J = 7.4 Hz, 1H) |
| 21 | 400 MHz $CDCl_3$ | 8.96 (dd, J = 4.1, 1.2 Hz, 1H), 8.88 (d, J = 4.5 Hz, 1H), 8.54 (s, 1H), 8.42 (d, J = 8.0 Hz, 1H), 8.17 (d, J = 8.2 Hz, 1H), 8.08 (dd, J = 8.4, 1.4 Hz, 1H), 7.99 (d, J = 7.8 Hz, 1H), 7.87 (d, J = 8.6 Hz, 1H), 7.46 (dd, J = 8.3, 4.2 Hz, 1H), 7.40 (dd, J = 7.8, 4.9 Hz, 1H), 7.30 (s, 1H), 7.24 (s, 1H), 7.18 (t, J = 7.6 Hz, 1H), 7.05 (d, J = 7.4 Hz, 1H), 6.89 (d, J = 8.0 Hz, 1H), 2.31 (s, 3H) |
| 22 | 400 MHz $CDCl_3$ | 8.97 (dd, J = 4.3, 1.6 Hz, 1H), 8.95 (d, J = 4.5 Hz, 1H), 8.87 (dd, J = 4.1, 1.6 Hz, 1H), 8.64 (d, J = 7.8 Hz, 1H), 8.56 (s, 1H), 8.18 (d, J = 8.2 Hz, 1H), 8.13 (d, J = 7.6 Hz, 1H), 8.09 (dd, J = 8.6, 1.6 Hz, 1H), 8.05 (s, 1H), 8.03 (s, 1H), 7.93 (s, 1H), 7.83-7.91 (m, 2H), 7.44-7.51 (m, 2H), 7.37 (dd, J = 8.3, 4.2 Hz, 1H), 7.10 (d, J = 7.6 Hz, 1H) |
| 23 | 400 MHz $d_4$-MeOH | 9.05 (d, J = 2.0 Hz, 1H), 8.97 (dd, J = 4.1, 1.6 Hz, 1H), 8.94 (d, J = 4.5 Hz, 1H), 8.68 (d, J = 7.6 Hz, 1H), 8.57 (s, 1H), 8.24 (d, J = 2.0 Hz, 1H), 8.18 (d, J = 8.2 Hz, 1H), 8.01-8.09 (m, 2H), 7.87 (d, J = 8.6 Hz, 1H), 7.44-7.50 (m, 2H), 7.42 (d, J = 7.6 Hz, 1H), 7.36 (dd, J = 8.2, 1.0 Hz, 1H), 7.08 (d, J = 7.6 Hz, 1H), 7.00 (d, J = 7.4 Hz, 1H), 4.03 (s, 3H) |
| 24 | 400 MHz $CDCl_3$ | 8.88-8.95 (m, 1H), 8.76-8.82 (m, 1H), 8.51 (br. s., 1H), 8.11-8.25 (m, 2H), 7.94-8.09 (m, 2H), 7.87 (dd, J = 8.5, 2.8 Hz, 1H), 7.44-7.51 (m, 1H), 7.38 (dt, J = 7.7, 3.7 Hz, 1H), 7.19-7.33 (m, 3H), 6.85-6.94 (m, 2H), 3.82 (s, 3H) |

TABLE 6-continued

| Ex. # | Freq., Solvent | $^1$HNMR Data (δ ppm) |
|---|---|---|
| | | $^1$H NMR Data of Examples 1-261 and 287-424. |
| 25 | 400 MHz $CDCl_3$ | 8.97 (dd, J = 4.2, 1.7 Hz, 1H), 8.89 (dd, J = 4.9, 0.8 Hz, 1H), 8.53 (s, 1H), 8.47 (d, J = 7.8 Hz, 1H), 8.18 (dd, J = 8.2, 0.8 Hz, 1H), 8.08 (dd, J = 8.5, 1.7 Hz, 1H), 8.02 (dd, J = 7.8, 0.8 Hz, 1H), 7.88 (d, J = 8.6 Hz, 1H), 7.41-7.49 (m, 2H), 7.21-7.26 (m, 1H), 7.19 (dd, J = 12.2, 2.1 Hz, 1H), 6.89 (t, J = 8.6 Hz, 1H), 6.83 (d, J = 7.8 Hz, 1H), 3.83 (s, 3H) |
| 26 | 400 MHz $CDCl_3$ | 8.96 (dd, J = 4.1, 1.4 Hz, 1H), 8.88 (d, J = 4.3 Hz, 1H), 8.54 (s, 1H), 8.50 (d, J = 7.8 Hz, 1H), 8.22 (d, J = 8.2 Hz, 1H), 8.08 (dd, J = 8.5, 1.3 Hz, 1H), 8.01 (d, J = 7.8 Hz, 1H), 7.89 (d, J = 8.4 Hz, 1H), 7.49 (dd, J = 8.2, 4.3 Hz, 1H), 7.39-7.47 (m, 3H), 7.28-7.35 (m, 2H), 6.89 (d, J = 7.8 Hz, 1H), 4.85 (q, J = 6.5 Hz, 1H), 2.47 (br. s., 1H), 1.44 (d, J = 6.5 Hz, 3H) |
| 27 | 400 MHz $CDCl_3$ | 8.98 (d, J = 4.1 Hz, 1H), 8.89 (d, J = 4.7 Hz, 1H), 8.45-8.56 (m, 2H), 8.19 (d, J = 8.2 Hz, 1H), 8.08 (d, J = 8.4 Hz, 1H), 8.02 (d, J = 7.8 Hz, 1H), 7.88 (d, J = 8.6 Hz, 1H), 7.39-7.50 (m, 4H), 6.98 (t, J = 8.6 Hz, 2H), 6.88 (d, J = 7.8 Hz, 1H) |
| 28 | 400 MHz, DMSO-$d_6$ | 9.50 (d, J = 7.8 Hz, 1H), 9.01 (dd, J = 4.2, 1.7 Hz, 1H), 8.61 (s, 1H), 8.45 (d, J = 7.6 Hz, 1H), 8.23 (dd, J = 4.6, 1.1 Hz, 1H), 8.00-8.12 (m, 2H), 7.59-7.77 (m, 5H), 7.47-7.56 (m, 1H), 7.39 (dd, J = 8.4, 4.7 Hz, 1H), 6.81 (d, J = 8.0 Hz, 1H), 3.67 (s, 3H) |
| 29 | 400 MHz, DMSO-$d_6$ | 9.73 (d, J = 7.6 Hz, 1H), 9.04 (d, J = 4.5 Hz, 1H), 8.35 (dd, J = 4.8, 1.9 Hz, 1H), 8.29 (d, J = 7.6 Hz, 1H), 8.25 (dd, J = 7.4, 2.0 Hz, 1H), 7.66-7.77 (m, 3H), 7.57 (d, J = 8.2 Hz, 2H), 7.16 (dd, J = 7.4, 4.9 Hz, 1H), 6.75 (d, J = 7.6 Hz, 1H), 4.06 (s, 3H) |
| 30 | 400 MHz, DMSO-$d_6$ | 9.37 (d, J = 7.4 Hz, 1H), 8.91 (d, J = 4.5 Hz, 1H), 8.71 (d, J = 2.3 Hz, 1H), 8.25 (d, J = 7.4 Hz, 1H), 8.18 (dd, J = 8.7, 2.4 Hz, 1H), 7.66-7.76 (m, J = 8.2 Hz, 2H), 7.62 (dd, J = 7.9, 4.8 Hz, 1H), 7.47-7.58 (m, J = 8.0 Hz, 2H), 6.86 (d, J = 8.6 Hz, 1H), 6.79 (d, J = 7.4 Hz, 1H), 3.89 (s, 3H) |
| 31 | 400 MHz, DMSO-$d_6$ | 9.84 (d, J = 8.2 Hz, 1H), 9.45 (dd, J = 4.9, 1.6 Hz, 1H), 9.06 (d, J = 4.3 Hz, 1H), 8.32 (d, J = 7.8 Hz, 1H), 8.24 (dd, J = 8.5, 1.7 Hz, 1H), 7.95 (dd, J = 8.4, 5.1 Hz, 1H), 7.68-7.77 (m, 3H), 7.61 (d, J = 8.2 Hz, 2H), 6.80 (d, J = 8.2 Hz, 1H) |
| 32 | 400 MHz, DMSO-$d_6$ | 9.55 (d, J = 8.4 Hz, 1H), 9.04 (d, J = 4.3 Hz, 1H), 8.49 (d, J = 5.9 Hz, 1H), 8.30 (d, J = 7.8 Hz, 1H), 7.65-7.76 (m, 3H), 7.48-7.60 (m, 3H), 7.20 (dd, J = 5.7, 2.7 Hz, 1H), 6.74 (d, J = 8.6 Hz, 1H), 3.89 (s, 3H) |
| 33 | 400 MHz, DMSO-$d_6$ | 9.54 (d, J = 8.4 Hz, 1H), 9.02 (d, J = 4.5 Hz, 1H), 8.31 (d, J = 7.6 Hz, 1H), 7.90 (t, J = 7.8 Hz, 1H), 7.67-7.75 (m, 3H), 7.65 (d, J = 7.2 Hz, 1H), 7.55 (d, J = 8.2 Hz, 2H), 7.08 (d, J = 8.2 Hz, 1H), 6.72 (d, J = 8.4 Hz, 1H), 3.97 (s, 3H) |
| 34 | 400 MHz, DMSO-$d_6$ | 9.61 (d, J = 7.4 Hz, 1H), 8.91 (d, J = 4.7 Hz, 1H), 8.20-8.32 (m, 2H), 7.66-7.76 (m, J = 8.2 Hz, 2H), 7.63 (dd, J = 7.8, 4.9 Hz, 1H), 7.47-7.56 (m, J = 8.2 Hz, 2H), 7.38 (d, J = 5.3 Hz, 1H), 7.25 (s, 1H), 6.76 (d, J = 7.4 Hz, 1H), 3.87 (s, 3H) |
| 35 | 400 MHz, DMSO-$d_6$ | 9.40 (d, J = 7.8 Hz, 1H), 8.74 (d, J = 2.2 Hz, 1H), 8.45 (d, J = 4.7 Hz, 1H), 8.21 (dd, J = 8.7, 2.4 Hz, 1H), 7.74-7.80 (m, 1H), 7.72 (d, J = 8.2 Hz, 2H), 7.63 (d, J = 8.2 Hz, 2H), 7.48 (dt, J = 8.5, 4.4 Hz, 1H), 6.89 (d, J = 8.8 Hz, 1H), 6.74 (d, J = 7.6 Hz, 1H), 3.91 (s, 3H) |
| 36 | 400 MHz, DMSO-$d_6$ | 10.00 (d, J = 6.8 Hz, 1H), 8.60 (d, J = 4.5 Hz, 1H), 8.39 (dd, J = 4.9, 2.0 Hz, 1H), 8.27 (dd, J = 7.4, 2.0 Hz, 1H), 7.82 (td, J = 9.2, 1.1 Hz, 1H), 7.68-7.77 (m, J = 8.2 Hz, 2H), 7.60-7.68 (m, J = 8.2 Hz, 2H), 7.54 (dt, J = 8.5, 4.4 Hz, 1H), 7.19 (dd, J = 7.4, 4.9 Hz, 1H), 6.60 (d, J = 5.9 Hz, 1H), 4.15 (s, 3H) |
| 37 | 400 MHz, DMSO-$d_6$ | 9.64 (d, J = 8.2 Hz, 1H), 9.05 (d, J = 4.3 Hz, 1H), 8.32 (d, J = 7.8 Hz, 1H), 8.12 (d, J = 9.2 Hz, 1H), 7.66-7.79 (m, 3H), 7.59 (d, J = 8.2 Hz, 2H), 7.40 (d, J = 9.2 Hz, 1H), 6.76 (d, J = 8.2 Hz, 1H), 4.12 (s, 3H) |
| 38 | 400 MHz, DMSO-$d_6$ | 9.62 (d, J = 7.4 Hz, 1H), 8.94 (d, J = 4.1 Hz, 1H), 8.67 (d, J = 1.6 Hz, 1H), 8.44 (d, J = 2.9 Hz, 1H), 8.24-8.33 (m, 1H), 7.78-7.87 (m, 1H), 7.70-7.78 (m, J = 8.2 Hz, 2H), 7.65 (dd, J = 7.8, 4.9 Hz, 1H), 7.50-7.59 (m, J = 8.2 Hz, 2H), 6.83 (d, J = 7.4 Hz, 1H), 3.88 (s, 3H) |
| 39 | 400 MHz, DMSO-$d_6$ | 9.58 (d, J = 6.7 Hz, 1H), 8.91 (d, J = 4.5 Hz, 1H), 8.55 (d, J = 5.1 Hz, 1H), 8.26 (d, J = 7.8 Hz, 1H), 7.66-7.75 (m, 3H), 7.63 (dd, J = 7.8, 4.9 Hz, 1H), 7.58 (d, J = 4.9 Hz, 1H), 7.53 (d, J = 8.2 Hz, 2H), 6.78 (d, J = 6.5 Hz, 1H), 2.51 (s, 3H) |
| 40 | 400 MHz, DMSO-$d_6$ | 9.49 (d, J = 7.4 Hz, 1H), 8.87-8.97 (m, 2H), 8.26 (d, J = 7.2 Hz, 1H), 8.14 (dd, J = 8.2, 2.3 Hz, 1H), 7.67-7.75 (m, J = 8.2 Hz, 2H), 7.62 (dd, J = 7.8, 4.9 Hz, 1H), 7.49-7.57 (m, J = 8.2 Hz, 2H), 7.33 (d, J = 8.0 Hz, 1H), 6.80 (d, J = 7.2 Hz, 1H), 2.51 (s, 3H) |

TABLE 6-continued

¹H NMR Data of Examples 1-261 and 287-424.

| Ex. # | Freq., Solvent | ¹HNMR Data (δ ppm) |
|---|---|---|
| 41 | 400 MHz, DMSO-$d_6$ | 9.12 (d, J = 7.4 Hz, 1H), 8.92 (d, J = 3.9 Hz, 1H), 8.22-8.36 (m, 1H), 8.17 (d, J = 2.5 Hz, 1H), 7.90 (dd, J = 9.7, 2.6 Hz, 1H), 7.68-7.75 (m, J = 8.2 Hz, 2H), 7.63 (dd, J = 7.8, 4.9 Hz, 1H), 7.41-7.57 (m, J = 8.0 Hz, 2H), 6.76 (d, J = 7.4 Hz, 1H), 6.33 (d, J = 9.6 Hz, 1H) |
| 42 | 400 MHz, DMSO-$d_6$ | 9.62 (br. s., 1H), 9.06 (s, 2H), 8.94 (d, J = 4.1 Hz, 1H), 8.22-8.33 (m, 1H), 7.69-7.78 (m, J = 8.2 Hz, 2H), 7.65 (dd, J = 7.6, 4.9 Hz, 1H), 7.50-7.60 (m, J = 8.2 Hz, 2H), 6.81 (br. s., 1H), 3.99 (s, 3H) |
| 43 | 400 MHz, DMSO-$d_6$ | 12.14 (br. s., 1H), 8.92 (d, J = 4.3 Hz, 1H), 8.84 (d, J = 8.0 Hz, 1H), 8.46 (s, 1H), 8.39 (dd, J = 7.8, 1.6 Hz, 1H), 8.17-8.32 (m, 2H), 7.66-7.75 (m, J = 8.4 Hz, 2H), 7.62 (dd, J = 7.9, 4.8 Hz, 1H), 7.46-7.58 (m, J = 8.0 Hz, 2H), 7.15 (dd, J = 7.8, 4.7 Hz, 1H), 6.89 (d, J = 7.8 Hz, 1H) |
| 44 | 400 MHz, DMSO-$d_6$ | 11.76 (br. s., 1H), 9.50 (d, J = 7.2 Hz, 1H), 8.90 (d, J = 4.5 Hz, 1H), 8.25 (d, J = 7.4 Hz, 1H), 7.66-7.75 (m, J = 8.2 Hz, 2H), 7.62 (dd, J = 7.9, 4.8 Hz, 1H), 7.46-7.55 (m, J = 8.2 Hz, 2H), 7.42 (d, J = 6.8 Hz, 1H), 6.75-6.80 (m, 1H), 6.69 (d, J = 6.7 Hz, 1H), 6.44 (dd, J = 6.8, 1.4 Hz, 1H) |
| 45 | 400 MHz, DMSO-$d_6$ | 12.42 (br. s., 1H), 9.34 (s, 1H), 9.09 (d, J = 7.8 Hz, 1H), 8.95 (d, J = 4.3 Hz, 1H), 8.76-8.88 (m, 1H), 8.47-8.62 (m, 1H), 8.29 (d, (d J = 7.8 Hz, 1H), 7.69-7.78 (m, J = 8.0 Hz, 2H), 7.65 (dd, J = 7.8, 4.9 Hz, 1H), 7.50-7.60 (m, J = 8.0 Hz, 2H), 6.91 (d, J = 7.8 Hz, 1H) |
| 46 | 400 MHz, DMSO-$d_6$ | 9.41 (d, J = 7.8 Hz, 1H), 8.76 (d, J = 2.3 Hz, 1H), 8.40-8.53 (m, 1H), 8.22 (dd, J = 8.8, 2.5 Hz, 1H), 7.76-7.82 (m, 1H), 7.74 (d, J = 8.4 Hz, 2H), 7.65 (d, J = 8.2 Hz, 2H), 7.50 (dt, J = 8.5, 4.4 Hz, 1H), 6.90 (d, J = 8.6 Hz, 1H), 6.76 (d, J = 7.6 Hz, 1H), 3.93 (s, 3H) |
| 47 | 400 MHz, DMSO-$d_6$ | 10.01 (d, J = 7.0 Hz, 1H), 8.60 (d, J = 4.7 Hz, 1H), 8.38 (dd, J = 4.9, 2.0 Hz, 1H), 8.27 (dd, J = 7.4, 2.0 Hz, 1H), 7.82 (t, J = 8.9 Hz, 1H), 7.69-7.77 (m, J = 8.2 Hz, 2H), 7.60-7.69 (m, J = 8.0 Hz, 2H), 7.50-7.60 (m, 1H), 7.18 (dd, J = 7.6, 4.9 Hz, 1H), 6.60 (d, J = 6.3 Hz, 1H), 4.15 (s, 3H) |
| 48 | 400 MHz, DMSO-$d_6$ | 9.72 (d, J = 7.6 Hz, 1H), 9.02 (d, J = 4.5 Hz, 1H), 8.59 (s, 1H), 8.33 (d, J = 4.7 Hz, 1H), 8.29 (d, J = 7.6 Hz, 1H), 7.72 (d, J = 8.4 Hz, 2H), 7.68 (dd, J = 8.1, 5.0 Hz, 1H), 7.64 (d, J = 4.7 Hz, 1H), 7.57 (d, J = 8.2 Hz, 2H), 6.74 (d, J = 7.6 Hz, 1H), 4.08 (s, 3H) |
| 49 | 400 MHz, DMSO-$d_6$ | 9.52 (d, J = 7.0 Hz, 1H), 8.90 (d, J = 4.7 Hz, 1H), 8.25 (d, J = 7.8 Hz, 1H), 7.75 (d, J = 7.0 Hz, 1H), 7.67-7.73 (m, J = 8.2 Hz, 2H), 7.62 (dd, J = 8.0, 4.9 Hz, 1H), 7.46-7.54 (m, J = 8.0 Hz, 2H), 6.83-6.92 (m, 1H), 6.70 (d, J = 7.0 Hz, 1H), 6.50 (dd, J = 7.0, 1.8 Hz, 1H), 3.43 (s, 3H) |
| 50 | 400 MHz, DMSO-$d_6$ | 9.05 (d, J = 7.6 Hz, 1H), 8.91 (d, J = 4.3 Hz, 1H), 8.50 (d, J = 2.5 Hz, 1H), 8.25 (d, J = 7.4 Hz, 1H), 7.88 (dd, J = 9.6, 2.5 Hz, 1H), 7.66-7.74 (m, J = 8.4 Hz, 2H), 7.62 (dd, J = 7.9, 4.8 Hz, 1H), 7.46-7.55 (m, J = 8.2 Hz, 2H), 6.76 (d, J = 7.6 Hz, 1H), 6.37 (d, J = 9.6 Hz, 1H), 3.45 (s, 3H) |
| 51 | 400 MHz, DMSO-$d_6$ | 12.01 (br. s., 1H), 9.15 (d, J = 7.8 Hz, 1H), 8.46 (d, J = 4.5 Hz, 1H), 8.19 (d, J = 2.5 Hz, 1H), 7.92 (dd, J = 9.7, 2.6 Hz, 1H), 7.77 (td, J = 9.3, 1.0 Hz, 1H), 7.73 (d, J = 8.4 Hz, 2H), 7.61 (d, J = 8.0 Hz, 2H), 7.49 (dt, J = 8.5, 4.4 Hz, 1H), 6.71 (d, J = 7.8 Hz, 1H), 6.35 (d, J = 9.8 Hz, 1H) |
| 52 | 400 MHz, DMSO-$d_6$ | 9.54 (d, J = 7.6 Hz, 1H), 8.96 (d, J = 2.0 Hz, 1H), 8.45 (d, J = 4.7 Hz, 1H), 8.21 (dd, J = 8.1, 2.2 Hz, 1H), 7.74-7.81 (m, 1H), 7.69-7.74 (m, J = 8.2 Hz, 2H), 7.61-7.66 (m, J = 8.2 Hz, 2H), 7.48 (dt, J = 8.5, 4.3 Hz, 1H), 7.40 (d, J = 8.2 Hz, 1H), 6.75 (d, J = 7.6 Hz, 1H), 2.54 (s, 3H) |
| 53 | 400 MHz, DMSO-$d_6$ | 9.69 (d, J = 7.6 Hz, 1H), 8.64 (d, J = 5.3 Hz, 1H), 8.45 (d, J = 4.7 Hz, 1H), 7.82 (s, 1H), 7.77 (t, J = 9.8 Hz, 1H), 7.68-7.75 (m, 3H), 7.60-7.67 (m, 2H), 7.49 (dt, J = 8.5, 4.4 Hz, 1H), 6.73 (d, J = 7.6 Hz, 1H), 2.57 (s, 3H) |
| 54 | 400 MHz, DMSO-$d_6$ | 12.15 (br. s., 1H), 8.90 (d, J = 8.0 Hz, 1H), 8.42-8.51 (m, 2H), 8.40 (dd, J = 8.0, 1.6 Hz, 1H), 8.26 (dd, J = 4.7, 1.6 Hz, 1H), 7.74-7.81 (m, 1H), 7.69-7.74 (m, J = 8.2 Hz, 2H), 7.60-7.67 (m, J = 8.2 Hz, 2H), 7.48 (dt, J = 8.5, 4.3 Hz, 1H), 7.16 (dd, J = 7.9, 4.6 Hz, 1H), 6.82 (d, J = 8.0 Hz, 1H) |
| 55 | 400 MHz, DMSO-$d_6$ | 9.54 (d, J = 7.6 Hz, 1H), 9.02 (d, J = 4.3 Hz, 1H), 8.79 (s, 1H), 8.56 (d, J = 5.9 Hz, 1H), 8.29 (d, J = 7.2 Hz, 1H), 7.65-7.74 (m, 3H), 7.56 (d, J = 8.2 Hz, 2H), 7.23 (d, J = 5.9 Hz, 1H), 6.76 (d, J = 7.6 Hz, 1H), 4.03 (s, 3H) |
| 56 | 400 MHz, DMSO-$d_6$ | 10.61 (br. s., 1H), 9.07 (d, J = 7.4 Hz, 1H), 8.90 (d, J = 4.5 Hz, 1H), 8.25 (d, J = 7.8 Hz, 1H), 7.75-7.84 (m, 2H), 7.66-7.73 (m, J = 8.2 Hz, 2H), 7.61 (dd, J = 7.9, 4.8 Hz, 1H), |

TABLE 6-continued

| $^1$H NMR Data of Examples 1-261 and 287-424. | | |
|---|---|---|
| Ex. # | Freq., Solvent | $^1$HNMR Data (δ ppm) |
| | | 7.47-7.55 (m, J = 8.2 Hz, 2H), 6.83 (d, J = 8.0 Hz, 1H), 6.78 (d, J = 7.4 Hz, 1H), 3.51 (s, 2H) |
| 57 | 400 MHz, DMSO-$d_6$ | 9.74 (d, J = 5.9 Hz, 1H), 9.08 (s, 2H), 8.92 (d, J = 4.3 Hz, 1H), 8.27 (d, J = 8.0 Hz, 1H), 7.68-7.76 (m, J = 8.2 Hz, 2H), 7.63 (dd, J = 7.8, 4.9 Hz, 1H), 7.50-7.60 (m, J = 8.2 Hz, 2H), 6.80 (d, J = 5.5 Hz, 1H), 2.67 (s, 3H) |
| 58 | 400 MHz, DMSO-$d_6$ | 10.34 (br. s., 1H), 9.47 (d, J = 7.4 Hz, 1H), 8.90 (d, J = 4.5 Hz, 1H), 8.48 (d, J = 1.8 Hz, 1H), 8.25 (d, J = 7.4 Hz, 1H), 8.22 (d, J = 2.7 Hz, 1H), 7.70 (d, J = 8.4 Hz, 2H), 7.62 (dd, J = 7.8, 4.9 Hz, 1H), 7.48-7.56 (m, 3H), 6.77 (d, J = 7.4 Hz, 1H) |
| 59 | 400 MHz, DMSO-$d_6$ | 12.46 (br. s., 1H), 11.21 (d, J = 8.2 Hz, 1H), 8.96 (d, J = 4.5 Hz, 1H), 8.32 (dd, J = 7.2, 2.2 Hz, 1H), 8.26 (d, J = 7.4 Hz, 1H), 7.66-7.78 (m, 3H), 7.64 (dd, J = 7.8, 4.9 Hz, 1H), 7.53 (d, J = 8.0 Hz, 2H), 6.80 (d, J = 8.2 Hz, 1H), 6.47 (t, J = 6.7 Hz, 1H) |
| 60 | 400 MHz, DMSO-$d_6$ | 9.77 (d, J = 6.7 Hz, 1H), 9.07 (s, 1H), 8.92 (d, J = 4.1 Hz, 1H), 8.69 (s, 1H), 8.22-8.32 (m, 1H), 7.69-7.78 (m, J = 8.2 Hz, 2H), 7.63 (dd, J = 7.8, 4.9 Hz, 1H), 7.55-7.61 (m, J = 8.2 Hz, 2H), 6.74 (d, J = 6.3 Hz, 1H), 2.43 (s, 3H) |
| 61 | 400 MHz, DMSO-$d_6$ | 10.88 (d, J = 8.0 Hz, 1H), 9.00 (d, J = 4.3 Hz, 1H), 8.63 (s, 1H), 8.39-8.48 (m, 1H), 8.29 (d, J = 7.0 Hz, 1H), 7.73 (d, J = 8.4 Hz, 2H), 7.67 (dd, J = 7.9, 5.0 Hz, 1H), 7.55 (d, J = 8.0 Hz, 2H), 6.81 (d, J = 8.0 Hz, 1H) |
| 62 | 400 MHz, DMSO-$d_6$ | 11.27 (br. s., 1H), 9.52 (d, J = 8.4 Hz, 1H), 9.04 (d, J = 4.5 Hz, 1H), 8.21-8.41 (m, 2H), 7.64-7.79 (m, 3H), 7.53 (d, J = 8.2 Hz, 2H), 7.41 (d, J = 2.2 Hz, 1H), 6.92 (d, J = 3.7 Hz, 1H), 6.71 (d, J = 8.6 Hz, 1H) |
| 63 | 400 MHz, DMSO-$d_6$ | 11.39 (br. s., 1H), 9.26 (d, J = 8.0 Hz, 1H), 9.00 (d, J = 4.5 Hz, 1H), 8.30 (d, J = 8.0 Hz, 1H), 7.62-7.84 (m, 4H), 7.51 (d, J = 8.0 Hz, 2H), 7.44 (d, J = 6.3 Hz, 1H), 6.82 (d, J = 8.2 Hz, 1H), 6.75 (d, J = 8.2 Hz, 1H) |
| 64 | 400 MHz, DMSO-$d_6$ | 11.39 (br. s., 1H), 9.26 (d, J = 8.6 Hz, 1H), 9.03 (d, J = 4.5 Hz, 1H), 8.29 (d, J = 7.8 Hz, 1H), 8.16 (d, J = 2.5 Hz, 1H), 7.90 (d, J = 8.4 Hz, 1H), 7.64-7.77 (m, 3H), 7.53 (d, J = 8.0 Hz, 2H), 7.29 (dd, J = 8.6, 2.7 Hz, 1H), 6.73 (d, J = 8.6 Hz, 1H) |
| 65 | 400 MHz, DMSO-$d_6$ | 9.06 (dd, J = 7.4, 5.9 Hz, 1H), 8.89 (d, J = 4.5 Hz, 1H), 8.24 (d, J = 8.0 Hz, 1H), 7.69 (d, J = 7.6 Hz, 2H), 7.61 (dd, J = 7.8, 4.9 Hz, 1H), 7.34-7.51 (m, 3H), 6.57 (d, J = 7.0 Hz, 1H), 3.20-3.27 (m, 1H), 2.72-2.86 (m, 1H), 2.03-2.24 (m, 2H), 1.85-2.00 (m, 1H), 1.64-1.85 (m, 2H) |
| 66 | 400 MHz, DMSO-$d_6$ | 12.19 (br. s., 1H), 9.34 (d, J = 7.4 Hz, 1H), 8.94 (d, J = 4.5 Hz, 1H), 8.33 (d, J = 3.5 Hz, 1H), 8.27 (d, J = 7.6 Hz, 1H), 8.05 (d, J = 7.0 Hz, 1H), 7.68-7.78 (m, J = 8.2 Hz, 2H), 7.64 (dd, J = 7.8, 4.9 Hz, 1H), 7.52-7.59 (m, J = 8.2 Hz, 2H), 7.28 (s, 1H), 7.10 (dd, J = 7.8, 4.7 Hz, 1H), 6.84 (d, J = 7.0 Hz, 1H) |
| 67 | 400 MHz, DMSO-$d_6$ | 11.89 (br. s., 1H), 9.33 (d, J = 7.4 Hz, 1H), 8.92 (d, J = 4.5 Hz, 1H), 8.74 (d, J = 2.0 Hz, 1H), 8.52 (d, J = 2.2 Hz, 1H), 8.26 (d, J = 7.8 Hz, 1H), 7.71 (d, J = 8.2 Hz, 2H), 7.62 (dd, J = 7.8, 4.9 Hz, 1H), 7.51-7.59 (m, 3H), 6.84 (d, J = 7.4 Hz, 1H), 6.54 (d, J = 3.5 Hz, 1H) |
| 68 | 400 MHz, DMSO-$d_6$ | 9.08 (d, J = 7.8 Hz, 1H), 8.51 (d, J = 2.5 Hz, 1H), 8.45 (d, J = 4.7 Hz, 1H), 7.90 (dd, J = 9.5, 2.6 Hz, 1H), 7.68-7.82 (m, 3H), 7.60 (d, J = 8.2 Hz, 2H), 7.47 (dt, J = 8.5, 4.4 Hz, 1H), 6.70 (d, J = 7.8 Hz, 1H), 6.39 (d, J = 9.4 Hz, 1H), 3.47 (s, 3H) |
| 69 | 400 MHz, DMSO-$d_6$ | 10.49 (s, 1H), 9.27 (d, J = 7.4 Hz, 1H), 8.90 (d, J = 4.7 Hz, 1H), 8.25 (d, J = 7.8 Hz, 1H), 7.70 (d, J = 8.2 Hz, 2H), 7.62 (dd, J = 8.0, 4.9 Hz, 1H), 7.45-7.56 (m, 3H), 7.21-7.33 (m, 2H), 6.78 (d, J = 7.4 Hz, 1H), 3.52 (s, 2H) |
| 70 | 400 MHz, DMSO-$d_6$ | 10.62 (s, 1H), 9.13 (d, J = 7.8 Hz, 1H), 8.44 (d, J = 4.7 Hz, 1H), 7.79-7.85 (m, 2H), 7.75 (t, J = 9.3 Hz, 1H), 7.71 (d, J = 8.2 Hz, 2H), 7.62 (d, J = 8.2 Hz, 2H), 7.47 (dt, J = 8.5, 4.4 Hz, 1H), 6.86 (d, J = 7.8 Hz, 1H), 6.71 (d, J = 7.6 Hz, 1H), 3.53 (s, 2H) |
| 71 | 400 MHz, DMSO-$d_6$ | 10.50 (s, 1H), 9.31 (d, J = 7.6 Hz, 1H), 8.45 (d, J = 4.7 Hz, 1H), 7.76 (t, J = 9.3 Hz, 1H), 7.68-7.73 (m, J = 8.4 Hz, 2H), 7.59-7.65 (m, J = 8.2 Hz, 2H), 7.51-7.56 (m, 1H), 7.45-7.51 (m, 1H), 7.32 (s, 1H), 7.28 (d, J = 7.8 Hz, 1H), 6.71 (d, J = 7.6 Hz, 1H), 3.53 (s, 2H) |
| 72 | 400 MHz, DMSO-$d_6$ | 12.50 (br. s., 1H), 11.32 (d, J = 7.8 Hz, 1H), 8.47-8.55 (m, 1H), 8.34 (dd, J = 7.2, 2.2 Hz, 1H), 7.69-7.85 (m, 4H), 7.59 (d, J = 8.0 Hz, 2H), 7.50 (dt, J = 8.5, 4.4 Hz, 1H), 6.69 (d, J = 7.4 Hz, 1H), 6.50 (dd, J = 7.0, 6.5 Hz, 1H) |
| 73 | 400 MHz, DMSO-$d_6$ | 10.92 (s, 1H), 9.21 (d, J = 7.6 Hz, 1H), 8.44 (d, J = 4.7 Hz, 1H), 7.72-7.79 (m, 1H), 7.71 (d, J = 8.2 Hz, 2H), 7.61 (d, J = 8.2 Hz, 2H), 7.53-7.59 (m, 2H), 7.47 (dt, J = 8.5, 4.3 Hz, 1H), 6.93 (d, J = 8.8 Hz, 1H), 6.70 (d, J = 7.6 Hz, 1H), 4.61 (s, 2H) |

TABLE 6-continued

| Ex. # | Freq., Solvent | $^1$HNMR Data (δ ppm) |
|---|---|---|
| | | $^1$H NMR Data of Examples 1-261 and 287-424. |
| 74 | 400 MHz, DMSO-$d_6$ | 9.60 (d, J = 7.8 Hz, 1H), 8.45 (d, J = 4.7 Hz, 1H), 8.05-8.15 (m, J = 8.4 Hz, 2H), 7.82-7.89 (m, J = 8.4 Hz, 2H), 7.74-7.81 (m, 1H), 7.69-7.74 (m, J = 8.2 Hz, 2H), 7.61-7.68 (m, J = 8.2 Hz, 2H), 7.58 (d, J = 5.1 Hz, 1H), 7.44-7.52 (m, 1H), 6.74 (d, J = 7.6 Hz, 1H), 2.42 (d, J = 5.1 Hz, 3H) |
| 75 | 400 MHz, DMSO-$d_6$ | 10.81 (s, 1H), 9.22 (d, J = 7.6 Hz, 1H), 8.44 (d, J = 4.7 Hz, 1H), 7.73-7.79 (m, 1H), 7.68-7.73 (m, J = 8.2 Hz, 2H), 7.59-7.65 (m, J = 8.2 Hz, 2H), 7.57 (dd, J = 8.4, 2.0 Hz, 1H), 7.47 (dt, J = 8.5, 4.4 Hz, 1H), 7.43 (d, J = 2.0 Hz, 1H), 7.00 (d, J = 8.4 Hz, 1H), 6.69 (d, J = 7.6 Hz, 1H), 4.63 (s, 2H) |
| 76 | 400 MHz, DMSO-$d_6$ | 11.84 (br. s., 1H), 9.37 (d, J = 7.6 Hz, 1H), 8.45 (d, J = 4.5 Hz, 1H), 7.73-7.80 (m, 1H), 7.71 (d, J = 8.2 Hz, 3H), 7.59-7.66 (m, 3H), 7.47 (dt, J = 8.5, 4.4 Hz, 1H), 7.34 (d, J = 8.4 Hz, 1H), 6.73 (d, J = 7.6 Hz, 1H) |
| 77 | 400 MHz, DMSO-$d_6$ | 10.89 (s, 1H), 9.79 (d, J = 7.2 Hz, 1H), 8.57 (d, J = 4.7 Hz, 1H), 7.75-7.82 (m, 1H), 7.68-7.74 (m, J = 8.4 Hz, 2H), 7.59-7.65 (m, J = 8.2 Hz, 2H), 7.51 (dt, J = 8.6, 4.4 Hz, 1H), 7.43 (dd, J = 6.7, 2.8 Hz, 1H), 7.00-7.11 (m, 2H), 6.58 (d, J = 6.7 Hz, 1H), 4.75-4.99 (m, 2H) |
| 78 | 400 MHz, DMSO-$d_6$ | 9.28 (d, J = 7.8 Hz, 1H), 8.45 (d, J = 4.5 Hz, 1H), 7.87 (s, 1H), 7.78 (t, J = 9.4 Hz, 2H), 7.69-7.74 (m, 3H), 7.59-7.67 (m, 2H), 7.43-7.53 (m, 1H), 7.13 (d, J = 8.0 Hz, 1H), 6.73 (d, J = 7.6 Hz, 1H) |
| 79 | 400 MHz, DMSO-$d_6$ | 11.86 (br. s., 1H), 9.34 (d, J = 7.6 Hz, 1H), 8.46 (d, J = 4.7 Hz, 1H), 7.68-7.82 (m, 2H), 7.65 (s, 1H), 7.54 (d, J = 8.6 Hz, 2H), 7.47 (dt, J = 8.5, 4.3 Hz, 1H), 7.35 (d, J = 8.2 Hz, 3H), 6.68 (d, J = 7.6 Hz, 1H) |
| 80 | 400 MHz, DMSO-$d_6$ | 11.87 (br. s., 1H), 9.24 (d, J = 7.8 Hz, 1H), 8.37-8.52 (m, 1H), 7.89 (d, J = 1.4 Hz, 1H), 7.81 (dd, J = 8.2, 1.6 Hz, 1H), 7.76 (ddd, J = 10.0, 8.6, 1.2 Hz, 1H), 7.51-7.59 (m, J = 8.6 Hz, 2H), 7.44-7.51 (m, 1H), 7.31-7.40 (m, J = 8.0 Hz, 2H), 7.15 (d, J = 8.0 Hz, 1H), 6.70 (d, J = 7.6 Hz, 1H) |
| 81 | 400 MHz, DMSO-$d_6$ | 10.92 (br. s., 1H), 9.15 (d, J = 7.6 Hz, 1H), 8.44 (d, J = 4.5 Hz, 1H), 7.74 (t, J = 9.3 Hz, 1H), 7.54-7.59 (m, 2H), 7.48-7.54 (m, J = 8.6 Hz, 2H), 7.46 (dt, J = 8.5, 4.3 Hz, 1H), 7.26-7.39 (m, J = 8.4 Hz, 2H), 6.93 (d, J = 8.6 Hz, 1H), 6.65 (d, J = 7.8 Hz, 1H), 4.61 (s, 2H) |
| 82 | 400 MHz, DMSO-$d_6$ | 11.98 (br. s., 1H), 9.07 (d, J = 7.4 Hz, 1H), 8.46 (d, J = 4.3 Hz, 1H), 8.15 (d, J = 2.3 Hz, 1H), 7.90 (dd, J = 9.7, 2.6 Hz, 1H), 7.76 (d, J = 7.4 Hz, 1H), 7.65-7.73 (m, J = 8.2 Hz, 2H), 7.53-7.60 (m, J = 8.2 Hz, 2H), 7.37 (dd, J = 7.4, 5.1 Hz, 1H), 6.59 (d, J = 7.4 Hz, 1H), 6.33 (d, J = 9.6 Hz, 1H), 2.24-2.40 (m, 3H) |
| 83 | 400 MHz, DMSO-$d_6$ | 9.01 (d, J = 7.4 Hz, 1H), 8.41-8.57 (m, 2H), 7.90 (dd, J = 9.5, 2.6 Hz, 1H), 7.77 (d, J = 7.4 Hz, 1H), 7.66-7.75 (m, J = 8.2 Hz, 2H), 7.54-7.63 (m, J = 8.2 Hz, 2H), 7.38 (dd, J = 7.3, 5.0 Hz, 1H), 6.62 (d, J = 7.4 Hz, 1H), 6.39 (d, J = 9.6 Hz, 1H), 3.46 (s, 3H), 2.35 (s, 3H) |
| 84 | 400 MHz, DMSO-$d_6$ | 11.82 (br. s., 1H), 9.27 (d, J = 7.8 Hz, 1H), 8.43 (d, J = 3.9 Hz, 1H), 7.68 (d, J = 8.4 Hz, 3H), 7.65 (d, J = 7.6 Hz, 1H), 7.56-7.62 (m, 3H), 7.33 (d, J = 8.4 Hz, 1H), 7.28 (dd, J = 7.6, 4.7 Hz, 1H), 6.47-6.69 (m, 1H), 2.22-2.41 (m, 3H) |
| 85 | 400 MHz, DMSO-$d_6$ | 10.92 (br. s., 1H), 9.12 (d, J = 7.6 Hz, 1H), 8.43 (d, J = 4.3 Hz, 1H), 7.68 (d, J = 8.2 Hz, 2H), 7.64 (d, J = 7.4 Hz, 1H), 7.50-7.60 (m, 4H), 7.27 (dd, J = 7.5, 4.8 Hz, 1H), 6.93 (d, J = 8.2 Hz, 1H), 6.58 (d, J = 7.6 Hz, 1H), 4.61 (s, 2H), 2.32 (s, 3H) |
| 86 | 400 MHz DMSO-$d_6$ | 9.58 (d, J = 7.6 Hz, 1 H), 8.59-8.65 (m, 1 H), 8.45-8.51 (m, 1 H), 8.32 (s, 1 H), 8.09 (s, 1 H), 7.72-7.83 (m, 4 H), 7.66-7.70 (m, 2 H), 7.50 (dt, J = 8.5, 4.4 Hz, 1H), 7.37 (dd, J = 7.1, 1.7 Hz, 1H), 6.77 (d, J = 7.6 Hz, 1H) |
| 87 | 400 MHz DMSO-d6 | 9.52 (d, J = 7.8 Hz, 1 H), 8.62 (d, J = 7.0 Hz, 1 H), 8.48 (d, J = 4.5 Hz, 1 H), 8.31 (s, 1 H), 8.08 (s, 1 H), 7.72-7.82 (m, 2 H), 7.58 (d, J = 8.6 Hz, 2 H), 7.49 (dt, J = 8.5, 4.3 Hz, 1 H), 7.37 (td, J = 4.8, 2.5 Hz, 3 H), 6.71 (d, J = 7.6 Hz, 1 H) |
| 88 | 400 MHz DMSO-$d_6$ | 9.52 (d, J = 7.8 Hz, 1 H), 8.62 (d, J = 7.0 Hz, 1 H), 8.48 (d, J = 4.5 Hz, 1 H), 8.31 (s, 1 H), 8.08 (s, 1 H), 7.72-7.82 (m, 2 H), 7.58 (d, J = 8.6 Hz, 2 H), 7.49 (dt, J = 8.5, 4.3 Hz, 1 H), 7.37 (td, J = 4.8, 2.5 Hz, 3 H), 6.71 (d, J = 7.6 Hz, 1 H) |
| 89 | 300 MHz $CDCl_3$ | 9.23 (s, 1H), 9.02 (d, J = 6.7 Hz, 1H), 8.54 (d, J = 4.5 Hz, 1H), 8.14-8.33 (m, 2H), 7.94 (s, 2H), 7.56-7.70 (m, 1H), 7.37-7.54 (m, 3H), 7.17 (d, J = 8.2 Hz, 2H), 6.70 (d, J = 6.3 Hz, 1H) |
| 90 | 300 MHz DMSO-$d_6$ | 10.50 (s, 1H), 9.25 (d, J = 7.7 Hz, 1H), 8.46 (d, J = 4.7 Hz, 1H), 7.75 (ddd, J = 10.0, 8.5, 1.2 Hz, 1H), 7.42-7.64 (m, 4H), 7.20-7.39 (m, 4H), 6.66 (d, J = 6.9 Hz, 1H), 3.54 (s, 2H) |
| 91 | 300 MHz $CDCl_3$ | 8.63 (br. s., 4H), 8.49 (d, J = 4.7 Hz, 5H), 8.39 (d, J = 7.2 Hz, 4H), 7.67-7.89 (m, 2H), 7.42-7.55 (m, 3H), 7.30-7.41 (m, |

TABLE 6-continued

| Ex. # | Freq., Solvent | $^{1}$HNMR Data (δ ppm) |
|---|---|---|
| | | $^{1}$H NMR Data of Examples 1-261 and 287-424. |
| | | 1H), 7.15 (d, J = 8.0 Hz, 2H), 6.94 (d, J = 8.0 Hz, 1H), 6.68 (dd, J = 7.1, 1.7 Hz, 1H), 3.60 (s, 2H) |
| 92 | 400 MHz $CDCl_3$ | 13.23 (br. s., 1H), 8.54 (dd, J = 4.9, 1.6 Hz, 1H), 8.43 (d, J = 6.8 Hz, 1H), 8.11 (d, J = 2.5 Hz, 1H), 7.95 (dd, J = 9.6, 2.5 Hz, 1H), 7.69 (dd, J = 7.8, 1.6 Hz, 1H), 7.48-7.60 (m, 4H), 7.23 (dd, J = 7.8, 4.9 Hz, 1H), 6.69 (d, J = 6.8 Hz, 1H), 6.61 (d, J = 9.4 Hz, 1H), 2.11 (s, 3H) |
| 93 | 400 MHz DMSO-$d_6$ | 8.99 (dd, J = 4.3, 1.6 Hz, 1H), 8.76 (d, J = 6.8 Hz, 1H), 8.58 (dd, J = 4.9, 1.6 Hz, 1H), 8.41 (s, 1H), 8.28 (dd, J = 8.2, 1.6 Hz, 1H), 8.18 (s, 2H), 7.72 (dd, J = 7.8, 1.6 Hz, 1H), 7.60-7.68 (m, J = 8.0 Hz, 2H), 7.52-7.59 (m, J = 8.4 Hz, 2H), 7.47 (dd, J = 8.2, 4.3 Hz, 1H), 7.18-7.25 (m, 1H), 6.83 (d, J = 6.8 Hz, 1H), 2.15 (s, 3H) |
| 94 | 300 MHz $CDCl_3$ | 8.94 (d, J = 4.4 Hz, 1H), 8.48 (d, J = 7.6 Hz, 1H), 8.22-8.36 (m, 2H), 8.16 (br. s., 1H), 8.08 (d, J = 7.7 Hz, 1H), 7.94 (d, J = 7.7 Hz, 1H), 7.39-7.73 (m, 5H), 6.88 (d, J = 7.6 Hz, 1H) |
| 95 | 300 MHz $CDCl_3$ | 8.60-8.92 (m, 2H), 8.03 (dd, J = 8.0, 1.2 Hz, 1H), 7.91 (d, J = 8.9 Hz, 2H), 7.42-7.68 (m, 5H), 7.08 (d, J = 7.7 Hz, 1H), 6.93 (d, J = 8.8 Hz, 2H), 3.85 (s, 3H), 2.17 (s, 3H) |
| 96 | 400 MHz $CDCl_3$ | 8.73 (d, J = 2.3 Hz, 1H), 8.53 (dd, J = 4.8, 1.5 Hz, 2H), 8.06 (dd, J = 8.7, 2.4 Hz, 1H), 7.69 (dd, J = 7.8, 1.6 Hz, 1H), 7.44-7.63 (m, 4H), 7.22 (dd, J = 7.8, 4.9 Hz, 1H), 6.46-6.85 (m, 2H), 3.91-4.01 (m, 3H), 2.13 (s, 3H) |
| 97 | 400 MHz $CDCl_3$ | 9.18-9.50 (m, 2H), 9.11 (br. s., 1H), 8.60-8.90 (m, 2H), 8.38 (d, J = 8.4 Hz, 1H), 8.17 (d, J = 8.4 Hz, 1H), 7.86-8.08 (m, 2H), 7.37-7.80 (m, 5H), 7.02 (d, J = 6.5 Hz, 1H), 2.18 (s, 3H) |
| 98 | 300 MHz $CDCl_3$ | 8.49-8.69 (m, 2H), 7.83-8.06 (m, 2H), 7.76 (dd, J = 7.9, 1.6 Hz, 1H), 7.37-7.66 (m, 7H), 7.26-7.32 (m, 1H), 6.86 (d, J = 7.2 Hz, 1H), 2.14 (s, 3H) |
| 99 | 400 MHz $d_4$-MeOH | 8.97 (d, J = 3.5 Hz, 1H), 8.65 (d, J = 3.5 Hz, 1H), 8.31-8.49 (m, 2H), 8.24 (d, J = 7.6 Hz, 1H), 8.09 (d, J = 7.0 Hz, 2H), 7.32-7.92 (m, 7H), 6.98 (br. s., 1H) |
| 100 | 400 MHz $CDCl_3$ | 8.93 (d, J = 4.7 Hz, 1H), 8.29 (d, J = 7.8 Hz, 1H), 8.01-8.16 (m, 2H), 7.95 (d, J = 8.2 Hz, 1H), 7.81 (dd, J = 8.1, 1.7 Hz, 1H), 7.39-7.65 (m, 5H), 6.87 (d, J = 7.8 Hz, 1H) |
| 101 | 300 MHz $CDCl_3$ | 9.33 (d, J = 4.2 Hz, 1H), 9.20 (d, J = 7.3 Hz, 1H), 8.88 (d, J = 8.3 Hz, 1H), 8.65-8.79 (m, 2H), 8.43-8.65 (m, 2H), 8.05 (dd, J = 7.9, 1.3 Hz, 1H), 7.95 (dd, J = 8.3, 5.1 Hz, 1H), 7.40-7.69 (m, 5H), 7.06 (d, J = 7.3 Hz, 1H), 4.91 (dd, J = 10.4, 5.6 Hz, 2H), 4.56 (dd, J = 5.6, 2.6 Hz, 2H), 1.75 (s, 3H) |
| 102 | 300 MHz $d_4$-MeOH | 8.48 (d, J = 4.5 Hz, 1H), 8.14 (d, J = 2.2 Hz, 1H), 8.04 (dd, J = 9.6, 2.6 Hz, 1H), 7.63 (td, J = 9.1, 1.3 Hz, 1H), 7.34-7.51 (m, 3H), 7.26-7.34 (m, 1H), 6.65 (s, 1H), 6.53 (d, J = 9.6 Hz, 1H) |
| 103 | 300 MHz $d_4$-MeOH | 8.50 (d, J = 4.7 Hz, 1H), 8.42 (d, J = 2.6 Hz, 1H), 8.00 (dd, J = 9.4, 2.6 Hz, 1H), 7.65 (td, J = 9.1, 1.2 Hz, 1H), 7.27-7.52 (m, 4H), 6.67 (s, 1H), 6.56 (d, J = 9.5 Hz, 1H), 3.63 (s, 3H) |
| 104 | 300 MHz $d_4$-MeOH | 8.70 (d, J = 2.8 Hz, 1H), 8.51 (d, J = 4.7 Hz, 1H), 8.43 (s, 1H), 7.99-8.11 (m, 2H), 7.85 (d, J = 2.6 Hz, 1H), 7.59-7.71 (m, 5H), 7.46 (dt, J = 8.4, 4.3 Hz, 1H), 6.81 (s, 1H) |
| 105 | 300 MHz $d_4$-MeOH | 8.50 (d, J = 4.8 Hz, 1H), 8.01 (d, J = 9.5 Hz, 1H), 7.85 (s, 1H), 7.69-7.82 (m, 2H), 7.58-7.69 (m, 5H), 7.46 (dt, J = 8.4, 4.3 Hz, 1H), 6.76 (s, 1H), 6.70 (d, J = 9.5 Hz, 1H) |
| 106 | 300 MHz $d_4$-MeOH | 8.93 (d, J = 4.2 Hz, 1H), 8.21 (d, J = 6.9 Hz, 1H), 8.00 (d, J = 9.5 Hz, 1H), 7.80 (s, 1H), 7.72-7.78 (m, 1H), 7.51-7.71 (m, 6H), 6.93 (s, 1H), 6.69 (d, J = 9.6 Hz, 1H) |
| 107 | 300 MHz $d_4$-MeOH | 8.91 (d, J = 4.8 Hz, 1H), 8.15-8.27 (m, 1H), 7.81-7.90 (m, 2H), 7.64-7.70 (m, 1H), 7.51-7.64 (m, 2H), 7.41-7.51 (m, 2H), 7.31-7.41 (m, 2H), 6.90 (s, 1H) |
| 108 | 300 MHz $d_4$-MeOH | 8.89-9.01 (m, 3H), 8.60 (d, J = 1.8 Hz, 1H), 8.13-8.31 (m, 3H), 7.55-7.73 (m, 2H), 7.36-7.48 (m, 2H), 6.96 (s, 1H) |
| 109 | 300 MHz $d_4$-MeOH | 8.94 (d, J = 4.4 Hz, 1H), 8.82 (d, J = 1.9 Hz, 1H), 8.13-8.32 (m, 3H), 7.75 (d, J = 8.8 Hz, 1H), 7.53-7.70 (m, 5H), 6.96 (s, 1H), 6.59 (d, J = 7.3 Hz, 1H) |
| 110 | 300 MHz $d_4$-MeOH | 8.94 (d, J = 4.7 Hz, 1H), 8.90 (d, J = 2.5 Hz, 1H), 8.54 (s, 1H), 8.48 (d, J = 1.9 Hz, 1H), 8.21 (d, J = 8.0 Hz, 1H), 7.96-8.10 (m, 2H), 7.55-7.69 (m, 5H), 6.98 (s, 1H) |
| 111 | 300 MHz $d_4$-MeOH | 9.26 (d, J = 1.2 Hz, 1H), 8.98 (d, J = 4.2 Hz, 1H), 8.81 (d, J = 2.5 Hz, 1H), 8.65-8.75 (m, 1H), 8.23 (d, J = 7.9 Hz, 1H), 7.58-7.71 (m, 2H), 7.30-7.45 (m, 2H), 6.86 (s, 1H) |
| 112 | 300 MHz $d_4$-MeOH | 8.98 (d, J = 4.1 Hz, 1H), 8.59-8.71 (m, 1H), 8.18-8.28 (m, 1H), 8.11 (dt, J = 7.9, 1.0 Hz, 1H), 7.97 (td, J = 7.7, 1.7 Hz, 1H), 7.53-7.70 (m, 3H), 7.32-7.45 (m, 2H), 6.84 (s, 1H) |
| 113 | 300 MHz $d_4$-MeOH | 8.86-8.92 (m, 2H), 8.51 (d, J = 4.7 Hz, 1H), 8.34 (dd, J = 8.8, 1.9 Hz, 1H), 8.19 (d, J = 8.8 Hz, 1H), 7.82 (d, J = 5.0 Hz, 1H), 7.63-7.71 (m, 5H), 7.46 (dt, J = 8.4, 4.3 Hz, 1H), 6.84 (s, 1H) |

TABLE 6-continued $^1$H NMR Data of Examples 1-261 and 287-424.

| Ex. # | Freq., Solvent | $^1$HNMR Data (δ ppm) |
|---|---|---|
| 114 | 300 MHz $d_4$-MeOH | 8.87 (d, J = 1.8 Hz, 1H), 8.51 (d, J = 4.7 Hz, 1H), 8.25 (dd, J = 8.7, 2.1 Hz, 1H), 8.18 (d, J = 7.2 Hz, 1H), 7.75 (d, J = 8.8 Hz, 1H), 7.58-7.71 (m, 5H), 7.45 (dt, J = 8.5, 4.4 Hz, 1H), 6.79 (s, 1H), 6.56 (d, J = 7.3 Hz, 1H) |
| 115 | 400 MHz DMSO-$d_6$ | 9.52 (d, J = 7.6 Hz, 1H), 8.93-8.99 (m, 2H), 8.59 (s, 1H), 8.41 (d, J = 8.1 Hz, 1H), 8.21 (d, J = 8.0 Hz, 1H), 8.03 (s, 2H), 7.62 (m, 2H), 7.27 (d, J = 8 Hz, 2H), 7.18 (d, J = 8 Hz, 2H), 7.68 (d, J = 7.6 Hz, 1H), 2.59 (q, J = 8 Hz, 2H), 1.15 (t, J = 8 Hz, 3H) |
| 116 | 300 MHz $d_4$-MeOH | 8.94 (d, J = 4.8 Hz, 1H), 8.91 (d, J = 1.6 Hz, 1H), 8.64 (d, J = 6.9 Hz, 1H), 8.39 (dd, J = 8.9, 2.0 Hz, 1H), 8.16-8.27 (m, 1H), 7.98 (d, J = 9.1 Hz, 1H), 7.53-7.70 (m, 5H), 7.03 (d, J = 6.9 Hz, 1H), 6.97 (s, 1H) |
| 117 | 300 MHz $d_4$-MeOH | 8.91 (d, J = 4.4 Hz, 1H), 8.11-8.27 (m, 2H), 7.84 (d, J = 7.9 Hz, 1H), 7.89 (d, J = 7.9 Hz, 1H), 7.49-7.68 (m, 5H), 7.23 (t, J = 7.9 Hz, 1H), 6.89 (s, 1H) |
| 118 | 300 MHz $d_4$-MeOH | 8.88 (d, J = 4.2 Hz, 1H), 8.18 (d, J = 7.9 Hz, 1H), 7.87 (d, J = 7.9 Hz, 1H), 7.64 (s, 4H), 7.55 (dd, J = 7.7, 4.9 Hz, 1H), 7.42 (t, J = 7.5 Hz, 1H), 7.33 (d, J = 6.6 Hz, 1H), 7.15 (t, J = 7.2 Hz, 1H), 6.90 (s, 1H) |
| 119 | 300 MHz $d_4$-MeOH | 8.93 (d, J = 4.2 Hz, 1H), 8.20 (d, J = 8.2 Hz, 1H), 7.52-7.74 (m, 2H), 7.19-7.36 (m, 2H), 6.63 (s, 1H), 4.28-4.45 (m, 1H), 3.96-4.10 (m, 1H), 3.81-3.96 (m, 1H), 2.15-2.35 (m, 1H), 1.74-2.02 (m, 3H) |
| 120 | 300 MHz $d_4$-MeOH | 8.91 (d, J = 2.3 Hz, 1H), 8.60 (s, 1H), 8.46-8.54 (m, 2H), 8.10 (dd, J = 8.6, 1.7 Hz, 1H), 8.02 (d, J = 8.5 Hz, 1H), 7.58-7.72 (m, 5H), 7.46 (dt, J = 8.4, 4.4 Hz, 1H), 6.82 (s, 1H) |
| 121 | 300 MHz $d_4$-MeOH | 8.91 (d, J = 4.5 Hz, 1H), 8.19 (d, J = 7.9 Hz, 1H), 7.82 (d, J = 8.5 Hz, 2H), 7.49-7.68 (m, 7H), 6.92 (s, 1H), 1.53 (s, 6H) |
| 122 | 300 MHz $d_4$-MeOH | 8.90 (d, J = 4.4 Hz, 1H), 8.19 (d, J = 7.2 Hz, 1H), 7.84 (d, J = 8.5 Hz, 2H), 7.50-7.67 (m, 7H), 6.90 (s, 1H) |
| 123 | 300 MHz $d_4$-MeOH | 8.92 (d, J = 4.1 Hz, 1H), 8.11-8.29 (m, 1H), 7.52-7.71 (m, 2H), 7.28 (d, J = 9.9 Hz, 2H), 6.63 (s, 1H), 4.37 (dd, J = 8.3, 5.6 Hz, 1H), 3.77-4.04 (m, 2H), 2.14-2.35 (m, 1H), 1.70-2.03 (m, 3H) |
| 124 | 600 MHz DMSO-$d_6$ | 9.32 (d, J = 7.6 Hz, 1H), 8.92 (d, J = 4.7 Hz, 1H), 8.71 (d, J = 2.1 Hz, 1H), 8.28-8.17 (m, 2H), 7.61 (dd, J = 7.9, 4.9 Hz, 1H), 7.34 (dd, J = 8.6, 5.5 Hz, 2H), 7.17 (t, J = 8.9 Hz, 2H), 6.87 (d, J = 8.7 Hz, 1H), 6.71 (d, J = 7.5 Hz, 1H), 3.90 (s, 3H) |
| 125 | 300 MHz $d_4$-MeOH | 8.50 (d, J = 4.7 Hz, 1H), 8.40 (d, J = 8.6 Hz, 1H), 8.23 (d, J = 7.2 Hz, 1H), 8.18 (d, J = 1.2 Hz, 1H), 7.96 (dd, J = 8.6, 1.5 Hz, 1H), 7.59-7.72 (m, 5H), 7.46 (dt, J = 8.6, 4.4 Hz, 1H), 6.79 (s, 1H), 6.58 (d, J = 7.2 Hz, 1H) |
| 126 | 600 MHz DMSO-$d_6$ | 9.22 (d, J = 7.2 Hz, 1H), 8.92 (d, J = 4.2 Hz, 1H), 8.23 (d, J = 7.8 Hz, 1H), 7.89 (d, J = 7.2 Hz, 2H), 7.61 (dd, J = 7.8, 4.8 Hz, 1H), 7.54 (dd, J = 7.8, 1.2 Hz, 1H), 7.45 (t, J = 7.2 Hz, 2H), 7.34-7.37 (m, 2H), 7.16 (d, J = 9 Hz, 2H), 6.71 (d, J = 7.8 Hz, 1H) |
| 127 | 300 MHz $d_4$-MeOH | 8.91 (d, J = 4.2 Hz, 1H), 8.20 (d, J = 7.9 Hz, 1H), 7.78 (d, J = 8.2 Hz, 2H), 7.50-7.71 (m, 2H), 7.23-7.45 (m, 4H), 6.89 (s, 1H), 2.96 (dt, J = 13.6, 6.8 Hz, 1H), 1.25 (d, J = 6.9 Hz, 6H) |
| 128 | 300 MHz $d_4$-MeOH | 9.22 (dd, J = 4.4, 1.8 Hz, 1H), 9.00 (d, J = 4.7 Hz, 1H), 8.64-8.76 (m, 2H), 8.41 (d, J = 8.3 Hz, 1H), 8.22 (d, J = 7.9 Hz, 1H), 7.84 (dd, J = 8.2, 4.4 Hz, 1H), 7.56-7.72 (m, 5H), 6.94 (s, 1H) |
| 129 | 300 MHz $d_4$-MeOH | 9.23 (dd, J = 4.5, 1.8 Hz, 1H), 9.01 (d, J = 4.4 Hz, 1H), 8.63-8.76 (m, 2H), 8.42 (d, J = 8.3 Hz, 1H), 8.24 (d, J = 8.0 Hz, 1H), 7.85 (dd, J = 8.3, 4.5 Hz, 1H), 7.59-7.72 (m, 2H), 7.40-7.53 (m, 2H), 6.91 (s, 1H) |
| 130 | 300 MHz $CDCl_3$ | 9.31 (d, J = 4.2 Hz, 1H), 8.96 (d, J = 4.1 Hz, 1H), 8.81 (d, J = 8.3 Hz, 1H), 8.49-8.69 (m, 3H), 8.35 (dd, J = 8.9, 1.8 Hz, 1H), 8.11 (d, J = 7.0 Hz, 1H), 7.90 (dd, J = 8.3, 4.8 Hz, 1H), 7.49-7.64 (m, 2H), 7.38 (d, J = 8.0 Hz, 1H), 7.30 (d, J = 11.4 Hz, 1H), 6.89 (d, J = 7.6 Hz, 1H) |
| 131 | 300 MHz $CDCl_3$ | 9.26 (br. s., 1H), 8.77-9.14 (m, 4H), 8.39 (d, J = 8.6 Hz, 1H), 8.22 (d, J = 8.6 Hz, 1H), 7.91-8.16 (m, 2H), 7.46-7.65 (m, 2H), 7.28-7.46 (m, 2H), 6.84 (d, J = 7.0 Hz, 1H) |
| 132 | 300 MHz $d_4$-MeOH | 8.85-9.00 (m, 2 H), 8.52 (s, 1 H), 8.42 (d, J = 8.3 Hz, 1 H), 8.21 (d, J = 8.0 Hz, 1 H), 7.88-8.12 (m, 2 H), 7.48-7.73 (m, 6 H), 6.99 (s, 1 H) |
| 133 | 300 MHz $d_4$-MeOH | 8.93 (d, J = 4.1 Hz, 2 H), 8.38-8.56 (m, 2 H), 8.15-8.28 (m, 2 H), 7.96-8.15 (m, 1 H), 7.50-7.71 (m, 6 H), 6.99 (s, 1 H) |
| 134 | 400 MHz DMSO-$d_6$ | 8.95 (d, J = 7.4 Hz, 1H), 8.90 (d, J = 4.7 Hz, 1H), 8.51 (d, J = 2.0 Hz, 1H), 8.24 (d, J = 7.8 Hz, 1H), 7.86 (dd, J = 8.6, 2.3 Hz, 1H), 7.66-7.73 (m, J = 8.2 Hz, 2H), 7.61 (dd, J = 7.8, 4.7 Hz, 1H), 7.46-7.55 (m, J = 7.8 Hz, 2H), 6.78 (d, J = 7.8 Hz, 1H), 6.51 (s, 2H), 6.40 (d, J = 8.6 Hz, 1H) |

TABLE 6-continued

| Ex. # | Freq., Solvent | $^1$HNMR Data (δ ppm) |
|---|---|---|
| | | $^1$H NMR Data of Examples 1-261 and 287-424. |
| 135 | 300 MHz $CDCl_3$ | 8.90 (d, J = 3.9 Hz, 1H), 8.82 (d, J = 2.0 Hz, 1H), 8.30 (d, J = 7.6 Hz, 1H), 8.00-8.16 (m, 2H), 7.46-7.65 (m, 5H), 7.41 (d, J = 8.2 Hz, 1H), 6.85 (d, J = 7.6 Hz, 1H) |
| 136 | 300 MHz $CDCl_3$ | 8.87 (d, J = 3.9 Hz, 1H), 8.75 (d, J = 7.6 Hz, 1H), 8.00 (d, J = 8.0 Hz, 1H), 7.62-7.74 (m, J = 8.2 Hz, 2H), 7.51-7.61 (m, J = 8.3 Hz, 2H), 7.43 (dd, J = 8.0, 4.9 Hz, 1H), 7.37 (s, 1H), 6.79 (d, J = 7.6 Hz, 1H), 6.34 (br s, 2H) |
| 137 | 400 MHz DMSO-$d_6$ | 9.38 (d, J = 7.4 Hz, 1H), 8.90 (d, J = 4.3 Hz, 1H), 8.66 (s, 1H), 8.25 (d, J = 7.8 Hz, 1H), 7.70 (d, J = 7.8 Hz, 2H), 7.55-7.65 (m, 3H), 7.51 (d, J = 7.8 Hz, 3H), 6.74 (d, J = 7.4 Hz, 1H), 2.34 (s, 3H) |
| 138 | 300 MHz $CDCl_3$ | 8.89 (d, J = 3.8 Hz, 1H), 7.93-8.11 (m, 2H), 7.58 (dd, J = 3.7, 1.1 Hz, 1H), 7.54 (s, 4H), 7.43-7.50 (m, 2H), 7.08 (dd, J = 5.0, 3.8 Hz, 1H), 6.85 (d, J = 7.9 Hz, 1H) |
| 139 | 400 MHz DMSO-$d_6$ | 9.35 (d, J = 7.4 Hz, 1H), 8.91 (d, J = 4.3 Hz, 1H), 8.26 (d, J = 7.4 Hz, 1H), 8.12 (s, 1H), 7.67-7.76 (m, 3H), 7.63 (dd, J = 7.8, 5.1 Hz, 1H), 7.47-7.56 (m, 3H), 6.75 (d, J = 7.4 Hz, 1H), 6.37 (s, 2H) |
| 140 | 300 MHz $CDCl_3$ | 8.90 (d, J = 3.8 Hz, 1H), 8.27 (d, J = 7.6 Hz, 1H), 8.07-8.14 (m, 2H), 8.05 (d, J = 6.7 Hz, 1H), 7.83-7.94 (m, 2H), 7.55 (s, 4H), 7.48 (dd, J = 7.7, 4.8 Hz, 1H), 6.89 (d, J = 7.7 Hz, 1H), 3.94 (s, 3H) |
| 141 | 300 MHz $CDCl_3$ | 8.98 (d, J = 4.2 Hz, 1H), 8.50 (d, J = 7.5 Hz, 1H), 8.13-8.18 (m, 3H), 7.95 (d, J = 8.5 Hz, 2H), 7.49-7.69 (m, 5H), 6.95 (d, J = 7.3 Hz, 1H) |
| 142 | 300 MHz $CDCl_3$ | 8.84 (d, J = 4.8 Hz, 1H), 8.00 (d, J = 7.5 Hz, 1H), 7.37-7.60 (m, 6H), 6.66 (d, J = 7.6 Hz, 1H), 3.97-4.15 (m, 1H), 3.89 (d, J = 13.3 Hz, 1H), 2.95 (dd, J = 13.3, 10.4 Hz, 1H), 2.82 (br. s., 1H), 2.33 (d, J = 3.8 Hz, 1H), 1.88 (br. s., 1H), 1.58-1.81 (m, 2H), 1.43 (d, J = 2.2 Hz, 9H) |
| 143 | 400 MHz DMSO-$d_6$ | 13.13 (br. s., 1H), 8.81-8.99 (m, 2H), 8.34 (br. s., 1H), 8.25 (d, J = 8.2 Hz, 1H), 7.98 (br. s., 1H), 7.66-7.75 (m, J = 8.2 Hz, 2H), 7.62 (dd, J = 8.0, 4.9 Hz, 1H), 7.44-7.51 (m, J = 8.2 Hz, 2H), 6.81 (d, J = 7.8 Hz, 1H) |
| 144 | 400 MHz DMSO-$d_6$ | 9.44 (d, J = 8.6 Hz, 1H), 9.03 (d, J = 4.3 Hz, 1H), 8.30 (d, J = 8.2 Hz, 1H), 7.80-7.86 (m, 1H), 7.64-7.76 (m, 3H), 7.54 (d, J = 8.2 Hz, 2H), 7.28 (dd, J = 8.6, 4.3 Hz, 1H), 7.18 (dd, J = 8.6, 1.2 Hz, 1H), 6.83 (br. s., 2H), 6.71 (d, J = 8.6 Hz, 1H) |
| 145 | 400 MHz DMSO-$d_6$ | 8.96 (d, J = 8.2 Hz, 1H), 8.86 (d, J = 4.3 Hz, 1H), 8.73 (s, 1H), 8.22 (d, J = 7.8 Hz, 1H), 7.62-7.69 (m, J = 8.2 Hz, 2H), 7.59 (dd, J = 7.8, 4.7 Hz, 1H), 7.31-7.39 (m, J = 8.2 Hz, 2H), 6.58 (d, J = 7.8 Hz, 1H), 2.96 (q, J = 7.2 Hz, 2H), 2.52-2.61 (m, 2H), 2.23 (s, 3H) |
| 146 | 400 MHz DMSO-$d_6$ | 9.02 (d, J = 4.7 Hz, 1H), 8.97 (d, J = 8.6 Hz, 1H), 8.30 (d, J = 7.8 Hz, 1H), 7.63-7.77 (m, 3H), 7.54 (d, J = 8.2 Hz, 2H), 7.39 (s, 1H), 7.01 (s, 1H), 6.66 (d, J = 8.6 Hz, 1H), 3.93 (s, 3H) |
| 147 | 300 MHz $CDCl_3$ | 9.33 (s, 1H), 9.16 (s, 2H), 8.91 (d, J = 4.2 Hz, 1H), 8.40 (d, J = 7.6 Hz, 1H), 8.06 (d, J = 8.2 Hz, 1H), 7.56 (s, 4H), 7.51 (dd, J = 8.1, 4.8 Hz, 1H), 6.86 (d, J = 7.6 Hz, 1H) |
| 148 | 300 MHz $CDCl_3$ | 8.90 (d, J = 4.1 Hz, 1H), 8.74 (d, J = 1.8 Hz, 2H), 8.31 (d, J = 8.8 Hz, 1H), 8.23 (d, J = 7.7 Hz, 1H), 8.16 (dd, J = 8.8, 2.3 Hz, 1H), 8.05 (d, J = 7.0 Hz, 1H), 7.55 (s, 4H), 7.49 (dd, J = 7.8, 4.9 Hz, 1H), 6.87 (d, J = 7.6 Hz, 1H), 2.23 (s, 3H) |
| 149 | 400 MHz DMSO-$d_6$ | 8.92-9.06 (m, 2H), 8.30 (d, J = 8.2 Hz, 1H), 7.63-7.78 (m, 3H), 7.55 (d, J = 8.2 Hz, 2H), 7.01-7.06 (m, 1H), 6.95-6.99 (m, 1H), 6.81 (d, J = 8.2 Hz, 1H), 2.68-2.76 (m, 3H) |
| 150 | 400 MHz DMSO-$d_6$ | 9.00 (d, J = 4.3 Hz, 1H), 8.96 (d, J = 8.2 Hz, 1H), 8.30 (d, J = 8.2 Hz, 1H), 7.81 (d, J = 9.8 Hz, 1H), 7.63-7.76 (m, 4H), 7.53 (d, J = 8.2 Hz, 2H), 6.94 (d, J = 9.8 Hz, 1H), 6.68 (d, J = 8.2 Hz, 1H) |
| 151 | 400 MHz DMSO-$d_6$ | 9.34 (d, J = 7.8 Hz, 1H), 9.03 (br. s., 1H), 8.31 (d, J = 7.8 Hz, 1H), 7.65-7.78 (m, 4H), 7.58 (d, J = 8.2 Hz, 2H), 7.29 (d, J = 5.5 Hz, 1H), 6.76 (d, J = 8.2 Hz, 1H), 2.75 (s, 3H), 2.61 (s, 3H) |
| 152 | 400 MHz DMSO-$d_6$ | 8.77-8.95 (m, 2H), 8.14-8.31 (m, 1H), 7.66-7.72 (m, J = 8.2 Hz, 2H), 7.60 (dd, J = 7.8, 4.7 Hz, 1H), 7.36-7.53 (m, J = 7.8 Hz, 2H), 6.57 (d, J = 7.8 Hz, 1H), 3.75-3.92 (m, 2H), 3.21-3.31 (m, 2H), 2.56-2.67 (m, 1H), 1.47-1.66 (m, 4H) |
| 153 | 400 MHz DMSO-$d_6$ | 9.23 (d, J = 7.8 Hz, 1H), 8.94 (d, J = 4.7 Hz, 1H), 8.26 (d, J = 7.8 Hz, 1H), 7.68-7.77 (m, J = 8.2 Hz, 2H), 7.64 (dd, J = 7.8, 4.7 Hz, 1H), 7.46-7.55 (m, J = 7.8 Hz, 2H), 7.27 (s, 1H), 6.58 (d, J = 8.2 Hz, 1H), 6.00 (s, 1H), 4.77-4.99 (m, 2H), 2.15 (s, 3H) |

TABLE 6-continued

| Ex. # | Freq., Solvent | $^1$HNMR Data (δ ppm) |
|---|---|---|
| | | $^1$H NMR Data of Examples 1-261 and 287-424. |
| 154 | 400 MHz DMSO-$d_6$ | 9.21 (d, J = 8.2 Hz, 1H), 8.90 (d, J = 4.3 Hz, 1H), 8.23 (d, J = 7.8 Hz, 1H), 7.66-7.76 (m, J = 8.2 Hz, 2H), 7.61 (dd, J = 8.0, 4.9 Hz, 1H), 7.43-7.53 (m, J = 7.8 Hz, 2H), 6.59 (d, J = 7.8 Hz, 1H), 4.25 (t, J = 8.0 Hz, 2H), 3.84-4.03 (m, 2H) |
| 155 | 300 MHz $CDCl_3$ | 8.83 (d, J = 3.9 Hz, 1H), 8.36 (br. s., 1H), 8.01 (d, J = 8.0 Hz, 1H), 7.85 (d, J = 8.0 Hz, 1H), 7.36-7.61 (m, 5H), 7.05 (s, 1H), 6.64 (d, J = 7.5 Hz, 1H), 2.90-3.08 (m, 2H), 2.72 (d, J = 6.6 Hz, 2H) |
| 156 | 300 MHz $d_4$-MeOH | 8.95 (d, J = 3.9 Hz, 1H), 8.16-8.32 (m, 3H), 8.11 (td, J = 7.8, 1.2 Hz, 1H), 7.96 (s, 1H), 7.88 (td, J = 7.7, 1.1 Hz, 1H), 7.59-7.79 (m, 2H), 7.43-7.56 (m, 2H), 7.01 (s, 1H), 3.11 (d, J = 7.5 Hz, 2H), 2.19-2.44 (m, 1H), 1.06 (d, J = 6.6 Hz, 6H) |
| 157 | 400 MHz DMSO-$d_6$ | 8.95 (dd, J = 8.0, 3.7 Hz, 1H), 8.89 (d, J = 4.7 Hz, 1H), 8.24 (d, J = 7.8 Hz, 1H), 7.64-7.75 (m, J = 8.2 Hz, 2H), 7.60 (dd, J = 7.8, 5.1 Hz, 1H), 7.38-7.52 (m, J = 7.4 Hz, 2H), 6.59 (d, J = 7.8 Hz, 1H), 3.63-3.74 (m, 2H), 3.59 (qd, J = 7.6, 2.3 Hz, 1H), 3.15-3.29 (m, 1H), 2.39-2.49 (m, 1H), 2.21-2.39 (m, 2H), 1.83-1.96 (m, 1H), 1.38-1.53 (m, 1H) |
| 158 | 400 MHz DMSO-$d_6$ | 11.87 (br. s., 1H), 9.08 (d, J = 8.2 Hz, 1H), 8.91 (d, J = 4.3 Hz, 1H), 8.24 (d, J = 7.4 Hz, 1H), 7.65-7.72 (m, J = 8.2 Hz, 2H), 7.61 (dd, J = 8.0, 4.9 Hz, 2H), 7.44-7.49 (m, J = 8.2 Hz, 2H), 6.90 (br. s., 1H), 6.60 (d, J = 8.2 Hz, 1H), 3.48 (br. s., 2H) |
| 159 | 400 MHz DMSO-$d_6$ | 9.01 (d, J = 4.7 Hz, 1H), 8.65 (d, J = 8.2 Hz, 1H), 8.30 (d, J = 7.8 Hz, 1H), 7.63-7.77 (m, 3H), 7.51 (d, J = 8.2 Hz, 2H), 6.66 (d, J = 8.6 Hz, 1H), 6.26 (br. s., 2H) |
| 160 | 400 MHz DMSO-$d_6$ | 9.35 (d, J = 7.8 Hz, 1H), 8.94 (d, J = 4.3 Hz, 1H), 8.26 (d, J = 8.2 Hz, 1H), 7.69-7.76 (m, J = 8.2 Hz, 2H), 7.64 (dd, J = 7.8, 4.7 Hz, 1H), 7.46-7.56 (m, J = 7.8 Hz, 2H), 6.96 (s, 1H), 6.67 (s, 1H), 6.57 (d, J = 7.8 Hz, 1H), 4.61-4.83 (m, 2H), 2.13 (s, 3H) |
| 161 | 300 MHz $CDCl_3$ | 9.12 (br. s., 1H), 8.84 (d, J = 3.9 Hz, 1H), 8.52 (d, J = 7.5 Hz, 1H), 7.99 (d, J = 7.9 Hz, 1H), 7.47-7.58 (m, 4H), 7.43 (dd, J = 7.8, 4.8 Hz, 1H), 7.32 (s, 1H), 6.60 (d, J = 7.3 Hz, 1H), 4.93-5.23 (m, 2H) |
| 162 | 400 MHz DMSO-$d_6$ | 8.81-8.99 (m, 2H), 8.25 (dd, J = 7.4, 2.7 Hz, 1H), 8.05 (dd, J = 19.0, 7.6 Hz, 1H), 7.69 (dd, J = 8.2, 3.1 Hz, 2H), 7.58-7.66 (m, 1H), 7.45 (t, J = 7.4 Hz, 2H), 6.54 (dd, J = 17.8, 8.0 Hz, 1H), 4.32-4.56 (m, 1H), 1.81 (d, J = 7.4 Hz, 3H), 1.06-1.29 (m, 3H) |
| 163 | 400 MHz DMSO-$d_6$ | 9.06-9.16 (m, 1H), 8.87-8.95 (m, 1H), 8.24 (d, J = 7.8 Hz, 1H), 7.67-7.74 (m, J = 8.2 Hz, 2H), 7.62 (dd, J = 7.8, 4.7 Hz, 1H), 7.54 (d, J = 9.4 Hz, 1H), 7.42-7.49 (m, J = 8.2 Hz, 2H), 6.58 (dd, J = 7.8, 3.9 Hz, 1H), 3.41-3.49 (m, 1H), 3.11-3.25 (m, 1H), 2.29 (dd, J = 7.8, 5.5 Hz, 1H), 2.24 (t, J = 8.4 Hz, 1H) |
| 164 | 400 MHz $CDCl_3$ | 8.75 (br. s., 1H), 7.98 (d, J = 6.8 Hz, 1H), 7.14-7.61 (m, 9H), 6.66 (d, J = 6.8 Hz, 1H), 3.65 (br. s., 2H) |
| 165 | 400 MHz $d_4$-MeOH | 9.15 (d, J = 4.9 Hz, 1H), 8.43 (d, J = 7.8 Hz, 1H), 8.00 (s, 2H), 7.84-7.88 (m, 2H), 7.81-7.84 (m, 1H), 7.76-7.81 (m, 2H), 7.15 (s, 1H), 7.07 (d, J = 8.6 Hz, 2H) |
| 166 | 400 MHz $d_4$-MeOH | 8.53 (d, J = 4.7 Hz, 1H), 8.16 (s, 2H), 7.91 (d, J = 8.2 Hz, 1H), 7.60-7.72 (m, 6H), 7.49 (dt, J = 8.5, 4.4 Hz, 1H), 6.82 (s, 1H) |
| 167 | 400 MHz $d_4$-MeOH | 8.49 (d, J = 4.5 Hz, 1H), 8.04 (d, J = 8.4 Hz, 2H), 7.86 (d, J = 8.4 Hz, 2H), 7.58-7.69 (m, 5H), 7.45 (dt, J = 8.5, 4.4 Hz, 1H), 6.72-6.79 (m, 1H) |
| 168 | 400 MHz $d_4$-MeOH | 8.93 (d, J = 4.9 Hz, 1H), 8.17-8.25 (m, 2H), 8.15 (d, J = 8.0 Hz, 1H), 7.91 (d, J = 7.6 Hz, 1H), 7.62-7.71 (m, 3H), 7.54-7.61 (m, 3H), 6.92 (s, 1H) |
| 169 | 400 MHz $d_4$-MeOH | 8.37 (d, J = 4.7 Hz, 1H), 7.82 (d, J = 7.8 Hz, 1H), 7.42-7.53 (m, 5H), 7.33-7.42 (m, 1H), 7.28 (dt, J = 8.6, 4.4 Hz, 1H), 7.05 (d, J = 8.4 Hz, 1H), 6.91 (t, J = 7.5 Hz, 1H), 6.49 (s, 1H), 3.97 (s, 3H) |
| 170 | 400 MHz $d_4$-MeOH | 8.99 (d, J = 3.9 Hz, 2H), 8.68 (d, J = 1.6 Hz, 1H), 8.53 (d, J = 4.5 Hz, 1H), 8.28-8.35 (m, 1H), 8.17-8.26 (m, 1H), 7.61-7.75 (m, 5H), 7.48 (dt, J = 8.5, 4.4 Hz, 1H), 6.85 (s, 1H) |
| 171 | 400 MHz $d_4$-MeOH | 8.94 (d, J = 4.1 Hz, 1H), 8.22 (dd, J = 8.0, 1.0 Hz, 1H), 7.81-7.92 (m, 2H), 7.52-7.69 (m, 5H), 6.97-7.06 (m, 2H), 6.94 (s, 1H), 3.87 (s, 3H) |
| 172 | 400 MHz $d_4$-MeOH | 8.50 (d, J = 4.5 Hz, 1H), 7.90 (d, J = 9.0 Hz, 2H), 7.58-7.71 (m, 5H), 7.45 (dt, J = 8.5, 4.4 Hz, 1H), 7.02 (d, J = 8.8 Hz, 2H), 6.75 (s, 1H), 3.87 (s, 3H) |
| 173 | 400 MHz $d_4$-MeOH | 8.55 (d, J = 4.7 Hz, 1H), 8.24 (d, J = 2.7 Hz, 1H), 7.97 (d, J = 8.6 Hz, 1H), 7.60-7.70 (m, 5H), 7.47 (dt, J = 8.5, 4.4 Hz, 1H), 7.28 (dd, J = 8.5, 2.8 Hz, 1H), 6.67 (d, J = 1.6 Hz, 1H) |

TABLE 6-continued $^1H$ NMR Data of Examples 1-261 and 287-424.

| Ex. # | Freq., Solvent | $^1$HNMR Data (δ ppm) |
|---|---|---|
| 174 | 400 MHz $d_4$-MeOH | 9.22 (d, J = 7.6 Hz, 1H), 8.93 (d, J = 4.5 Hz, 1H), 8.21 (d, J = 7.8 Hz, 1H), 7.92 (d, J = 8.8 Hz, 2H), 7.50-7.71 (m, 5H), 7.23 (d, J = 8.6 Hz, 2H), 6.94 (d, J = 7.6 Hz, 1H), 2.31 (s, 3H) |
| 175 | 400 MHz $d_4$-MeOH | 8.96 (d, J = 4.3 Hz, 1H), 8.24 (dd, J = 8.0, 1.0 Hz, 1H), 8.12 (dd, J = 12.6, 0.9 Hz, 2H), 7.88 (dd, J = 8.5, 0.7 Hz, 1H), 7.56-7.72 (m, 6H), 7.00 (s, 1H) |
| 176 | 400 MHz $d_4$-MeOH | 9.00 (d, J = 4.7 Hz, 1H), 8.22 (d, J = 7.8 Hz, 1H), 8.01 (dd, J = 7.8, 1.6 Hz, 1H), 7.59-7.69 (m, 5H), 7.50-7.57 (m, 1H), 7.20 (d, J = 8.4 Hz, 1H), 7.09 (t, J = 7.5 Hz, 1H), 6.91 (s, 1H), 4.07 (s, 3H) |
| 177 | 400 MHz $d_6$-DMSO | 10.90 (s, 1H), 10.83 (s, 1H), 9.20 (d, J = 7.6 Hz, 1H), 8.45 (d, J = 4.7 Hz, 1H), 7.69-7.83 (m, 3H), 7.58-7.66 (m, 3H), 7.53 (s, 1H), 7.48 (dt, J = 8.4, 4.3 Hz, 1H), 6.97 (d, J = 8.2 Hz, 1H), 6.73 (d, J = 8.2 Hz, 1H) |
| 178 | 400 MHz $d_4$-MeOH | 8.94 (d, J = 4.7 Hz, 1H), 8.65-8.76 (m, 2H), 8.23 (d, J = 8.0 Hz, 1H), 7.79-7.88 (m, 2H), 7.65-7.70 (m, 2H), 7.56-7.64 (m, 3H), 6.94 (s, 1H) |
| 179 | 400 MHz $d_4$-MeOH | 8.95 (d, J = 4.3 Hz, 1H), 8.52 (s, 1H), 8.22 (dd, J = 7.2, 4.3 Hz, 2H), 8.09 (d, J = 7.8 Hz, 1H), 7.51-7.71 (m, 6H), 6.90-7.01 (m, 1H) |
| 180 | 400 MHz $d_4$-MeOH | 8.50 (d, J = 4.7 Hz, 1H), 7.91 (d, J = 7.2 Hz, 2H), 7.61-7.71 (m, 5H), 7.54-7.61 (m, 1H), 7.40-7.54 (m, 3H), 6.76 (s, 1H) |
| 181 | 400 MHz $d_4$-MeOH | 8.94 (d, J = 3.9 Hz, 1H), 8.22 (d, J = 7.2 Hz, 1H), 7.97-8.06 (m, 2H), 7.81-7.90 (m, 2H), 7.64-7.70 (m, 2H), 7.57-7.63 (m, 3H), 6.94 (s, 1H) |
| 182 | 400 MHz $d_4$-MeOH | 8.94 (s, 2H), 8.68 (s, 1H), 8.45 (s, 1H), 8.21 (d, J = 8.0 Hz, 1H), 7.63-7.69 (m, 2H), 7.55-7.62 (m, 3H), 6.93 (s, 1H), 2.51 (s, 3H) |
| 183 | 400 MHz $d_4$-MeOH | 8.93 (d, J = 4.5 Hz, 1H), 8.21 (d, J = 8.0 Hz, 1H), 7.93 (dd, J = 8.8, 5.3 Hz, 2H), 7.62-7.68 (m, 2H), 7.54-7.62 (m, 3H), 7.21 (t, J = 8.7 Hz, 2H), 6.93 (s, 1H) |
| 184 | 400 MHz $d_4$-MeOH | 8.52 (d, J = 4.7 Hz, 1H), 8.27-8.33 (m, 1H), 8.21 (dt, J = 7.9, 1.4 Hz, 1H), 7.95 (dt, J = 7.8, 1.3 Hz, 1H), 7.58-7.75 (m, 6H), 7.40-7.53 (m, 1H), 6.79 (s, 1H) |
| 185 | 400 MHz $d_4$-MeOH | 8.92 (d, J = 4.3 Hz, 1H), 8.20 (d, J = 8.0 Hz, 1H), 7.78-7.91 (m, 2H), 7.61-7.68 (m, 2H), 7.54-7.61 (m, 3H), 7.46-7.51 (m, 2H), 6.91 (s, 1H) |
| 186 | 400 MHz $d_4$-MeOH | 8.93 (d, J = 4.7 Hz, 1H), 8.22 (d, J = 8.0 Hz, 1H), 7.62-7.67 (m, 2H), 7.54-7.62 (m, 3H), 7.26-7.34 (m, 1H), 7.22 (s, 1H), 7.14 (d, J = 7.6 Hz, 1H), 6.90-6.98 (m, 2H), 2.98 (s, 6H) |
| 187 | 400 MHz $d_4$-MeOH | 8.50 (d, J = 4.7 Hz, 1H), 7.75 (d, J = 7.8 Hz, 1H), 7.59-7.69 (m, 6H), 7.52 (td, J = 8.0, 5.8 Hz, 1H), 7.45 (dt, J = 8.5, 4.4 Hz, 1H), 7.32 (td, J = 8.4, 2.0 Hz, 1H), 6.76 (br. s., 1H) |
| 188 | 400 MHz $d_4$-MeOH | 8.99-9.05 (m, 1H), 8.94 (d, J = 4.1 Hz, 1H), 8.71 (dd, J = 4.9, 1.6 Hz, 1H), 8.26-8.33 (m, 1H), 8.22 (dd, J = 7.9, 0.9 Hz, 1H), 7.64-7.69 (m, 2H), 7.58-7.63 (m, 3H), 7.56 (ddd, J = 7.9, 5.0, 0.8 Hz, 1H), 6.96 (s, 1H) |
| 189 | 400 MHz $d_4$-MeOH | 8.94 (d, J = 4.5 Hz, 1H), 8.50 (s, 1H), 8.21 (t, J = 7.5 Hz, 2H), 8.10 (d, J = 7.6 Hz, 1H), 7.53-7.71 (m, 6H), 6.95 (s, 1H), 3.95 (s, 3H) |
| 190 | 400 MHz $d_4$-MeOH | 8.96 (d, J = 4.3 Hz, 1H), 8.24 (s, 1H), 8.20-8.23 (m, 1H), 7.60-7.70 (m, 3H), 7.55-7.59 (m, 2H), 6.87 (s, 1H), 2.47 (s, 3H) |
| 191 | 400 MHz $d_4$-MeOH | 8.94 (d, J = 4.1 Hz, 1H), 8.23 (d, J = 8.2 Hz, 1H), 7.63-7.68 (m, 2H), 7.55-7.63 (m, 3H), 7.34-7.48 (m, 3H), 7.13 (dt, J = 6.7, 1.3 Hz, 1H), 6.94 (s, 1H), 3.86 (s, 3H) |
| 192 | 400 MHz $d_4$-MeOH | 8.95 (d, J = 4.7 Hz, 1H), 8.21 (d, J = 8.2 Hz, 1H), 7.51-7.69 (m, 6H), 6.86 (s, 1H), 6.73 (d, J = 2.3 Hz, 1H), 3.96 (s, 3H) |
| 193 | 400 MHz $d_4$-MeOH | 8.51 (d, J = 4.7 Hz, 1H), 7.91 (d, J = 7.2 Hz, 2H), 7.62-7.70 (m, 5H), 7.55-7.61 (m, 1H), 7.42-7.54 (m, 3H), 6.76 (s, 1H) |
| 194 | 400 MHz $d_4$-MeOH | 8.71 (d, J = 4.3 Hz, 1H), 8.54 (d, J = 4.5 Hz, 1H), 8.10 (d, J = 7.8 Hz, 1H), 7.97 (td, J = 7.7, 1.7 Hz, 1H), 7.55-7.70 (m, 6H), 7.46 (dt, J = 8.5, 4.4 Hz, 1H), 6.68 (s, 1H) |
| 195 | 400 MHz $d_6$-DMSO | 9.67 (d, J = 7.6 Hz, 1H), 9.01 (dd, J = 4.1, 1.8 Hz, 1H), 8.59-8.71 (m, 2H), 8.45 (dd, J = 8.3, 0.9 Hz, 1H), 8.17 (dd, J = 8.1, 1.5 Hz, 1H), 8.08 (s, 2H), 7.71-7.80 (m, 2H), 7.59-7.69 (m, 3H), 7.38 (dd, J = 8.0, 4.7 Hz, 1H), 6.88 (d, J = 7.6 Hz, 1H) |
| 196 | 400 MHz $d_4$-MeOH | 8.94 (d, J = 4.1 Hz, 1H), 8.22 (d, J = 7.0 Hz, 1H), 7.73-7.84 (m, 2H), 7.51-7.69 (m, 5H), 6.95 (s, 1H), 6.71-6.81 (m, 2H), 3.05 (s, 6H) |
| 197 | 400 MHz $d_4$-MeOH | 8.90 (d, J = 4.5 Hz, 1H), 8.20 (d, J = 8.0 Hz, 1H), 7.83 (d, J = 7.6 Hz, 1H), 7.71-7.79 (m, 2H), 7.60-7.70 (m, 5H), 7.57 (dd, J = 7.8, 4.9 Hz, 1H), 6.92 (s, 1H) |
| 198 | 400 MHz $d_4$-MeOH | 8.86 (d, J = 2.2 Hz, 1H), 8.61 (d, J = 2.2 Hz, 1H), 8.52 (d, J = 4.7 Hz, 1H), 7.59-7.73 (m, 5H), 7.47 (dt, J = 8.5, 4.4 Hz, 1H), 6.78 (s, 1H) |

TABLE 6-continued $^1$H NMR Data of Examples 1-261 and 287-424.

| Ex. # | Freq., Solvent | $^1$HNMR Data (δ ppm) |
|---|---|---|
| 199 | 400 MHz $d_4$-MeOH | 8.78 (d, J = 4.1 Hz, 1H), 7.98-8.11 (m, 2H), 7.50 (d, J = 8.4 Hz, 2H), 7.42-7.47 (m, 2H), 7.40 (d, J = 8.2 Hz, 2H), 6.77 (s, 1H), 6.74 (d, J = 1.0 Hz, 1H) |
| 200 | 400 MHz $d_4$-MeOH | 8.51 (d, J = 4.7 Hz, 1H), 8.02-8.10 (m, 2H), 7.85-7.91 (m, 2H), 7.62-7.72 (m, 5H), 7.47 (dt, J = 8.6, 4.4 Hz, 1H), 6.78 (s, 1H) |
| 201 | 400 MHz $d_4$-MeOH | 8.72 (dd, J = 5.3, 0.8 Hz, 1H), 8.15-8.25 (m, 2H), 8.08 (dd, J = 9.6, 2.7 Hz, 1H), 7.71-7.78 (m, 3H), 7.69 (dd, J = 7.0, 5.9 Hz, 1H), 7.61 (d, J = 8.2 Hz, 2H), 6.54-6.63 (m, 2H) |
| 202 | 400 MHz $d_4$-MeOH | 8.95-9.05 (m, 2H), 8.69 (d, J = 2.0 Hz, 1H), 8.50-8.58 (m, 1H), 8.32 (dd, J = 8.8, 2.0 Hz, 1H), 8.18-8.25 (m, 1H), 7.61-7.75 (m, 5H), 7.49 (dt, J = 8.5, 4.4 Hz, 1H), 6.86 (s, 1H) |
| 203 | 400 MHz $d_4$-MeOH | 9.05 (d, J = 1.8 Hz, 1H), 8.71 (dd, J = 5.0, 1.5 Hz, 1H), 8.49 (d, J = 4.7 Hz, 1H), 8.32 (dt, J = 8.0, 2.0 Hz, 1H), 7.59-7.69 (m, 5H), 7.56 (dd, J = 7.8, 5.1 Hz, 1H), 7.45 (dt, J = 8.5, 4.4 Hz, 1H), 6.78 (s, 1H) |
| 204 | 400 MHz $d_4$-MeOH | 8.99 (dd, J = 4.5, 1.6 Hz, 1H), 8.60 (s, 1H), 8.52 (d, J = 6.1 Hz, 2H), 8.11 (s, 2H), 7.61-7.74 (m, 6H), 7.47 (dt, J = 8.5, 4.4 Hz, 1H), 6.83 (s, 1H) |
| 205 | 400 MHz $d_4$-MeOH | 8.99 (d, J = 4.7 Hz, 1H), 8.78 (d, J = 1.8 Hz, 1H), 8.12-8.29 (m, 2H), 8.05 (d, J = 8.2 Hz, 1H), 7.55-7.68 (m, 5H), 6.87 (s, 1H) |
| 206 | 400 MHz $d_4$-MeOH | 9.10 (d, J = 1.4 Hz, 1H), 8.92 (d, J = 4.5 Hz, 1H), 8.38 (dd, J = 8.1, 2.2 Hz, 1H), 8.21 (d, J = 8.0 Hz, 1H), 7.97 (dd, J = 8.0, 0.6 Hz, 1H), 7.62-7.69 (m, 2H), 7.55-7.62 (m, 3H), 6.92 (s, 1H) |
| 207 | 400 MHz $d_4$-MeOH | 8.55 (s, 1H), 8.50 (d, J = 4.7 Hz, 1H), 8.21 (d, J = 7.8 Hz, 1H), 8.12 (d, J = 8.2 Hz, 1H), 7.55-7.70 (m, 6H), 7.45 (dt, J = 8.6, 4.3 Hz, 1H), 6.77 (s, 1H) |
| 208 | 400 MHz $d_4$-MeOH | 8.92 (d, J = 4.7 Hz, 1H), 8.20 (d, J = 7.8 Hz, 1H), 7.87 (s, 1H), 7.79 (d, J = 7.8 Hz, 1H), 7.61-7.67 (m, 2H), 7.53-7.61 (m, 4H), 7.42-7.50 (m, 1H), 6.91 (d, J = 7.6 Hz, 1H) |
| 209 | 400 MHz $d_4$-MeOH | 8.50 (d, J = 4.7 Hz, 1H), 7.75 (d, J = 7.8 Hz, 1H), 7.59-7.69 (m, 6H), 7.53 (td, J = 8.0, 5.8 Hz, 1H), 7.46 (dt, J = 8.5, 4.4 Hz, 1H), 7.29-7.37 (m, 1H), 6.76 (s, 1H) |
| 210 | 400 MHz $d_4$-MeOH | 8.97 (d, J = 4.9 Hz, 1H), 8.32 (d, J = 2.9 Hz, 1H), 8.21 (d, J = 7.2 Hz, 1H), 8.07 (d, J = 8.6 Hz, 1H), 7.54-7.68 (m, 5H), 7.48 (dd, J = 8.7, 2.8 Hz, 1H), 6.86 (s, 1H), 3.94 (s, 3H) |
| 211 | 400 MHz $d_4$-MeOH | 8.94 (d, J = 4.1 Hz, 1H), 8.18-8.26 (m, 2H), 8.15 (d, J = 7.6 Hz, 1H), 7.88 (d, J = 7.8 Hz, 1H), 7.64-7.74 (m, 3H), 7.55-7.64 (m, 3H), 6.96 (s, 1H) |
| 212 | 400 MHz $d_4$-MeOH | 9.53 (dd, J = 2.2, 1.3 Hz, 1H), 9.36 (dd, J = 5.3, 1.2 Hz, 1H), 8.93 (d, J = 4.5 Hz, 1H), 8.21 (d, J = 7.8 Hz, 1H), 8.06 (dd, J = 5.4, 2.2 Hz, 1H), 7.63-7.68 (m, 2H), 7.55-7.62 (m, 3H), 6.92 (s, 1H) |
| 213 | 400 MHz $d_6$-DMSO | 10.13 (s, 1H), 9.24 (d, J = 7.6 Hz, 1H), 8.45 (d, J = 4.7 Hz, 1H), 7.92 (d, J = 8.8 Hz, 2H), 7.74-7.81 (m, 1H), 7.72 (d, J = 8.2 Hz, 2H), 7.63 (d, J = 8.2 Hz, 2H), 7.48 (dt, J = 8.5, 4.4 Hz, 1H), 7.25 (d, J = 8.8 Hz, 2H), 6.73 (d, J = 7.6 Hz, 1H), 3.06 (s, 3H) |
| 214 | 400 MHz $d_4$-MeOH | $^1$H NMR (MeOH): 8.52 (d, J = 4.7 Hz, 1H), 7.61-7.71 (m, 5H), 7.36-7.53 (m, 4H), 7.10-7.19 (m, 1H), 6.77 (s, 1H), 3.87 (s, 3H) |
| 215 | 400 MHz $d_4$-MeOH | 9.01 (d, J = 4.1 Hz, 1H), 8.17-8.28 (m, 2H), 7.59-7.69 (m, 6H), 7.43-7.53 (m, 1H), 7.32 (t, J = 7.2 Hz, 1H), 6.98 (s, 1H), 4.18 (s, 3H) |
| 216 | 400 MHz $d_4$-MeOH | 8.50 (d, J = 4.7 Hz, 1H), 8.47 (s, 1H), 8.24 (d, J = 7.8 Hz, 1H), 8.15 (d, J = 7.8 Hz, 1H), 7.77 (t, J = 7.8 Hz, 1H), 7.60-7.70 (m, 5H), 7.46 (dt, J = 8.5, 4.4 Hz, 1H), 6.79 (s, 1H), 3.17 (s, 3H) |
| 217 | 400 MHz $d_4$-MeOH | 8.50 (d, J = 4.7 Hz, 1H), 8.10-8.14 (m, 2H), 8.05-8.10 (m, 2H), 7.58-7.72 (m, 5H), 7.46 (dt, J = 8.5, 4.4 Hz, 1H), 6.77 (s, 1H), 3.17 (s, 3H) |
| 218 | 400 MHz $d_4$-MeOH | 8.86 (d, J = 4.3 Hz, 1H), 8.16 (d, J = 8.0 Hz, 1H), 7.59 (d, J = 8.4 Hz, 2H), 7.55 (dd, J = 7.8, 4.9 Hz, 1H), 7.48 (d, J = 8.2 Hz, 2H), 7.20-7.35 (m, 5H), 6.70 (s, 1H), 3.64 (s, 2H) |
| 219 | 400 MHz $d_4$-MeOH | 8.94 (d, J = 3.9 Hz, 1H), 8.22 (dd, J = 8.0, 1.2 Hz, 1H), 7.86-7.94 (m, 1H), 7.80 (s, 1H), 7.64-7.68 (m, 2H), 7.56-7.63 (m, 4H), 7.47-7.53 (m, 1H), 6.94 (s, 1H) |
| 220 | 400 MHz $d_4$-MeOH | 8.96 (d, J = 4.9 Hz, 1H), 8.54 (d, J = 1.8 Hz, 1H), 8.22 (d, J = 7.2 Hz, 1H), 7.53-7.69 (m, 5H), 7.06 (d, J = 2.0 Hz, 1H), 6.88 (s, 1H) |
| 221 | 400 MHz $d_4$-MeOH | 8.50 (d, J = 4.5 Hz, 1H), 8.23 (s, 1H), 7.57-7.69 (m, 5H), 7.46 (dt, J = 8.5, 4.4 Hz, 1H), 6.65 (s, 1H), 2.45 (s, 3H) |
| 222 | 400 MHz $d_4$-MeOH | 8.96 (d, J = 4.5 Hz, 1H), 8.23 (d, J = 8.0 Hz, 1H), 8.10-8.15 (m, 1H), 7.86-7.98 (m, 2H), 7.64-7.70 (m, 2H), 7.57-7.63 (m, 3H), 7.39-7.50 (m, 2H), 6.94 (s, 1H) |
| 223 | 400 MHz $d_4$-MeOH | 8.89 (d, J = 4.1 Hz, 1H), 8.17 (d, J = 8.0 Hz, 1H), 7.63 (d, J = 7.8 Hz, 2H), 7.47-7.58 (m, 3H), 6.69 (s, 1H), 2.82-3.02 (m, |

TABLE 6-continued $^{1}$H NMR Data of Examples 1-261 and 287-424.

| Ex. # | Freq., Solvent | $^{1}$HNMR Data (δ ppm) |
|---|---|---|
| | | 1H), 2.48-2.72 (m, 1H), 2.24-2.45 (m, 2H), 1.14-2.18 (m, 5H) |
| 224 | 400 MHz $d_4$-MeOH | 8.89 (d, J = 4.5 Hz, 1H), 8.18 (d, J = 8.2 Hz, 1H), 7.59-7.64 (m, 2H), 7.55-7.59 (m, 1H), 7.51-7.55 (m, 2H), 6.74 (s, 1H), 3.57-3.78 (m, 2H), 2.36-2.76 (m, 2H) |
| 225 | 400 MHz $d_4$-MeOH | 8.91 (d, J = 4.7 Hz, 1H), 8.18 (d, J = 8.0 Hz, 1H), 7.60-7.68 (m, 2H), 7.50-7.60 (m, 3H), 6.73 (s, 1H), 3.64-4.17 (m, 4H), 3.21 (quin, J = 7.4 Hz, 1H), 2.00-2.21 (m, 2H) |
| 226 | 400 MHz $d_4$-MeOH | 9.27 (d, J = 2.0 Hz, 1H), 9.19 (d, J = 2.2 Hz, 1H), 8.95 (d, J = 3.9 Hz, 1H), 8.81 (t, J = 2.1 Hz, 1H), 8.23 (d, J = 7.4 Hz, 1H), 7.65-7.69 (m, 2H), 7.58-7.64 (m, 3H), 6.94-7.00 (m, 1H) |
| 227 | 400 MHz $d_4$-MeOH | 8.94 (d, J = 4.1 Hz, 1H), 8.22 (dd, J = 8.1, 0.9 Hz, 1H), 7.69-7.75 (m, 1H), 7.56-7.68 (m, 6H), 7.51 (td, J = 8.0, 5.6 Hz, 1H), 7.28-7.37 (m, 1H), 6.94 (s, 1H) |
| 228 | 400 MHz $d_4$-MeOH | 9.00 (d, J = 4.5 Hz, 1H), 8.68 (d, J = 4.7 Hz, 1H), 8.23 (d, J = 8.0 Hz, 1H), 8.14 (s, 1H), 7.99 (td, J = 7.7, 1.6 Hz, 1H), 7.53-7.69 (m, 6H), 6.90 (s, 1H) |
| 229 | 400 MHz $d_4$-MeOH | 8.91 (d, J = 4.5 Hz, 1H), 8.18 (d, J = 7.4 Hz, 1H), 7.64 (d, J = 8.2 Hz, 2H), 7.50-7.60 (m, 3H), 6.71 (s, 1H), 3.95-4.09 (m, 2H), 3.59-3.68 (m, 2H), 2.86-2.97 (m, 1H), 2.64 (d, J = 7.8 Hz, 2H), 1.44 (s, 9H) |
| 230 | 400 MHz $d_4$-MeOH | 9.28 (d, J = 2.2 Hz, 1H), 8.97 (d, J = 3.9 Hz, 1H), 8.89 (d, J = 1.6 Hz, 1H), 8.24 (d, J = 7.2 Hz, 1H), 8.11 (t, J = 9.1 Hz, 2H), 7.84-7.97 (m, 1H), 7.57-7.77 (m, 6H), 7.03 (s, 1H) |
| 231 | 400 MHz $d_4$-MeOH | 8.94 (d, J = 4.3 Hz, 1H), 8.20-8.25 (m, 1H), 7.96-8.02 (m, 2H), 7.64-7.70 (m, 2H), 7.55-7.63 (m, 3H), 7.39 (d, J = 8.0 Hz, 2H), 6.94 (s, 1H) |
| 232 | 300 MHz $d_4$-MeOH | 8.94 (d, J = 3.1 Hz, 1 H), 8.56 (s, 1 H), 8.43 (d, J = 8.0 Hz, 1 H), 8.06 (s, 2 H), 7.53-7.74 (m, 6 H), 7.34 (dd, J = 7.6, 5.0 Hz, 1 H), 6.91 (s, 1 H), 1.70 (t, J = 7.1 Hz, 1 H), 1.52 (s, 3 H), 0.87-1.01 (m, 2 H), 0.83 (s, 3 H) |
| 233 | 400 MHz $d_4$-MeOH | 8.90-9.00 (m, 1 H), 8.44-8.62 (m, 3 H), 8.25 (dd, J = 8.9, 1.9 Hz, 1 H), 8.13 (d, J = 8.8 Hz, 1 H), 7.52-7.73 (m, 6 H), 7.35 (dd, J = 7.7, 4.8 Hz, 1 H), 6.95 (s, 1 H), 1.62-1.76 (m, 1 H), 1.54 (s, 3 H), 0.86-0.98 (m, 2 H), 0.77-0.86 (m, 3 H) |
| 234 | 400 MHz $d_4$-MeOH | 8.94 (d, J = 4.5 Hz, 1 H), 8.20 (d, J = 8.0 Hz, 1 H), 7.57-7.69 (m, 3 H), 7.51 (d, J = 8.0 Hz, 2 H), 6.68 (s, 1 H), 4.28-4.42 (m, 1 H), 4.03 (q, J = 6.5 Hz, 1 H), 3.91 (q, J = 6.8 Hz, 1 H), 2.18-2.36 (m, 1 H), 1.74-2.01 (m, 3 H) |
| 235 | 400 MHz $d_4$-MeOH | 8.37 (d, J = 4.5 Hz, 1H), 7.52-7.66 (m, 3H), 7.46 (d, J = 8.0 Hz, 2H), 7.14-7.34 (m, 6H), 6.46 (s, 1H), 5.80 (ddt, J = 16.8, 10.4, 6.2 Hz, 1H), 4.97 (d, J = 10.0 Hz, 1H), 4.89 (d, J = 17.2 Hz, 1H), 3.81 (q, J = 7.0 Hz, 1H), 3.32-3.44 (m, 2H), 1.46 (d, J = 7.0 Hz, 3H) |
| 236 | 400 MHz $d_4$-MeOH | 8.89-9.01 (m, 1 H), 8.56-8.61 (m, 1 H), 8.48-8.56 (m, 2 H), 8.23 (dd, J = 8.9, 1.9 Hz, 1 H), 8.13 (d, J = 8.8 Hz, 1 H), 7.70 (d, J = 7.8 Hz, 1 H), 7.54-7.66 (m, 5 H), 7.35 (dd, J = 7.6, 4.7 Hz, 1 H), 6.96 (s, 1 H), 2.93 (d, J = 13.7 Hz, 1 H), 2.51-2.78 (m, 1 H), 1.03 (s, 9 H) |
| 237 | 300 MHz $d_4$-MeOH | 8.86 (d, J = 4.5 Hz, 1 H), 8.17 (d, J = 8.0 Hz, 1 H), 7.28-7.67 (m, 10 H), 6.68 (s, 1 H), 3.38 (s, 3 H) |
| 238 | 300 MHz $d_4$-MeOH | 8.87 (d, J = 4.5 Hz, 1 H), 8.45 (s, 1 H), 8.40 (d, J = 4.5 Hz, 1 H), 8.14 (d, J = 7.9 Hz, 1 H), 7.75 (d, J = 7.7 Hz, 1 H), 7.57-7.63 (m, 2 H), 7.52-7.57 (m, 1 H), 7.44-7.52 (m, 2 H), 7.36 (dd, J = 7.7, 5.0 Hz, 1 H), 6.68 (s, 1 H), 3.68 (s, 2 H) |
| 239 | 400 MHz $CDCl_3$ | 9.11 (s, 1H), 8.92 (d, J = 3.9 Hz, 1H), 8.52 (d, J = 1.5 Hz, 1H), 8.32 (d, J = 7.7 Hz, 1H), 8.18 (d, J = 8.5 Hz, 1H), 8.02-8.09 (m, 1H), 7.95 (dd, J = 8.6, 1.7 Hz, 1H), 7.52-7.63 (m, 4H), 7.48 (dd, J = 7.7, 5.1 Hz, 1H), 6.93 (d, J = 7.7 Hz, 1H) |
| 240 | 400 MHz $CDCl_3$ | 8.85 (dd, J = 4.7, 1.2 Hz, 1H), 8.32 (d, J = 7.9 Hz, 1H), 7.99 (dd, J = 8.0, 1.0 Hz, 1H), 7.44-7.58 (m, 4H), 7.41 (dd, J = 7.7, 5.0 Hz, 1H), 6.64 (d, J = 8.2 Hz, 1H), 3.24 (s, 3H), 1.35 (s, 3H), 1.35 (s, 3H) |
| 241 | 400 MHz $CDCl_3$ | 8.84 (d, J = 4.2 Hz, 1H), 8.00 (d, J = 7.9 Hz, 1H), 7.35-7.59 (m, 6H), 6.69 (d, J = 7.7 Hz, 1H), 3.51 (d, J = 6.9 Hz, 2H), 2.29-2.49 (m, 1H), 1.76-1.94 (m, 2H), 1.36-1.76 (m, 7H) |
| 242 | 400 MHz $CDCl_3$ | 8.87 (d, J = 4.2 Hz, 1H), 8.13 (d, J = 7.7 Hz, 1H), 7.49-7.61 (m, 4H), 7.46 (d, J = 8.3 Hz, 2H), 6.70 (d, J = 7.7 Hz, 1H), 3.49-3.68 (m, 1H), 2.18 (tt, J = 11.9, 3.5 Hz, 1H), 1.86-2.10 (m, 3H), 1.42-1.65 (m, 2H), 1.17-1.38 (m, 2H) |
| 243 | 400 MHz $CDCl_3$ | 8.84 (d, J = 4.2 Hz, 1H), 8.36 (d, J = 7.6 Hz, 1H), 8.05 (d, J = 7.2 Hz, 1H), 7.35-7.62 (m, 5H), 6.65 (d, J = 7.5 Hz, 1H), 1.54 (s, 3H), 1.51 (s, 3H) |
| 244 | 300 MHz $CDCl_3$ | 8.83 (d, J = 3.9 Hz, 1H), 8.01 (d, J = 8.2 Hz, 1H), 7.35-7.60 (m, 6H), 6.68 (d, J = 7.9 Hz, 1H), 2.59 (t, J = 4.6 Hz, 1H), |

TABLE 6-continued

| Ex. # | Freq., Solvent | $^1$HNMR Data (δ ppm) |
|---|---|---|
| | | $^1$H NMR Data of Examples 1-261 and 287-424. |
| | | 2.20-2.38 (m, 1H), 2.01-2.20 (m, 2H), 1.75 (d, J = 5.1 Hz, 3H), 1.48-1.66 (m, 2H) |
| 245 | 400 MHz $NCCD_3$ | 8.58 (d, J = 4.3 Hz, 1H), 8.00 (d, J = 7.2 Hz, 1H), 7.81-7.88 (m, 1H), 7.73-7.81 (m, 2H), 7.18-7.39 (m, 6H), 6.54 (d, J = 7.6 Hz, 1H), 2.81-2.92 (m, 2H), 2.32-2.41 (m, 2H) |
| 246 | 400 MHz $d_6$-DMSO | 9.58 (d, J = 7.4 Hz, 1H), 8.89 (d, J = 3.9 Hz, 1H), 8.22-8.30 (m, 2H), 8.19 (dt, J = 7.8, 1.3 Hz, 1H), 7.87 (dt, J = 7.7, 1.2 Hz, 1H), 7.48-7.78 (m, 11H), 6.81 (d, J = 7.4 Hz, 1H) |
| 247 | 400 MHz $d_4$-MeOH | 9.86 (s, 1H), 8.83 (s, 1H), 8.72 (d, J = 4.7 Hz, 1H), 8.64-8.70 (m, 1H), 8.56-8.64 (m, 2H), 8.43 (dd, J = 8.7, 1.5 Hz, 1H), 8.16 (td, J = 7.8, 1.6 Hz, 1H), 7.75 (d, J = 8.0 Hz, 1H), 7.68 (d, J = 2.2 Hz, 1H), 7.61-7.67 (m, 1H), 7.58 (d, J = 8.4 Hz, 1H), 7.42 (dd, J = 8.3, 2.1 Hz, 1H), 6.58 (s, 1H) |
| 248 | 300 MHz $d_6$-DMSO | 9.10 (d, J = 7.7 Hz, 1H), 8.57 (dd, J = 4.7, 1.5 Hz, 1H), 8.15 (d, J = 2.5 Hz, 1H), 7.97 (dd, J = 8.1, 1.4 Hz, 1H), 7.90 (dd, J = 9.6, 2.6 Hz, 1H), 7.64-7.76 (m, J = 8.3 Hz, 2H), 7.48-7.62 (m, J = 8.2 Hz, 2H), 7.43 (dd, J = 8.1, 4.6 Hz, 1H), 6.77 (d, J = 7.7 Hz, 1H), 6.33 (d, J = 9.6 Hz, 1H) |
| 249 | 300 MHz $d_6$-DMSO | 9.03 (d, J = 7.7 Hz, 1H), 8.58 (dd, J = 4.6, 1.4 Hz, 1H), 8.50 (d, J = 2.5 Hz, 1H), 7.99 (dd, J = 8.2, 1.5 Hz, 1H), 7.90 (dd, J = 9.5, 2.6 Hz, 1H), 7.65-7.78 (m, J = 8.2 Hz, 2H), 7.51-7.62 (m, J = 8.2 Hz, 2H), 7.43 (dd, J = 8.2, 4.7 Hz, 1H), 6.79 (d, J = 7.9 Hz, 1H), 6.39 (d, J = 9.5 Hz, 1H), 3.47 (s, 3H) |
| 250 | 300 MHz $d_6$-DMSO | 9.10 (d, J = 7.7 Hz, 1H), 8.38-8.50 (m, 1H), 8.15 (d, J = 2.5 Hz, 1H), 7.89 (dd, J = 9.6, 2.8 Hz, 1H), 7.75 (ddd, J = 10.1, 8.6, 1.2 Hz, 1H), 7.68 (d, J = 2.0 Hz, 1H), 7.61 (d, J = 8.3 Hz, 1H), 7.42-7.54 (m, 1H), 7.38 (dd, J = 8.4, 2.0 Hz, 1H), 6.61 (d, J = 7.9 Hz, 1H), 6.34 (d, J = 9.6 Hz, 1H) |
| 251 | 300 MHz $d_6$-DMSO | 9.05 (d, J = 7.9 Hz, 1H), 8.49 (d, J = 2.5 Hz, 1H), 8.40-8.47 (m, 1H), 7.90 (dd, J = 9.5, 2.6 Hz, 1H), 7.76 (ddd, J = 10.0, 8.5, 1.3 Hz, 1H), 7.69 (d, J = 2.0 Hz, 1H), 7.62 (d, J = 8.3 Hz, 1H), 7.47 (dt, J = 8.6, 4.3 Hz, 1H), 7.39 (dd, J = 8.3, 2.0 Hz, 1H), 6.63 (d, J = 7.6 Hz, 1H), 6.40 (d, J = 9.5 Hz, 1H), 3.47 (s, 3H) |
| 252 | 300 MHz $CDCl_3$ | 8.51 (d, J = 4.8 Hz, 1H), 8.44 (d, J = 7.0 Hz, 1H), 8.25 (d, J = 2.3 Hz, 1H), 7.88 (dd, J = 9.5, 2.5 Hz, 1H), 7.53-7.65 (m, 1H), 7.36-7.50 (m, 3H), 7.17 (d, J = 8.2 Hz, 2H), 6.78 (d, J = 9.5 Hz, 1H), 6.66 (d, J = 7.2 Hz, 1H), 3.66 (s, 3H) |
| 253 | 300 MHz $CDCl_3$ | 9.18 (s, 1H), 9.00 (d, J = 6.6 Hz, 1H), 8.52 (d, J = 4.4 Hz, 1H), 8.16-8.39 (m, 2H), 7.94 (d, J = 14.3 Hz, 2H), 7.49-7.73 (m, 5H), 7.36-7.49 (m, 1H), 6.68 (d, J = 5.4 Hz, 1H) |
| 254 | 300 MHz $CDCl_3$ | 9.15 (s, 1H), 8.93 (d, J = 4.1 Hz, 1H), 8.77 (d, J = 7.2 Hz, 1H), 8.04-8.38 (m, 3H), 7.94 (d, J = 18.1 Hz, 2H), 7.38-7.65 (m, 5H), 6.86 (d, J = 7.3 Hz, 1H) |
| 255 | 300 MHz $CDCl_3$ | 8.39-8.56 (m, 1H), 8.08-8.34 (m, 2H), 7.72 (dd, J = 9.5, 2.6 Hz, 1H), 7.27-7.54 (m, 4H), 7.14 (d, J = 7.9 Hz, 2H), 6.35-6.73 (m, 2H), 4.03 (dd, J = 7.2, 3.7 Hz, 2H), 1.37 (t, J = 7.2 Hz, 3H) |
| 256 | 300 MHz $d_4$-MeOH | 9.09 (d, J = 3.5 Hz, 1H), 8.79 (d, J = 8.2 Hz, 1H), 8.64 (s, 1H), 8.36 (d, J = 7.7 Hz, 1H), 8.19 (d, J = 9.1 Hz, 1H), 7.83 (dd, J = 8.3, 4.7 Hz, 1H), 7.70 (d, J = 8.2 Hz, 3H), 7.52 (d, J = 8.2 Hz, 2H), 7.33-7.47 (m, 2H), 7.30 (d, J = 7.6 Hz, 1H), 6.88 (s, 1H) |
| 257 | 400 MHz $CDCl_3$ | 8.97 (dd, J = 4.1, 1.6 Hz, 1H), 8.43 (s, 1H), 8.19-8.26 (m, 1H), 8.07 (dd, J = 8.5, 1.7 Hz, 1H), 7.93 (d, J = 8.6 Hz, 1H), 7.80 (d, J = 7.6 Hz, 1H), 7.60 (q, J = 7.0 Hz, 2H), 7.48-7.54 (m, 2H), 7.38 (d, J = 7.8 Hz, 1H), 7.11-7.25 (m, 2H), 6.83-6.93 (m, 2H) |
| 258 | 300 MHz $d_4$-MeOH | 9.03 (d, J = 7.7 Hz, 1H), 8.13 (d, J = 2.3 Hz, 1H), 8.04 (dd, J = 9.6, 2.6 Hz, 1H), 7.59-7.72 (m, J = 8.2 Hz, 2H), 7.46-7.54 (m, J = 8.2 Hz, 2H), 7.36-7.46 (m, 1H), 7.05 (t, J = 8.4 Hz, 2H), 6.87 (d, J = 4.8 Hz, 1H), 6.53 (d, J = 9.5 Hz, 1H) |
| 259 | 300 MHz $d_4$-MeOH | 9.01-9.16 (m, 2H), 8.80 (d, J = 8.3 Hz, 1H), 8.66 (s, 1H), 8.36 (d, J = 9.2 Hz, 1H), 8.19 (d, J = 8.9 Hz, 1H), 7.83 (dd, J = 8.5, 4.7 Hz, 1H), 7.57-7.73 (m, 4H), 6.79 (s, 1H) |
| 260 | 300 MHz $d_4$-MeOH | 9.14 (dd, J = 4.8, 1.3 Hz, 1H), 8.76-8.92 (m, 3H), 8.61 (s, 1H), 8.17-8.32 (m, 2H), 7.92 (dd, J = 8.4, 4.9 Hz, 1H), 7.84 (d, J = 5.1 Hz, 1H), 7.68-7.79 (m, J = 8.2 Hz, 2H), 7.46-7.58 (m, J = 8.0 Hz, 2H), 6.99 (s, 1H) |
| 261 | 400 MHz $CDCl_3$ | 9.00 (dd, J = 4.2, 1.5 Hz, 1H), 8.84 (d, J = 4.7 Hz, 1H), 8.62 (s, 1H), 8.26 (d, J = 8.0 Hz, 1H), 8.21 (d, J = 7.6 Hz, 1H), 8.13 (dd, J = 8.4, 1.6 Hz, 1H), 8.06 (d, J = 7.6 Hz, 1H), 7.92 (d, J = 8.4 Hz, 1H), 7.44-7.51 (m, 2H), 7.35-7.42 (m, 2H), 7.20-7.30 (m, 3H), 6.79 (d, J = 8.0 Hz, 1H) |
| 287 | 400 MHz DMSO-$d_6$ | 11.99 (br. s., 1H), 9.14 (d, J = 7.8 Hz, 1H), 8.44 (d, J = 4.7 Hz, 1H), 8.16 (d, J = 2.5 Hz, 1H), 7.90 (dd, J = 9.6, 2.7 Hz, 1H), 7.73-7.80 (m, 1H), 7.71 (d, J = 8.2 Hz, 2H), 7.60 (d, J = 8.0 Hz, |

TABLE 6-continued

| $^{1}$H NMR Data of Examples 1-261 and 287-424. | | |
|---|---|---|
| Ex. # | Freq., Solvent | $^{1}$HNMR Data (δ ppm) |
| | | 2H), 7.47 (dt, J = 8.5, 4.3 Hz, 1H), 6.69 (d, J = 7.8 Hz, 1H), 6.33 (d, J = 9.6 Hz, 1H) |
| 288 | 400 MHz DMSO-$d_6$ | 9.31 (d, J = 8.0 Hz, 1H), 8.47 (t, J = 2.8 Hz, 2H), 7.37-7.42 (m, 1H), 7.69-7.81 (m, 2H), 7.45-7.65 (m, 3H), 7.26-7.32 (m, 3H), 3.65 (s, 2H) |
| 289 | 400 MHz DMSO-$d_6$ | 8.54 (s, 2H), 8.35-8.37 (d, J = 4.8 Hz, 1H), 7.78 (d, J = 6.8 Hz, 1H), 7.67 (d, J = 7.6 Hz, 1H), 7.37-7.42 (m, 1H), 7.28-7.32 (m, 2H), 7.13-7.20 (m, 3H), 6.38 (dd, J = 6.8 Hz, 1H), 3.65 (s, 2H) |
| 290 | 400 MHz DMSO-$d_6$ | 9.33 (d, J = 8.4 Hz, 1H), 8.45-8.46 (m, 3H), 7.76 (m, 1H), 7.50-7.55 (m, 1H), 7.46-7.48 (m, 2H), 7.25-7.28 (m, 3H), 6.47 (d, J = 8.0 Hz, 1H), 3.64 (s, 2H) |
| 291 | 400 MHz DMSO-$d_6$ | 12.00 (s, 1H), 9.19 (d, J = 8.0 Hz, 1H), 8.19 (s, 1H), 7.99-8.03 (m, 1H), 7.90 (dd, J = 9.6, 2.4 Hz, 1H), 7.77 (d, J = 8.4 Hz, 2H), 7.64 (d, J = 8.0 Hz, 2H), 7.27-7.29 (m, 1H), 6.65 (d, J = 7.6 Hz, 1H), 6.38 (d, J = 9.6 Hz, 1H) |
| 292 | 400 MHz DMSO-$d_6$ | 12.05 (br. s., 1H), 9.07 (d, J = 8.0 Hz, 1H), 8.55 (d, J = 2.8 Hz, 1H), 8.15 (br. s., 1H), 7.91 (dd, J = 9.6, 2.4 Hz, 1H,), 7.73-7.78 (m, 1H), 7.52-7.61 (m, 3H) 7.32 (d, J = 8.4 Hz, 1H), 6.43 (d, J = 8.0 Hz, 1H), 6.35 (d, J = 9.6 Hz, 1H) |
| 293 | 400 MHz DMSO-$d_6$ | 12.02 (br. s., 1H), 9.05 (d, J = 8.0 Hz, 1H), 8.55 (dd, J = 4.7, 0.8 Hz, 1H), 8.16 (d, J = 2.3 Hz, 1H), 7.91 (dd, J = 9.7, 2.6 Hz, 1H), 7.82 (td, J = 7.7, 1.8 Hz, 1H), 7.46-7.63 (m, 3H), 7.22-7.39 (m, 2H), 6.27-6.50 (m, 2H) |
| 294 | 400 MHz $CDCl_3$ | 8.63 (d, J = 4.7 Hz, 1H), 8.38 (d, J = 5.9 Hz, 1H), 8.14 (d, J = 2.3 Hz, 1H), 7.64-7.84 (m, 2H), 7.27-7.32 (m, 1H), 7.16-7.25 (m, 3H), 6.60 (d, J = 9.6 Hz, 1H), 6.19 (d, J = 6.1 Hz, 1H), 3.60 (s, 3H) |
| 295 | 400 MHz DMSO-$d_6$ | 12.02 (br. s., 1H), 9.02 (d, J = 7.4 Hz, 1H), 8.14 (br. s., 1H), 7.90 (d, J = 9.4 Hz, 1H), 7.51-7.65 (m, 1H), 7.30-7.50 (m, 3H), 7.12-7.29 (m, 3H), 6.58 (d, J = 7.4 Hz, 1H), 6.35 (d, J = 9.4 Hz, 1H) |
| 296 | 400 MHz $CDCl_3$ | 8.15 (d, J = 2.3 Hz, 1H), 7.61 (dd, J = 9.6, 2.5 Hz, 1H), 7.30-7.42 (m, 2H), 6.97-7.26 (m, 5H), 6.71 (d, J = 8.0 Hz, 1H), 6.55 (dd, J = 8.8, 4.1 Hz, 2H), 3.60 (s, 3H) |
| 297 | 400 MHz DMSO-$d_6$ | 9.08 (d, J = 6.8 Hz, 1H), 8.43 (d, J = 20.0 Hz, 2H), 7.94 (d, J = 9.2 Hz, 1H), 7.77 (br. s., 1H), 7.43-7.65 (m, 3H), 7.33 (d, J = 8.2 Hz, 1H), 6.67 (d, J = 7.0 Hz, 1H), 6.40 (d, J = 8.8 Hz, 1H), 4.91 (br. s., 1H), 3.97 (br. s., 2H), 3.63 (br. s., 2H) |
| 298 | 400 MHz DMSO-$d_6$ | 9.10 (d, J = 7.8 Hz, 1H), 8.31-8.60 (m, 2H), 7.94 (dd, J = 9.5, 2.6 Hz, 1H), 7.77 (ddd, J = 9.9, 8.6, 1.1 Hz, 1H), 7.42-7.66 (m, 3H), 7.33 (d, J = 8.4 Hz, 1H), 6.69 (d, J = 7.6 Hz, 1H), 6.39 (d, J = 9.6 Hz, 1H), 4.94 (d, J = 5.3 Hz, 1H), 4.08 (dd, J = 12.9, 3.3 Hz, 1H), 3.82-3.97 (m, 1H), 3.55 (dd, J = 12.8, 8.5 Hz, 1H), 1.08 (d, J = 6.5 Hz, 3H) |
| 299 | 400 MHz DMSO-$d_6$ | 9.07 (d, J = 7.0 Hz, 1H), 8.32-8.59 (m, 2H), 7.95 (d, J = 9.6 Hz, 1H), 7.76 (t, J = 9.1 Hz, 1H), 7.39-7.63 (m, 3H), 7.33 (d, J = 8.2 Hz, 1H), 6.67 (d, J = 7.4 Hz, 1H), 6.39 (d, J = 9.4 Hz, 1H), 4.91 (br. s., 1H), 4.07 (d, J = 12.7 Hz, 1H), 3.90 (br. s., 1H), 3.59 (d, J = 10.2 Hz, 1H), 1.08 (d, J = 3.5 Hz, 3H) |
| 300 | 400 MHz DMSO-$d_6$ | 9.13 (d, J = 7.8 Hz, 1H), 8.34-8.54 (m, 2H), 7.95 (dd, J = 9.6, 2.7 Hz, 1H), 7.65-7.87 (m, 3H), 7.60 (d, J = 8.2 Hz, 2H), 7.48 (dt, J = 8.5, 4.4 Hz, 1H), 6.72 (d, J = 7.8 Hz, 1H), 6.39 (d, J = 9.6 Hz, 1H), 4.94 (d, J = 5.3 Hz, 1H), 4.07 (dd, J = 12.8, 3.2 Hz, 1H), 3.90 (td, J = 5.8, 2.5 Hz, 1H), 3.55 (dd, J = 12.9, 8.4 Hz, 1H), 1.08 (d, J = 6.5 Hz, 3H) |
| 301 | 400 MHz DMSO-$d_6$ | 9.09 (d, J = 7.0 Hz, 1H), 8.26-8.63 (m, 2H), 7.95 (d, J = 9.4 Hz, 1H), 7.67-7.82 (m, 3H), 7.60 (d, J = 7.0 Hz, 2H), 7.48 (d, J = 3.9 Hz, 1H), 6.71 (d, J = 6.8 Hz, 1H), 6.39 (d, J = 9.6 Hz, 1H), 4.91 (br. s., 1H), 4.07 (d, J = 12.7 Hz, 1H), 3.90 (br. s., 1H), 3.46-3.70 (m, 1H), 1.08 (d, J = 2.9 Hz, 3H) |
| 302 | 400 MHz DMSO-$d_6$ | 9.08 (d, J = 7.8 Hz, 1H), 8.24-8.60 (m, 2H), 7.97 (dd, J = 9.5, 2.6 Hz, 1H), 7.76 (ddd, J = 10.0, 8.6, 1.2 Hz, 1H), 7.42-7.63 (m, 3H), 7.33 (d, J = 8.6 Hz, 1H), 6.67 (d, J = 7.6 Hz, 1H), 6.41 (d, J = 9.6 Hz, 1H), 4.80 (s, 1H), 3.92 (s, 2H), 1.06 (s, 6H) |
| 303 | 400 MHz DMSO-$d_6$ | 9.12 (d, J = 7.8 Hz, 1H), 8.43-8.53 (m, 1H), 8.39 (d, J = 2.5 Hz, 1H), 7.98 (dd, J = 9.6, 2.7 Hz, 1H), 7.68-7.84 (m, 3H), 7.60 (d, J = 8.2 Hz, 2H), 7.37-7.54 (m, 1H), 6.71 (d, J = 7.6 Hz, 1H), 6.41 (d, J = 9.6 Hz, 1H), 4.81 (s, 1H), 3.92 (s, 2H), 1.06 (s, 6H) |
| 304 | 400 MHz DMSO-$d_6$ | 9.30 (d, J = 7.8 Hz, 1H), 8.36-8.55 (m, 2H), 7.94 (dd, J = 9.5, 2.4 Hz, 1H), 7.68-7.84 (m, 1H), 7.44-7.65 (m, 3H), 7.33 (d, J = 8.6 Hz, 1H), 6.71 (d, J = 7.8 Hz, 1H), 6.42 (d, J = 9.6 Hz, 1H), 5.50 (t, J = 7.2 Hz, 1H), 4.57-5.03 (m, 4H) |

TABLE 6-continued

| $^1$H NMR Data of Examples 1-261 and 287-424. | | |
|---|---|---|
| Ex. # | Freq., Solvent | $^1$HNMR Data (δ ppm) |
| 305 | 400 MHz DMSO-$d_6$ | 9.35 (d, J = 7.8 Hz, 1H), 8.31-8.61 (m, 2H), 7.94 (dd, J = 9.6, 2.5 Hz, 1H), 7.68-7.84 (m, 3H), 7.60 (d, J = 8.2 Hz, 2H), 7.48 (dt, J = 8.5, 4.4 Hz, 1H), 6.76 (d, J = 7.8 Hz, 1H), 6.42 (d, J = 9.6 Hz, 1H), 5.51 (t, J = 7.2 Hz, 1H), 4.57-5.03 (m, 4H) |
| 306 | 400 MHz $CDCl_3$ | 8.94 (dd, J = 4.1, 1.4 Hz, 1H), 8.87 (d, J = 4.3 Hz, 1H), 8.53 (s, 1H), 8.49 (d, J = 8.0 Hz, 1H), 8.15 (d, J = 7.8 Hz, 1H), 8.07 (dd, J = 8.4, 1.6 Hz, 1H), 7.99 (d, J = 7.6 Hz, 1H), 7.85 (d, J = 8.6 Hz, 1H), 7.36-7.51 (m, 4H), 7.20-7.33 (m, 3H), 6.93 (d, J = 8.0 Hz, 1H) |
| 307 | 400 MHz DMSO-$d_6$ | 9.95 (s, 1 H), 9.82 (br. s., 1 H), 8.47 (d, J = 4.7 Hz, 1 H), 8.19-8.30 (m, 2 H), 7.72-7.83 (m, 3 H), 7.66-7.71 (m, 2 H), 7.50 (dt, J = 8.5, 4.4 Hz, 1 H), 6.78 (br. s., 1 H) |
| 308 | 400 MHz DMSO-$d_6$ | 9.93 (br. s., 1 H), 9.38 (d, J = 7.2 Hz, 1 H), 8.82 (s, 1 H), 8.47 (d, (d J = 4.7 Hz, 1 H), 7.72-7.83 (m, 4 H), 7.66-7.71 (m, 2 H), 7.50 (dt, J = 8.5, 4.4 Hz, 1 H), 6.77 (br. s., 1 H) |
| 309 | 400 MHz DMSO-$d_6$ | 9.95 (s, 1 H), 9.72-9.81 (m, 1 H), 8.47 (d, J = 4.5 Hz, 1 H), 8.19-8.29 (m, 2 H), 7.78 (t, J = 9.2 Hz, 1 H), 7.59 (m, J = 8.6 Hz, 2 H), 7.48 (dt, J = 8.4, 4.3 Hz, 1 H), 7.37 (m, J = 8.2 Hz, 2 H), 6.69-6.75 (m, 1 H) |
| 310 | 400 MHz DMSO-$d_6$ | 9.87 (d, J = 7.4 Hz, 1 H), 9.38 (d, J = 7.0 Hz, 1 H), 8.81 (s, 1 H), 8.47 (d, J = 4.5 Hz, 1 H), 7.73-7.82 (m, 2 H), 7.58 (m, J = 8.6 Hz, 2 H), 7.45-7.52 (m, 1 H), 7.37 (m, J = 8.2 Hz, 2 H), 6.71 (d, J = 7.4 Hz, 1 H) |
| 311 | 400 MHz DMSO-$d_6$ | 9.94 (s, 1 H), 9.82 (br. s., 1 H), 8.94 (d, J = 4.5 Hz, 1 H), 8.18-8.31 (m, 3 H), 7.73 (d, J = 8.4 Hz, 2 H), 7.65 (dd, J = 7.8, 4.9 Hz, 1 H), 7.59 (d, J = 8.2 Hz, 2 H), 6.82 (s, 1 H) |
| 312 | 400 MHz DMSO-$d_6$ | 9.93 (s, 1 H), 9.37 (d, J = 7.0 Hz, 1 H), 8.94 (d, J = 4.3 Hz, 1 H), 8.80 (s, 1 H), 8.28 (d, J = 7.4 Hz, 1 H), 7.78 (dd, J = 7.1, 1.5 Hz, 1 H), 7.73 (m, J = 8.2 Hz, 2 H), 7.65 (dd, J = 8.0, 4.9 Hz, 1 H), 7.58 (d, J = 8.2 Hz, 2 H), 6.81 (s, 1 H) |
| 313 | 400 MHz DMSO-$d_6$ | 9.17 (d, J = 7.6 Hz, 1 H), 8.43 (d, J = 4.3 Hz, 1 H), 7.81 (s, 1 H), 7.75 (d, J = 8.0 Hz, 1 H), 7.62-7.71 (m, 3 H), 7.59 (d, J = 8.2 Hz, 2 H), 7.27 (dd, J = 7.5, 4.8 Hz, 1 H), 7.11 (d, J = 8.0 Hz, 1 H), 6.61 (d, J = 7.6 Hz, 1 H), 2.33 (s, 3 H) |
| 314 | 400 MHz DMSO-$d_6$ | 9.35 (d, J = 7.6 Hz, 1 H), 9.22 (s, 1 H), 8.44 (d, J = 4.1 Hz, 1 H), 8.04 (s, 1 H), 7.56-7.72 (m, 8 H), 7.28 (dd, J = 7.5, 4.8 Hz, 1 H), 6.65 (d, J = 7.6 Hz, 1 H), 2.36 (s, 3 H) |
| 315 | 400 MHz DMSO-$d_6$ | 13.09 (br. s., 1 H), 9.58 (d, J = 7.6 Hz, 1 H), 8.42-8.52 (m, 1 H), 8.12 (m, 2 H), 7.92 (m, 2 H), 7.72-7.83 (m, 3 H), 7.64-7.69 (m, 2 H), 7.50 (dt, J = 8.5, 4.4 Hz, 1 H), 6.77 (d, J = 7.6 Hz, 1 H) |
| 316 | 400 MHz DMSO-$d_6$ | 13.09 (br. s., 1 H), 9.52 (d, J = 7.8 Hz, 1 H), 8.45-8.51 (m, 1 H), 8.11 (m, 2 H), 7.92 (m, 2 H), 7.78 (ddd, J = 10.0, 8.6, 1.2 Hz, 1 H), 7.57 (m, 2 H), 7.49 (dt, J = 8.5, 4.3 Hz, 1 H), 7.37 (m, 2 H), 6.71 (d, J = 7.6 Hz, 1 H) |
| 317 | 400 MHz DMSO-$d_6$ | 13.51 (s, 1 H), 9.22 (d, J = 7.4 Hz, 1 H), 8.53 (d, J = 4.7 Hz, 1 H), 7.76-7.85 (m, 2 H), 7.70 (m, 2 H), 7.60 (m, 2 H), 7.53 (dt, J = 8.6, 4.4 Hz, 1 H), 6.98 (dd, J = 9.9, 2.2 Hz, 1 H), 6.51 (d, J = 6.5 Hz, 1 H) |
| 318 | 400 MHz DMSO-$d_6$ | 10.31 (s, 1 H), 9.14 (d, J = 7.8 Hz, 1 H), 8.42-8.50 (m, 1 H), 7.83 (s, 1 H), 7.70-7.81 (m, 4 H), 7.63 (d, J = 8.2 Hz, 2 H), 7.49 (dt, J = 8.5, 4.4 Hz, 1 H), 6.90 (d, J = 8.4 Hz, 1 H), 6.74 (d, J = 7.6 Hz, 1 H), 2.94 (t, J = 7.5 Hz, 2 H), 2.47-2.51 (m, 2H) |
| 319 | 400 MHz DMSO-$d_6$ | 12.76 (br. s., 1 H), 9.29 (d, J = 7.6 Hz, 1 H), 8.58 (d, J = 4.7 Hz, 1 H), 8.06 (d, J = 1.2 Hz, 1 H), 7.99 (s, 1 H), 7.82 (ddd, J = 9.9, 8.6, 1.1 Hz, 1 H), 7.72 (m, 2 H), 7.60 (m, 2 H), 7.54 (dt, J = 8.5, 4.4 Hz, 1 H), 6.55 (dd, J = 7.4, 1.4 Hz, 1 H) |
| 320 | 400 MHz DMSO-$d_6$ | 8.80 (d, J = 7.6 Hz, 1 H), 8.52-8.58 (m, 1 H), 7.81 (ddd, J = 10.0, 8.5, 1.3 Hz, 1 H), 7.72 (m, 2 H), 7.58 (m, 2 H), 7.53 (dt, J = 8.6, 4.4 Hz, 1 H), 6.54 (dd, J = 7.6, 1.2 Hz, 1 H), 5.88 (s, 1 H), 4.27-4.37 (m, 2 H), 4.21 (t, J = 6.7 Hz, 2 H), 2.16-2.28 (m, 2 H) |
| 321 | 400 MHz DMSO-$d_6$ | 8.80 (d, J = 7.6 Hz, 1 H), 8.52-8.58 (m, 1 H), 7.81 (ddd, J = 10.0, 8.5, 1.3 Hz, 1 H), 7.72 (m, 2 H 7.58 (m, 2 H), 7.53 (dt, J = 8.6, 4.4 Hz, 1 H), 6.54 (dd, J = 7.6, 1.2 Hz, 1 H), 5.88 (s, 1 H), 4.27-4.37 (m, 2 H), 4.21 (t, J = 6.7 Hz, 2 H), 2.16-2.28 (m, 2 H) |
| 322 | 400 MHz DMSO-$d_6$ | 12.86 (br. s., 1 H), 8.82 (d, J = 7.6 Hz, 1 H), 8.56 (d, J = 4.7 Hz, 1 H), 7.81 (ddd, J = 9.9, 8.5, 1.2 Hz, 1 H), 7.72 (m, 2 H), 7.59 (m, 2 H), 7.53 (dt, J = 8.6, 4.4 Hz, 1 H), 6.54 (d, J = 7.2 Hz, 1 H), 2.61 (t, J = 5.7 Hz, 4 H), 1.61-1.77 (m, 4 H) |
| 323 | 400 MHz DMSO-$d_6$ | 13.08 (br. s., 1 H), 9.47 (d, J = 7.6 Hz, 1 H), 8.47 (d, J = 4.1 Hz, 1 H), 8.09 (m, 2 H), 7.90 (m, 2 H), 7.67-7.76 (m, 3 H), 7.61 (d, J = 8.2 Hz, 2 H), 7.34 (dd, J = 7.5, 4.8 Hz, 1 H), 6.65 (d, J = 7.4 Hz, 1 H), 2.35 (s, 3 H) |
| 324 | 400 MHz DMSO-$d_6$ | 11.98 (br. s., 1 H), 8.95 (d, J = 8.0 Hz, 1 H), 8.45 (d, J = 4.5 Hz, 1 H), 8.17 (d, J = 2.3 Hz, 1 H), 7.90 (dd, J = 9.6, 2.5 Hz, 1 H), 7.70 (t, J = 9.3 Hz, 1 H), 7.43 (dt, J = 8.5, 4.3 Hz, 1 H), 6.97 (s, 2 H), |

TABLE 6-continued

| $^1$H NMR Data of Examples 1-261 and 287-424. | | |
|---|---|---|
| Ex. # | Freq., Solvent | $^1$HNMR Data (δ ppm) |
| | | 6.90 (s, 1 H), 6.52 (d, J = 7.8 Hz, 1 H), 6.31 (d, J = 9.6 Hz, 1 H), 2.23 (s, 6 H) |
| 325 | 400 MHz DMSO-$d_6$ | 12.00 (br. s., 1 H), 9.05 (d, J = 8.0 Hz, 1 H), 8.43-8.49 (m, 1 H), 8.18 (d, J = 2.5 Hz, 1 H), 7.92 (dd, J = 9.6, 2.7 Hz, 1 H), 7.74 (ddd, J = 10.1, 8.5, 1.2 Hz, 1 H), 7.46 (1 dt, J = 8.5, 4.3 Hz, 1 H), 7.00-7.07 (m, 2 H), 6.95 (d, J = 9.6 Hz, 1 H), 6.59 (d, J = 7.8 Hz, 1 H), 6.35 (d, J = 9.6 Hz, 1 H), 2.30 (s, 3 H) |
| 326 | 400 MHz DMSO-$d_6$ | 8.98 (d, J = 8.0 Hz, 1 H), 8.52 (d, J = 2.3 Hz, 1 H), 8.46 (d, J = 4.7 Hz, 1 H), 7.91 (dd, J = 9.4, 2.5 Hz, 1 H), 7.74 (t, J = 9.3 Hz, 1 H), 7.46 (dt, J = 8.5, 4.4 Hz, 1 H), 7.00-7.07 (m, 2 H), 6.95 (d, J = 9.6 Hz, 1 H), 6.60 (d, J = 8.0 Hz, 1 H), 6.40 (d, J = 9.6 Hz, 1 H), 3.48 (s, 3 H), 2.29 (s, 3 H) |
| 327 | 400 MHz DMSO-$d_6$ | 12.01 (br. s., 1 H), 9.20 (d, J = 7.8 Hz, 1 H), 8.42-8.48 (m, 1 H), 8.17 (d, J = 2.5 Hz, 1 H), 7.91 (dd, J = 9.6, 2.7 Hz, 1 H), 7.78 (ddd, J = 10.0, 8.5, 1.3 Hz, 1 H), 7.58-7.70 (m, 3 H), 7.49 (dt, J = 8.5, 4.4 Hz, 1 H), 6.76 (d, J = 7.8 Hz, 1 H), 6.36 (d, J = 9.6 Hz, 1 H) |
| 328 | 400 MHz DMSO-$d_6$ | 9.16 (d, J = 7.8 Hz, 1 H), 8.50 (d, J = 2.3 Hz, 1 H), 8.44 (d, J = 4.7 Hz, 1 H), 7.91 (dd, J = 9.5, 2.4 Hz, 1 H), 7.78 (t, J = 9.3 Hz, 1 H), 7.59-7.69 (m, 3 H), 7.49 (dt, J = 8.5, 4.3 Hz, 1 H), 6.76 (d, J = 7.6 Hz, 1 H), 6.41 (d, J = 9.4 Hz, 1 H), 3.48 (s, 3 H) |
| 329 | 400 MHz DMSO-$d_6$ | 12.01 (br. s., 1 H), 9.10 (d, J = 8.0 Hz, 1 H), 8.45 (dt, J = 4.5, 1.3 Hz, 1 H), 8.18 (d, J = 2.5 Hz, 1 H), 7.91 (dd, J = 9.7, 2.6 Hz, 1 H), 7.77 (ddd, J = 10.1, 8.5, 1.2 Hz, 1 H), 7.49 (dt, J = 8.5, 4.3 Hz, 1 H), 7.10-7.22 (m, 3 H), 6.65 (d, J = 7.6 Hz, 1 H), 6.36 (d, J = 9.6 Hz, 1 H) |
| 330 | 400 MHz DMSO-$d_6$ | 9.05 (d, J = 7.8 Hz, 1 H), 8.52 (d, J = 2.5 Hz, 1 H), 8.43-8.49 (m, 1 H), 7.92 (dd, J = 9.5, 2.6 Hz, 1 H), 7.78 (ddd, J = 10.0, 8.6, 1.2 Hz, 1 H), 7.49 (dt, J = 8.4, 4.4 Hz, 1 H), 7.10-7.23 (m, 3 H), 6.67 (d, J = 7.6 Hz, 1 H), 6.41 (d, J = 9.4 Hz, 1 H), 3.49 (s, 3 H) |
| 331 | 400 MHz DMSO-$d_6$ | 12.01 (br. s., 1 H), 9.07 (d, J = 8.0 Hz, 1 H), 8.44 (d, J = 4.5 Hz, 1 H), 8.16 (d, J = 2.5 Hz, 1 H), 7.90 (dd, J = 9.6, 2.5 Hz, 1 H), 7.74 (t, J = 9.3 Hz, 1 H), 7.34-7.56 (m, 3 H), 7.19-7.27 (m, 1 H), 6.61 (d, J = 7.8 Hz, 1 H), 6.34 (d, J = 9.6 Hz, 1 H) |
| 332 | 400 MHz DMSO-$d_6$ | 9.02 (d, J = 7.8 Hz, 1 H), 8.50 (d, J = 2.5 Hz, 1 H), 8.45 (d, J = 4.5 Hz, 1 H), 7.90 (dd, J = 9.5, 2.6 Hz, 1 H), 7.75 (ddd, J = 10.0, 8.6, 1.0 Hz, 1 H), 7.35-7.56 (m, 3 H), 7.19-7.28 (m, 1 H), 6.63 (d, J = 7.6 Hz, 1 H), 6.40 (d, J = 9.4 Hz, 1 H), 3.48 (s, 3 H) |
| 333 | 400 MHz DMSO-$d_6$ | 11.95 (br. s., 1 H), 9.15 (d, J = 8.0 Hz, 1 H), 8.45 (d, J = 4.5 Hz, 1 H), 8.16 (d, J = 2.5 Hz, 1 H), 7.90 (dd, J = 9.6, 2.7 Hz, 1 H), 7.69-7.78 (m, 1 H), 7.53 (d, J = 9.6 Hz, 2 H), 7.41-7.49 (m, 2 H), 6.66 (d, J = 7.8 Hz, 1 H), 6.33 (d, J = 9.6 Hz, 1 H), 2.37 (s, 3 H) |
| 334 | 400 MHz DMSO-$d_6$ | 11.97 (br. s., 1 H), 9.02 (d, J = 7.8 Hz, 1 H), 8.43 (d, J = 4.7 Hz, 1 H), 8.16 (d, J = 2.3 Hz, 1 H), 7.90 (dd, J = 9.7, 2.6 Hz, 1 H), 7.67-7.76 (m, 1 H), 7.44 (dt, J = 8.5, 4.4 Hz, 1 H), 7.19-7.26 (m, 1 H), 7.16 (d, J = 11.2 Hz, 1 H), 7.08 (d, J = 7.8 Hz, 1 H), 6.57 (d, J = 7.8 Hz, 1 H), 6.33 (d, J = 9.6 Hz, 1 H), 2.19 (s, 3 H) |
| 335 | 400 MHz DMSO-$d_6$ | 8.95 (d, J = 7.8 Hz, 1 H), 8.51 (d, J = 2.5 Hz, 1 H), 8.44 (d, J = 4.5 Hz, 1 H), 7.90 (dd, J = 9.5, 2.6 Hz, 1 H), 7.68-7.77 (m, 1 H), 7.44 (dt, J = 8.5, 4.3 Hz, 1 H), 7.20-7.27 (m, 1 H), 7.17 (d, J = 11.0 Hz, 1 H), 7.09 (d, J = 7.8 Hz, 1 H), 6.59 (d, J = 7.8 Hz, 1 H), 6.39 (d, J = 9.4 Hz, 1 H), 3.47 (s, 3 H), 2.19 (s, 3 H) |
| 336 | 400 MHz DMSO-$d_6$ | 11.96 (br. s., 1 H), 8.99 (d, J = 8.0 Hz, 1 H), 8.44 (d, J = 4.7 Hz, 1 H), 8.15 (d, J = 2.5 Hz, 1 H), 7.89 (dd, J = 9.7, 2.6 Hz, 1 H), 7.66-7.76 (m, 1 H), 7.43 (dt, J = 8.5, 4.4 Hz, 1 H), 7.21-7.29 (m, 1 H), 7.07-7.15 (m, 2 H), 6.53 (d, J = 7.8 H, 1 Hz), 6.33 (d, J = 9.6 Hz, 1 H), 3.80 (s, 1 H) |
| 337 | 400 MHz DMSO-$d_6$ | 8.92 (d, J = 8.0 Hz, 1 H), 8.50 (d, J = 2.3 Hz, 1 H), 8.44 (d, J = 4.5 Hz, 1 H), 7.89 (dd, J = 9.6, 2.5 Hz, 1 H), 7.72 (t, J = 9.0 Hz, 1 H), 7.44 (dt, J = 8.5, 4.3 Hz, 1 H), 7.22-7.29 (m, 1 H), 7.06-7.17 (m, 2 H), 6.54 (d, J = 7.8 Hz, 1 H), 6.39 (d, J = 9.6 Hz, 1 H), 3.81 (s, 3 H), 3.47 (s, 3 H) |
| 338 | 400 MHz DMSO-$d_6$ | 11.97 (br. s., 1 H), 9.00 (d, J = 8.0 Hz, 1 H), 8.44 (d, J = 4.7 Hz, 1 H), 8.15 (d, J = 2.5 Hz, 1 H), 7.90 (dd, J = 9.7, 2.6 Hz, 1 H, 7.67-7.75 (m, 1 H), 7.43 (dt, J = 8.5, 4.4 Hz, 1 H), 7.26-7.33 (m, 1 H), 7.16-7.24 (m, 1 H), 7.03-7.12 (m, 1 H), 6.55 (d, J = 7.8 Hz, 1 H), 6.33 (d, J = 9.6 Hz, 1 H), 2.08-2.30 (m, 3 H) |
| 339 | 400 MHz DMSO-$d_6$ | 8.93 (d, J = 7.8 Hz, 1 H), 8.50 (d, J = 2.5 Hz, 1 H), 8.45 (d, J = 4.5 Hz, 1 H), 7.90 (dd, J = 9.5, 2.6 Hz, 1 H), 7.67-7.76 (m, 1 H), 7.44 (dt, J = 8.4, 4.4 Hz, 1 H), 7.26-7.34 (m, 1 H), 7.17-7.25 (m, 1 H), 7.09 (t, J = 9.1 Hz, 1 H), 6.56 (d, J = 7.8 Hz, 1 H), 6.39 (d, J = 9.6 Hz, 1 H), 3.47 (s, 3 H), 2.17-2.23 (m, 3 H) |
| 340 | 400 MHz DMSO-$d_6$ | 11.94 (br. s., 1 H), 9.03 (d, J = 7.8 Hz, 1 H), 8.44 (d, J = 4.7 Hz, 1 H), 8.16 (d, J = 2.5 Hz, 1 H), 7.89 (dd, J = 9.6, 2.5 Hz, 1 H), 7.67-7.76 (m, 1 H), 7.36-7.48 (m, 3 H), 7.16 (t, J = 8.8 Hz, 2 H), 6.59 (d, J = 7.8 Hz, 1 H), 6.32 (d, J = 9.6 Hz, 1 H) |

TABLE 6-continued

| Ex. # | Freq., Solvent | $^1$HNMR Data (δ ppm) |
|---|---|---|
| | | $^1$H NMR Data of Examples 1-261 and 287-424. |
| 341 | 400 MHz DMSO-$d_6$ | 8.97 (d, J = 8.0 Hz, 1 H), 8.50 (d, J = 2.5 Hz, 1 H), 8.45 (d, J = 4.7 Hz, 1 H), 7.90 (dd, J = 9.5, 2.6 Hz, 1 H), 7.73 (ddd, J = 10.0, 8.6, 1.2 Hz, 1 H), 7.38-7.49 (m, 3 H), 7.12-7.21 (m, 2 H), 6.61 (d, J = 7.8 Hz, 1 H), 6.39 (d, J = 9.4 Hz, 1 H), 3.47 (s, 3 H) |
| 342 | 400 MHz DMSO-$d_6$ | 11.96 (br. s., 1 H), 8.97 (d, J = 7.8 Hz, 1 H), 8.43 (d, J = 4.7 Hz, 1 H), 8.15 (d, J = 2.5 Hz, 1 H), 7.90 (dd, J = 9.7, 2.6 Hz, 1 H), 7.64-7.73 (m, 1 H), 7.41 (dt, J = 8.4, 4.4 Hz, 1 H), 7.28 (m, 2 H), 6.88 (m, 2 H), 6.52 (d, J = 7.6 Hz, 1 H), 6.32 (d, J = 9.6 Hz, 1 H), 3.72 (s, 3 H) |
| 343 | 400 MHz DMSO-$d_6$ | 8.88 (d, J = 7.8 Hz, 1 H), 8.48-8.53 (m, 1 H), 8.44 (d, J = 4.3 Hz, 1 H), 7.90 (dd, J = 9.5, 2.2 Hz, 1 H), 7.70 (t, J = 9.2 Hz, 1 H), 7.42 (dt, J = 8.3, 4.3 Hz, 1 H), 7.29 (m, 2 H), 6.89 (m, 2 H), 6.54 (d, J = 7.6 Hz, 1 H), 6.38 (d, J = 9.4 Hz, 1 H), 3.72 (s, 3 H), 3.47 (s, 3 H) |
| 344 | 400 MHz DMSO-$d_6$ | 12.00 (br. s., 1 H), 9.08 (d, J = 7.8 Hz, 1 H), 8.43 (d, J = 4.7 Hz, 1 H), 8.15 (d, J = 2.3 Hz, 1 H), 7.89 (dd, J = 9.6, 2.7 Hz, 1 H), 7.75 (ddd, J = 10.0, 8.6, 1.2 Hz, 1 H), 7.55 (t, J = 8.0 Hz, 1 H), 7.42-7.50 (m, 2 H), 7.21-7.27 (m, 1 H), 6.62 (d, J = 7.8 Hz, 1 H), 6.33 (d, J = 9.8 Hz, 1 H) |
| 345 | 400 MHz DMSO-$d_6$ | 9.03 (d, J = 7.8 Hz, 1 H), 8.49 (d, J = 2.5 Hz, 1 H), 8.44 (d, J = 4.5 Hz, 1 H), 7.89 (dd, J = 9.6, 2.7 Hz, 1 H), 7.75 (ddd, J = 10.0, 8.6, 1.2 Hz, 1 H), 7.56 (t, J = 8.0 Hz, 1 H), 7.43-7.51 (m, 2 H), 7.25 (dd, J = 8.2, 1.6 Hz, 1 H), 6.64 (d, J = 7.8 Hz, 1 H), 6.39 (d, J = 9.4 Hz, 1 H), 3.47 (s, 3 H) |
| 346 | 400 MHz DMSO-$d_6$ | 10.65 (br. s., 1 H), 9.14 (d, J = 7.8 Hz, 1 H), 8.37-8.54 (m, 1 H), 7.81-7.86 (m, 2 H), 7.77 ddd, J = 10.0, 8.6, 1.2 Hz, 1 H), 7.53-7.63 (m, 2 H), 7.49 (dt, J = 8.5, 4.4 Hz, 1 H), 7.37 (d, J = 8.4 Hz, 1 H), 6.88 (d, J = 8.0 Hz, 1 H), 6.70 (d, J = 7.6 Hz, 1 H), 3.55 (s, 2 H) |
| 347 | 400 MHz DMSO-$d_6$ | 11.96 (br. s., 1 H), 9.01 (d, J = 8.0 Hz, 1 H), 8.39-8.43 (m, 1 H), 8.14 (d, J = 2.5 Hz, 1 H), 7.89 (dd, J = 9.6, 2.7 Hz, 1 H), 7.63 (d, J = 6.8 Hz, 1 H), 7.46-7.54 (m, 2 H), 7.23-7.32 (m, 2 H), 6.55 (d, J = 7.8 Hz, 1 H), 6.32 (d, J = 9.6 Hz, 1 H), 2.35 s, 3 H) |
| 348 | 400 MHz DMSO-$d_6$ | 8.96 (d, J = 7.8 Hz, 1 H), 8.49 (d, J = 2.5 Hz, 1 H), 8.38-8.45 (m, 1 H), 7.89 (dd, J = 9.5, 2.6 Hz, 1 H), 7.61-7.67 (m, 1 H), 7.47-7.55 (m, 2 H), 7.22-7.33 (m, 2 H), 6.56 (d, J = 7.8 Hz, 1 H), 6.38 (d, J = 9.6 Hz, 1 H), 3.46 (s, 3 H), 2.36 (s, 3 H) |
| 349 | 400 MHz DMSO-$d_6$ | 13.38-13.60 (m, 1 H), 9.22 (d, J = 7.2 Hz, 1 H), 8.52 (d, J = 4.7 Hz, 1 H), 7.75-7.86 (m, 2 H), 7.48-7.58 (m, 3 H), 7.33 (d, J = 8.6 Hz, 1 H), 6.98 (dd, J = 9.9, 2.2 Hz, 1 H), 6.47-6.52 (m, 1 H) |
| 350 | 400 MHz DMSO-$d_6$ | 13.38-13.60 (m, 1 H), 9.17 (d, J = 7.4 Hz, 1 H), 8.53 (d, J = 4.7 Hz, 1 H), 7.75-7.85 (m, 2 H), 7.46-7.56 (m, 3 H), 7.33 (d, J = 8.0 Hz, 2 H), 6.98 (dd, J = 9.9, 2.1 Hz, 1 H), 6.47 (dd, J = 7.3, 1.5 Hz, 1 H) |
| 351 | 400 MHz DMSO-$d_6$ | 10.29 (s, 1 H), 9.12 (d, J = 7.8 Hz, 1 H), 8.44 (d, J = 4.7 Hz, 1 H), 7.70-7.83 (m, 3 H), 7.50-7.62 (m, 2 H), 7.47 (dt, J = 8.5, 4.4 Hz, 1 H), 7.35 (d, J = 8.4 Hz, 1 H), 6.89 (d, J = 8.2 Hz, 1 H), 6.69 (d, J = 7.8 Hz, 1 H), 2.92 (t, J = 7.5 Hz, 2 H), 2.44-2.50 (m, 2 H) |
| 352 | 400 MHz DMSO-$d_6$ | 10.29 (1 H, s, 1 H), 9.07 (1 H, d, J = 7.8 Hz, 1 H), 8.45 (1 H, d, J = 4.7 Hz, 1 H), 7.67-7.84 (3 H, m, 3 H), 7.52 (2 H, m, 2 H), 7.46 (1 H, dt, J = 8.5, 4.4 Hz, 1 H), 7.34 (2 H, m, 2 H), 6.88 (1 H, d, J = 8.4 Hz, 1 H), 6.67 (1 H, d, J = 7.6 Hz, 1 H), 2.91 (2 H, t, J = 7.5 Hz, 2 H), 2.44-2.49 (2 H, m, 2 H) |
| 353 | 400 MHz DMSO-$d_6$ | 12.78 (br. s., 1 H), 9.25 (d, J = 7.4 Hz, 1 H), 8.55 (d, J = 4.7 Hz, 1 H), 8.02-8.07 (m, 1 H), 7.97 (br. s., 1 H), 7.76-7.84 (m, 1 H), 7.46-7.57 (m, 3 H), 7.30 (d, J = 8.4 Hz, 1 H), 6.49 (dd, J = 7.4, 1.4 Hz, 1 H) |
| 354 | 400 MHz DMSO-$d_6$ | 12.78 (br. s., 1 H), 9.23 (d, J = 7.6 Hz, 1 H), 8.55 (d, J = 4.7 Hz, 1 H), 8.05 (d, J = 1.2 Hz, 1 H), 7.97 (s, 1 H), 7.79 (ddd, J = 9.9, 8.6, 1.1 Hz, 1 H), 7.44-7.56 (m, 3 H), 7.32 (d, J = 8.0 Hz, 2 H), 6.48 (dd, J = 7.6, 1.6 Hz, 1 H) |
| 355 | 400 MHz DMSO-$d_6$ | 8.79 (1 H, d, J = 7.6 Hz, 1 H), 8.52 (1 H, d, J = 4.7 Hz, 1 H), 7.74-7.84 (1 H, m, 1 H), 7.44-7.58 (3 H, m, 3 H), 7.29 (1 H, d, J = 8.6 Hz, 1 H), 6.50 (1 H, dd, J = 7.6, 1.2 Hz, 1 H), 5.87 (1 H, s, 1 H), 4.28-4.33 (2 H, m, 2 H), 4.18 (2 H, t, J = 6.4 Hz, 2 H), 2.16-2.25 (m, 1 H) |
| 356 | 400 MHz DMSO-$d_6$ | 8.72 (1 H, d, J = 7.8 Hz, 1 H), 8.53 (1 H, d, J = 4.7 Hz, 1 H), 7.69-7.85 (1 H, m, 1 H), 7.44-7.54 (3 H, m, 3 H), 7.33 (2 H, d, J = 8.2 Hz, 2 H), 6.44-6.52 (1 H, m, 1 H), 5.86 (1 H, s, 1 H), 4.28-4.33 (2 H, m, 2 H), 4.19 (2 H, t, J = 6.3 Hz, 2 H), 2.16-2.25 (2 H, m, 2 H) |

TABLE 6-continued $^{1}$H NMR Data of Examples 1-261 and 287-424.

| Ex. # | Freq., Solvent | $^{1}$HNMR Data (δ ppm) |
|---|---|---|
| 357 | 400 MHz DMSO-$d_6$ | 10.92 (s, 1 H), 9.11 (d, J = 7.6 Hz, 1 H), 8.44 (d, J = 3.7 Hz, 1 H), 7.67 (d, J = 7.6 Hz, 1 H), 7.45-7.59 (m, 4 H), 7.26-7.34 (m, 2 H), 6.93 (d, J = 8.0 Hz, 1 H), 6.56 (d, J = 7.6 Hz, 1 H), 4.61 (s, 2 H), 2.34 (s, 3 H) |
| 358 | 400 MHz DMSO-$d_6$ | 11.83 (s, 1 H), 9.27 (d, J = 7.6 Hz, 1 H), 8.44 (d, J = 3.7 Hz, 1 H), 7.66-7.74 (m, 2 H), 7.63 (d, J = 1.6 Hz, 1 H), 7.47-7.58 (m, 2 H), 7.26-7.39 (m, 3 H), 6.59 (d, J = 7.8 Hz, 1 H), 2.35 (s, 3 H) |
| 359 | 300 MHz DMSO-$d_6$ | 11.92 (br. s., 1 H), 9.01 (d, J = 7.7 Hz, 1 H), 8.39-8.46 (m, 1 H), 8.14 (d, J = 2.5 Hz, 1 H), 7.90 (dd, J = 9.6, 2.6 Hz, 1 H), 7.57-7.66 (m, 1 H), 7.46 (d, J = 8.8 Hz, 2 H), 7.21-7.35 (m, 3 H), 6.53 (d, J = 7.9 Hz, 1 H), 6.32 (d, J = 9.6 Hz, 1 H), 2.31 (s, 3 H) |
| 360 | 300 MHz DMSO-$d_6$ | 8.94 (d, J = 7.9 Hz, 1 H), 8.50 (d, J = 2.3 Hz, 1 H), 8.44 (d, J = 3.8 Hz, 1 H), 7.89 (dd, J = 9.5, 2.5 Hz, 1 H), 7.63 (d, J = 7.0 Hz, 1 H), 7.47 (d, J = 8.6 Hz, 2 H), 7.21-7.36 (m, 3 H), 6.55 (d, J = 7.9 Hz, 1 H), 6.39 (d, J = 9.4 Hz, 1 H), 3.47 (s, 3 H), 2.33 (s, 3 H) |
| 361 | 400 MHz DMSO-$d_6$ | 9.35 (d, J = 8.0 Hz, 1 H), 8.57 (d, J = 4.1 Hz, 1 H), 7.83 (td, J = 7.7, 1.7 Hz, 1 H), 7.68-7.75 (m, 3 H), 7.61-7.67 (m, 3 H), 7.54 (d, J = 7.8 Hz, 1 H), 7.29-7.40 (m, 2 H), 6.51 (d, J = 8.0 Hz, 1 H) |
| 362 | 400 MHz DMSO-$d_6$ | 10.84-12.61 (m, 1 H), 9.30 (d, J = 8.2 Hz, 1 H), 8.57 (d, J = 4.3 Hz, 1 H), 7.83 (td, J = 7.7, 1.8 Hz, 1 H), 7.71 (dd, J = 8.2, 1.6 Hz, 1 H), 7.62-7.66 (m, 1 H), 7.53 (d, J = 8.4 Hz, 3 H), 7.28-7.38 (m, 4 H), 6.46 (d, J = 8.2 Hz, 1 H) |
| 363 | 300 MHz $CDCl_3$ | 13.05 (br. s., 1H), 8.45-8.87 (m, 2H), 8.09 (d, J = 2.5 Hz, 1H), 7.94 (dd, J = 9.6, 2.6 Hz, 1H), 7.81 (dd, J = 7.9, 1.5 Hz, 1H), 7.40-7.63 (m, 4H), 7.32 (dd, J = 7.7, 4.8 Hz, 1H), 6.92 (dd, J = 17.2, 11.0 Hz, 1H), 6.44-6.71 (m, 2H), 5.65 (d, J = 17.2 Hz, 1H), 5.44 (d, J = 11.3 Hz, 1H) |
| 364 | 300 MHz $CDCl_3$ | 8.47 (d, J = 4.5 Hz, 1H), 8.32 (d, J = 6.6 Hz, 1H), 8.15 (d, J = 2.6 Hz, 1H), 7.73 (dd, J = 9.5, 2.6 Hz, 1H), 7.56 (s, 4H), 7.39-7.48 (m, 1H), 7.29-7.38 (m, 1H), 6.44-6.65 (m, 2H), 4.02 (qd, J = 7.1, 4.2 Hz, 2H), 1.37 (t, J = 7.2 Hz, 3H) |
| 365 | 300 MHz $CDCl_3$ | 8.46 (dt, J = 4.6, 1.2 Hz, 1H), 8.26 (d, J = 6.7 Hz, 1H), 8.15 (d, J = 2.5 Hz, 1H), 7.72 (dd, J = 9.6, 2.7 Hz, 1H), 7.27-7.58 (m, 5H), 6.58 (d, J = 9.5 Hz, 1H), 6.47 (dd, J = 6.7, 2.0 Hz, 1H), 3.91-4.10 (m, 2H), 1.38 (t, J = 7.2 Hz, 3H) |
| 366 | 300 MHz $CDCl_3$ | 8.47 (d, J = 4.7 Hz, 1H), 8.26 (d, J = 6.6 Hz, 1H), 8.16 (d, J = 2.5 Hz, 1H), 7.72 (dd, J = 9.5, 2.6 Hz, 1H), 7.41-7.52 (m, 1H), 7.31-7.40 (m, 1H), 7.16-7.27 (m, 3H), 6.37-6.64 (m, 2H), 4.04 (qd, J = 7.2, 4.0 Hz, 2H), 1.38 (t, J = 7.2 Hz, 3H) |
| 367 | 300 MHz $CDCl_3$ | 8.47 (d, J = 4.7 Hz, 1H), 8.35 (d, J = 6.6 Hz, 1H), 8.22 (d, J = 2.3 Hz, 1H), 7.70 (dd, J = 9.5, 2.6 Hz, 1H), 7.56 (s, 4H), 7.39-7.48 (m, 1H), 7.28-7.39 (m, 1H), 6.34-6.67 (m, 2H), 5.11-5.34 (m, 1H), 1.37 (dd, J = 6.7, 4.2 Hz, 6H) |
| 368 | 300 MHz $CDCl_3$ | 13.23 (br. s., 1H), 8.50 (d, J = 4.5 Hz, 1H), 8.30-8.42 (m, 2H), 8.18 (d, J = 2.2 Hz, 1H), 7.50-7.67 (m, 4H), 7.31-7.49 (m, 2H), 6.57 (dd, J = 6.6, 1.8 Hz, 1H) |
| 369 | 300 MHz $CDCl_3$ | 11.69 (dd, J = 13.2, 6.9 Hz, 1H), 8.55 (d, J = 4.7 Hz, 1H), 7.60-7.70 (m, 2H), 7.53-7.59 (m, 2H), 7.40-7.50 (m, 2H), 7.29-7.38 (m, 1H), 6.91 (d, J = 9.8 Hz, 1H), 6.07 (d, J = 6.7 Hz, 1H), 5.84 (d, J = 9.6 Hz, 1H), 4.03 (s, 3H) |
| 370 | 400 MHz $d_6$-DMSO | 9.12 (d, J = 7.8 Hz, 1H), 8.35-8.51 (m, 2H), 7.94 (dd, J = 9.5, 2.6 Hz, 1H), 7.66-7.84 (m, 3H), 7.60 (d, J = 8.2 Hz, 2H), 7.36-7.54 (m, 1H), 6.71 (d, J = 7.8 Hz, 1H), 6.40 (d, J = 9.6 Hz, 1H), 4.91 (t, J = 5.5 Hz, 1H), 3.85-4.27 (m, 2H), 3.63 (q, J = 5.5 Hz, 2H) |
| 371 | 300 MHz $CDCl_3$ | 8.36-8.52 (m, 1H), 8.30 (d, J = 6.6 Hz, 1H), 8.16 (d, J = 2.5 Hz, 1H), 7.73 (dd, J = 9.6, 2.6 Hz, 1H), 7.53 (s, 4H), 7.27-7.47 (m, 7H), 6.62 (d, J = 9.5 Hz, 1H), 6.54 (dd, J = 6.7, 1.9 Hz, 1H), 5.15 (d, J = 3.7 Hz, 2H) |
| 372 | 300 MHz $CDCl_3$ | 8.41-8.51 (m, 1H), 8.35 (d, J = 6.7 Hz, 1H), 8.10 (d, J = 2.3 Hz, 1H), 7.77 (dd, J = 9.7, 2.6 Hz, 1H), 7.49-7.65 (m, 5H), 7.39-7.48 (m, 1H), 7.30-7.39 (m, 1H), 6.66 (d, J = 9.6 Hz, 1H), 6.57 (dd, J = 6.7, 2.0 Hz, 1H), 4.64 (q, J = 8.5 Hz, 2H) |
| 373 | 300 MHz $CDCl_3$ | 12.78 (br. s., 1H), 8.48 (d, J = 4.7 Hz, 1H), 8.27 (d, J = 6.7 Hz, 1H), 8.02 (d, J = 2.3 Hz, 1H), 7.80 (d, J = 1.0 Hz, 1H), 7.55 (s, 4H), 7.39-7.49 (m, 1H), 7.29-7.39 (m, 1H), 6.60 (dd, J = 6.8, 2.0 Hz, 1H), 2.22 (s, 3H) |
| 374 | 300 MHz $CDCl_3$ | 8.45 (d, J = 3.4 Hz, 1H), 8.28 (d, J = 5.8 Hz, 1H), 7.64 (d, J = 2.3 Hz, 1H), 7.21-7.56 (m, 5H), 6.97-7.20 (m, 3H), 6.61 (d, J = 6.4 Hz, 1H) |
| 375 | 300 MHz $CDCl_3$ | 8.47 (br. s., 1H), 8.32 (br. s., 1H), 7.21-7.88 (m, 8H), 7.10 (br. s., 1H), 6.63 (d, J = 5.7 Hz, 1H) |
| 376 | 300 MHz $d_6$-DMSO | 11.97 (br. s., 1H), 9.02 (d, J = 7.7 Hz, 1H), 8.90 (d, J = 3.7 Hz, 1H), 8.22 (d, J = 8.2 Hz, 1H), 8.13 (br. s., 1H), 7.88 (dd, J = 9.6, 2.8 Hz, 1H), 7.65-7.75 (m, J = 8.3 Hz, 2H), 7.60 (dd, J = 7.8, |

TABLE 6-continued

| Ex. # | Freq., Solvent | $^1$HNMR Data (δ ppm) |
|---|---|---|
| | | $^1$H NMR Data of Examples 1-261 and 287-424. |
| | | 4.6 Hz, 1H), 6.99-7.14 (m, J = 8.3 Hz, 2H), 6.61 (d, J = 7.3 Hz, 1H), 6.31 (d, J = 9.4 Hz, 1H) |
| 377 | 300 MHz $d_6$-DMSO | 9.03 (d, J = 8.2 Hz, 1H), 8.55 (dd, J = 4.8, 0.9 Hz, 1H), 8.16 (d, J = 2.5 Hz, 1H), 7.91 (dd, J = 9.6, 2.7 Hz, 1H), 7.81 (td, J = 7.7, 1.9 Hz, 1H), 7.42-7.56 (m, 3H), 7.24-7.40 (m, 3H), 6.39 (d, J = 8.2 Hz, 1H), 6.33 (d, J = 9.6 Hz, 1H) |
| 378 | 300 MHz $d_6$-DMSO | 9.00 (d, J = 8.0 Hz, 1H), 8.57 (dd, J = 4.9, 0.8 Hz, 1H), 8.50 (d, J = 2.6 Hz, 1H), 7.92 (dd, J = 9.5, 2.6 Hz, 1H), 7.84 (td, J = 7.7, 1.8 Hz, 1H), 7.44-7.57 (m, 3H), 7.28-7.40 (m, 3H), 6.33-6.49 (m, 2H) |
| 379 | 300 MHz $d_4$-MeOH | 8.39-8.50 (m, 1H), 8.13 (d, J = 2.6 Hz, 1H), 8.04 (dd, J = 9.5, 2.6 Hz, 1H), 7.54-7.66 (m, 1H), 7.41 (dt, J = 8.6, 4.4 Hz, 1H), 7.20-7.31 (m, J = 8.2 Hz, 2H), 7.09-7.20 (m, J = 8.0 Hz, 2H), 6.59 (s, 1H), 6.53 (d, J = 9.5 Hz, 1H), 2.30 (s, 3H) |
| 380 | 300 MHz $d_4$-MeOH | 8.44 (d, J = 4.7 Hz, 1H), 8.13 (d, J = 2.6 Hz, 1H), 8.04 (dd, J = 9.6, 2.7 Hz, 1H), 7.58 (ddd, J = 9.9, 8.5, 1.2 Hz, 1H), 7.40 (dt, J = 8.6, 4.3 Hz, 1H), 7.13 (s, 1H), 7.01-7.11 (m, 2H), 6.47-6.59 (m, 2H), 2.22 (s, 6H) |
| 381 | 300 MHz $d_4$-MeOH | 8.46 (dt, J = 4.8, 1.2 Hz, 1H), 8.10-8.18 (m, 1H), 8.04 (dd, J = 9.6, 2.7 Hz, 1H), 7.60 (ddd, J = 9.9, 8.4, 1.3 Hz, 1H), 7.42 (dt, J = 8.5, 4.4 Hz, 1H), 7.34-7.38 (m, 1H), 7.29 (dd, J = 8.6, 2.0 Hz, 1H), 7.20 (dd, J = 8.5, 1.3 Hz, 1H), 6.58-6.65 (m, 1H), 6.53 (dd, J = 9.6, 0.6 Hz, 1H), 2.28 (s, 3H) |
| 382 | 300 MHz $d_4$-MeOH | 8.57-8.68 (m, 1H), 8.13 (d, J = 2.5 Hz, 1H), 7.97-8.09 (m, 2H), 7.23-7.44 (m, 4H), 6.77 (s, 1H), 6.53 (d, J = 9.6 Hz, 1H) |
| 383 | 300 MHz $d_4$-MeOH | 8.90 (d, J = 4.1 Hz, 1H), 8.13-8.23 (m, 1H), 8.11 (d, J = 2.2 Hz, 1H), 8.01 (dd, J = 9.6, 2.7 Hz, 1H), 7.57 (dd, J = 7.7, 5.1 Hz, 1H), 7.30-7.42 (m, 2H), 7.19-7.30 (m, 1H), 6.80 (s, 1H), 6.51 (d, J = 9.6 Hz, 1H) |
| 384 | 300 MHz $d_4$-MeOH | 8.65 (br. s., 1H), 8.08 (d, J = 8.2 Hz, 1H), 7.69 (d, J = 8.0 Hz, 1H), 7.59 (br. s., 1H), 7.19-7.48 (m, 5H), 6.81 (s, 1H) |
| 385 | 300 MHz $d_4$-MeOH | 8.92 (br. s., 1H), 8.20 (d, J = 6.3 Hz, 1H), 7.66 (d, J = 7.5 Hz, 1H), 7.57 (br. s., 2H), 7.36 (br. s., 2H), 7.28 (br. s., 2H), 6.84 (br. s., 1H) |
| 386 | 300 MHz $d_4$-MeOH | 8.43 (dt, J = 4.6, 1.3 Hz, 1H), 8.10-8.19 (m, 1H), 8.04 (dd, J = 9.6, 2.7 Hz, 1H), 7.57-7.70 (m, 1H), 7.38-7.54 (m, 2H), 7.06-7.18 (m, 2H), 6.91 (s, 1H), 6.48-6.59 (m, 1H) |
| 387 | 300 MHz $d_4$-MeOH | 8.45-8.57 (m, 1H), 7.64 (ddd, J = 9.8, 8.4, 1.2 Hz, 1H), 7.31-7.52 (m, 5H), 7.28 (d, J = 1.2 Hz, 1H), 6.59 (s, 1H), 4.03 (s, 3H) |
| 388 | 300 MHz $d_4$-MeOH | 8.46-8.58 (m, 1H), 7.64 (ddd, J = 9.8, 8.5, 1.3 Hz, 1H), 7.29-7.53 (m, 4H), 7.22 (s, 1H), 6.62 (s, 1H), 2.27-2.42 (m, 3H) |
| 389 | 300 MHz $d_4$-MeOH | 8.53 (d, J = 4.7 Hz, 1H), 8.22 (d, J = 2.6 Hz, 1H), 7.98 (d, J = 8.6 Hz, 1H), 7.64 (td, J = 9.1, 1.2 Hz, 1H), 7.26-7.51 (m, 6H), 6.53-6.64 (m, 1H) |
| 390 | 300 MHz $d_4$-MeOH | 8.47-8.52 (m, 1H), 7.95 (d, J = 8.9 Hz, 1H), 7.64 (ddd, J = 9.8, 8.5, 1.3 Hz, 1H), 7.30-7.48 (m, 7H), 6.63-6.66 (m, 1H), 2.20 (s, 3H) |
| 391 | 400 MHz $d_6$-DMSO | 9.21 (d, J = 8.0 Hz, 1H), 8.52-8.63 (m, 1H), 7.73-7.93 (m, 3H), 7.50-7.65 (m, 3H), 7.40 (d, J = 8.6 Hz, 1H), 7.34 (ddd, J = 7.5, 4.8, 1.0 Hz, 1H), 7.16 (s, 1H), 6.49 (d, J = 8.0 Hz, 1H) |
| 392 | 400 MHz $d_6$-DMSO | 12.67 (br. s., 1H), 9.31 (d, J = 7.8 Hz, 1H), 8.46 (d, J = 4.5 Hz, 1H), 8.34 (s, 1H), 8.25 (br. s., 1H), 7.74-7.83 (m, 2H), 7.70-7.74 (m, 2H), 7.58-7.68 (m, 3H), 7.48 (dt, J = 8.5, 4.4 Hz, 1H), 6.76 (d, J = 7.6 Hz, 1H) |
| 393 | 400 MHz $d_6$-DMSO | 12.70 (br. s., 1H), 9.28 (d, J = 7.0 Hz, 1H), 8.58 (d, J = 4.3 Hz, 1H), 8.09-8.46 (m, 2H), 7.76-7.92 (m, 2H), 7.49-7.75 (m, 4H), 7.42 (d, J = 8.6 Hz, 1H), 7.34 (dd, J = 7.1, 5.2 Hz, 1H), 6.52 (d, J = 8.2 Hz, 1H) |
| 394 | 400 MHz $d_6$-DMSO | 9.33 (d, J = 7.8 Hz, 1H), 8.46 (d, J = 4.7 Hz, 1H), 8.33 (s, 2H), 7.88 (dd, J = 8.6, 1.4 Hz, 1H), 7.70-7.82 (m, 3H), 7.61-7.69 (m, 3H), 7.48 (dt, J = 8.4, 4.4 Hz, 1H), 6.77 (d, J = 7.4 Hz, 1H), 3.87 (s, 3H) |
| 395 | 400 MHz $d_6$-DMSO | 9.33 (d, J = 7.8 Hz, 1H), 8.47 (d, J = 4.7 Hz, 1H), 8.24-8.35 (m, 2H), 7.63-7.88 (m, 7H), 7.49 (dt, J = 8.5, 4.4 Hz, 1H), 6.82 (d, J = 7.6 Hz, 1H), 3.90 (s, 3H) |
| 396 | 400 MHz $d_6$-DMSO | 9.52 (d, J = 7.8 Hz, 1H), 8.60 (d, J = 2.3 Hz, 1H), 8.46 (d, J = 4.5 Hz, 1H), 7.97-8.04 (m, 1H), 7.70-7.91 (m, 4H), 7.62 (d, J = 8.0 Hz, 2H), 7.49 (dt, J = 8.5, 4.4 Hz, 1H), 6.72 (d, J = 7.4 Hz, 1H), 6.58 (d, J = 9.8 Hz, 1H) |
| 397 | 400 MHz $d_6$-DMSO | 12.45 (br. s., 1H), 9.27 (d, J = 7.6 Hz, 1H), 8.43-8.54 (m, 1H), 8.11 (s, 1H), 7.71-7.85 (m, 4H), 7.63-7.70 (m, 2H), 7.45-7.54 (m, 2H), 6.78 (d, J = 7.6 Hz, 1H), 2.53 (s, 3H) |

TABLE 6-continued $^1$H NMR Data of Examples 1-261 and 287-424.

| Ex. # | Freq., Solvent | $^1$HNMR Data (δ ppm) |
|---|---|---|
| 398 | 400 MHz $d_6$-DMSO | 9.87 (d, J = 7.4 Hz, 1H), 9.21 (dd, J = 2.0, 0.8 Hz, 1H), 8.56-8.63 (m, 1H), 8.52 (dd, J = 8.1, 2.1 Hz, 1H), 8.20 (dd, J = 8.1, 0.7 Hz, 1H), 7.79-7.89 (m, 1H), 7.52-7.63 (m, 3H), 7.37 (d, J = 8.6 Hz, 1H), 6.59 (dd, J = 7.4, 1.4 Hz, 1H), 3.95 (s, 3H) |
| 399 | 400 MHz $d_6$-DMSO | 9.46 (d, J = 7.6 Hz, 1H), 8.58 (d, J = 2.3 Hz, 1H), 8.46 (d, J = 4.5 Hz, 1H), 7.97-8.06 (m, 1H), 7.88 (s, 0H), 7.72-7.83 (m, 1H), 7.53-7.64 (m, 2H), 7.49 (dt, J = 8.5, 4.4 Hz, 1H), 7.34 (d, J = 8.4 Hz, 1H), 6.68 (d, J = 7.6 Hz, 1H), 6.58 (d, J = 9.8 Hz, 1H) |
| 400 | 400 MHz $d_4$-MeOH | 8.51 (d, J = 4.5 Hz, 1H), 8.05 (s, 1H), 7.88 (d, J = 11.2 Hz, 1H), 7.66 (t, J = 9.1 Hz, 1H), 7.38-7.53 (m, 3H), 7.28-7.37 (m, 1H), 6.68 (s, 1H) |
| 401 | 400 MHz $d_4$-MeOH | 8.49 (br. s., 1H), 8.26 (br. s., 1H), 8.14 (br. s., 1H), 7.64 (t, J = 8.4 Hz, 1H), 7.36-7.52 (m, 3H), 7.27-7.35 (m, 1H), 6.67 (br. s., 1H) |
| 402 | 400 MHz $d_6$-DMSO | 12.78 (br. s., 1H), 9.36 (d, J = 7.0 Hz, 1H), 8.29-8.53 (m, 3H), 7.77 (t, J = 9.2 Hz, 1H), 7.43-7.64 (m, 3H), 7.33 (d, J = 8.2 Hz, 1H), 6.68 (d, J = 6.7 Hz, 1H) |
| 403 | 400 MHz $d_6$-DMSO | 11.92 (br. s., 1H), 9.06 (d, J = 7.8 Hz, 1H), 8.44 (d, J = 4.7 Hz, 1H), 8.03 (d, J = 2.2 Hz, 1H), 7.82 (d, J = 1.2 Hz, 1H), 7.76 (ddd, J = 10.0, 8.6, 1.2 Hz, 1H), 7.51-7.63 (m, 2H), 7.48 (dt, J = 8.4, 4.4 Hz, 1H), 7.33 (d, J = 8.8 Hz, 1H), 6.66 (d, J = 7.6 Hz, 1H), 1.99 (s, 3H) |
| 404 | 400 MHz $d_6$-DMSO | 11.09-11.51 (s, 1H), 9.80 (d, J = 7.2 Hz, 1H), 8.50 (d, J = 4.5 Hz, 1H), 7.79-7.88 (m, 1H), 7.44-7.62 (m, 3H), 7.31 (d, J = 8.4 Hz, 1H), 7.22 (d, J = 7.2 Hz, 1H), 6.60 (d, J = 6.3 Hz, 1H), 6.55 (d, J = 7.2 Hz, 1H), 3.40-3.61 (s, 3H) |
| 405 | 400 MHz $d_6$-DMSO | 12.00 (br. s., 1H), 9.15 (d, J = 7.8 Hz, 1H), 8.43 (dt, J = 4.7, 1.4 Hz, 1H), 8.16 (d, J = 2.3 Hz, 1H), 7.89 (dd, J = 9.6, 2.7 Hz, 1H), 7.70-7.81 (m, 2H), 7.57 (d, J = 11.9 Hz, 1H), 7.48 (dt, J = 8.5, 4.4 Hz, 1H), 7.42 (d, J = 8.2 Hz, 1H), 6.70 (d, J = 7.8 Hz, 1H), 6.34 (d, J = 9.6 Hz, 1H) |
| 406 | 400 MHz $d_6$-DMSO | 9.88 (d, J = 7.6 Hz, 1H), 9.20 (dd, J = 2.0, 0.8 Hz, 1H), 8.65 (d, J = 3.9 Hz, 1H), 8.50 (dd, J = 8.0, 2.2 Hz, 1H), 8.18 (dd, J = 8.0, 0.8 Hz, 1H), 7.85 (td, J = 7.7, 1.9 Hz, 1H), 7.59-7.67 (m, 2H), 7.48-7.58 (m, 1H), 7.32-7.44 (m, 2H), 6.43 (d, J = 7.6 Hz, 1H), 3.93 (s, 3H) |
| 407 | 400 MHz DMSO-$d_6$ | 9.12 (d, J = 7.6 Hz, 1H), 8.45 (d, J = 2.5 Hz, 2H), 7.98 (dd, J = 9.5, 2.4 Hz, 1H), 7.77 (t, J = 9.1 Hz, 1H), 7.51-7.63 (m, 2H), 7.48 (dt, J = 8.5, 4.3 Hz, 1H), 7.33 (d, J = 8.2 Hz, 1H), 6.67 (d, J = 7.6 Hz, 1H), 6.41 (d, J = 9.4 Hz, 1H), 5.63 (s, 1H), 4.03 (s, 2H), 0.67-0.78 (m, 2H), 0.61 (br. s., 2H) |
| 408 | 400 MHz DMSO-$d_6$ | 9.12 (dd, J = 10.3, 8.1 Hz, 1H), 8.35-8.61 (m, 2H), 7.99 (dd, J = 9.6, 1.4 Hz, 1H), 7.68-7.85 (m, 1H), 7.42-7.65 (m, 3H), 7.33 (d, J = 8.6 Hz, 1H), 6.61-6.82 (m, 2H), 6.46 (d, J = 9.4 Hz, 1H), 4.17-4.51 (m, 2H), 3.58-3.94 (m, 1H) |
| 409 | 400 MHz DMSO-$d_6$ | 8.95-9.32 (m, 1H), 8.33-8.55 (m, 2H), 7.94-8.09 (m, 1H), 7.71-7.84 (m, 1H), 7.52-7.64 (m, 2H), 7.42-7.55 (m, 1H), 7.33 (d, J = 8.4 Hz, 1H), 6.63-6.82 (m, 2H), 6.46 (d, J = 9.6 Hz, 1H), 4.22-4.52 (m, 2H), 3.69-3.87 (m, 1H) |
| 410 | 400 MHz DMSO-$d_6$ | 12.00 (s, 1H), 9.10 (d, J = 7.6 Hz, 1H), 8.16 (s, 1H), 7.91 (dd, J = 10, 2.8 Hz, 1H), 7.71 (d, J = 8.4 Hz, 2H), 7.64-7.56 (m, 3H), 6.30-6.27 (m, 1H), 6.30 (d, J = 7.6 Hz, 1H), 6.35 (d, J = 9.6 Hz, 1H), 2.43 (s, 3H) |
| 411 | 400 MHz DMSO-$d_6$ | 12.15 (br. s., 1H), 9.0 (d, J = 8.4 Hz, 1H), 8.13 (d, J = 2.4 Hz, 1H), 7.92 (dd, J = 10.0, 2.8 Hz, 1H), 7.47-7.58 (m, 2H), 7.36-7.39 (m, 2H), 7.27 (d, J = 8.8 Hz, 1H), 7.17-7.22 (m, 2H), 6.34-6.38 (m, 2H) |
| 412 | 400 MHz DMSO-$d_6$ | 12.13 (br. s., 1H), 9.08 (d, J = 8.0 Hz, 1H), 8.14 (d, J = 2.4 Hz, 1H), 7.91 (dd, J = 9.6, 2.4 Hz, 1H), 7.56-7.58 (m, 1H), 7.41-7.52 (m, 2H), 7.16-7.25 (m, 3H), 6.59 (d, J = 7.6 Hz, 1H), 6.36 (d, J = 9.6 Hz, 1H) |
| 413 | 400 MHz DMSO-$d_6$ | 12.15 (br. s., 1H), 9.05 (d, J = 8.0 Hz, 1H), 8.16 (d, J = 2.4 Hz, 1H), 7.93 (dd, J = 9.6, 2.4 Hz, 1H), 7.57-7.61 (m, 1H), 7.47-7.49 (m, 1H), 7.37-7.43 (m, 1H), 7.23-7.34 (m, 2H), 7.13-7.17 (m, 1H), 6.55 (d, J = 8.0 Hz, 1H), 6.37 (d, J = 9.6 Hz, 1H) |
| 414 | 400 MHz DMSO-$d_6$ | 12.14 (br. s., 1H), 9.04 (d, J = 7.6 Hz, 1H), 8.17 (d, J = 2.0 Hz, 1H), 7.93 (dd, J = 9.6, 2.4 Hz, 1H), 7.58-7.62 (m, 1H), 7.49-7.52 (m, 1H), 7.24-7.33 (m, 4H), 6.56 (d, J = 8.0 Hz, 1H), 6.38 (d, J = 9.6 Hz, 1H) |
| 415 | 400 MHz $d_4$-MeOH | 8.52 (br. s., 1H), 8.36 (d, J = 7.8 Hz, 2H), 8.12-8.24 (m, 1H), 7.67 (t, J = 8.9 Hz, 1H), 7.32-7.55 (m, 4H), 6.77 (br. s., 1H) |
| 416 | 300 MHz $d_4$-MeOH | 8.44-8.56 (m, 2H), 7.71 (dd, J = 6.3, 2.2 Hz, 1H), 7.63 (ddd, J = 9.9, 8.5, 1.2 Hz, 1H), 7.35-7.49 (m, 5H), 6.66 (d, J = 1.6 Hz, 1H), 6.59 (dd, J = 7.2, 6.4 Hz, 1H) |

TABLE 6-continued

| $^1$H NMR Data of Examples 1-261 and 287-424. | | |
|---|---|---|
| Ex. # | Freq., Solvent | $^1$HNMR Data (δ ppm) |
| 417 | 400 MHz DMSO-$d_6$ | 12.15 (br. s., 1H), 9.01 (d, J = 8.0 Hz, 1H), 8.14 (br. s., 1H), 7.91 (d, J = 9.6 Hz, 1H), 7.49-7.59 (m, 3H), 7.12-7.31 (m, 4H), 6.40 (dd, J = 14.4, 10.0 Hz, 2H) |
| 418 | 400 MHz DMSO-$d_6$ | 12.12 (br. s., 1H), 9.04 (d, J = 7.2 Hz, 1H), 8.18 (d, J = 2.4 Hz, 1H), 7.92 (dd, J = 9.6, 2.4 Hz, 1H), 7.53-7.57 (m, 1H), 7.45-7.49 (m, 2H), 7.12-7.18 (m, 3H), 6.64 (d, J = 7.2 Hz, 1H), 6.34 (d, J = 9.6 Hz, 1H) |
| 419 | 300 MHz $d_4$-MeOH | 8.48 (dt, J = 4.7, 1.3 Hz, 1H), 8.14 (dd, J = 2.7, 0.5 Hz, 1H), 8.04 (dd, J = 9.6, 2.7 Hz, 1H), 7.63 (ddd, J = 9.8, 8.4, 1.3 Hz, 1H), 7.34-7.51 (m, 3H), 7.25-7.34 (m, 1H), 6.65 (s, 1H), 6.53 (dd, J = 9.6, 0.6 Hz, 1H) |
| 420 | 400 MHz DMSO-$d_6$ | 12.05 (br. s., 1H), 8.96 (d, J = 8.0 Hz, 1H), 8.14 (br. s., 1H), 7.92 (d, J = 11.6 Hz, 1H), 7.70 (t, J = 8.0 Hz, 1H), 7.61-7.52 (m, 2H), 7.38 (d, J = 8.0 Hz, 1H), 7.06 (d, J = 7.2 Hz, 1H), 6.74 (d, J = 8.0 Hz, 1H), 6.37 (d, J = 9.6 Hz, 1H), 6.29 (d, J = 8.0 Hz, 1H), 3.81 (s, 3H) |
| 421 | 400 MHz DMSO-$d_6$ | 12.02 (br. s., 1H), 9.01 (d, J = 8.4 Hz, 1H), 8.26 (d, J = 2.4 Hz, 1H), 8.15 (br. s., 1H), 7.92 (dd, J = 9.6, 2.4 Hz, 1H), 7.51-7.54 (m, 2H), 7.41-7.45 (m, 2H), 7.31 (d, J = 8.4 Hz, 1H), 6.37 (dd, J = 9.2, 5.6 Hz, 2H), 3.81 (s, 3H) |
| 422 | 400 MHz DMSO-$d_6$ | 12.05 (br. s., 1H), 9.01 (d, J = 8.0 Hz, 1H), 8.37 (d, J = 5.6 Hz, 1H), 8.16 (d, J = 2.4 Hz, 1H), 7.92 (dd, J = 9.6, 2.8 Hz, 1H), 7.50-7.58 (m, 2H), 7.35 (d, J = 8.8 Hz, 1H), 7.14 (d, J = 2.4 Hz, 1H), 6.92 (dd, J = 6.0, 2.8 Hz, 1H), 6.36 (dd, J = 8.0, 3.2 Hz, 2H), 3.82 (s, 3H) |
| 423 | 400 MHz DMSO-$d_6$ | 12.02 (br. s., 1H), 9.03 (d, J = 8.2 Hz, 1H), 8.42 (d, J = 4.9 Hz, 1H), 8.17 (d, J = 2.2 Hz, 1H), 7.93 (dd, J = 9.7, 2.6 Hz, 1H), 7.46-7.62 (m, 2H), 7.30-7.44 (m, 2H), 7.17 (d, J = 4.7 Hz, 1H), 6.25-6.44 (m, 2H), 2.34 (s, 3H) |
| 424 | 400 MHz DMSO-$d_6$ | 12.00 (br. s., 1H), 9.01 (d, J = 8.0 Hz, 1H), 8.33-8.48 (m, 1H), 8.15 (d, J = 2.5 Hz, 1H), 7.91 (dd, J = 9.6, 2.8 Hz, 1H), 7.63 (dd, J = 8.0, 1.8 Hz, 1H), 7.46-7.59 (m, 2H), 7.40 (d, J = 7.9 Hz, 1H), 7.32 (d, J = 8.5 Hz, 1H), 6.36 (dd, J = 8.9, 4.5 Hz, 2H), 2.28 (s, 3H) |

Stereochemistry

Absolute stereochemistry, where noted, was determined by comparison of either (I) quantum-mechanically predicted optical rotation values (Stephens, P. J. et. al, J. Phys. Chem. A 2001, 105, 5356) or (II) VCD spectra (Stephens, P. J. et. al, Chirality 2008, 20, 643) to those measured experimentally. A single-crystal X-ray structure of (S)-tert-butyl((3-bromopyridin-2-yl)(4-(trifluoromethyl)phenyl)-methyl)carbamate (Intermediate 46, Step 5) provided confirmation of the absolute stereochemistry.

Computed and observed optical rotation for a subset of examples in this invention are shown in Table 7. Optical rotations were measured in $CHCl_3$ at room temperature using a Perkin-Elmer digital polarimeter at 589 nm (sodium D line) in a 1.0 dm cell.

TABLE 7

| Computed and Measured Optical Rotation for Absolute Stereochemistry Assignment | | |
|---|---|---|
| Example | Computed Rotation | Measured Rotation |
| 41 | (S) = + | +78° |
| 50 | (S) = + | +57° |
| 92 | (S) = + | +16° |

The experimental vibrational circular dichroism (VCD) spectrum of Example 28 was obtained on a Biotools, Inc. ChiralIR spectrometer (BaF2 cell, 100 um path length, 48 mg/mL, 4 h acquisition time in $CDCl_3$). Comparison of the experimental spectrum to those computed quantum mechanically for the (S) and (R) stereoisomers, using the B3LYP hybrid density functional and 6-31G* basis set, led to the assignment of 28 as the (S) configuration.

Assays

Luminescence Readout Assay for Measuring Intracellular Calcium

A stable Chinese hamster ovary cell line expressing human TRPM8 was generated using tetracycline inducible T-REx™ expression system from Invitrogen, Inc. (Carlsbad, Calif.). In order to enable a luminescence readout based on intracellular increase in calcium (Le Poul et al., 2002), the cell line was also co-transfected with pcDNA3.1 plasmid containing jelly fish aequorin cDNA. Twenty four hours before the assay, cells were seeded in 96-well plates and TRPM8 expression was induced with 0.5 μg/mL tetracycline. On the day of the assay, culture media was removed and cells were incubated with assay buffer (Ham's F12 containing 30 mM HEPES) that contained 15 μM coelenterazine (P.J.K, Germany) for 2 h. Potential antagonists were added 2.5 min prior to the addition of agonist, 1 μM icilin, 100 μM L-menthol, or 1 min prior to the addition of cold buffer (<10° C.). The luminescence was measured by a CCD camera based FLASH-luminometer built by Amgen, Inc. A cooling device attached to FLASH luminometer was used for cold activation. Compound activity was calculated using either GraphPad Prism 4.01 (GraphPad Software Inc, San Diego, Calif.) or Genedata Screener.

The following compounds exhibit $IC_{50}$ values of less than 10 μM in the assay described above with icilin activation. Results are shown in Table 8.

TABLE 8 hTRPM8 $IC_{50}$'s for Examples 1-438

| Example | $IC_{50}$ (μM) |
|---|---|
| 1 | 0.0098 |
| 2 | 0.0170 |
| 3 | 0.0177 |
| 4 | 0.0440 |
| 5 | 0.0219 |
| 6 | 0.0739 |
| 7 | 0.0758 |
| 8 | 0.0543 |
| 9 | 0.146 |
| 10 | 0.0205 |
| 11 | 0.0785 |
| 12 | 0.0754 |
| 13 | 0.0833 |
| 14 | 0.0749 |
| 15 | 0.117 |
| 16 | 0.0807 |
| 17 | 0.230 |
| 18 | 0.157 |
| 19 | 0.0952 |
| 20 | 0.187 |
| 21 | 0.0918 |
| 22 | 0.418 |
| 23 | 1.06 |
| 24 | 0.318 |
| 25 | 0.0368 |
| 26 | 3.29 |
| 27 | 0.129 |
| 28 | 0.194 |
| 29 | 0.0324 |
| 30 | 0.0149 |
| 31 | 0.162 |
| 32 | 0.143 |
| 33 | 0.125 |
| 34 | 0.0322 |
| 35 | 0.0196 |
| 36 | 0.073 |
| 37 | 0.146 |
| 38 | 0.0777 |
| 39 | 0.0178 |
| 40 | 0.0134 |
| 41 | 0.0063 |
| 42 | 0.0539 |
| 43 | 0.0245 |
| 44 | 0.229 |
| 45 | 0.0635 |
| 46 | 0.0123 |
| 47 | 0.0201 |
| 48 | 0.0215 |
| 49 | 0.127 |
| 50 | 0.0105 |
| 51 | 0.0101 |
| 52 | 0.0401 |
| 53 | 0.0455 |
| 54 | 0.0231 |
| 55 | 0.0304 |
| 56 | 0.0092 |
| 57 | 0.0631 |
| 58 | 0.0639 |
| 59 | 0.0416 |
| 60 | 0.0784 |
| 61 | 0.312 |
| 62 | 0.172 |
| 63 | 0.134 |
| 64 | 0.02 |
| 65 | 0.245 |
| 66 | 0.405 |
| 67 | 0.04 |
| 68 | 0.0142 |
| 69 | 0.0129 |
| 70 | 0.0152 |
| 71 | 0.0092 |
| 72 | 0.167 |
| 73 | 0.017 |
| 74 | 0.0853 |
| 75 | 0.0391 |
| 76 | 0.0045 |

TABLE 8-continued hTRPM8 $IC_{50}$'s for Examples 1-438

| Example | $IC_{50}$ (μM) |
|---|---|
| 77 | 0.053 |
| 78 | 0.0148 |
| 79 | 0.0051 |
| 80 | 0.0231 |
| 81 | 0.0248 |
| 82 | 0.0177 |
| 83 | 0.0392 |
| 84 | 0.0053 |
| 85 | 0.0289 |
| 86 | 0.0102 |
| 87 | 0.0089 |
| 88 | 0.0121 |
| 89 | 0.0103 |
| 90 | 0.0062 |
| 91 | 0.0137 |
| 92 | 0.0103 |
| 93 | 0.0178 |
| 94 | 0.0414 |
| 95 | 0.0572 |
| 96 | 0.0376 |
| 97 | 0.119 |
| 98 | 0.125 |
| 99 | 0.129 |
| 100 | 0.0615 |
| 101 | 0.395 |
| 102 | 0.0081 |
| 103 | 0.0078 |
| 104 | 0.0062 |
| 105 | 0.0108 |
| 106 | 0.0089 |
| 107 | 0.0267 |
| 108 | 0.0241 |
| 109 | 0.0639 |
| 110 | 0.0644 |
| 111 | 0.0559 |
| 112 | 0.0844 |
| 113 | 0.0311 |
| 114 | 0.0506 |
| 115 | 0.0562 |
| 116 | 0.0429 |
| 117 | 0.0700 |
| 118 | 0.0905 |
| 119 | 0.100 |
| 120 | 0.0594 |
| 121 | 0.247 |
| 122 | 0.107 |
| 123 | 0.149 |
| 124 | 0.190 |
| 125 | 0.176 |
| 126 | 0.194 |
| 127 | 0.584 |
| 128 | 0.125 |
| 129 | 0.114 |
| 130 | 0.0247 |
| 131 | 0.0189 |
| 132 | 0.0175 |
| 133 | 0.0200 |
| 134 | 0.0310 |
| 135 | 0.0194 |
| 136 | 0.121 |
| 137 | 0.0949 |
| 138 | 0.0464 |
| 139 | 0.0659 |
| 140 | 0.0527 |
| 141 | 0.160 |
| 142 | 0.144 |
| 143 | 0.0874 |
| 144 | 0.200 |
| 145 | 0.0852 |
| 146 | 0.180 |
| 147 | 0.148 |
| 148 | 0.257 |
| 149 | 0.398 |
| 150 | 0.178 |
| 151 | 0.395 |
| 152 | 0.459 |

TABLE 8-continued hTRPM8 $IC_{50}$'s for Examples 1-438

| Example | $IC_{50}$ (μM) |
|---|---|
| 153 | 0.373 |
| 154 | 2.53 |
| 155 | 1.44 |
| 156 | 0.301 |
| 157 | 0.716 |
| 158 | 1.95 |
| 159 | 2.21 |
| 160 | 3.32 |
| 161 | 3.37 |
| 162 | 4.38 |
| 163 | 3.18 |
| 164 | 0.294 |
| 165 | 0.0051 |
| 166 | 0.0076 |
| 167 | 0.0215 |
| 168 | 0.0384 |
| 169 | 0.0104 |
| 170 | 0.0235 |
| 171 | 0.0173 |
| 172 | 0.0181 |
| 173 | 0.0153 |
| 174 | 0.0229 |
| 175 | 0.0303 |
| 176 | 0.0219 |
| 177 | 0.0208 |
| 178 | 0.0262 |
| 179 | 0.0398 |
| 180 | 0.0297 |
| 181 | 0.0266 |
| 182 | 0.0418 |
| 183 | 0.0396 |
| 184 | 0.0529 |
| 185 | 0.0290 |
| 186 | 0.0492 |
| 187 | 0.0453 |
| 188 | 0.0351 |
| 189 | 0.0806 |
| 190 | 0.0331 |
| 191 | 0.0789 |
| 192 | 0.0790 |
| 193 | 0.0348 |
| 194 | 0.0756 |
| 195 | 0.0506 |
| 196 | 0.0671 |
| 197 | 0.115 |
| 198 | 0.0560 |
| 199 | 0.0776 |
| 200 | 0.0493 |
| 201 | 0.0293 |
| 202 | 0.0352 |
| 203 | 0.135 |
| 204 | 0.104 |
| 205 | 0.140 |
| 206 | 0.0675 |
| 207 | 0.121 |
| 208 | 0.0417 |
| 209 | 0.105 |
| 210 | 0.150 |
| 211 | 0.115 |
| 212 | 0.0815 |
| 213 | 0.0430 |
| 214 | 0.121 |
| 215 | 0.0845 |
| 216 | 0.143 |
| 217 | 0.147 |
| 218 | 0.230 |
| 219 | 0.137 |
| 220 | 0.164 |
| 221 | 0.105 |
| 222 | 0.119 |
| 223 | 0.599 |
| 224 | 1.4 |
| 225 | 0.487 |
| 226 | 2.31 |
| 227 | 0.0414 |
| 228 | 0.0397 |

TABLE 8-continued hTRPM8 $IC_{50}$'s for Examples 1-438

| Example | $IC_{50}$ (μM) |
|---|---|
| 229 | 0.354 |
| 230 | 0.0837 |
| 231 | 0.461 |
| 232 | 0.0159 |
| 233 | 0.0831 |
| 234 | 0.169 |
| 235 | 0.226 |
| 236 | 0.239 |
| 237 | 0.733 |
| 238 | 0.547 |
| 239 | 0.016 |
| 240 | 0.081 |
| 241 | 0.59 |
| 242 | 1.03 |
| 243 | 1.44 |
| 244 | 3.38 |
| 245 | 0.0774 |
| 246 | 0.210 |
| 247 | 0.0427 |
| 248 | 0.0119 |
| 249 | 0.0132 |
| 250 | 0.0192 |
| 251 | 0.0193 |
| 252 | 0.0247 |
| 253 | 0.0114 |
| 254 | 0.0118 |
| 255 | 0.0176 |
| 256 | 0.302 |
| 257 | 0.109 |
| 258 | 0.0407 |
| 259 | 0.128 |
| 260 | 0.311 |
| 261 | 0.375 |
| 262 | 0.114 |
| 263 | 0.133 |
| 264 | 0.253 |
| 265 | 0.0622 |
| 266 | 0.223 |
| 267 | 0.0099 |
| 268 | 0.156 |
| 269 | 0.136 |
| 270 | 0.0191 |
| 271 | 0.0089 |
| 272 | 0.0119 |
| 273 | 0.0161 |
| 274 | 0.198 |
| 275 | 0.0686 |
| 276 | 0.177 |
| 277 | 0.188 |
| 278 | 0.317 |
| 279 | 1.81 |
| 280 | 0.0221 |
| 281 | 0.0101 |
| 282 | 0.0117 |
| 283 | 0.0218 |
| 284 | 0.346 |
| 285 | 2.16 |
| 286 | 1.11 |
| 287 | 2.37 |
| 288 | 0.139 |
| 289 | 1.61 |
| 290 | 0.944 |
| 291 | 0.332 |
| 292 | 0.0524 |
| 293 | 0.0137 |
| 294 | 0.0145 |
| 295 | 0.0180 |
| 296 | 0.0231 |
| 297 | 0.0168 |
| 298 | 0.0361 |
| 299 | 0.0175 |
| 300 | 0.0697 |
| 301 | 0.0417 |
| 302 | 0.0709 |
| 303 | 0.143 |
| 304 | 0.0144 |

TABLE 8-continued hTRPM8 $IC_{50}$'s for Examples 1-438

| Example | $IC_{50}$ (μM) |
|---|---|
| 305 | 0.0296 |
| 306 | 0.389 |
| 307 | 0.0454 |
| 308 | 0.0269 |
| 309 | 0.0308 |
| 310 | 0.0160 |
| 311 | 0.0278 |
| 312 | 0.0252 |
| 313 | 0.0259 |
| 314 | 0.0218 |
| 315 | 0.0363 |
| 316 | 0.0314 |
| 317 | 0.0389 |
| 318 | 0.0297 |
| 319 | 0.132 |
| 320 | 0.132 |
| 321 | 0.164 |
| 322 | 0.202 |
| 323 | 0.0367 |
| 324 | 1.05 |
| 325 | 0.644 |
| 326 | 3.21 |
| 327 | 0.302 |
| 328 | 1.06 |
| 329 | 0.841 |
| 330 | 2.68 |
| 331 | 0.965 |
| 332 | 0.268 |
| 333 | 0.658 |
| 334 | 0.103 |
| 335 | 0.209 |
| 336 | 0.136 |
| 337 | 0.313 |
| 338 | 0.264 |
| 339 | 0.915 |
| 340 | 0.808 |
| 341 | 4.28 |
| 342 | 0.255 |
| 343 | 1.48 |
| 344 | 0.0451 |
| 345 | 0.102 |
| 346 | 0.0111 |
| 347 | 0.0100 |
| 348 | 0.0154 |
| 349 | 0.0156 |
| 350 | 0.0227 |
| 351 | 0.0159 |
| 352 | 0.0188 |
| 353 | 0.0277 |
| 354 | 0.0681 |
| 355 | 0.0385 |
| 356 | 0.0784 |
| 357 | 0.0466 |
| 358 | 0.0141 |
| 359 | 0.0136 |
| 360 | 0.0200 |
| 361 | 0.0058 |
| 362 | 0.0042 |
| 363 | 0.0295 |
| 364 | 0.0158 |
| 365 | 0.0401 |
| 366 | 0.0097 |
| 367 | 0.0683 |
| 368 | 0.0210 |
| 369 | 3.71 |
| 370 | 0.0337 |
| 371 | 0.190 |
| 372 | 0.0894 |
| 373 | 0.0206 |
| 374 | 0.0524 |
| 375 | 0.0303 |
| 376 | 0.0530 |
| 377 | 0.0207 |
| 378 | 0.0503 |
| 379 | 0.270 |
| 380 | 0.245 |

TABLE 8-continued hTRPM8 $IC_{50}$'s for Examples 1-438

| Example | $IC_{50}$ (μM) |
|---|---|
| 381 | 0.0104 |
| 382 | 0.0069 |
| 383 | 0.0079 |
| 384 | 0.0058 |
| 385 | 0.0067 |
| 386 | 0.0105 |
| 387 | 0.279 |
| 388 | 2.98 |
| 389 | 0.0183 |
| 390 | 0.136 |
| 391 | 0.0117 |
| 392 | 0.0076 |
| 393 | 0.0061 |
| 394 | 0.0354 |
| 395 | 0.0066 |
| 396 | 0.0201 |
| 397 | 0.0103 |
| 398 | 0.189 |
| 399 | 0.0165 |
| 400 | 0.0069 |
| 401 | 0.0128 |
| 402 | 0.120 |
| 403 | 0.0178 |
| 404 | 3.55 |
| 405 | 0.0175 |
| 406 | 0.241 |
| 407 | 0.0596 |
| 408 | 0.0781 |
| 409 | 0.0892 |
| 410 | 0.0718 |
| 411 | 0.14 |
| 412 | 0.048 |
| 413 | 0.197 |
| 414 | 0.150 |
| 415 | 0.648 |
| 416 | 0.054 |
| 417 | 0.083 |
| 418 | 0.065 |
| 419 | 2.02 |
| 420 | 0.118 |
| 421 | 0.611 |
| 422 | 0.841 |
| 423 | 0.137 |
| 424 | 0.092 |
| 425 | 0.0105 |
| 426 | 0.0097 |
| 427 | 0.0140 |
| 428 | 1.29 |
| 429 | 2.66 |
| 430 | 0.0124 |
| 431 | 0.0564 |
| 432 | 0.0195 |
| 433 | 0.0079 |
| 434 | 0.0121 |
| 435 | 6.24 |
| 436 | 0.0224 |
| 437 | 0.225 |
| 438 | 0.0114 |

Icilin Biochemical Challenge Models

Inhibition of Icilin Induced Jumping in Mice

Example compounds at doses ranging from 0.01 to 10 mg/kg were administered to male C57BL/6 mice (18-25 g, Taconic, n=10/treatment) 1 h before icilin to assess the ability to block the spontaneous jumps induced by icilin (i.p. suspended in 100% PEG400 at 20 mg/kg, 5 mL/kg). The total number of jumps were recorded during the 10 min post-icilin administration based on the number of photocell beam breaks from the vertical array of open field boxes (Kinder Scientific)

while movement of the mice was restricted within a clear Plexiglas cylinder 9.5 cm diameter×30 cm height.

Inhibition of Icilin Induced Shaking in Rats

Example compounds at doses ranging from 0.01 to 3 mg/kg (p.o, suspended in 5% Tween80/Oralplus or suspended in 2% HPMC-1% Tween-80 pH2.2 with MSA, 5 mL/kg) were administered to male Sprague Dawley rats (200-300 g, Harlan, n=6-8/treatment) 2 h before icilin to assess the ability to block the spontaneous wet-dog shake phenomena induced by icilin (i.p., suspended in 100% PEG400 at 0.5 mg/kg, 1 mL/kg or p.o., suspended in 2% HPMC-1% Tween-80 at 3 mg/kg, 2.5 mL/kg). Spontaneous wet-dog shakes were counted manually by two blinded observers or using LABORAS automation (Metris) for 30 min post-icilin. Results are shown in Table 9.

TABLE 9

Inhibition of icilin induced wet dog shakes in rats by select Examples

| Example # | Dose (mg/kg) | % Inhibition of Wet-Dog Shakes |
|---|---|---|
| 1 | 1 | 100 |
| 51 | 1 | 99 |
| 68 | 1 | 100 |
| 76 | 1 | 100 |
| 79 | 1 | 99 |
| 91 | 1 | 100 |
| 102 | 1 | 99 |
| 103 | 1 | 97 |
| 132 | 1 | 95 |
| 293 | 1 | 96 |
| 295 | 1 | 77 |
| 297 | 1 | 78 |
| 299 | 1 | 56 |
| 348 | 1 | 51 |
| 362 | 1 | 98 |
| 370 | 1 | 50 |
| 373 | 1 | 64 |
| 377 | 1 | 94 |
| 386 | 1 | 97 |
| 426 | 1 | 53 |
| 432 | 1 | 60 |
| 434 | 1 | 91 |

Cold Pressor Test (CPT) as a Translatable PD Model for TRPM8

The cold pressor test (CPT) was developed as a method to measure blood pressure response following exposure to a cold stimulus and has been used over 70 years in the diagnosis of hypertension and other cardiac autonomic disorders (Hines and Brown 1936). In healthy human subjects, the CPT is typically performed by immersing a subject's hand into ice water (0-5° C.) which triggers, through a vascular sympathetic activation of afferent pain and temperature neurons, an increase in blood pressure. With some modifications, this test has also been utilized in rat to delineate the medullary and spinal pathways mediating the cardio-vascular responses to cold pressor test and to identify neurotransmitters in these pathways (Sapru N et al 2008) or to characterize analgesic compounds (Koltzenburg M et al 2006 and Player M R et al 2011).

TRPM8 antagonists were evaluated in rat CPT to determine whether TRPM8 antagonists would attenuate the increase in blood pressure resulting from exposure to cold stimulation of the paws and ventral half of the body. Male Sprague-Dawley rats weighing 350-450 g were instrumented with a unilateral carotid artery-cannula connected to a transducer for measuring blood pressure using a Digi-Med Blood Pressure Analyzer, Model 400. Animals were orally administrated with Vehicle (2% HPMC 1% Tween 80 pH 2.2 with MSA) or test compounds at 120 min prior to cold challenge and anesthetized with sodium pentobarbital at 60 mg/kg ip at 100 min prior to cold. Blood pressure was recorded for 5 min for pre-cold baseline and additional 5 min during immersion of the paws and ventral half of body in ice water. Percent inhibition attributed to treatment with test compound was then determined using the following Formula: [1−(cold evoked change in MBP/cold evoked change in MBP post-vehicle)]×100. Plasma was collected through artery catheter immediately after CPT for pk analysis and IC50/90 determination.

REFERENCES

Hines, E A and Brown G E. The cold pressor test for measuring the reactability of the blood pressure. Am. Heart J. 1936, 11:1-9

Nakamura T, Kawabe K, and Sapru H N. Cold pressor test in the rat: medullary and spinal pathways and neurotransmitters. Am J Physiol Heart Circ Physiol 2008, 295:H1780-H1787

Koltzenburg M, Pokorny R, Gasser U and Richarz U. Differential sensitivity of three experimental pain models in detecting the analgesic effects of transdermal fentanyl and buprenorphine. Pain 2006, 126:165-174

Parks D, Parsons W, Colburn R, Meegala S, Ballentine S, Illig C, Qin N, Liu Y, Hutchinson T, Lubin M, Stone D, Baker J, Schneider C, Ma J, Damiano B, Flores C, and Player M. Design and optimization of benzimidazole-containing transient receptor potentiate melastatin 8 (TRPM8) antagonists. J. Med. Chem. 2011, 54:233-247

CCI Model

Surgery—A chronic constriction injury (CCI) can be produced as previously described (Bennett & Xie, 1988). Under gaseous anesthesia with a mixture of isoflurane (3% for induction and 2% for maintenance) in $O_2$, the sciatic nerve can be exposed at the mid-thigh level proximal to the sciatic trifurcation. Four chromic gut ligatures (4-0) can be tied loosely around nerve, 1-2 mm apart such that the vascular supply will not be compromised.

Behavioral testing—A behavioral test can be performed to estimate cold-induced ongoing pain as previously described (Choi et al., 1994). The rat can be placed under a transparent plastic cover on an aluminum plate (IITC PE34, Woodland, Calif.) which can be kept at a cold temperature (5±0.5° C.). After 2 min of adaptation, the cumulative duration of time that the rat lifts its foot off the plate for the next 5 min can be measured. Foot lifts associated with locomotion or grooming are not counted. Seven to 9 days after the CCI surgery, baseline of the cold-induced ongoing pain can be measured. Any rat showing a cold-induced ongoing pain less than 100 sec out of 300 sec observation period can be eliminated from the study. Twenty four hours after the baseline measurement, test compound, positive control, morphine (2 mg/kg, Sigma, St. Louis) or a vehicle (saline or 2% HPMC/1% Tween 80) can be administered orally (test compound) or subcutaneously (morphine). Two hours (test compound) or 30 mins (morphine) after the drug administration, the cold-induced ongoing pain can be measured again.

Chung Model

Surgery—Spinal nerve ligation surgery can be performed as previously described (Kim & Chung, 1992). Briefly, under gaseous anesthesia with a mixture of isoflurane (3% for induction and 2% for maintenance) in $O_2$, the spinal nerve injury can be produced by ligating the left L5 and L6 spinal nerves taking special care to avoid any possible damage to the L4 spinal nerve or surrounding area. Additional treatments can be performed to increase the development of mechanical allodynia. First, L5 spinal nerve can be cut approximately 1 mm distal to the suture as described by Li et al. (2000). Second, immediately after ligation and cut, the L4 spinal nerve can be lightly manipulated by slightly stretching it with a fine hooked glass rod and gently sliding the hook back and forth 20 times along the nerve as described by Lee et al. (2003). The whole surgery procedure from anesthesia to the clipping of the incised skin can take at most 15 min.

Behavioral testing—Two weeks later, mechanical sensitivity can be measured by determining the median 50% foot withdrawal threshold for von Frey filaments using the up-down method (Chaplan et al., 1994). The rats can be placed under a plastic cover (9×9×20 cm) on a metal mesh floor. The area tested consists of the middle glabrous area between the footpads of the plantar surface of the hind paw. The plantar area can be touched with a series of 9 von Frey hairs with approximately exponentially incremental bending forces (von Frey values: 3.61, 3.8, 4.0, 4.2, 4.41, 4.6, 4.8, 5.0 and 5.2; equivalent to: 0.41, 0.63, 1.0, 1.58, 2.51, 4.07, 6.31, 10 and 15.8 g). The von Frey hair can be presented perpendicular to the plantar surface with sufficient force to cause slight bending, and held for approximately 3-4 sec. Abrupt withdrawal of the foot (paw flinching, shaking or licking for more than 1 sec) can be recorded as a response. Any rat showing a mechanical threshold of more than 3.16 g or less than 0.7 g after surgery can be eliminated from the study. After measuring basal threshold, test compound, positive control gabapentin (Sigma, St. Louis) or a vehicle (saline or 2% HPMC/1% Tween 80) can be administered orally (test compound) or intraperitoneally (gabapentin). The measurement of the tactile threshold can be reassessed at 1.5 and 2 h after drug administration.

Data—Since the von Frey filament set is calibrated on a logarithmic scale by the vendor (Stoelting) and our selection of 9 filaments for the up-down method is also based on near equal logarithmic intervals (Dixon et al., 1980), data can be treated using logarithmic values in every aspect (statistical treatment as well as plotting). However, an equivalent gram value scale is labeled on the Y-axis of the figures for convenience. Data are expressed as mean±standard error of the mean (S.E.M.).

For the treatment of TRPM8-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating TRPM8-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to $^{2}$% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I having the structure:

I

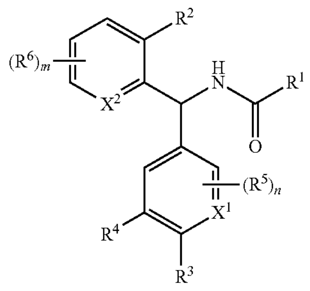

a pharmaceutically-acceptable salt thereof, a tautomer thereof, a pharmaceutically-acceptable salt of the tautomer, a stereoisomer thereof, or a mixture thereof, wherein:

m is 0, 1, 2 or 3;

n is 0 or 1;

$X^1$ is C($R^4$);

$X^2$ is N;

$R^1$ is $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one 0 or S atom, the $C_{1-6}$alk and ring being substituted by 0, 1, 2 or 3 substituents independently selected from halo, oxo, $C_{1-6}$alk, $C_{1-6}$alkOH, $C_{1-6}$alk-C(═O)$R^a$, $C_{1-6}$alk-C(═O)O$R^a$, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —OC(═O)N$R^aR^a$, —OC(═O)N($R^a$)S(═O)$_2R^a$, —O$C_{2-6}$alkN$R^aR^a$, —O$C_{2-6}$alkO$R^a$, —S$R^a$, ═S, —S(═O)$R^a$, —S(═O)$_2R^a$, —S(═O)$_2$N$R^aR^a$, —S(═O)$_2$N($R^a$)C(═O)$R^a$, —S(═O)$_2$N($R^a$)C(═O)O$R^a$, —S(═O)$_2$N($R^a$)C(═O)N$R^aR^a$, —N$R^aR^a$, —N($R^a$)C(═O)$R^a$, —N($R^a$)C(═O)O$R^a$, —N($R^a$)C(═O)N$R^aR^a$, —N($R^a$)C(═N$R^a$)N$R^aR^a$, —N($R^a$)S(═O)$_2R^a$, —N($R^a$)S(═O)$_2$N$R^aR^a$, —N$R^a$$C_{2-6}$alkN$R^aR^a$ and —N$R^a$$C_{2-6}$alkO$R^a$, wherein the ring is additionally substituted by 0 or 1 directly bonded, $SO_2$ linked, C(═O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one 0 or S atom, and substituted by 0, 1, 2 or 3 groups selected from halo, oxo, $C_{1-6}$alk, $C_{1-4}$haloalk, cyano, nitro, —C(═O)$R^a$, —C(═O)O$R^a$, —C(═O)N$R^aR^a$, —C(═N$R^a$)N$R^aR^a$, —O$R^a$, —OC(═O)$R^a$, —S$R^a$, —S(═O)$R^a$, —S(═O)$_2R^a$, —S(═O)$_2$N$R^aR^a$, —N$R^aR^a$, and —N($R^a$)C(═O)$R^a$;

$R^2$ is —F or —$CF_3$;

$R^3$ is —O$CF_3$ or —$CF_3$;

$R^4$ is independently, at each instance, H, $C_{1-6}$alk, —$C_{1-3}$haloalk, —$OC_{1-6}$alk, —$OC_{1-3}$haloalk, —N($C_{1-6}$alk)$C_{1-6}$alk, —$NHC_{1-6}$alk, —NC(═O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, halo, $OR^a$, $CH_3$ or $CF_3$;

$R^6$ is F, $C_{1-6}$alk, or $OR^a$;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —N($C_{1-4}$alk)$C_{1-4}$alk.

2. The compound of claim 1 or the pharmaceutically-acceptable salt thereof, the tautomer thereof, the pharmaceutically-acceptable salt of the tautomer, or the mixture thereof, wherein the compound of Formula I has the Formula IA:

IA

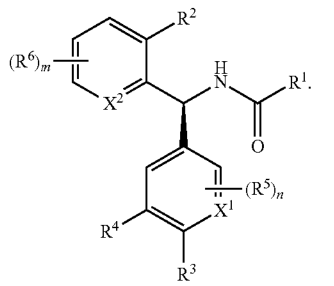

3. The compound of claim 1 or the pharmaceutically-acceptable salt thereof, the tautomer thereof, the pharmaceutically-acceptable salt of the tautomer, or the mixture thereof, wherein $R^1$ is the saturated, partially-saturated or unsaturated 3-, 4-, 5-, 6- or 7-membered monocyclic or 7-, 8-, 9-, 10- or 11-membered bicyclic ring and the monocyclic or bicyclic ring is substituted by 0, 1, 2, or 3 substituents, wherein the substituents are selected from F, Cl, Br, I, oxo, cyano, —$CH_3$, —$CH_2CH_3$, —$CH_2CH_2CH_3$, —C(H)$(CH_3)_2$, —$CH_2$C(H)$(CH_3)_2$, —$CH_2$C(H)═$CH_2$, —$CH_2CO_2H$, —$CH_2CF_3$, —C(OH)$(CH_3)_2$, —$SO_2$N(H)$CH_3$, —N(H)$SO_2CH_3$, —$OCH_3$, —$OCF_3$, —OH, —$OCH_2CO_2H$, —$CH_2OH$, —$CH_2CH_2OH$, —$CH_2$C(H)($CH_3$)OH, —$CO_2H$, —$CO_2CH_3$, —$CO_2CH_2CH_3$, —$CO_2C(CH_3)_3$, —$CO_2NH_2$, —$CO_2$N(H)$CH_3$, —$SO_2CH_3$, —OC(═O)$CH_3$, —$NH_2$, —NHC(═O)$CH_3$, —N$(CH_3)_2$, —N(H)$CH_2CH_3$, —$CF_3$, —$CHF_2$, —$CH_2$C(H)($CF_3$)OH, —$CH_2C(CH_3)_2OH$, —$CH_2$-phenyl, —C(═O)-phenyl, tetrazolyl, oxadiazolonyl, pyridyl, oxetanyl,

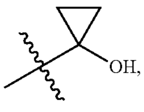 or 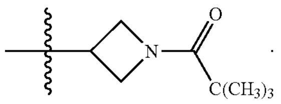 .

4. The compound of claim 1 or the pharmaceutically-acceptable salt thereof, the tautomer thereof, the pharmaceutically-acceptable salt of the tautomer, or the mixture thereof, wherein $R^1$ is a phenyl, pyridyl, pyridinonyl, piperidinonyl, pyridazinonyl, pyrazinonyl, pyridazinyl, pyrimidinyl, pyrazinyl, tetradyrofuranyl, tetrahydropyranyl, thiazolyl, furanyl, thiophenyl, pyrazolyl, isoxazolyl, triazolyl, oxazolyl, imidazolyl, pyrrolidinonyl, piperidinyl, cyclohexyl, cyclohexanonyl, quinolinyl, isoquinolinyl, naphthyridinyl, pyrrolopyridinyl, pyrrolopyrimidinyl, benzothiophenyl, pyrazolopyrimidinyl, triazolopyrimidinyl, indazolyl, tetrahydroindazolyl, tetrahydrocyclopentapyrazolyl, dihydropyrazolooxazinyl, indolinonyl, isoindolinonyl, benzooxazolonyl, oxazolopyridinonyl, benzoimidazolonyl, isoindolindionyl, tetrahydroquinolinyl, dihydroquinolinonyl, benzooxazinonyl, dihydrobenzooxazinonyl, dihydroindenonyl, benzothiazolyl, benzimidazolyl, imidazopyridinyl, tetrazolopyridinyl, quinolinonyl, quinoxalinyl, or quinoxalindionyl substituted by 0, 1, 2, or 3 substituents.

5. The compound of claim 4 or the pharmaceutically-acceptable salt thereof, the tautomer thereof, the pharmaceutically-acceptable salt of the tautomer, or the mixture thereof, wherein $R^1$ is a pyridinonyl substituted by 0, or 1 substituent.

6. The compound of claim 4 or the pharmaceutically-acceptable salt thereof, the tautomer thereof, the pharmaceutically-acceptable salt of the tautomer, or the mixture thereof, wherein $R^1$ is a pyridyl substituted by 0, or 1 substituent.

7. The compound of claim 1 or the pharmaceutically-acceptable salt thereof, the tautomer thereof, the pharmaceutically-acceptable salt of the tautomer, or the mixture thereof, wherein $R^1$ is a group of formula

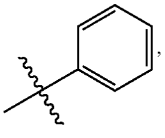, 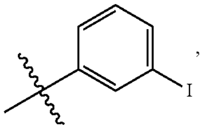, 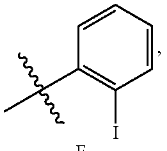,

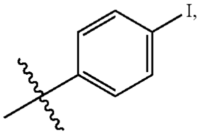 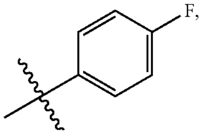

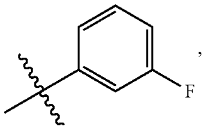, 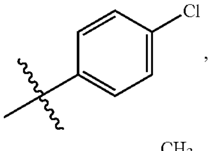,

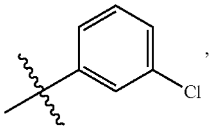, 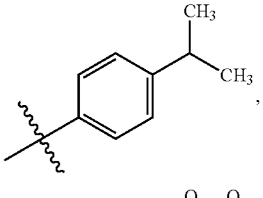,

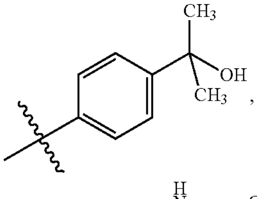, 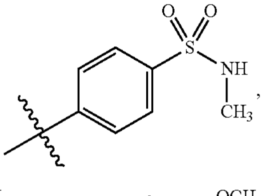,

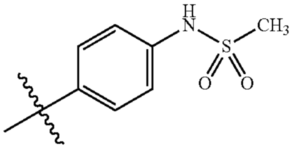, 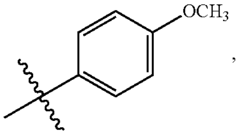,

-continued
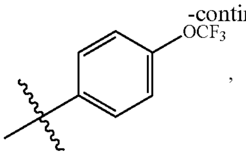, 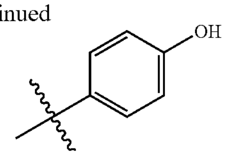, 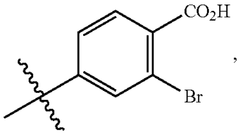, 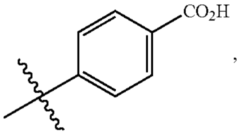, 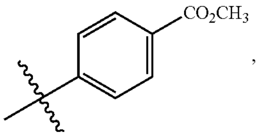, 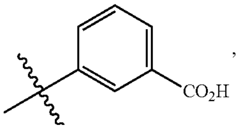, 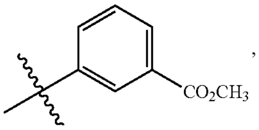, 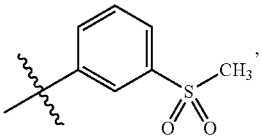, 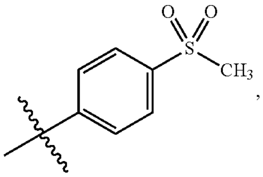, 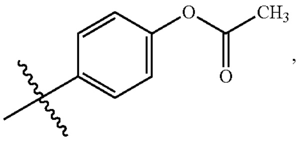, 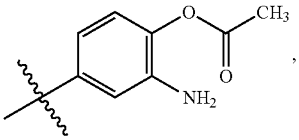, 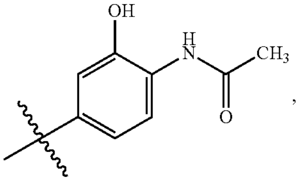, 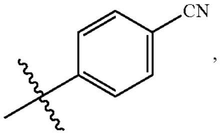, 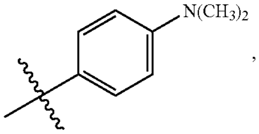, 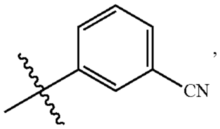, 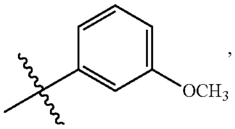, 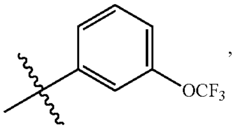, 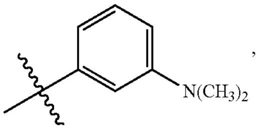, 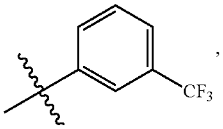, 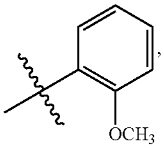, 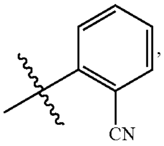,
-continued
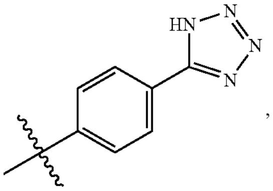, 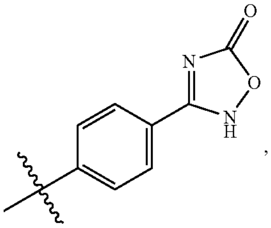, 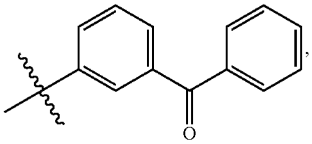, 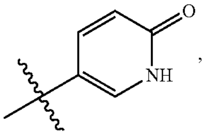, 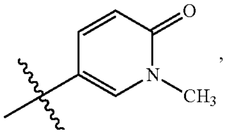, 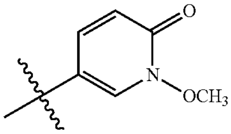, 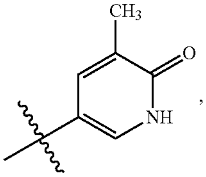, 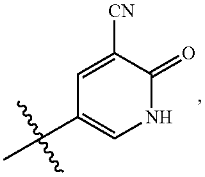, 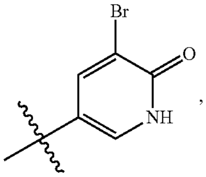, 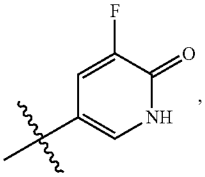, 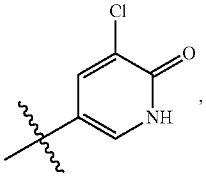, 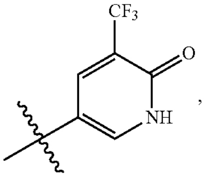, 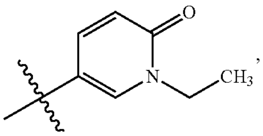, 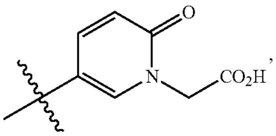, 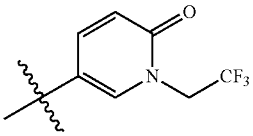, 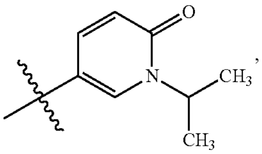, 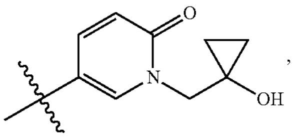, 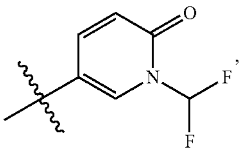, 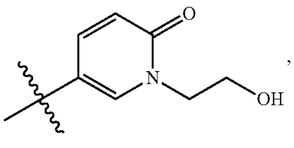, -continued
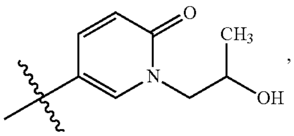
,
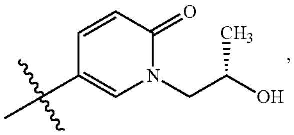
,
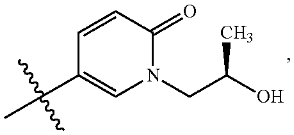
,
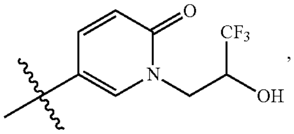
,
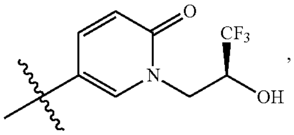
,
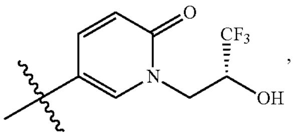
,
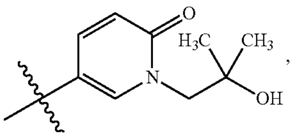
,
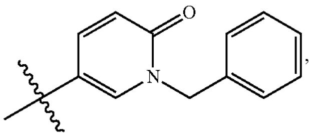
,
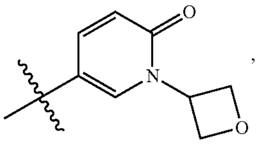
,
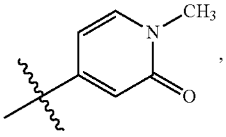
,
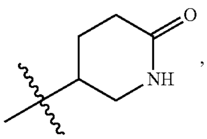
,
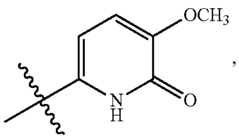
,
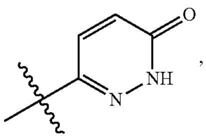
,
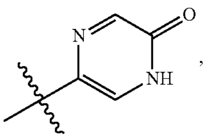
,
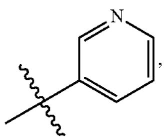
,
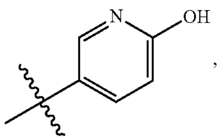
,
-continued
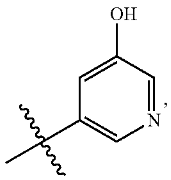
,
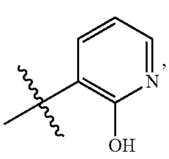
,
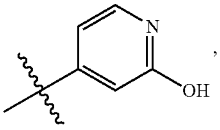
,
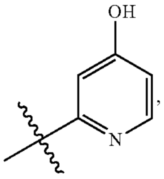
,
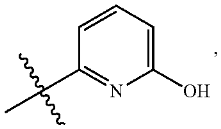
,
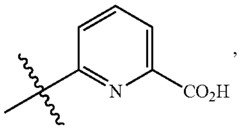
,
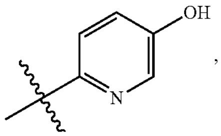
,
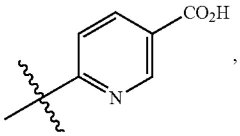
,
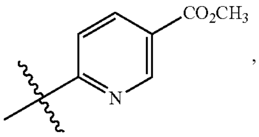
,
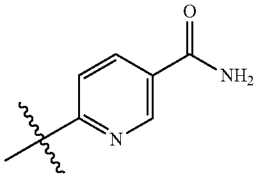
,
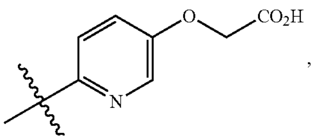
,
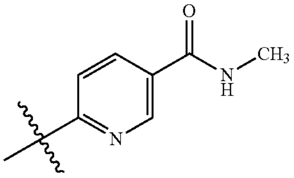
,
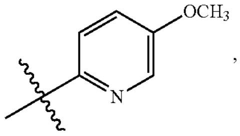
,
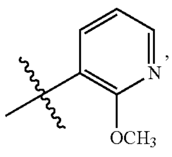
,
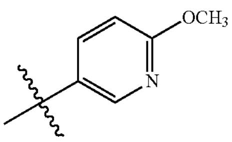
,
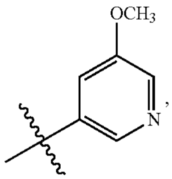
,
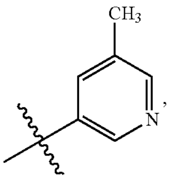
,
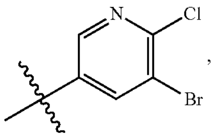
,
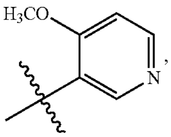
, -continued
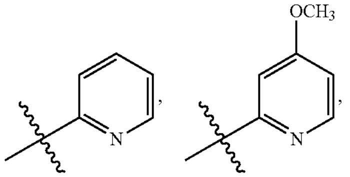
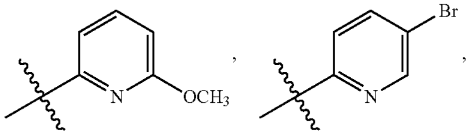
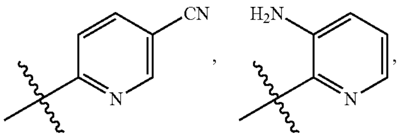
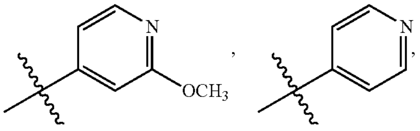
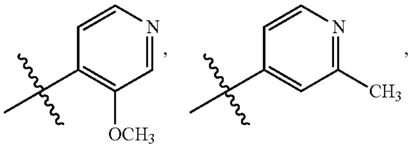
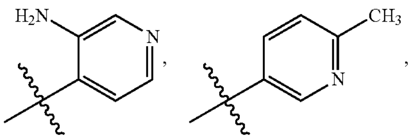
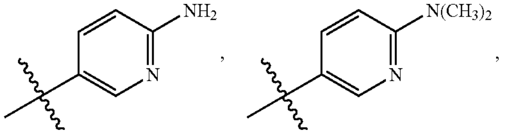
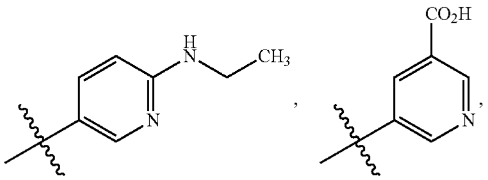
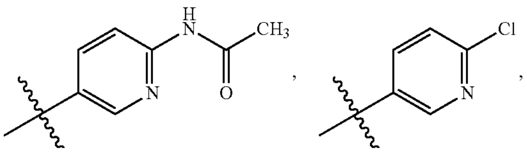
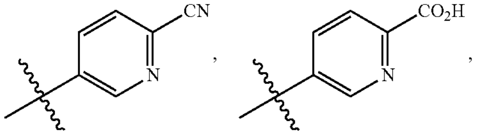
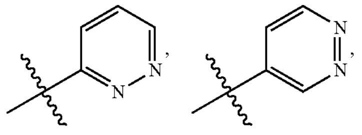
-continued
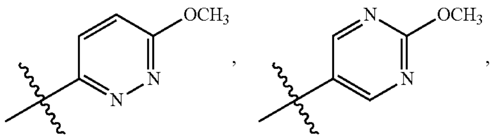
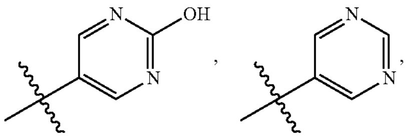
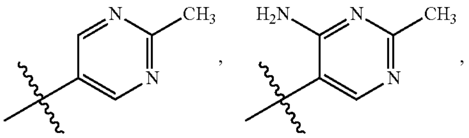
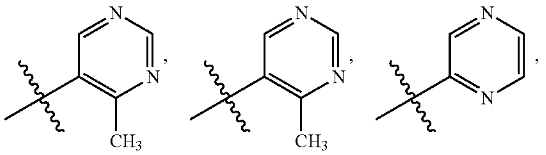
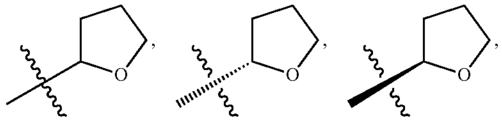
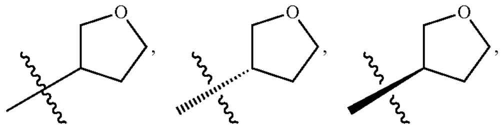
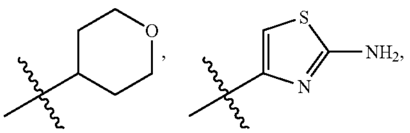
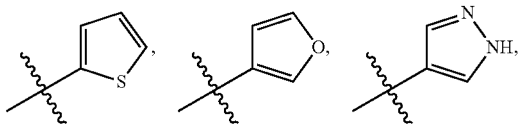
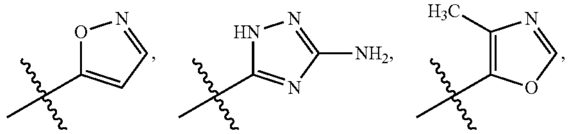
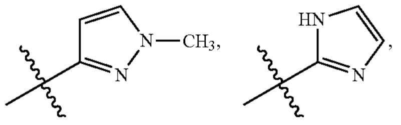
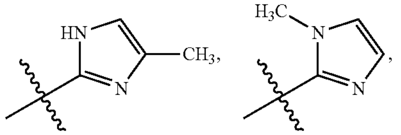
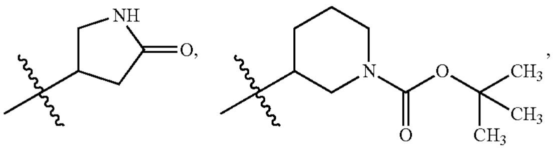

-continued
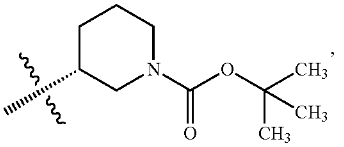,
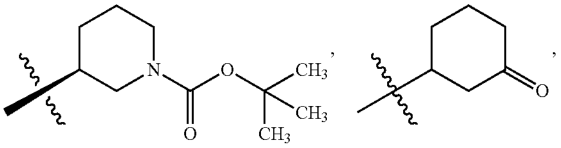,
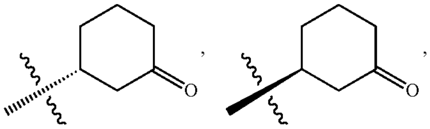,
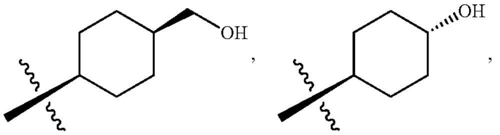,
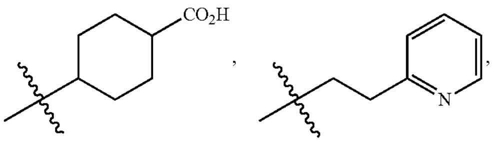,
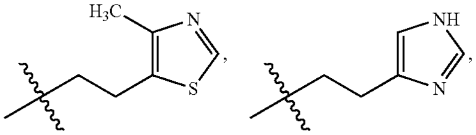,
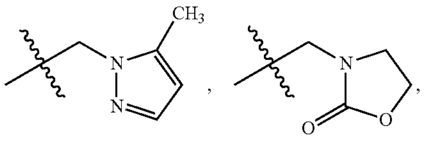,
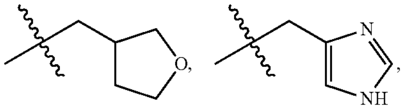,
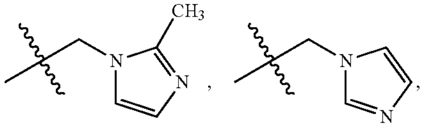,
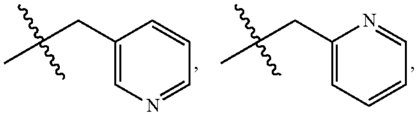,
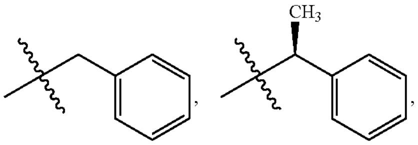,
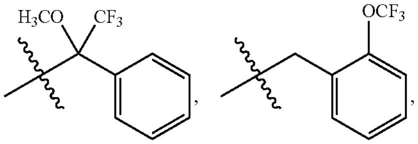,
-continued
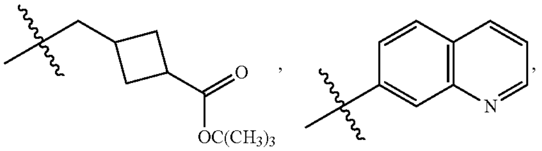,
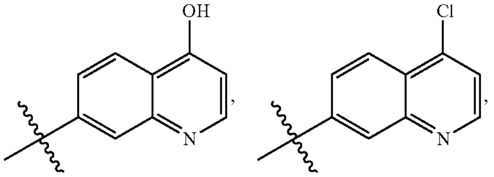,
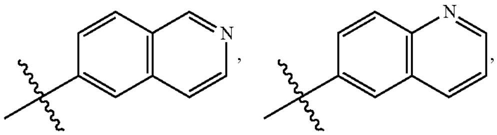,
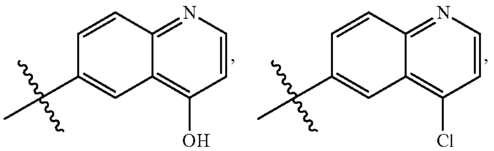,
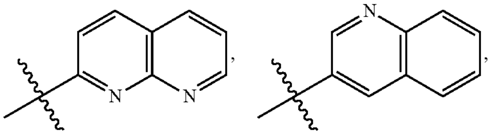,
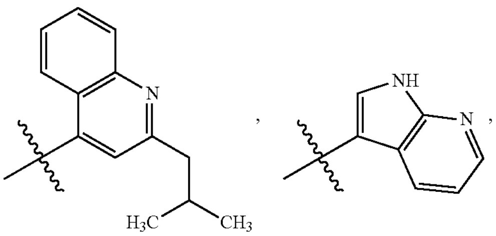,
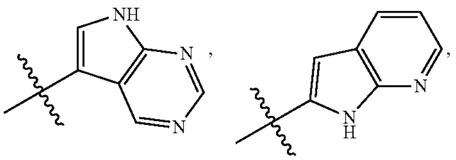,
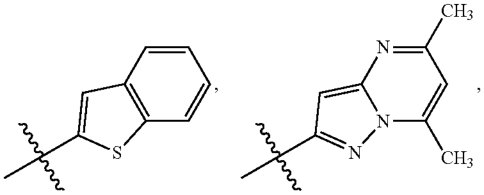,
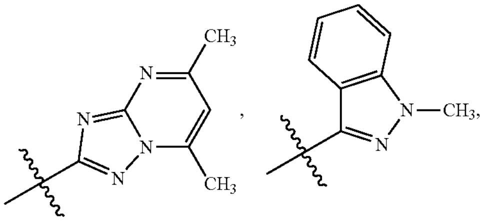, -continued
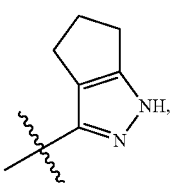
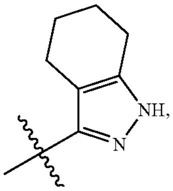
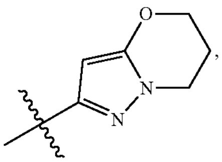
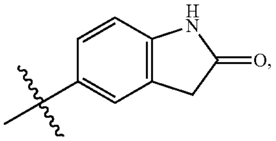
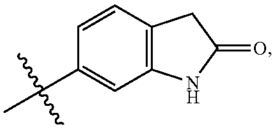
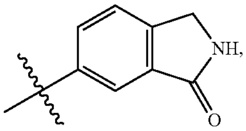
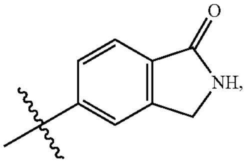
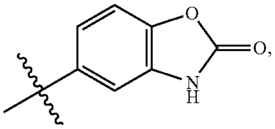
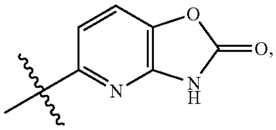
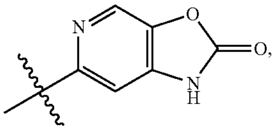
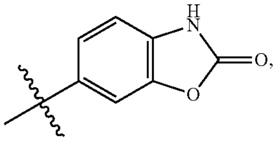
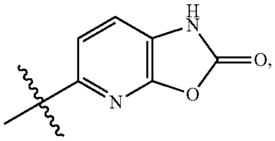
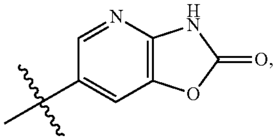
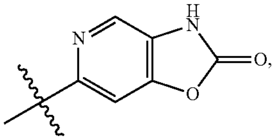
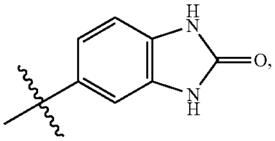
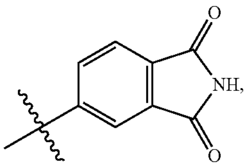
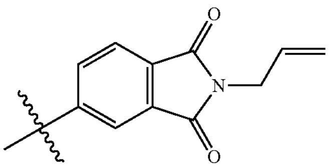
,
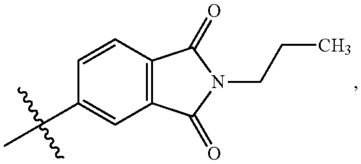
,
-continued
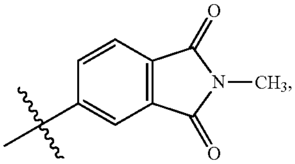
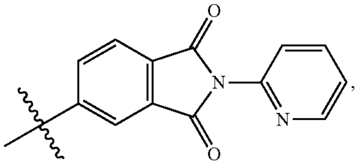
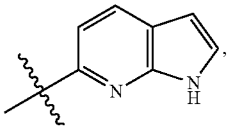
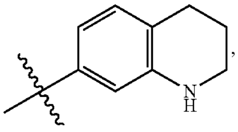
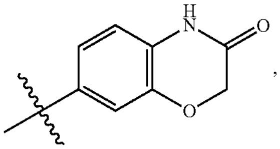
,
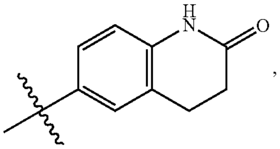
,
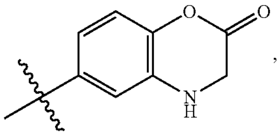
,
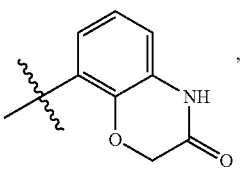
,
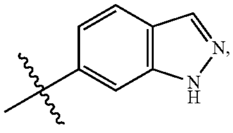
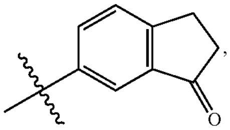
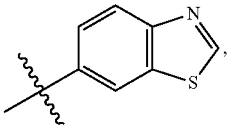
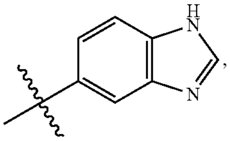
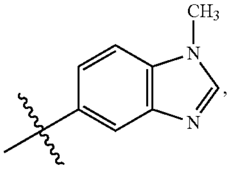
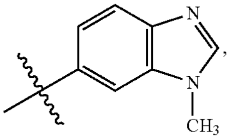
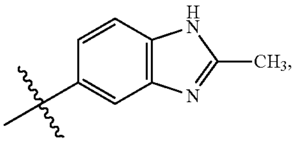
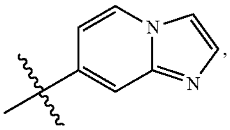
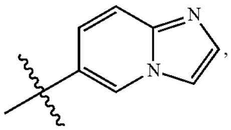
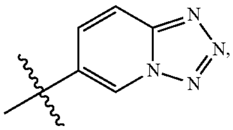
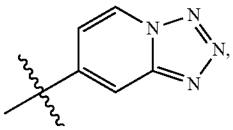
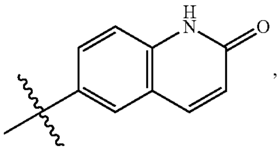
, -continued

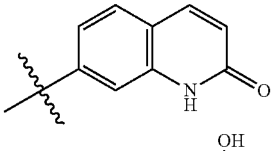,

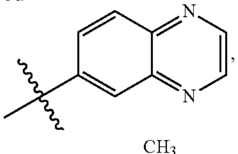,

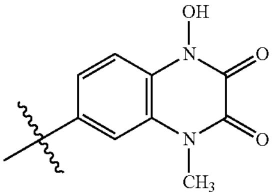,

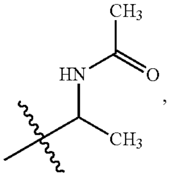,

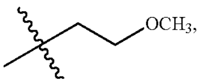,

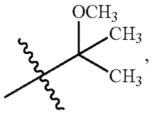, or

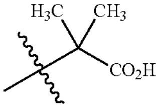

and the symbol , when drawn across a bond, indicates the point of attachment to the rest of the molecule.

8. The compound of claim 1 or the pharmaceutically-acceptable salt thereof, the tautomer thereof, the pharmaceutically-acceptable salt of the tautomer, or the mixture thereof, wherein $R^1$ is

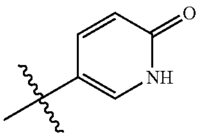 [SMILES: *c1ccc(=O)[nH]c1]

and the symbol , when drawn across a bond, indicates the point of attachment to the rest of the molecule.

9. The compound of claim 1 or the pharmaceutically-acceptable salt thereof, the tautomer thereof, the pharmaceutically-acceptable salt of the tautomer, or the mixture thereof, wherein $R^2$ is —F.

10. The compound of claim 1 or the pharmaceutically-acceptable salt thereof, the tautomer thereof, the pharmaceutically-acceptable salt of the tautomer, or the mixture thereof, wherein $R^2$ is —$CF_3$.

11. The compound of claim 1 or the pharmaceutically-acceptable salt thereof, the tautomer thereof, the pharmaceutically-acceptable salt of the tautomer, or the mixture thereof, wherein $R^3$ is —$OCF_3$.

12. The compound of claim 1 or the pharmaceutically-acceptable salt thereof, the tautomer thereof, the pharmaceutically-acceptable salt of the tautomer, or the mixture thereof, wherein $R^3$ is —$CF_3$.

13. The compound of claim 1 or the pharmaceutically-acceptable salt thereof, the tautomer thereof, the pharmaceutically-acceptable salt of the tautomer, or the mixture thereof, wherein $R^4$ is —F, —Cl, $C_{1-6}$alk, —$OC_{1-6}$alk, or —$C_{1-3}$haloalk.

14. The compound of claim 13 or the pharmaceutically-acceptable salt thereof, the tautomer thereof, the pharmaceutically-acceptable salt of the tautomer, or the mixture thereof, wherein $R^4$ is —F.

15. The compound of claim 1 or the pharmaceutically-acceptable salt thereof, the tautomer thereof, the pharmaceutically-acceptable salt of the tautomer, or the mixture thereof, wherein $X^1$ is CH.

16. The compound of claim 1 or the pharmaceutically-acceptable salt thereof, the tautomer thereof, the pharmaceutically-acceptable salt of the tautomer, or the mixture thereof, wherein $R^2$ is —F; $X^1$ is CH; and $R^4$ is —F.

17. The compound of claim 16 or the pharmaceutically-acceptable salt thereof, the tautomer thereof, the pharmaceutically-acceptable salt of the tautomer, or the mixture thereof, wherein $R^3$ is —$CF_3$.

18. The compound of claim 17 or the pharmaceutically-acceptable salt thereof, the tautomer thereof, the pharmaceutically-acceptable salt of the tautomer, or the mixture thereof, wherein $R^1$ is a pyridinonyl substituted by 0, or 1 substituent.

19. The compound of claim 17 or the pharmaceutically-acceptable salt thereof, the tautomer thereof, the pharmaceutically-acceptable salt of the tautomer, or the mixture thereof, wherein $R^1$ is a pyridyl substituted by 0, or 1 substituent.

20. The compound of claim 16 or the pharmaceutically-acceptable salt thereof, the tautomer thereof, the pharmaceutically-acceptable salt of the tautomer, or the mixture thereof, wherein $R^3$ is —$OCF_3$.

21. The compound of claim 20 or the pharmaceutically-acceptable salt thereof, the tautomer thereof, the pharmaceutically-acceptable salt of the tautomer, or the mixture thereof, wherein $R^1$ is a pyridinonyl substituted by 0, or 1 substituent.

22. The compound of claim 20 or the pharmaceutically-acceptable salt thereof, the tautomer thereof, the pharmaceutically-acceptable salt of the tautomer, or the mixture thereof, wherein $R^1$ is a pyridyl substituted by 0, or 1 substituent.

23. The compound of claim 16 or the pharmaceutically-acceptable salt thereof, the tautomer thereof, the pharmaceutically-acceptable salt of the tautomer, or the mixture thereof, wherein $R^1$ is a group of formula

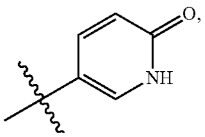,

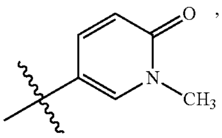,

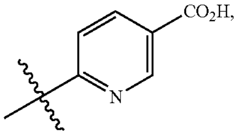,

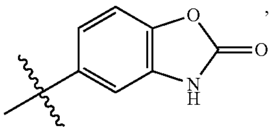,

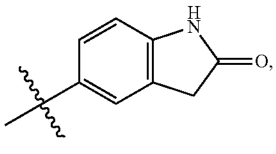,

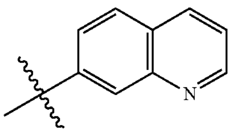,

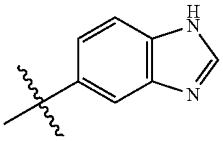, or

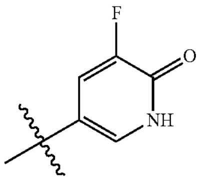

and the symbol , when drawn across a bond, indicates the point of attachment to the rest of the molecule.

24. The compound of claim 23 or the pharmaceutically-acceptable salt thereof, the tautomer thereof, the pharmaceutically-acceptable salt of the tautomer, or the mixture thereof, wherein m is 0 and n is 0.

25. The compound of claim 1 or the pharmaceutically-acceptable salt thereof, the tautomer thereof, the pharmaceutically-acceptable salt of the tautomer, or the mixture thereof, wherein $R^2$ is F; m is 0; $X^1$ is CH; $R^4$ is F or H; and $R^1$ is

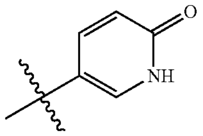 [SMILES: *c1ccc(=O)[nH]c1]

and the symbol , when drawn across a bond, indicates the point of attachment to the rest of the molecule.

26. The compound of claim 1, wherein the compound is
(S)—N-((3-fluoropyridin-2-yl)(4-(trifluoromethoxy)phenyl)methyl)-6-oxo-1,6-dihydropyridine-3-carboxamide;
(S)-6-oxo-N-((4-(trifluoromethyl)phenyl)(3-(trifluoromethyl)pyridin-2-yl)methyl)-1,6-dihydropyridine-3-carboxamide;
(S)—N-((3-fluoropyridin-2-yl)(4-(trifluoromethyl)phenyl)methyl)-6-oxo-1,6-dihydropyridine-3-carboxamide;
(S)—N-((3-fluoropyridin-2-yl)(4-(trifluoromethyl)phenyl)methyl)-1-methyl-6-oxo-1,6-dihydropyridine-3-carboxamide;
(S)—N-((3-fluoropyridin-2-yl)(4-(trifluoromethyl)phenyl)methyl)-2-oxo-2,3-dihydrobenzo[d]oxazole-5-carboxamide;
(S)—N-((3-fluoropyridin-2-yl)(4-(trifluoromethoxy)phenyl)methyl)-2-oxo-2,3-dihydrobenzo[d]oxazole-5-carboxamide;
(S)—N-((3-fluoropyridin-2-yl)(4-(trifluoromethoxy)phenyl)methyl)-2-oxoindoline-5-carboxamide;
(S)—N-((3-fluoro-4-(trifluoromethoxy)phenyl)(3-fluoropyridin-2-yl)methyl)-6-oxo-1,6-dihydropyridine-3-carboxamide;
(S)—N-((3-fluoro-4-(trifluoromethoxy)phenyl)(3-fluoropyridin-2-yl)methyl)-1-methyl-6-oxo-1,6-dihydropyridine-3-carboxamide; or
(S)—N-((4-(trifluoromethyl)phenyl)(3-(trifluoromethyl)pyridin-2-yl)methyl)quinoline-7-carboxamide; or the pharmaceutically-acceptable salt thereof, the tautomer thereof, the pharmaceutically-acceptable salt of the tautomer, or the mixture thereof.

27. The compound of claim 1, wherein the compound is
(S)—N-((3-fluoro-4-(trifluoromethoxy)phenyl)(3-fluoropyridin-2-yl)methyl)-6-oxo-1,6-dihydropyridine-3-carboxamide;
(S)—N-((3-fluoro-4-(trifluoromethoxy)phenyl)(3-(trifluoromethyl)pyridin-2-yl)methyl)-6-oxo-1,6-dihydropyridine-3-carboxamide;
(S)—N-((2-fluoro-4-(trifluoromethoxy)phenyl)(3-fluoropyridin-2-y)methyl)-6-oxo-1,6-dihydropyridine-3-carboxamide;
(S)-5-fluoro-N-((3-fluoro-4-(trifluoromethoxy)phenyl)(3-fluoropyridin-2-yl)methyl)-6-oxo-1,6-dihydropyridine-3-carboxamide;
(S)—N-((3-fluoro-4-(trifluoromethyl)phenyl)(3-fluoropyridin-2-yl)methyl)-6-oxo-1,6-dihydropyridine-3-carboxamide; or
(S)-6-(((3-fluoro-4-(trifluoromethoxy)phenyl)(3-fluoropyridin-2-yl)methyl)carbamoyl)nicotinic acid; or the pharmaceutically-acceptable salt thereof, the tautomer thereof, the pharmaceutically-acceptable salt of the tautomer, or the mixture thereof.

28. A pharmaceutical composition comprising the compound according to claim 1 or the pharmaceutically-acceptable salt thereof, the tautomer thereof, the pharmaceutically-acceptable salt of the tautomer, or the mixture thereof, and a pharmaceutically-acceptable diluent or carrier.

29. A pharmaceutical composition comprising the compound according to claim 16 or the pharmaceutically-acceptable salt thereof, the tautomer thereof, the pharmaceutically-acceptable salt of the tautomer, or the mixture thereof, and a pharmaceutically-acceptable diluent or carrier.

30. A pharmaceutical composition comprising the compound according to claim 17 or the pharmaceutically-acceptable salt thereof, the tautomer thereof, the pharmaceutically-acceptable salt of the tautomer, or the mixture thereof, and a pharmaceutically-acceptable diluent or carrier.

31. A pharmaceutical composition comprising the compound according to claim 18 or the pharmaceutically-acceptable salt thereof, the tautomer thereof, the pharmaceutically-acceptable salt of the tautomer, or the mixture thereof, and a pharmaceutically-acceptable diluent or carrier.

32. A pharmaceutical composition comprising the compound according to claim 19 or the pharmaceutically-acceptable salt thereof, the tautomer thereof, the pharmaceutically-acceptable salt of the tautomer, or the mixture thereof, and a pharmaceutically-acceptable diluent or carrier.

33. A pharmaceutical composition comprising the compound according to claim 20 or the pharmaceutically-acceptable salt thereof, the tautomer thereof, the pharmaceutically-acceptable salt of the tautomer, or the mixture thereof, and a pharmaceutically-acceptable diluent or carrier.

34. A pharmaceutical composition comprising the compound according to claim 21 or the pharmaceutically-acceptable salt thereof, the tautomer thereof, the pharmaceutically-acceptable salt of the tautomer, or the mixture thereof, and a pharmaceutically-acceptable diluent or carrier.

35. A pharmaceutical composition comprising the compound according to claim 22 or the pharmaceutically-acceptable salt thereof, the tautomer thereof, the pharmaceutically-acceptable salt of the tautomer, or the mixture thereof, and a pharmaceutically-acceptable diluent or carrier.

36. A pharmaceutical composition comprising the compound according to claim 23 or the pharmaceutically-acceptable salt thereof, the tautomer thereof, the pharmaceutically-acceptable salt of the tautomer, or the mixture thereof, and a pharmaceutically-acceptable diluent or carrier.

37. A pharmaceutical composition comprising the compound according to claim 24 or the pharmaceutically-acceptable salt thereof, the tautomer thereof, the pharmaceutically-acceptable salt of the tautomer, or the mixture thereof, and a pharmaceutically-acceptable diluent or carrier.

38. A pharmaceutical composition comprising the compound according to claim 25 or the pharmaceutically-acceptable salt thereof, the tautomer thereof, the pharmaceutically-acceptable salt of the tautomer, or the mixture thereof, and a pharmaceutically-acceptable diluent or carrier.

* * * * *